US012733927B2

(12) United States Patent
Fanelli et al.

(10) Patent No.: US 12,733,927 B2
(45) Date of Patent: Sep. 15, 2026

(54) METHOD OF SURGICAL STAPLING

(71) Applicant: Cilag GmbH International, Zug (CH)

(72) Inventors: Nicholas Fanelli, Morrow, OH (US); Kevin M. Fiebig, Cincinnati, OH (US); Jeffery D. Bruns, Cincinnati, OH (US); John K. Bruce, Morrow, OH (US); Pierre R. Mesnil, Newport, KY (US); Shannon L. Jones, Cincinnati, OH (US); John W. Stodghill, Cincinnati, OH (US); Gregory G. Scott, Cincinnati, OH (US); Devanathan Raghavan, Mason, OH (US); John P. May, Mason, OH (US); Nicholas A. Wilson, Montgomery, OH (US); Cory G. Kimball, Hamilton, OH (US); Kristin L. Jambor, Cincinnati, OH (US); Scott A. Jenkins, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/245,562

(22) Filed: Jun. 23, 2025

(65) Prior Publication Data

US 2025/0312036 A1 Oct. 9, 2025

Related U.S. Application Data

(63) Continuation of application No. 18/588,684, filed on Feb. 27, 2024, now Pat. No. 12,471,913.

(Continued)

(51) Int. Cl.

| | |
|---|---|
| ***A61B 17/064*** | (2006.01) |
| ***A61B 17/072*** | (2006.01) |

(52) U.S. Cl.

CPC .... *A61B 17/0644* (2013.01); *A61B 17/07207* (2013.01); *A61B 2017/07271* (2013.01)

(58) Field of Classification Search

CPC ...................... A61B 17/0644; A61B 17/07207

(Continued)

(56) References Cited

U.S. PATENT DOCUMENTS

| | | | |
|---|---|---|---|
| 7,401,721 | B2 | 7/2008 | Holsten et al. |
| 7,735,703 | B2 | 6/2010 | Morgan et al. |

(Continued)

FOREIGN PATENT DOCUMENTS

| | | | |
|---|---|---|---|
| CN | 105919642 | A | 9/2016 |
| CN | 105997172 | A | 10/2016 |

(Continued)

OTHER PUBLICATIONS

International Search Report and Written Opinion dated Aug. 16, 2024, for International Application No. PCT/IB2024/054893, 16 pages.

(Continued)

*Primary Examiner* — Nathaniel C Chukwurah

(74) *Attorney, Agent, or Firm* — FBT Gibbons LLP

(57) ABSTRACT

A method of operating a surgical instrument includes clamping tissue with a surgical instrument end effector and actuating the end effector to drive staples into the clamped tissue, including a first longitudinal row having at least one first formed staple with a first formed shape in which the first legs are aligned laterally with each other and with the first crown; a second longitudinal row having at least one second formed staple with a second formed shape in which each second leg is skewed laterally away from the second crown at a first angle; and a third longitudinal row of third formed staples having at least one third formed staple with a third formed (Continued)

shape in which each third leg is skewed laterally away from the third crown at a second angle.

20 Claims, 117 Drawing Sheets

Related U.S. Application Data

(60) Provisional application No. 63/467,615, filed on May 19, 2023, provisional application No. 63/467,622, filed on May 19, 2023, provisional application No. 63/467,623, filed on May 19, 2023, provisional application No. 63/467,648, filed on May 19, 2023, provisional application No. 63/467,649, filed on May 19, 2023, provisional application No. 63/459,739, filed on Apr. 17, 2023.

(58) Field of Classification Search
USPC .......................................................... 227/175.1
See application file for complete search history.

(56) References Cited

U.S. PATENT DOCUMENTS

| | | | |
|---|---|---|---|
| 8,393,514 | B2 | 3/2013 | Shelton, IV et al. |
| 8,453,914 | B2 | 6/2013 | Laurent et al. |
| 8,733,613 | B2 | 5/2014 | Huitema et al. |
| 9,186,142 | B2 | 11/2015 | Fanelli et al. |
| 9,717,497 | B2 | 8/2017 | Zerkle et al. |
| 9,808,248 | B2 | 11/2017 | Hoffman |
| 9,839,421 | B2 | 12/2017 | Zerkle et al. |
| 9,844,369 | B2 | 12/2017 | Huitema et al. |
| 9,924,944 | B2 | 3/2018 | Shelton, IV et al. |
| 10,092,292 | B2 | 10/2018 | Boudreaux et al. |
| 10,130,359 | B2 | 11/2018 | Hess et al. |
| 10,166,023 | B2 | 1/2019 | Vendely et al. |
| 10,349,939 | B2 | 7/2019 | Shelton, IV et al. |
| 10,357,252 | B2 | 7/2019 | Harris et al. |
| 10,537,325 | B2 | 1/2020 | Bakos et al. |
| 10,542,981 | B2 | 1/2020 | Miller et al. |
| 10,561,422 | B2 | 2/2020 | Schellin et al. |
| 11,045,191 | B2 | 6/2021 | Shelton, IV et al. |
| 11,058,426 | B2 | 7/2021 | Nalagatla et al. |
| 11,166,724 | B2 | 11/2021 | McGiveron et al. |
| 11,202,628 | B2 | 12/2021 | Posey et al. |
| 11,229,433 | B2 | 1/2022 | Schings et al. |
| 11,272,937 | B2 | 3/2022 | Fernandes et al. |
| D967,421 | S | 10/2022 | Shelton, IV et al. |
| 11,517,315 | B2 | 12/2022 | Huitema et al. |
| D974,560 | S | 1/2023 | Shelton, IV et al. |
| D976,401 | S | 1/2023 | Shelton, IV et al. |
| 11,576,672 | B2 | 2/2023 | Shelton, IV et al. |
| 11,849,944 | B2 | 12/2023 | Shelton, IV et al. |
| 11,896,218 | B2 | 2/2024 | Bakos et al. |
| 11,918,210 | B2 | 3/2024 | Shelton, IV et al. |
| 12,035,913 | B2 | 7/2024 | Shelton, IV et al. |
| 12,285,170 | B2 | 4/2025 | Wilson et al. |
| 12,324,583 | B2 | 6/2025 | Scott et al. |
| 12,390,220 | B2 | 8/2025 | Scott et al. |
| 12,414,771 | B2 | 9/2025 | Fanelli et al. |
| 12,426,880 | B2 | 9/2025 | Fanelli et al. |
| 12,471,913 | B2 | 11/2025 | Fanelli et al. |
| 2015/0297234 | A1* | 10/2015 | Schellin ............. A61B 17/0644 227/176.1 |
| 2024/0382196 | A1 | 11/2024 | Fanelli et al. |

FOREIGN PATENT DOCUMENTS

| | | | |
|---|---|---|---|
| CN | 105997173 | A | 10/2016 |
| CN | 106037848 | A | 10/2016 |
| CN | 108542454 | A | 9/2018 |
| CN | 111195142 | A | 5/2020 |

OTHER PUBLICATIONS

International Search Report and Written Opinion dated Aug. 22, 2024, for International Application No. PCT/IB2024/054894, 18 pages.

U.S. Appl. No. 63/459,739, entitled “Surgical Stapler Anvil Having Staple Forming Pockets with Laterally Varying Orientations,” filed Apr. 17, 2023.

* cited by examiner 58
56
46
50
54
52
82
84
86
44

42
86
62
84
40
70

A234
A232
A308
A236
A306
A230
A240
A302

A338
A412
A346
A410
A416
A414
A348
A422
A350

T1
T2
D110
D112
D126
D122
D126
86

44
T1
T2
D126
D122
70
84
86
66
D110
D112

44
D110
66
T1
T2
D112
74
D126
D122
86
84
70

D818
D861
D834
D860
D866
D846
D820
D830
D814
D856
D850
D854
D832
D810
D812

D860
D834
D866
D830
D846
D814
D856
D832
D854
D810
D812

E410
E420
E460c
E430
E412
E434
E450
E432
E460a
E460b
E414
E454
E452

E1312
E1313
E1320
126
E1326
E1324
E1310

E1320
E1324
E1313
L4
E1326
E1310
H2

D1
F114a
F134a
F122
F112
F134d
F114d
F134e
F114e
F116
F111
F110
D3

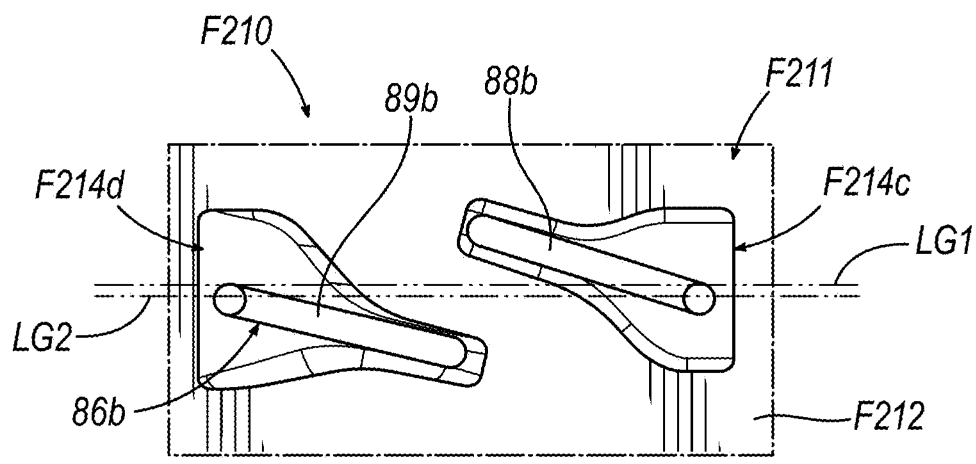
FIG. 139
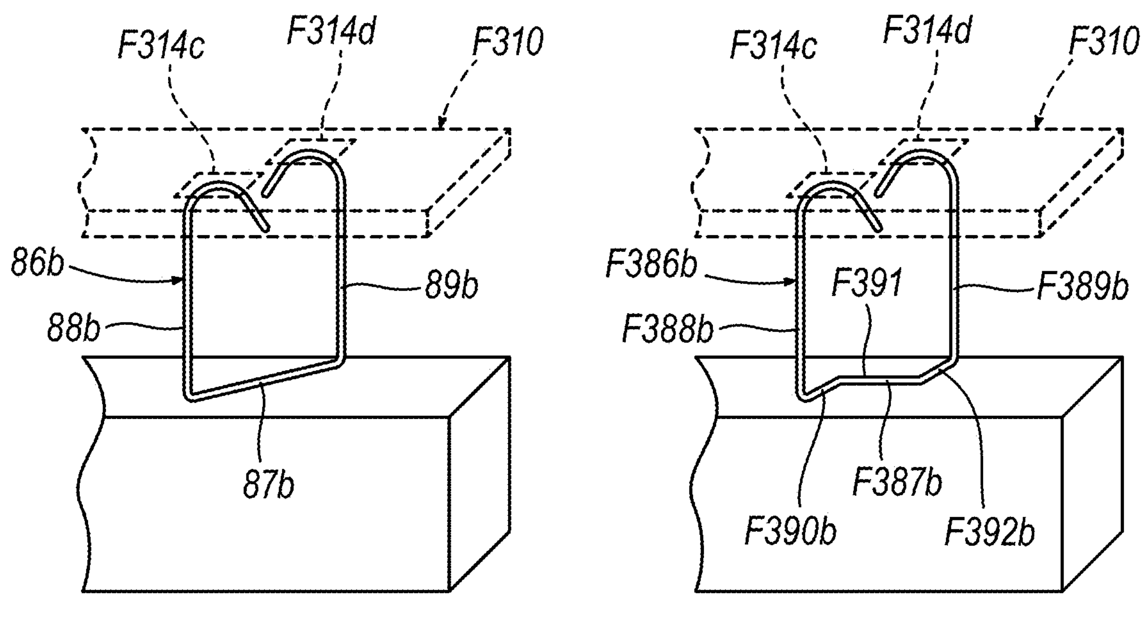
FIG. 140
FIG. 141

METHOD OF SURGICAL STAPLING

PRIORITY

This application us a continuation of U.S. patent application Ser. No. 18/588,684, entitled "Method of Surgical Stapling," filed Feb. 27, 2024 now U.S. Pat. No. 12,471,913, published as U.S. Pat. Pub. No. 2024/0350137 on Oct. 24, 2024; which claims priority to each of U.S. Provisional Pat. App. No. 63/467,615, entitled "Incompatible Staple Cartridge Use Prevention Features for Surgical Stapler," filed May 19, 2023; U.S. Provisional Pat. App. No. 63/467,622, entitled "Surgical Stapler Cartridge Having Intermediate Raised Tissue Engagement Protrusions," filed May 19, 2023; U.S. Provisional Pat. App. No. 63/467,623, entitled "Surgical Stapler Cartridge Having Tissue Engagement Protrusions with Enlarged Engagement Surface," filed May 19, 2023; U.S. Provisional Pat. App. No. 63/467,648, entitled "Surgical Stapler Cartridge Having Raised Surface to Promote Buttress Adhesion," filed May 19, 2023; U.S. Provisional Pat. App. No. 63/467,649, entitled "Surgical Stapler Cartridge Having Cartridge Retention Features," filed May 19, 2023; and U.S. Provisional Pat. App. No. 63/459,739, entitled "Surgical Stapler Anvil Having Staple Forming Pockets with Laterally Varying Orientations," filed Apr. 17, 2023. The disclosure of each of the above patent applications is incorporated by reference herein in its entirety.

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In a surgical procedure setting in which multiple different types of surgical staplers and/or multiple different types of staple cartridges are made available to a clinician for use in the procedure, a theoretical scenario could arise in which the clinician inadvertently selects a staple cartridge that is not designed for use with the particular surgical stapler selected by the clinician. In other words, the staple cartridge selected by the clinician could be incompatible with the surgical stapler. Nevertheless, the incompatible staple cartridge could be structurally similar enough to a compatible staple cartridge (i.e., one designed specifically for use with the selected surgical stapler) that the incompatible staple cartridge is capable of being at least partially seated within the cartridge jaw of the surgical stapler by the clinician. Additionally, the end effector of the surgical stapler may be capable of at least partially closing with the incompatible staple cartridge loaded, which could result in the clinician mistakenly believing that the end effector is properly loaded and ready for firing on patient tissue. Furthermore, if the incompatible staple cartridge has not previously been fired (or "spent"), the surgical stapler could be capable of at least partially firing the incompatible staple cartridge in response to the clinician's input. The incompatibility of the staple cartridge with the surgical stapler could result in the staples ejected by the incompatible staple cartridge being improperly formed by surgical stapler's anvil jaw, and thus being ineffective to properly seal the patient tissue being fired upon.

The surgical stapling features of the present disclosure seek to protect against inadvertent clinician misuse by inhibiting loading of an incompatible staple cartridge into a selected surgical stapler, and subsequent firing of the incompatible staple cartridge with the surgical stapler. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

FIG. 109 depicts a partial side elevational view of another example of a lower pan of a staple cartridge for use with the end effector of FIG. 2 and having a retention tab extending laterally outwardly from a sidewall of the lower pan, the retention tab being longitudinally flanked by proximal and distal T-shaped relief slots;

FIG. 110 depicts an end cross-sectional view of the lower pan of FIG. 109, taken along line 110-110 of FIG. 109, further showing an example of a channel of the lower cartridge jaw of the end effector of FIG. 2;

Figure 2:
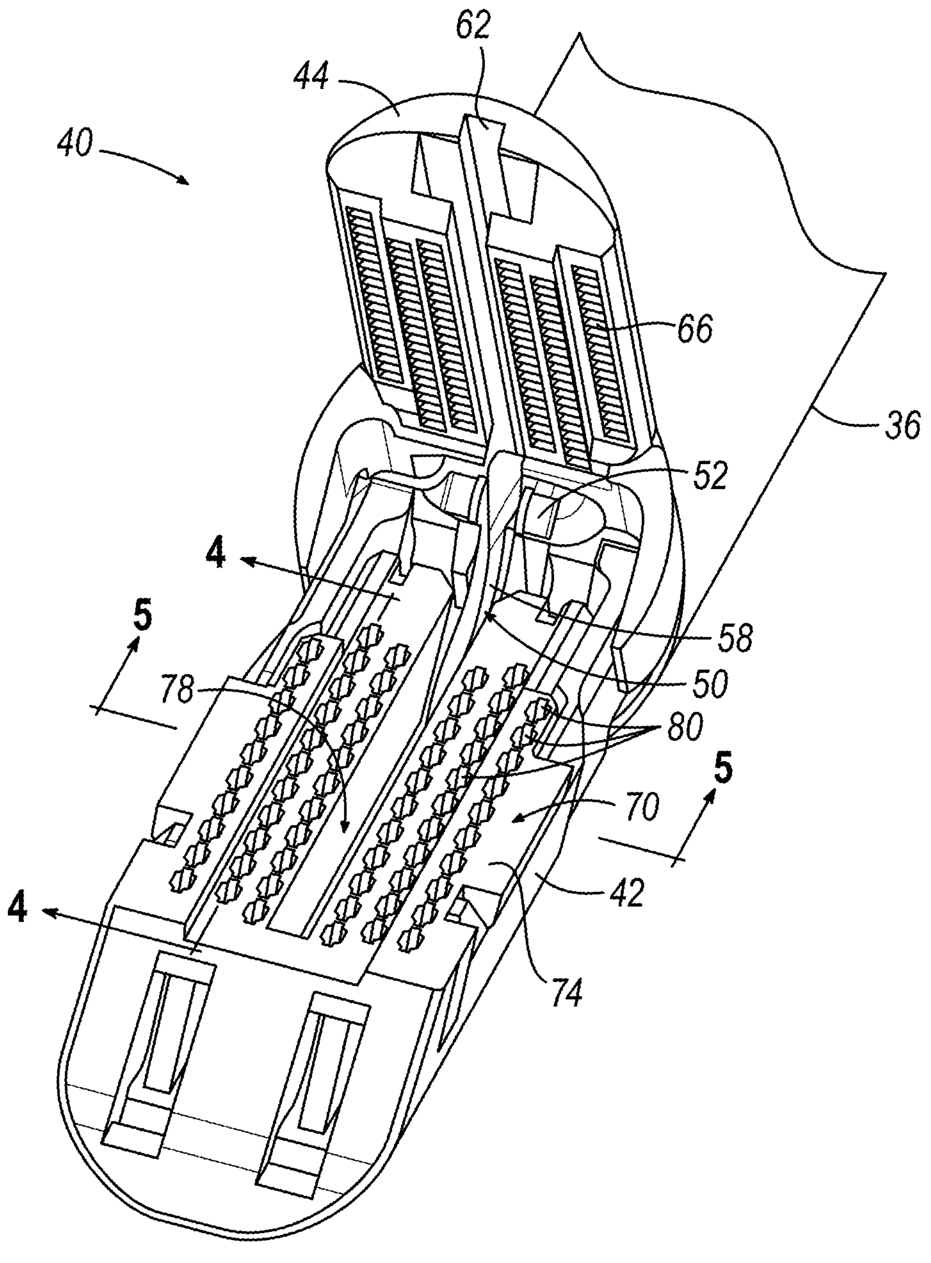
FIG. 2 depicts a perspective view of an end effector of the surgical stapler of FIG. 1, shown in an open state.
Figures 109, 110:
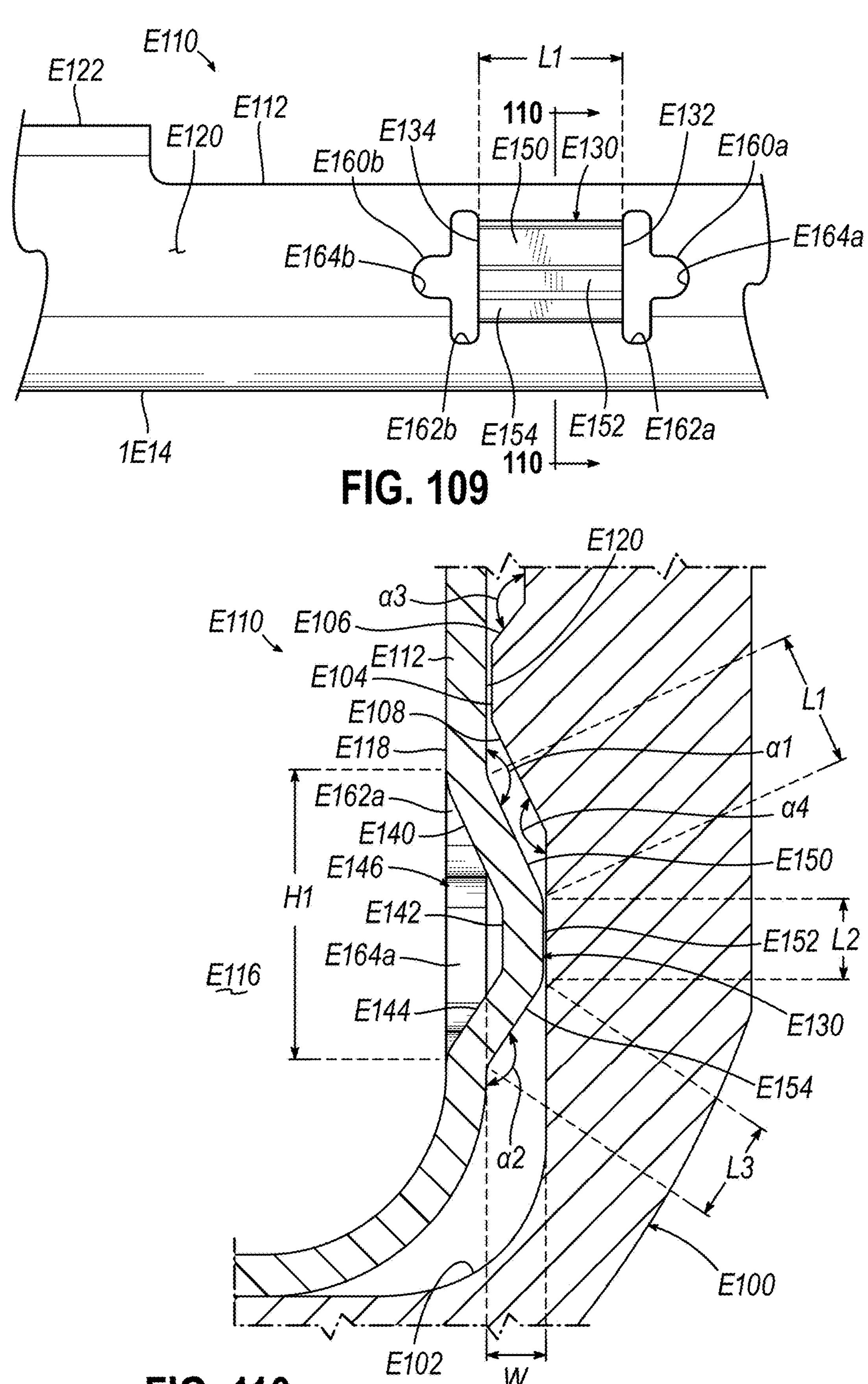
Figure 111:
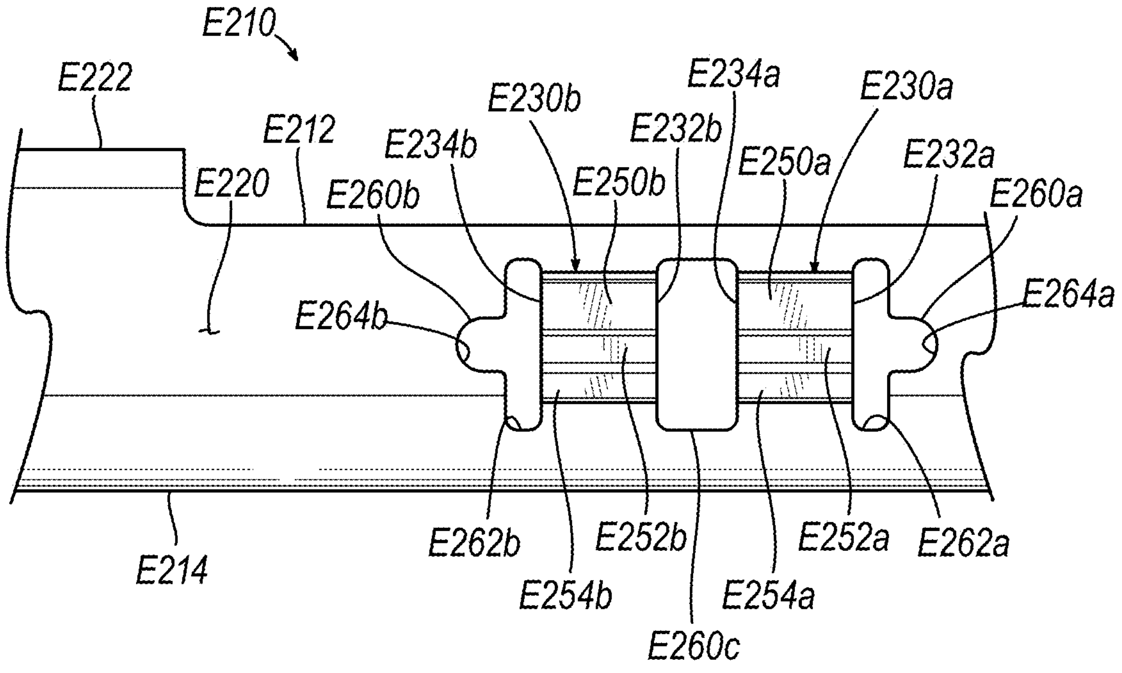
Figures 112, 113:
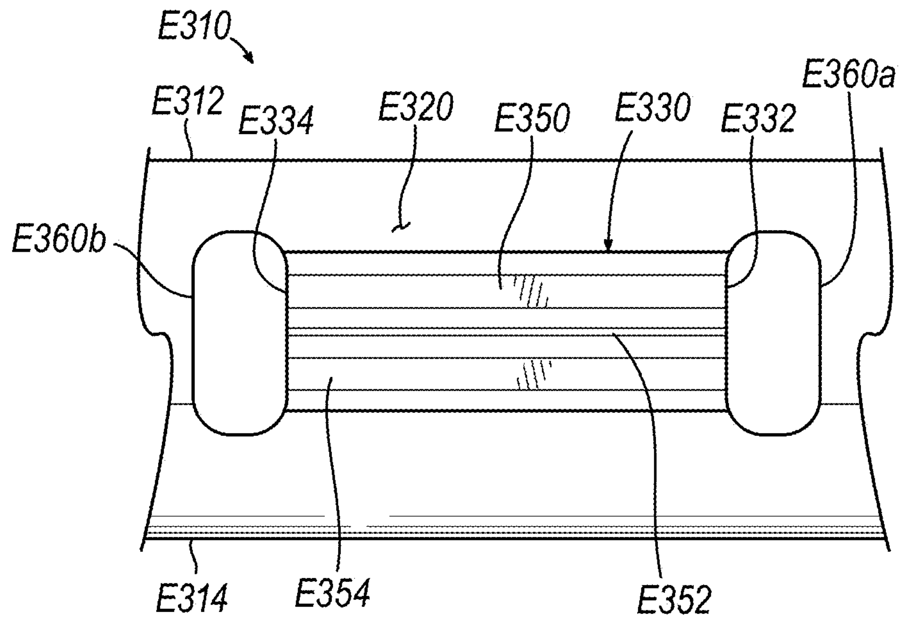
Figure 114:
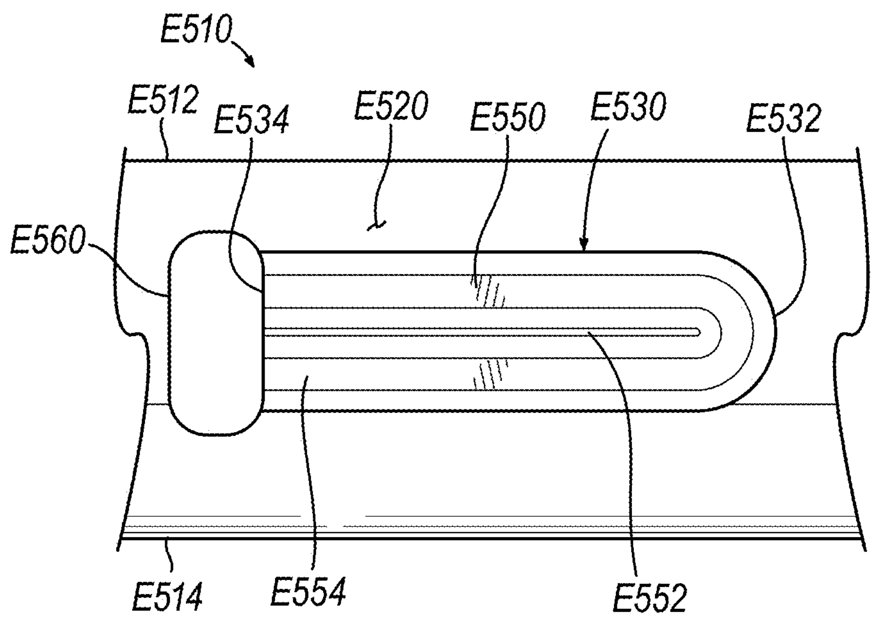
Figure 115:
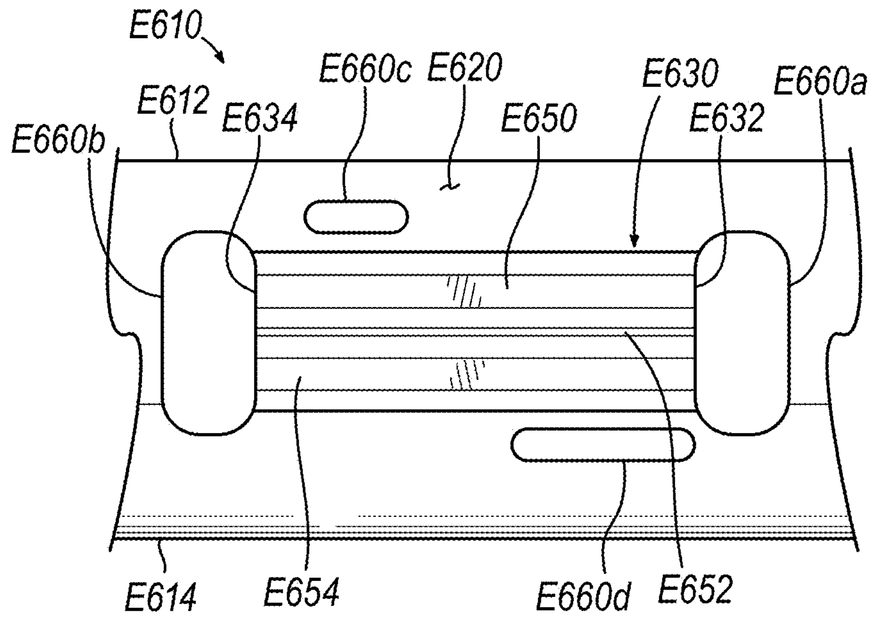
Figure 116:
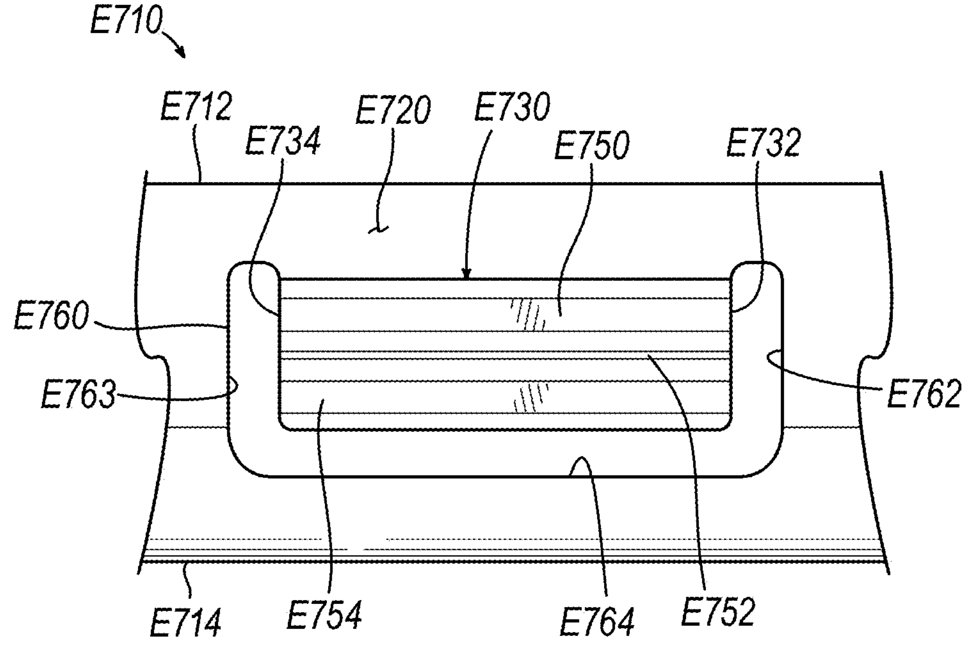
Figure 117:
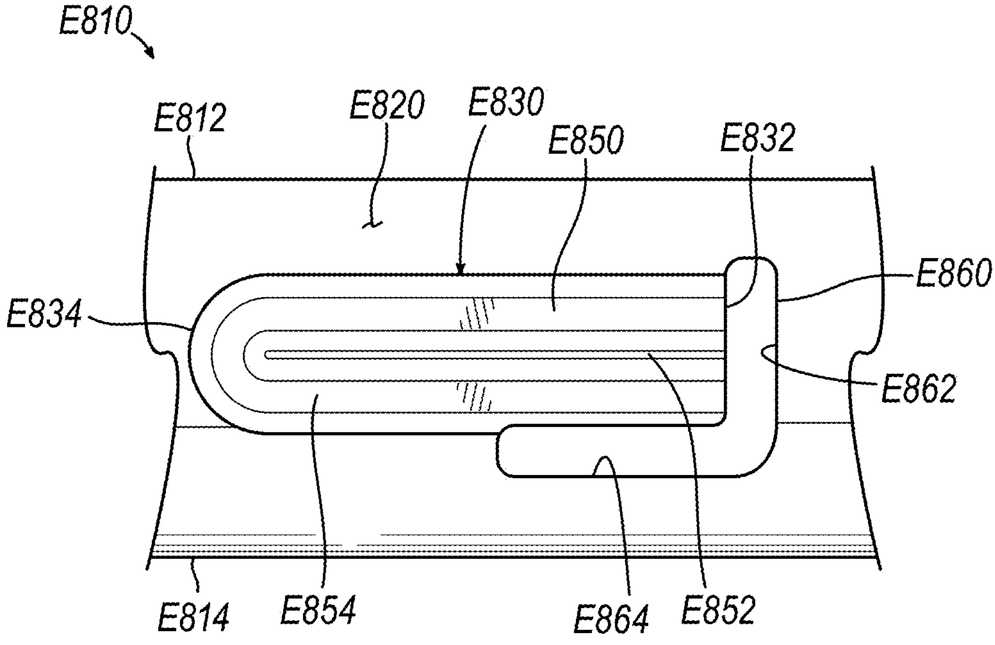
Figure 118:
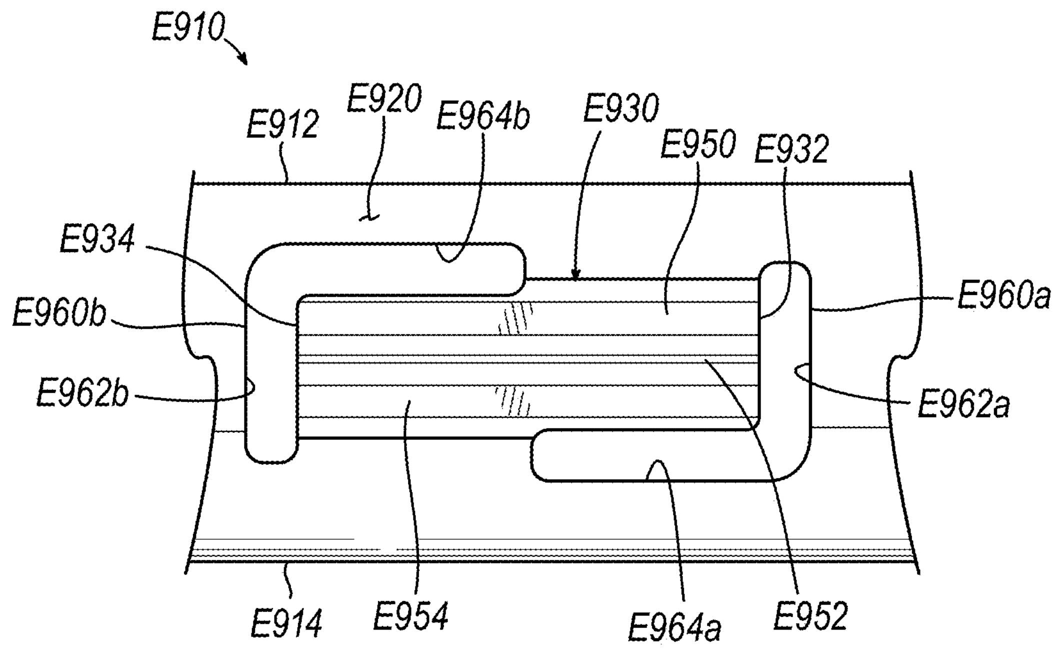
Figure 119:
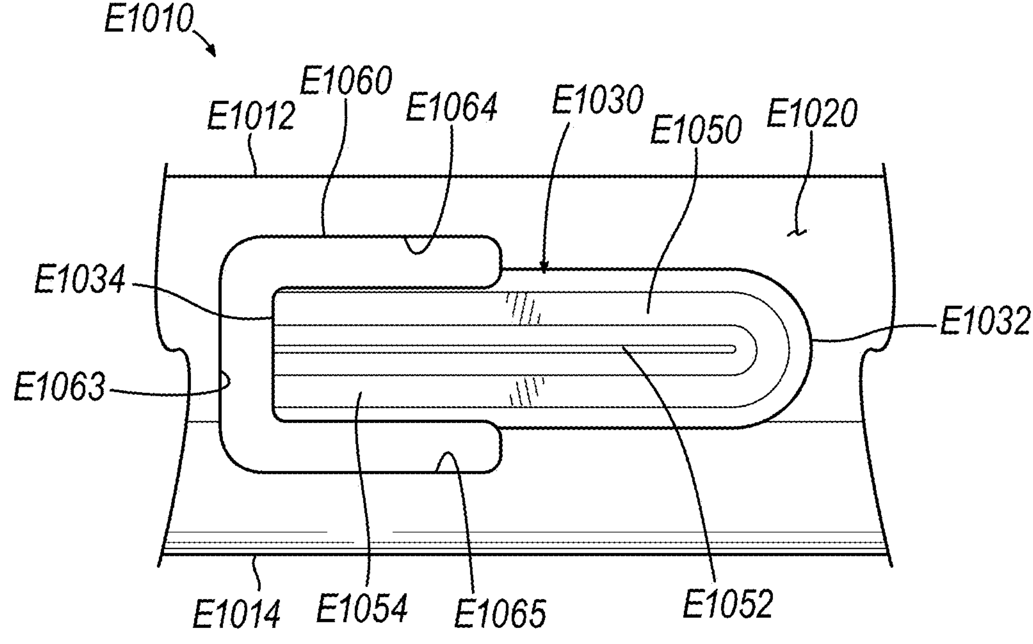
Figure 120:
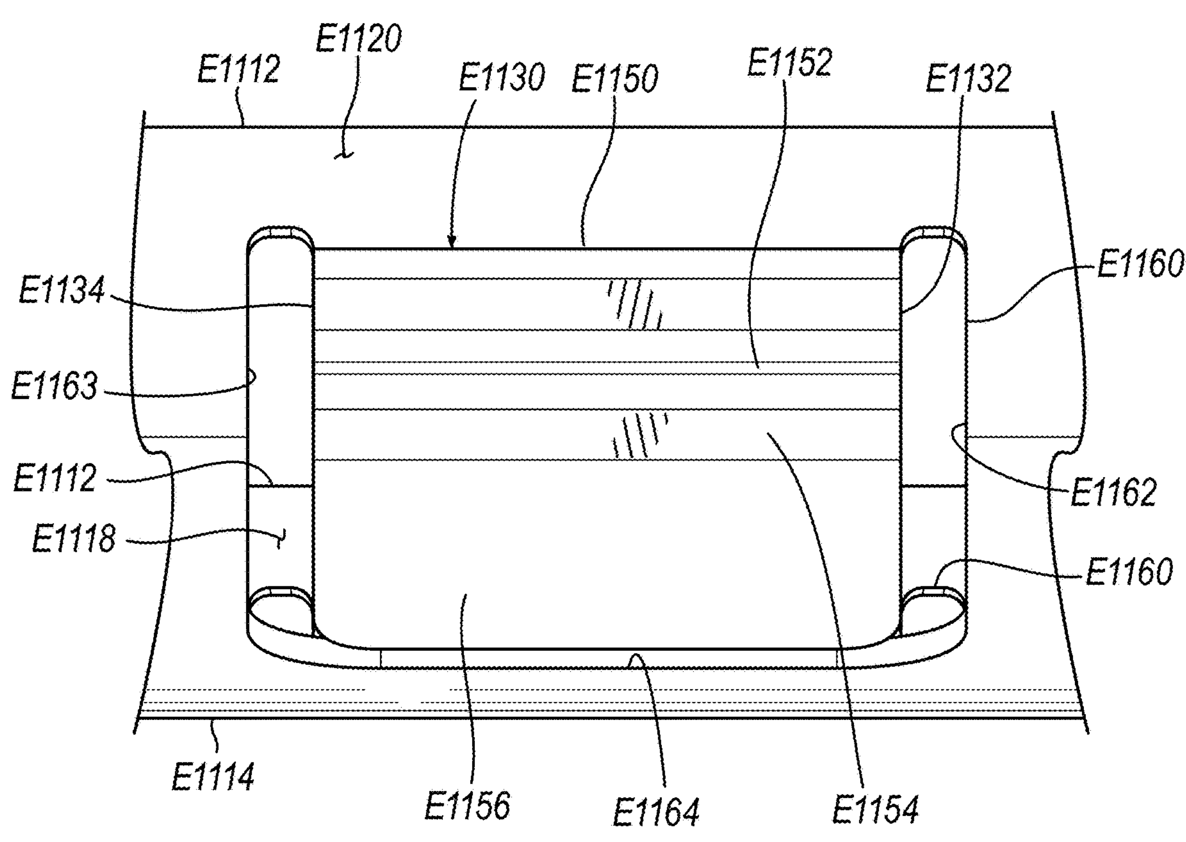
Figures 121, 122:
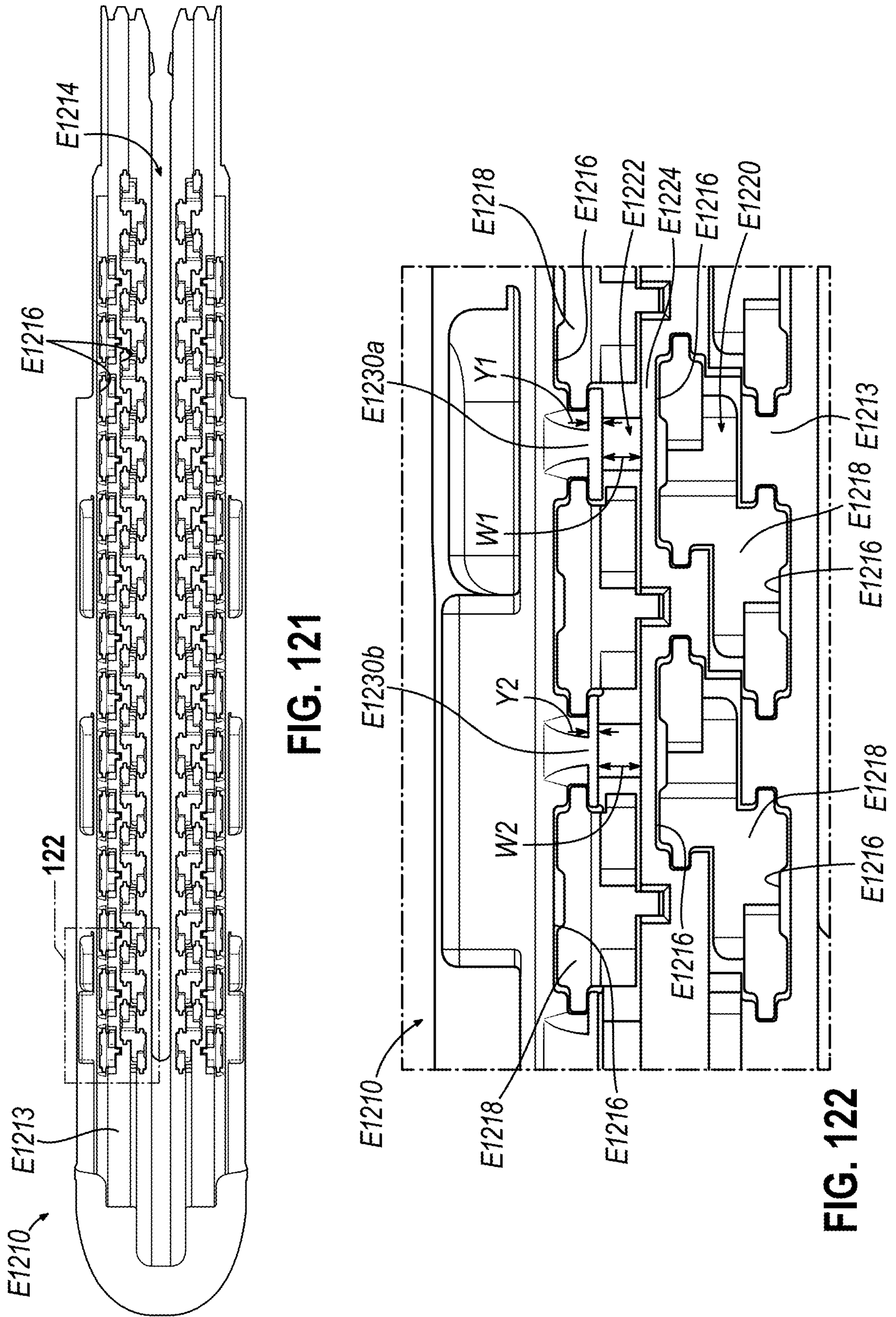
Figure 123:
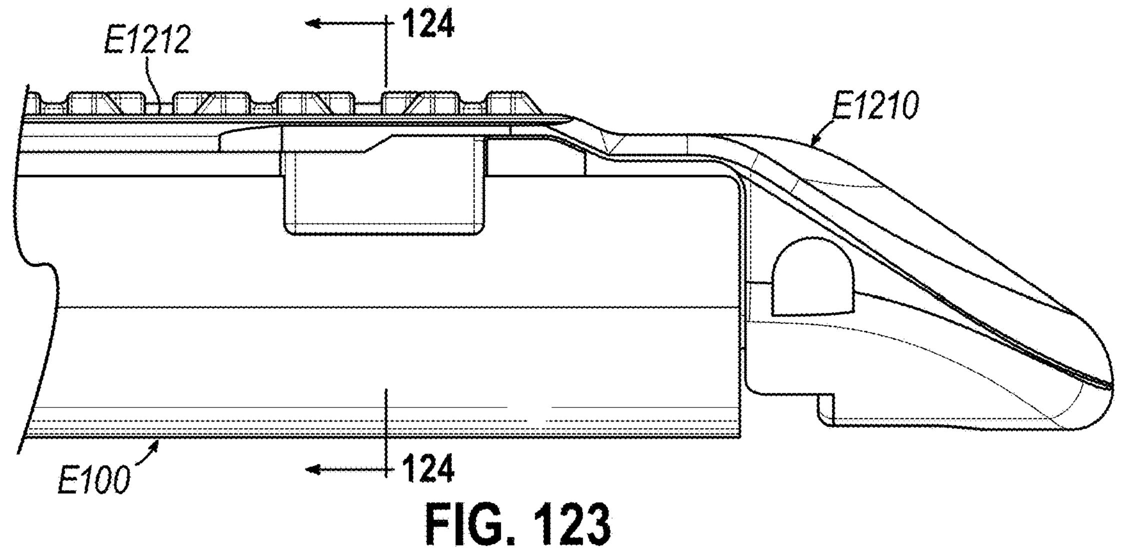
Figure 124:
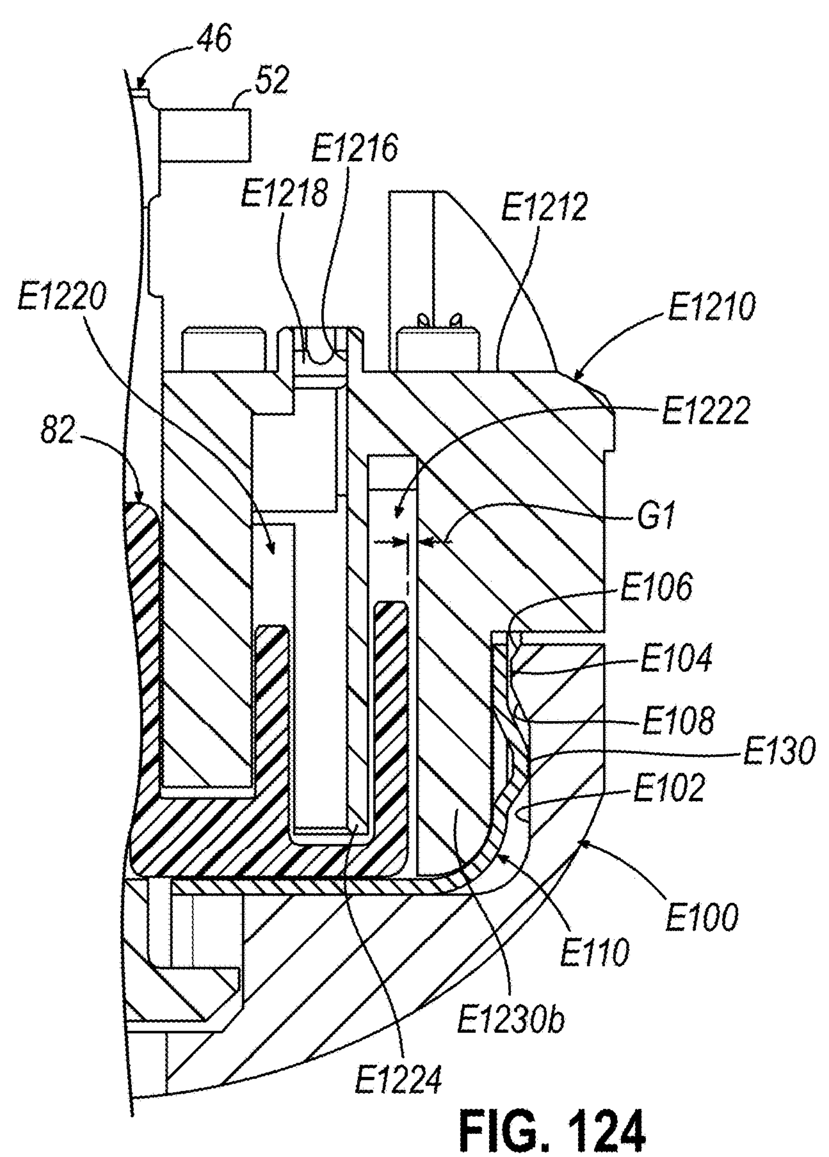
Figures 125, 126:
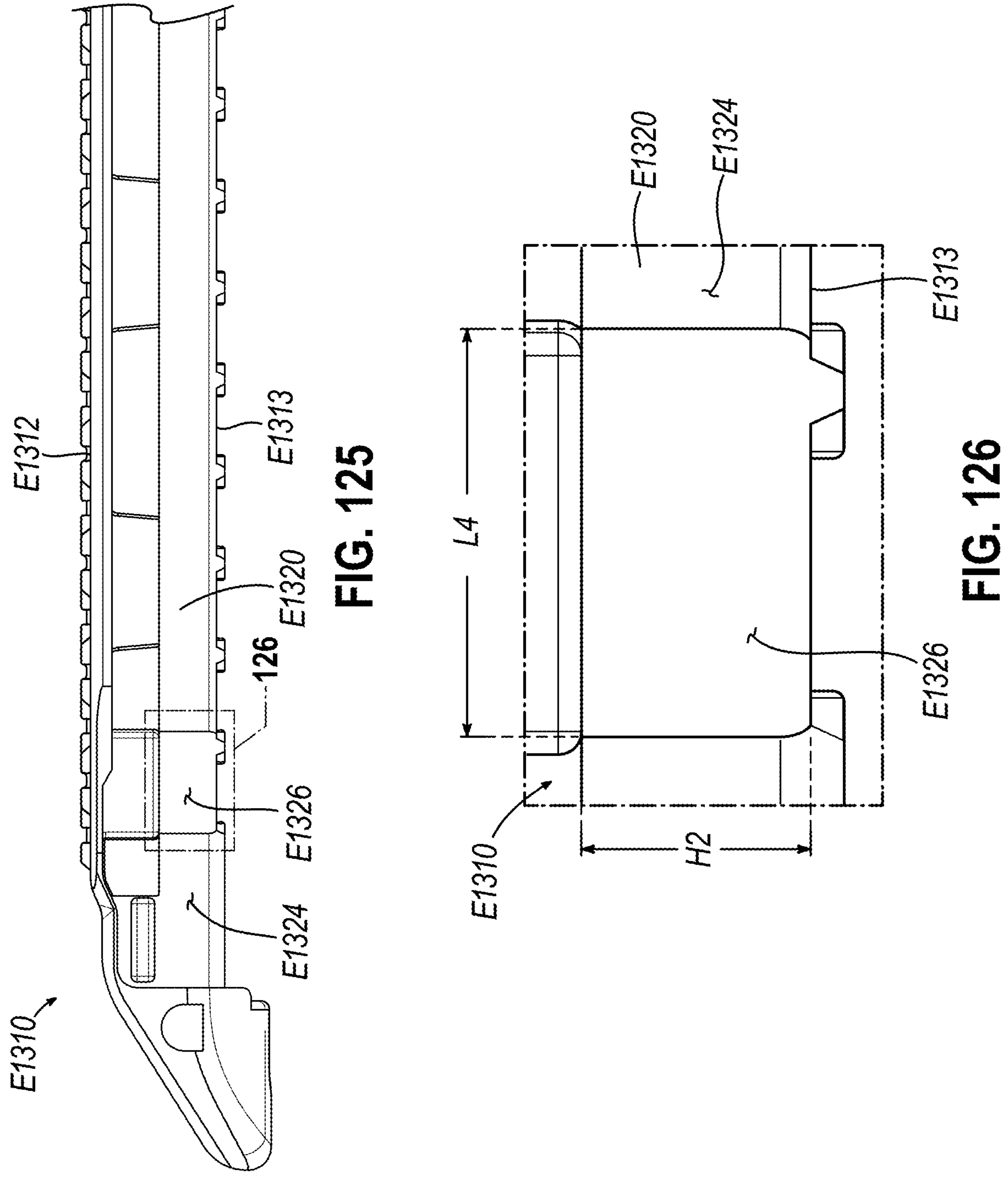
Figure 127:
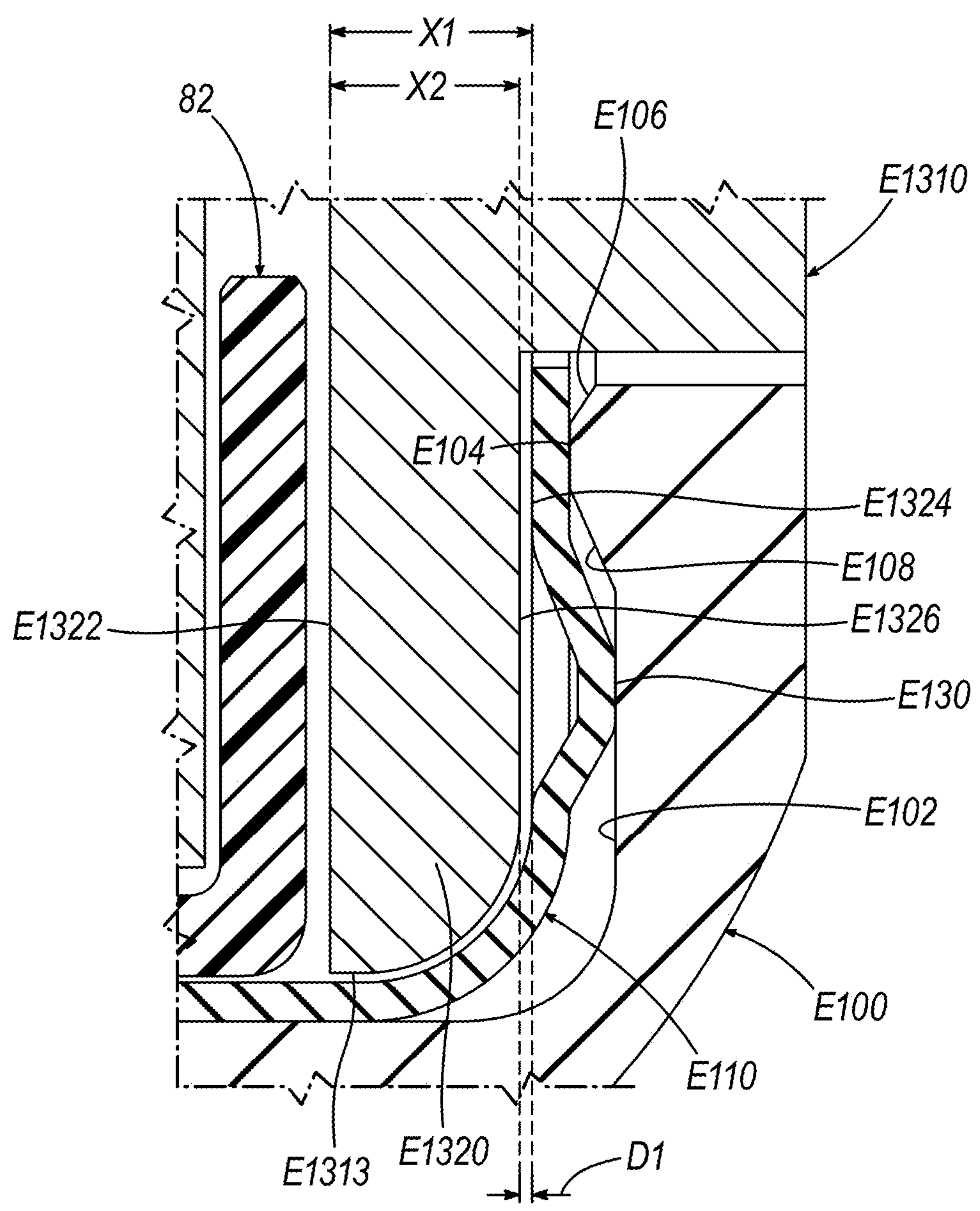
Figure 128:
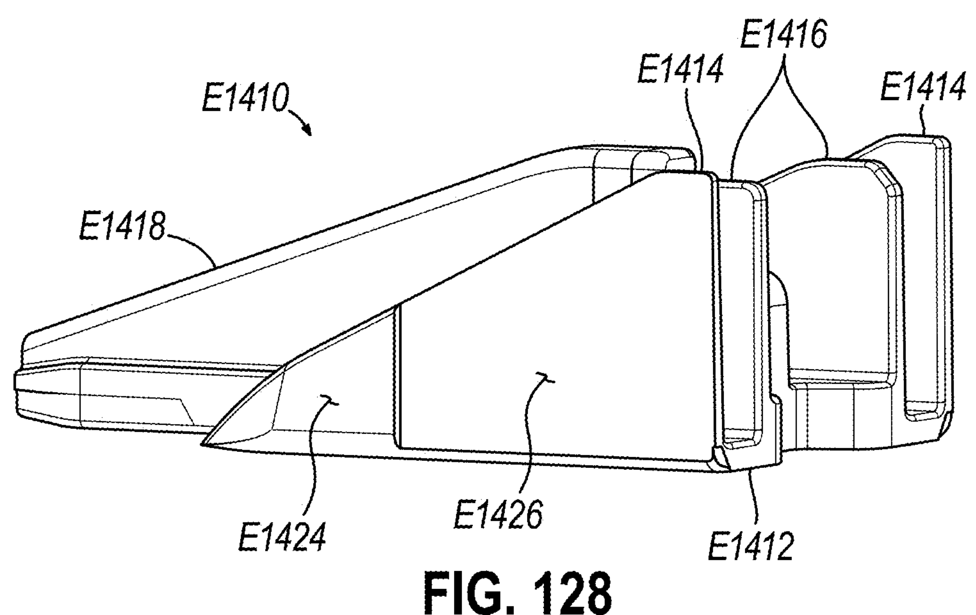
Figure 129:
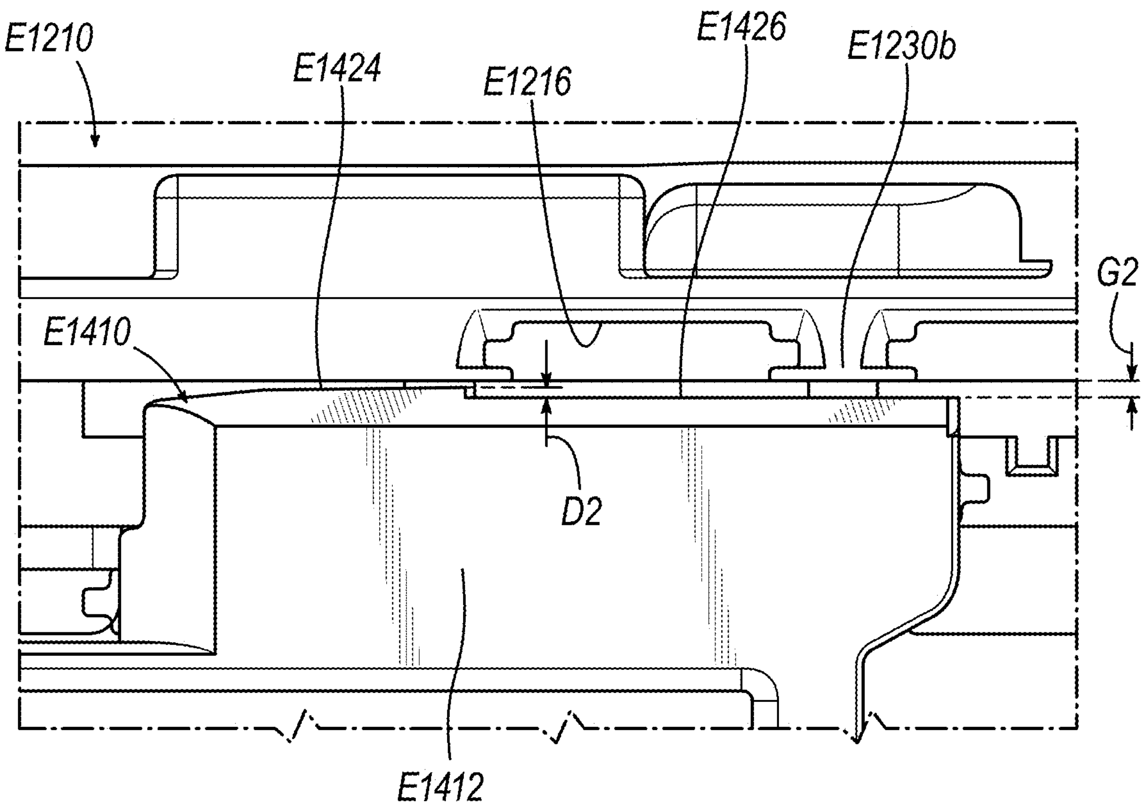
Figure 130:
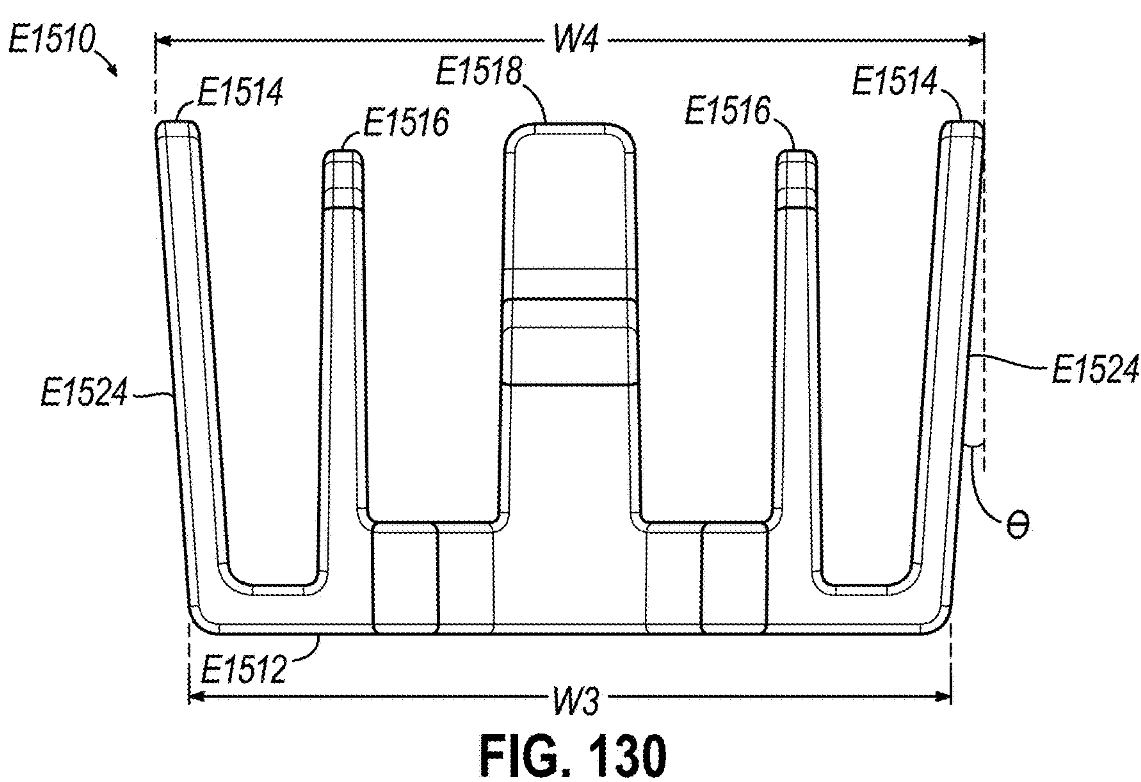
Figure 131:
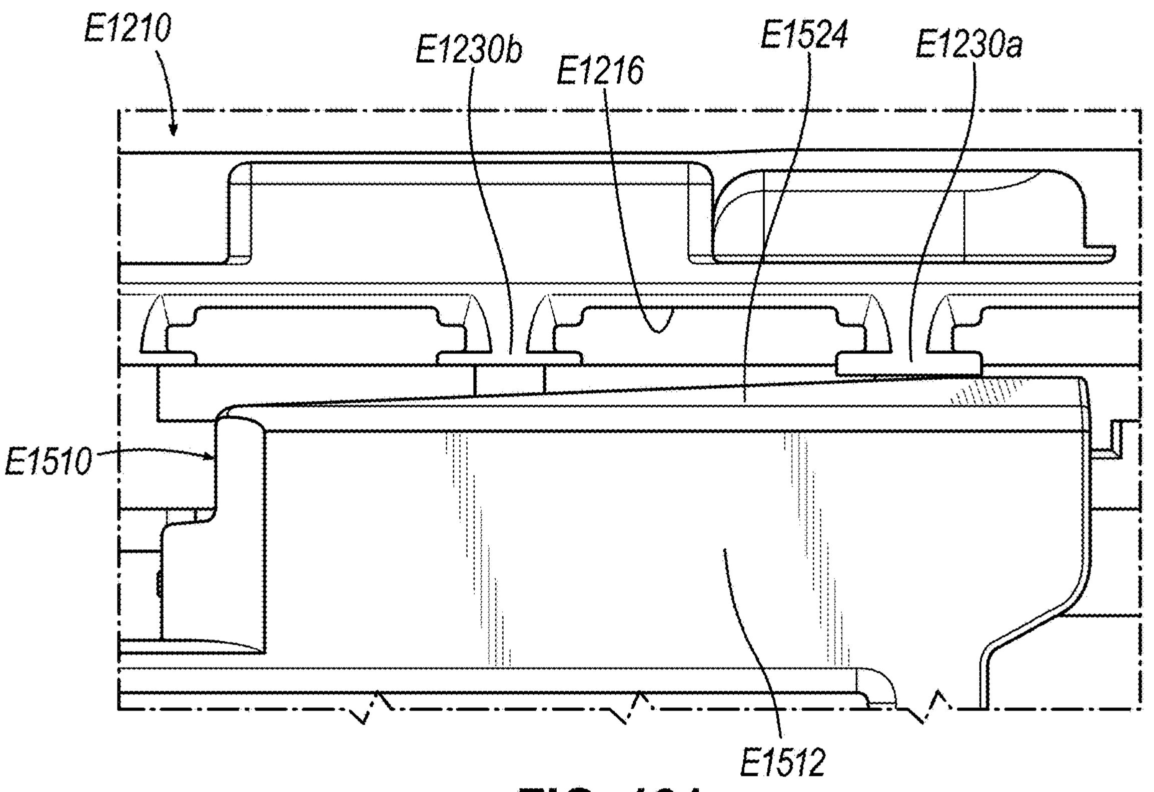
Figure 132:
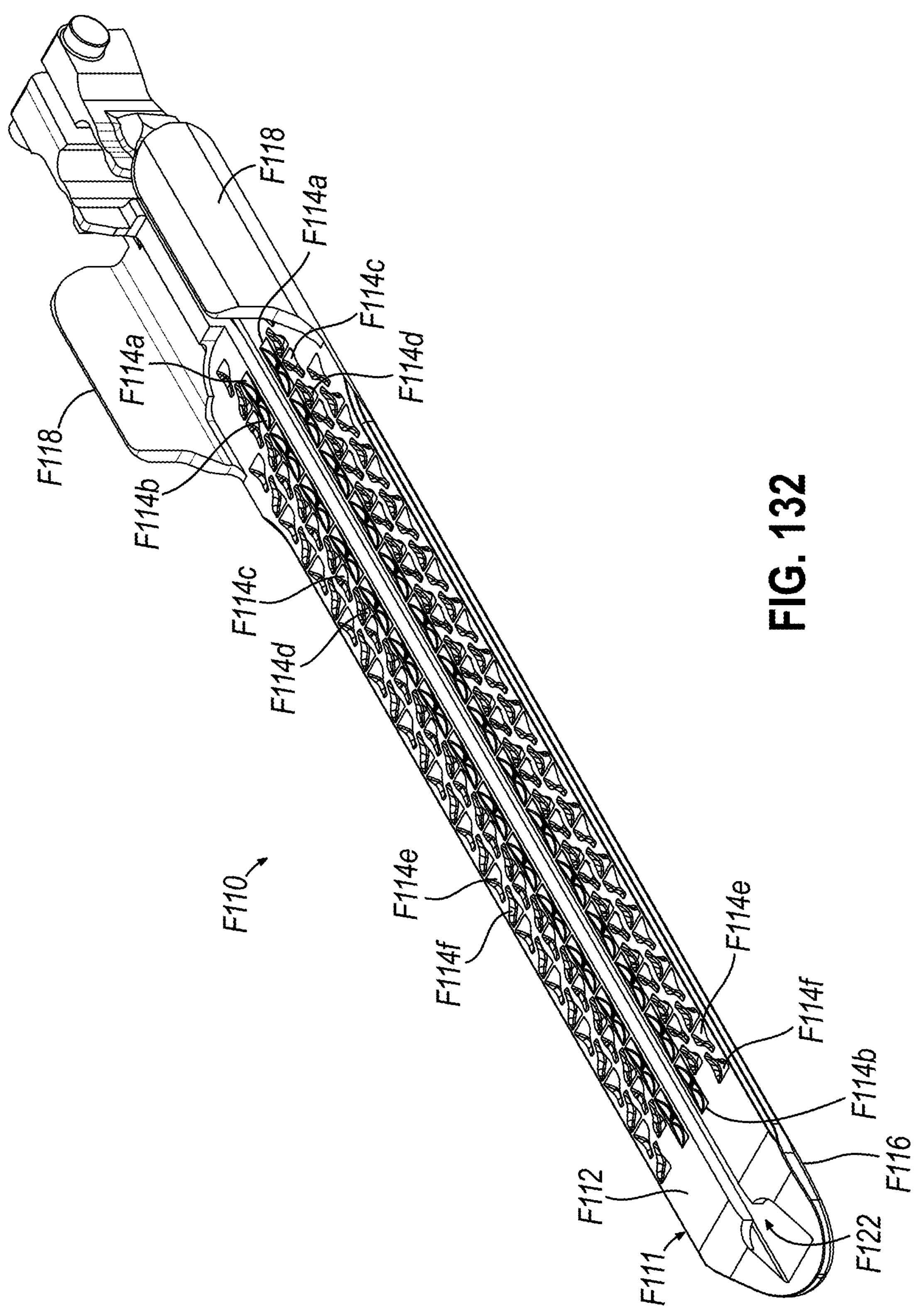
Figure 133:
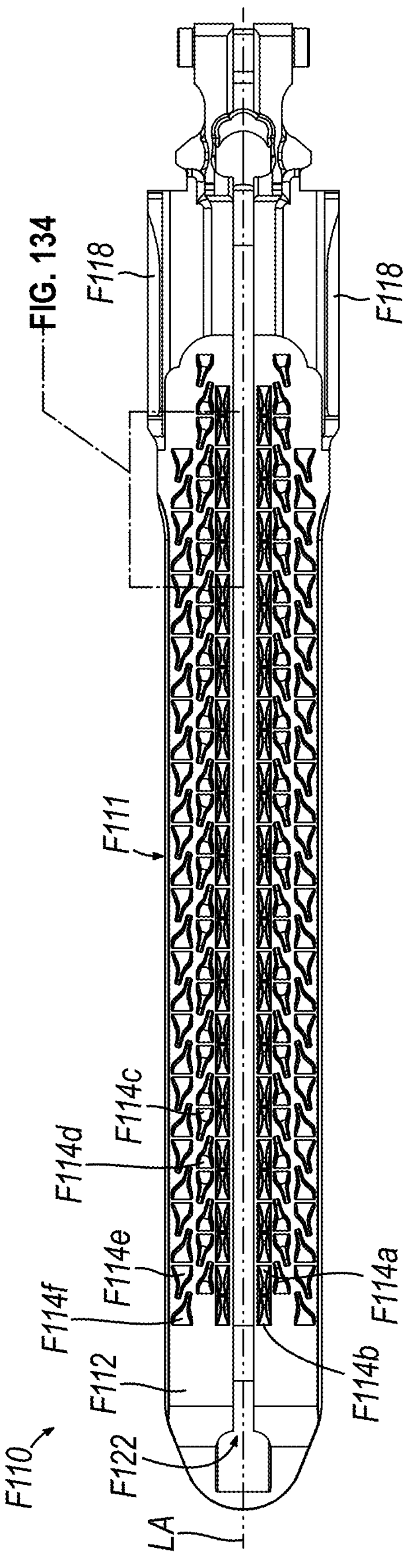
Figure 134:
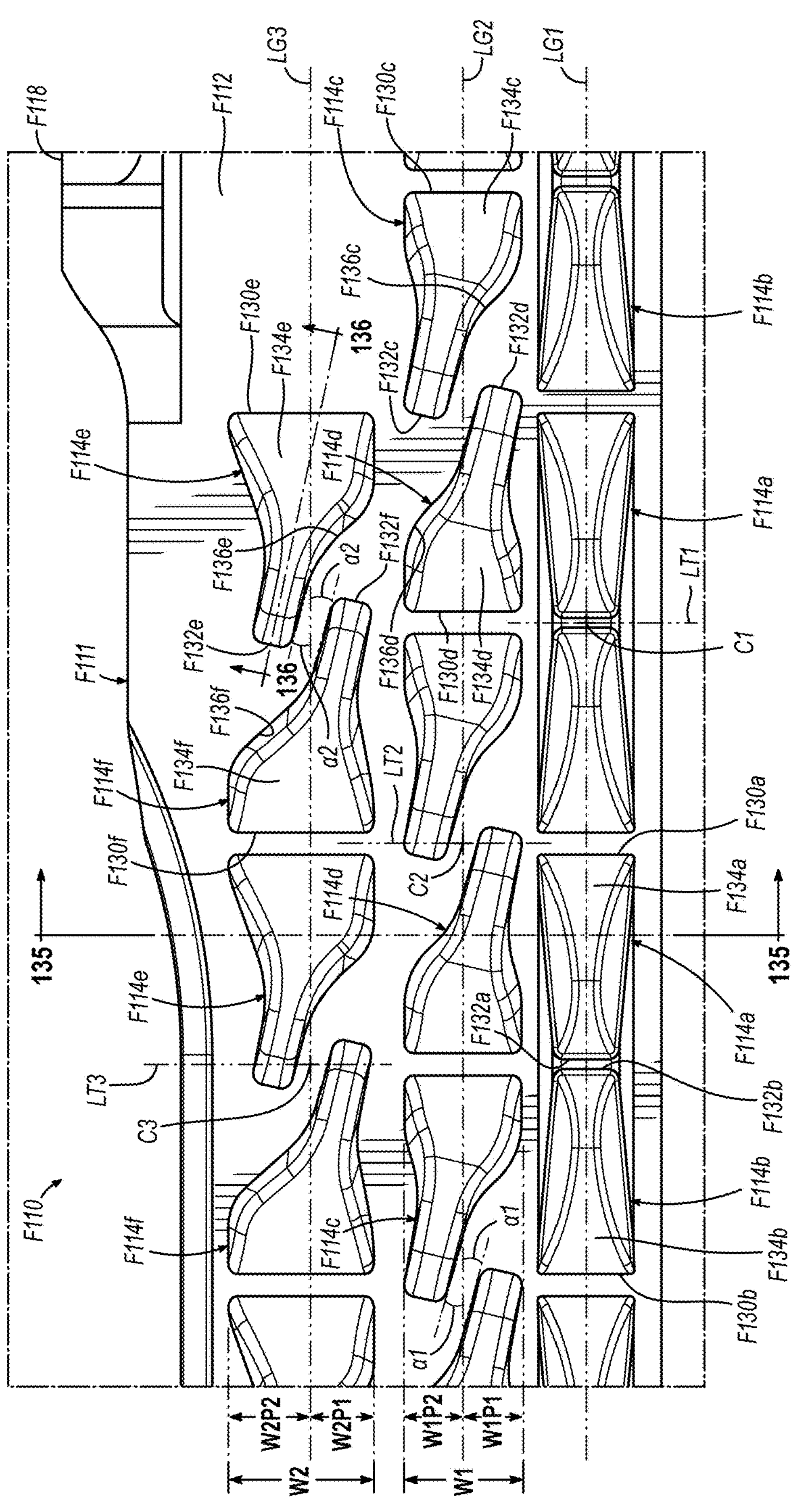
Figure 135:
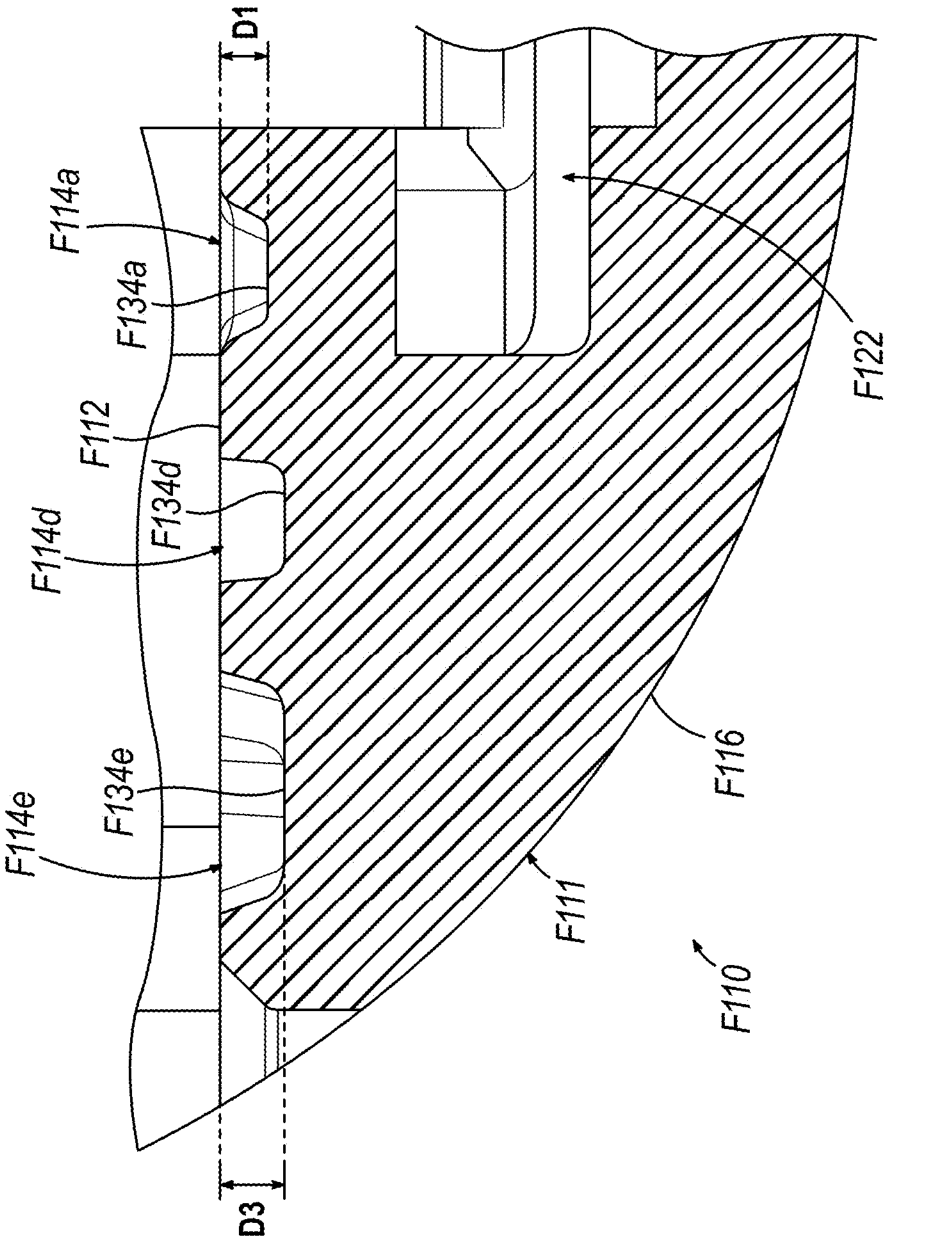
Figure 136:
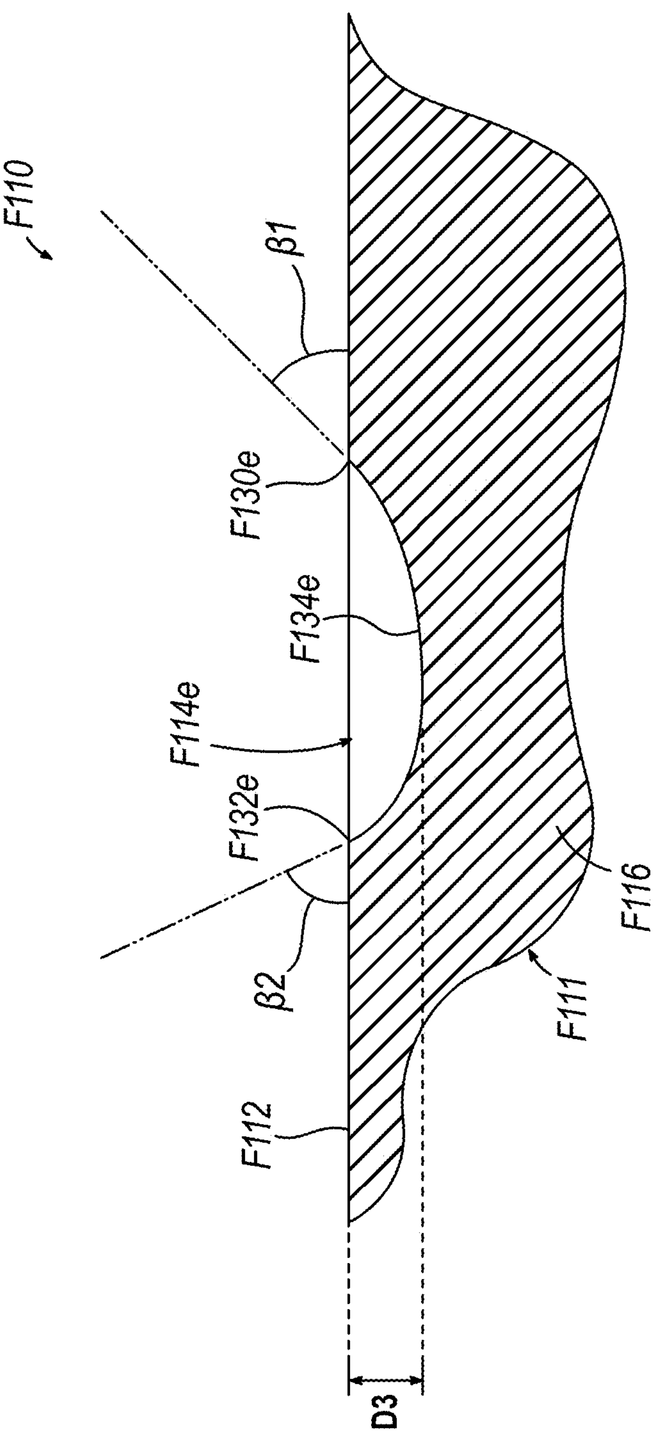
Figure 137:
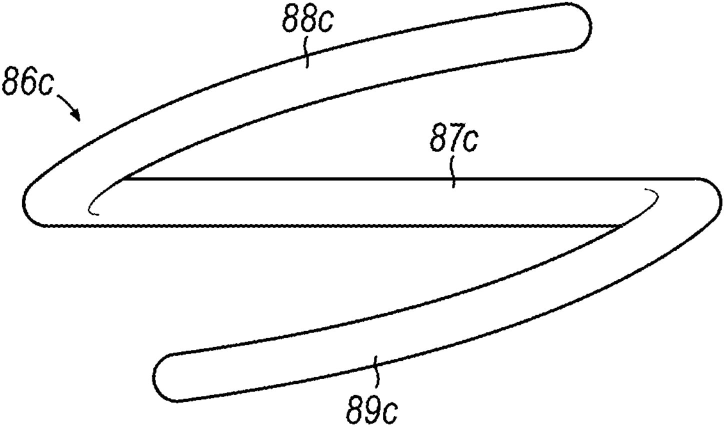
Figure 137:
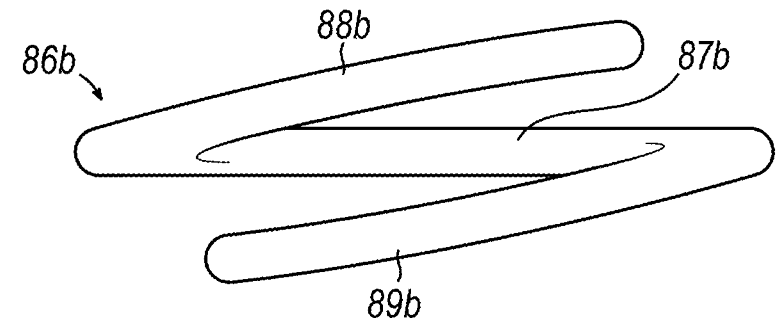
Figure 137:
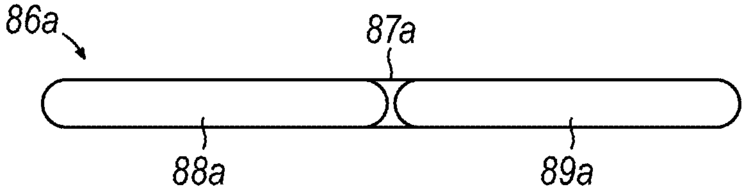
Figure 138:
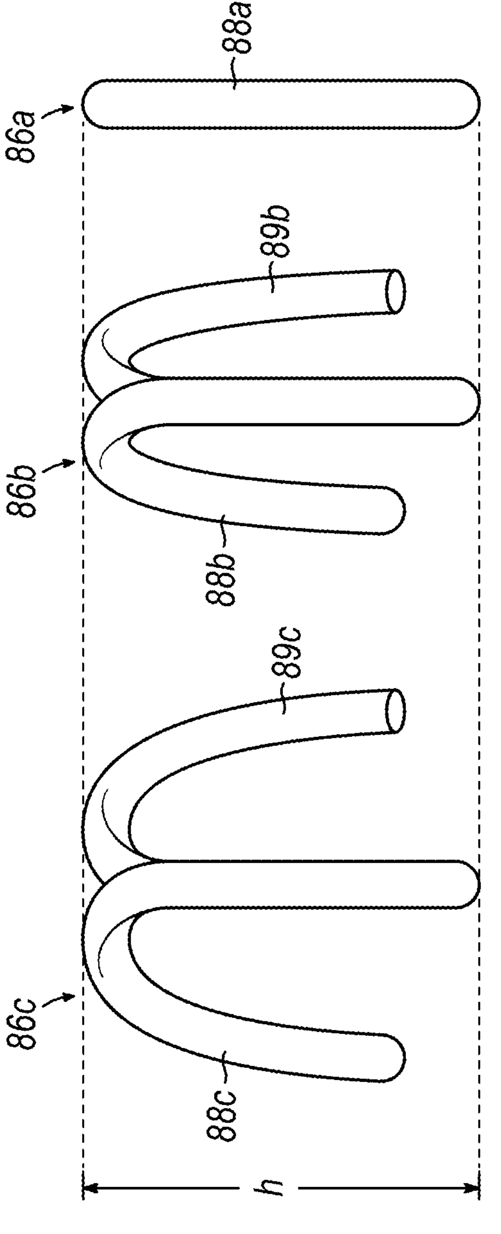

FIG. 111 depicts a partial side elevational view of another example of a lower pan of a staple cartridge for use with the end effector of FIG. 2 and having a pair of retention tabs extending laterally outwardly from a sidewall of the lower pan, the retention tabs being collectively longitudinally flanked by proximal and distal T-shaped relief slots and being spaced apart from each other by an intermediate elongate relief slot and;

FIG. 112 depicts a partial side elevational view of another example of a lower pan of a staple cartridge for use with the end effector of FIG. 2 and having a retention tab extending laterally outwardly from a sidewall of the lower pan, the retention tab being longitudinally flanked by proximal and distal elongate relief slots;

FIG. 113 depicts a partial side elevational view of another example of a lower pan of a staple cartridge for use with the end effector of FIG. 2 and having a retention tab extending laterally outwardly from a sidewall of the lower pan, the retention tab being partially surrounded by proximal, distal, and upper elongate relief slots;

FIG. 114 depicts a partial side elevational view of another example of a lower pan of a staple cartridge for use with the end effector of FIG. 2 and having a retention tab extending laterally outwardly from a sidewall of the lower pan, the lower pan further having a distal elongate relief slot adjacent a distal end of the retention tab;

FIG. 115 depicts a partial side elevational view of another example of a lower pan of a staple cartridge for use with the end effector of FIG. 2 and having a retention tab extending laterally outwardly from a sidewall of the lower pan, the retention tab being partially surrounded by proximal, distal, upper, and lower elongate relief slots;

FIG. 116 depicts a partial side elevational view of another example of a lower pan of a staple cartridge for use with the end effector of FIG. 2 and having a retention tab extending laterally outwardly from a sidewall of the lower pan, the retention tab being partially surrounded by a U-shaped relief slot;

FIG. 117 depicts a partial side elevational view of another example of a lower pan of a staple cartridge for use with the end effector of FIG. 2 and having a retention tab extending laterally outwardly from a sidewall of the lower pan, the lower pan further having a proximal L-shaped relief slot adjacent a proximal end of the retention tab;

FIG. 118 depicts a partial side elevational view of another example of a lower pan of a staple cartridge for use with the end effector of FIG. 2 and having a retention tab extending laterally outwardly from a sidewall of the lower pan, the retention tab being partially surrounded by a pair of L-shaped relief slots;

FIG. 119 depicts a partial side elevational view of another example of a lower pan of a staple cartridge for use with the end effector of FIG. 2 and having a retention tab extending laterally outwardly from a sidewall of the lower pan, the lower pan further having a distal C-shaped relief slot adjacent a distal end of the retention tab;

FIG. 120 depicts a partial side perspective view of another example of a lower pan of a staple cartridge for use with the end effector of FIG. 2 and having a retention tab extending laterally outwardly from a sidewall of the lower pan, the retention tab being partially surrounded by a U-shaped relief slot defined in both the sidewall and a bottom wall of the lower pan;

FIG. 121 depicts a bottom plan view of another example of a cartridge body of a staple cartridge for use with the end effector of FIG. 2 and having a thinned distal staple driver pocket support;

FIG. 122 depicts a magnified view of area 122 of the cartridge body of FIG. 121 as indicated in FIG. 121;

FIG. 123 depicts a partial side elevational view of a staple cartridge including the cartridge body of FIG. 121 and the lower pan of FIG. 110, showing the staple cartridge removably installed into the channel of FIG. 110;

FIG. 124 depicts an end cross-sectional view of the staple cartridge and channel of FIG. 123, taken along line 124-124 of FIG. 123, showing a sled of the staple cartridge in a distal fired position;

FIG. 125 depicts a partial side elevational view of another example of a cartridge body of a staple cartridge for use with the end effector of FIG. 2 and having a recessed laterally outer surface;

FIG. 126 depicts a magnified view of area 126 of the cartridge body of FIG. 125 as indicated in FIG. 125;

FIG. 127 depicts an end cross-sectional view of a staple cartridge including the cartridge body of FIG. 125 and the lower pan of FIG. 110, showing the staple cartridge removably installed into the channel of FIG. 110;

FIG. 128 depicts a perspective view of another example of a sled of a staple cartridge for use with the end effector of FIG. 2 and having a recessed laterally outer surface;

FIG. 129 depicts a partial bottom plan view of a staple cartridge including the sled of FIG. 128 and the cartridge body of FIG. 121, showing the sled in a distal fired position;

FIG. 130 depicts a rear elevational view of another example of a sled of a staple cartridge for use with the end effector of FIG. 2 and having tapered laterally outer surfaces;

FIG. 131 depicts a partial bottom plan view of a staple cartridge including the sled of FIG. 130 and the cartridge body of FIG. 121, showing the sled in a distal fired position;

FIG. 132 depicts a perspective view of another example of an upper anvil jaw for use with the end effector of FIG. 2 and having 2D and 3D staple forming pockets;

FIG. 133 depicts a bottom plan view of the upper anvil jaw of FIG. 132;

FIG. 134 depicts a magnified view of an area of the upper anvil jaw of FIG. 132 as indicated in FIG. 133;

FIG. 135 depicts an end cross-sectional view of the upper anvil jaw of FIG. 132, taken along line 135-135 of FIG. 134;

FIG. 136 depicts a cross-sectional view of the upper anvil jaw of FIG. 132, taken along line 136-136 of FIG. 134;

FIG. 137 depicts a top plan view of a plurality of staples formed by the upper anvil jaw of FIG. 132;

FIG. 138 depicts a front elevational view of the plurality of staples of FIG. 137;

FIG. 139 depicts a bottom plan view of another example of an upper anvil jaw for use with the end effector of FIG.

Figure 5:
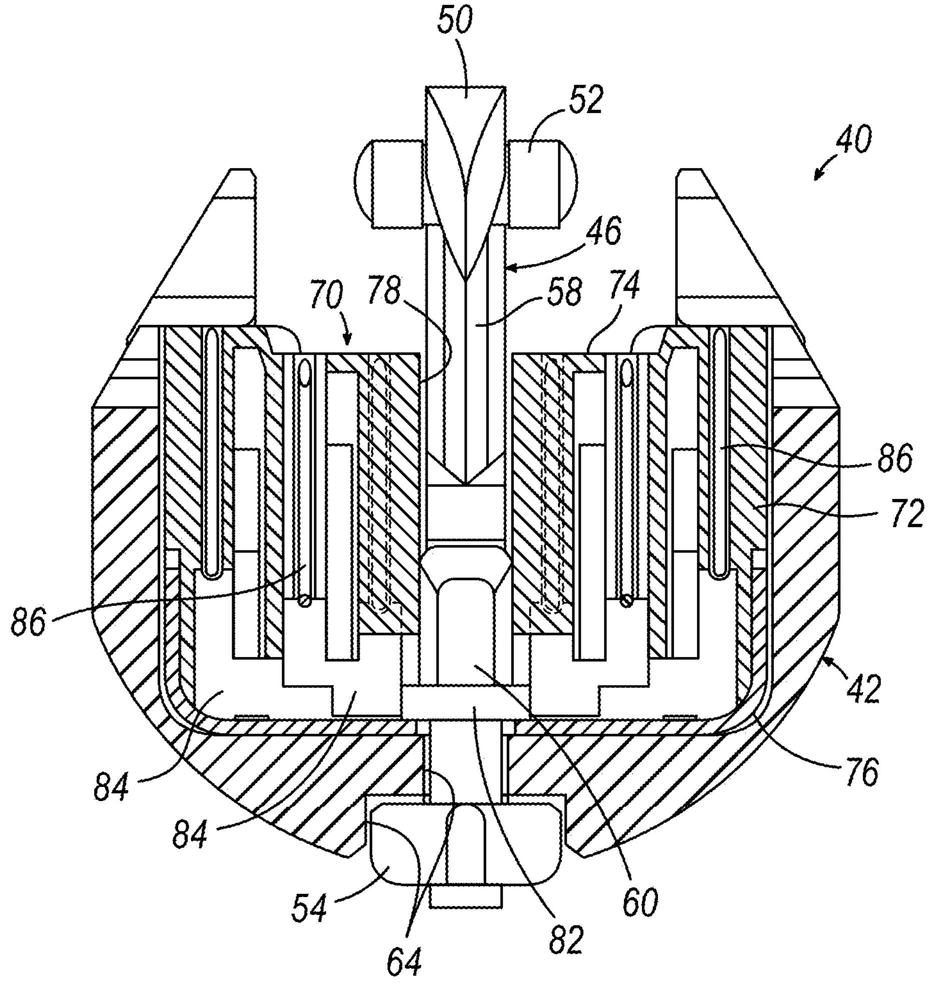
FIG. 5 depicts an end cross-sectional view of the end effector of FIG. 2, taken along line 5-5 of FIG. 2 and omitting an upper anvil jaw, showing further details of a distal knife portion of the firing beam and the sled.
Figure 142:
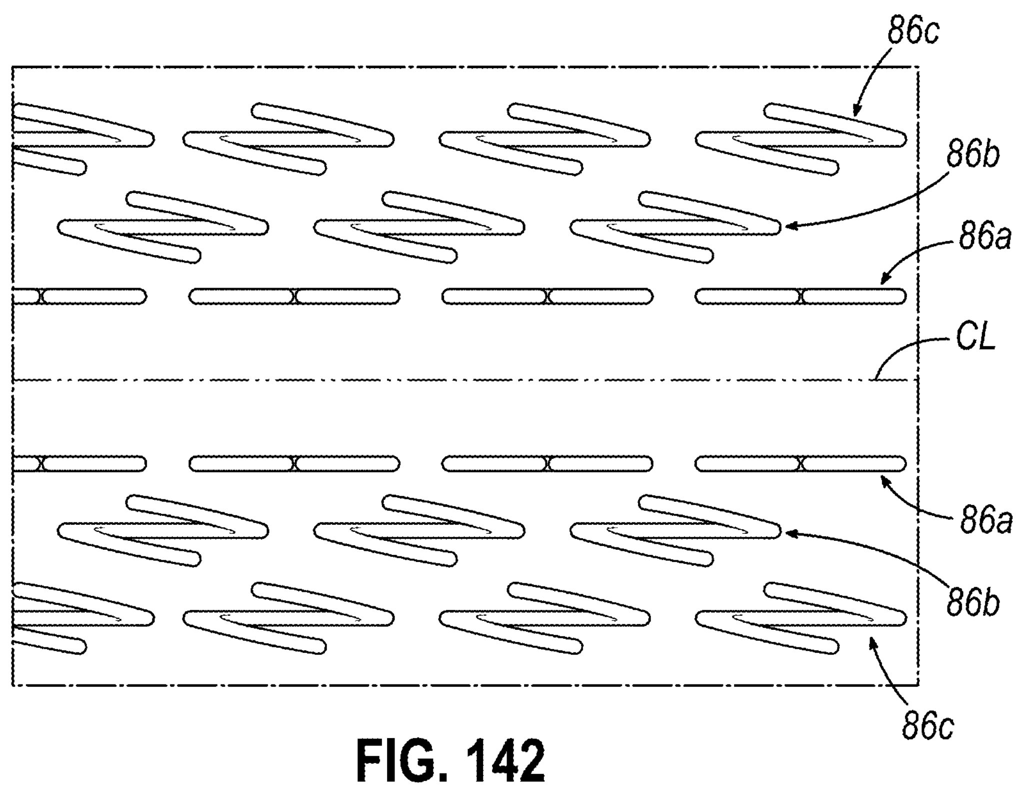
Figure 143:
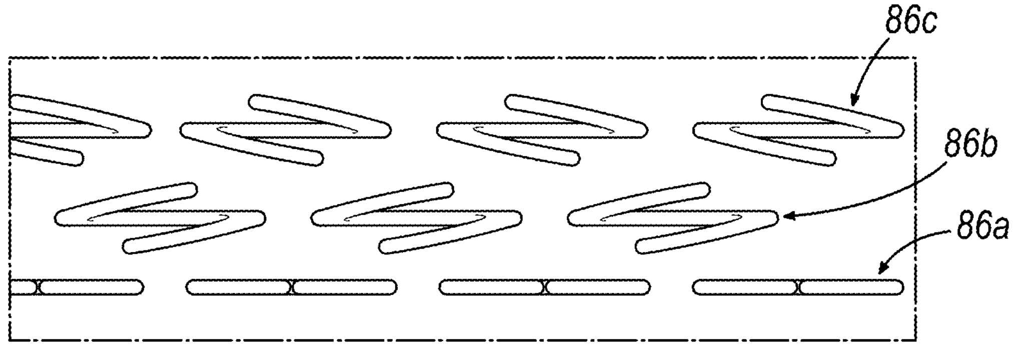
Figure 144:
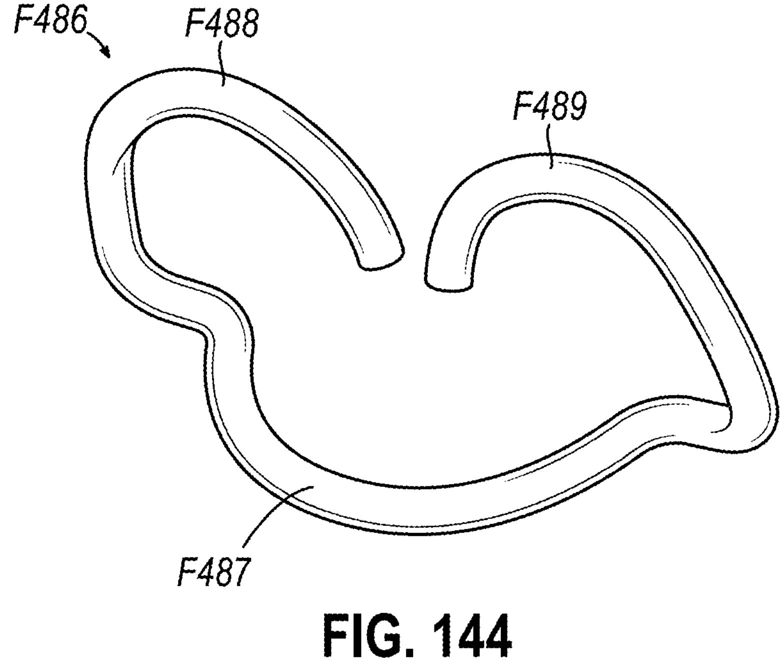
Figure 145:
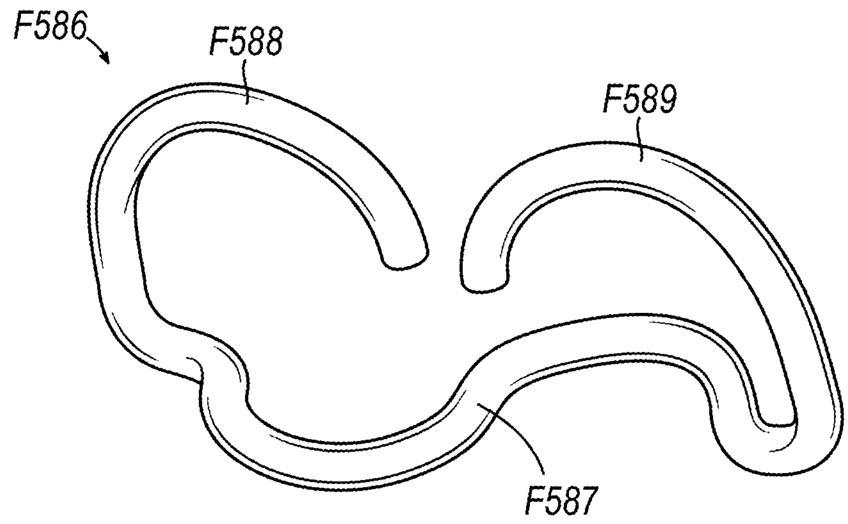

2 and having a row of staple forming pockets with laterally offset proximal and distal pockets;

FIG. 140 depicts a schematic view of an anvil having laterally offset proximal and distal staple forming pockets, in conjunction with a staple having a crown that is oriented obliquely relative to the anvil slot;

FIG. 141 depicts a schematic view of an anvil having laterally offset proximal and distal staple forming pockets, in conjunction with a staple having a zigzag-shaped crown;

FIG. 142 depicts a top plan view of a plurality of formed staples that are asymmetric relative to a cut line produced by the distal knife portion of FIG. 5;

FIG. 143 depicts a top plan view of a plurality of formed staples including a laterally intermediate row of 3D-formed staples that are oriented in an inverted manner relative to a laterally outer row of 3D-formed staples;

FIG. 144 depicts a perspective view of another example of a staple for use with the end effector of FIG. 2 and having a generally C-shaped crown; and FIG. 145 depicts a perspective view of another example of a staple for use with the end effector of FIG. 2 and having a generally S-shaped crown.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms “proximal” and “distal” are defined herein relative to a human or robotic operator of the surgical instrument. The term “proximal” refers the position of an element closer to the human or robotic operator of the surgical instrument and further away from the surgical end effector of the surgical instrument. The term “distal” refers to the position of an element closer to the surgical end effector of the surgical instrument and further away from the human or robotic operator of the surgical instrument. In addition, the terms “upper,” “lower,” “lateral,” “transverse,” “bottom,” “top,” are relative terms to provide additional clarity to the figure descriptions provided below. The terms “upper,” “lower,” “lateral,” “transverse,” “bottom,” “top,” are thus not intended to unnecessarily limit the invention described herein.

Furthermore, the terms “about,” “approximately,” “substantially,” and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, “substantially parallel” encompasses nominally parallel structures, and “substantially equal” values encompass nominally equal values.

I. Illustrative Surgical Stapler

A. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Figure 1:
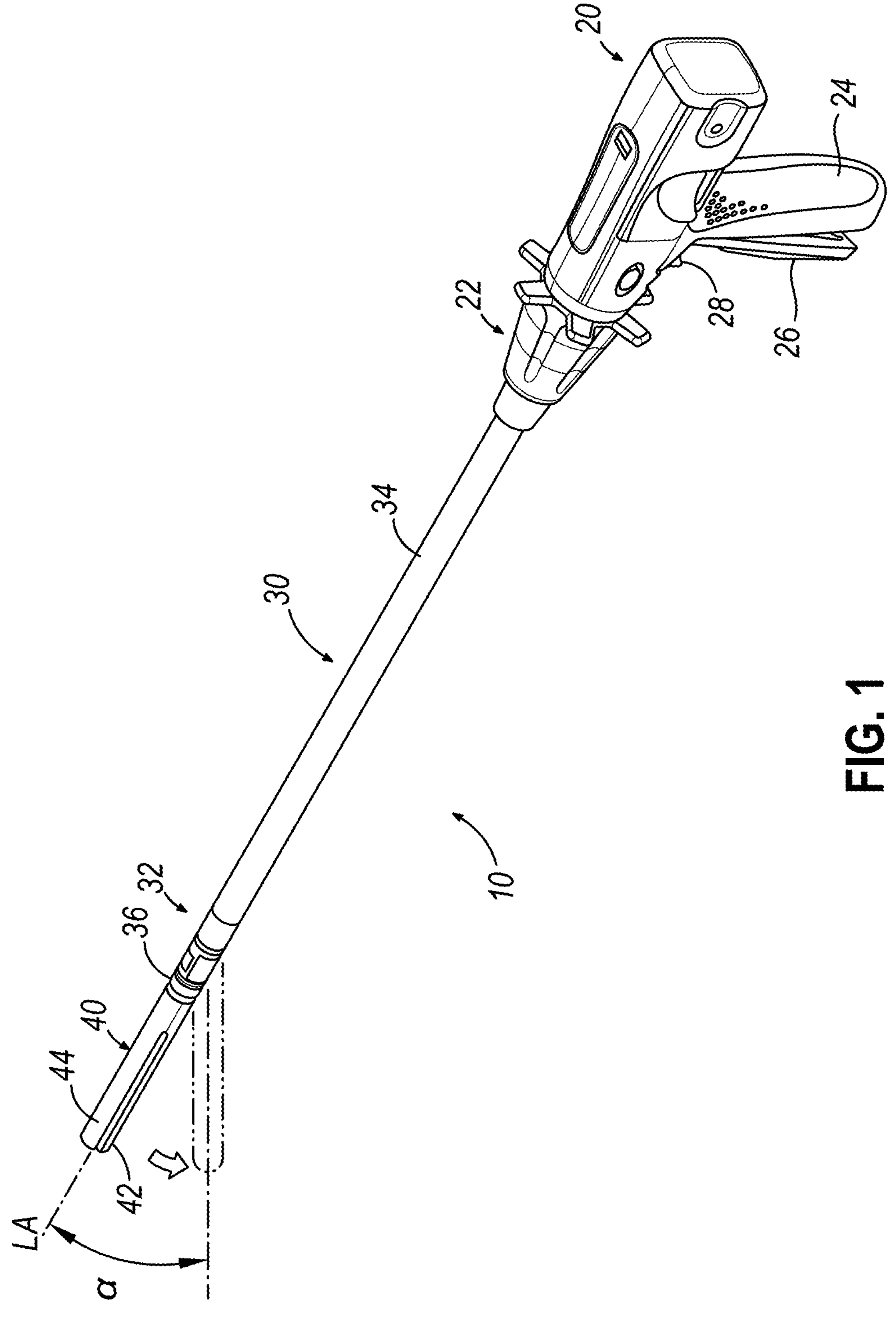
FIG. 1 depicts a perspective view of an example of a surgical stapler.

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle ($\alpha$). Articulation joint (32) and related features for manipulating articulation joint (32) may be further configured in accordance with the teachings of U.S. Pat. No. 9,186,142, entitled “Surgical Instrument End Effector Articulation Drive with Pinion and Opposing Racks,” issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a “reload”), and an upper jaw exemplified as an anvil jaw (44)) (also referred to as an “anvil”) that pivots relative to cartridge jaw (42) to clamp tissue therebetween. In other versions, end effector (40) may be alternatively configured such that cartridge jaw (42) pivots relative to anvil jaw (44). Unless otherwise described, the term “pivot” (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term “pivot” and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member (also referred to as a firing driver) exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 3:
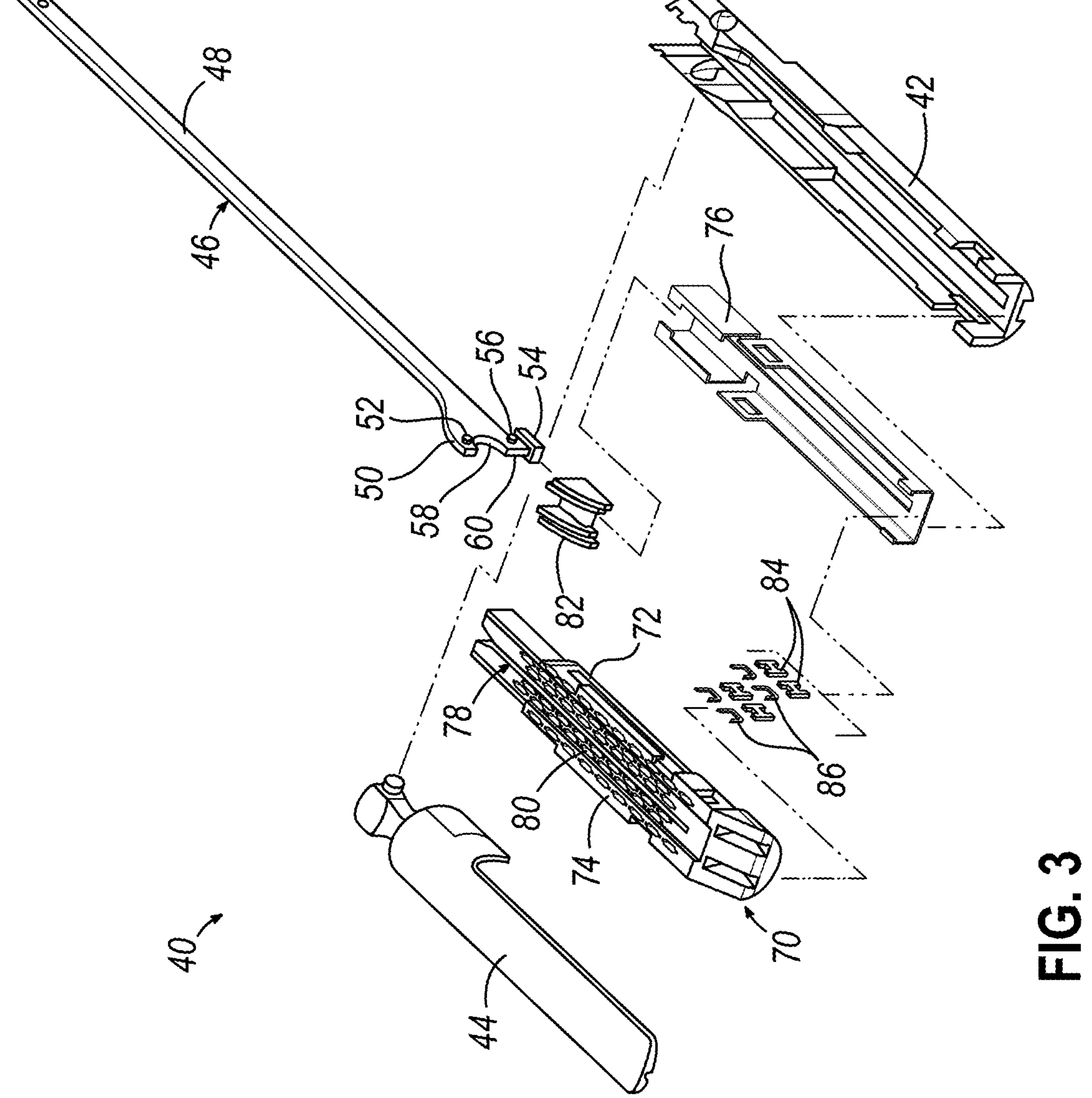
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably seated within a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
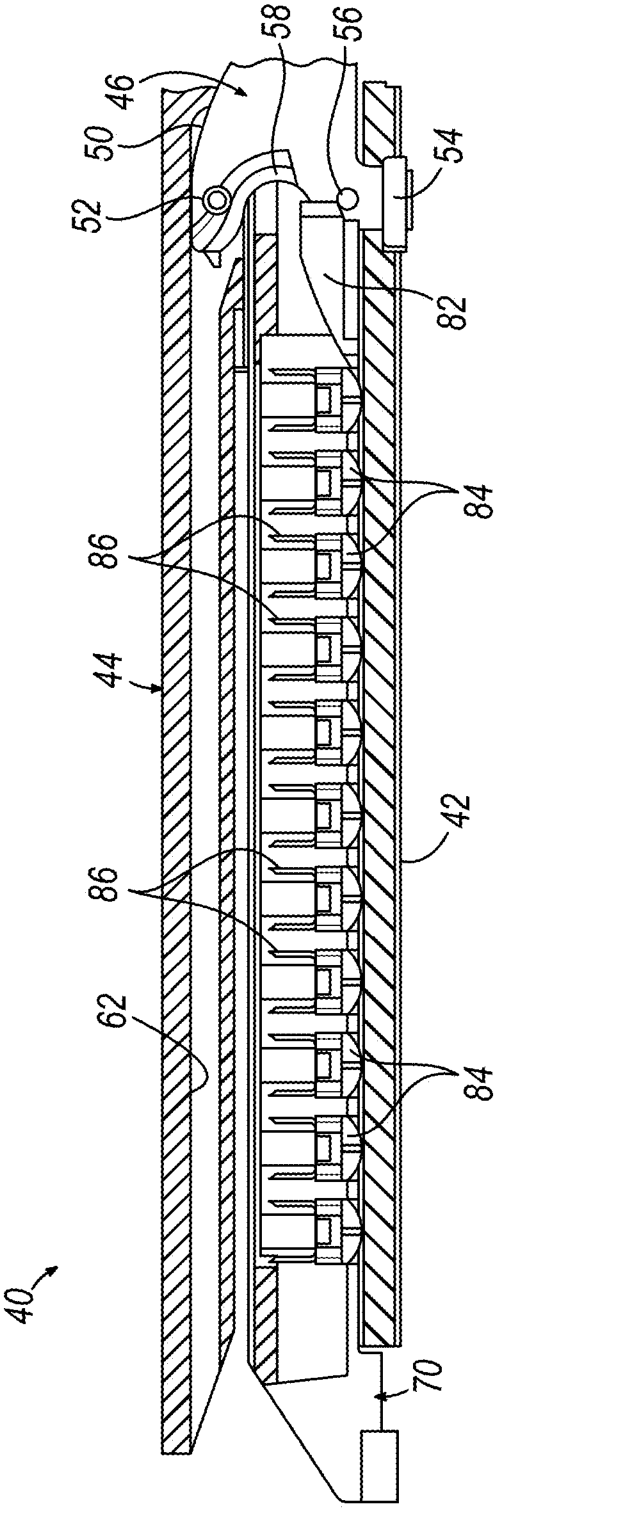
FIG. 4A depicts a side cross-sectional view of the end effector of FIG. 2, taken along line 4-4 of FIG. 2, showing a firing beam and sled in a proximal undisplaced position.
Figure 4B:
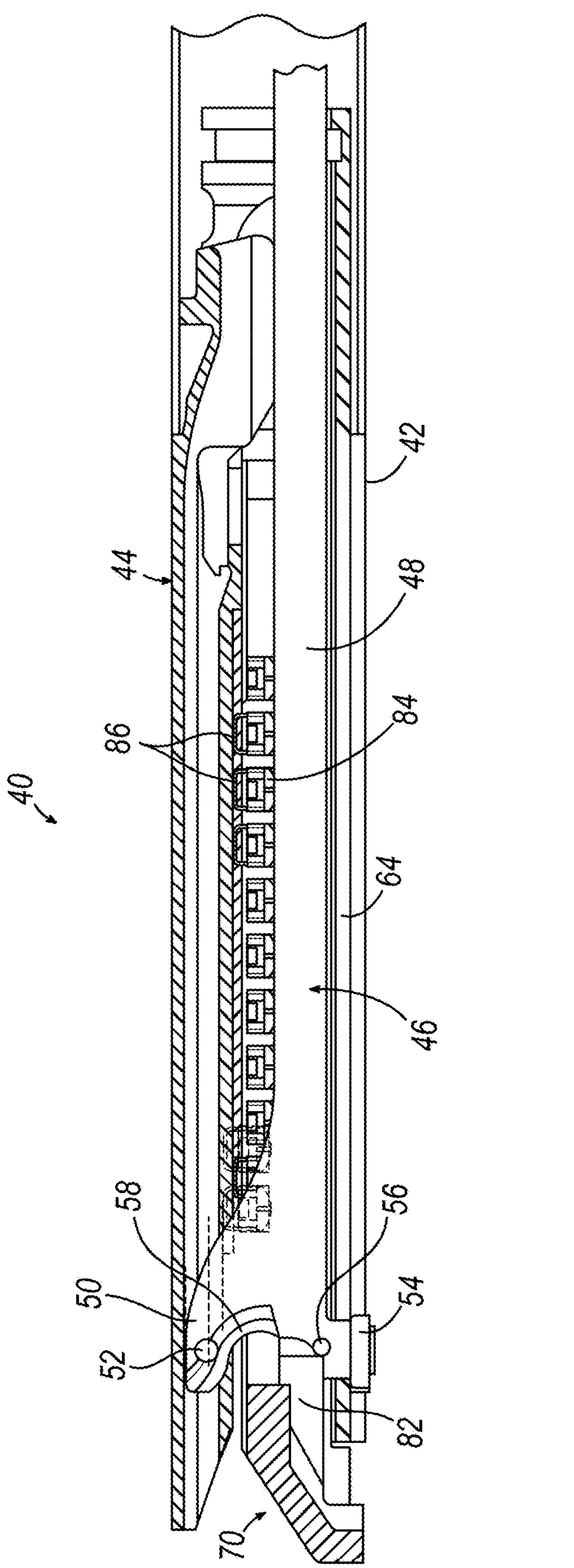
FIG. 4B depicts a side cross-sectional view of the end effector of FIG. 2, taken along line 4-4 of FIG. 2, showing the firing beam and sled in a distal fired position.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (43) is aligned with and movable vertically within a respective cartridge pocket (51). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
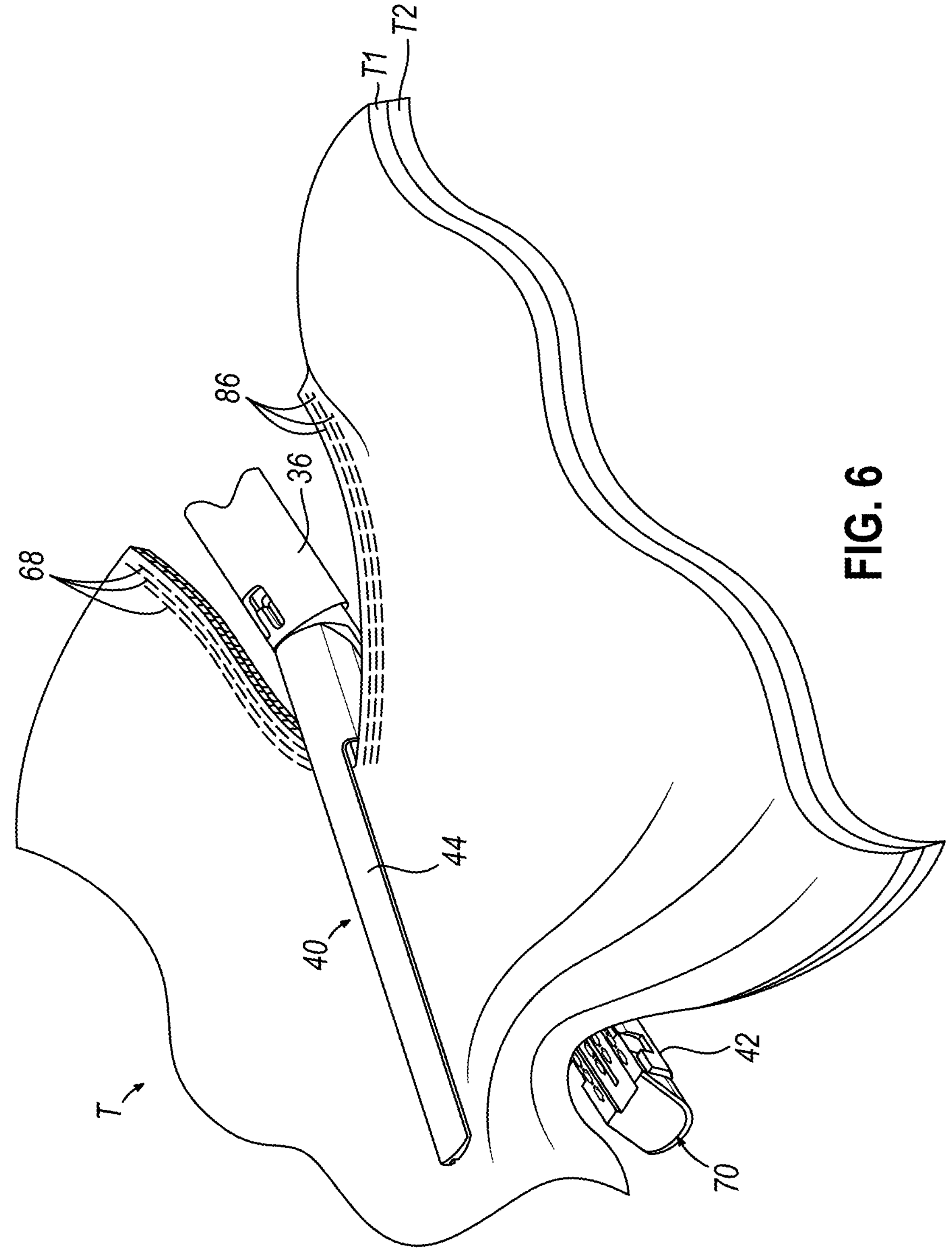
FIG. 6 depicts a perspective view of the end effector of FIG. 3, shown after having been fired once on a first section of tissue and being positioned to clamp and fire on a second section of tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

B. Illustrative End Effector Firing Lockout Features

In some instances, it may be desirable to provide a firing lockout feature for end effector (40) to prevent clamped tissue from being severed without being stapled. In particular, it may be desirable to prevent sled (82) and cutting edge

(58) from advancing distally if staple cartridge (70) is spent (i.e., has already been fired), or if a staple cartridge (70) is entirely absent from cartridge jaw (42).

Figure 7:
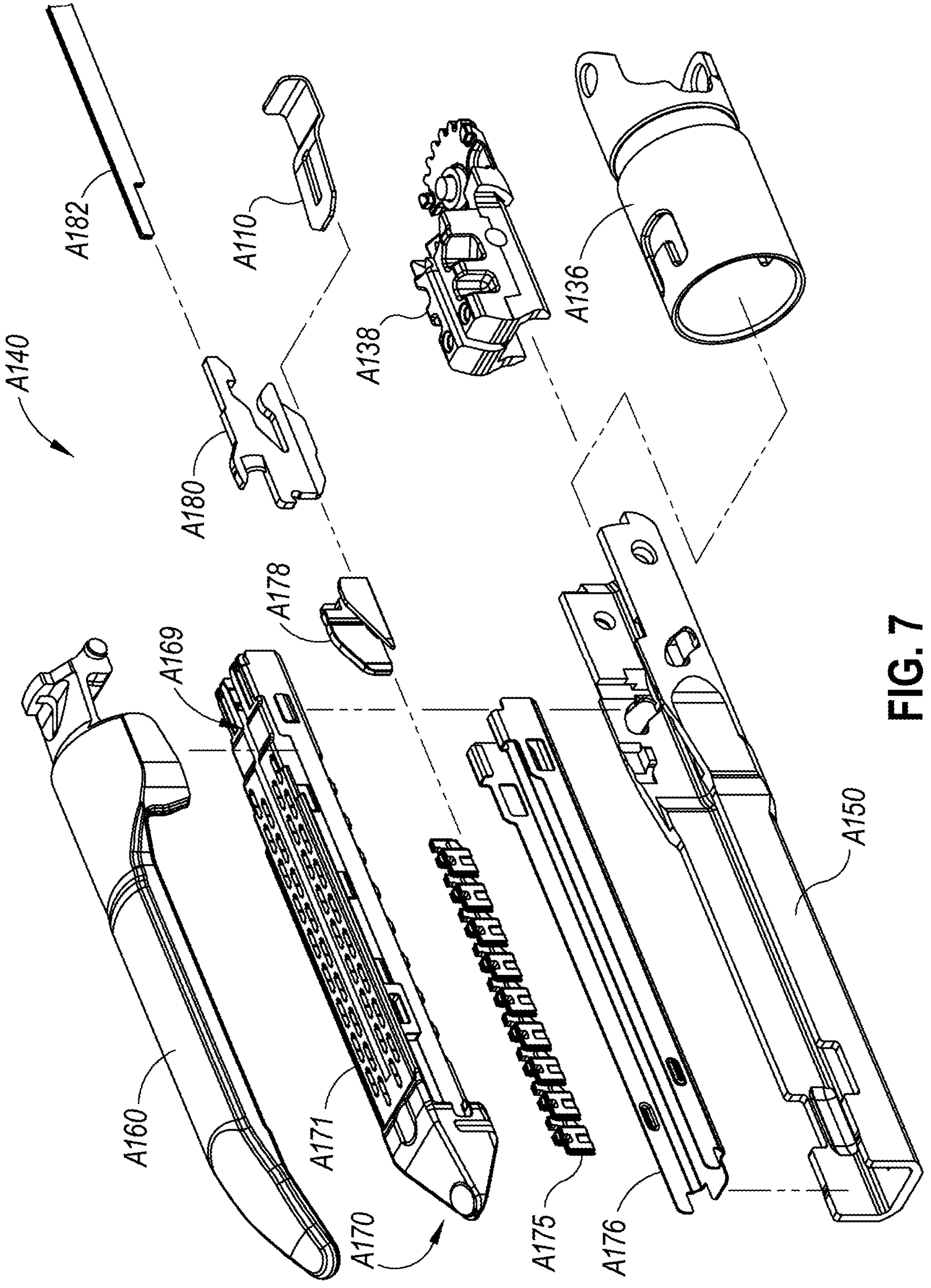
FIG. 7 depicts an exploded perspective view of another example of an end effector with a staple cartridge configured for use with the surgical stapler of FIG. 1.

FIG. 7 shows another illustrative end effector (140) that may be readily incorporated into surgical stapler (10) in place of end effector (40). End effector (140) includes a lower cartridge jaw (150), a pivotable anvil jaw (160), and a closure ring (A236), which are similar to cartridge jaw (42), anvil jaw (44), and closure ring (36) of end effector (40). A staple cartridge (170) similar to staple cartridge (70) may be removably installed into cartridge jaw (150) and includes a cartridge body (171), a lower cartridge pan (176), a sled (178), a plurality of staple drivers (175), and a plurality of staples (not shown) similar to staples (86). A firing beam (182) is coupled to a proximal end of knife (180) and is configured to drive knife (180) distally and/or proximally. A resilient member exemplified as a leaf spring (110) is positioned proximal to knife (180) and is configured to releasably engage and resiliently bias knife (180) downwardly. A frame member (138) supports leaf spring (110) and is positioned within closure ring (136) and is coupled to a proximal end of cartridge jaw (150) such that frame member (138) couples with an articulation joint similar to articulation joint (32).

Knife (180) includes a cutting edge (184), an upper extension (190), and a lower extension (186). Upper extension (190) extends proximally from cutting edge (184) and includes a downwardly extending tab (198) configured to lockingly engage frame member (138) such that frame member (138) may prevent tab (198) and knife (180) from advancing distally in the absence of an unspent staple cartridge (170), as will be described in greater detail below. Lower extension (186) extends proximally underneath cutting edge (184) and includes a distal end projection (197) and a distal wall (181). Distal end projection (197) extends distally and downwardly from lower extension (186) such that and underside of distal end projection (197) is configured to vertically engage an upwardly facing knife engagement surface at the proximal end of sled (178). Distal end projection (197) and distal wall (181) are configured to engage sled (178) when knife (180) is translated distally within cartridge jaw (150) to thereby drive sled (178) distally within cartridge jaw (150) to fire staple cartridge (170). A proximal portion of lower extension (186) includes a rounded tab that extends upwardly and is configured to engage leaf spring (110) such that leaf spring (110) may bias lower extension (186) and knife (180) downwardly so that tab (198) of upper extension (190) engages frame member (138) to prevent knife (180) from advancing distally in the absence of an unloaded staple cartridge (170).

Figure 8A:
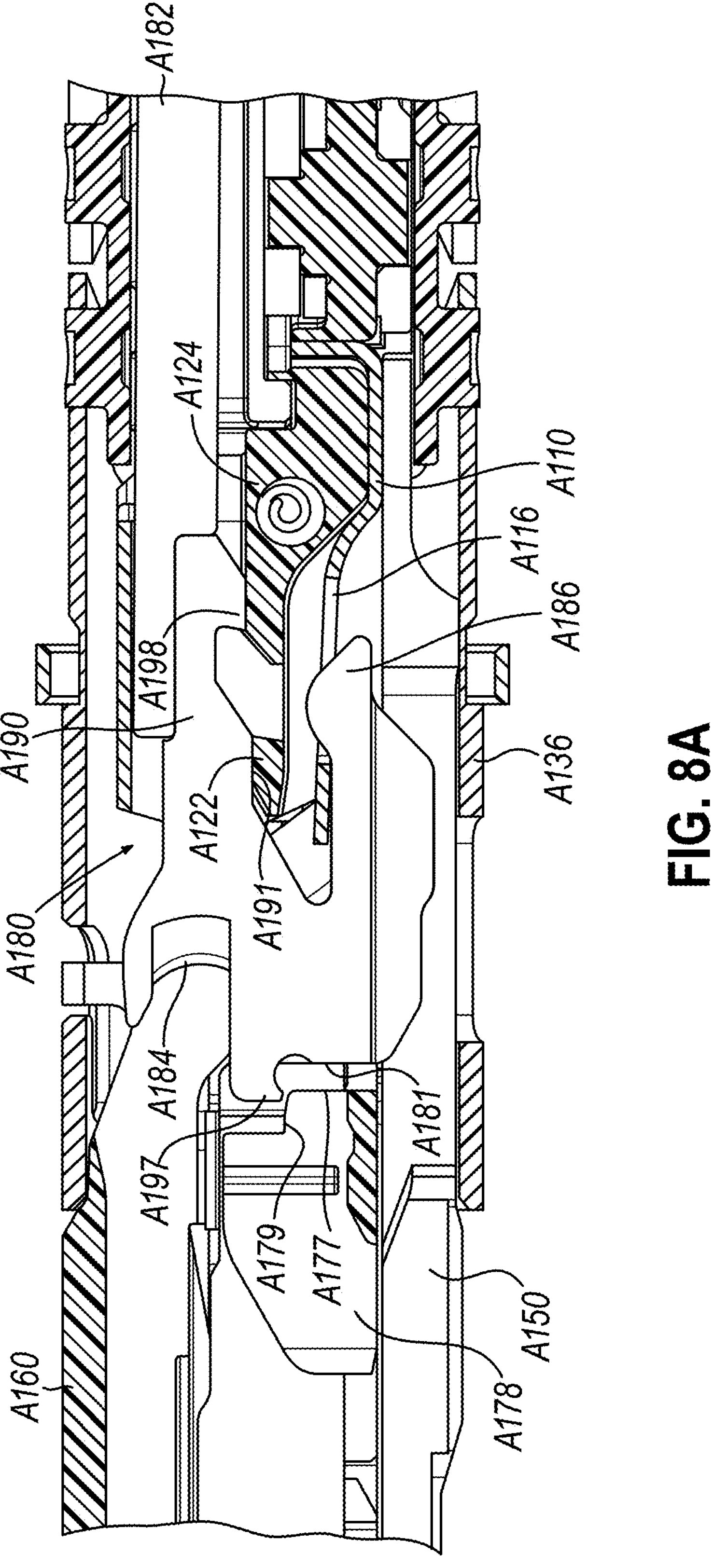
FIG. 8A depicts a side cross-sectional view of the end effector of FIG. 7, showing the compatible staple cartridge in an unspent state seated in a cartridge jaw, and showing a knife and a sled in unactuated proximal positions before firing of the unspent staple cartridge.
Figure 8B:
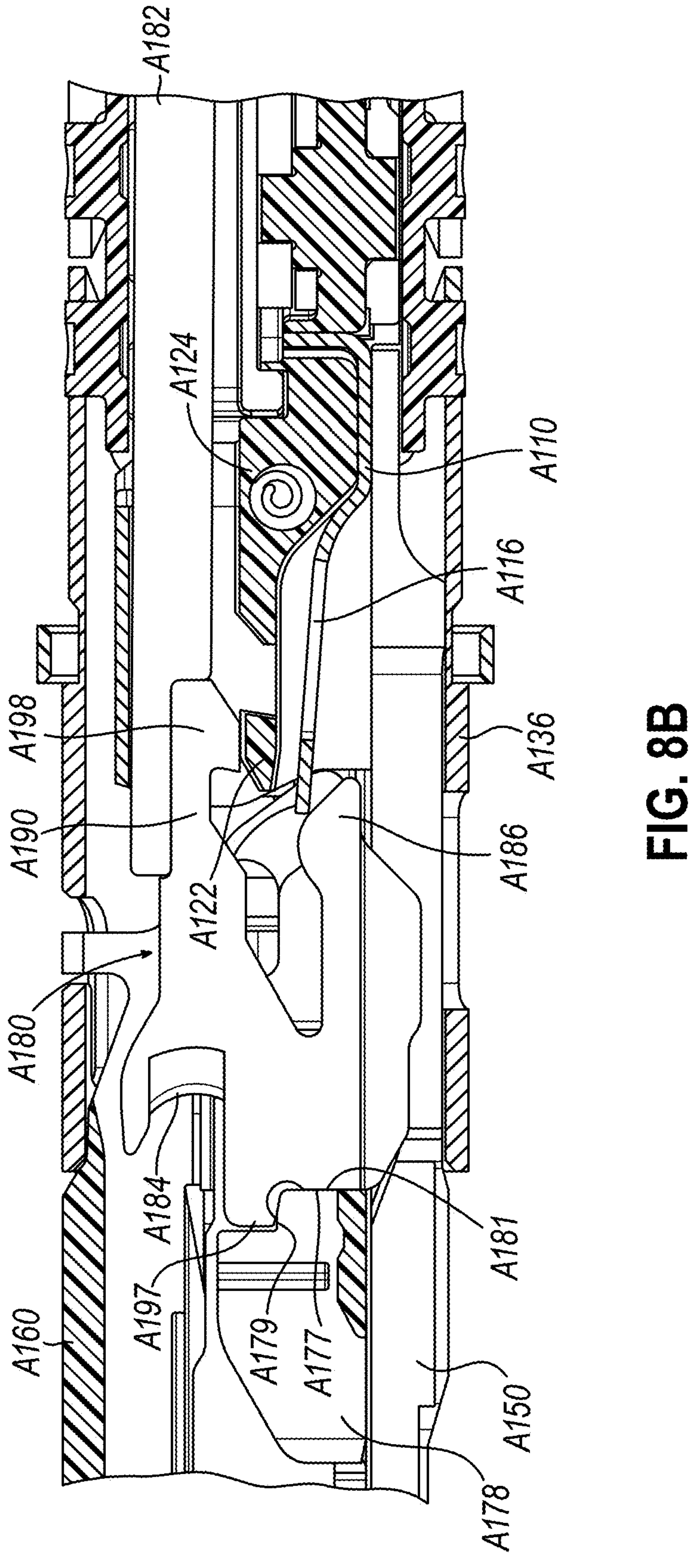
FIG. 8B depicts another side cross-sectional view of the end effector and unspent staple cartridge of FIG. 8A, showing distal actuation of the knife and sled to initiate firing of the unspent staple cartridge.

FIGS. 8A-8B show knife (180) being fired with an unspent staple cartridge (170) loaded in cartridge jaw (150) of end effector (140). FIG. 8A shows knife (180) in a proximal position in which upper extension (190) of knife (180) is positioned above engagement features (122, 124) of frame member (138). Wall (191) of upper extension (190) is resting on a top surface of first engagement feature (122), while tab (198) of upper extension (190) is resting on a top surface of second engagement feature (124). Leaf spring (110) is positioned between lower jaw (150) and frame member (138). An opening (116) of leaf spring (110) is positioned above lower extension (186) of knife (180) such that the tab of lower extension (186) tab is positioned within opening (116) of leaf spring (110).

As shown in FIG. 8B, in response to actuation of firing trigger (28), firing beam (182) drives knife (180) distally through staple cartridge (170), which in turn drives sled (178) distally through staple cartridge (170). As knife (180) is driven distally, a lower surface of distal end projection (197) of knife (180) engages an upwardly facing knife engagement surface (179) at the proximal end of sled (178), such that sled (178) vertically supports knife (180). Simultaneously, distal wall (181) of knife (180) engages a proximal end (177) of sled (178). Because sled (178) maintains the vertical position of knife (180) against the downward resilient bias of leaf spring (110), tab (198) of knife (180) translates distally above engagement features (122, 124) of frame member (138) and avoids falling into a lockout position between engagement features (122, 124), thus permitting end effector (140) to be fired.

Figure 9A:
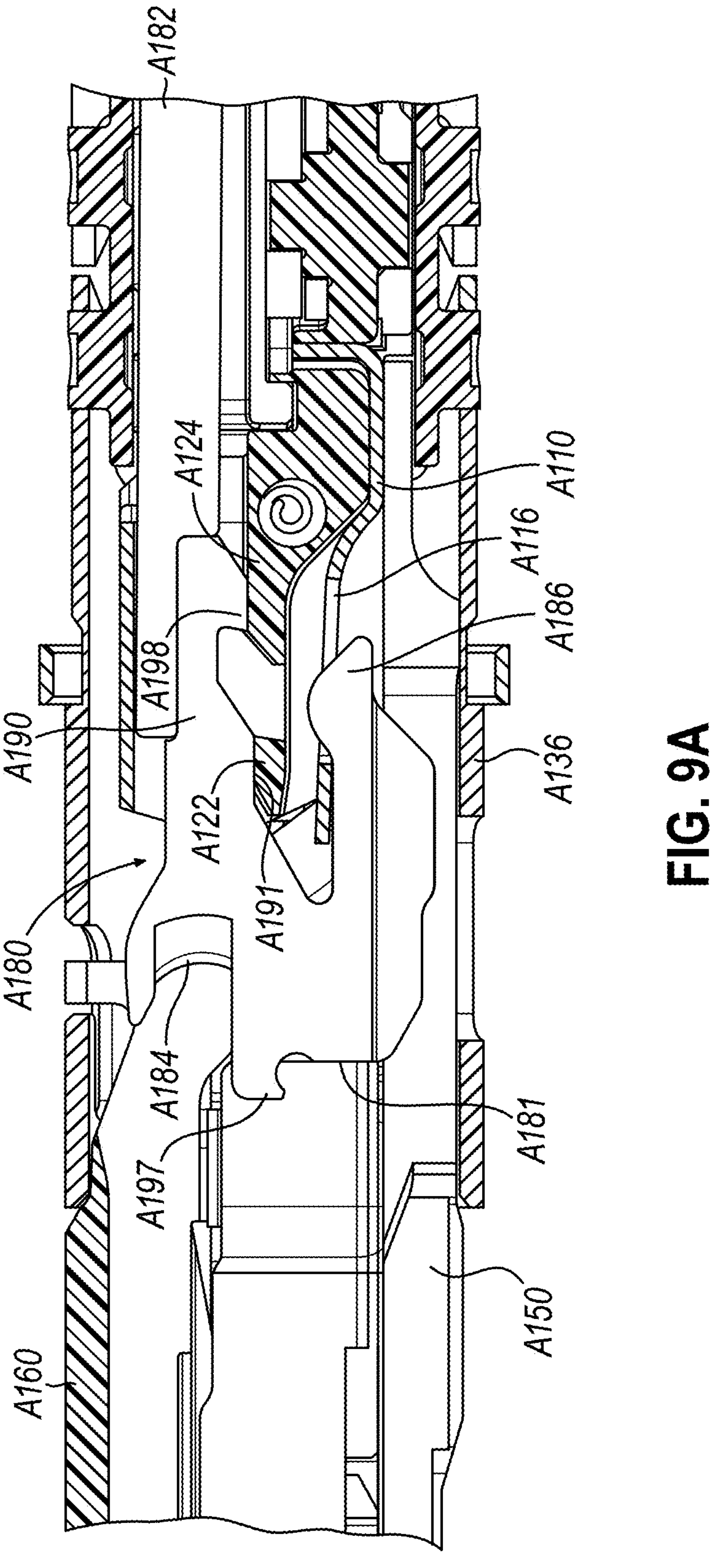
FIG. 9A depicts a side cross-sectional view of the end effector of FIG. 7, showing the staple cartridge in a spent state and the knife in an unactuated proximal position before attempted firing of the spent staple cartridge.
Figure 9B:
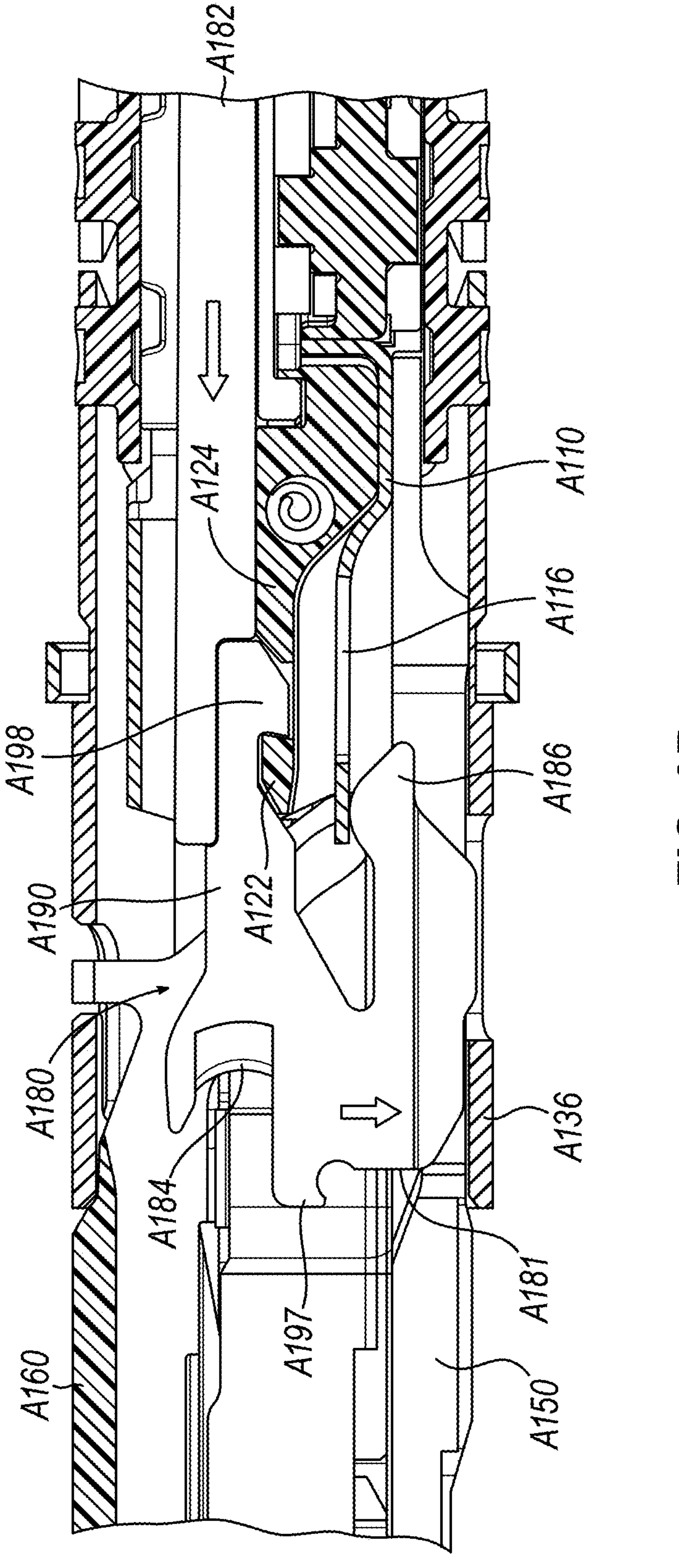
FIG. 9B depicts another side cross-sectional view of the end effector and spent staple cartridge of FIG. 9A, showing the knife assuming a lockout position in response to distal actuation of the knife by a firing beam.

After end effector (140) is fired, knife (180) is retracted to its proximal position and the spent staple cartridge (170) may be replaced with a fresh (aka unspent) staple cartridge (170). However, in some instances the user may forget to install an unspent staple cartridge (170). FIG. 9A shows an example of such a scenario in which knife (180) is positioned proximally, but a cartridge sled (178) is not, due to either a spent staple cartridge (170) being loaded in cartridge jaw (150) or a staple cartridge (170) being entirely absent from cartridge jaw (150). Accordingly, sled (178) is not vertically supported against the resilient bias of leaf spring (110). As a result, when knife (180) is actuated distally for an attempted firing stroke, tab (198) falls between engagement features (122, 124) of frame member (138), thus constraining tab (198) longitudinally in a lockout position such that knife (180) is inhibited from advancing sled (178) distally to fire staple cartridge (170). Accordingly, knife (180) is inhibited from severing the clamped tissue.

End effector (140) may be further configured and operable in accordance with the teachings of U.S. Pat. No. 10,335,147, entitled "Method of Using Lockout Features for Surgical Stapler Cartridge," issued Jul. 2, 2019, the disclosure of which is incorporated by reference herein in its entirety.

II. Illustrative Features for Inhibiting Use of an Incompatible Staple Cartridge with Surgical Stapler As discussed above in connection with FIGS. 7-9B, it may be desirable to inhibit actuation of the firing assembly of a surgical stapler if the end effector is loaded with spent staple cartridge, and also if a staple cartridge is entirely absent from the end effector. Additionally, it may also be desirable to inhibit use of an incompatible staple cartridge with a surgical stapler, including where the incompatible staple cartridge is in an unspent state and is capable of being at least partially seated within the cartridge jaw of the surgical stapler end effector.

The illustrative safety features shown and described below in connection with FIGS. 10-21 provide at least two barriers to such misuse by a clinician. As described in greater detail below, the first safety feature inhibits a distal end portion of an incompatible staple cartridge from being substantially seated within the cartridge jaw. The second safety feature serves as a fallback to the first safety feature and inhibits a firing driver of the surgical stapler from driving a sled of the incompatible staple cartridge to deploy staples, even when the incompatible staple cartridge is unspent and its sled is in a proximal undisplaced position.

A. Staple Cartridge Lugs that Inhibit Full Seating of Staple Cartridge

Figure 10:
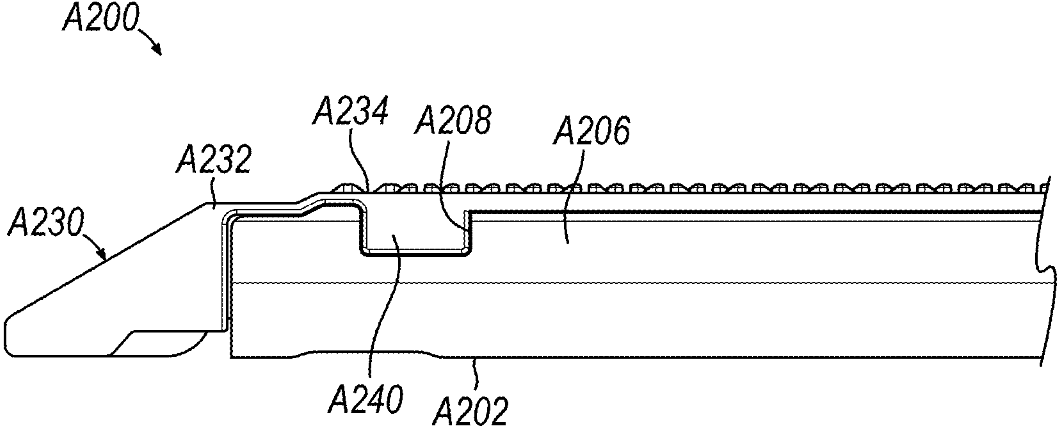
FIG. 10 depicts a side elevational view of a first cartridge jaw of an alternative first surgical stapler properly loaded with a first staple cartridge configured for use with the first surgical stapler.

FIG. 10 shows a first cartridge jaw (A202) of a first end effector (A200) (see FIG. 15), and a corresponding first staple cartridge (A230) intended for use with first end effector (A200) such that first end effector (A200) and first staple cartridge (A230) are compatible. First staple cartridge (A230) includes a first cartridge body (A232) that defines a first deck (A234) and includes a plurality of cartridge pockets (not shown) that house a corresponding plurality of staples (not shown) and a corresponding plurality of staple drivers (not shown). First staple cartridge (A230) further includes a first pan (A236) and a first sled (A238) slidably coupled with first cartridge body (A232) and constrained vertically by first pan (A236).

Figure 11:
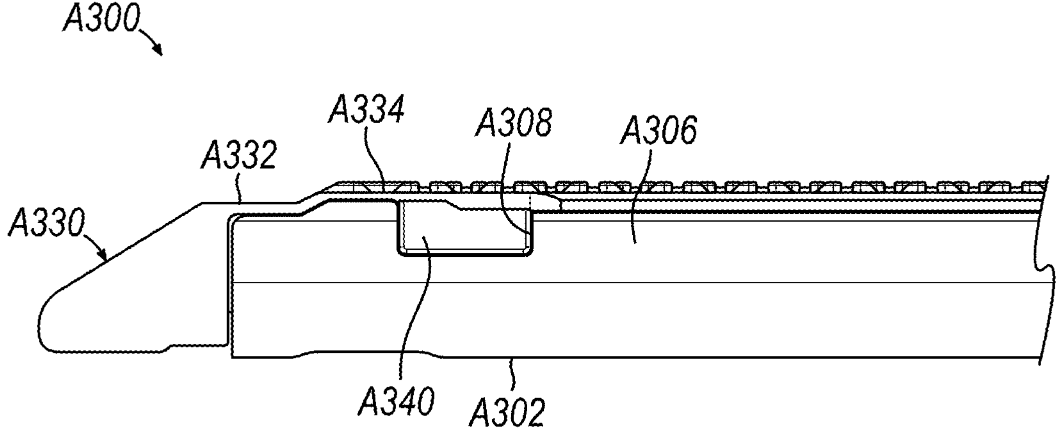
FIG. 11 depicts a side elevational view of a second cartridge jaw of an alternative second surgical stapler properly loaded with a second staple cartridge configured for use with the second surgical stapler.

Similarly, FIG. 11 shows a second cartridge jaw (A302) of a second end effector (A300) (see FIG. 16), and a corresponding second staple cartridge (A330) configured for use with second end effector (A300). Second staple cartridge (A330) includes a second cartridge body (A332) that defines a second deck (A334) and includes a plurality of cartridge pockets (not shown) that house a corresponding plurality of staples (not shown) and a corresponding plurality of staple drivers (not shown). Second staple cartridge (A330) further includes a second pan (A336) and a second sled (A338) slidably coupled with second cartridge body (A332) and constrained vertically by second pan (A336).

In the present example, first staple cartridge (A230) has exterior dimensions that are substantially equal to those of second staple cartridge (A330). For instance, first staple cartridge (A230) has a first maximum width and second staple cartridge (A330) has a second maximum width that is substantially equal to the first maximum width. However, first staple cartridge (A230) is specifically configured to cooperate with a first anvil jaw (A204) (see FIG. 15) of first end effector (A200) to form staples with a two-dimensional shape. In contrast, second staple cartridge (A330) is specifically configured to cooperate with a second anvil jaw (A304) (see FIG. 16) of second end effector (A300) to form staples with a three-dimensional shape. Examples of such a three-dimensional formed staple shape and corresponding staple forming features are disclosed in U.S. Pat. No. 11,406,379, entitled "Surgical End Effectors with Staple Cartridges," issued Aug. 9, 2022, the disclosure of which is incorporated by reference herein in its entirety. Due to structural differences in the two-dimensional staple forming features of first anvil jaw (A204) and first staple cartridge (A230) and relative to the three-dimensional staple forming features of second anvil jaw (A304) and second staple cartridge (A330), attempted use of first staple cartridge (A230) in second end effector (A300) or second staple cartridge (A330) in first end effector (A200) would yield malformed staples that are ineffective to seal patient tissue being fired upon.

First cartridge jaw (A202) includes a pair of first sidewalls (A206) each having a first compatibility recess (A208) that opens to an upper edge of the first sidewall (A206). Each first compatibility recess (A208) is suitably sized, shaped, and located to receive a respective first compatibility lug (A240) that protrudes laterally from a corresponding side of first cartridge body (A232), thereby permitting a distal end portion of first staple cartridge (A230) to be substantially seated within first cartridge jaw (A202). Similarly, second cartridge jaw (A302) includes a pair of second sidewalls (A306) each having a second compatibility recess (A308) that opens to an upper edge of the second sidewall (A306). Each second compatibility recess (A308) is suitably sized, shaped, and located to receive a respective second compatibility lug (A340) that protrudes laterally from a corresponding side of a second cartridge body (A332), thereby permitting a distal end portion of second staple cartridge (A330) to be substantially seated within second cartridge jaw (A302). While first and second compatibility lugs (A240, A340) are shown as generally rectangular in the present example, they may be formed with various other shapes in other examples.

Figure 12:
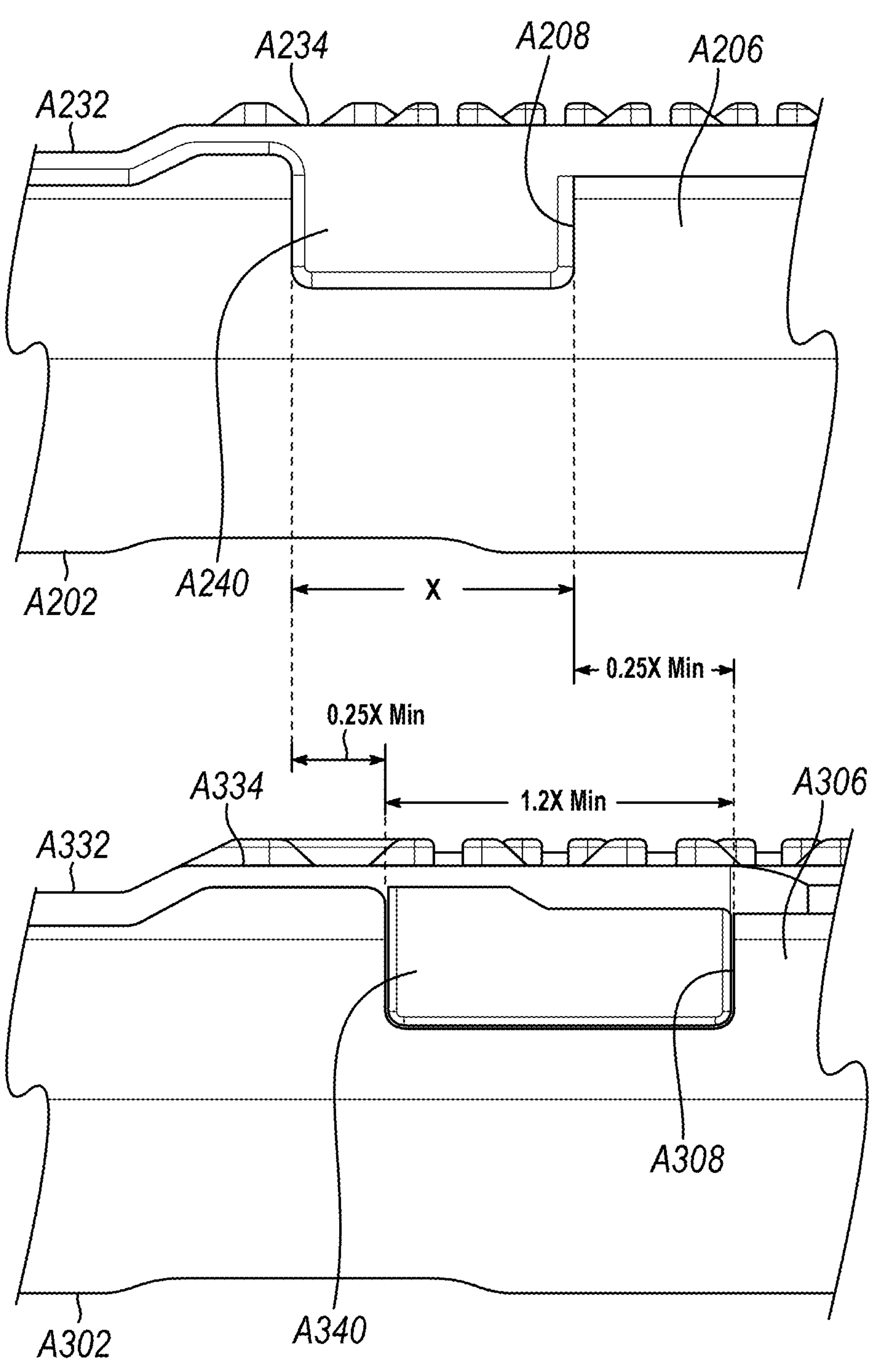
FIG. 12 depicts an enlarged side elevational view of the first cartridge jaw and first staple cartridge of FIG. 10 positioned alongside the second cartridge jaw and second staple cartridge of FIG. 11, showing a dimensional comparison of corresponding lugs of the cartridges and recesses of the cartridge jaws.

Each first compatibility lug (A240) of first staple cartridge (A230) and its respective first compatibility recess (A208) of first cartridge jaw (A202) differ from the corresponding second compatibility lug (A340) of second staple cartridge (A330) and its respective second compatibility recess (A308) of second cartridge jaw (A302) in at least one of size, shape, or longitudinal location. More specifically, as shown in FIG. 12, each first compatibility lug (A240) differs from the corresponding second compatibility lug (A340) in length and longitudinal location. In particular, second compatibility lug (A340) is approximately 20% longer than first compatibility lug (A240) and is proximally displaced relative to second compatibility lug (A340) such that a distal end of second compatibility lug (A340) is displaced proximal to a distal end of first compatibility lug (A240) by a longitudinal distance equal to at least approximately 25% of the length of first compatibility lug (A240). Similarly, a proximal end of second compatibility lug (A340) is displaced proximal to a proximal end of first compatibility lug (A240) by a longitudinal distance equal to at least approximately 25% of the length of first compatibility lug (A240).

Figures 13, 14:
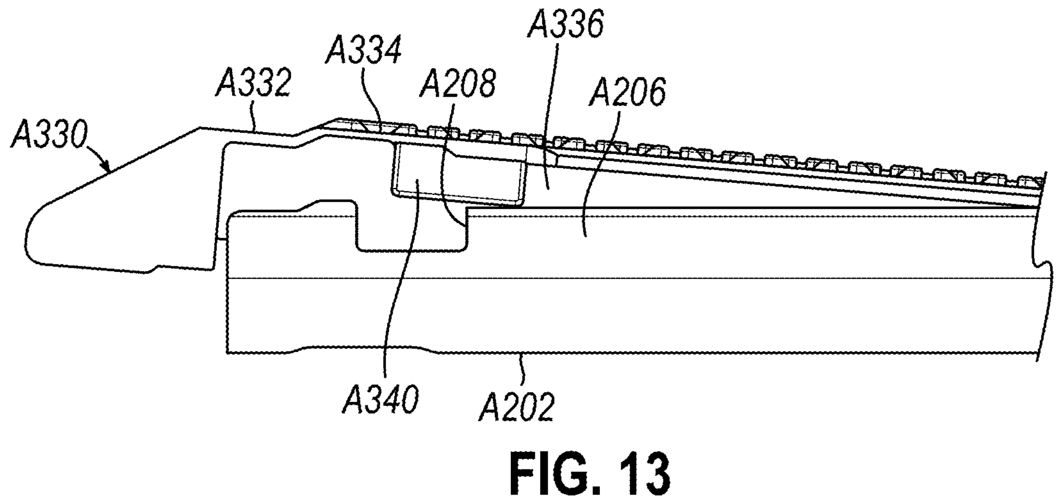
FIG. 13 depicts a side elevational view of the second staple cartridge partially seated within the first cartridge jaw as a result of user error, where the lug of the second staple cartridge is non-receivable by the recess of the first cartridge jaw such that only a proximal end portion of the second staple cartridge is substantially seated within the first cartridge jaw.
FIG. 14 depicts a side elevational view of the first staple cartridge partially seated within the second cartridge jaw as a result of user error, where the lug of the first staple cartridge is non-receivable by the recess of the second cartridge jaw such that only a proximal end portion of the first staple cartridge is substantially seated within the second cartridge jaw.

As shown in FIGS. 13-14, the structural differences between first compatibility lugs (A240) of first staple cartridge (A230) and second compatibility lugs (A340) of second staple cartridge (A330) described above render first compatibility recesses (A208) of first cartridge jaw (A202) incapable of receiving second compatibility lugs (A340), and render second compatibility recesses (A308) of second staple cartridge (A330) incapable of receiving first compatibility lugs (A240). Accordingly, the distal end portion of second staple cartridge (A330) is incapable of being substantially seated within first cartridge jaw (A202), as depicted in FIG. 13 where an underside of second compatibility lug (A340) is shown abutting an upper edge of first sidewall (A206) proximal to first compatibility recess (A208). Similarly, the distal end portion of first staple cartridge (A230) is incapable of being substantially seated within second cartridge jaw (A302), as depicted in FIG. 14 where an underside of first compatibility lug (A240) is shown abutting an upper edge of second sidewall (A306) distal to second compatibility recess (A308). Advantageously, this provides a clear visual indication to the clinician that first staple cartridge (A230) is incompatible with second end effector (A300) and that second staple cartridge (A330) is incompatible with first end effector (A200) such that the clinician should not proceed with conducting a surgical procedure with such a mis-matched cartridge-stapler configuration.

B. Staple Cartridge Sled Features that Promote Firing Lockout when Loaded in Incompatible Stapler While first and second cartridge jaw recesses (A208, A308) and first and second staple cartridge lugs (A240, A240) described above are specifically designed to provide a clear visual indication to a clinician of cartridge incompatibility when a staple cartridge (A230, A330) is loaded into an incompatible end effector (A300, A200), a clinician may nonetheless attempt to fire on patient tissue with the incompatible cartridge-stapler combination. The illustrative features described below in connection with FIGS. 15-21 provide a firing lockout condition to inhibit firing in such a scenario of clinician misuse.

Figure 15:
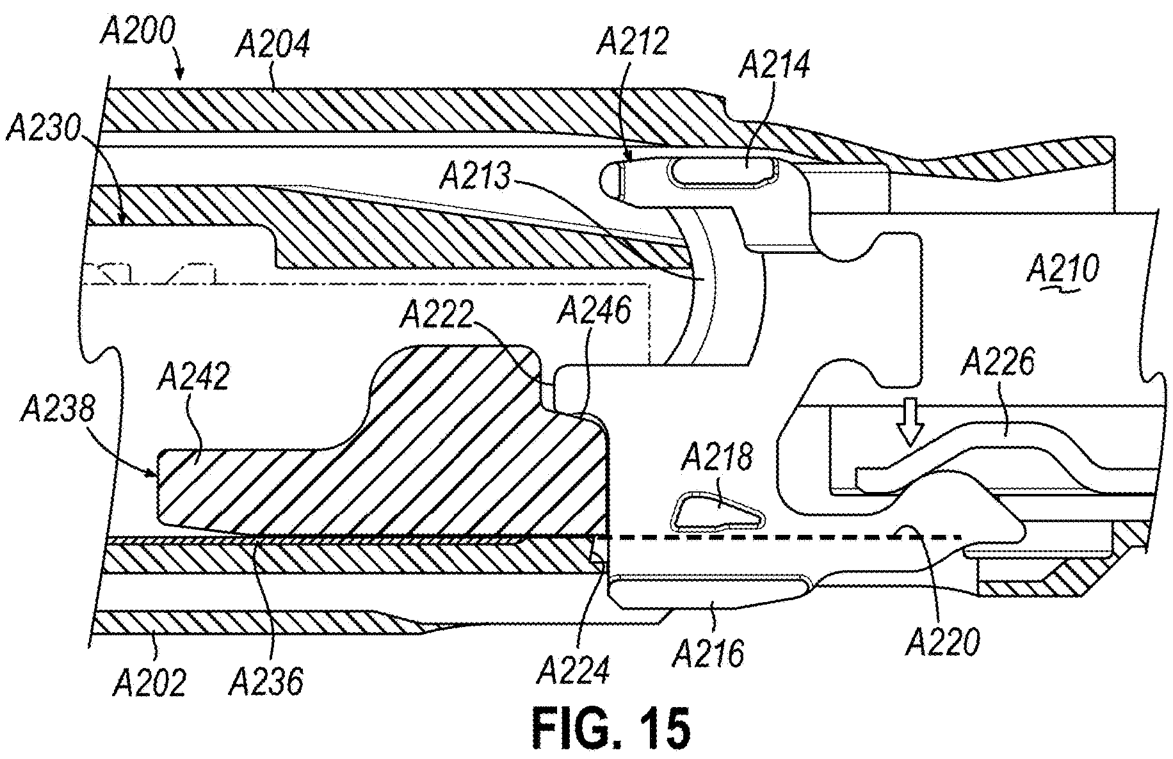
FIG. 15 depicts a partial side cross-sectional view of the end effector of the first surgical stapler properly loaded with the first staple cartridge of FIG. 10 in an unspent state, showing a sled of the first staple cartridge vertically supporting a distal end projection of the knife of the first surgical stapler to bypass a knife lockout position and permit firing.

FIG. 15 shows first staple cartridge (A230) in an unspent and undisturbed state such that first sled (A238) is positioned in a proximal undisplaced position, where first staple cartridge (A230) has been substantially seated within first cartridge jaw (A202) of first end effector (A200) such that first anvil jaw (A204) has been permitted to fully close onto tissue (not shown) positioned between first anvil jaw (A204) and first staple cartridge (A230). As shown in FIG. 15, first end effector (A200) includes a first firing beam (A210) and a first knife (A212) secured to a distal end of first firing beam (A210). First knife (A212) includes a cutting edge (A213), a transversely oriented upper protrusion (A214) slidable within a longitudinal slot of first anvil jaw (A204), a transversely oriented lower protrusion (A216) slidable within a longitudinal slot of first cartridge jaw (A202), and a transversely oriented middle protrusion (A218) slidable along a floor (A220) of first cartridge jaw (A202). First knife (A212) further includes a first distal end projection (A222) configured to be vertically supported by a first knife engagement surface (A246) of first sled (A238), as described in greater detail below. First end effector (A200) further includes a first lockout recess (A224) formed in first cartridge jaw floor (A220) at its proximal end, and a first lockout spring (A226) positioned proximal to first lockout recess (A224) and configured to bias first knife (A212) downwardly toward first cartridge jaw floor (A220) such that middle protrusion (A218) of first knife (A212) is biased downwardly toward first lockout recess (A224).

Figure 20:
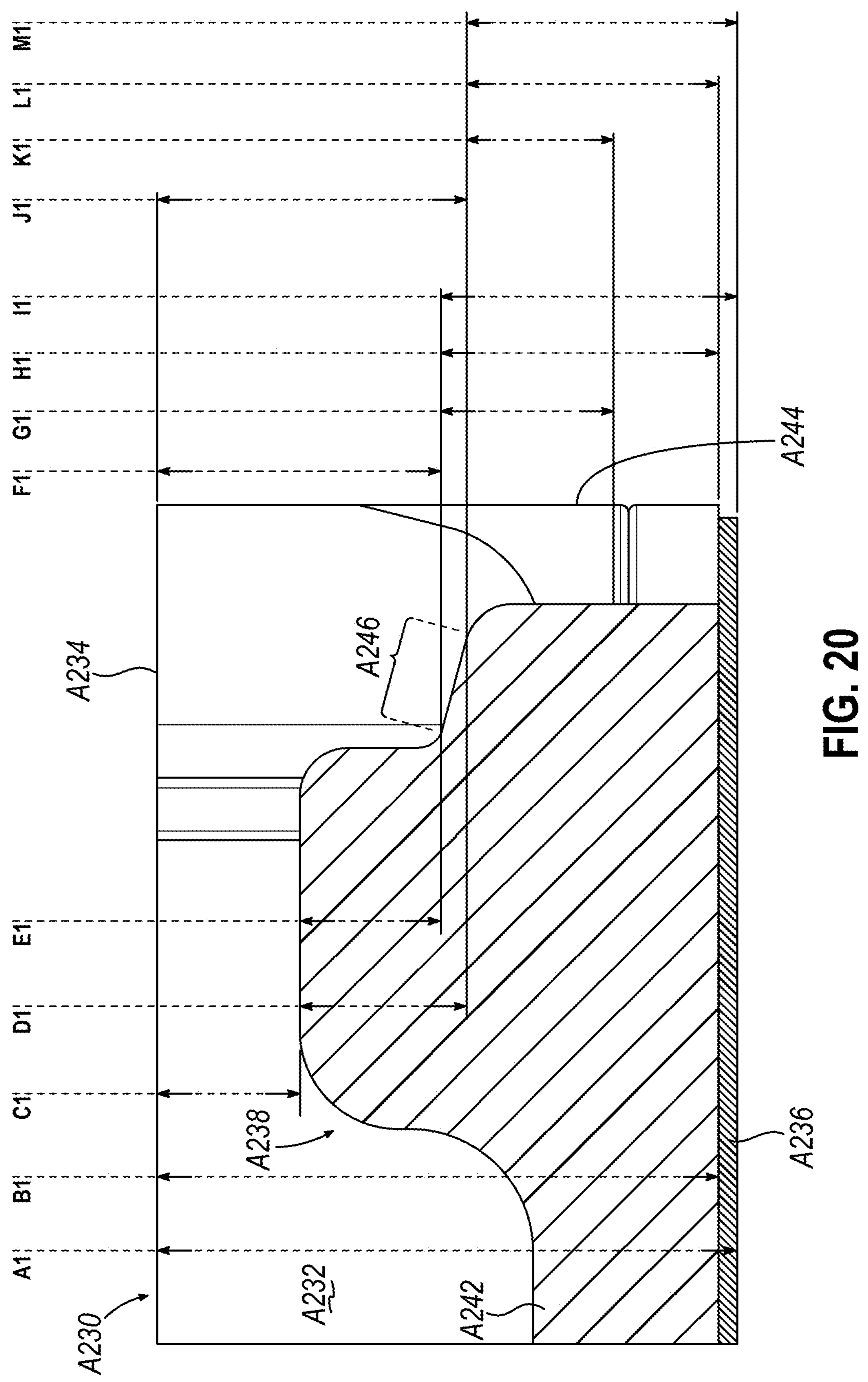
FIG. 20 depicts a partial side cross-sectional view of a proximal portion of the first staple cartridge of FIG. 10, showing select dimensions.

As shown in FIGS. 15 and 20, first sled (A238) of first staple cartridge (A230) includes a first central body portion (A242) and a pair of first fins (A244) (see FIG. 20) disposed on each lateral side of first central body portion (A242). Though not shown, each first fin (A244) includes an angled distal surface configured to cammingly engage a respective row of staple drivers of first staple cartridge (A230) and actuate the staple drivers upwardly to thereby deploy staples from the cartridge pockets as first sled (A238) is driven distally within first staple cartridge (A230) during a firing stoke. A proximal end of first central body portion (A242) is recessed distally relative to first fins (A244) and defines a first knife engagement surface (A246) that is substantially planar and angled downwardly in a proximal direction.

As shown in FIG. 15, first sled (A238) is in its proximal undisplaced position such that first knife engagement surface (A246) directly contacts an underside of first distal end projection (A222) to vertically support first knife (A212) in an upward direction and thereby overcome the downward bias imposed by first lockout spring (A226). As a result, in response to a clinician's firing input, first firing beam (A210) may then actuate first knife (A212) distally within first end effector (A200), which in turn drives first sled (A238) distally within first staple cartridge (A230) to deploy staples into the clamped tissue. If first sled (A238) were positioned distal to its proximal undisplaced position, for example as a result of first staple cartridge (A230) having been previously fired or first sled (A238) having been bumped distally during handling or transport, then first knife (A212) would assume a lockout position in response to attempted firing of first end effector (A200). Specifically, first sled (A238) would not be appropriately positioned to vertically support first knife (A212), which would in turn drop downwardly under the bias of first lockout spring (A226) such that middle protrusion (A218) of first knife (A212) would advance downwardly and distally into first lockout recess (A224), which would inhibit further distal advancement of first knife (A212).

Figure 16:
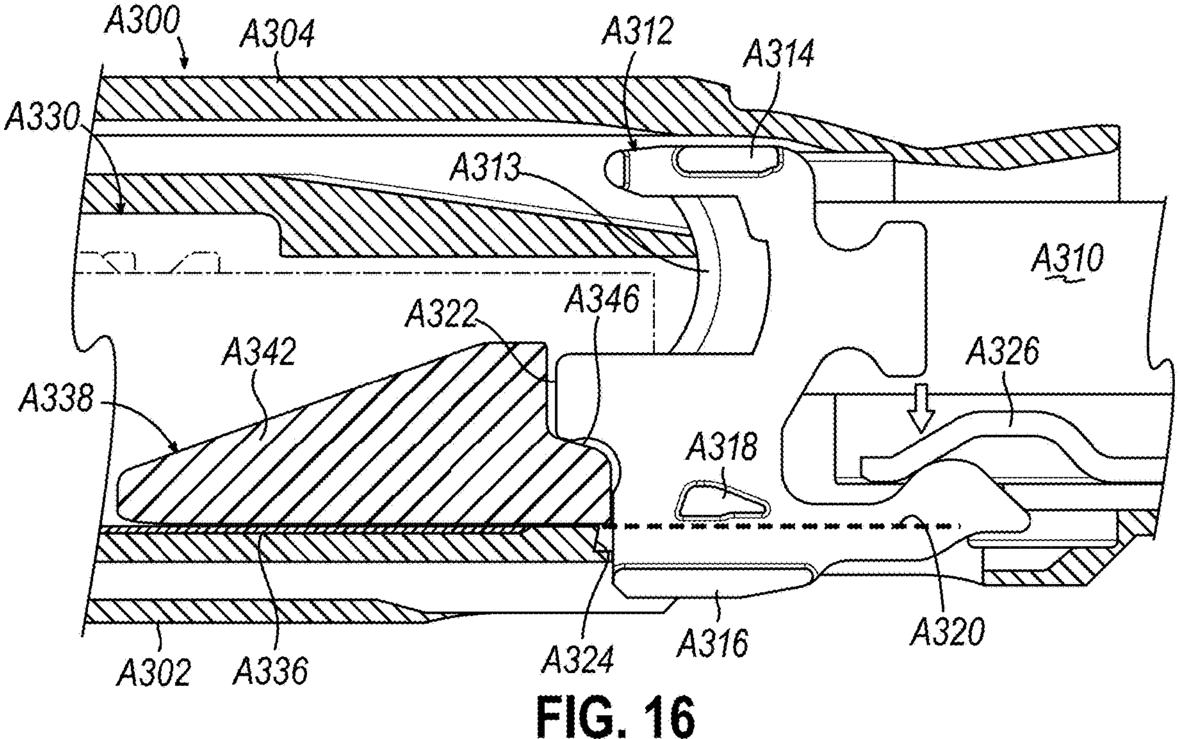
FIG. 16 depicts a partial side cross-sectional view of the end effector of the second surgical stapler properly loaded with the second staple cartridge of FIG. 11 in an unspent state, showing a sled of the second staple cartridge vertically supporting a distal end projection of the knife of the second surgical stapler to bypass a knife lockout position and permit firing.

FIG. 16 shows second staple cartridge (A330) in an unspent and undisturbed state such that second sled (A338) is positioned in a proximal undisplaced position, where second staple cartridge (A330) has been substantially seated within second cartridge jaw (A302) of second end effector (A300) such that second anvil jaw (A304) has been permitted to fully close onto tissue (not shown) positioned between second anvil jaw (A304) and second staple cartridge (A330). Similar to first end effector (A200), second end effector (A300) includes a second firing beam (A310) and a second knife (A312) secured to a distal end of second firing beam (A310). Second knife (A312) includes a cutting edge (A313), a transversely oriented upper protrusion (A314) slidable within a longitudinal slot of second anvil jaw (A304), a transversely oriented lower protrusion (A316) slidable within a longitudinal slot of second cartridge jaw (A302), and a transversely oriented middle protrusion (A318) slidable along a floor (A320) of second cartridge jaw (A302). Second knife (A312) further includes a second distal end projection (A322) configured to be vertically supported by a second knife engagement surface (A346) of second sled (A338), as described in greater detail below. Second end effector (A300) further includes a second lockout recess (A324) formed in second cartridge jaw floor (A320) at its proximal end, and a second lockout spring (A326) positioned proximal to second lockout recess (A324) and configured to bias second knife (A312) downwardly toward second cartridge jaw floor (A320) such that middle protrusion (A318) of second knife (A312) is biased downwardly toward second lockout recess (A324).

Figure 21:
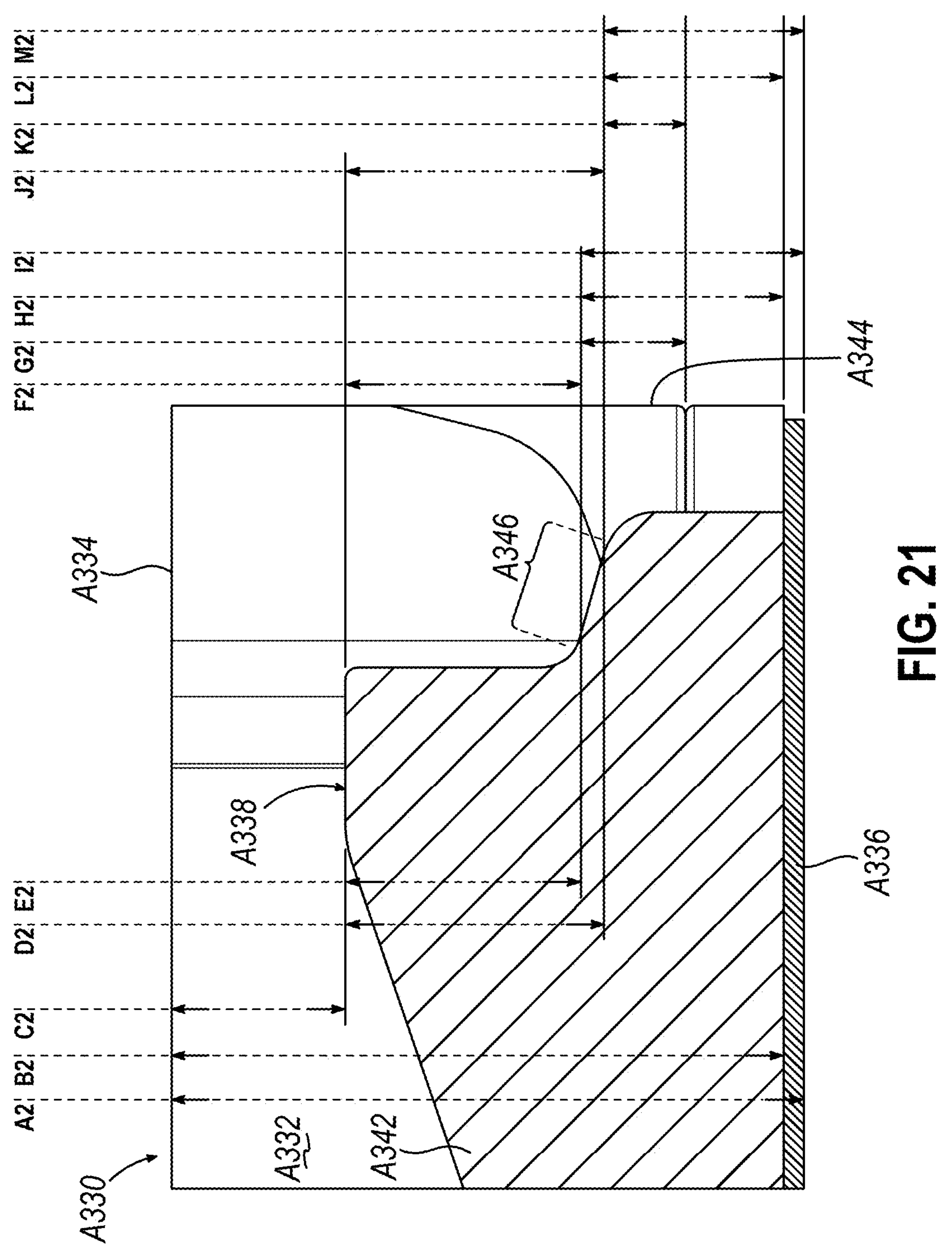
FIG. 21 depicts a partial side cross-sectional view of a proximal portion of the second staple cartridge of FIG. 11, showing select dimensions.

As shown in FIGS. 16 and 21, second sled (A338) of second staple cartridge (A330) includes a second central body portion (A342) and a pair of second fins (A344) (see FIG. 20) disposed on each lateral side of second central body portion (A342). Similar to first fins (A244), each second fin (A344) includes an angled distal surface configured to cammingly engage a respective row of staple drivers of second staple cartridge (A330) and actuate the staple drivers upwardly to thereby deploy staples from the cartridge pockets as second sled (A338) is driven distally within second staple cartridge (A330) during a firing stoke. A proximal end of second central body portion (A342) is recessed distally relative to second fins (A344) and defines a second knife engagement surface (A346) that is substantially planar and angled downwardly in a proximal direction. Second sled (A338) may be further configured in accordance with one or more teachings of U.S. Pat. No. 11,540,826, entitled "Surgical Stapler End Effector Sled Having Cartridge Wall Support Feature," issued Jan. 3, 2023, the disclosure of which is incorporated by reference herein in its entirety.

As shown in FIG. 16, second sled (A338) is in its proximal undisplaced position such that second knife engagement surface (A346) directly contacts an underside of second distal end projection (A322) to vertically support second knife (A312) in an upward direction and thereby overcome the downward bias imposed by second lockout spring (A326). As a result, in response to a clinician's firing input, second firing beam (A310) may then actuate second knife (A312) distally within second end effector (A300), which in turn drives second sled (A338) distally within second staple cartridge (A330) to deploy staples into the clamped tissue. If second sled (A338) were positioned distal to its proximal undisplaced position, for example as a result of second staple cartridge (A330) having been previously fired or second sled (A338) having been bumped distally during handling or transport, then second knife (A312) would assume a lockout position in response to attempted firing of second end effector (A300). Specifically, second sled (A338) would not be appropriately positioned to vertically support second knife (A312), which would in turn drop downwardly under the bias of second lockout spring (A326) such that middle protrusion (A318) of second knife (A312) would advance downwardly and distally into second lockout recess (A324), which would inhibit further distal advancement of second knife (A312).

As shown in FIGS. 17-21, first and second end effectors (A200, A300) and first and second staple cartridges (A230, A330) are configured such that first staple cartridge (A230) may be fired only by first end effector (A200) and second staple cartridge (A330) may be fired only by second end effector (A300). In other words, first end effector (A200) is incapable of firing second staple cartridge (A330) and second end effector (A300) is incapable of firing first staple cartridge (A230), even when first and second sleds (A238, A338) are located in their proximal undisplaced positions. This functionality is provided by strategically designed structural differences between first and second knives (A212, A312) and first and second sleds (A238, A338), as described below.

Figure 17:
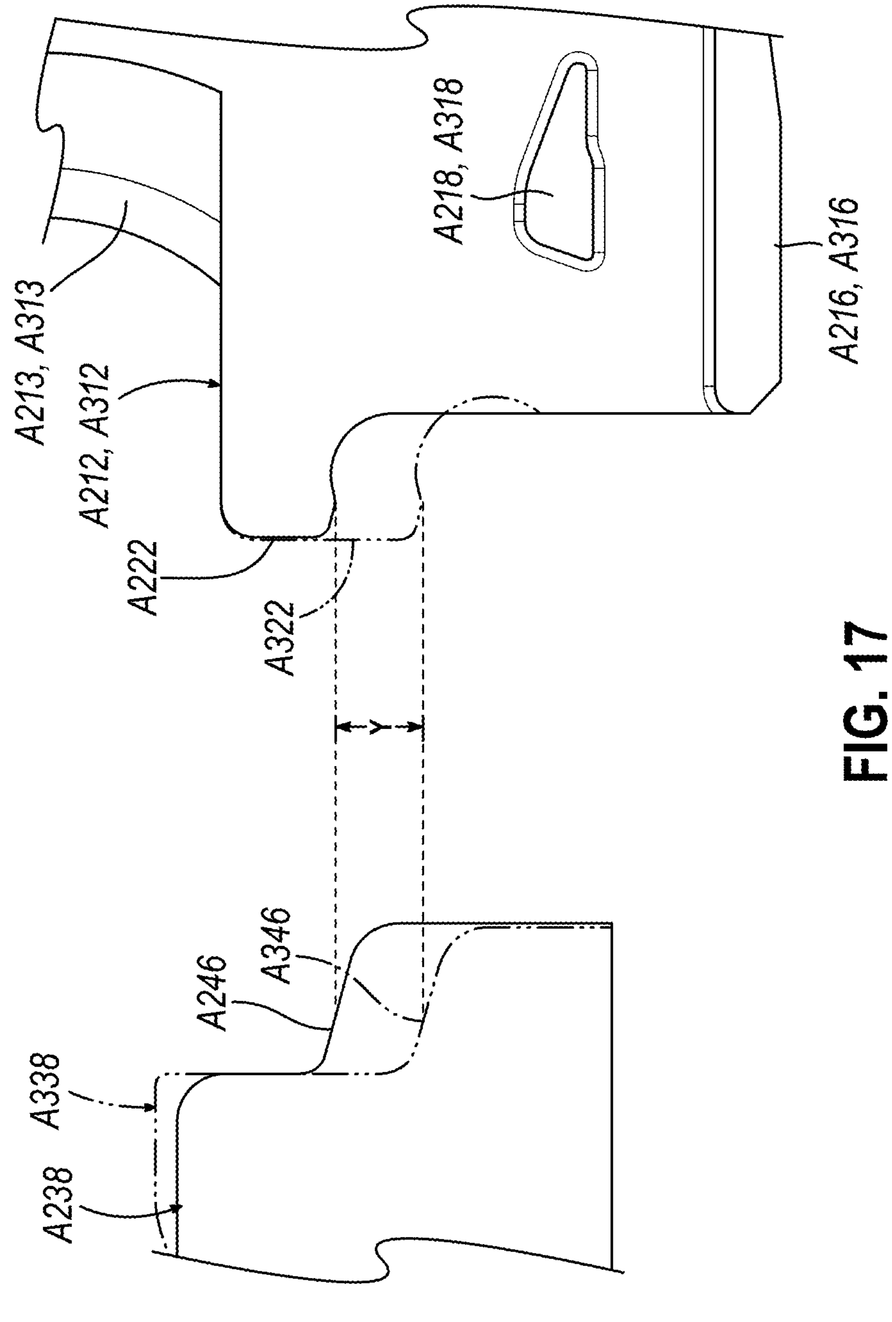
FIG. 17 depicts a partial side elevational view of the sleds of the first and second cartridges and the knives of the first and second surgical staplers of FIGS. 15 and 16, showing differing features of the second sled and the second knife in phantom relative to the corresponding features of the first sled and the first knife, where such differences inhibit firing of the first staple cartridge by the second surgical stapler and firing of the second staple cartridge by the first surgical stapler.

As shown in FIG. 17, second knife engagement surface (A346) of second sled (A338) is positioned lower than first knife engagement surface (A246) of first sled (A238), relative to a bottom surface of each sled (A238, A338), by a vertical distance (Y). Additionally, second distal end projection (A322) of second knife (A312) is vertically thicker than second distal end projection (A322) of second knife (A312) such that the sled-contacting underside of second distal end projection (A322) is positioned lower than the sled-contacting underside of first distal end projection (A222) of first knife (A212), relative to a top surface of each distal end projection (A222, A322), by vertical distance (Y). First and second knife engagement surfaces (A246, A346) are substantially parallel to one another such that vertical distance (Y) may be evaluated at any longitudinal location along knife engagement surfaces (A246, A346). In the present example, vertical distance (Y) is approximately 0.030 in (0.76 mm) as calculated from the dimensions provided below in Table 1 in connection with FIGS. 20 and 21.

Accordingly, first sled (A238) is capable of vertically supporting only first distal end projection (A222) of first knife (A212), and not second distal end projection (A322) of second knife (A312), in a manner sufficient to bypass the lockout state of first knife (A212) during an attempted firing stroke on first staple cartridge (A230). Similarly, second sled (A338) is capable of vertically supporting only second distal end projection (A322) of second knife (A312), and not first distal end projection (A222) of first knife (A212), in a manner sufficient to bypass the lockout state of second knife (A312) during an attempted firing stroke on second staple cartridge (A330).

Figure 18A:
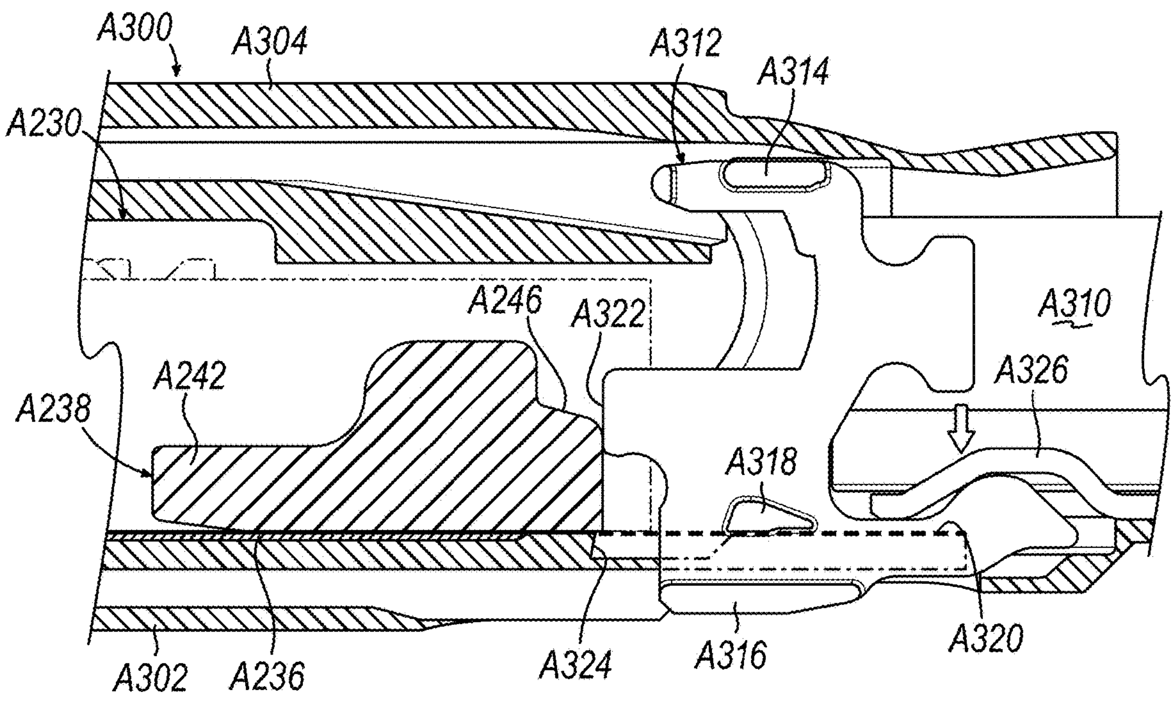
FIG. 18A depicts a partial side cross-sectional view of the second surgical stapler end effector of FIG. 16 improperly loaded with the first staple cartridge of FIG. 10 as a result of user error, showing the knife and sled in unactuated proximal positions before attempted firing.
Figure 18B:
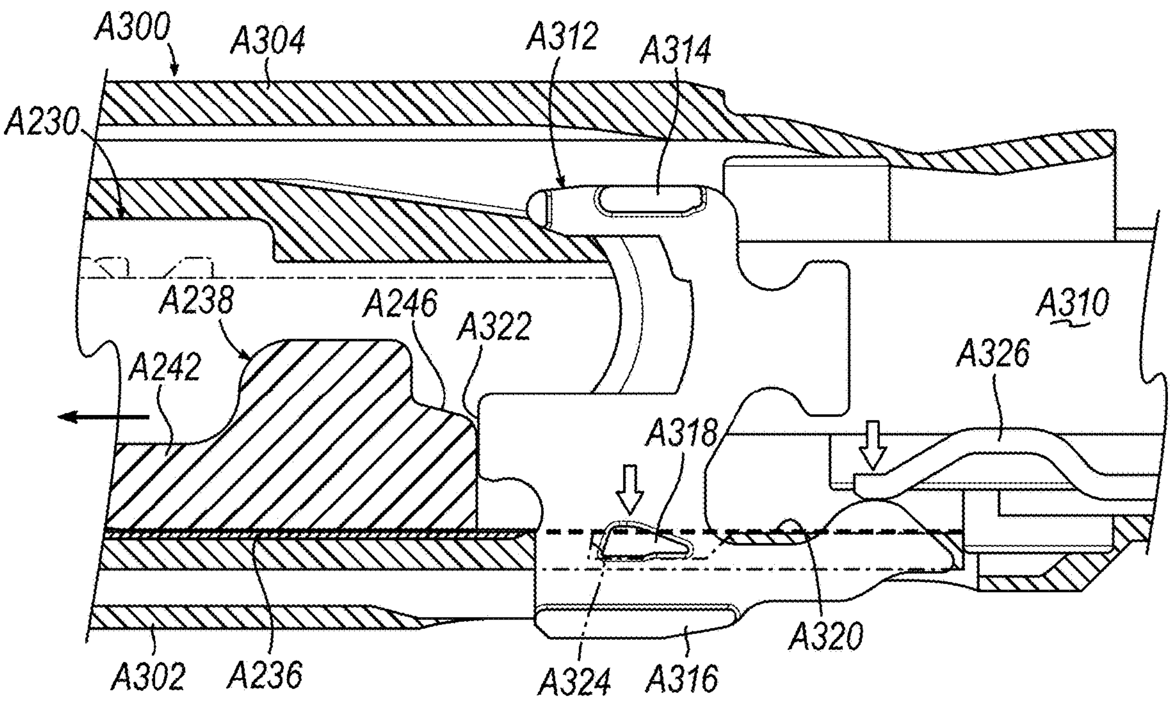
FIG. 18B depicts another partial side cross-sectional view of the second surgical stapler end effector and first staple cartridge of FIG. 18A, showing the knife advanced distally into a lockout position as a result of attempted firing.

FIGS. 18A-18B show an illustrative case of clinician misuse in which a clinician has installed first staple cartridge (A230) into second cartridge jaw (A302) of second end effector (A300). As shown and described above in connection with FIG. 14, only the proximal end portion of first staple cartridge (A230) is capable of being substantially seated in second cartridge jaw (A302), whereas its distal end portion is inhibited from being substantially seated due to the inability of second compatibility recesses (A308) of second cartridge jaw (A302) to receive first compatibility lugs (A240) of first staple cartridge (A230). Accordingly, first staple cartridge (A230) is capable of being only partially seated within second cartridge jaw (A302). Nevertheless, because the proximal end portion of first staple cartridge (A230) is substantially seated within second cartridge jaw (A302) and first sled (A238) is in its proximal undisplaced position, it is desirable to actively inhibit second knife (A312) from driving first sled (A238) distally enough to deploy staples from first staple cartridge (A230) and yield malformation of the deployed staples against second anvil jaw (A304). The structural uniqueness of first sled (A238) and first knife (A212) relative to second sled (A338) and second knife (A312) as discussed above provides such a safeguard.

As shown in FIGS. 17 and 18A, an entirety of first knife engagement surface (A246) of first sled (A238) is positioned higher than the sled-contacting underside of second distal end projection (A322) of second knife (A312) by vertical distance (Y), such that first knife engagement surface (A246) is incapable of vertically supporting second distal end projection (A322). Rather, a distal end surface of second distal end projection (A322) abuts a proximal end surface of first sled (A238). In response to an attempted firing stroke by the clinician, second knife (A312) advances distally and drives first sled (A238) distally a minute distance while second lockout spring (A326) biases second knife (A312) downwardly against second cartridge jaw floor (A320). As shown in FIG. 18B, before first sled (A238) engages any staple drivers to deploy staples from first staple cartridge (A230), middle protrusion (A318) of second knife (A312) advances downwardly into second lockout recess (A324), which inhibits further distal advancement of second knife (A312) and thus halts firing of the incompatible first staple cartridge (A230).

Figure 19:
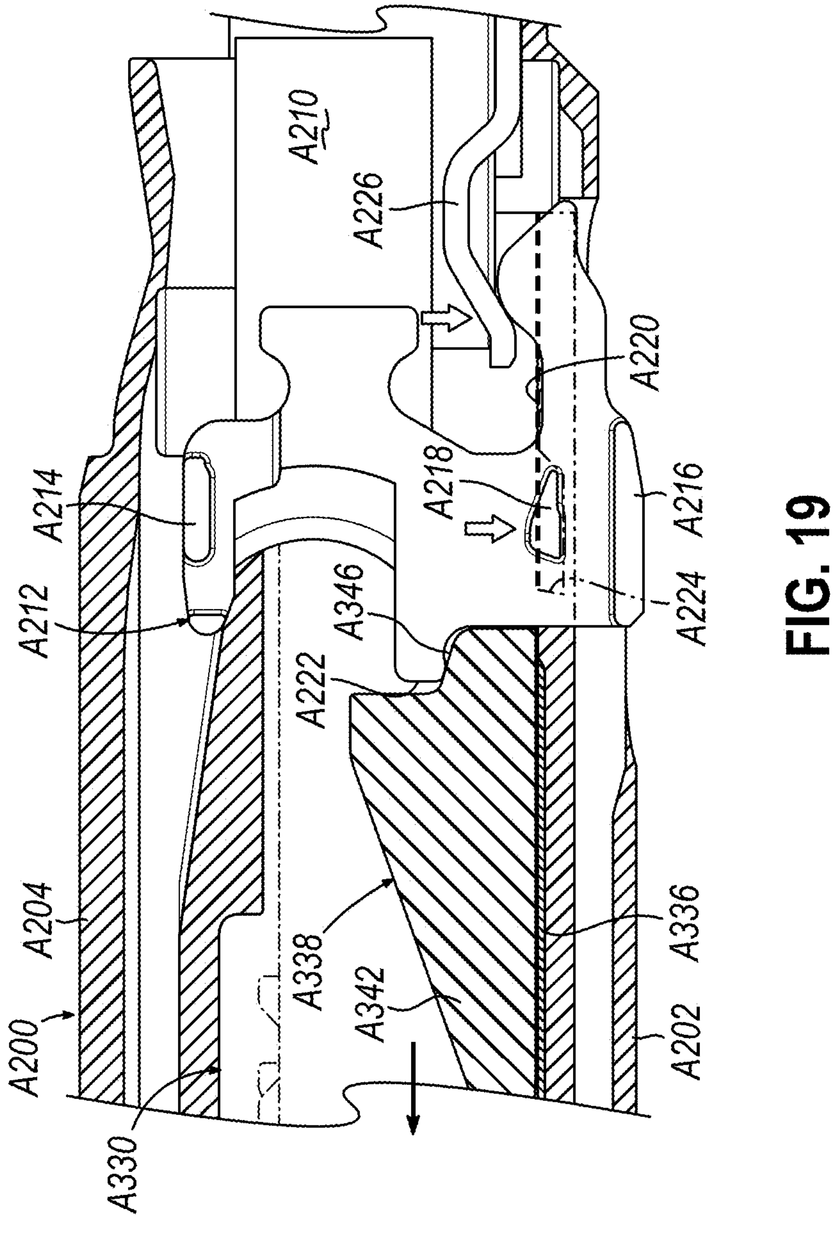
FIG. 19 depicts a partial side cross-sectional view of the first surgical stapler end effector of FIG. 15 improperly loaded with the second staple cartridge of FIG. 11 as a result of user error, showing the knife advanced distally into a lockout position as a result of attempted firing.

FIG. 19 shows another illustrative case of clinician misuse in which a clinician has installed second staple cartridge (A330) into first cartridge jaw (A202) of first end effector (A200). As shown and described above in connection with FIG. 13, only the proximal end portion of second staple cartridge (A330) is capable of being substantially seated in first cartridge jaw (A202), whereas its distal end portion is inhibited from being substantially seated due to the inability of first compatibility recesses (A208) of first cartridge jaw (A202) to receive second compatibility lugs (A340) of second staple cartridge (A330). Accordingly, second staple cartridge (A330) is capable of being only partially seated within first cartridge jaw (A202). Nevertheless, because the proximal end portion of second staple cartridge (A330) is substantially seated within first cartridge jaw (A202) and second sled (A338) is in its proximal undisplaced position, it is desirable to actively inhibit first knife (A212) from driving second sled (A338) distally enough to deploy staples from second staple cartridge (A330) and yield malformation of the deployed staples against first anvil jaw (A204). The structural uniqueness of first sled (A238) and first knife (A212) relative to second sled (A338) and second knife (A312) as discussed above provides such a safeguard.

As shown in FIG. 17, an entirety of second knife engagement surface (A346) of second sled (A338) is spaced vertically below the sled-contacting underside of first distal end projection (A222) of first knife (A212) by vertical distance (Y), such that second knife engagement surface (A346) is incapable of vertically supporting first distal end projection (A222). In response to an attempted firing stroke by the clinician, first knife (A212) advances distally while first lockout spring (A226) biases first knife (A212) downwardly against first cartridge jaw floor (A220). As shown in FIG. 19, before second sled (A338) engages any staple drivers to deploy staples from first staple cartridge (A230), middle protrusion (A218) of first knife (A212) advances downwardly into first lockout recess (A224), which inhibits further distal advancement of first knife (A212) and thus halts firing of the incompatible second staple cartridge (A330).

FIGS. 20 and 21 in combination with Table 1 below show various dimensions for first sled (A238) and second sled (A338), with a particular focus on dimensions relative to knife engagement surfaces (A246, A346), that specifically enable first and second sleds (A238, A338) to operate in the manner described above to cause a firing lockout condition and inhibit firing when first staple cartridge (A230) is mistakenly loaded by a clinician into second end effector (A300) or when second staple cartridge (A330) is mistakenly loaded by a clinician into first end effector (A200). Due to the angled planar configuration of each knife engagement surface (A246, A346), its vertical midpoint is understood to coincide with its longitudinal midpoint. Additionally, because each knife engagement surface (A246, A346) slopes downwardly in a proximal direction, it has a maximum height relative to the bottom surface of the respective sled (A238, A338) at a distal end of the knife engagement surface (A246, A346), and a minimum height relative to the bottom surface of the respective sled (A238, A338) at a proximal end of the knife engagement surface (A246, A346).

As evidenced by these dimensions, second knife engagement surface (A346) of second sled (A338) spans a vertical distance of approximately 5% of the total height of second sled (A338), or approximately 0.009 inches (0.23 mm). The vertical midpoint of second knife engagement surface (A346) is positioned at approximately 44% of a total height of second sled (A338), or approximately 0.073 inches (1.9 mm) vertically from a bottom surface of second sled (A338). The vertical midpoint of second knife engagement surface (A346) is also positioned at approximately 0.093 inches (2.4 mm) vertically from a top surface of the second sled (A338). Additionally, an upper distal end of second knife engagement surface (A346) is positioned at approximately 47% of the total sled height measured from the bottom surface of second sled (A338), and a lower proximal end of second knife engagement surface (A346) is positioned at approximately 41% of the total sled height measured vertically from the bottom surface. More specifically, the upper distal end of second knife engagement surface (A346) is positioned at approximately 0.077 inches (2.0 mm) vertically from the bottom surface of second sled (A338), and the lower proximal end of second knife engagement surface (A346) is positioned at approximately 0.068 inches (1.7 mm) vertically from the bottom surface of second sled (A338). Additionally, the vertical midpoint of the second knife engagement surface (A346) is positioned at approximately 0.036 inches (0.91 mm) vertically from an upwardly facing floor of second sled (A338).

In the case of a first version of second staple cartridge (A330) having a relatively shorter second deck (A334) for firing on relatively thicker tissues, the vertical midpoint of second knife engagement surface (A346) is positioned at approximately 34% of a total height of second staple cartridge (A330) measured vertically from the bottom surface of second pan (A336) to the top surface of second deck (A334). In the case of a second version of second staple cartridge (A330) having a relatively taller second deck (A334) for firing on relatively thinner tissues, the vertical midpoint of second knife engagement surface (A346) is positioned at approximately 30% of a total height of second staple cartridge (A330) measured vertically from the bottom surface of second pan (A336) to the top surface of second deck (A334).

It will be appreciated that similar ratios and measurements may be determined for first staple cartridge (A230) based on the dimensions provided in FIG. 20 and Table 1. For instance, the vertical midpoint of first knife engagement surface (A246) is determined to be positioned at approximately 63% of a total height of first sled (A238), or approximately 0.108 inches (2.74 mm) vertically from a bottom surface of first sled (A238).

TABLE 1

| | | First Sled (A238) | | Second Sled (A338) | |
|---|---|---|---|---|---|
| Dimension | Description | in (±0.005) | mm (±0.13) | in (±0.005) | mm (±0.13) |
| A | Bottom of pan to top of deck | 0.A238 | 6.05 | 0.A238 | 6.05 |
| B | Bottom of sled to top of deck | 0.A230 | 5.84 | 0.231 | 5.87 |
| C | Top of sled to top of deck | 0.059 | 1.50 | 0.066 | 1.68 |
| D | Lower end of knife engagement surface to top of sled | 0.068 | 1.73 | 0.097 | 2.46 |
| E | Upper end of knife engagement surface to top of sled | 0.058 | 1.47 | 0.088 | 2.24 |
| F | Upper end of knife engagement surface to top of deck | 0.117 | 2.97 | 0.154 | 3.91 |
| G | Upper end of knife engagement surface to sled floor | 0.070 | 1.78 | 0.040 | 1.02 |
| H | Upper end of knife engagement surface to bottom of sled | 0.113 | 2.87 | 0.077 | 1.96 |
| I | Upper end of knife engagement surface to bottom of pan | 0.121 | 3.07 | 0.084 | 2.13 |
| J | Lower end of knife engagement surface to top of deck | 0.127 | 3.23 | 0.163 | 4.14 |
| K | Lower end of knife engagement surface to sled floor | 0.060 | 1.52 | 0.031 | 0.79 |
| L | Lower end of knife engagement surface to bottom of sled | 0.103 | 2.62 | 0.068 | 1.73 |
| M | Lower end of knife engagement surface to bottom of pan | 0.111 | 2.82 | 0.075 | 1.91 |

C. Knife Having Machined Surfaces to Optimize Engagement with Sled

Figure 22:
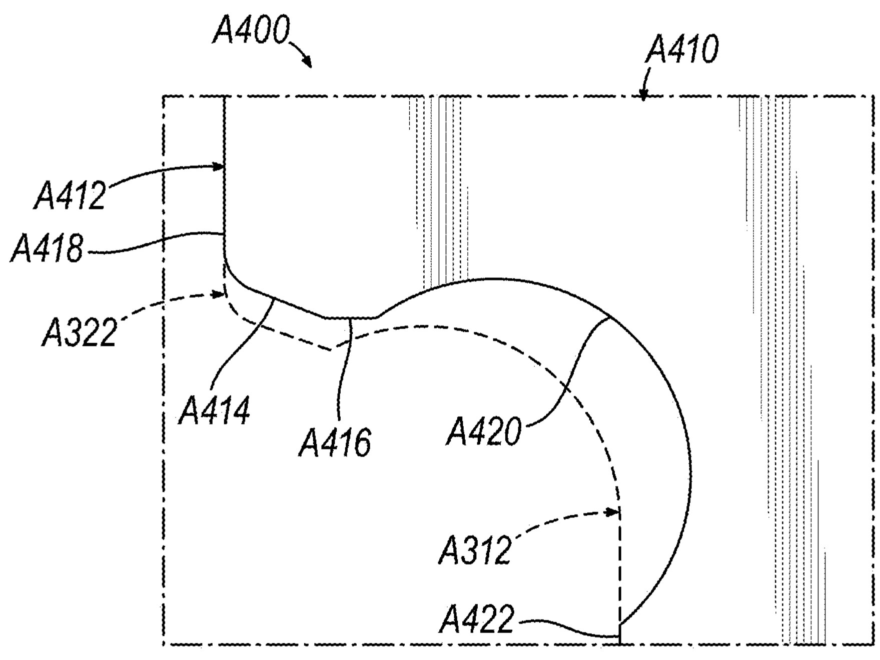
FIG. 22 depicts an enlarged side elevational view of a distal end portion of another illustrative knife in combination with a distal end portion of the knife of FIG. 16 shown in phantom.

As described above in connection with FIG. 16, the underside of second distal end projection (A322) of second knife (A312) is configured to directly contact and be vertically supported by second knife engagement surface (A346) of second sled (A338) when second end effector (A300) is fired. FIGS. 22-23C show an illustrative alternative end effector (A400) that includes a cartridge jaw (not shown) similar to cartridge jaw (A302) and configured to fully receive second staple cartridge (A330), an anvil jaw (not shown) similar to anvil jaw (A304), and a knife (A410). As described in greater detail below, knife (A410) includes a distal end projection (A412) having a geometry that slightly differs from that of second distal end projection (A322) of second knife (A312) so as to optimize an interface between its distal end projection (A412) and second knife engagement surface (A346) of second sled (A338). End effector (A400), including knife (A410), is otherwise similar in structure and function to second end effector (A300) described above.

As shown in FIG. 22, distal end projection (A412) of knife (A410) includes an underside that faces toward a floor of the cartridge jaw and includes a distal planar underside surface (A414) and a proximal planar underside surface (A416). Distal planar underside surface (A414) extends proximally from a distal-most end surface (A418) of knife (A410), and proximal planar underside surface (A416) extends proximally from distal planar underside surface (A414) and terminates at a relief recess (A420) formed in the body of knife (A410). Planar underside surfaces (A414, A416) are angled relative to one another, and each planar underside surface (A414, A416) is angled relative to a floor and a longitudinal jaw axis of the cartridge jaw. More specifically, proximal planar underside surface (A416) defines a first, smaller distally-opening angle relative to the cartridge jaw axis, and distal planar underside surface (A414) defines a second, larger distally-opening angle relative to the cartridge jaw axis. Planar underside surfaces (A414, A416) may be formed by machining, for example.

Figure 23A:
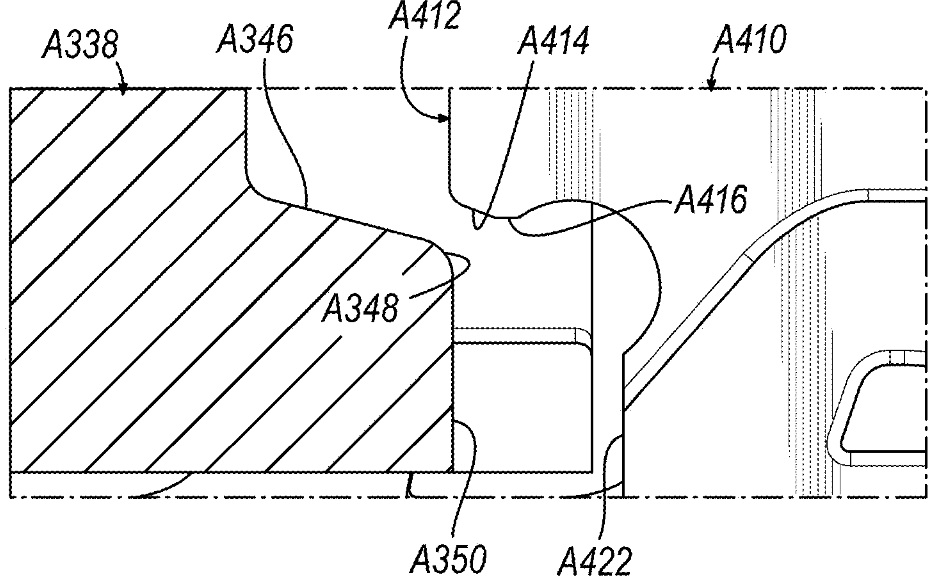
FIG. 23A depicts an enlarged side cross-sectional view of a surgical stapler end effector having the knife of FIG. 22 and properly loaded with the second staple cartridge of FIG. 11 in an unspent state, showing the knife and sled in unactuated proximal positions prior to firing.
Figures 23B, 23C:
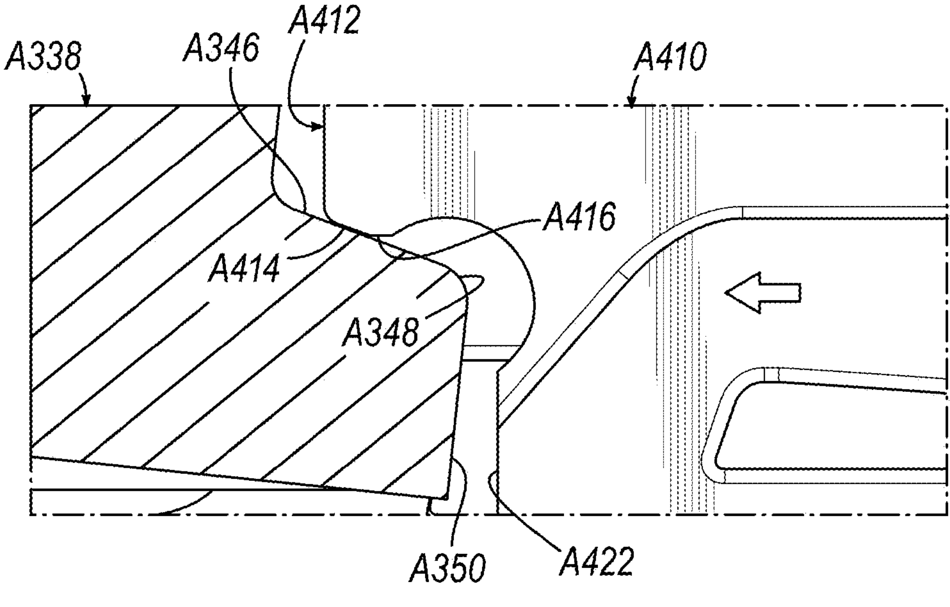
FIG. 23B depicts another enlarged side cross-sectional view of the surgical stapler end effector of FIG. 23A, showing initial engagement between the knife and the sled as the knife is advanced distally during firing.
FIG. 23C depicts another enlarged side cross-sectional view of the surgical stapler end effector of FIG. 23A, showing engagement between the knife and the sled as they advance distally during a firing stroke.

As shown in FIG. 23A, planar underside surfaces (A414, A416) are each spaced vertically above a radiused proximal edge (A348) of second sled (A338) as knife (A410) advances distally toward second sled (A338) in its unactuated proximal position. This arrangement ensures that distal end projection (A412) does not contact radiused proximal edge (A348) and cause second sled (A338) to prematurely advance distally, which could result in knife (A410) dropping downwardly into a lockout position that inhibits firing.

As shown in FIG. 23B, upon initial engagement between knife (A410) and second sled (A338), distal end projection (A412) exerts a downward force on second knife engagement surface (A346) that may result in second sled (A338) tilting slightly proximally such that a distal end of second sled (A338) raises slightly. In this orientation, distal planar underside surface (A414) of knife (A410) maintains surface-to-surface contact with second knife engagement surface (A346), as opposed to edge-to-surface contact, which ensures that the force exerted by distal end projection (A412) on second knife engagement surface (A346) as the former distally mounts the latter is directed substantially vertically downward rather than distally. This again helps to ensure that second sled (A338) does not prematurely advance distally as knife (A410) initially engages second sled (A338), particularly in configurations where second knife engagement surface (A346) has a relatively low coefficient of friction, for example when second sled (A338) is formed of metal.

As shown in FIG. 23C, knife (A410) has been actuated further distally relative to second sled (A338) such that distal end projection (A412) has advanced further distally along second knife engagement surface (A346), and such that a distal driving surface (A422) of knife (A410) now engages a proximal end surface (A350) of second sled (A338) for firing. As knife (A410) and second sled (A338) advance distally together the distal end of second sled (A338) engages one or more initial staple drivers (not shown) of second staple cartridge (A330), which results in second sled (A338) resuming a leveled state that it maintains throughout the remainder of the distal firing stroke.

III. Examples of Stapling Assemblies Including Engagement Protrusions

In some instances, it may be desirable in predetermined areas to incorporate raised features that extend upwardly from the deck thereof for enhancing the gripping of tissue by the stapling assembly (e.g., a staple cartridge) when the end effector is closed, and/or for guiding the legs of the staples as the legs exit the respective staple openings during deployment of the staples. Utilizing raised features in predetermined areas may provide increased localized compression applied to tissue (T) in those predetermined areas while simultaneously minimizing the overall increase in total compression applied to tissue (T). It may be desirable to affect the interaction between the raised feature(s) and tissue (T) or between the raised features and a buttress. For example, it may be desirable to resist relative movement between the buttress to the deck prior to contacting tissue, and encourage release of the buttress and/or tissue from the raised features after contacting tissue.

It will be understood that while the features shown and described above are presented in the context of a stapling assembly (e.g., a staple cartridge (C110)) for surgical stapler (10), such features may also be applied to staple cartridges configured for use with various other types of surgical staplers, such as linear surgical staplers. Staple cartridge (C110) described below provides such functionality. FIGS. 24-35 are shown to scale.

A. Example of Staple Cartridge

Figure 24:
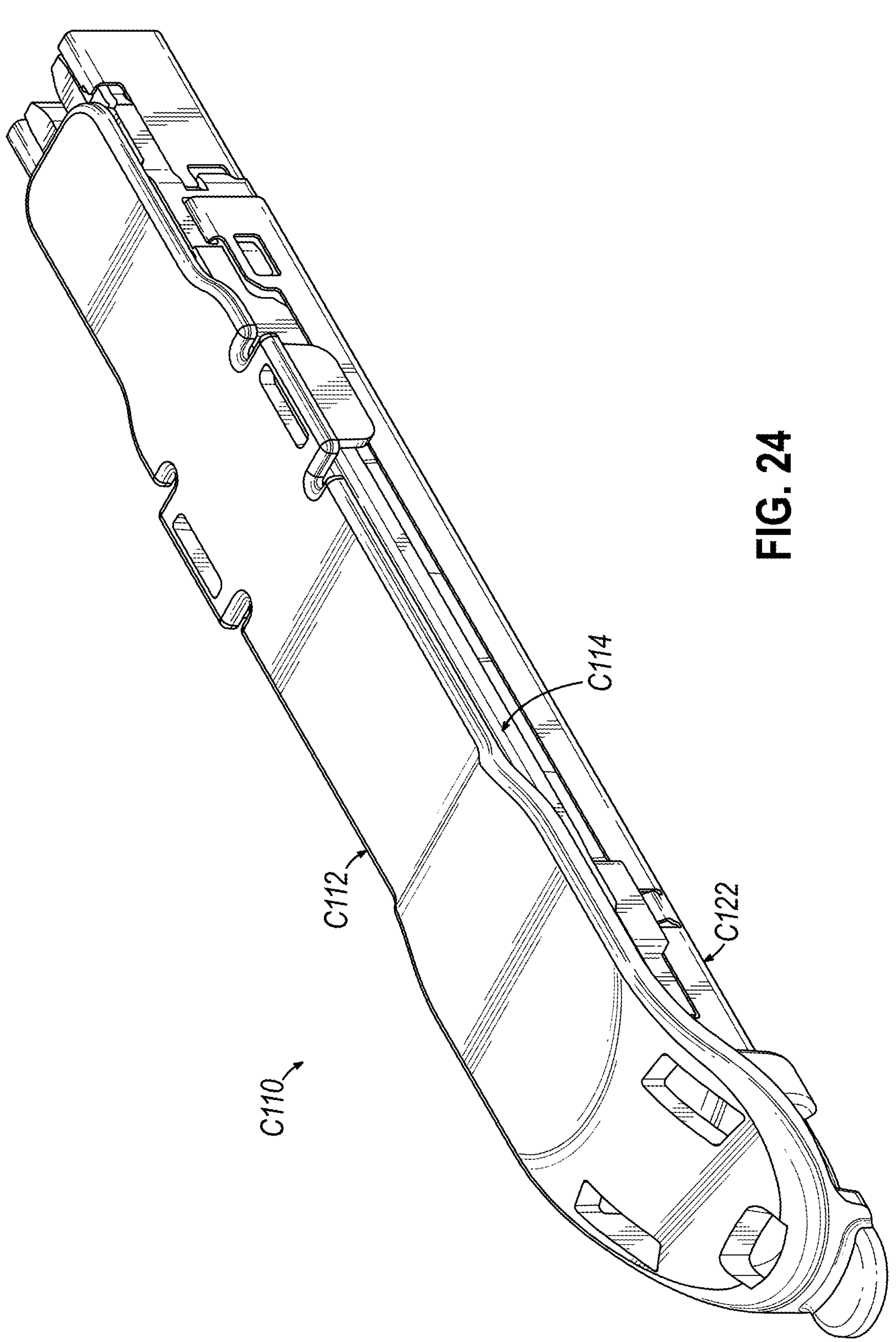
FIG. 24 depicts a perspective view of another example of a staple cartridge for use with the end effector of FIG. 2.
Figure 25:
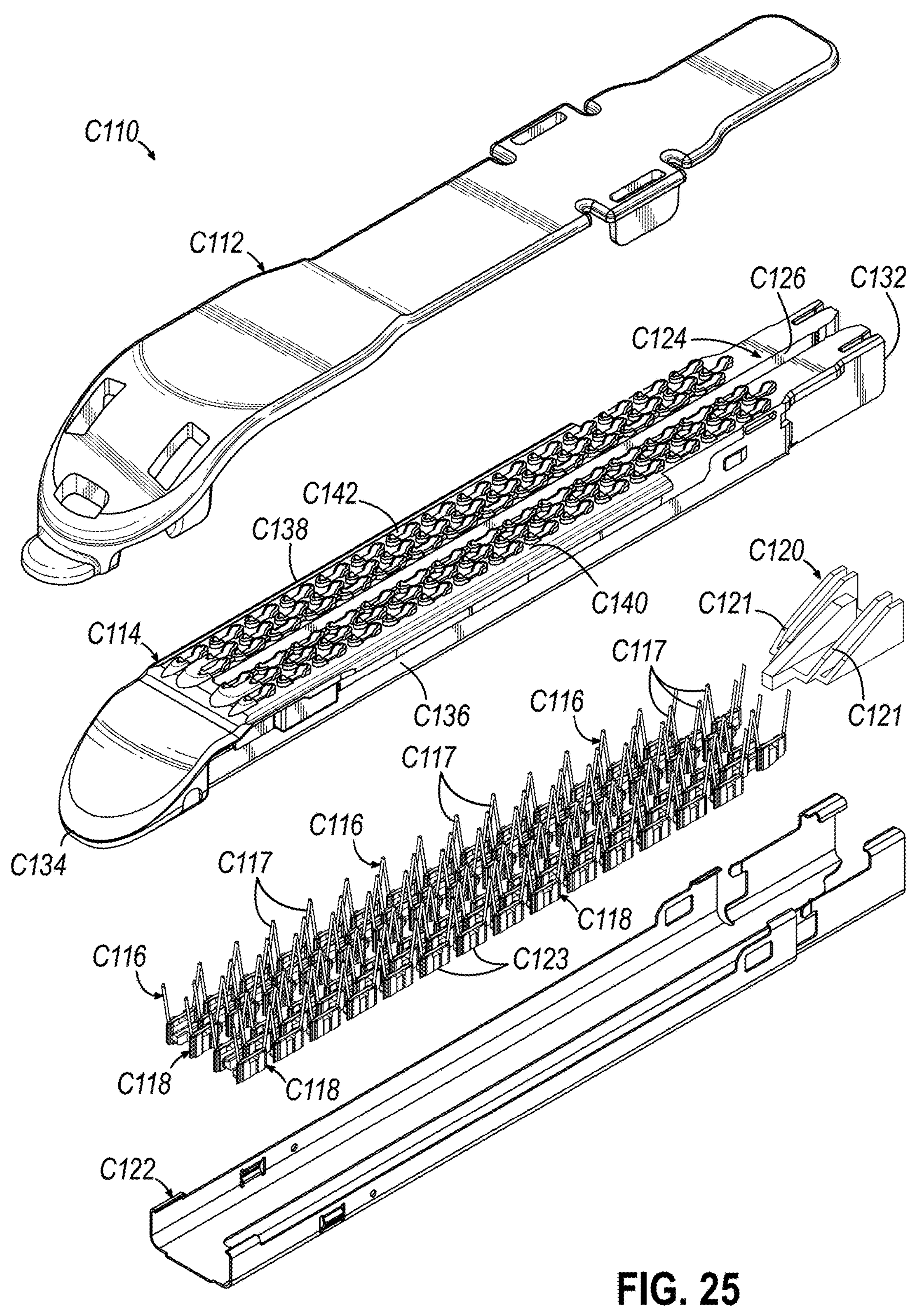
FIG. 25 depicts an exploded perspective view of the staple cartridge of FIG. 24, where the staple cartridge includes a retainer, a cartridge body, staples, staple drivers, a sled, and a tray.

FIGS. 24-35 show an example of a staple cartridge (C110) configured for use with end effector (40) of FIG. 2. As shown in FIGS. 24-25, staple cartridge (C110) includes a retainer (C112), a cartridge body (C114), a plurality of staples (C116), a plurality of staple drivers (C118), a wedge sled (C120), and a tray (C122). Staple cartridge (C110) is similar to staple cartridge (70) described above except as otherwise described below. Staple cartridge (C110) is configured to deploy staples (C116) toward corresponding staple forming pockets of an anvil (not shown), but similar to staple forming pockets (66) of anvil (44). Staples (C116) are similar to staples (86), and staple drivers (C118) are similar to staple drivers (84). Tray (C122) is similar to lower tray (76). Tray (C122) encloses an underside of cartridge body (C114) to retain staples (C116) and staple drivers (C118) within staple cartridge (C110). Wedge sled (C120) is similar to wedge sled (82) and is slidably disposed within cartridge body (C114). Wedge sled (C120) includes upwardly presented cam surfaces (C121) configured to engage the undersides (C123) of staple drivers (C118).

As will be described in greater detail below, cartridge body (C114) includes a deck (C124), an elongate slot (C126) formed in deck (C124), a plurality of cartridge pockets (C128) formed in deck (C124), and a plurality of engagement protrusions (C130*a*-*f*) extending outwardly from deck (C124). Cartridge body (C114) includes a proximal end (C132), a distal end (C134), a first lateral side (C136), and a second lateral side (C138). Second lateral side (C138) of cartridge body (C114) is disposed opposite first lateral side (C136). Deck (C124) is similar to upper deck (74) and is configured to compress tissue (T) against an anvil (not shown), but similar to anvil (44). Deck (C124) is defined by cartridge body (C114) and is shown as being substantially planar. Elongate slot (C126) is similar to knife slot (78). Elongate slot (C126) extends along a longitudinal axis (LA) of cartridge body (C114). Elongate slot (C126) opens upwardly through deck (C124) and terminates at a connecting portion (C131). Elongate slot (C126) is configured to slidably receive a knife therein. The knife may be a distal knife portion of a firing beam (not shown), such as distal knife portion (50) of firing beam (46). Cartridge pockets (C128) are configured to house a plurality of staples (C116). As shown, each cartridge pocket (C128) slidably houses an unformed staple (C116) and a respective staple driver (C118) similar to staple drivers (84) positioned beneath staples (86). While FIG. 25 shows a 1:1 relationship of cartridge pockets (C128) to staples (C116), this may vary.

Figure 26:
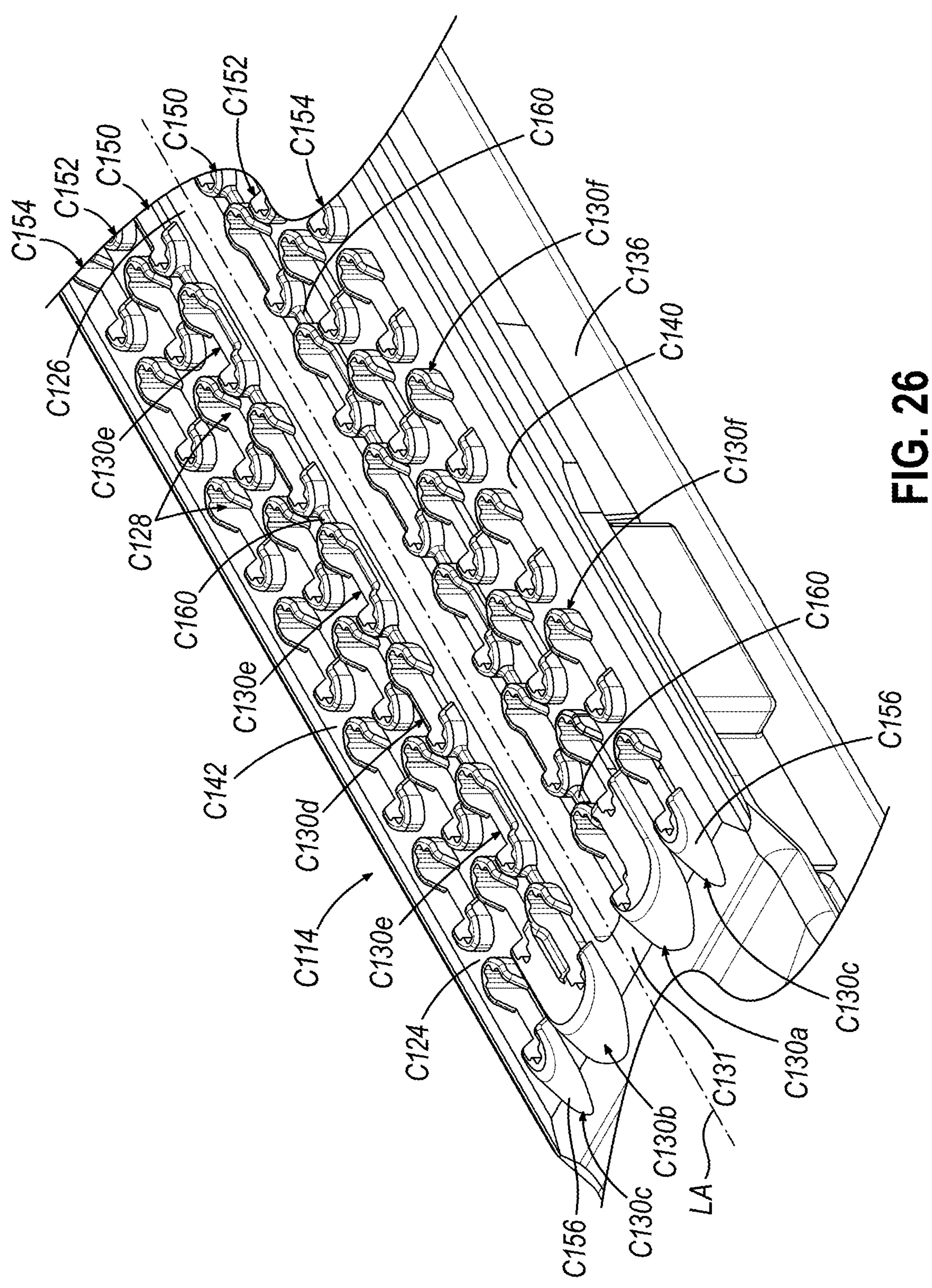
FIG. 26 depicts a perspective view of an enlarged portion of the cartridge body of FIG. 25.
Figures 27, 28:
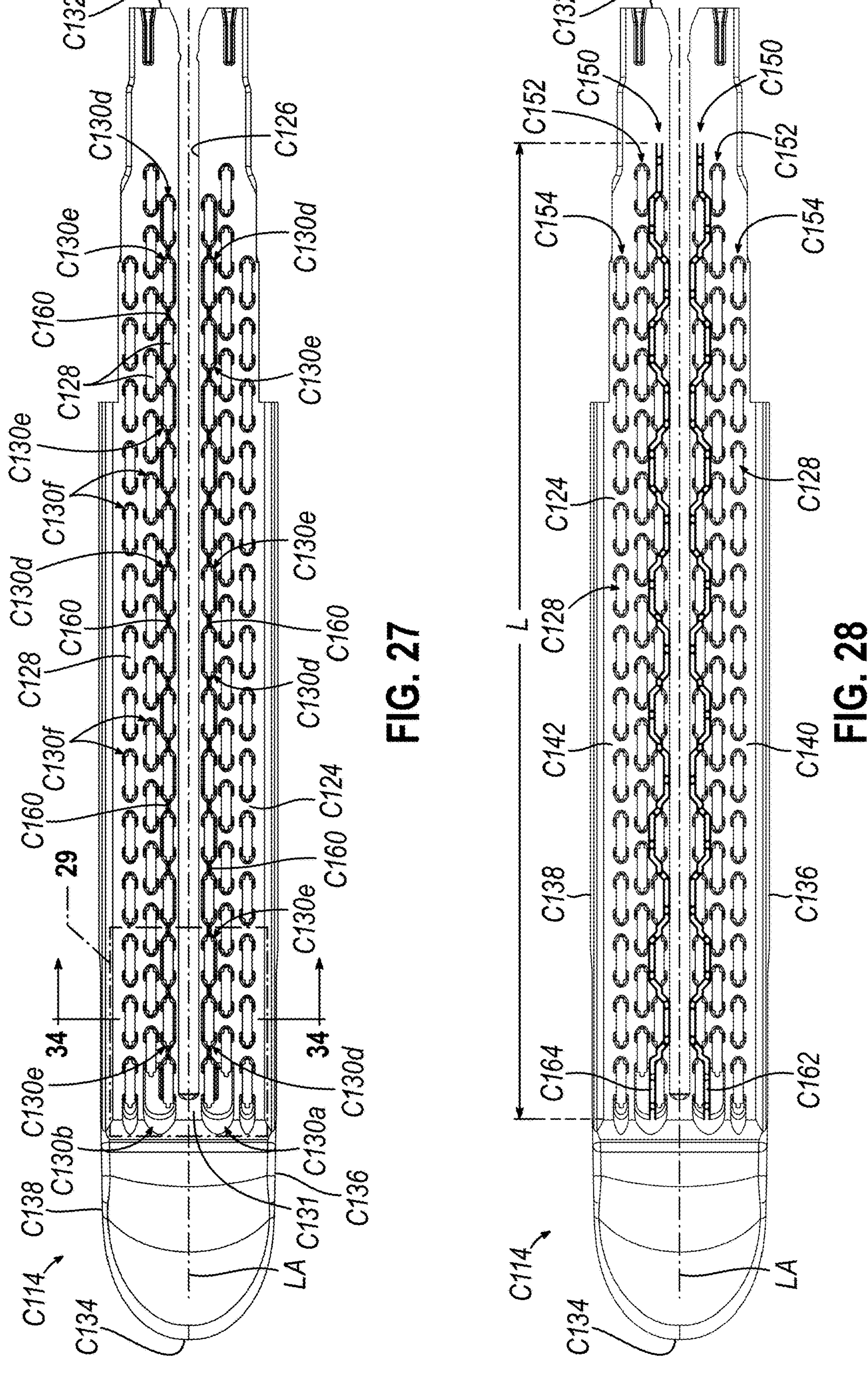
FIG. 27 depicts a top plan view of the cartridge body of FIG. 25.
FIG. 28 depicts a top plan view of the cartridge body of FIG. 27 but showing first and second continuous non-linear paths having first and second continuous non-linear cross-sectional areas along the length of inner rows of cartridge pockets.
Figure 29:
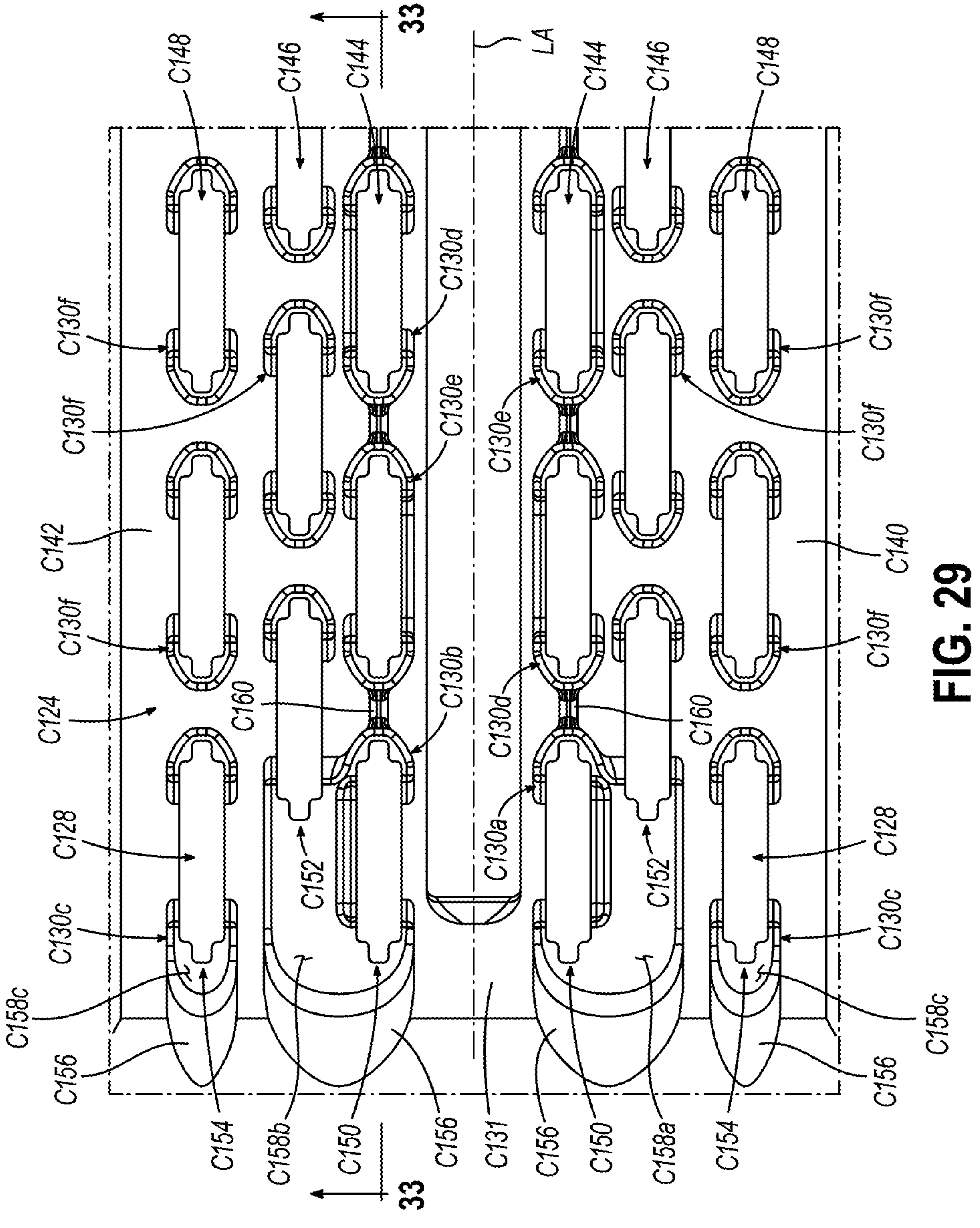
FIG. 29 depicts an enlarged partial top plan view of the cartridge body of FIG. 27.

FIG. 27 shows cartridge pockets (C128) arranged into six longitudinally extending rows. Elongate slot (C126) separates three rows positioned on a first deck side (C140) from three additional rows are positioned a second deck side (C142). Second deck side (C142) of deck (C124) is a mirror image of first deck side (C140). As shown in FIGS. 26 and 29, these longitudinal rows include inner rows (C144), middle rows (C146), and outer rows (C148). While two inner rows (C144), two middle rows (C146), and two outer rows (C148) are shown, more or fewer rows are envisioned. Inner rows (C144) are the closest cartridge pockets (C128) relative to elongate slot (C126). In other words, inner rows (C144) are positioned closer to elongate slot (C126) than middle rows (C146). Similarly, middle rows (C146) are positioned closer to elongate slot (C126) than outer rows (C148) of cartridge pockets (C128). Elongate slot (C126) separates and bisects inner rows (C144) of cartridge pockets (C128). Inner rows (C144) and middle rows (C146) are shown as including fifteen cartridge pockets (C128); however, more or fewer cartridge pockets (C128) are envisioned. Outer rows (C148) are shown as including fourteen cartridge pockets (C128); however, more or fewer cartridge pockets (C128) are envisioned.

As shown in FIGS. 26 and 29, engagement protrusions (C130*a-f*) extend from deck (C124) and are configured to grip tissue (T) or an adjunct material (e.g., a buttress) positioned thereon. As will be described below, cartridge body (C114) includes six different configurations of engagement protrusions (C130*a-f*). The arrangement of these engagement protrusions (C130*a-f*) is symmetric about elongate slot (C126). Each engagement protrusion (C130*a-f*) partially surrounds a respective cartridge pocket (C128). Similar to cartridge pockets (C128), engagement protrusions (C130*a-f*) are arranged into a plurality of longitudinally extending rows. These longitudinal rows include inner rows (C150), middle rows (C152), and outer rows (C154). While two inner rows (C150), two middle rows (C152), and two outer rows (C154) are shown, more or fewer rows are also envisioned. Inner rows (C150) generally correspond with inner rows (C144) of cartridge pockets (C128). Similarly, middle rows (C152) generally correspond with middle rows (C146) of cartridge pockets (C128), and outer rows (C154) generally correspond with outer rows (C148) of cartridge pockets (C128). Inner rows (C150) are the closest engagement protrusions relative to elongate slot (C126). In other words, inner rows (C150) of engagement protrusions are positioned closer to elongate slot (C126) than middle rows (C152), and middle rows (C152) are positioned closer to elongate slot (C126) than outer rows (C154) of engagement protrusions. As shown, inner rows (C150), middle rows (C152), and outer rows (C154) each extend substantially parallel to elongate slot (C126).

As best shown in FIGS. 26 and 29, engagement protrusions (C130*a-c*) are the distal most engagement protrusions. Each engagement protrusion (C130*a-c*) includes a distal lead-in portion (C156). Engagement protrusions (C130*a-b*) extend between multiple rows. Particularly, engagement protrusion (C130*a*) extends between inner row (C150) and middle row (C152) on first deck side (C140). Similarly, engagement protrusion (C130*b*) extends between inner row (C150) and middle row (C152) on second deck side (C142). Engagement protrusions (C130*a-c*) include planar surfaces (C158*a-c*) (see FIG. 29). Engagement protrusions (C130*c*) are the distal most engagement protrusions for outer rows (C154) on first and second deck sides (C140, C142). Each engagement protrusion (C130*c-f*) extends within a single row (e.g., one of inner row (C150), middle row (C152), and outer rows (C154)) and does not connect with an adjacent row. As shown, longitudinally adjacent engagement protrusions (C130*d-f*) of inner rows (C150) on first and second deck sides (C140, C142) are linked together (also referred to as joined together) by interconnections (C160). Interconnections (C160) effectively daisy chain together adjacent engagement protrusions (C130*d-f*) of inner rows (C150).

As shown in FIG. 27, inner row (C150) on first deck side (C140) includes engagement protrusion (C130*a*) followed by interconnection (C160), engagement protrusion (C130*d*), interconnection (C160), and engagement protrusion (C130*e*) in an alternating manner. Particularly, moving proximally, this arrangement is engagement protrusion (C130*a*), interconnection (C160), engagement protrusion (C130*d*), interconnection (C160), engagement protrusion (C130*e*), interconnection (C160), engagement protrusion (C130*d*), interconnection (C160), engagement protrusion (C130*e*), interconnection (C160), engagement protrusion (C130*d*), interconnection (C160), engagement protrusion (C130*e*), interconnection (C160), engagement protrusion (C130*d*), interconnection (C160), engagement protrusion (C130*e*), interconnection (C160), engagement protrusion (C130*d*), interconnection (C160), engagement protrusion (C130*e*), interconnection (C160), engagement protrusion (C130*d*), interconnection (C160), engagement protrusion (C130*e*), interconnection (C160), engagement protrusion (C130*d*), interconnection (C160), and engagement protrusion (C130*e*). Moving proximally, inner row (C150) on second deck side (C142) includes engagement protrusion (C130*b*) followed by interconnection (C160), engagement protrusion (C130*e*), interconnection (C160), and engagement protrusion (C130*d*) in an alternating manner. This difference is because inner row (C150) of second deck side (C142) is a mirror image of inner row (C150) of first deck side (C140). While inner rows (C150) are shown as alternating every engagement protrusion, it is also envisioned that this pattern may vary (e.g., two engagement protrusions (C130*d*) followed by two engagement protrusions (C130*e*) each separated by interconnections (C160) etc.).

Moving proximally, middle row (C152) on first deck side (C140) includes engagement protrusion (C130*a*) followed by a series of longitudinally extending engagement protrusions (C130*f*). Moving proximally, middle row (C152) on second deck side (C142) includes engagement protrusion (C130*b*) followed by a series of longitudinally extending engagement protrusions (C130*f*). As shown, no longitudinally adjacent engagement protrusion (C130*a*-C130*f*) of middle rows (C152) is joined together by an interconnection (C160) or any other feature extending from deck (C124). Moving proximally, outer rows (C148) include engagement protrusion (C130*c*) followed by a series of longitudinally extending engagement protrusions (C130*f*). Similarly, no longitudinally adjacent engagement protrusion (C130*c*, C130*f*) of outer rows (C154) is joined together by an interconnection (C160) or any other feature extending from deck (C124). Except for engagement protrusion (C130*a*) connecting inner and middle rows (C150, C152) on first deck side (C140) and engagement protrusion (C130*b*) connecting inner and middle rows (C150, C152) on second deck side (C142), inner rows (C150) are not otherwise linked with either middle row (C146) or outer row (C148) above deck (C124). Engagement protrusions (C130*a-f*) and interconnections (C160) are integrally formed together as a unitary piece with deck (C124).

FIG. 28 shows first and second continuous non-linear raised cross-sectional areas (C162, C164) forming first and second continuous non-linear paths. First continuous non-linear raised cross-sectional area (C162) extends from deck (C124) between adjacent engagement protrusions (C130*a*, C130*d*, C130*e*) joined by interconnections (C160) along an entire length (L) of inner row (C144) of cartridge pockets (C128). Second continuous non-linear raised cross-sectional area (C164) extends from deck (C124) between adjacent engagement protrusions (C130*a*, C130*d*, C130*c*) joined by interconnections (C160) along entire length (L) of inner row (C144) of cartridge pockets (C128). First and second continuous non-linear raised cross-sectional areas (C162, C164) are configured to provide increased stiffness to inner rows (C150) of engagement protrusions (C130*a-b*, C130*d-c*). First and second continuous non-linear raised cross-sectional areas (C162, C164) increase localized clamping pressure along each adjacent side elongate slot (C126). While first and second continuous non-linear raised cross-sectional areas (C162, C164) are shown as extending along entire length (L) of inner row (C144) of cartridge pockets (C128), first and/or second continuous non-linear raised cross-sectional areas (C162, C164) may extend along a select portion of inner row (C144) of cartridge pockets (C128) that is less than entire length (L) of inner row (C144).

Figure 30:
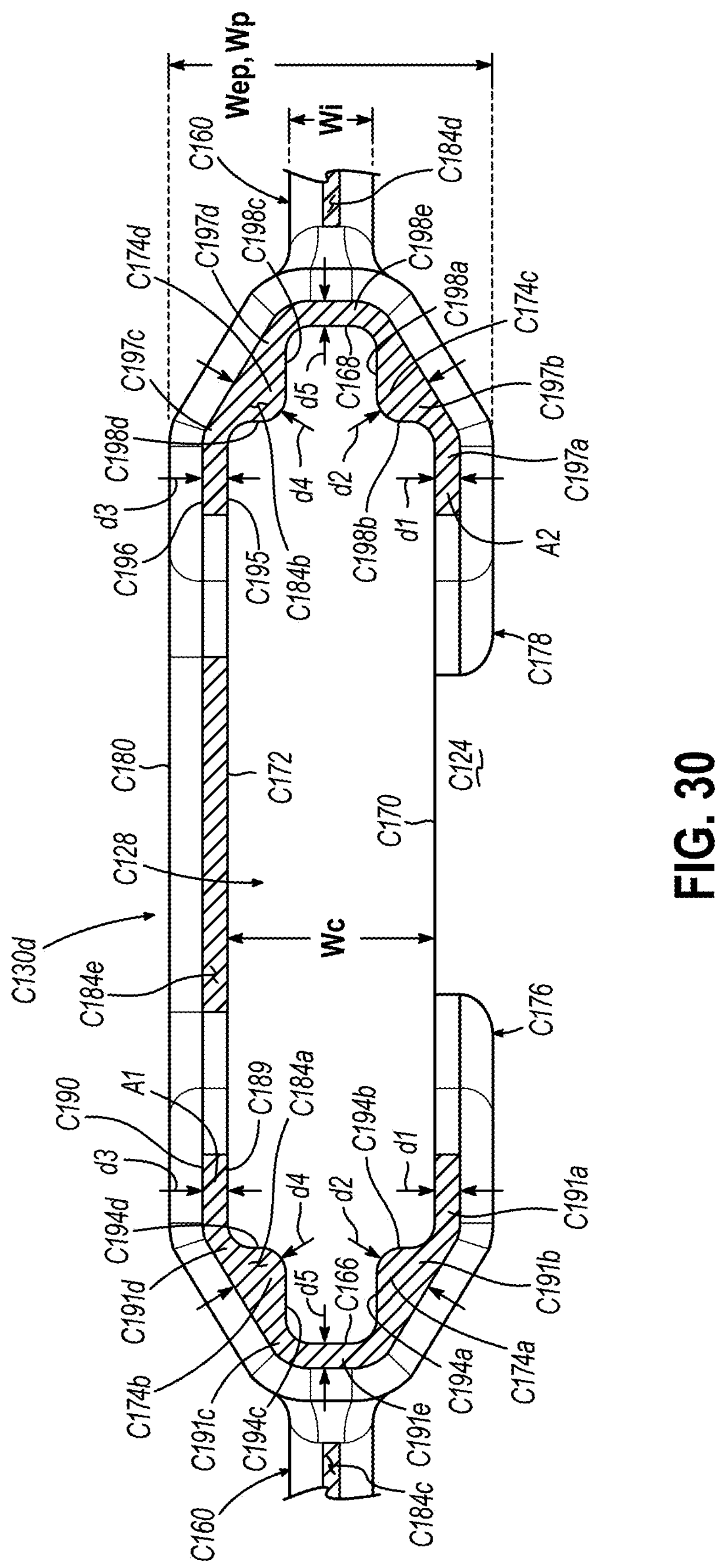
FIG. 30 depicts an enlarged top view of an engagement protrusion and accompanying interconnections partially surrounding a cartridge pocket of the cartridge body of FIG. 29.

FIG. 30 shows an enlarged top view of cartridge pocket (C128), engagement protrusion (C130*d*), and adjacent interconnections (C160) of inner rows (C150) of FIGS. 26 and 29. Engagement protrusion (C130*d*) is associated with cartridge pocket (C128). Cartridge pocket (C128) includes a first longitudinal end (C166), a second longitudinal end (C168), a first lateral side (C170), and a second lateral side (C172). Between first and second ends (C166, C168) and first and second lateral sides (C170, C172) are inwardly facing projections (C174*a-d*) of engagement protrusions (C130*a-f*). Second longitudinal end (C168) is disposed opposite first longitudinal end (C166). First and second ends (C166, C168) and inwardly facing projections (C174*a-d*) are configured to guide legs (C117) of staples (C116). First lateral side (C170) is disposed between first and second ends (C166, C168). Second lateral side (C172) is disposed between first and second ends (C166, C168) and opposite to first lateral side (C170). As shown, first and second lateral sides (C170, C172) of cartridge pocket (C128) extend substantially parallel to elongate slot (C126).

With continued reference to FIG. 30, engagement protrusion (C130*d*) includes a first end portion (C176), a second end portion (C178), and a lateral portion (C180). First end portion (C176) wraps around first longitudinal end (C166) of cartridge pocket (C128). Similarly, second end portion (C178) wraps around second longitudinal end (C168) of cartridge pocket (C128). Lateral portion (C180) extends longitudinally between first and second end portions (C176, C178) longitudinally along at least one of first or second lateral sides (C170, C172) of cartridge pocket (C128). For example, the lateral portion may extend longitudinally between first and second end portions (C176, C178) along first lateral side (C170), the lateral portion may extend longitudinally between first and second end portions (C176, C178) along second lateral side (C172), or the lateral portion may extend longitudinally between first and second end portions (C176, C178) along both of first and second lateral sides (C170, C172). As shown, lateral portion (C180) extends longitudinally along second lateral side (C172) of cartridge pocket (C128). Engagement protrusion (C130*d*) does not extend along first lateral side (C170) of cartridge pocket (C128) such that first lateral side (C170) opens directly to deck (C124). Lateral portion (C180) extends continuously between first and second end portions (C176, C178) of engagement protrusion (C130*d*). Interconnections (C160) extend continuously between second end portion (C178) of engagement protrusion (C130*d*) and a first end portion (C176) of an adjacent engagement protrusion (e.g., engagement protrusions (C130*a-b*, C130*e*)). Interconnections (C160) and lateral portion (C180) being adjacent to elongate slot (C126) provide additional compression near the cutline and assist in preventing movement of tissue (T) during firing.

As previously described, engagement protrusions (C130*a-f*) are associated with cartridge pockets (C128). First and second lateral sides (C170, C172) extend substantially parallel to elongate slot (C126). Engagement protrusions (C130*a-f*) at least partially surround respective cartridge pockets (C128). First end portion (C176) is tapered inwardly towards the first longitudinal end (C166) such that the first end portion (C176) is narrower at the first longitudinal end (C166) than at the first and second lateral sides (C170, C172) of the cartridge pocket (C128). More specifically, the portions of the first end portion (C176) that extend from the first and second lateral sides (C170, C172) towards the first longitudinal end (C166) provide a substantially frustoconical shape for the first end portion (C176) at the first longitudinal end (C166). First end portion (C176) includes a first inwardly facing projection (C174*a*), a second inwardly facing projection (C174*b*), and a first planar surface (C184*a*). First inwardly facing projection (C174*a*) extends inwardly between first longitudinal end (C166) and first lateral side (C170). First inwardly facing projection (C174*a*) extends toward second longitudinal end (C168) and second lateral side (C172) of cartridge pocket (C128). Second inwardly facing projection (C174*b*) extends inwardly between first longitudinal end (C166) and second lateral side (C172). Second inwardly facing projection (C174*b*) extends toward second longitudinal end (C168) and first lateral side (C170).

First planar surface (C184*a*) wraps around first longitudinal end (C166) of cartridge pocket (C128). First planar surface (C184*a*) defines a maximum height (hep) of engagement protrusion (C130*a-f*) relative to deck (C124). First planar surface (C184*a*) extends substantially parallel to deck (C124). First planar surface (C184*a*) is partially defined by first inwardly facing projection (C174*a*). First planar surface (C184*a*) has a non-uniform area (A1) (shown by shaded region) defined at least in part by first inwardly facing projection (C174*a*). As shown, first planar surface (C184*a*) has a non-uniform area (A1) due to first and second inwardly facing projections (C174*a-b*). First planar surface (C184*a*) includes an inner boundary (C189), an outer boundary (C190), a first portion (C191*a*), a second portion (C191*b*), a third portion (C191*c*), a fourth portion (C191*d*), and a fifth portion (C191*e*). Inner boundary (C189) defines the innermost portion of first planar surface (C184*a*). Outer boundary (C189) defines the outermost portion of first planar surface (C184*a*). Inner boundary (C189) is stepped relative to outer boundary (C190). Inner boundary (C189) includes first, second, third, and fourth inner walls (C194*a-d*). First inner wall (C194*a*) and third inner wall (C194*c*) extend parallel to first and second lateral sides (C170, C172). Second inner wall (C194*b*) partially defines first inwardly facing projection (C174*a*) together with first inner wall (C194*a*). As shown, second inner wall (C194*b*) extends perpendicular to first inner wall (C194*a*) and first lateral side (C170). Third inner wall (C194*c*) extends parallel to first and second lateral side (C170). Second inner wall (C194*b*) partially defines first inwardly facing projection (C174*a*) together with first inner wall (C194*a*). As shown, second inner wall (C194*b*) extends perpendicular to first inner wall (C194*a*) and first lateral side (C170).

First portion (C191*a*) defines a first distance (d1) between inner and outer boundaries (C189, C190) in a direction perpendicular to outer boundary (C190). Second portion (C191*b*) includes first inwardly facing projection (C174*a*). Second portion (C191*b*) defines a second distance (d2) between the inner and outer boundaries (C189, C190) in the direction perpendicular to the outer boundary (C190). Second distance (d2) is greater than first distance (d1). As shown, second distance (d2) is at least about double first distance (d1). Third portion (C191*c*) defines a third distance (d3) between inner and outer boundaries (C189, C190) in the direction perpendicular to outer boundary (C190). Fourth portion (C191*d*) defines a fourth distance (d4) between the inner and outer boundaries (C189, C190) in the direction perpendicular to the outer boundary (C190). Fourth portion (C191*d*) includes second inwardly facing projection (C174*b*). Fourth distance (d4) is greater than third distance (d3). Fifth portion (C191*e*) defines a first distance (d5) between inner and outer boundaries (C189, C190) in a direction perpendicular to outer boundary (C190). As shown, first distance (d1) is equal to third distance (d3) and fifth distance (d5). Similarly, fourth distance (d4) is equal to second distance (d2). First, third, and fifth portions (C191*a*, C191*c*, C191*e*) each define generally rectangular shapes. Second and fourth portions (C191*b*, C191*d*) each define generally triangular shapes. As shown, without the inclusion of first and second inwardly facing projection (C174*a-b*), area (A1) would be substantially uniform along first end portion (C176).

Second end portion (C178) is a mirror image of first end portion (C176). Second end portion (C178) is tapered inwardly towards the second longitudinal end (C168) such that the second end portion (C178) is narrower at the second longitudinal end (C168) than at the first and second lateral sides (C170, C172) of the cartridge pocket (C168). More specifically, the portions of the second end portion (C178) that extend from the first and second lateral sides (C170, C172) towards the second longitudinal end (C168) provide a substantially frustoconical shape for the second end portion (C178) at the second longitudinal end (C168) Second end portion (C178) includes a third inwardly facing projection (C174*c*), a fourth inwardly facing projection (C174*d*), and second planar surface (C184*b*). Third inwardly facing projection (C174*c*) is similar to first inwardly facing projection (C174*a*), and fourth inwardly facing projection (C174*d*) is similar to second inwardly facing projection (C174*b*). Third and fourth inwardly facing projections (C174*c-d*) extend away from second end portion (C178) inwardly toward first end portion (C176). Third inwardly facing projection (C174*c*) extends inwardly between second longitudinal end (C168) and first lateral side (C170). Third inwardly facing projection (C174*c*) extends toward first longitudinal end (C166) and second lateral side (C172) of cartridge pocket (C128). Fourth inwardly facing projection (C174*d*) extends inwardly between second longitudinal end (C168) and second lateral side (C172). Fourth inwardly facing projection (C174*d*) extends toward first longitudinal end (C166) and first lateral side (C170).

Second planar surface (C184*b*) wraps around second longitudinal end (C168) of cartridge pocket (C128). Second planar surface (C184*b*) defines a maximum height (hep) of engagement protrusion (C130*a-f*) relative to deck (C124). Second planar surface (C184*b*) extends substantially parallel to deck 124). Second planar surface (C184*b*) is partially defined by third inwardly facing projection (C174*c*). Second planar surface (C184*b*) has a non-uniform area (A2) defined at least in part by third inwardly facing projection (C174*c*). As shown, second planar surface (C184*b*) has a non-uniform area (A) due to third and fourth and second inwardly facing projections (C174*c-d*). Second planar surface (C184*b*) includes an inner boundary (C195), an outer boundary (C196), a first portion (C197*a*), a second portion (C197*b*), a third portion (C197*c*), a fourth portion (C197*d*), and a fifth portion (C197*e*). Inner boundary (C195) defines the innermost portion of second planar surface (C184*b*). Outer boundary (C195) defines the outermost portion of second planar surface (C184*b*). Inner boundary (C195) is stepped relative to outer boundary (C196). Inner boundary (C195) includes first and second inner walls (C198*a-b*). First inner wall (C198*a*) partially defines third inwardly facing projection (C174*c*). First inner wall (C198*a*) extends parallel to first lateral side (C170). Second inner wall (C198*b*) partially defines third inwardly facing projection (C174*c*) together with first inner wall (C198*a*). As shown, second inner wall (C198*b*) extends perpendicular to first inner wall (C198*a*) and first lateral side (C170).

Similar to first planar surface (C184*a*), first portion (C197*a*) of second planar surface (C184*b*) defines first distance (d1), second portion (C197*b*) defines second distance (d2), third portion (C197*c*) defines third distance (d3), fourth portion (C197*d*) defines fourth distance (d4), and fifth portion (C197*e*) defines a first distance (d5). First, second, third, fourth, and fifth distances (d1-d5) are measured between the inner and outer boundaries (C195, 196) in the direction perpendicular to the outer boundary (C196). Similar to second portion (C191*b*), second portion (C197*b*) includes third inwardly facing projection (C174*c*). Similar to fourth portion (C191*d*), fourth portion (C197*d*) includes fourth inwardly facing projection (C174*d*). First, third, and fifth portions (C197*a*, C197*c*, C197*e*) each define generally rectangular shapes. Second and fourth portions (C197*b*, C197*d*) each define generally triangular shapes. As shown, without the inclusion of third and fourth inwardly facing projections (C174*c-d*), area (A2) of second planar surface (C184*b*) would be substantially uniform.

Inwardly facing projections (C174*a-d*) increase the cross-sectional area of planar surfaces (C184*a-b*). Inwardly facing projections (C174*a-d*) increase the surface area configured contact tissue (T) and/or buttress (C188). For example, by increasing the cross-sectional area of planar surfaces (C184*a-b*), inwardly facing projections (C174*a-d*) may increase the adhesion of buttress (C188) (see FIGS. 33-34) to engagement protrusions (C130*a-f*) and/or prevent movement of tissue (T) during firing. Inwardly facing projections (C174*a-d*) increase the area (A1, A2) which may encourage release of buttress (C188) and/or tissue (T) from engagement protrusions (C130*a-f*) after contacting tissue (T).

The shaded surfaces of FIG. 30 depict planar surfaces (C184*a-e*) of engagement protrusion (C130*d*) and adjacent interconnections (C160). Planar surfaces (C184*a-e*) are substantially parallel to deck (C124). Planar surfaces (C184*a-b*) are generally U-shaped with an increased area due to inwardly facing projections (C174). Planar surface (C184*c*) is formed by interconnection (C160) and first end portion (C176). Planar surface (C184*d*) is formed by interconnection (C160) and second end portion (C178). Planar surface (C184*e*) is formed between second lateral side (C172) of cartridge pocket (C128) and lateral portion (C180) of engagement protrusion (C130*d*). Planar surfaces (C184*c-e*) are substantially rectangular.

With continued reference to FIG. 30, engagement protrusion (C130*d*) has a maximum width (Wep) in the direction transverse to longitudinal axis (LA). Interconnection (C160) has a maximum width (Wi) in the direction transverse to longitudinal axis (LA). Maximum width (Wp) of engagement protrusion (C130*d*) is greater than maximum width (Wi) of interconnection (C160). Cartridge pocket (C128) has a maximum width (Wc) defined by a distance between first and second lateral sides (C170, C172) of cartridge pocket (C128) in the direction transverse to longitudinal axis (LA). Maximum width (Wc) of cartridge pocket (C128) is greater than maximum width (Wi) of interconnection (C160). First and second end portions (C176, C178) have a maximum width (Wep) in the direction transverse to longitudinal axis (LA) that is greater than maximum width (Wi) of interconnection (C160).

Figure 31:
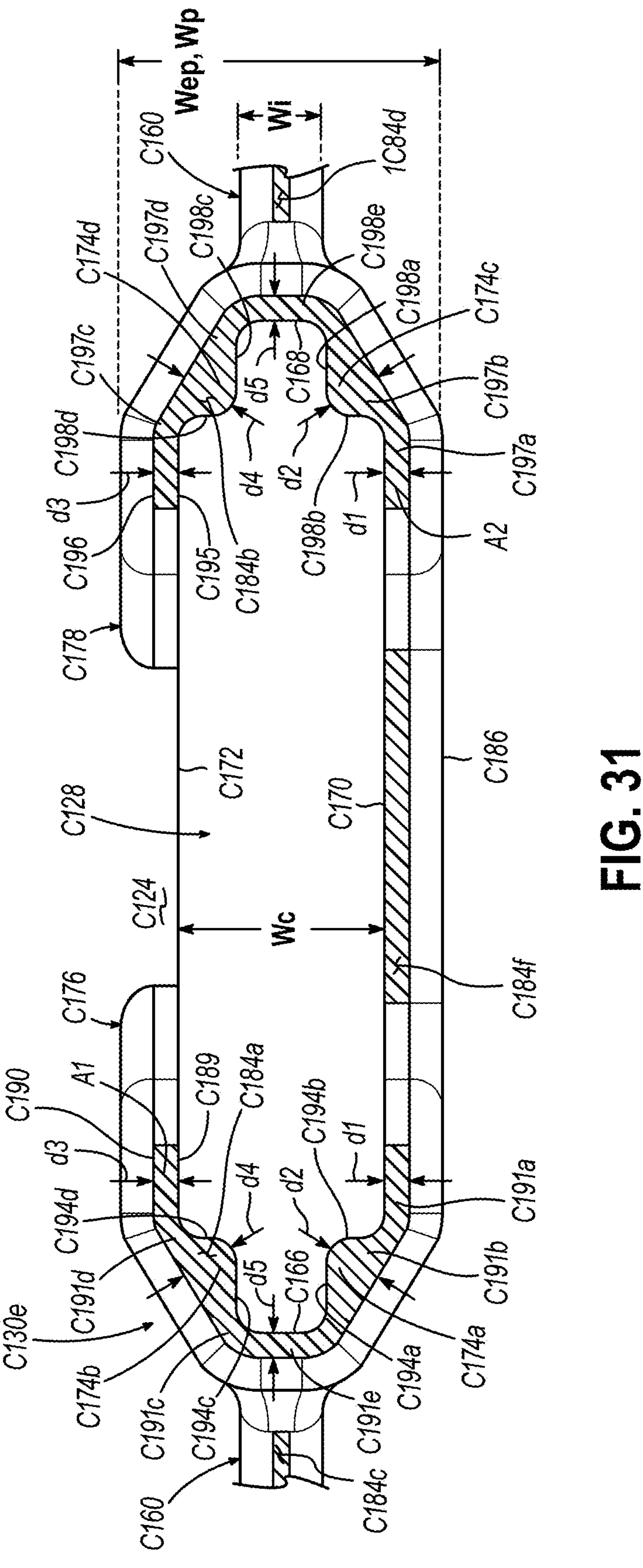
FIG. 31 depicts an enlarged top view of another engagement protrusion and accompanying interconnections partially surrounding a cartridge pocket of the cartridge body of FIG. 29.

FIG. 31 shows an enlarged top view of cartridge pocket (C128), engagement protrusion (C130*e*), and adjacent interconnections (C160) of inner rows (C150) of FIGS. 26 and 29. Engagement protrusion (C130*e*) is a mirror image of engagement protrusion (C130*d*). Similar to engagement protrusion (C130*d*) includes a first end portion (C176) and a second end portion (C178). Unlike engagement protrusion (C130*d*) where lateral portion (C180) extends longitudinally along second lateral side (C172), lateral portion (C186) extends longitudinally along first lateral side (C170) of cartridge pocket (C128). Engagement protrusion (C130*e*) does not extend along second lateral side (C172) of cartridge pocket (C128) such that second lateral side (C172) opens directly to deck (C124). Similar to lateral portion (C180), lateral portion (C186) extends continuously between first and second end portions (C176, C178) of engagement protrusion (C130*e*). Engagement protrusion (C130*e*) and adjacent interconnections (C160) includes planar surfaces (C184*a-d*). Engagement protrusion (C130*e*) includes planar surface (C184*f*) instead of planar surface (C184*e*). Planar surface (C184*f*) is formed between first lateral side (C170) of cartridge pocket (C128) and lateral portion (C186) of engagement protrusion (C130*e*). Planar surface (C184*f*) is substantially rectangular.

Figure 32:
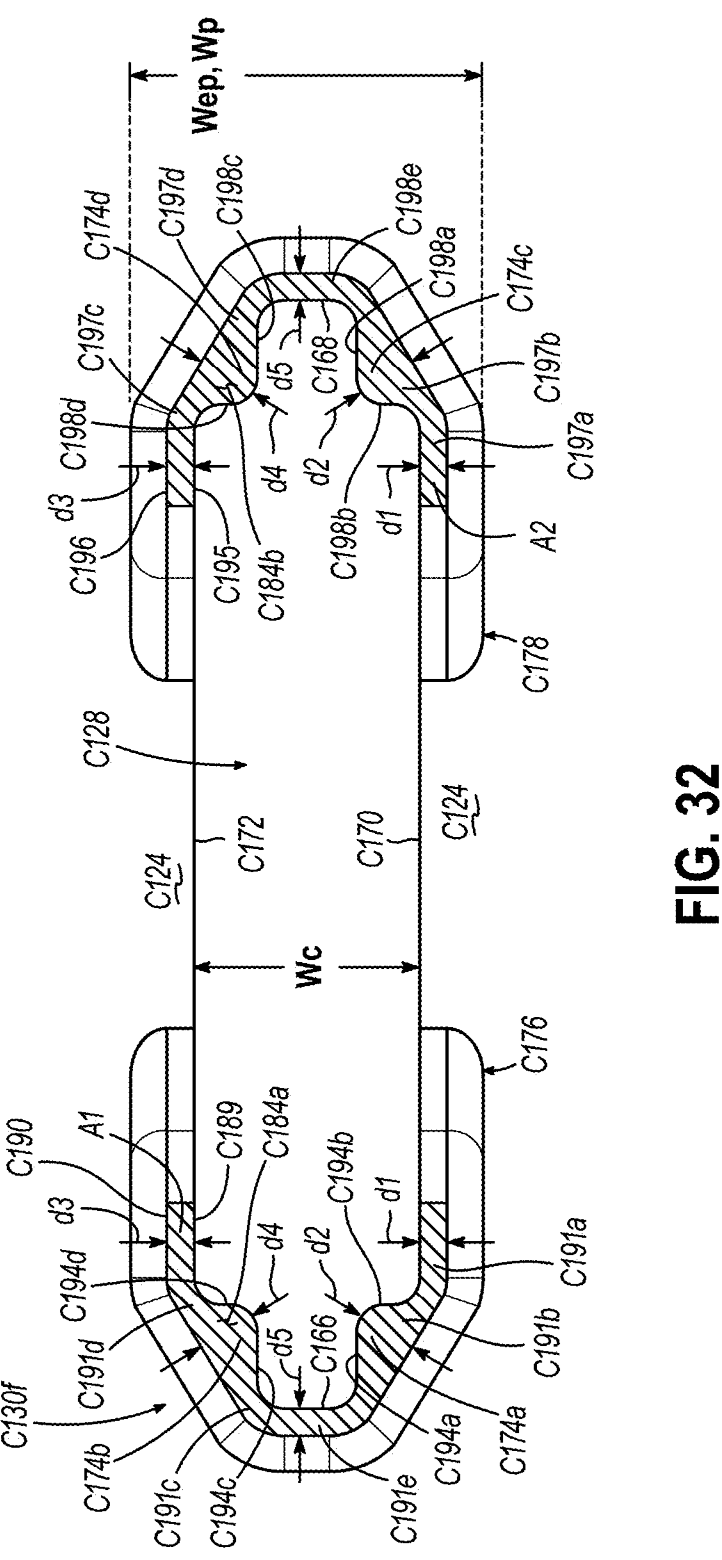
FIG. 32 depicts an enlarged top view of another engagement protrusion partially surrounding a cartridge pocket of the cartridge body of FIG. 29.

FIG. 32 shows an enlarged top view of cartridge pocket (C128) and engagement protrusion (C130*f*) of middle and outer rows (C152, C154) of FIG. 29. Similar to engagement protrusions (C130*d-e*), engagement protrusion (C130*f*) includes a first end portion (C176) and a second end portion (C178). Unlike engagement protrusions (C130*d-e*), engagement protrusion (C130*f*) does not include a lateral portion (e.g., lateral portions (C180, C186)). Instead, both first and second lateral sides (C170, C172) of cartridge pocket (C128) open directly to deck (C124). First and second end portions (C176) are not linked together above deck (C124). Additionally, engagement protrusion (C130*f*) is not linked with another engagement protrusion (C130*a-f*) using interconnections (C160).

Similar to engagement protrusion (C130*d*), first end portion (C176) of engagement protrusions (C130*d*, C130*f*) of FIGS. 31 and 32 includes first inwardly facing projection (C174*a*), second inwardly facing projection (C174*b*), and first planar surface (C184*a*). Similar to engagement protrusion (C130*d*), second end portion (C178) of engagement protrusions (C130*d*, C130*f*) includes third inwardly facing projection (C174*c*), fourth inwardly facing projection (C174*d*), and second planar surface (C184*d*). First planar surface (C184*a*) includes inner boundary (C189), outer boundary (C190), first portion (C191*a*), second portion (C191*b*), third portion (C191*c*), fourth portion (C191*d*), and fifth portion (C191*e*). Second planar surface (C184*b*) includes inner boundary (C195), outer boundary (C196), first portion (C197*a*), second portion (C197*b*), third portion (C197*c*), fourth portion (C197*d*), and fifth portion (C197*e*). These features are shown and described above with reference to FIG. 30. While FIGS. 30-32 show engagement protrusions (C130*d-f*), certain aspects also apply to engagement protrusions (C130*a-c*) shown and described above with reference to FIGS. 26 and 29. For example, engagement protrusions (C130*a-c*) each include a second end portion similar to second end portion (C178). Engagement protrusions (C130*a-c*) respectively include planar surfaces (C158*a-c*) instead of first planar surface (C184*a*). Planar surfaces (C158*a-c*) include inwardly facing projections similar to first and second inwardly facing projections (C174*a-b*).

Figures 33, 34:
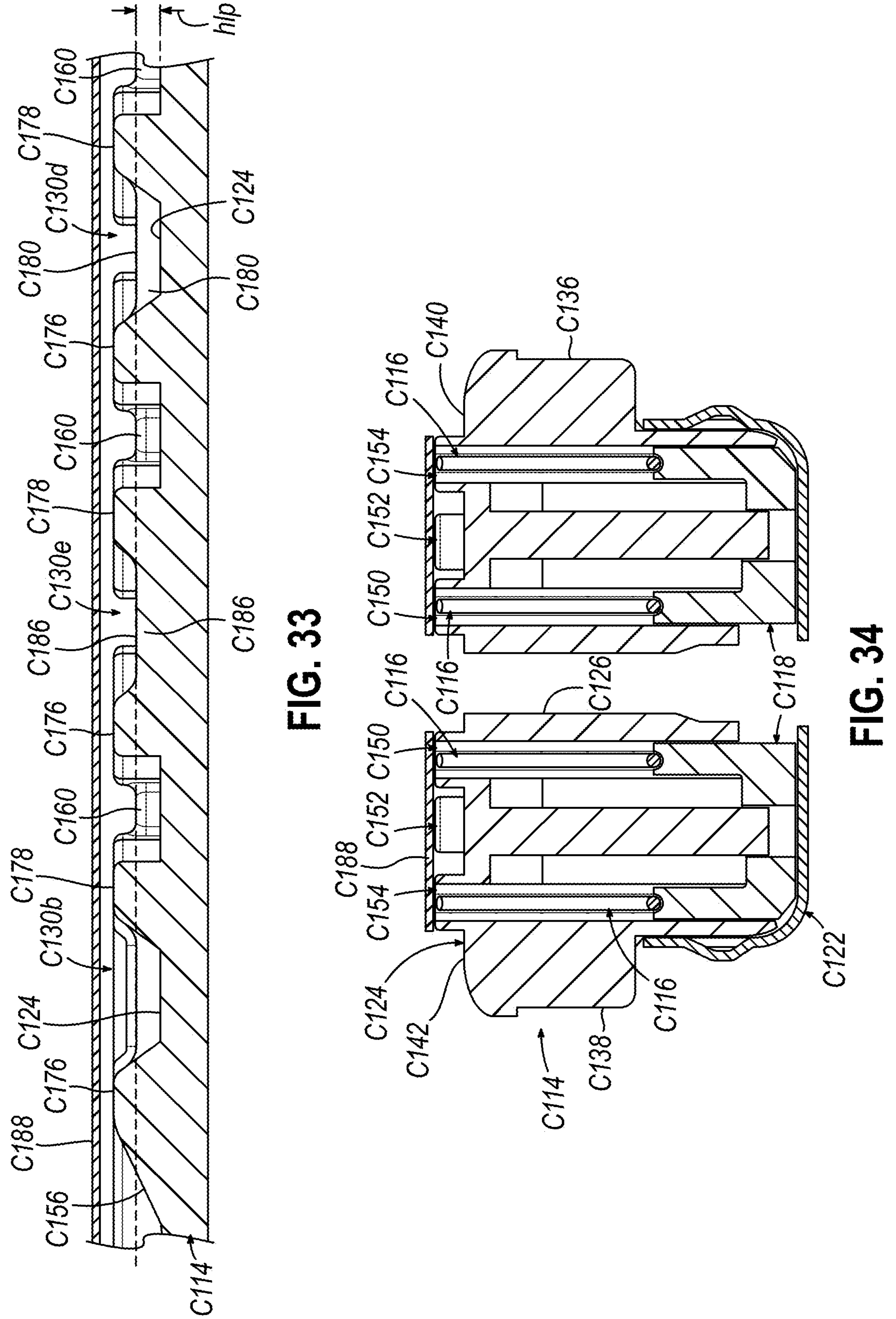
FIG. 33 depicts a partial sectional view of the cartridge body of FIG. 29 taken along line 33-33 of FIG. 29 prior to adhesion of a buttress onto the engagement protrusions of the cartridge body of FIG. 29.
FIG. 34 depicts a partial sectional view of the staple cartridge of FIG. 24 after adhesion of the buttress of FIG. 33 onto the engagement protrusions.

FIG. 33 shows a partial sectional view of cartridge body (C114) of FIG. 29 taken along line 33-33 prior to adhesion of a buttress (C188) onto engagement protrusions (C130*a-f*) of FIG. 29. As shown, lateral portions (C180, C186) connect first and second end portions (C176, C178). Lateral portions (C180, C186) alternate between adjacent cartridge pockets (C128) along an entire length of inner row (C144). Considering first row (C150) on second deck side (C140), lateral portions (C180, C186) alternate from first lateral side (C170) (e.g., side adjacent to elongate slot (C126)) to second lateral side (C172) (e.g., side opposite to elongate slot (C126)) moving proximally along elongate slot (C126). Alternating lateral portions (C180, C186) on inner row (C144) of cartridge pockets (C128) may influence tissue retainment during clamping and firing.

FIG. 34 shows a partial sectional view of staple cartridge (C110) of FIG. 24 after adhesion of buttress (C188) onto engagement protrusions (C130*a-f*). In some instances, it may be desirable to equip end effector (40) of surgical stapler (10) with an adjunct material, such as a buttress, to reinforce the mechanical fastening of tissue (T) provided by staples (86). In addition to or as an alternative to providing structural support and integrity to a line of staples (86), a buttress (C188) may provide various other kinds of effects such as spacing or gap-filling, administration of therapeutic agents, and/or other effects. In some instances, a buttress may be provided on engagement protrusions (C130*d-e*). As described above, deck (C124) houses staples (C116), which are driven by staple driver (C118). In some other instances, buttress (C188) may be provided on the surface of an anvil (e.g., anvil (44)) that faces staple cartridge (C110). It should also be understood that a first buttress (C188) may be provided on deck (C124) and a second buttress (not shown) but similar to buttress (C188) is provided on anvil (44) of the same end effector. Illustrative buttress assemblies, illustrative materials and techniques for applying buttress assemblies, and illustrative buttress applier cartridges may be configured in accordance with at least some of the teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and/or U.S. Pat. No. 11,166,724, entitled "Adhesive Distribution on Buttress for Surgical Stapler," issued Nov. 9, 2021, the disclosures of which are incorporated by reference herein. Increased contact area of planar surfaces (C158*a-c*, C184*a-f*) may affect adhesion of buttress (C188) to engagement protrusions (C130*a-f*). While planar surfaces (C158*a-c*, C184*a-f*) were the upper most surfaces configured to contact buttress (C188), it is also envisioned that lateral portions (C180, C186) and/or protrusions (C160) may contact buttress (C188).

Figure 35:
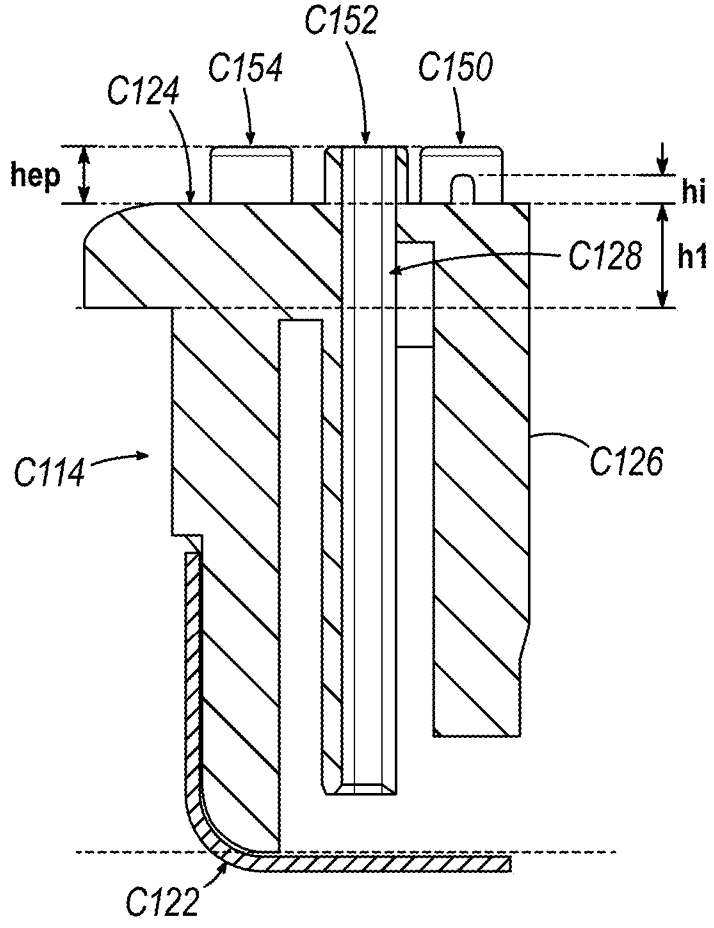
FIG. 35 depicts a partial sectional view of the cartridge body of FIG. 25 taken along a different portion of the cartridge body than FIG. 34.

FIG. 35 shows a partial sectional view of cartridge body (C114) taken along a different portion than FIG. 34. As shown, each engagement protrusion (C130*a-f*) has the same height (e.g., extends away from deck (C124) the same distance). Particularly, first and second end portions (C176, C178) of engagement protrusions (C130*a-f*) extend from deck (C124) a maximum height (hep). As shown, maximum height (hep) is about 0.020 inches (0.508 millimeters). Increasing maximum height (hep) accommodates thicker tissue (T). While first and second end portions (C176, C178) are shown as extending from deck (C124) the same maximum height (hep), first end portion (C176) may extend from deck (C124) a greater or lesser amount than second end portion (C178). Lateral portions (C180, C186) of engagement protrusions (C130*d-e*) extend from deck (C124) a maximum height (hlp) (see FIG. 33). Interconnection (C160) extends from deck (C124) a maximum height (hi). As shown, maximum height (hep) of first and second end portions (C176, C178) is greater than maximum height (hi) of interconnection. In other words, maximum height (hi) of interconnections (C160) and maximum height of (hlp) of lateral portions (C180, C186) are each less than maximum height (hep) of first and second end portions (C176, C178). For example, maximum height (hi) of interconnections (C160) and maximum height of (hlp) of lateral portions (C180, C186) may be each about half of maximum height (hep) of first and second end portions (C176, C178). Deck (C124) is planar between engagement protrusions (C130*a-c*) to proximal end (C132) of cartridge body (C114). Height (h1) is about 0.037 inches (0.9398 millimeters).

B. Second Example of a Cartridge Body

Figure 36:
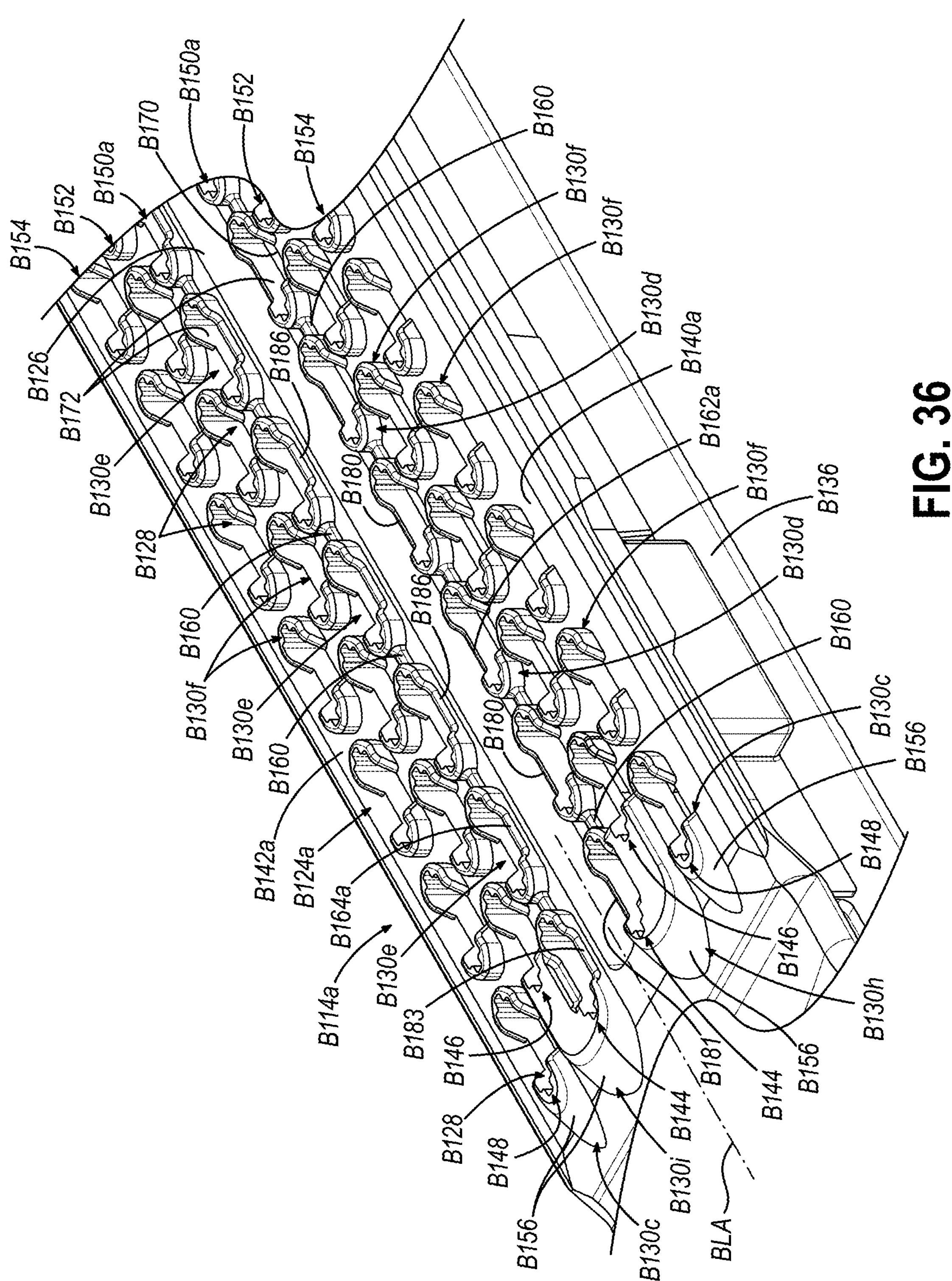
FIG. 36 depicts a partial perspective view of another example of a cartridge body configured to be incorporated into the staple cartridge of FIG. 24 and the end effector of FIG. 2.

FIG. 36 shows a partial perspective view of another example of a cartridge body (B114*a*) configured to be incorporated into staple cartridge (C110) of FIG. 24 for use with end effector (40) of FIG. 2. Similar to cartridge body (C114), cartridge body (B114*a*) includes a deck (B124*a*), elongate slot (B126) formed in deck (B124*a*), cartridge pockets (B128) formed in deck (B124*a*), and engagement protrusions (B130*c-f*, B130*h-i*) extending outwardly from deck (B124*a*). Similar to cartridge body (C114), cartridge body (B114*a*) include inner rows (B144), middle rows (B146), and outer rows (B148) of cartridge pockets (B128). Similar to cartridge body (C114), cartridge body (B114*a*) includes engagement protrusions (B130*c-f*, B130*h-i*) extending from deck (B124*a*) that are configured to grip tissue or an adjunct material (e.g., a buttress) positioned thereon. Second deck side (B142*a*) is a mirror image of first deck side (B140*a*). Longitudinal rows of engagement protrusions include inner rows (B150*a*), middle rows (B152), and outer rows (B154) and generally correspond to inner rows (B144), middle rows (B146), and outer rows (B148) of cartridge pockets (B128).

Engagement protrusions (B130*c*, B130*h-i*) are the distal most engagement protrusions. Engagement protrusion (B130*h*) is similar to engagement protrusions (C130*a*), except that engagement protrusion (B130*h*) includes a lateral portion (B181) instead of opening onto deck (B124*a*). Engagement protrusion (B130*i*) is similar to engagement protrusions (C130*a*), except that engagement protrusion (B130*h*) includes a lateral portion (B183) instead of opening onto deck (B124*a*). Engagement protrusions (B130*h-i*) each completely surround a cartridge pocket (B128). Engagement protrusion (B130*c-f*) each partially surround a cartridge pocket (B128). Longitudinally adjacent engagement protrusions (B130*d-e*) of inner rows (B150*a*) on first and second deck sides (B140*a*, B142*a*) are linked together by interconnections (B160). Moving proximally, inner row (B150*a*) on first deck side (B140*a*) includes engagement protrusion (B130*a*) then alternates between interconnection (B160) and engagement protrusion (B130*d*). This is different from inner row (C150) on first deck side (C140) of FIGS. 26 and 29 that repeats the sequence of engagement protrusion (C130*d*), interconnection (C160), engagement protrusion (C130*e*), and interconnection (C160). Moving proximally, inner row (B150*a*) on second deck side (B142*a*) includes engagement protrusion (B130*b*) and then alternates between interconnection (B160) and engagement protrusion (B130*c*). This is different from inner row (C150) on second deck side (C142*a*) of FIGS. 26 and 29 that repeats the sequence of engagement protrusion (C130*e*), interconnection (C160), engagement protrusion (C130*d*), and interconnection (C160).

As shown in FIG. 36, lateral portions (B180, B186) of engagement protrusions (B130*d-e*) are adjacent to elongate slot (B126) to provide additional compression near the cutline. As shown, lateral portion (B180) of engagement protrusion (B130*d*) extends longitudinally along second lateral side (B172) of cartridge pocket (B128) continuously between first and second end portions (B176, B178). Engagement protrusion (B130*d*) does not extend along first lateral side (B170) of cartridge pocket (B128) such that first lateral side (B170) opens directly to deck (B124*a*). Lateral portion (B186) extends longitudinally along first lateral side (B170) of cartridge pocket (B128) continuously between first and second end portions (B176, B178). Engagement protrusion (B130*e*) does not extend along first lateral side (B170) of cartridge pocket (B128) such that first lateral side (B170) opens directly to deck (B124*a*).

FIG. 36 shows first and second continuous non-linear raised cross-sectional areas (B162*a*, B164*a*) forming first and second continuous non-linear paths. First continuous non-linear raised cross-sectional area (B162*a*) extends from deck (B124*a*) between longitudinally adjacent engagement protrusions (B130*a*, B130*d*) joined by interconnections (B160) along inner row (B144) of cartridge pockets (B128) on first deck side (B140*a*). Second continuous non-linear raised cross-sectional area (B164*a*) extends from deck (B124*a*) between adjacent engagement protrusions (B130*a*, B130*e*) joined by interconnections (B160) along the entire length of inner row (B144) of cartridge pockets (B128) on second deck side (B142*a*). To form first and second continuous non-linear raised cross-sectional areas (B162*a*, B164*a*), lateral portions (B180, B186) do not alternate and are adjacent to elongate slot (B126). First and second continuous non-linear raised cross-sectional areas (B162*a*, B164*a*) extend along the entire length (not shown) of first and second deck sides (B140*a*, B142*a*), but similar to length (L) of FIG. 28.

C. Third Example of a Cartridge Body

Figure 37:
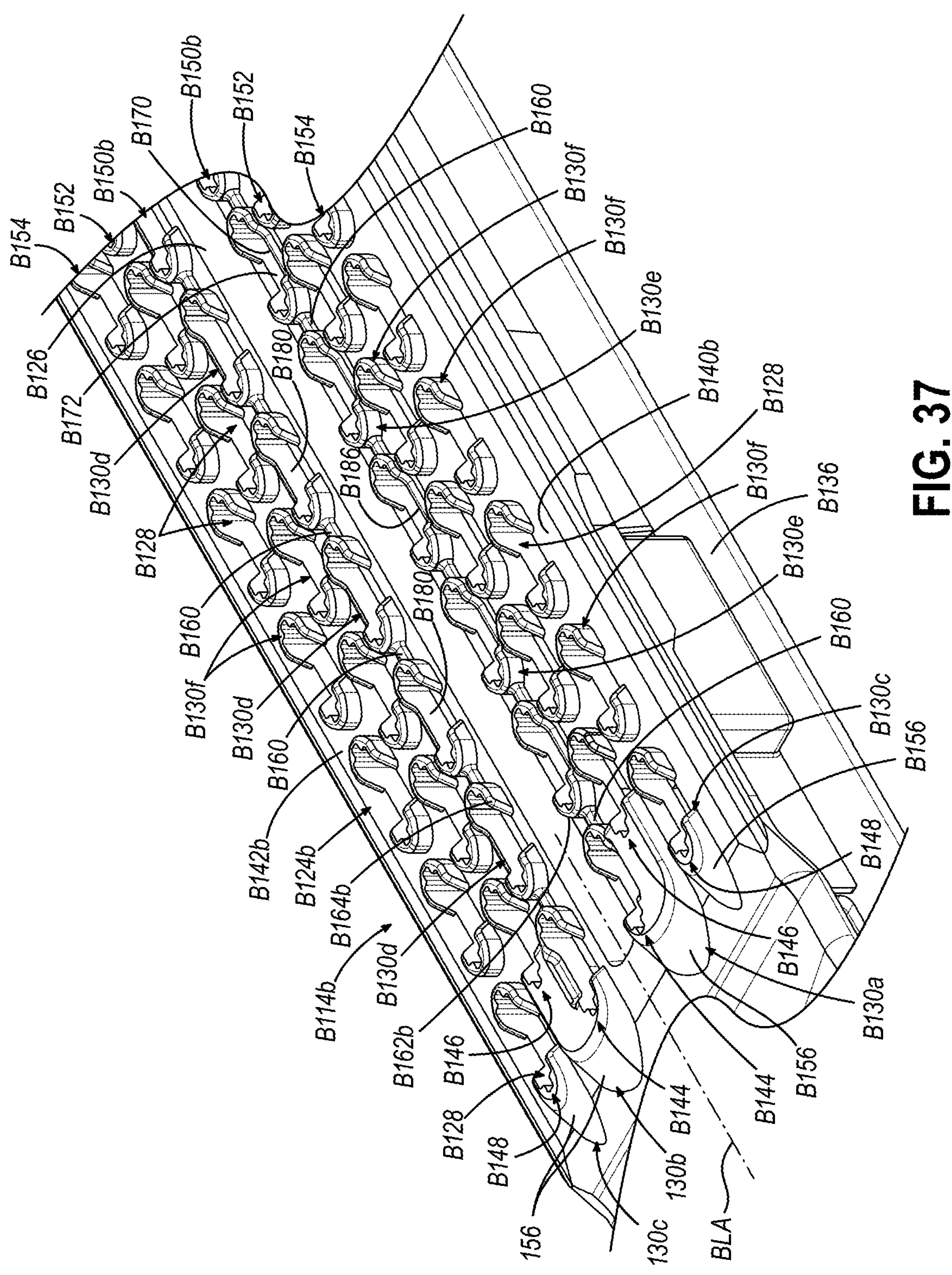
FIG. 37 depicts a partial perspective view of another example of a cartridge body configured to be incorporated into the staple cartridge of FIG. 24 and the end effector of FIG. 2.

FIG. 37 shows a partial perspective view of another example of a cartridge body (B114*b*) configured to be incorporated into staple cartridge (C110) of FIG. 24 for use with end effector (40) of FIG. 2. Similar to cartridge body (C114), cartridge body (B114*b*) includes a deck (B124*b*), an elongate slot (B126) formed in deck (B124*b*), a plurality of cartridge pockets (B128) formed in deck (B124*b*), and a plurality of engagement protrusions (B130*a-f*) extending outwardly from deck (B124*b*). Each cartridge pocket (B128) is configured to slidably house an unformed staple such as staple (B116) and a respective staple driver such as staple driver (B118). Similar to cartridge body (C114), cartridge body (B114*b*) include inner rows (B144), middle rows (B146), and outer rows (B148) of cartridge pockets (B128). Similar to cartridge body (C114), cartridge body (B114*b*) includes engagement protrusions (B130*a-f*) extending from deck (B124*b*) that are configured to grip tissue or an adjunct material (e.g., a buttress) positioned thereon. Each engagement protrusion (B130*a-f*) partially surrounds a respective cartridge pocket (B128). The arrangement of these engagement protrusions (B130*a-f*) is symmetric about elongate slot (B126). Second deck side (B140) of cartridge body (C114) is a mirror image of first deck side (B140) of cartridge body (C114). Longitudinal rows of engagement protrusions include inner rows (B150*b*), middle rows (B152), and outer rows (B154) and generally correspond to inner rows (B144), middle rows (B146), and outer rows (B148), respectively.

Similar to cartridge body (C114), engagement protrusions (B130*a-c*) are the distal most engagement protrusions. Longitudinally adjacent engagement protrusions (B130*d-f*) of inner rows (B150) on first and second deck sides (B140, B142) are linked together by interconnections (B160). Moving proximally, inner row (B150*b*) on first deck side (B140*b*) includes engagement protrusion (B130*a*) then alternates between interconnection (B160) and engagement protrusion (B130*e*). This is different from inner row (C150) on first deck side (C140*b*) of FIGS. 26 and 29 that repeats the sequences of engagement protrusion (C130*e*), interconnection (C160), engagement protrusion (C130*c*), and interconnection (C160). Moving proximally, inner row (B150*b*) on second deck side (B142*b*) includes engagement protrusion (B130*b*) and then alternates between interconnection (B160) and engagement protrusion (B130*d*). This is different from inner row (C150) on second deck side (C142) of FIGS. 26 and 29 that alternates between engagement protrusion (C130*e*), interconnection (C160), engagement protrusion (C130*d*), and interconnection (C160).

As shown in FIG. 37, lateral portions (B180, B186) are disposed opposite to elongate slot (B126). On first deck side (B140*b*), lateral portion (B186) of engagement protrusion (B130*e*) extends longitudinally along first lateral side (B170) of cartridge pocket (B128). Engagement protrusion (B130*e*) does not extend along second lateral side (B172) of cartridge pocket (B128) such that second lateral side (B172) opens directly to deck (B124*b*) adjacent elongate slot (B126). Lateral portion (B186) extends continuously between first and second end portions (B176, B178) of engagement protrusion (B130*e*). On second deck side (B142*b*), lateral portion (B180) of engagement protrusion (B130*d*) extends longitudinally along second lateral side (B172) of cartridge pocket (B128). Engagement protrusion (B130*d*) does not extend along first lateral side (B170) of cartridge pocket (B128) such that first lateral side (B170) opens directly to deck (B124*b*) adjacent elongate slot (B126). Lateral portion (B180) extends continuously between first and second end portions (B176, B178) of engagement protrusion (B130*d*). As shown in FIG. 37, lateral portions (B180, B186) do not alternate and are on the side opposite to elongate slot (B126).

FIG. 37 shows first and second continuous non-linear raised cross-sectional areas (B162*b*, B164*b*) forming first and second continuous non-linear paths. First continuous non-linear raised cross-sectional area (B162*b*) extends from deck (B124*b*) between adjacent engagement protrusions (B130*a*, B130*e*) joined by interconnections (B160) along inner row (B144) of cartridge pockets (B128) on first deck side (B140*b*). Second continuous non-linear raised cross-sectional area (B164*a*) extends from deck (B124) between adjacent engagement protrusions (B130*b*,130*d*) joined by interconnections (B160) along inner row (B144) of cartridge pockets (B128) on second deck side (B142*b*). First and second continuous non-linear raised cross-sectional areas (B162*b*, B164*b*) extend along the entire length (not shown) of first and second deck sides (B140*b*, B142*b*), but similar to length (L) of FIG. 28.

D. Fourth Example of a Cartridge Body

Figure 38:
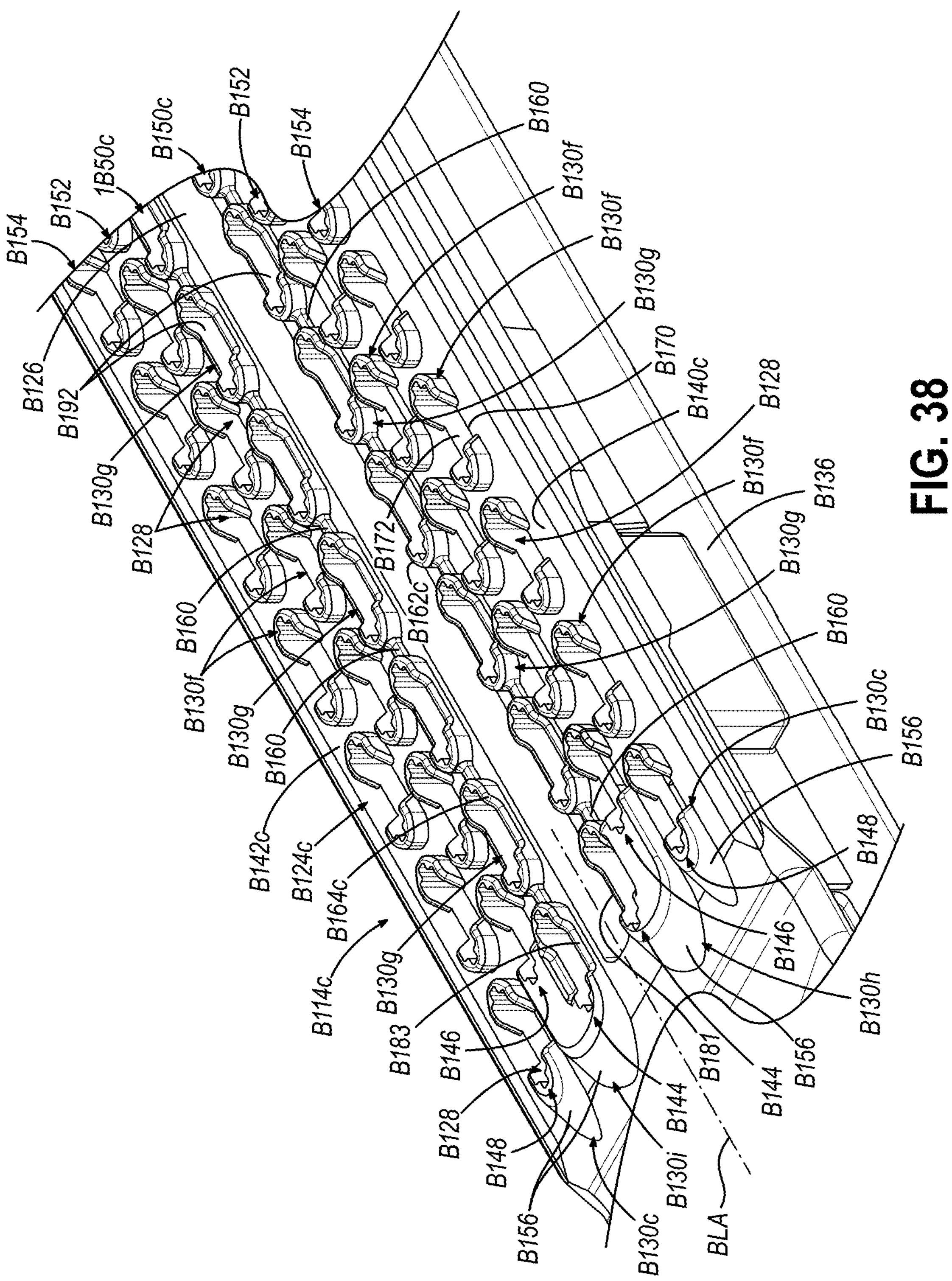
FIG. 38 depicts a partial perspective view of another example of a cartridge body configured to be incorporated into the staple cartridge of FIG. 24 and the end effector of FIG. 2.

FIG. 38 shows a partial perspective view of another example of a cartridge body (B114*c*) configured to be incorporated into staple cartridge (C110) of FIG. 24 for use with end effector (40) of FIG. 2. Similar to cartridge body (C114), cartridge body (B114*c*) includes a deck (B124*c*), an elongate slot (B126) formed in deck (B124*c*), a plurality of cartridge pockets (B128) formed in deck (B124*c*), and a plurality of engagement protrusions (B130*c*, B130*f-i*) extending outwardly from deck (B124*c*). Each cartridge pocket (B128) is configured to slidably house an unformed staple similar to staple (C116) and a respective staple driver similar to staple driver (C118). Similar to cartridge body (C114), cartridge body (B114*c*) includes inner rows (B144), middle rows (B146), and outer rows (B148) of cartridge pockets (B128). Engagement protrusions (B130*c*, B130*f-i*) extend from deck (B124*c*) and are configured to grip tissue or an adjunct material (e.g., a buttress) positioned thereon. The arrangement of these engagement protrusions (B130*c*, B130*f-i*) is symmetric about elongate slot (B126). Second deck side (B140) of cartridge body (C114) is a mirror image of first deck side (B140) of cartridge body (C114). Longitudinal rows of engagement protrusions include inner rows (B150*c*), middle rows (B152), and outer rows (B154) and generally correspond to inner rows (B144), middle rows (B146), and outer rows (B148), respectively.

Similar to cartridge body (B114*a*), engagement protrusions (B130*c*, B130*h-i*) are the distal most engagement protrusions. Longitudinally adjacent engagement protrusions (B130*g-i*) of inner rows (B150) on first and second deck sides (B140*c*, B142*c*) are linked together by interconnections (B160). Moving proximally, inner row (B150*c*) on first deck side (B140*c*) includes engagement protrusion (B130*h*) then alternates between interconnection (B160) and engagement protrusion (B130*g*). Moving proximally, inner row (B150*c*) on second deck side (B142*c*) includes engagement protrusion (B130*i*) and then alternates between interconnection (B160) and engagement protrusion (B130*g*).

FIG. 38 shows first and second continuous non-linear raised cross-sectional areas (B162*c*, B164*c*) forming first and second continuous non-linear paths. First continuous non-linear raised cross-sectional area (B162*c*) extends from deck (B124*c*) between adjacent engagement protrusions (B130*g-h*) joined by interconnections (B160) along inner row (B144) of cartridge pockets (B128) on first deck side (B140*c*). Second continuous non-linear raised cross-sectional area (B164*c*) extends from deck (B124*c*) between adjacent engagement protrusions (B130*g*, B130*i*) joined by interconnections (B160) along inner row (B144) of cartridge pockets (B128) on second deck side (B142*c*). Each engagement protrusion (B130*g-i*) of inner row (B150*c*) surrounds a respective cartridge pocket (B128) of inner rows (B144) of cartridge pockets (B128). First and second continuous non-linear raised cross-sectional areas (B162*c*, B164*c*) increase the localized pressure in the area adjacent to elongate slot (B126). First and second continuous non-linear raised cross-sectional areas (B162*c*, B164*c*) extend along the entire length (not shown) of first and second deck sides (B140*c*, B142*c*), but similar to length (L) of FIG. 28.

Figure 39:
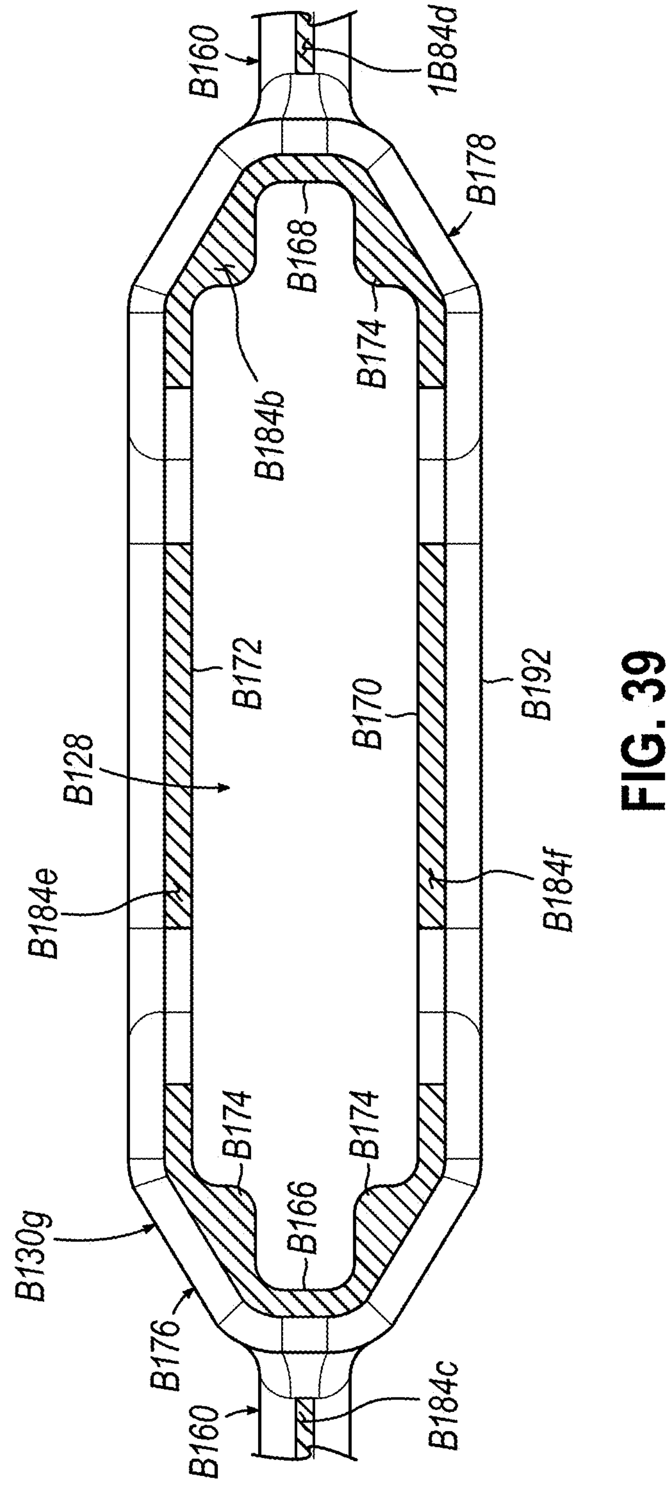
FIG. 39 depicts an enlarged top view of another engagement protrusion and accompanying interconnections completely surrounding a cartridge pocket of FIG. 38.

FIG. 39 shows an enlarged top view of cartridge pocket (B128), engagement protrusion (B130*g*), and adjacent interconnections (B160). Similar to engagement protrusions (C130*d-e*), engagement protrusion (B130*g*) includes a first end portion (B176) and a second end portion (B178). Unlike engagement protrusion (B130*d-e*), engagement protrusion (B130*g*) includes lateral portion (B192). Lateral portion (B192) extends longitudinally along both first lateral side (B170) and second lateral side (B172) of cartridge pocket (B128). In other words, first end portion (B176), second end portion (B178), and lateral portion (B192) collectively surround cartridge pocket (B128). Engagement protrusion (B130*g*) includes planar surfaces (B184*e-f*) that are substantially rectangular. As shown, lateral portion (B192) is both adjacent to and opposite to elongate slot (B126) to provide additional compression near the cutline.

E. Fifth Example of a Cartridge Body

Figure 40:
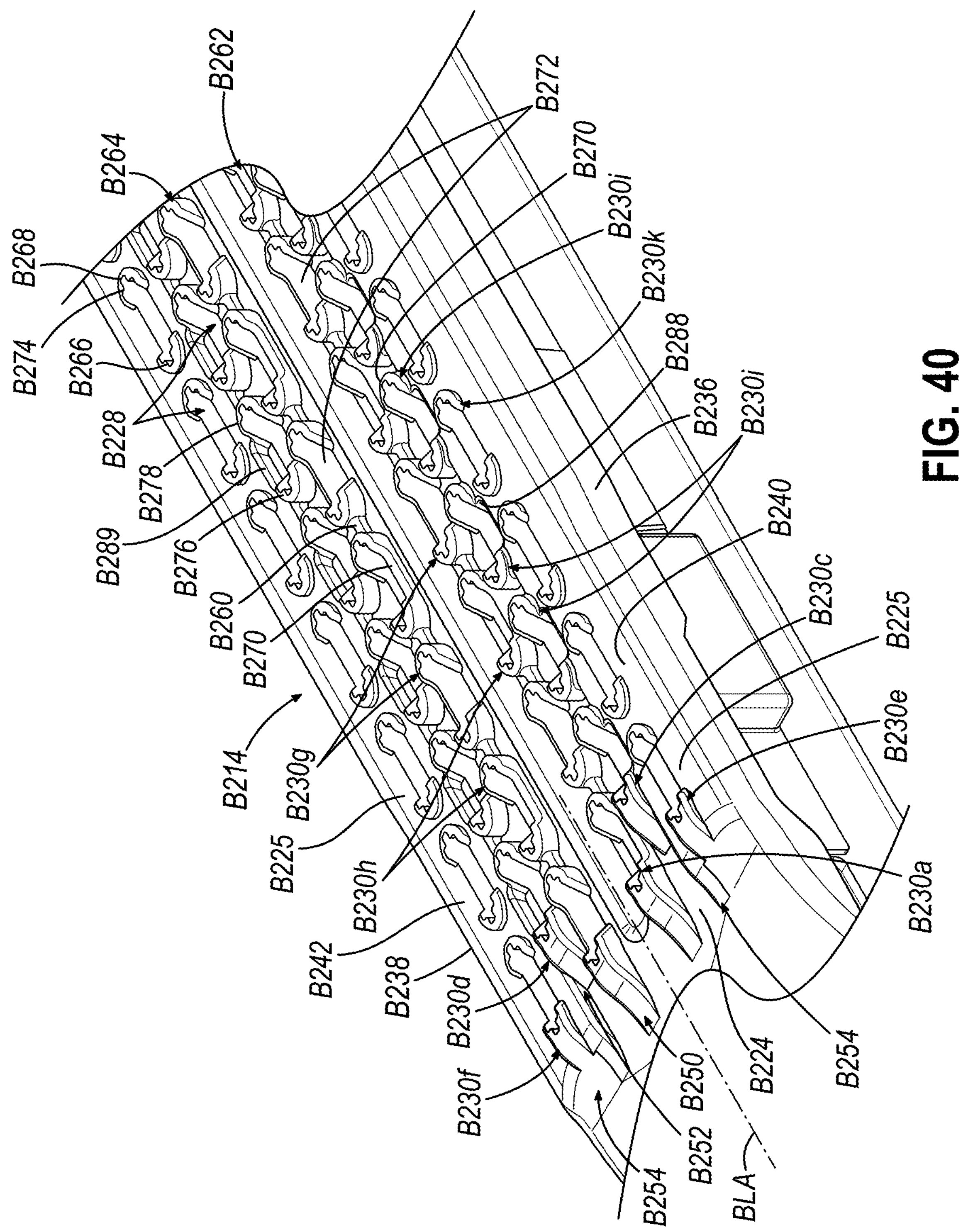
FIG. 40 depicts a partial perspective view of another example of a cartridge body configured to be incorporated into the staple cartridge of FIG. 24 and the end effector of FIG. 2.
Figure 41:
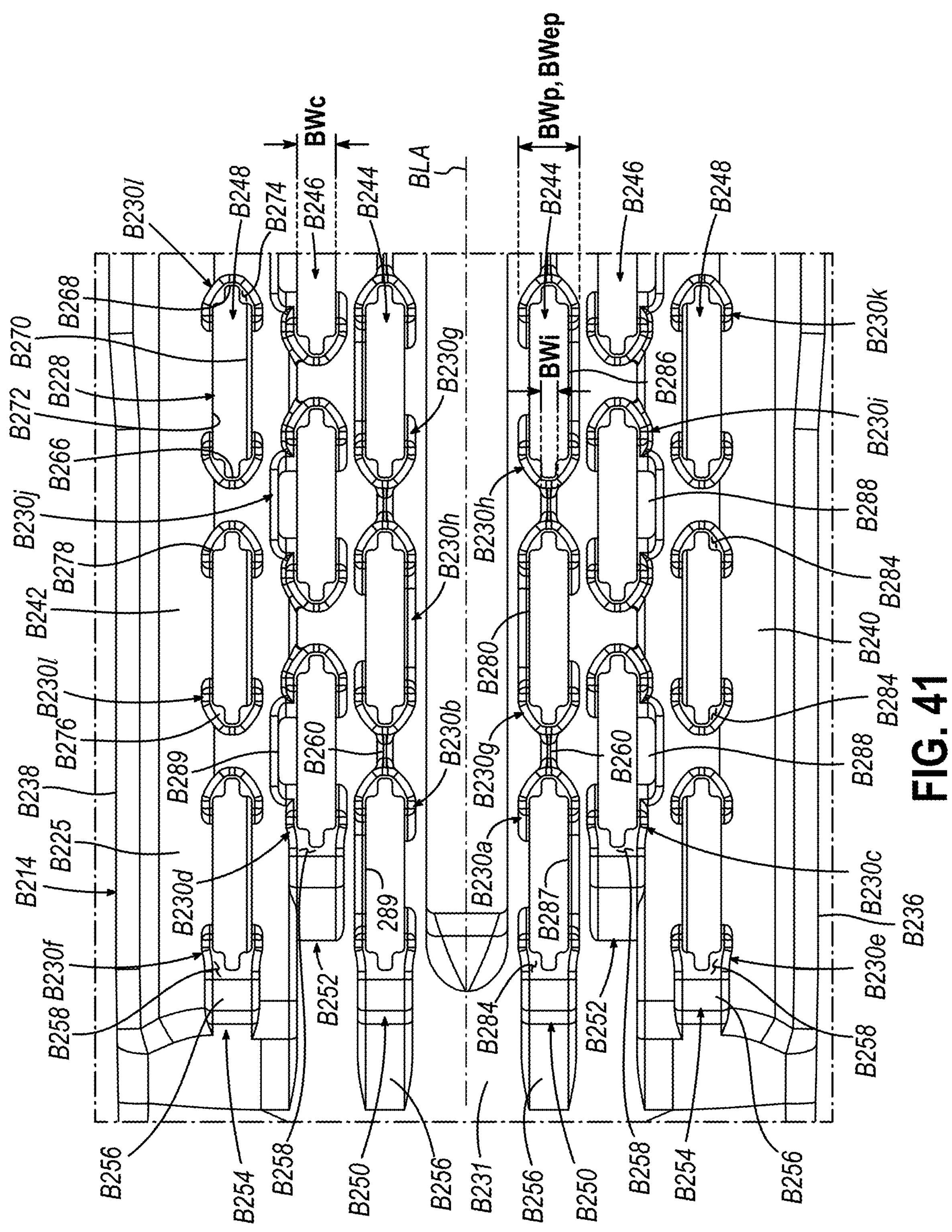
FIG. 41 depicts a partial top plan view of the cartridge body of FIG. 40.
Figure 42:
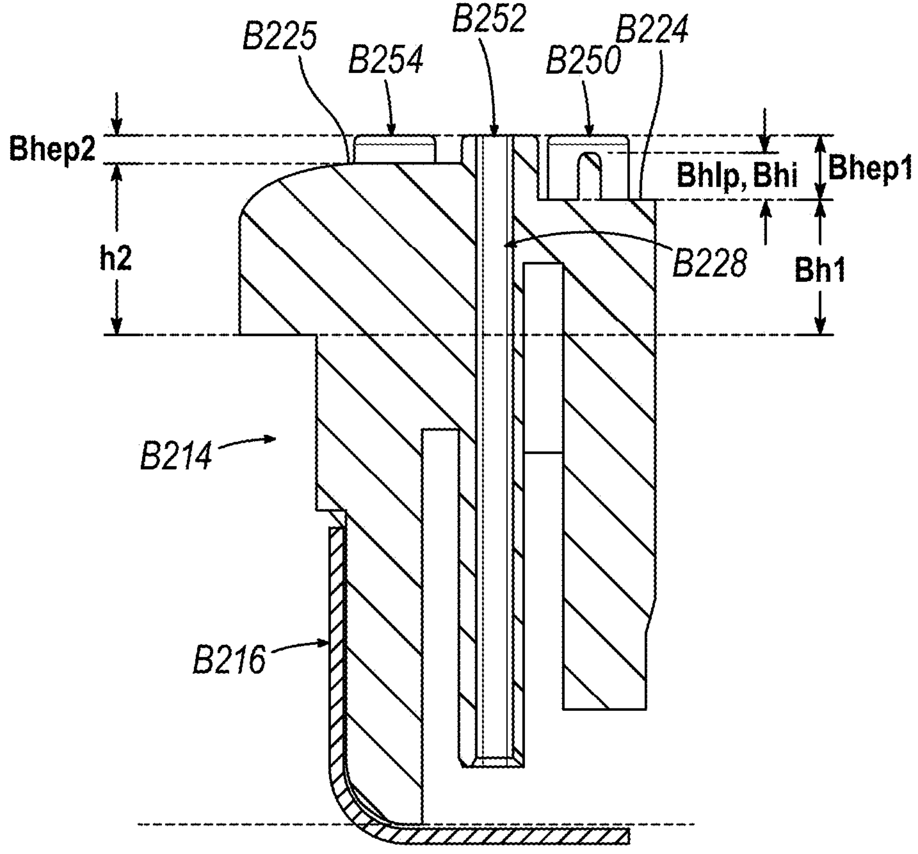
FIG. 42 depicts a partial sectional view of the cartridge body of FIG. 40 and an accompanying tray.

FIGS. 40-42 show another example of a cartridge body (B214) configured to be incorporated into staple cartridge (C110) of FIG. 24 for use with end effector (40) of FIG. 2. Cartridge body (B214) is similar to cartridge body (C114) described above except as otherwise described below. Similar to cartridge body (C114), cartridge body (B214) includes a deck (B224), an elongate slot (B226) formed in deck (B224), a plurality of cartridge pockets (B228) formed in deck (B224), and a plurality of engagement protrusions (B230*a*-1) extending outwardly from deck (B224). Deck (B224) is configured to compress tissue against an anvil (not shown), but similar to anvil (44). Deck (B224) is defined by cartridge body (B214) and is shown as upwardly facing. Unlike decks (B124, B124*a-c*) which are substantially planar, deck (B224) has a stepped orientation and is non-planar. Particularly, deck (B224) has a step (B225) extending from between middle and outer rows (B246, B248). Elongate slot (B226) extends along a longitudinal axis (LA) of cartridge body (B214). Elongate slot (B226) opens upwardly through deck (B224) and terminates at a connecting portion (B231). Elongate slot (B226) is configured to slidably receive a knife therein similar to elongate slot (C126). Cartridge pockets (B228) are configured to house staples (not shown) but similar to staples (C116) and staple drivers (not shown) but similar to staple drivers (C118). As shown, cartridge body (B214) includes a first lateral side (B236) and a second lateral side (B238) disposed opposite first lateral side (B236).

FIGS. 40-41 show cartridge pockets (B228) arranged into six longitudinally extending rows. Elongate slot (B226) separates three rows on a first deck side (B240) from three additional rows on a second deck side (B242). These longitudinal rows include inner rows (B244), middle rows (B246), and outer rows (B248). Similar to cartridge body (C114), inner row (B250) of second deck side (B242) is a mirror image of inner row (B250) of first deck side (B240). Inner rows (B244) are the closest cartridge pockets (B228) relative to elongate slot (B226). Engagement protrusions (B230*a*-1) extend from deck (B224) and are configured to grip tissue (T) or an adjunct material (e.g., buttress (B188)) positioned thereon. Cartridge body (B214) includes twelve different configurations of engagement protrusions (B230*a*-1). The arrangement of these engagement protrusions (B230*a*-1) is symmetric about elongate slot (B226). In other words, second deck side (B242) of cartridge body (B214) is a mirror image of first deck side (B240) of cartridge body (B214). Similar to cartridge pockets (B228), engagement protrusions (B230*a*-1) are arranged into a plurality of longitudinally extending rows. These longitudinal rows include inner rows (B250), middle rows (B252), and outer rows (B254). Inner rows (B250) generally correspond with inner rows (B244) of cartridge pockets (B228), middle rows (B252) generally correspond with middle rows (B246) of cartridge pockets (B228), and outer rows (B254) generally correspond with outer rows (B248) of cartridge pockets (B228). As shown, inner rows (B250), middle rows (B252), and outer rows (B254) each extend substantially parallel to elongate slot (B226). Inner rows (B250) are the closest engagement protrusions relative to elongate slot (B226).

With continued reference to FIGS. 40-41, engagement protrusions (B230*a-f*) are the distal most engagement protrusions. Each engagement protrusion (B230*a-f*) includes a distal lead-in portion (B256). Engagement protrusions (B230*a-f*) include planar surfaces (B258). Engagement protrusions (B230*a-b*, B230*g-h*) extend within a single row and do not connect with an adjacent row. As shown in FIG. 41, engagement protrusion (B230*a*) includes a lateral portion (B287), and engagement protrusion (B230*a*) includes a lateral portion (B289). Engagement protrusion (B230*g*) is similar to engagement protrusion (C130*d*) and includes a lateral portion (B280) (see FIG. 41) similar to lateral portion (C180). Engagement protrusion (B230*h*) is similar to engagement protrusions (C130*c*) and includes a lateral portion (B286) (see FIG. 41) similar to lateral portion (C186). Engagement protrusions (B230*c-f*, B230*i*-1) in middle and outer rows (B252, B254) connect due to step (B225) but are not linked together above step (B225) or outside of step (B225). As shown, longitudinally adjacent engagement protrusions (B230*a-b*, B230*g-h*) of inner rows (B250) on first and second deck sides (B240, B242) are linked together by interconnections (B260). Interconnections (B260) are similar to interconnections (C160). Moving proximally, inner row (B250) on first deck side (B240) includes engagement protrusion (B230*a*) followed by interconnection (B260), followed by engagement protrusion (B230*g*), followed by interconnection (B260), followed by engagement protrusion (B230*h*), with the sequence of engagement protrusion (B230*g*), interconnection (B260), and engagement protrusion (B230*h*) interconnection (B260) repeating in an alternating manner. Moving proximally, inner row (B250) on second deck side (B242) includes engagement protrusion (B230*b*) followed by interconnection (B260), followed by engagement protrusion (B230*h*), followed by interconnection (B260), followed by engagement protrusion (B230*g*), with the sequence of interconnection (B260), engagement protrusion (B230*h*), interconnection (B260), and engagement protrusion (B230*g*) repeating in an alternating manner.

Similar to first and second continuous non-linear raised cross-sectional areas (C162, C164), cartridge body (B214) includes first and second continuous non-linear raised cross-sectional areas (B262, B264) (see FIG. 41) that form first and second continuous non-linear paths. The first continuous non-linear raised cross-sectional area (B262) extends from deck (B224) between adjacent engagement protrusions (B230*a*, B230*g*, B230*h*) joined by interconnections (B260) along the entire length of inner row (B244) of cartridge pockets (B228). The second continuous non-linear raised cross-sectional area (B264) extends from deck (B224) between longitudinally adjacent engagement protrusions (B230*b*, B230*h*, B230*g*) joined by interconnections (B260) along the inner row (B244) of cartridge pockets (B228).

These continuous non-linear raised cross-sectional areas (B262, B264) are configured to provide increased stiffness to inner rows (B250) and/or increased localized clamping pressure around elongate slot (B226).

Similar to cartridge pockets (C128), cartridge pockets (B228) each include a first longitudinal end (B266), a second longitudinal end (B268), a first lateral side (B270), and a second lateral side (B272). Between first and second longitudinal ends (B266, B268) and first and second lateral sides (B270, B272) are inwardly facing projections (B274), similar to inwardly facing projections (C174). As shown, first and second lateral sides (B270, B272) of cartridge pocket (B228) extend substantially parallel to elongate slot (B226).

Inner rows (B250) are not linked with either middle row (B246) or outer rows (B248) above deck (B224). Except for step (B225), middle and outer rows (B252, B254) are not otherwise linked together. Engagement protrusions (B230*a*-1) and interconnections (B260) are integrally formed together as a unitary piece with deck (B224). Engagement protrusion (B230*g*) includes a first end portion (B276), a second end portion (B278), and lateral portion (B280). First end portion (B276) wraps around first longitudinal end (B266) of cartridge pocket (B228). Lateral portion (B280) being adjacent to elongate slot (B226) provides additional compression near the cutline. As shown, lateral portion (B280) extends longitudinally along first lateral side (B270) of cartridge pocket (B228) but not on second lateral side (B272) of cartridge pocket (B228) which instead opens directly to deck (B224). Interconnections (B260) extend between second end portion (B278) of engagement protrusion (B230*d*) and a first end portion (B276) of an adjacent engagement protrusion. Planar surfaces (B284) are substantially parallel to deck (B224).

Middle row (B252) on first deck side (B240) includes engagement protrusion (B230*c*) followed by a series of engagement protrusions (B230*i*). Middle row (B252) on second deck side (B242) includes engagement protrusion (B230*d*) followed by a series of engagement protrusions (B230*j*). As shown, no longitudinally adjacent engagement protrusion of middle or outer rows (B252, B254) is joined together by an interconnection (B260) or any other feature extending from deck (B224) other than step (B225) of deck (B224). Engagement protrusions (B230*c*, B230*i*) open to deck (B224) on second lateral side (B272), and include a U-shaped wall (B288) on first lateral side (B270) of cartridge pocket (B228). Engagement protrusions (B230*d*, B230*j*) include a U-shaped wall (B291) on second lateral side (B272), and open to deck (B224) on first lateral side (B270) of cartridge pocket (B228).

Outer row (B254) on first deck side (B240) includes engagement protrusion (B230*e*) followed by a series of engagement protrusions (B230*k*). Outer row (B254) on second deck side (B242) includes engagement protrusion (B230*f*) followed by a series of engagement protrusions (B2301). For each of engagement protrusions (B230*e-f*, B230*k*-1), both first and second lateral sides (B270, B272) of cartridge pocket (B228) open directly onto deck (B224). Unlike engagement protrusions (B230*g-h*), engagement protrusions (B230*e-f*, B230*k*-1) do not include a lateral portion (e.g., lateral portions (B280, B286)). As shown, no longitudinally adjacent engagement protrusion of middle or outer rows (B252, B254) is joined together by an interconnection (B260) or any other feature extending from deck (B224) other than step (B225) of deck (B224).

As shown in FIG. 41, engagement protrusions (B230*a-h*, B230*k*) have a maximum width (BWp) in the direction transverse to longitudinal axis (LA). Interconnection (B260) has a maximum width (BWi) in the direction transverse to longitudinal axis (LA). Maximum width (BWp) of engagement protrusions (B230*a-h*, B230*k*) is greater than maximum width (BWi) of interconnection (B260). Cartridge pockets (B228) have a maximum width (BWc) defined by a distance between first and second lateral sides (B270, B272) of cartridge pocket (B228) in the direction transverse to longitudinal axis (LA). Maximum width (BWc) of cartridge pocket (B228) is greater than maximum width (BWi) of interconnection (B260). First and second end portions (B276, B278) have a maximum width (BWep) in the direction transverse to longitudinal axis (LA) that is greater than maximum width (BWi) of interconnection (B260).

FIG. 42 shows cartridge body (B214) and tray (B216). As shown, for inner row (B250), first and second end portions (B276, B278) extend from deck (B224) a maximum height (Bhep1). Interconnection (B260) extends from deck (B224) a maximum height (Bhi). As shown, maximum height (Bhep1) of first and second end portions (B276, B278) of inner row (B250) is greater than maximum height (Bhi) of interconnection (B260). For middle row (B252), inner side extends from deck (B224) a maximum height (Bhep1), and outer row (B254) extends from step (B225) of deck (B224) a maximum height (Bhep2). Maximum height (Bhep1) of first and second end portions (B276, B278) of inner row (B250) is about 0.025 inches (0.635 millimeters). As shown, maximum height (Bhep2) of first and second end portions (B276, B278) of outer row (B254) is about 0.010 inches (0.254 millimeters). As shown, height (Bh1) is about 0.052 inches (1.3208 millimeters), height (Bh2) is about 0.067 inches (1.7018 millimeters).

F. Sixth Example of a Cartridge Body

Figure 43:
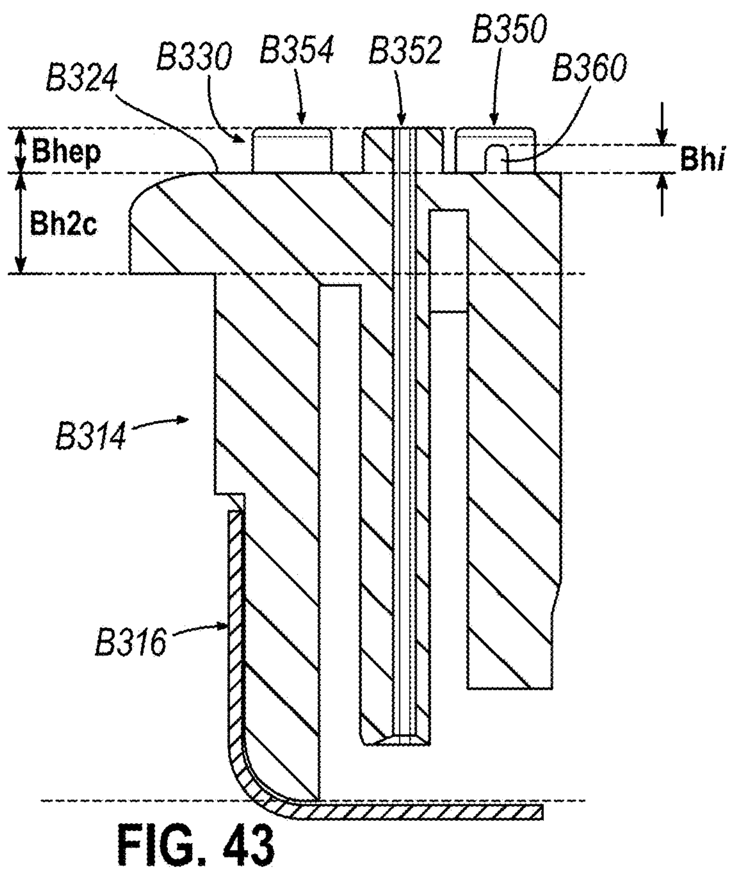
FIG. 43 depicts a partial sectional view of another example of a cartridge body and an accompanying tray configured to be incorporated into the staple cartridge of FIG. 24 and the end effector of FIG. 2.

FIG. 43 shows a partial sectional view of another example of a cartridge body (B314) and accompanying tray (B316) configured to be incorporated into staple cartridge (C110) of FIG. 24 for use with end effector (40) of FIG. 2. Cartridge body (B314) is similar to cartridge body (C114) described and shown above with reference to FIGS. 24-35. Engagement protrusions (B330), similar to engagement protrusions (C130*a-f*), include inner rows (B350), middle rows (B352), and outer rows (B354) that extend from a deck (B324). As shown in FIG. 43, maximum height (Bhep) of engagement protrusions (B330) is about 0.016 inches (0.4064 millimeters), and height (Bh2*c*) is about 0.037 inches (0.9398 millimeters). Interconnections (B360) have a max height (Bhi) that is about half of maximum height (Bhep) of engagement protrusions (B330). Interconnections (B360) are similar to interconnections (C160). Deck (B324) is shown as being substantially planar.

G. Seventh Example of a Cartridge Body

Figure 44:
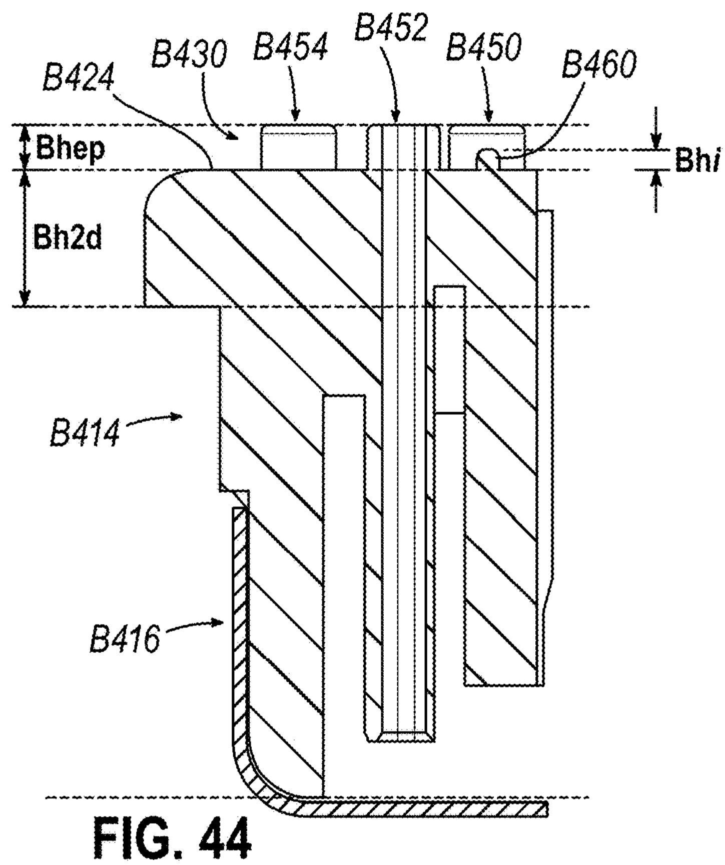
FIG. 44 depicts a partial sectional view of another example of a cartridge body and an accompanying tray configured to be incorporated into the staple cartridge of FIG. 24 and the end effector of FIG. 2.
Figure 45:
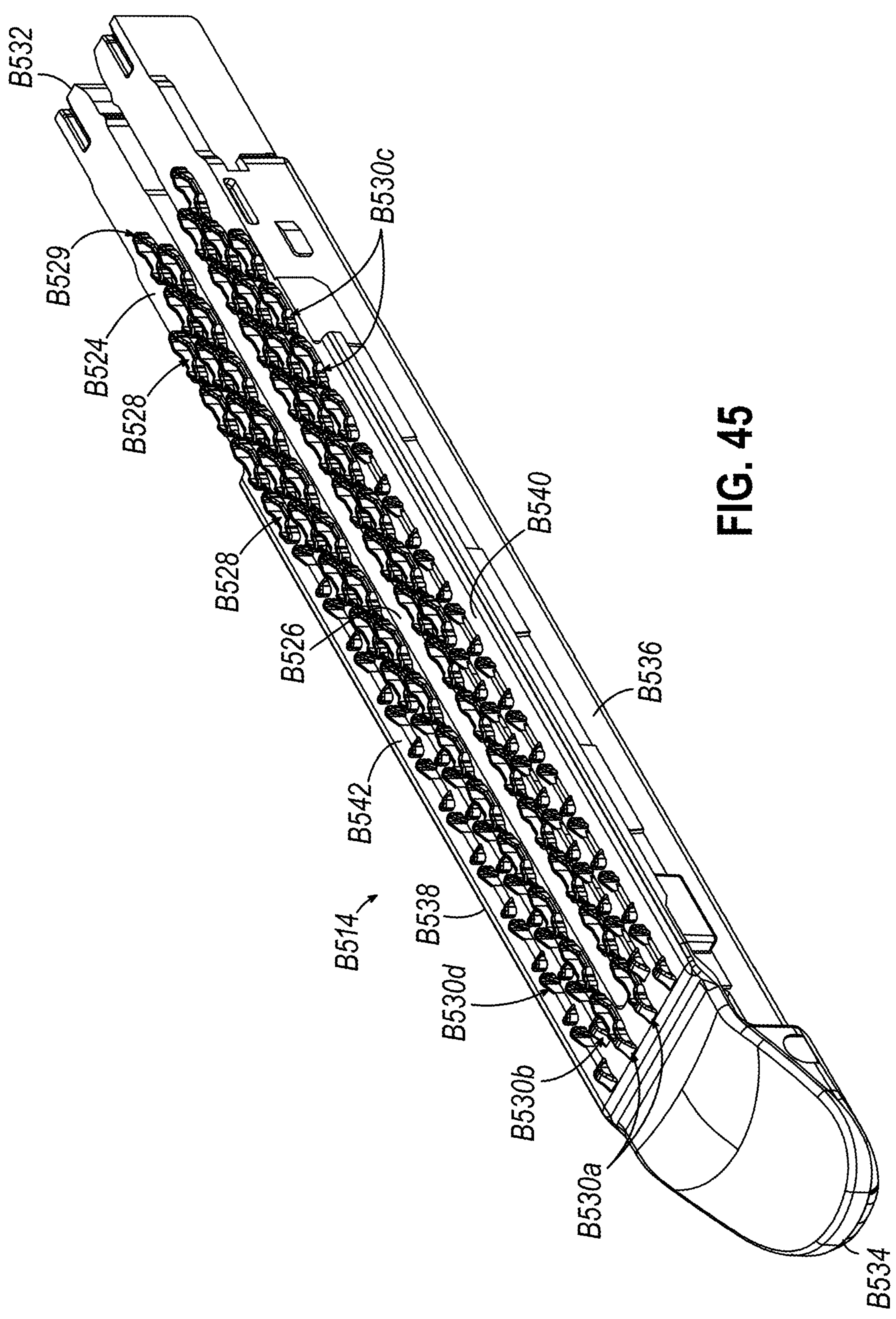
FIG. 45 depicts a perspective view of another example of a cartridge body configured to be incorporated into the staple cartridge of FIG. 24 and the end effector of FIG. 2.

FIG. 44 shows a partial sectional view of another example of a cartridge body (B414) and accompanying tray (B416) configured to be incorporated into staple cartridge (C110) of FIG. 24 for use with end effector (40) of FIG. 2. Cartridge body (B414) is similar to cartridge body (C114) described and shown above with reference to FIGS. 24-35. Engagement protrusions (B430), similar to engagement protrusions (C130*a-f*), include inner rows (B450), middle rows (B452), and outer rows (B454) that extend from a deck (B424). As shown in FIG. 44, maximum height (Bhep) of engagement protrusions (B430) is about 0.020 inches (0.508 millimeters), and height (Bh2*d*) is about 0.037 inches (0.9398 millimeters). Interconnections (B460) have a maximum height (Bhi) that is about half of maximum height (Bhep) of engagement protrusions (B430). Interconnections (B460) are similar to interconnections (C160). Deck (B424) is shown as being substantially planar.

H. Eighth Example of a Cartridge Body

FIGS. 45-49 show another example of a cartridge body (B514) configured to be incorporated into staple cartridge (C110) of FIG. 24 for use with end effector (40) of FIG. 2. Cartridge body (B512) includes a deck (B524), an elongate slot (B526) formed in deck (B524), a plurality of cartridge pockets (B528) formed in deck (B524), and a plurality of engagement protrusions (B530*a-d*) extending outwardly from deck (B524). Engagement protrusions (B530*a-d*) collectively form an array (B529). Cartridge body (B514) includes a proximal end (B532), a distal end (B534), a first lateral side (B536), and a second lateral side (B538). Second lateral side (B538) is disposed opposite first lateral side (B536). Deck (B524) is configured to compress tissue against an anvil (not shown) but similar to anvil (44). Deck (B524) is defined by cartridge body (B514) and is shown as substantially planar. Elongate slot (B526) extends along a longitudinal axis (LA) of cartridge body (B514). Elongate slot (B526) opens upwardly through deck (B524) and terminates at a connecting portion (B531). Elongate slot (B526) is configured to slidably receive a knife therein. The knife may be a distal knife portion of a firing beam (not shown), such as distal knife portion (50) of firing beam (46).

Cartridge pockets (B528) are configured to house a plurality of staples (not shown) but similar to staples (C116). Cartridge pockets (B528) are arranged into six longitudinally extending rows. Elongate slot (B526) separates three rows on a first deck side (B540) from three additional rows on a second deck side (B542). These longitudinal rows include inner rows (B544), middle rows (B546), and outer rows (B548). While two inner rows (B544), two middle rows (B546), and two outer rows (B548) are shown, more or fewer rows are also envisioned. Inner rows (B544) are the closest cartridge pockets (B528) relative to elongate slot (B526). In other words, inner rows (B544) are positioned closer to elongate slot (B526) than middle rows (B546). Similarly, middle rows (B546) are positioned closer to elongate slot (B526) than outer rows (B548) of cartridge pockets (B528).

Engagement protrusions (B530*a-d*) extend from deck (B524) and are configured to grip tissue (T) or an adjunct material (e.g., a buttress) positioned thereon. As will be described below, cartridge body (B514) includes four different configurations of engagement protrusions (B530*a-d*). The arrangement of these engagement protrusions (B530*a-d*) is symmetric about elongate slot (B526). Second deck side (B542) of cartridge body (B514) is a mirror image of first deck side (B540) of cartridge body (B514). Engagement protrusions (B530*a-d*) are arranged into a plurality of longitudinally extending rows. These longitudinal rows include inner rows (B550), middle rows (B552), and outer rows (B554). Inner rows (B550) generally correspond with inner rows (B544) of cartridge pockets (B528). Similarly, middle rows (B552) generally correspond with middle rows (B546) of cartridge pockets (B528), and outer rows (B554) generally correspond with outer rows (B548) of cartridge pockets (B528). Inner rows (B550) are the closest engagement protrusions relative to elongate slot (B526). In other words, inner rows (B550) of engagement protrusions are positioned closer to elongate slot (B526) than middle rows (B552). Similarly, middle rows (B552) are positioned closer to elongate slot (B526) than outer rows (B554) of engagement protrusions. As shown, inner rows (B550), middle rows (B552), and outer rows (B554) each extend substantially parallel to elongate slot (B526). Each engagement protrusion (B530*a-d*) extends within a single row (e.g., one of inner row (B550), middle row (B552), and outer rows (B554)) and does not connect with an adjacent row. Engagement protrusions (B530*a*) surround a respective cartridge pocket (B528) of inner row (B544) of cartridge pockets (B528). Engagement protrusions (B530*c*) surround a respective cartridge pocket (B528) of inner rows (B544), middle rows (B546), and outer rows (B548) of cartridge pockets (B528).

Figure 47:
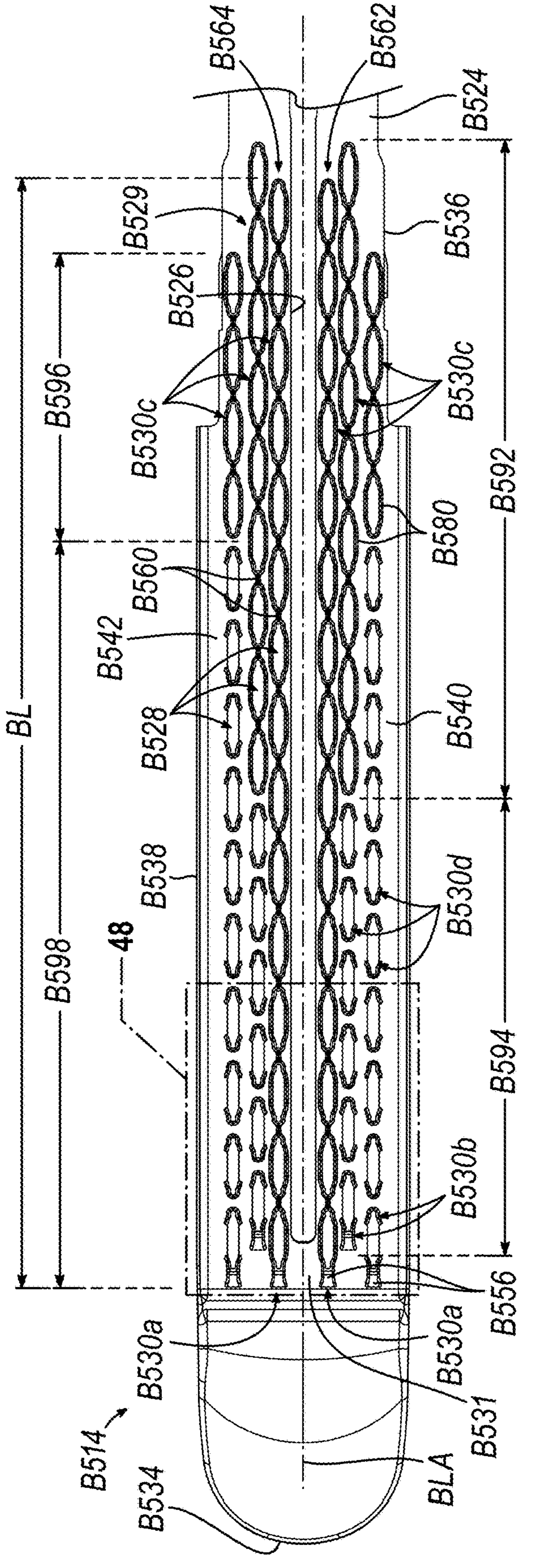
FIG. 47 depicts a partial top plan view of the partial cartridge body of FIG. 45.

FIG. 47 shows first and second continuous non-linear raised cross-sectional areas (B562, B564) forming first and second continuous non-linear paths along the entire length of cartridge pockets (B528). First and second continuous non-linear raised cross-sectional areas (B562, B564) extend from deck (B524) between adjacent engagement protrusions (B530*a*, B530*c*) joined by interconnections (B560) along the entire length of inner row (B544) of cartridge pockets (B528). First and second continuous non-linear raised cross-sectional areas (B562, B564) are configured to provide increased stiffness to inner rows (B550) of engagement protrusions (B530*a-b*, B530*d-e*) and/or increased localized clamping pressure around elongate slot (B526). Increasing the clamping pressure around elongate slot (B526) may keep tissue (T) taught and orient the tissue for cutting. For example, this may orient tissue (T) to be pierced by the knife and reduce transverse forces in tissue (T).

Middle rows (B552) include a first portion (B592) of longitudinally adjacent engagement protrusions (B530*c*) joined by interconnections (B560), and a second portion (B594) of adjacent engagement protrusions (B530*b*, B530*d*) that is not linked by interconnections (B560). Instead, longitudinally adjacent engagement protrusions (B530*b*, B530*d*) are spaced apart from each other. As shown, first portion (B592) of middle rows (B552) includes nine longitudinally adjacent engagement protrusions (B530*d*) linked by interconnections (B560). As shown, second portion (B594) of middle rows (B552) includes one engagement protrusion (B530*b*) and five longitudinally adjacent engagement protrusions (B530*d*) not linked together. In other words, first portion (B592) extends longitudinally along about 60% of middle rows (B552), and second portion (B594) extends longitudinally along about 40% of middle rows (B552). These percentages may vary, for example, first portion (B592) extends longitudinally along about 50% of middle rows (B552), and second portion (B594) extends longitudinally along about 50% of middle rows (B552).

With continued reference to FIG. 47, first portion (B596) of outer rows (B554) includes four adjacent engagement protrusions (B530*d*) longitudinally linked by interconnections (B560). As shown, second portion (B598) of outer rows (B554) includes ten longitudinally adjacent engagement protrusions (B530*a*, B530*d*). In other words, first portion (B592) extends longitudinally along about 29% of outer rows (B554), and second portion (B594) extends longitudinally along about 71% of outer rows (B554). These percentages may vary, for example, first portion (B592) may extend longitudinally along about 25% of outer rows (B554), and second portion (B594) extends longitudinally along about 75% of outer rows (B554). First portions (B592, B596) form continuous non-linear raised cross-sectional areas that apply greater proximal compression as compared to distal compression as the raised cross-sectional area is greater moving proximally.

Figure 46:
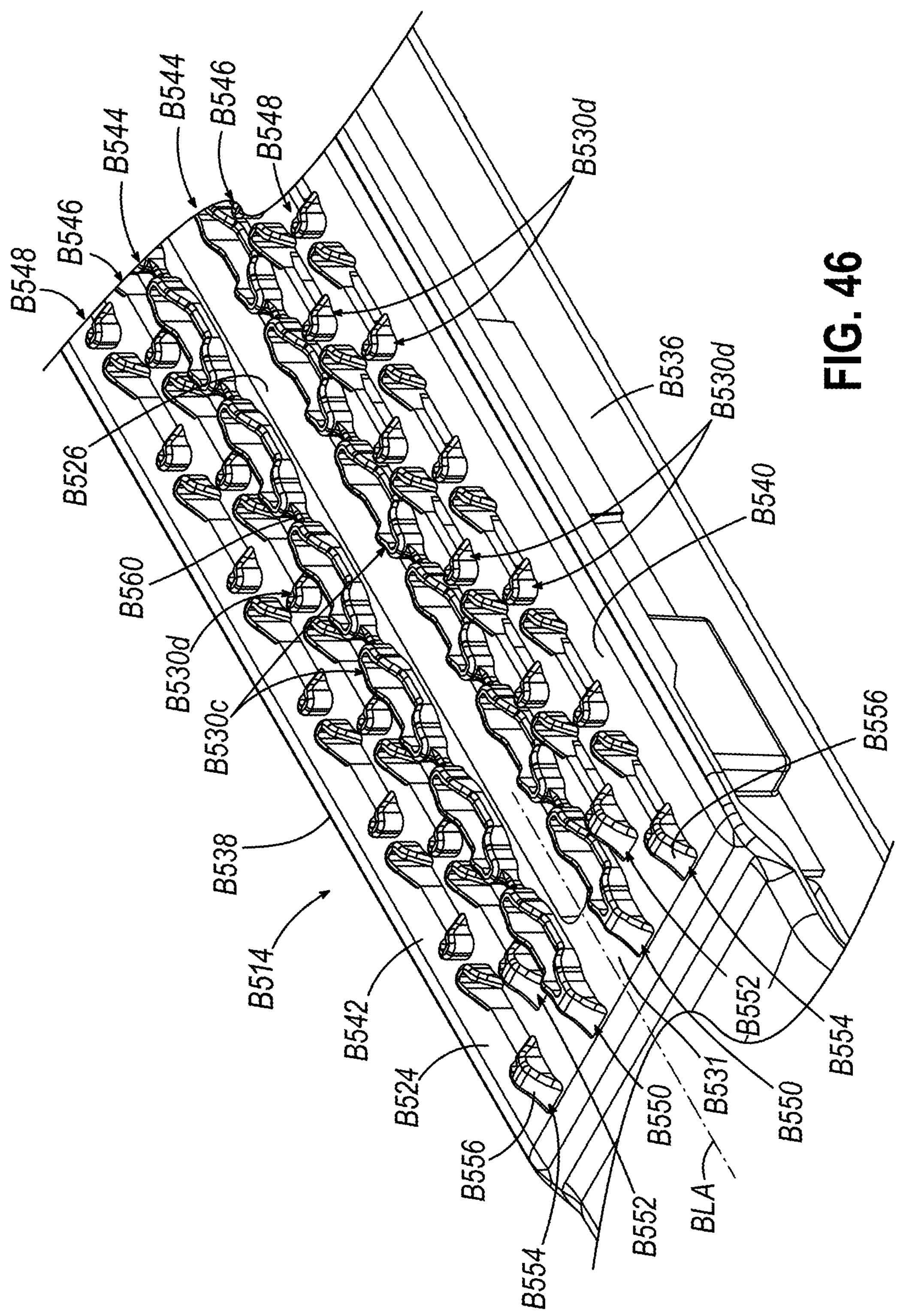
FIG. 46 depicts an enlarged perspective view of a portion of the cartridge body of FIG. 45.
Figure 48:
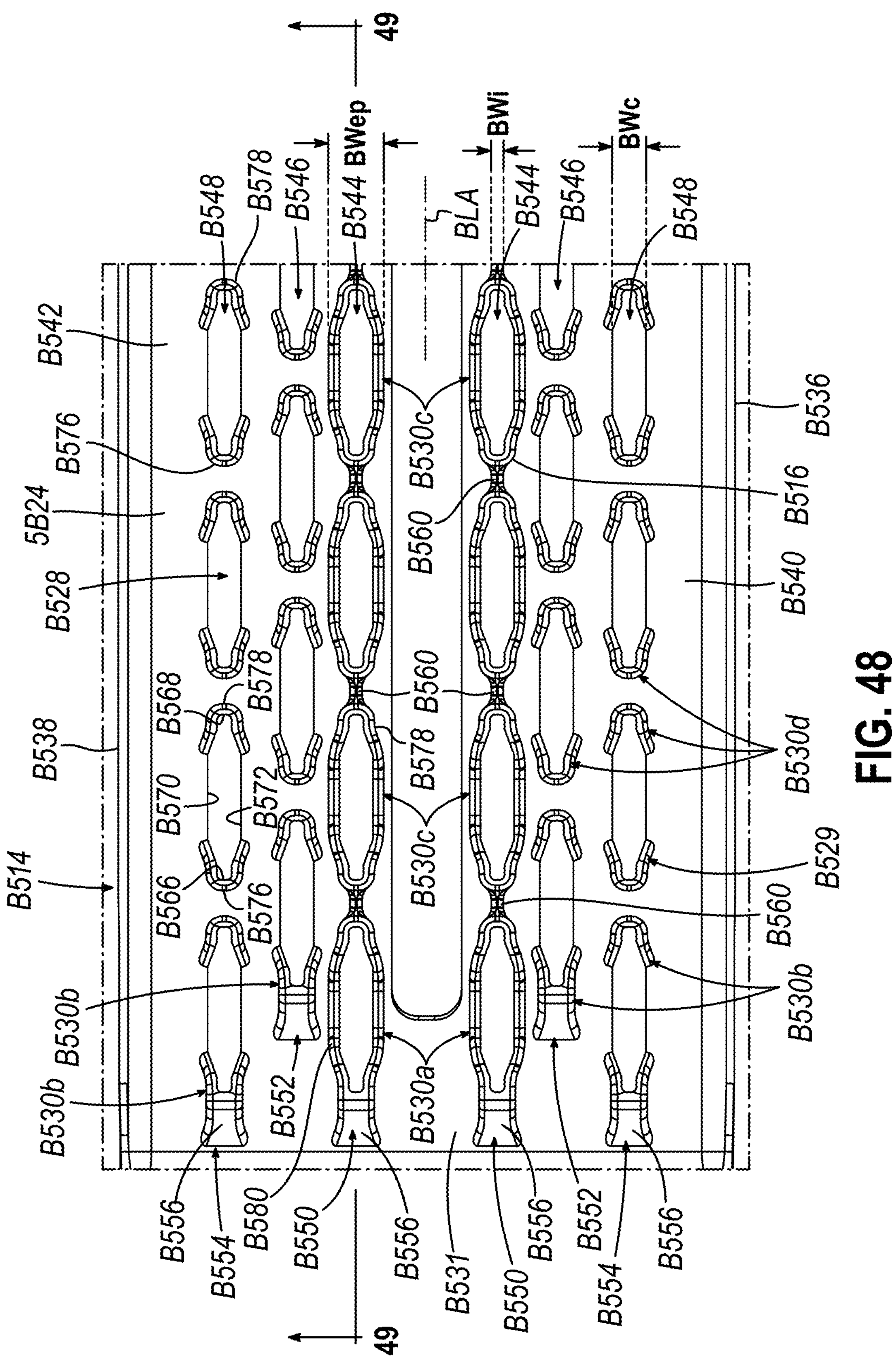
FIG. 48 depicts an enlarged top plan view of the cartridge body of FIG. 47.

As shown in FIGS. 46 and 48, engagement protrusions (B530*a-b*) are the distal most engagement protrusions on first and second deck sides (B540, B542). Each engagement protrusion (B530*a-b*) includes a distal lead-in portion (B556). As shown, longitudinally adjacent engagement protrusions (B530*a*, B530*c*) of inner rows (B550) on first and second deck sides (B540, B542) are linked together (also referred to as joined together) by interconnections (B560). Similar to cartridge pocket (C128), FIG. 48 shows cartridge pocket (B528) including a first longitudinal end (B566), a second longitudinal end (B568), a first lateral side (B570), and a second lateral side (B572). Second longitudinal end (B568) is disposed opposite first longitudinal end (B566). First and second longitudinal ends (B566, B568) are configured to guide legs (B117) of staples (B116) (see FIG. 24). First lateral side (B570) is disposed between first and second longitudinal ends (B566, B568). Second lateral side (B572) is disposed between first and second longitudinal ends (B566, B568) and opposite to first lateral side (B570). As shown, first and second lateral sides (B570, B572) of cartridge pocket (B528) extend substantially parallel to elongate slot (B526).

Engagement protrusions (B530*a*, B530*c*) include a first end portion (B576), a second end portion (B578), and a lateral portion (B580). First end portion (B576) wraps around first longitudinal end (B566) of cartridge pocket (B528). Similarly, second end portion (B578) wraps around second longitudinal end (B568) of cartridge pocket (B528). Lateral portion (B580) extends continuously between first and second end portions (B576, B578) on both of first and second lateral sides (B570, B572) of cartridge pocket (B528). Engagement protrusions (B530*b*, B530*d*) include first end portion (B576) and a second end portion (B578). Engagement protrusions (B530*b*, B530*d*) do not extend along first lateral side (B570) or second lateral side (B572) of cartridge pocket (B528) such that first lateral side (B570) and second lateral side (B572) open directly to deck (B524). Engagement protrusions (B530*a*, B530*c*) are configured to provide greater compression than engagement protrusions (B530*b*, B530*d*). Interconnections (B560) extend between second end portion (B578) of engagement protrusion (B530*a*) and a first end portion (B576) of an adjacent engagement protrusion (e.g., engagement protrusion (B530*c*)) and then between adjacent engagement protrusion (B530*c*) moving proximally.

Tighter tissue compression at the proximal end near elongate slot (B526) encourages the knife (e.g., distal knife portion of a firing beam (not shown), such as distal knife portion (50) of firing beam (46)) to pierce and cleanly cut tissue (T) and/or buttress (e.g., B118) at the proximal end of elongate slot (B526). Guiding of the fluid-phase of the tissue outwards both laterally and longitudinally during the clamping wait time (e.g., which may be about 15 seconds). Due to a natural tendance of fluid to flow in the path of least resistance, more fluid evacuates the tissue sooner during clamping phase to provide less fluid flow during firing. This selectively applies greater tissue pressures in localized regions and encourages fluid-flow-out of tissue (T).

As shown in FIG. 48, engagement protrusion (B530*d*) has a maximum width (BWp) in the direction transverse to longitudinal axis (LA). Interconnection (B560) has a maximum width (BWi) in the direction transverse to longitudinal axis (LA). Maximum width (BWp) of engagement protrusion (B530*a-d*) is greater than maximum width (BWi) of interconnection (B560). Cartridge pocket (B528) has a maximum width (BWc) defined by a distance between first and second lateral sides (B570, B572) of cartridge pocket (B528) in the direction transverse to longitudinal axis (LA). Maximum width (BWp) of cartridge pocket (B528) is greater than maximum width (BWi) of interconnection (B560). First and second end portions (B576, B578) have a maximum width (BWep) in the direction transverse to longitudinal axis (LA) that is greater than maximum width (BWi) of interconnection (B560).

Figure 49:
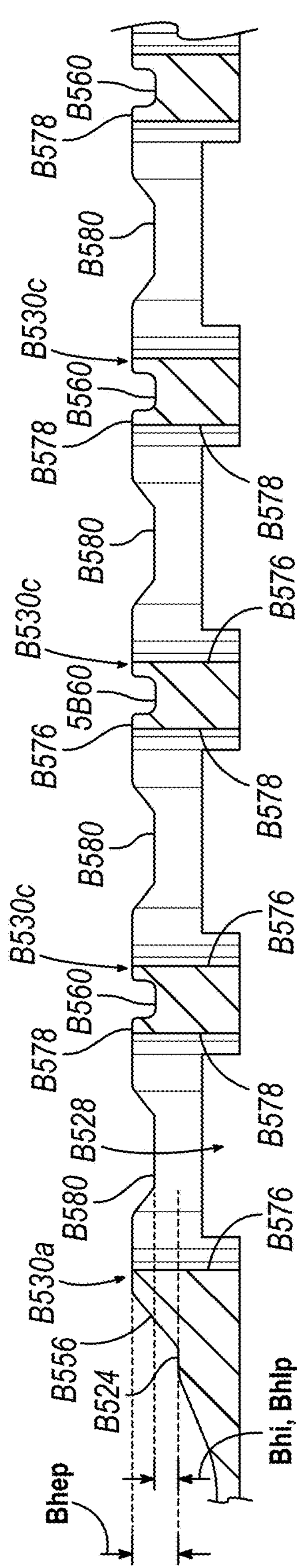
FIG. 49 depicts a partial side sectional view of the portion of the cartridge body of FIG. 48 taken along line 49-49 of FIG. 48.

As shown in FIG. 49, each engagement protrusion (B530*a-d*) has the same height (e.g., extends away from deck (B524) the same distance). First and second end portions (B576, B578) of engagement protrusions (B530*a-d*) extend from deck (B524) a maximum height (Bhep). Lateral portions (B580) of engagement protrusions (B530*a*, B530*c*) extend from deck (B524) a maximum height (Bhlp). Interconnection (B560) extends from deck (B524) a maximum height (Bhi). As shown, maximum height (Bhep) of first and second end portions (B576, B578) is greater than maximum height (Bhi) of interconnection. For example, maximum height (Bhi) of interconnections (B560) and maximum height of (Bhlp) of lateral portions (B580) may be each about half of maximum height (Bhep) of first and second end portions (B576, B578).

I. Ninth Example of a Cartridge Body

Figure 50:
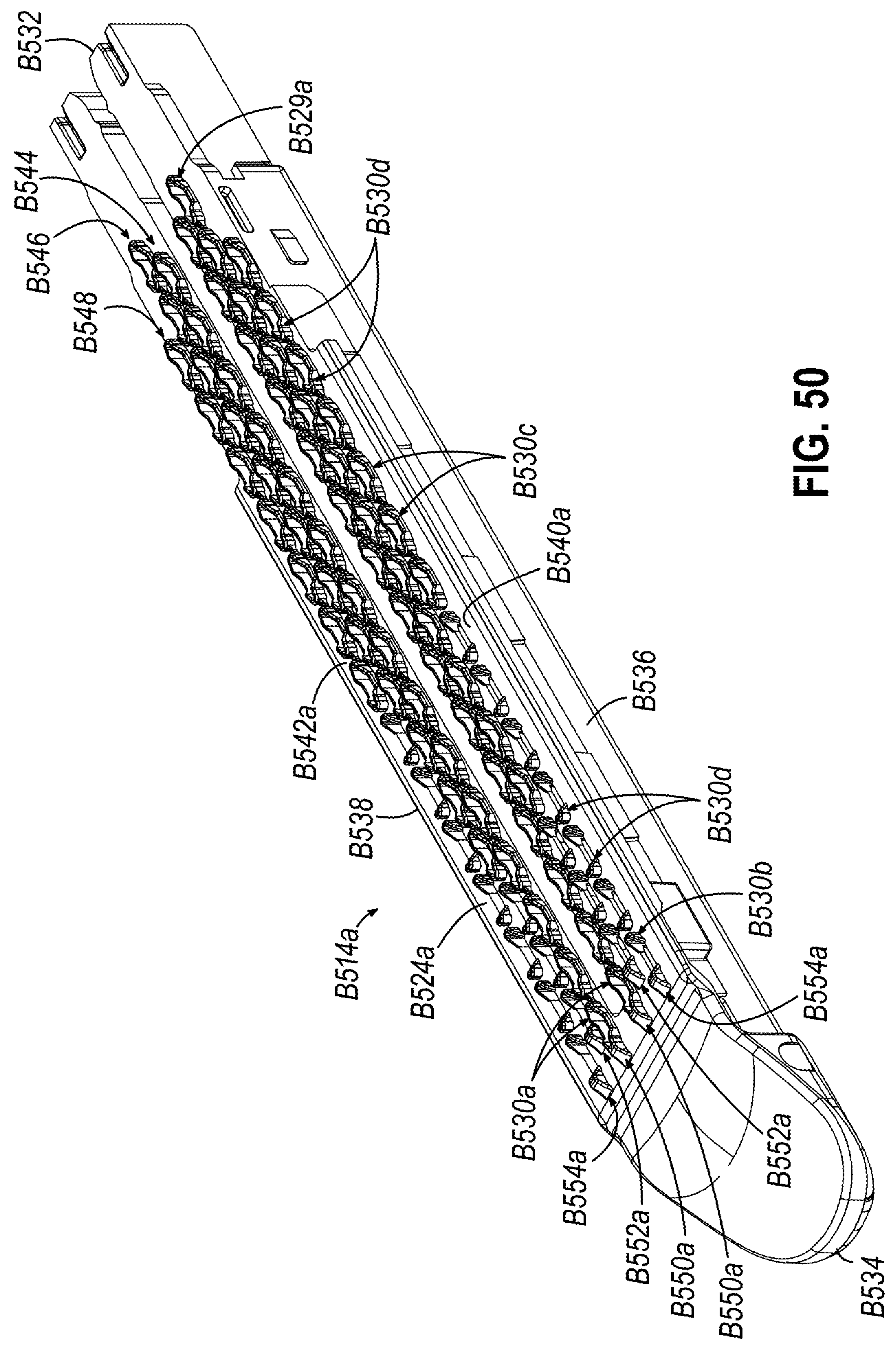
FIG. 50 depicts a perspective view of another example of a cartridge body configured to be incorporated into the staple cartridge of FIG. 24 and the end effector of FIG. 2.
Figure 51:
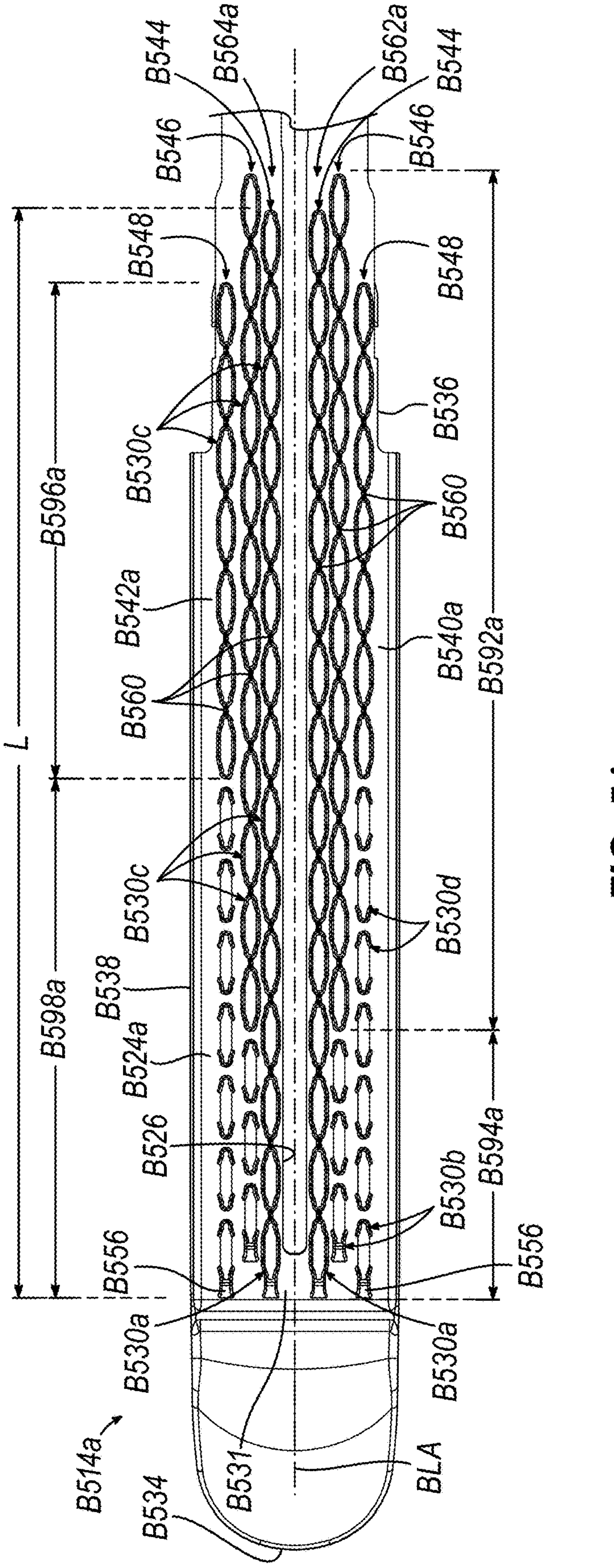
FIG. 51 depicts a partial top plan view of the cartridge body of FIG. 50.

FIGS. 50-51 show another example of a cartridge body (B514*a*) configured to be incorporated into staple cartridge (C110) of FIG. 24 for use with end effector (40) of FIG. 2. Similar to cartridge body (B514), cartridge body (B514*a*) includes a deck (B524*a*), an elongate slot (B526) formed in deck (B524*a*), a plurality of cartridge pockets (B528) formed in deck (B524*a*), and a plurality of engagement protrusions (B530*a-d*) extending outwardly from deck (B524*a*). Engagement protrusions (B530*a-d*) collectively form an array (B529*a*). Similar to cartridge body (B514), cartridge body (B514*a*) include inner rows (B544), middle rows (B546), and outer rows (B548) of cartridge pockets (B528). Similar to cartridge body (B514), cartridge body (B514*a*) includes engagement protrusions (B530*a-d*) extending from deck (B524*a*) that are configured to grip tissue (T) or an adjunct material (e.g., a buttress) positioned thereon. Second deck side (B542*a*) of cartridge body (B514*a*) is a mirror image of first deck side (B540*a*) of cartridge body (B514*a*). Longitudinal rows of engagement protrusions include inner rows (B550*a*), middle rows (B552*a*), and outer rows (B554*a*) and generally correspond to inner rows (B544), middle rows (B546), and outer rows (B548) of cartridge pockets (B528).

FIG. 51 shows first and second continuous non-linear raised cross-sectional areas (B562*a*, B564*a*) forming first and second continuous non-linear paths along an entire length (L) of cartridge pockets (B528). Middle rows (B552*a*) include a first portion (B592*a*) of longitudinally adjacent engagement protrusions (B530*b*) joined by interconnections (B560), and a second portion (B594*a*) of adjacent engagement protrusions (B530*d*) that is not linked by interconnections (B560). Instead, longitudinally adjacent engagement protrusions (B530*d*) are spaced apart from each other. As shown, first portion (B592*a*) of middle rows (B552*a*) includes nine longitudinally adjacent engagement protrusions (B530*d*) linked by interconnections (B560). As shown, second portion (B594*a*) of middle rows (B552*a*) includes one engagement protrusion (B530*b*) and two longitudinally adjacent engagement protrusions (B530*d*). In other words, first portion (B592*a*) extends longitudinally along about 80% of middle rows (B552*a*), and second portion (B594*a*) extends longitudinally along about 20% of middle rows (B552*a*). These percentages may vary, for example, first portion (B592*a*) may extend longitudinally along about 75% of middle rows (B552*a*), and second portion (B594*a*) extends longitudinally along about 25% of middle rows (B552*a*).

With continued reference to FIG. 51, first portion (B596*a*) of outer rows (B554*a*) includes seven adjacent engagement protrusions (B530*d*) longitudinally linked by interconnections (B560). As shown, second portion (B598*a*) of outer rows (B554*a*) includes one engagement protrusion (B530*b*) and six longitudinally adjacent engagement protrusions (B530*d*). In other words, first and second portions (B592*a*, B596*a*) each extend longitudinally along about 50% of outer rows (B554*a*). First portions (B592*a*, B596*a*) form continuous non-linear raised cross-sectional areas. Increasing the clamping pressure around elongate slot (B526) may keep the tissue taught and orient the tissue for cutting. For example, this may orient the tissue to be pierced by the knife and reduce transverse forces in the tissue. Cartridge body (B514*a*) may provide greater compression than cartridge body (B514) since cartridge body (B514*a*) has a greater raised cross-sectional area.

J. Tenth Example of a Cartridge Body

Figure 52:
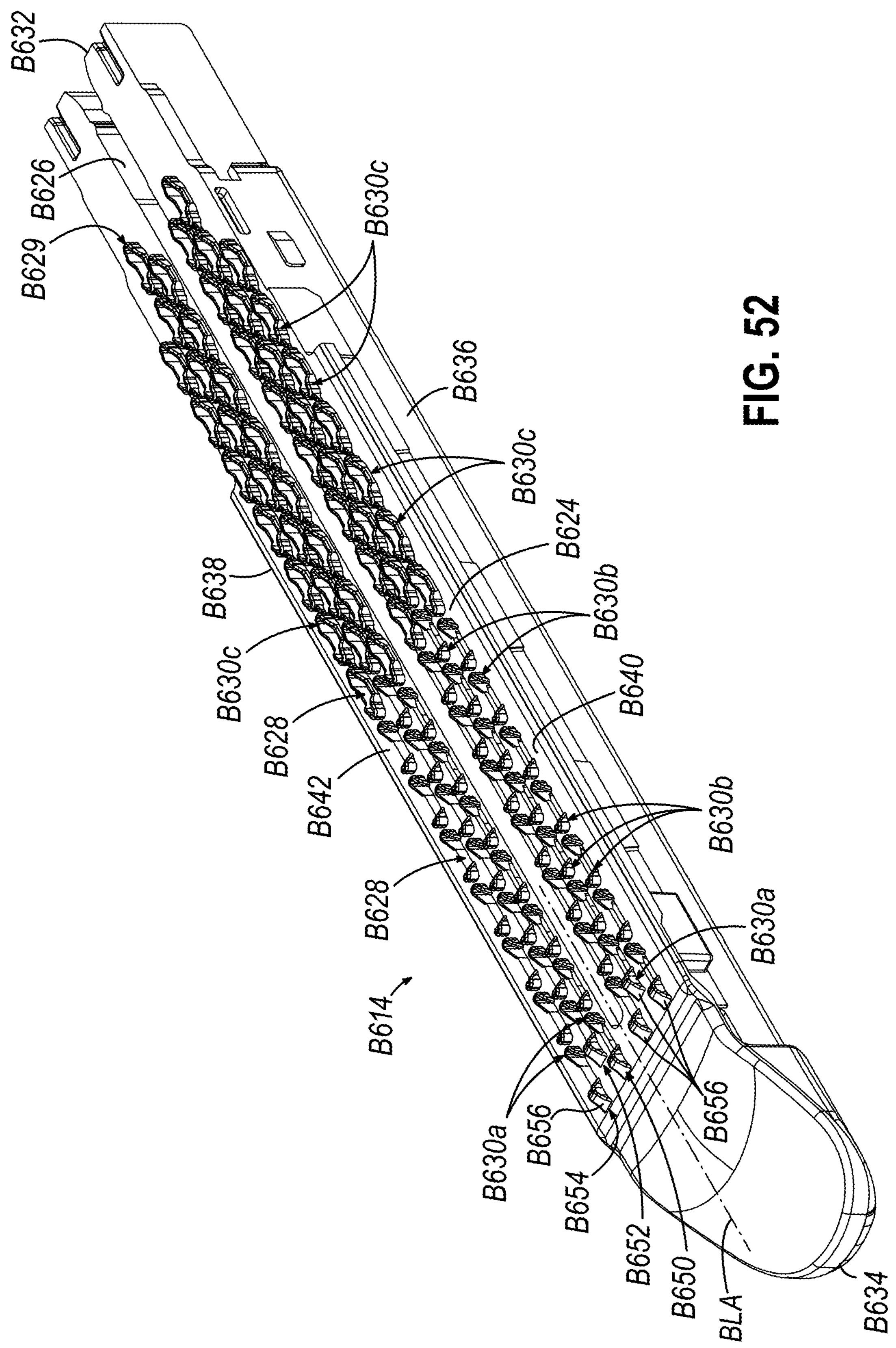
FIG. 52 depicts a perspective view of another example of a cartridge body configured to be incorporated into the staple cartridge of FIG. 24 and the end effector of FIG. 2.
Figure 53:
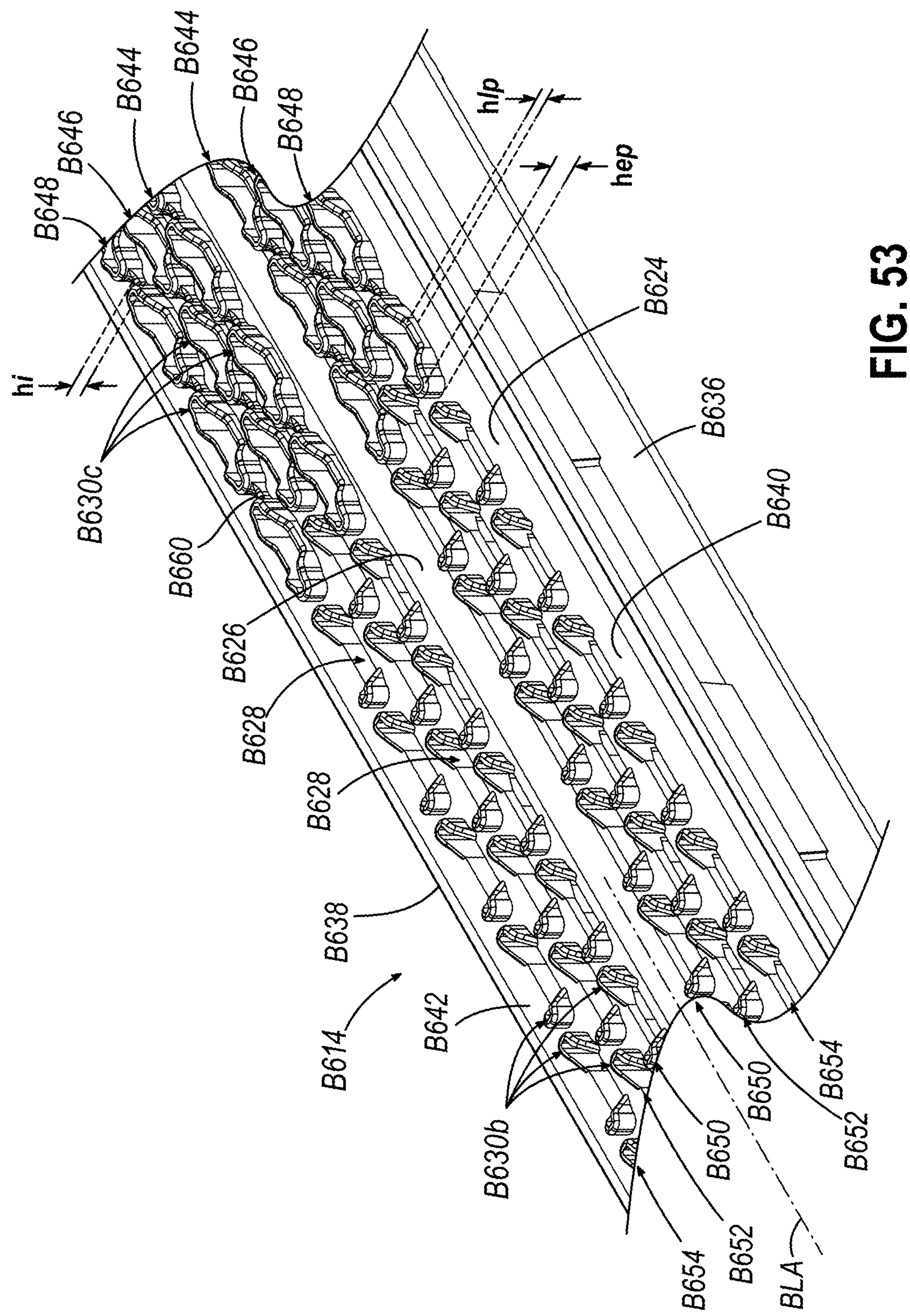
FIG. 53 depicts an enlarged perspective view of the cartridge body of FIG. 52.
Figure 54:
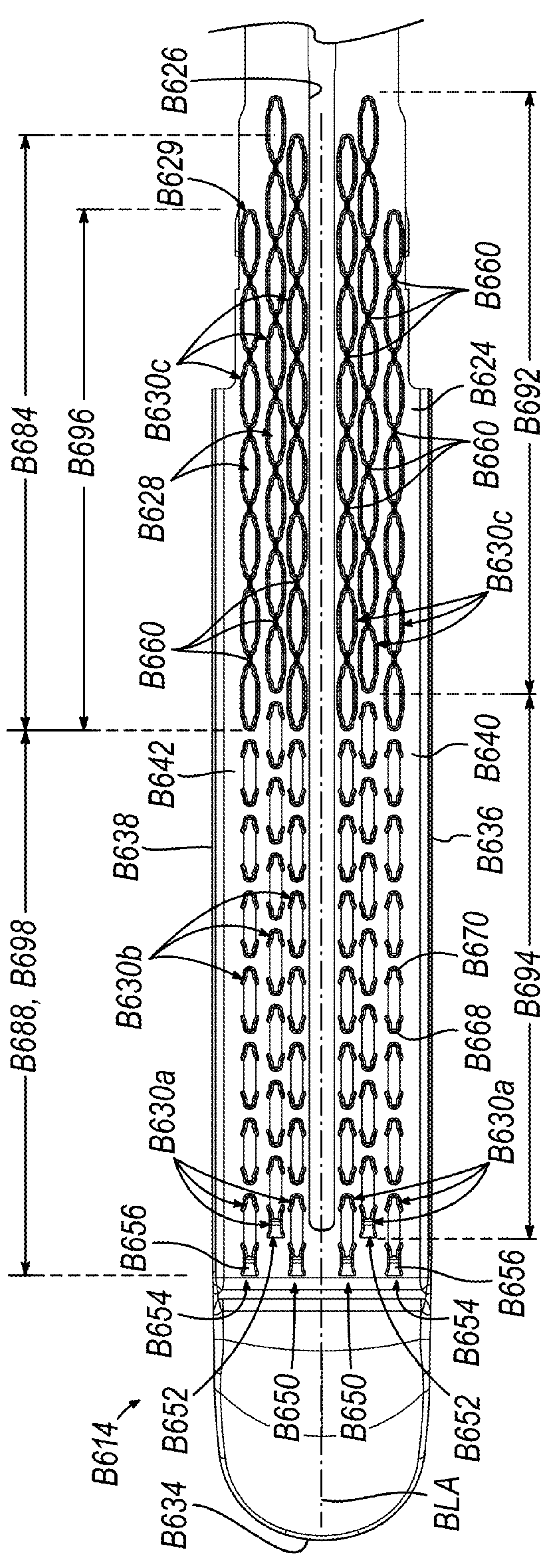
FIG. 54 depicts a partial top plan view of the cartridge body of FIG. 52.

FIGS. 52-54 show another example of a cartridge body (B614) configured to be incorporated into staple cartridge (C110) of FIG. 24 for use with end effector (40) of FIG. 2. Cartridge body (B612) includes a deck (B624), an elongate slot (B626) formed in deck (B624), a plurality of cartridge pockets (B628) formed in deck (B624), and a plurality of engagement protrusions (B630*a*-*c*) extending outwardly from deck (B624). Engagement protrusions (B630*a*-*c*) collectively form an array (B629). Cartridge body (B614) includes a proximal end (B632), a distal end (B634), a first lateral side (B636), and a second lateral side (B638). Second lateral side (B638) is disposed opposite first lateral side (B636). Deck (B624) is configured to compress tissue against an anvil (not shown) but similar to anvil (44). Deck (B624) is defined by cartridge body (B614) and is shown as upwardly facing and substantially planar. Elongate slot (B626) extends along a longitudinal axis (LA) of cartridge body (B614). Elongate slot (B626) opens upwardly through deck (B624) and terminates at a connecting portion (B633). Elongate slot (B626) is configured to slidably receive a knife therein. The knife may be a distal knife portion of a firing beam (not shown), such as distal knife portion (60) of firing beam (46).

Cartridge pockets (B628) are configured to house a plurality of staples (not shown) but similar to staples (C116) and staple drivers (not shown) but similar to staple drivers (C118). Cartridge pockets (B628) are arranged into six longitudinally extending rows. Elongate slot (B626) separates three rows positioned on a first deck side (B640) from three additional rows are positioned a second deck side (B642). These longitudinal rows include inner rows (B644), middle rows (B646), and outer rows (B648). While two inner rows (B644), two middle rows (B646), and two outer rows (B648) are shown, more or fewer rows are also envisioned. Inner rows (B644) are the closest cartridge pockets (B628) relative to elongate slot (B626). In other words, inner rows (B644) are positioned closer to elongate slot (B626) than middle rows (B646), and middle rows (B646) are positioned closer to elongate slot (B626) than outer rows (B648) of cartridge pockets (B628).

Engagement protrusions (B630*a*-*c*) extend from deck (B624) and are configured to grip tissue (T) or an adjunct material (e.g., a buttress) positioned thereon. As will be described below, cartridge body (B614) includes three different configurations of engagement protrusions (B630*a*-*c*). The arrangement of these engagement protrusions (B630*a*-*c*) is symmetric about elongate slot (B626). Second deck side (B642) of cartridge body (B614) is a mirror image of first deck side (B640). Engagement protrusions (B630*a*-*c*) are arranged into a plurality of longitudinally extending rows. These longitudinal rows include inner rows (B650), middle rows (B652), and outer rows (B654). Inner rows (B650) generally correspond with inner rows (B644) of cartridge pockets (B628). Similarly, middle rows (B652) generally correspond with middle rows (B646) of cartridge pockets (B628). Similarly, outer rows (B654) generally correspond with outer rows (B648) of cartridge pockets (B628).

Inner rows (B650) are the closest engagement protrusions relative to elongate slot (B626). In other words, inner rows (B650) of engagement protrusions are positioned closer to elongate slot (B626) than middle rows (B652). Similarly, middle rows (B652) are positioned closer to elongate slot (B626) than outer rows (B654) of engagement protrusions. As shown, inner rows (B650), middle rows (B652), and outer rows (B654) each extend substantially parallel to elongate slot (B626). Each engagement protrusion (B630*a*-*c*) extends within a single row (e.g., one of inner row (B650), middle row (B652), and outer rows (B654)) and does not connect with an adjacent row. Each engagement protrusions (B630*a*) partially surrounds a respective cartridge pocket (B628) of inner row (B644) of cartridge pockets (B628). Each engagement protrusion (B630*c*) completely surrounds a respective cartridge pocket (B628) of inner rows (B644), middle rows (B646), and outer rows (B648) of cartridge pockets (B628). As shown in FIGS. 52 and 54, engagement protrusions (B630*a*) are the distal most engagement protrusions on first and second deck sides (B640, B642). Each engagement protrusion (B630*a*) includes a distal lead-in portion (B656).

As shown in FIG. 54, inner rows (B650) include a first portion (B684) of longitudinally adjacent engagement protrusions (B630*c*) joined by interconnections (B660), and a second portion (B688) of adjacent engagement protrusions (B630*a*-*b*) that are not linked by interconnections (B660). Instead, longitudinally adjacent engagement protrusions (B630*a*-*b*) are spaced apart from each other. As shown, first portion (B684) of inner rows (B650) includes eight longitudinally adjacent engagement protrusions (B630*c*) linked by interconnections (B660). As shown, second portion (B688) of middle rows (B652) includes one engagement protrusion (B630*a*) and six longitudinally adjacent engagement protrusions (B630*b*) not linked together. In other words, first portion (B684) extends longitudinally along about 53% of middle rows (B652), and second portion (B688) extends longitudinally along about 47% middle rows (B652). First portion (B684) is positioned entirely proximal to second portion (B688).

Middle rows (B652) include a first portion (B692) of longitudinally adjacent engagement protrusions (B630*b*) joined by interconnections (B660), and a second portion (B694) of adjacent engagement protrusions (B630*a*-*b*) that are not linked by interconnections (B660). Instead, longitudinally adjacent engagement protrusions (B630*a*-b) are spaced apart from each other. As shown, first portion (B692) of middle rows (B652) includes eight longitudinally adjacent engagement protrusions (B630*d*) linked by interconnections (B660). Second portion (B694) of middle rows (B652) includes one engagement protrusions (B630*a*) and six longitudinally adjacent engagement protrusions (B630*d*) not linked together. In other words, first portion (B692) extends longitudinally along about 53% of middle rows (B652), and second portion (B694) extends longitudinally along about 47% middle rows (B652). These percentages may vary. First portion (B692) is positioned entirely proximal to second portion (B694).

With continued reference to FIG. 54, first portion (B696) of outer rows (B654) includes four adjacent engagement protrusions (B630*d*) longitudinally linked by interconnections (B660). As shown, second portion (B698) of outer rows (B654) includes ten longitudinally adjacent engagement protrusions (B630*a*, B630*d*). In other words, first and second portions (B692, B696) each extend longitudinally along about 50% of outer rows (B654). First portions (B684, B692, B696) form continuous non-linear raised cross-sectional areas. Engagement protrusions (B630*a-d*) and interconnections (B660) selectively apply greater compression along only a predetermined longitudinal length of cartridge body (B614). First portion (B696) is positioned entirely proximal to second portion (B698). Engagement protrusions (B630*a-d*) and interconnections (B660) apply greater compression during initial knife travel and staples (e.g., staples (B116) located adjacent proximal end (B632). This may provide greater clamping pressure adjacent the proximal region where the knife starts cutting tissue (T).

Figure 55:
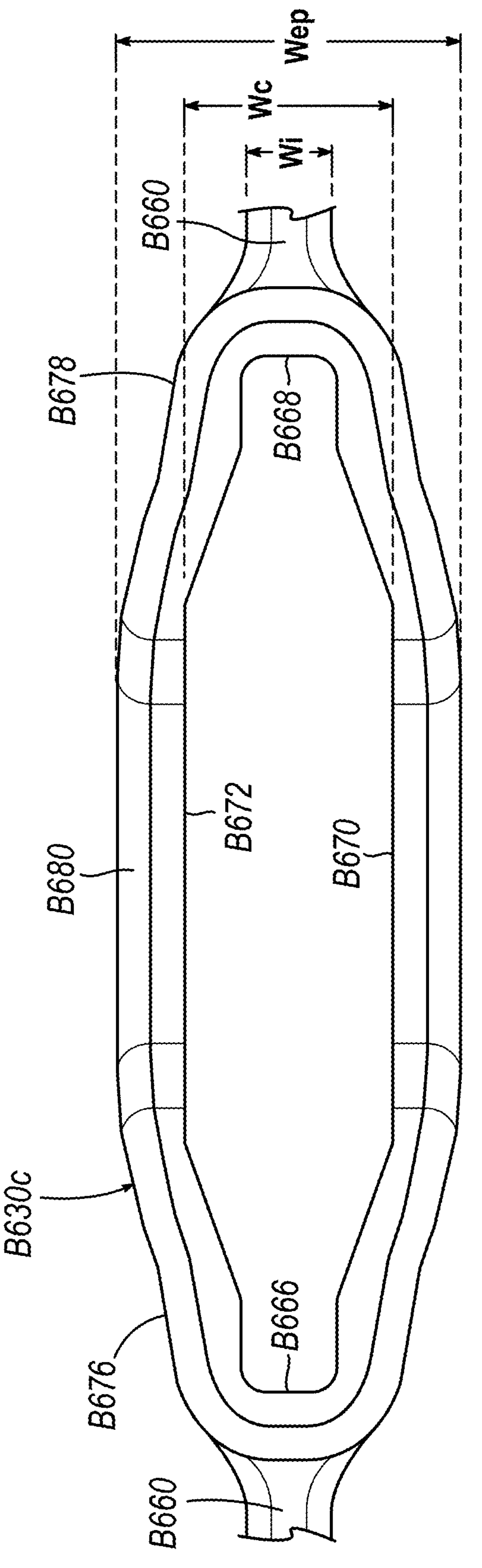
FIG. 55 depicts an enlarged top view of an engagement protrusion and accompanying interconnections completely surrounding a cartridge pocket of the cartridge body of FIG. 54.

As shown in FIG. 55 and as similar to cartridge pocket (C128), cartridge pocket (B628) includes a first longitudinal end (B666), a second longitudinal end (B668), a first lateral side (B670), and a second lateral side (B672). Second longitudinal end (B668) is disposed opposite first longitudinal end (B666). First and second longitudinal ends (B666, B668) are configured to guide legs (C117) of staples (C116) (see FIG. 24). First lateral side (B670) is disposed between first and second longitudinal ends (B666, B668). Second lateral side (B672) is disposed between first and second longitudinal ends (B666, B668) and opposite to first lateral side (B670). As shown, first and second lateral sides (B670, B672) of cartridge pocket (B628) extend substantially parallel to elongate slot (B626). Engagement protrusion (B630*c*) includes a first end portion (B676), a second end portion (B678), and a lateral portion (B680). First end portion (B676) wraps around first longitudinal end (B666) of cartridge pocket (B628). Similarly, second end portion (B678) wraps around second longitudinal end (B668) of cartridge pocket (B628). Lateral portion (B680) extends longitudinally between first and second end portions (B676, B678) on both of first and second lateral sides (B670, B672) of cartridge pocket (B628). Lateral portion (B680) extends continuously between first and second end portions (B676, B678) of engagement protrusion (B630*c*). Engagement protrusions (B630*c*) are configured to provide greater compression than engagement protrusions (B630*a-b*). Interconnections (B660) extend between second end portion (B678) of engagement protrusion (B630*a*) and first end portion (B676) of adjacent engagement protrusion (B630*c*). Similar to engagement protrusion (B630*c*), engagement protrusions (B630*a-b*) include a first end portion (B676) and a second end portion (B678). Engagement protrusions (B630*a-b*) do not extend along first lateral side (B670) or second lateral side (B672) of cartridge pocket (B628) such that first lateral side (B670) and second lateral side (B672) open directly to deck (B624).

As shown in FIG. 53, each engagement protrusion (B630*a-c*) has the same height (e.g., extends away from deck (B624) the same distance). First and second end portions (B676, B678) of engagement protrusions (B630*d-c*) extend from deck (B624) a maximum height (Bhep). Lateral portions (B680) of engagement protrusions (B630*c*) extend from deck (B624) a maximum height (Bhlp). Interconnections (B660) extend from deck (B624) a maximum height (Bhi). As shown, maximum height (Bhep) of first and second end portions (B676, B678) is greater than maximum height (Bhi) of interconnections (B660). For example, maximum height (Bhi) of interconnections (B660) and maximum height of (Bhlp) of lateral portions (B680) may be each about half of maximum height (Bhep) of first and second end portions (B676, B678).

As shown in FIG. 55, engagement protrusions (B630*a-c*) have a maximum width (BWp) in the direction transverse to longitudinal axis (LA). Interconnection (B660) has a maximum width (BWi) in the direction transverse to longitudinal axis (LA). Maximum width (BWp) of engagement protrusion (B630*d*) is greater than maximum width (BWi) of interconnection (B660). Cartridge pocket (B628) has a maximum width (BWc) defined by a distance between first and second lateral sides (B670, B672) of cartridge pocket (B628) in the direction transverse to longitudinal axis (LA). Maximum width (BWc) of cartridge pocket (B628) is greater than maximum width (BWi) of interconnection (B660). First and second end portions (B676, B678) have a maximum width (BWep) in the direction transverse to longitudinal axis (LA) that is greater than maximum width (BWi) of interconnection (B660).

K. Eleventh Example of a Cartridge Body

Figure 56:
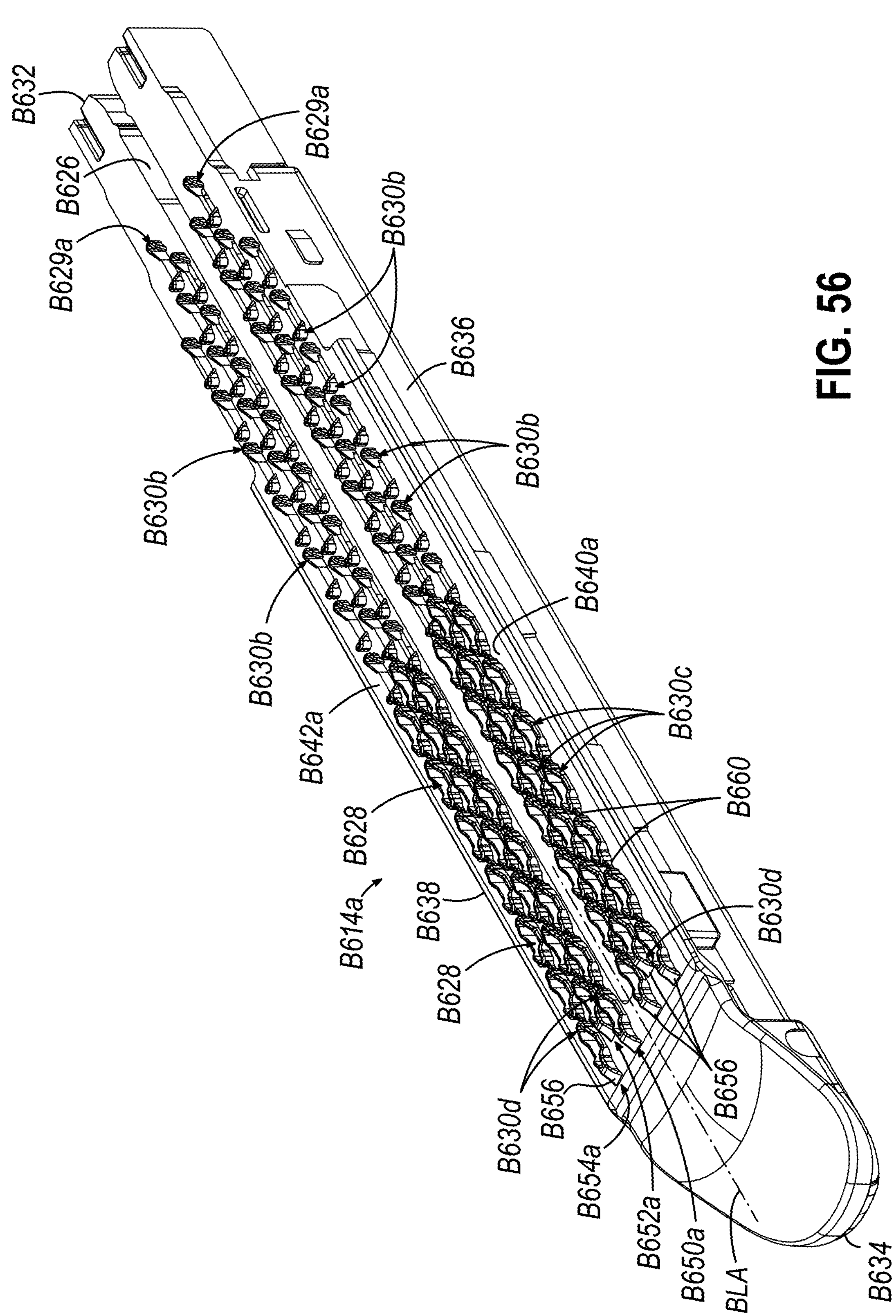
FIG. 56 depicts a perspective view of another example of a cartridge body configured to be incorporated into the staple cartridge of FIG. 24 and the end effector of FIG. 2.
Figure 57:
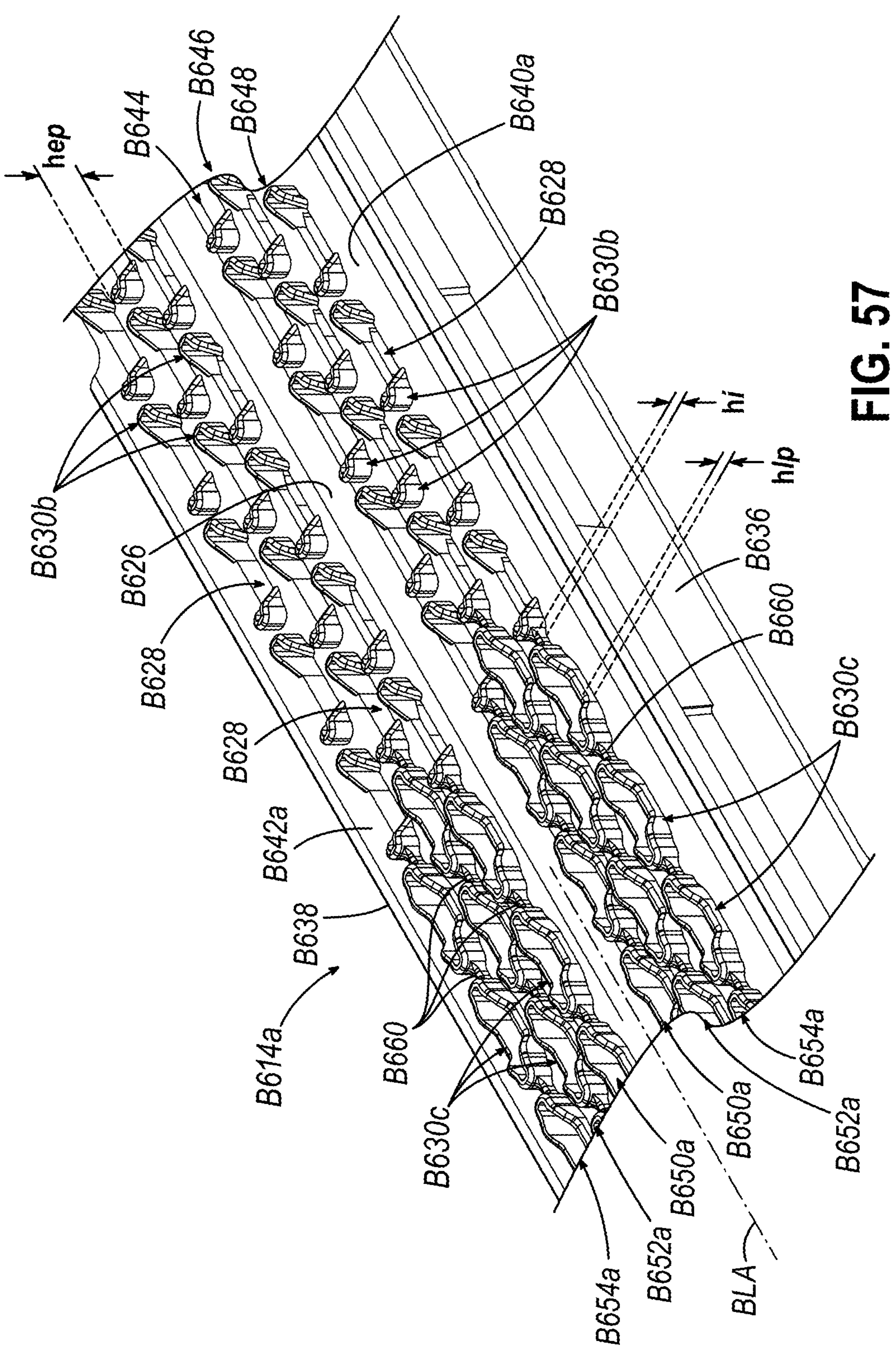
FIG. 57 depicts an enlarged perspective view of a portion of the cartridge body of FIG. 56.
Figure 58:
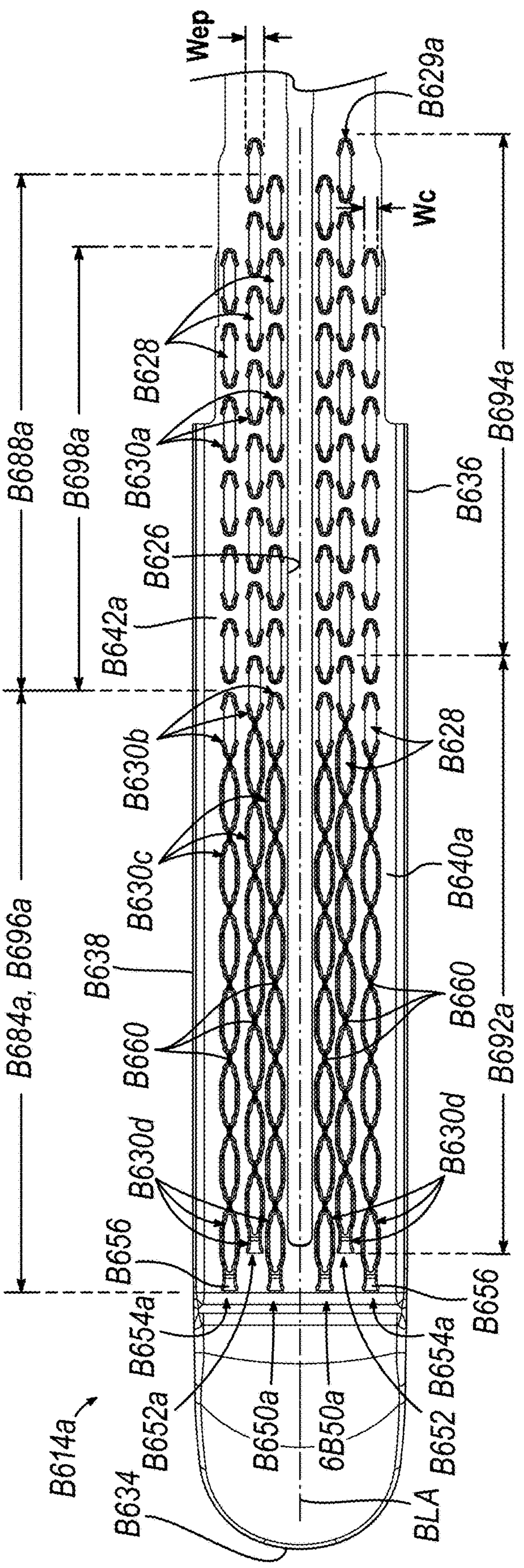
FIG. 58 depicts a top plan view of the cartridge body of FIG. 55.

FIGS. 56-58 show another example of a cartridge body (B614*a*) configured to be incorporated into staple cartridge (C110) of FIG. 24 for use with end effector (40) of FIG. 2. Similar to cartridge body (B614), cartridge body (B614*a*) includes a deck (B624*a*), an elongate slot (B626) formed in deck (B624*a*), a plurality of cartridge pockets (B628) formed in deck (B624*a*), and a plurality of engagement protrusions (B630*b-d*) extending outwardly from deck (B624*a*). Engagement protrusions (B630*a-c*) collectively form an array (B629*a*). Each cartridge pocket (B628) is configured to slidably house an unformed staple (not shown) but similar to staple (B116) and a respective staple driver (not shown) but similar to staple driver (C118). Similar to cartridge body (B614), cartridge body (B614*a*) include inner rows (B644), middle rows (B646), and outer rows (B648) of cartridge pockets (B628). Similar to cartridge body (B614), cartridge body (B614*a*) includes engagement protrusions (B630*a-d*) extending from deck (B624*a*) that are configured to grip tissue (T) or an adjunct material (e.g., a buttress) positioned thereon. Second deck side (B642*a*) is a mirror image of first deck side (B640*a*). Longitudinal rows of engagement protrusions include inner rows (B650*a*), middle rows (B652*a*), and outer rows (B654*a*) that generally correspond to inner rows (B644), middle rows (B646), and outer rows (B648), respectively.

Inner rows (B650*a*) include a first portion (B684*a*) of longitudinally adjacent engagement protrusions (B630*b-d*) joined by interconnections (B660), and a second portion (B688*a*) of adjacent engagement protrusions (B630*b*) that are not linked by interconnections (B660). Instead, longitudinally adjacent engagement protrusions (B630*b*) of second portion (B688*a*) are spaced apart from each other. Moving proximally, first portion (B684*a*) of inner rows (B650*a*) includes one engagement protrusions (B630*d*), six longitudinally adjacent engagement protrusions (B630*c*), and one engagement protrusion (B630*b*) linked by interconnections (B660). As shown, second portion (B688*a*) of inner rows (B650*a*) includes six longitudinally adjacent engagement protrusions (B630*b*) not linked together. In other words, first portion (B684*a*) extends longitudinally along about 53% of inner rows (B650*a*), and second portion (B688*a*) extends longitudinally along about 47% of inner rows (B650*a*). Unlike first and second portions (B684, B688) of FIGS. 52-54, first portion (B684*a*) is positioned entirely distal to second portion (B688*a*).

Middle rows (B652*a*) include a first portion (B692*a*) of longitudinally adjacent engagement protrusions (B630*b*-*d*) joined by interconnections (B660), and a second portion (B694*a*) of adjacent engagement protrusions (B630*b*) that are not linked by interconnections (B660). Instead, longitudinally adjacent engagement protrusions (B630*b*) of second portion (B694*a*) are spaced apart from each other. Moving proximally, first portion (B692*a*) of middle rows (B652*a*) includes one engagement protrusions (B630*d*), six longitudinally adjacent engagement protrusions (B630*c*), and one engagement protrusion (B630*b*) linked by interconnections (B660). As shown, second portion (B688*a*) of middle rows (B652*a*) includes seven longitudinally adjacent engagement protrusions (B630*b*) not linked together. In other words, first portion (B692*a*) extends longitudinally along about 53% of middle rows (B652*a*), and second portion (B694*a*) extends longitudinally along about 47% of middle rows (B652*a*). Unlike first and second portions (B692, B694) of FIGS. 52-54, first portion (B692*a*) is positioned entirely distal to second portion (B694*a*).

Outer rows (B654*a*) include a first portion (B696*a*) of longitudinally adjacent engagement protrusions (B630*b*-*d*) joined by interconnections (B660), and a second portion (B698*a*) of adjacent engagement protrusions (B630*b*) that are not linked by interconnections (B660). Instead, longitudinally adjacent engagement protrusions (B630*b*) of second portion (B698*a*) are spaced apart from each other. Moving proximally, first portion (B696*a*) of outer rows (B654*a*) includes one engagement protrusions (B630*d*), six longitudinally adjacent engagement protrusions (B630*c*), and one engagement protrusion (B630*b*) linked by interconnections (B660). As shown, second portion (B698*a*) of outer rows (B654*a*) includes seven longitudinally adjacent engagement protrusions (B630*b*) not linked together. In other words, first portion (B696*a*) extends longitudinally along about 57% of outer rows (B654*a*), and second portion (B698*a*) extends longitudinally along about 43% of outer rows (B654*a*). Unlike first and second portions (B696, B698) of FIGS. 52-54, first portion (B692*a*) is positioned entirely distal to second portion (B694*a*). First portions (B684, B692, B696) each form continuous non-linear raised cross-sectional areas, except along engagement protrusions (B630*b*) that do not include a lateral portion. First portions (B684*a*, B692*a*, B696*a*) selectively apply greater compression along a distal portion as compared to second portions (B686*a*, B694*a*, B698*a*) along a proximal portion. Similar to cartridge body (B614), maximum height (Bhep) of first and second end portions (B676, B678) is greater than maximum height (Bhi) of interconnections (B660) and maximum height of (Bhlp) of lateral portions (B680). Similar to cartridge body (B614), first and second end portions (B676, B678) have a maximum width (BWep) that is greater than maximum width (BWc) of cartridge pocket (B628).

L. Twelfth Example of a Cartridge Body

FIGS. 59-62C show another example of a cartridge body (B80100) configured to be incorporated into stapler cartridge (C110) of FIG. 24 for use with end effector (40) of FIG. 2. Cartridge body (B80100) comprises a proximal end (B80102) and a distal end (B80104), a deck surface (B80106) that extends between proximal end (B80102) and distal end (B80104) and is configured to oppose an anvil of the end effector. The cartridge body further comprises a base surface (B80108) that is opposite the deck surface (B80106). A longitudinal slot (B80110) is defined in cartridge body (B80100). Longitudinal slot (B80110) extends from the proximal end (B80102) toward the distal end (B80104) and is sized to receive a sled driver, or firing actuator, to eject staples out of cartridge body (B80100) during a staple firing stroke. Various aspects of staple cartridges are described in greater detail in U.S. Pat. No. 9,844,369, the disclosure of which is herein incorporated by reference in its entirety.

Figure 59:
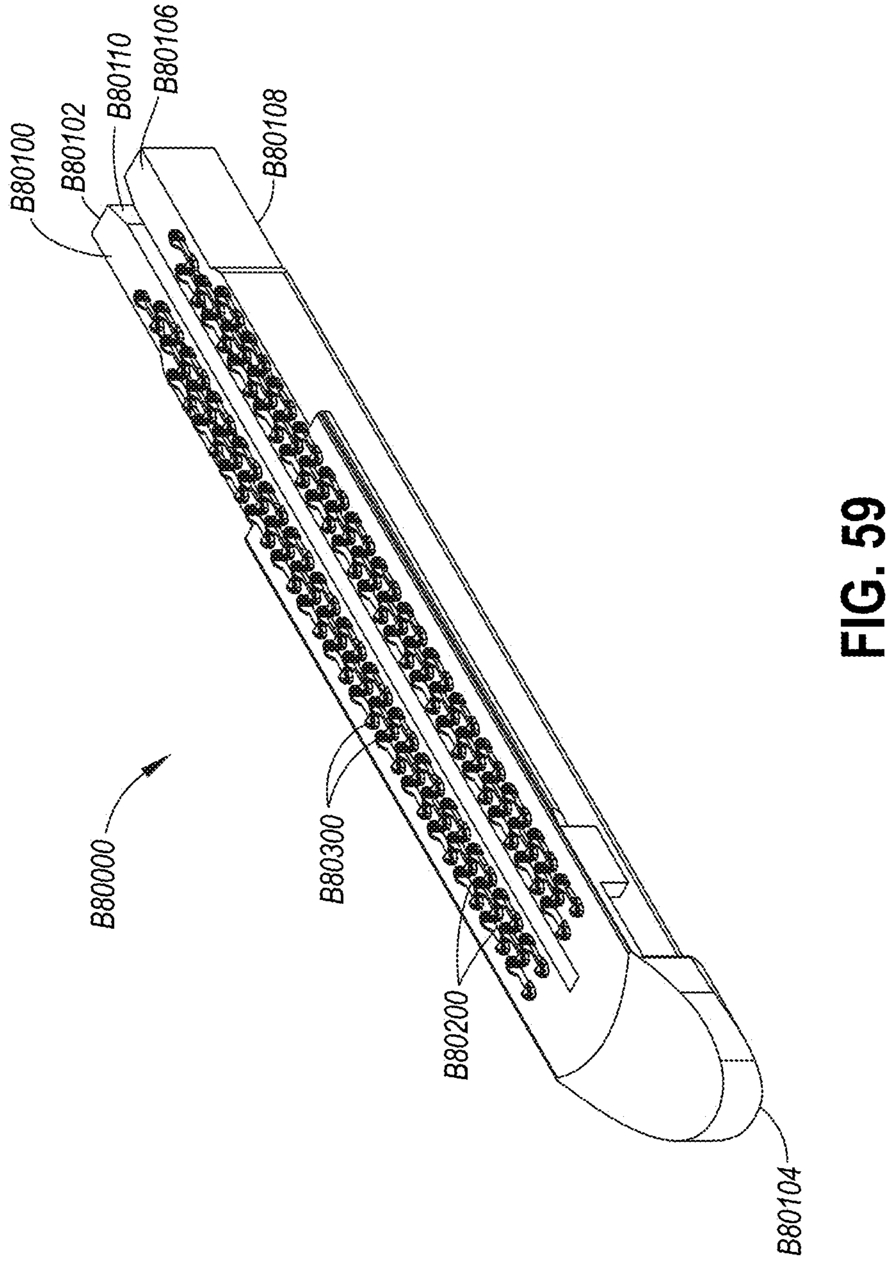
FIG. 59 depicts a perspective view of another example of a cartridge body configured to be incorporated into the staple cartridge of FIG. 24 and the end effector of FIG. 2.

Staples are removably stored in staple cavities (B80200) (also referred to as cartridge pockets) defined in the cartridge body (B80100). As illustrated in FIG. 59, six longitudinal rows of staple cavities are defined in the cartridge body (B80100); however, any suitable number of staple cavity rows and/or staple cavities is envisioned and can be selected based on the particular surgical procedure, for example. Out of the six longitudinal rows of staple cavities shown in FIG. 59, three longitudinal rows are defined on each side of the longitudinal slot (B80110).

As can be seen in FIG. 59, projections (B80300) (also referred to as engagement protrusions) are integrated, or integrally-formed, with the cartridge body (B80100) and extend away from the deck surface (B80106). Multiple, discrete projections (B80300) surround at least a portion of the staple cavities (B80200) defined in the cartridge body (B80100). As described in greater detail herein, various features of the projections (B80300) including projection width, height, and/or overall geometry (sometimes referred to herein as "projection configuration") can be modified to maximize a gripping strength of staple cartridge (B110) while also minimizing any damage to an adjacent article, such as patient tissue or an adjunct material. A geometry of proximal projections may comprise a sharp tissue-facing interface to prevent the adjacent article from unintentional displacement while a geometry of distal projections may comprise a smooth tissue-facing interface to prevent damage to the adjacent article as the adjacent article is positioned adjacent the cartridge deck.

Projections (B80300) allow for numerous benefits including gripping an adjacently positioned article, such as an adjunct layer or patient tissue, against the deck surface (B80106). The placement of the projections (B80300) around at least a portion of the staple cavities (B80200) secures the adjacent article in place, or otherwise prevents unwanted movement of the adjacent article, as staples are ejected from the cavities and/or the adjacent article is severed during a staple firing and tissue cutting stroke. An additional benefit realized by the placement of the projections (B80300) around at least a portion of the staple cavities includes guidance for the staples as the staples are fired, or otherwise ejected, from the cartridge body (B80100) and formed against an anvil during a staple firing stroke. The support provided by the projections (B80300) may also help to maintain a desired, upright orientation of the staples as the staples exit the staple cavities (B80200) during the firing stroke.

Maintenance of the adjacent article or adjunct material in its desired position by the staple cavities (B80200) is desirable to achieve a uniform staple line. In instances where the adjacent article slips or otherwise moves out of its desired position alongside the staple cavities (B80200), the staples ejected out of the staple cavities (B80200) may fail to encounter the adjacent article and/or encounter a thicker adjacent article as the staples are formed. Such inconsistencies in the adjacent article can result in a non-uniform staple line having staples formed to unwanted different heights which can lead to complications such as a non-sealed tissue cut line and/or tissue trauma, for example.

Given the universal desire for optimizing the integrity retention of the adjacent article, for example, the degree of gripping strength across the deck surface need not be uniform. As such, these considerations must be weighed against one another in designing a topography of the cartridge deck. For example, portions of an adjacent article positioned nearest the longitudinal slot of the staple cartridge are subject to greater displacement forces as the sled driver, or firing actuator, is longitudinally traversed through the staple cartridge during a staple firing stroke. In such instances, to avoid having the same intensity of gripping strength across the entire deck surface, and thus, risking the integrity of the entire adjacent article, the deck surface can provide a targeted, greater degree of gripping functionality alongside the longitudinal slot. In such instances, other lateral portions of the deck surface have a decreased, or non-enhanced, gripping functionality.

Additionally, a larger force is necessarily experienced by the adjacent article as a distally-advancing sled driver initially cuts, or otherwise traverses, through the adjacent article. For example, when cutting and stapling a target tissue requiring multiple firings, a first staple cartridge is employed to cut and attach a first adjunct or adjuncts to a first portion of the target tissue. Thereafter, the spent staple cartridge is replaced with a fresh cartridge and a corresponding second adjunct or second adjuncts are positioned in the end effector. The end effector jaws are positioned so that a proximal end of the second adjunct or adjuncts is overlapped with the distal end of the stapled first adjunct or adjuncts and then the jaws are closed to clamp the remaining portion of target tissue between the second adjunct(s) and the jaws. As the sled driver or firing actuator is driven distally, the knife on the firing actuator contacts the overlapping adjunct materials. If the second adjunct materials are permitted to move during this process, the second adjuncts may bunch or "plow" which could cause the second adjuncts to detrimentally affect the staple formation process. This undesirable plowing or bunching is more likely to occur when the knife of the firing actuator or sled driver initially contacts the second adjunct and somewhat diminishes as the sled driver proceeds through the staple cartridge. Thus, it is desirable for the projections located at the proximal end of the staple cartridge to be more aggressive than those in the middle and distal portion of the cartridge. For example, as will be discussed in further detail below, the proximal projections may be higher than the projections in a middle portion of the cartridge and the middle projections may extend higher than the distal projections located in the distal portion of the cartridge. The proximal projections may also be more robust than the middle and distal projections which can address such problem and prevent movement of the adjunct(s) during such stapling operations. As such, the deck surface can provide a greater degree of gripping strength in proximal portions of the deck surface. Given the location-specific benefits of having gripping strength across the cartridge deck, the features impacting the degree of gripping strength can vary longitudinally and/or laterally across the deck surface. Such variances are discussed in greater detail herein.

Figure 60:
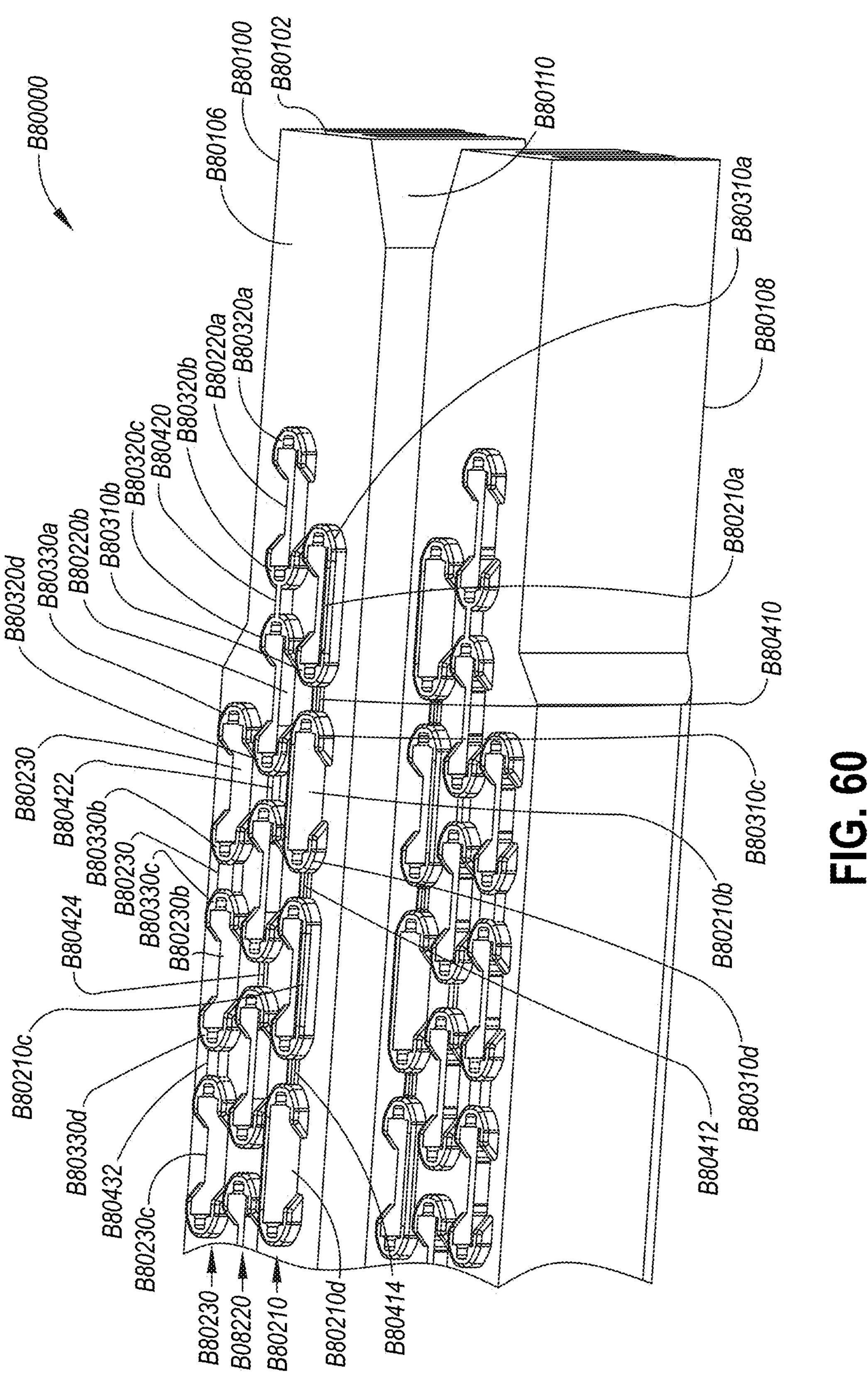
FIG. 60 depicts a partial perspective view of the cartridge body of FIG. 59, the cartridge body including a plurality of projections above a deck surface of the cartridge body.
Figure 61:
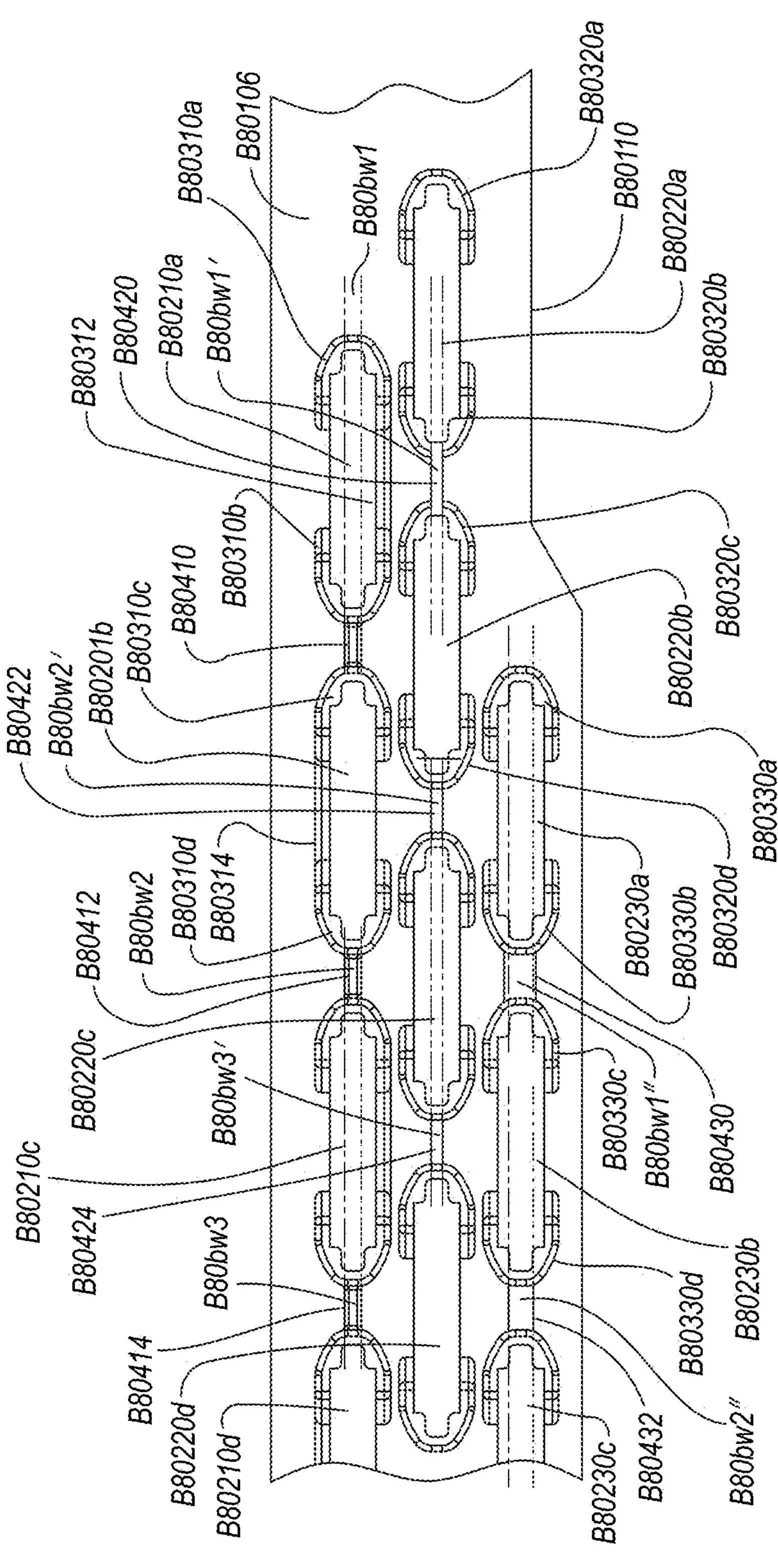
FIG. 61 depicts a partial plan view of the projections extending above the deck surface of the cartridge body of FIG. 59.

Referring now to FIGS. 60 and 61, a portion of cartridge body (B80100) is shown. As described with respect to FIG. 61, three longitudinal rows of staple cavities are defined in the cartridge body (B80100) on each side of the longitudinal slot (B80110). For brevity, the topography with respect to a first side of the longitudinal slot is discussed herein in detail; however, it is envisioned the topography of the deck surface on the first side of the longitudinal slot is mirrored onto the deck surface on the second side of the longitudinal slot. Other arrangements are contemplated wherein the topography of the deck surface on one side of the longitudinal slot differs from the topography of the deck surface on an opposite side of the longitudinal slot. As shown, a first longitudinal row of staple cavities (B80210) extends alongside the longitudinal slot (B80110), a second longitudinal row of staple cavities (B80220) extends alongside the first longitudinal row of staple cavities (B80210), and a third longitudinal row of staple cavities (B80230) extends alongside the second longitudinal row of staple cavities (B80220). The first, second, and third longitudinal rows of staple cavities (B80210, B80220, B80230) are defined on a first side of the longitudinal slot (B80110).

The first longitudinal row of staple cavities (B80210) includes a proximal-most staple cavity (B80210*a*). Each proximal-most staple cavity (B80210*a*) comprises corresponding first or proximal projection configuration (B80211*a*). Each first projection configuration (B80211*a*) comprises a first projection (B80310*a*) that surrounds a proximal portion of the proximal-most staple cavity (B80210*a*), and a second projection (B80310*b*) that surrounds a distal portion of the proximal-most staple cavity (B80210*a*). A first intermediate projection (B80312) surrounds an intermediate portion of the proximal-most staple cavity (B80210*a*) and extends between the first projection (B80310*a*) and the second projection (B80310*b*).

A second staple cavity (B80210*b*) is positioned distal to the proximal-most cavity (B80210*a*) in the first longitudinal row of staple cavities (B80210). Each staple cavity (B80210*b*) comprises a corresponding second or middle projection configuration (B80211*b*). Each second projection configuration (B80211*b*) comprises a third projection (B80310*c*) that surrounds a proximal portion of the second staple cavity (B80210*b*), and a fourth projection (B80310*d*) that surrounds a distal portion of the second staple cavity (B80210*b*). A second intermediate projection (B80314) surrounds an intermediate portion of the second staple cavity (B80210*b*) and extends between the third projection (B80310*c*) and the fourth projection (B80310*d*). As shown in FIG. 61, the second intermediate projection (B80314) surrounds an intermediate portion of the second staple cavity (B80210*b*) on a single side of the staple cavity. In other instances, the second intermediate projection (B80314) can surround an intermediate portion of the second staple cavity (B80210*b*) on both sides of the staple cavity. Furthermore, the second intermediate projection (B80314) is present on a side of the second staple cavity (B80210*b*) that is opposite from the side of the first staple cavity (B80210*a*) on which the first intermediate projection (B80312) is present. In such arrangement, the first projection configuration differs from the second projection configuration.

Figure 62A:
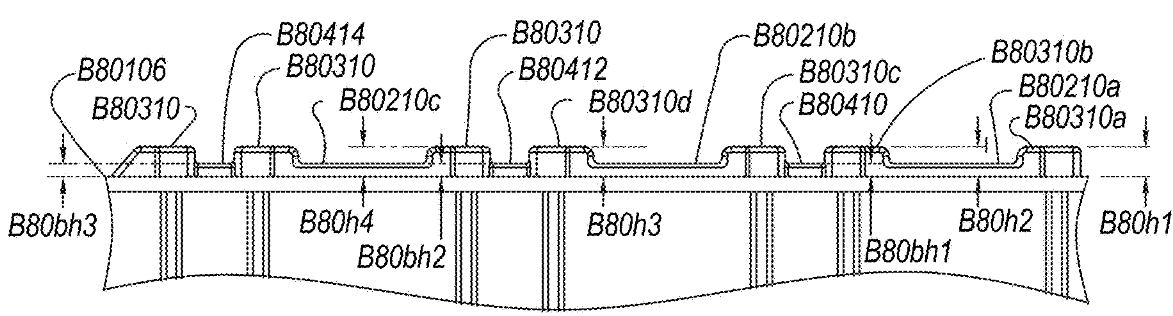
FIG. 62A depicts a partial elevational view of the projections extending above the deck surface of a first longitudinal row of staple cavities of the cartridge body of FIG. 59.

The first projection (B80310*a*) extends from the deck surface (B80106) to a first height (B80*h*1), the second projection (B80310*b*) extends from the deck surface (B80106) to a second height (B80*h*2). The third projection (B80310*c*) extends from the deck surface (B80106) to a third height (B80*h*3), and the fourth projection (B80310*d*) extends from the deck surface (B80106) to a fourth height (B80*h*4). As depicted in FIGS. 60 and 62A, the first, second, third, and fourth heights are the same.

The first intermediate projection (B80312) extends from the deck surface (B80106) to a fifth height, and the second intermediate projection (B80314) extends from the deck surface (B80106) to a sixth height. The fifth height is the same as the sixth height; however, in other instances, the heights to which the intermediate projections extend can differ across the staple cartridge.

The fifth height of the first intermediate projection (B80312) is different than the first and second heights of the first and second projections (B80310*a*, B80310*b*), respectively. In the illustrated arrangement, the fifth height is less than the first and second heights. The sixth height of the second intermediate projection (B80314) is different than the third and fourth heights of the third and fourth projections (B80310*c*, B80310*d*), respectively. In the illustrated arrangement, the sixth height is less than the third and fourth heights. In other instances, the intermediate projection can extend from the deck surface to a height that is the same as the projections between which the intermediate projection extends.

The projections surrounding adjacent staple cavities, or portions thereof, can be directly connected to one another by a bridge projection (also referred to as an interconnection). Stated another way, the second projection of the proximal-most staple cavity is connected to the third projection of the second staple cavity by a longitudinally-extending bridge projection. Connecting bridges improve the holding and/or gripping of the adjacent article to the cartridge body by providing increased surface area for the adjacent article to contact, or otherwise interact with. In the absence of such connecting bridges, the adjacent article requires application of a significant force to engage additional cartridge surfaces absent the projections. Stated another way, the adjacent article requires a significant force to become engaged with the deck surface in the crevices, or valleys, formed between surrounding projections. However, during such force application, the adjacent article is likely to move out its desired position and/or become damaged.

In particular, the second projection (B80310*b*) of the proximal-most staple cavity (B80210*a*) in the first longitudinal row of staple cavities (B80210) is directly connected to the third projection (B80310*c*) of the second staple cavity (B80210*b*) by the bridge projection (B80410). See FIGS. 61 and 62A. The bridge projection (B80410) extends from the deck surface (B80106) to a first bridge height (B80*bh*1) (FIG. 62A) and extends laterally a first bridge width (B80*bw*1) (FIG. 61). The first bridge height is different than the second and third heights of the second and third projections (B80310*b*, B80310*c*), respectively. More specifically, the first bridge height is shorter than the second and third heights of the second projection and third projection, respectively.

A second bridge projection (B80412) connects the fourth projection (B80310*d*) to a projection surrounding a third staple cavity (B80210*c*) that is distal to the second staple cavity (B80210*b*). Each third staple cavity (B80210*c*) comprises a corresponding third or distal projection configuration (B80211*c*). Each third projection configuration (B80211*c*) comprises a fifth projection (B80310*c*) that surrounds a proximal portion of the third staple cavity (B80210*c*), and a sixth projection (B80310*f*) that surrounds a distal portion of the third staple cavity (B80210*c*). The second bridge projection (B80412) extends from the deck surface (B80106) to a second bridge height (B80*bh*2) and extends laterally a second bridge width (b80*bw*2). A third bridge projection (B80414) connects a projection surrounding a distal portion of the third staple cavity (B80210*c*) to a projection surrounding a proximal portion of the fourth staple cavity (B80210*d*). The third bridge projection (B80414) extends from the deck surface (B80106) to a third bridge height (B80*bh*3) and extends laterally a third bridge width (B80*bw*3). As depicted in FIGS. 60-62A, the first bridge height, the second bridge height, and the third bridge height are the same. Furthermore as shown in FIG. 61, the first bridge width, the second bridge width, and the third bridge width are the same. While the bridge projections can continue to directly connect the projections of longitudinally-adjacent staple cavities, FIGS. 60, 61, and 62A depict bridge projections directly connecting the projections of only a proximal set of the first longitudinal row of staple cavities (B80210) (located only in a corresponding proximal portion of the staple cartridge body). Notably, no bridge projection is depicted distal to the fourth staple cavity (B80210*d*) in the first longitudinal row of staple cavities (B80210).

The second longitudinal row of second staple cavities (B80220) includes a second proximal-most staple cavity (B80220*a*). Each second proximal-most staple cavity (B80220*a*) comprises a corresponding second proximal projection configuration (B80221*a*). The second proximal projection configuration (B80221*a*) comprises a first projection (B80320*a*) that surrounds a proximal portion of the proximal-most staple cavity (B80220*a*), and a second projection (B80320*b*) that surrounds a distal portion of the proximal-most staple cavity (B80220*a*). A second staple cavity (B80220*b*) is positioned distal to the proximal-most staple cavity (B80220*a*) in the second longitudinal row of staple cavities (B80220). Each second staple cavity comprises a corresponding second projection configuration (B80221*b*). The second projection configuration comprises a third projection (B80320*c*) that surrounds a proximal portion of the second staple cavity (B80220*b*), and a fourth projection (B80320*d*) that surrounds a distal portion of the second staple cavity (B80220*b*).

Figure 62B:
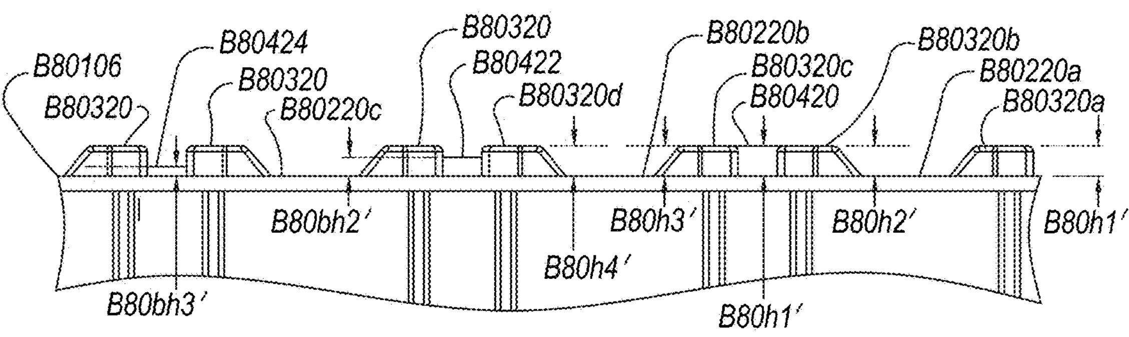
FIG. 62B depicts another partial elevational view of the projections extending above the deck surface of a second longitudinal row of staple cavities of the cartridge body of FIG. 59.

The first projection (B80320*a*) extends from the deck surface (B80106) to a first height (B80*h*1'), and the second projection (B80320*b*) extends from the deck surface (B80106) to a second height (B80*h*2'). The third projection (B80320*c*) extends from the deck surface (B80106) to a third height (B80*h*3'), and the fourth projection (B80320*d*) extends from the deck surface (B80106) to a fourth height (B80*h*4'). As depicted in FIGS. 60 and 62B, the first, second, third, and fourth heights are the same.

The second projection (B80320*b*) of the proximal-most staple cavity (B80220*a*) from the second longitudinal row of staple cavities (B80220) is directly connected to the third projection (B80320*c*) of the second staple cavity (B80220*b*) by a bridge projection (B80420). The bridge projection (B80420) extends from the deck surface (B80106) to a first bridge height (B80*bh*1') and extends laterally a first bridge width (B80*bw*1'). As depicted in FIGS. 60 and 62B, the first bridge height (B80*bh*1') is the same as the second and third heights (B80*h*1', B80*h*2', B80*h*3') of the second and third projections (B80320*b*, B80320*c*), respectively.

Still referring to FIG. 61, a third staple cavity (B80220*c*) is located distal to the second staple cavity (B80220*b*). The third staple cavity (B80220*c*) comprises a third projection configuration (B80221*c*) that is the same or similar to the second projection configuration (B80221*b*). In the illustrated arrangement, a second bridge projection (B80422) connects the fourth projection (B80320*d*) to a projection surrounding the third staple cavity (B80220*c*). The second bridge projection (B80422) extends from the deck surface (B80106) to a second bridge height (B80*bh*2') and extends laterally a second bridge width (B80*bw*2'). As depicted in FIGS. 60 and 62B, the second bridge height (B80*bh*2') is less than the first bridge height (B80*bh*1'), and the second bridge height (B80*bh*2') is less than the fourth height (B80*h*4') of the fourth projection (B80320*d*).

A fourth staple cavity (B80220*d*) is located distal to the third staple cavity (B80220*c*). The fourth staple cavity (B80220*d*) comprises a fourth projection configuration (B80221*d*) that is the same or similar to the third projection configuration (B80221*c*). A third bridge projection (B80424) connects a projection surrounding a distal portion of a third staple cavity (B80210*c*) to a projection surrounding a proximal portion of a fourth staple cavity (B80210*d*). The third bridge projection (B80424) extends from the deck surface (B80106) to a third bridge height (B80*bh*3') and extends laterally a third bridge width (B80*bw*3'). As depicted in FIGS. 60, 61, and 62B, the third bridge height (B80*bh*3') is less than the first and second bridge heights (B80*bh*1', B80*bh*2'); however, the first bridge width (B80*bw*1'), the second bridge width (B80*bw*2'), and the third bridge width (B80*bw*3') are the same. While the bridge projections can continue to directly connect the projections of longitudinally-adjacent staple cavities, FIGS. 60, 61, and 62B depict bridge projections directly connecting the projections of only a proximal set of the second longitudinal row of staple cavities (B80220). Notably, no bridge projection is depicted distal to the fourth staple cavity (B80220*d*) in the second longitudinal row of staple cavities (B80220).

The third longitudinal row of staple cavities (B80230) includes a proximal-most staple cavity (B80230*a*). Each staple cavity (B80230*a*) comprises a first projection configuration (B80231*a*). The first projection configuration (B80231*a*) comprises a first projection (B80330*a*) that surrounds a proximal portion of the proximal-most staple cavity (B80230*a*), and a second projection (B80330*b*) that surrounds a distal portion of the proximal-most staple cavity (B80230*a*). A second staple cavity (B80230*b*) is positioned distal to the proximal-most cavity (B80230*a*) in the second longitudinal row of staple cavities (B80230). Each second staple cavity (B80230*b*) comprises a second projection configuration (B80231*b*). The second projection configuration comprises a third projection (B80330*c*) that surrounds a proximal portion of the second staple cavity (B80230*b*), and a fourth projection (B80330*d*) that surrounds a distal portion of the second staple cavity (B80230*b*).

Figure 62C:
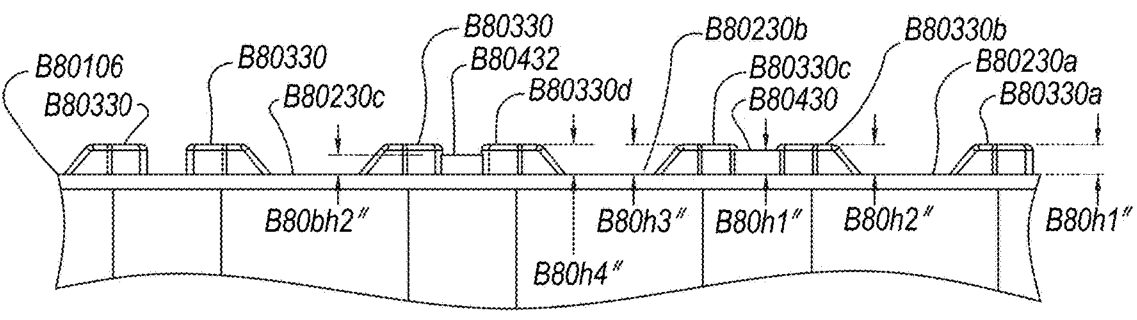
FIG. 62C depicts yet another partial elevational view of the projections extending above the deck surface of a third longitudinal row of staple cavities of the cartridge body of FIG. 59.

The first projection (B80330*a*) extends from the deck surface (B80106) to a first height (B80*h*1"), and the second projection (B80330*b*) extends from the deck surface (B80106) to a second height (B80*h*2"). The third projection (B80330*c*) extends from the deck surface (B80106) to a third height (B80*h*3"), and the fourth projection (B80330*d*) extends from the deck surface (B80106) to a fourth height (B80*h*4"). As depicted in FIGS. 60 and 62C, the first, second, third, and fourth heights are the same.

The second projection (B80330*b*) of the proximal-most staple cavity (B80230*a*) from the third longitudinal row of staple cavities (B80230) is directly connected to the third projection (B80330*c*) of the second staple cavity (B80230*b*) by a bridge projection (B80430). The bridge projection (B80430) extends from the deck surface (B80106) to a first bridge height (B80*bh*1") and extends laterally a first bridge width (B80*bw*1"). As depicted in FIGS. 60 and 62C, the first bridge height (B80*bh*1") is different than the second (B80*h*2") and third heights (B80*h*3") of the second and third projections (B80320*b*, B80320*c*), respectively. More specifically, the first bridge height (B80*bh*1") is less than the second and third heights (B80*h*2", B80*h*3") of the second and third projections, respectively.

A third staple cavity (B80230*c*) is located distal to the second staple cavity (B80230*b*). The third staple cavity comprises a third projection configuration (B80231*c*). A second bridge projection (B80432) connects the fourth projection (B80330*d*) to a projection surrounding a third staple cavity (B80230*c*). The second bridge projection (B80432) extends from the deck surface (B80106) to a second bridge height (B80*bh*2") and extends laterally a second bridge width (B80*bw*2"). As depicted in FIGS. 60, 61, and 62C, the second bridge height (B80*bh*2") is the same as the first bridge height (B80*bh*1"); however, the second bridge width (B80*bw*2") is less than the first bridge width (B80*bw*1"). Varying the width of the projections and/or bridge projections provides increased surface area and/or contact area with the adjacent article which thereby increases retention. While the bridge projections can continue to directly connect the projections of longitudinally-adjacent staple cavities, FIGS. 60, 61, and 62C depict bridge projections directly connecting the projections of only a proximal set of the third longitudinal row of staple cavities (B80230). Notably, no bridge projection is depicted distal to the third staple cavity (B80230*c*) in the third longitudinal row of staple cavities (B80230).

While the bridge connections are shown as connecting staple cavities from within the same longitudinal row, it is envisioned that such bridge connections could also, or alternatively, connect staple cavities from different longitudinal rows. Such connections could be in the form of diagonal bridge projections, for example. The diagonal bridge projections provide an added benefit as the distance covered necessarily involves a larger surface area than bridge projections connecting staple cavities within the same longitudinal row. Bridge connections can be used in varying locations along the cartridge deck to achieve a desired retention effect.

M. Thirteenth Example of a Cartridge Body

Figure 63:
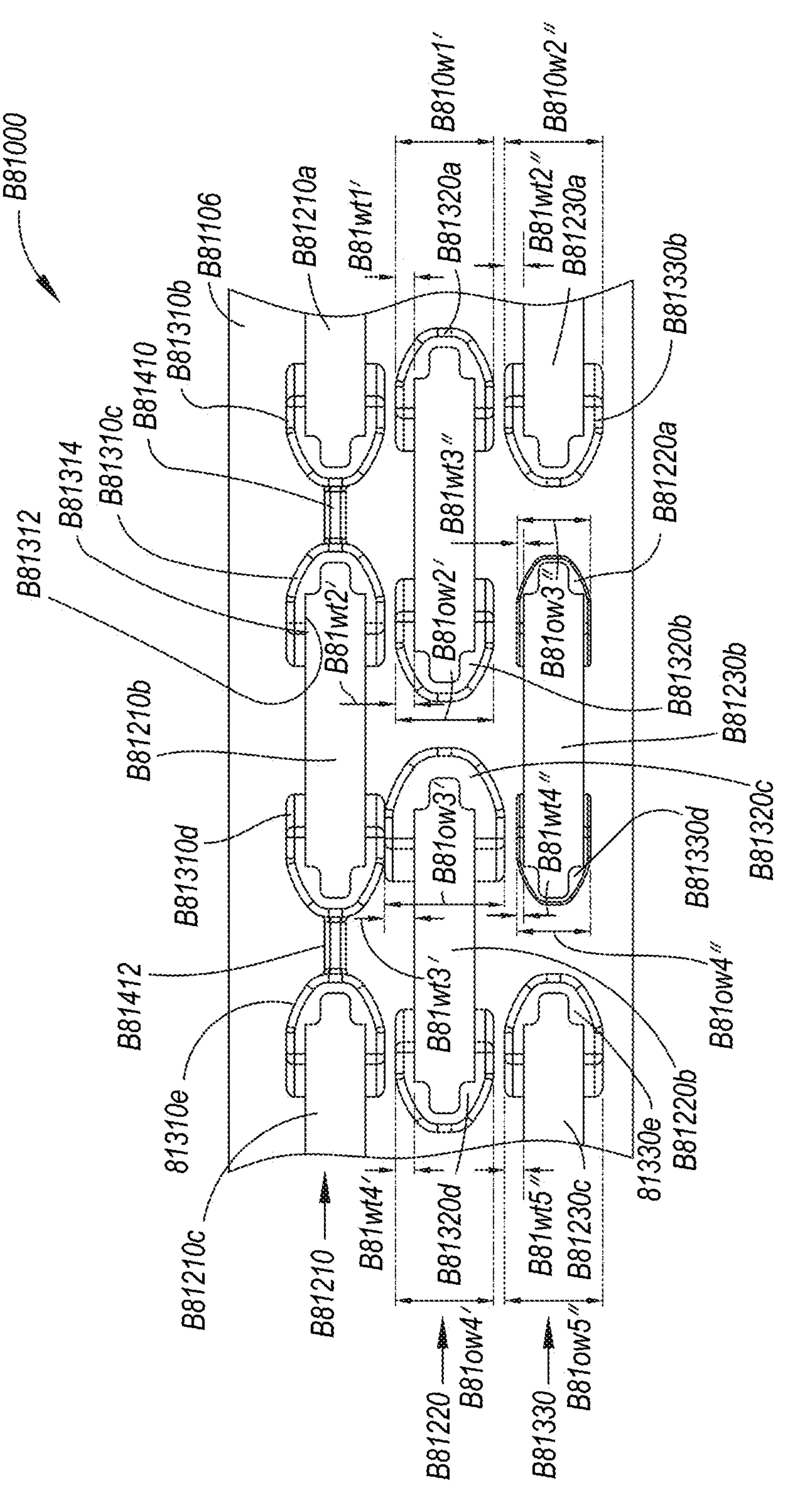
FIG. 63 depicts a partial plan view of another example of a cartridge body configured to be incorporated into the staple cartridge of FIG. 24 and the end effector of FIG. 2, the cartridge body including projections extending above a deck surface.
Figure 64:
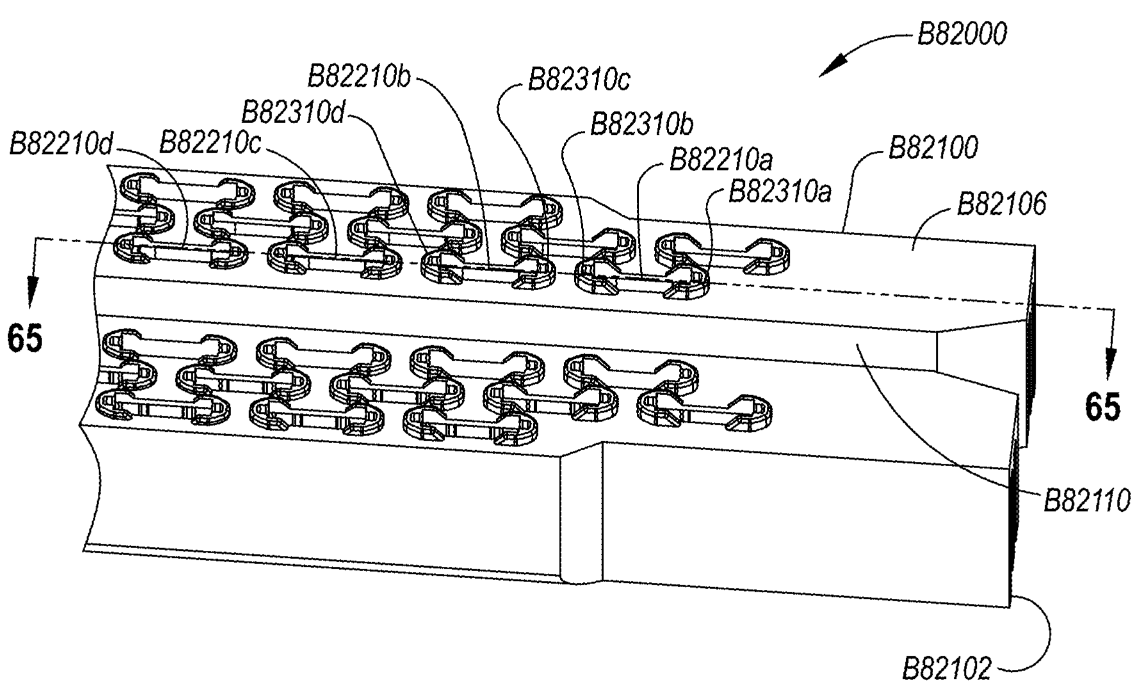
FIG. 64 depicts a partial perspective view of another example of a cartridge body configured to be incorporated into the staple cartridge of FIG. 24 and the end effector of FIG. 2, the cartridge body including projections extending above a deck surface.

FIG. 63 depicts a portion of a cartridge body (B81100) that is similar in many respects to cartridge body (B80100) described above. Cartridge body (B81100) defines a proximal end and a distal end and a deck surface (B81106) that extends therebetween. A first longitudinal row of staple cavities (B81210) extends alongside a longitudinal slot (B81110) defined in the cartridge body (B81100), a second longitudinal row of staple cavities (B81220) extends alongside the first longitudinal row of staple cavities (B81210), and a third longitudinal row of staple cavities (B81230) extends alongside the second longitudinal row of staple cavities (B81220). The first, second, and third longitudinal rows of staple cavities (B81210, B81220, B81230) are defined on a first side of the longitudinal slot.

The first longitudinal row of staple cavities (B81210) includes a first staple cavity (B81210*a*). A second projection (B81310*b*) surrounds a distal portion of the first staple cavity (B81210*a*) having a second overall width SW and a second projection wall thickness SPWT. The second projection wall thickness SPWT is defined by the thickness of the projection measured between a cavity-facing wall (B81312) and an opposite, external wall (B81314). A second staple cavity (B81210*b*) is positioned distal to the first cavity (B81210*a*) in the first longitudinal row of staple cavities (B81210). A third projection (B81310*c*) surrounds a proximal portion of the second staple cavity (B81210*b*), and a fourth projection (B81310*d*) surrounds a distal portion of the second staple cavity (B81210*b*). The third projection (B81310*c*) has a third overall width TW and a third projection wall thickness TPWT that is defined by the thickness of the projection (B81310*c*) measured between a cavity-facing wall (B81316) and an opposite, external wall (B81318). The fourth projection (B81310*d*) has a fourth overall width FW and a fourth projection wall thickness FPWT that is defined by the thickness of the fourth projection (B81310*d*) measured between a cavity-facing wall (B81317) and an opposite, external wall (B81319). A third staple cavity (B81210*c*) is positioned distal to the second cavity (B81210*b*) in the first longitudinal row of staple cavities (B81210). A fifth projection (B81310*e*) surrounds a proximal portion of the third staple cavity (B81210*c*). The fifth projection (81310*c*) has a fifth overall width FTW and a fifth projection wall thickness FTPWT. As shown in FIG. 63, the second, third, fourth, and fifth overall widths are the same, and the second, third, fourth, and fifth projection wall thicknesses are the same.

A first bridge projection (B81410) directly connects the second projection (B81310*b*) to the third projection (B81310*c*). The first bridge projection (B81410) extends to a first height above the deck surface (B81106) and has a first lateral width. A second bridge projection (B81412) directly connects the fourth projection (B81310*d*) to the fifth projection (B81310*e*). The second bridge projection (B81412) extends to a second height above the deck surface (B81106) and has a second lateral width. The first height is the same as the second height and, as shown in FIG. 63, the first lateral width is the same as the second lateral width.

The second longitudinal row of staple cavities (B81220) includes a first staple cavity (B81220*a*). A first projection (B81320*a*) surrounds a proximal portion of the first staple cavity (B81220*a*) having a first overall width (B81*ow*1') and a first projection wall thickness (B81*wt*1'), and a second projection (B81320*b*) surrounds a distal portion of the first staple cavity (B81220*a*) having a second overall width (B81*ow*2') and a second projection wall thickness (B81*wt*2'). As shown in FIG. 63, the first overall width (B81*ow*1') and the second overall width (B81*ow*2') are the same. Similarly, the first projection wall thickness (B81*wt*1') is the same as the second projection wall thickness (B81*wt*2').

A second staple cavity (B81220*b*) is positioned distal to the first cavity (B81220*a*) in the second longitudinal row of staple cavities (B81220). A third projection (B81320*c*) surrounds a proximal portion of the second staple cavity (B81220*b*), and a fourth projection (B81320*d*) surrounds a distal portion of the second staple cavity (B81220*b*). The third projection (B81320*c*) has a third overall width (B81*ow*3') and a third projection wall thickness (B81*wt*3'). The fourth projection (B81320*d*) has a fourth overall width (B81*ow*4') and a fourth projection wall thickness (B81*wt*4'). As shown in FIG. 63, the fourth overall width (B81*ow*4') is the same as the first and second overall widths (B81*ow*1', B81*ow*2') while the third overall width (B81*ow*3') is greater than the fourth overall width (B81*ow*4'). Similarly, the fourth projection wall thickness (B81*wt*4') is the same as the first and second projection wall thicknesses (B81*wt*1', B81*wt*2') while the third projection wall thickness (B81*wt*3') is greater than the fourth projection wall thickness (B81*wt*4').

The third longitudinal row of staple cavities (B81230) includes a first staple cavity (B81230*a*). A second projection (B81330*b*) surrounds a distal portion of the first staple cavity (B81230*a*) having a second overall width (B81*ow*2") and a second projection wall thickness (B81*wt*2"). A second staple cavity (B81230*b*) is positioned distal to the first cavity (B81230*a*) in the third longitudinal row of staple cavities (B81230). A third projection (B81330*c*) surrounds a proximal portion of the second staple cavity (B81230*b*), and a fourth projection (B81330*d*) surrounds a distal portion of the second staple cavity (B81230*b*). The third projection (B81330*c*) has a third overall width (B81*ow*3") and a third projection wall thickness (B81*wt*3"). The fourth projection (B81330*d*) has a fourth overall width (B81*ow*4") and a fourth projection wall thickness (B81*wt*4"). A third staple cavity (B81230*c*) is positioned distal to the second cavity (B81230*b*) in the third longitudinal row of staple cavities (B81230). A fifth projection (B81330*e*) surrounds a proximal portion of the third staple cavity (B81230*c*). The fifth projection (B81330*e*) has a fifth overall width (B81*ow*5") and a fifth projection wall thickness (B81*wt*5"). As shown in FIG. 63, the second and fifth overall widths are the same, and the second and fifth projection wall thicknesses are the same. However, while the third and fourth overall widths are the same, the third and fourth overall widths are less than the second and fifth overall widths. Similarly, while the third and fourth projection wall thicknesses are the same, the third and fourth projection wall thicknesses are less than the second and fifth projection wall thicknesses.

N. Fourteenth Example of a Cartridge Body

Figure 65:
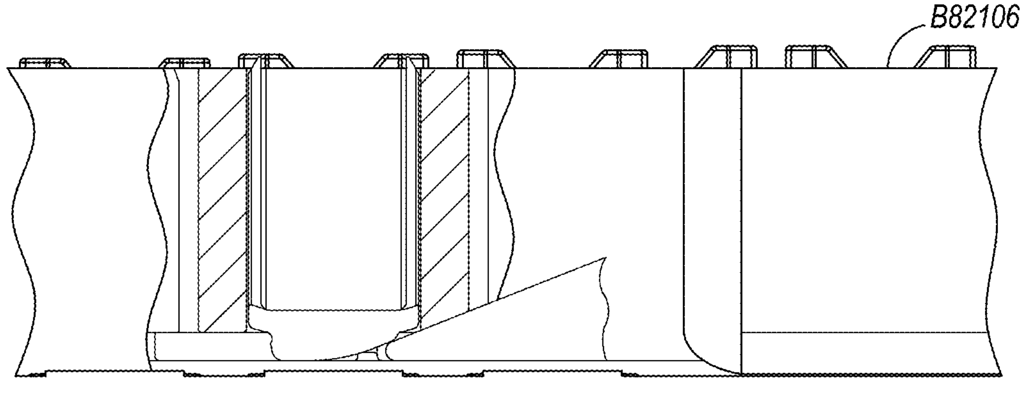
FIG. 65 depicts a partial cross-sectional view of the cartridge body of FIG. 64 taken along line 65-65 of FIG. 64.
Figure 66:
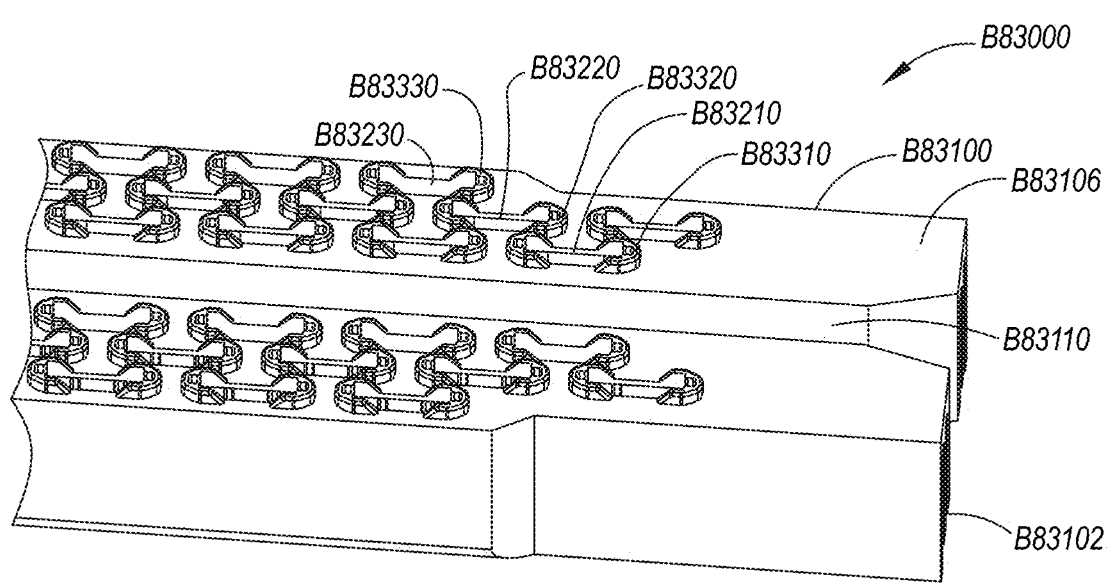
FIG. 66 depicts a partial perspective view of another example of a cartridge body configured to be incorporated into the staple cartridge of FIG. 24 and the end effector of FIG. 2, the cartridge body including projections extending above a deck surface.

FIGS. 65 and 66 show a cartridge body (B82100) that is similar in many respects to cartridge bodies (B80100, B81100) described above. Cartridge body (B82100) comprises a deck surface (B82106) and a longitudinal slot (B82110). Longitudinal slot (B82110) is defined in cartridge body (B82100) and extends from a proximal end (B82102) of the cartridge body (B82100) toward a distal end. A first longitudinal row of staple cavities (B82210) extends alongside the longitudinal slot (B82110) on a first side of the longitudinal slot (B82110). A proximal-most staple cavity (B82210*a*) is defined in the cartridge body (B82100) as part of the first longitudinal row of staple cavities (B82210). A first projection (B82310*a*) surrounds a proximal portion of the proximal-most staple cavity (B82210*a*), and the first projection (B82310*a*) extends a first height above the deck surface (B82106). A second projection (B82310*b*) surrounds a distal portion of the proximal-most staple cavity (B82210*a*), and the second projection (B82310*b*) extends a second height above the deck surface (B82106). As shown in FIG. 65, the first height is the same as the second height.

A second staple cavity (B82210*b*) is defined in the cartridge body (B82100) distal to the proximal-most staple cavity (B82210*a*). A third projection (B82310*c*) surrounds a proximal portion of the second staple cavity (B82210*b*), and the third projection (B82310*c*) extends a third height above the deck surface (B82106). A fourth projection (B82310*d*) surrounds a distal portion of the second staple cavity (B82210*b*), and the fourth projection (B82310*d*) extends a fourth height above the deck surface (B82106). As shown in FIG. 65, the third height is the same as the fourth height; however, the third and fourth heights are different than the first and second heights. More specifically, the third and fourth heights are less than the first and second heights.

A third staple cavity (B82210*c*) is defined in the cartridge body (B82100) distal to the second staple cavity (B82210*b*). A fifth projection (B82310*e*) surrounds a proximal portion of the third staple cavity (B82210*c*), and the fifth projection (B82310*c*) extends a fifth height above the deck surface (B82106). A sixth projection (B82310*f*) surrounds a distal portion of the third staple cavity (B82210*c*), and the sixth projection (B82310*f*) extends a sixth height above the deck surface (B82106). As shown in FIG. 65, the fifth height is the same as the fifth height; however, the fifth and sixth heights are different than the first, second, third, and fourth heights. More specifically, the fifth and sixth heights are less than the first, second, third, and fourth heights.

Although the heights of the projections associated with an individual staple cavity are illustrated as being the same, it is envisioned that the height of each projection can follow the gradient, such as a linear decrease in height, of the other projection heights. More specifically, the first height of the first projection (B82310*a*) could be greater than the second height of the second projection (B82310*b*) even though they surround portions of the same staple cavity (B82210*a*). When an adjunct material is used, an initial engagement of the knife with the adjunct material may tend to undesirably urge the adjunct material distally as the knife initially severs the material and continues to proceed distally through the material. Thus, by making the heights of the proximal-most projections greater than the distally-proceeding projections helps to retain the adjunct material in position during this portion of the firing procedure.

O. Fifteenth Example of a Cartridge Body

Figure 67:
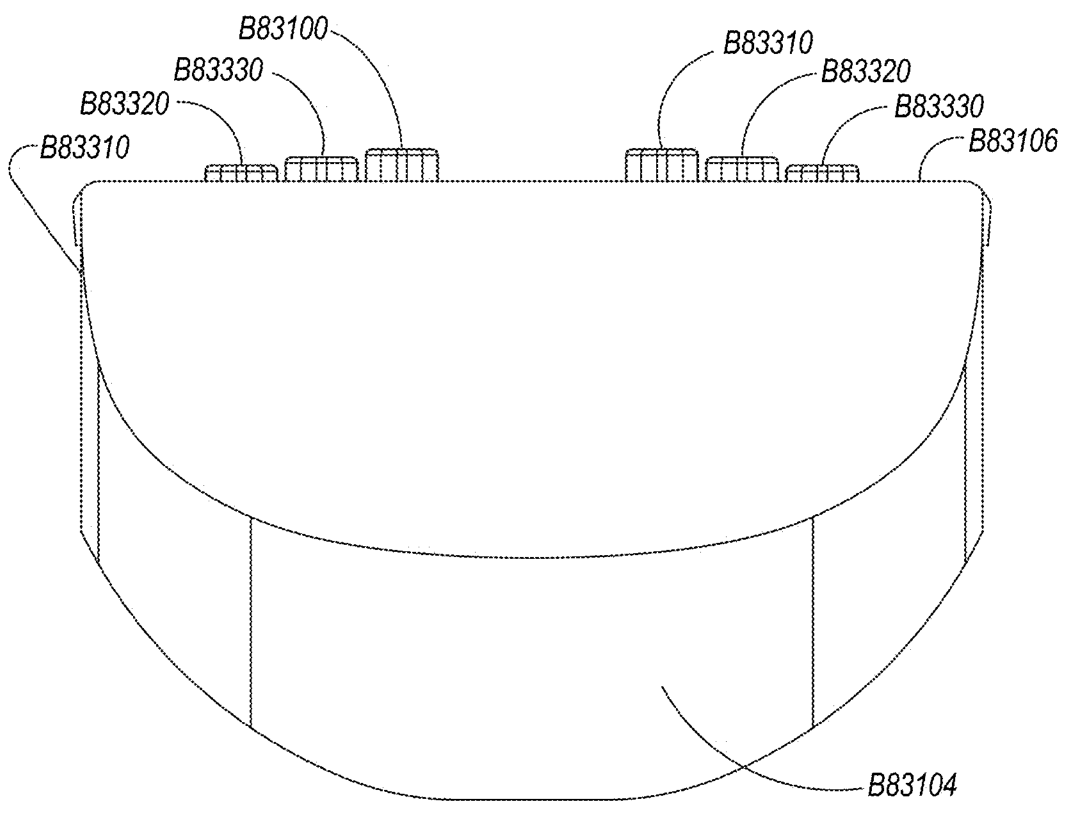
FIG. 67 depicts a front elevational view of the cartridge body of FIG. 66.

FIGS. 66 and 67 show a cartridge body (B83100) that is similar in many respects to cartridge bodies (B80100, B81100, B82100) described above. Cartridge body (B83100) comprises a deck surface (B83106) and a longitudinal slot (B83110). Longitudinal slot (B83110) is defined in the cartridge body (B83100) and extends from a proximal end (B83102) of the cartridge body (B83100) toward a distal end (B83104). A first longitudinal row of staple cavities (B83210) extends alongside the longitudinal slot (B83110) on a first side of the longitudinal slot (B83110). A first projection (B83310) surrounds at least a portion of a staple cavity (B83210) within the first longitudinal row. The first projection (B83310) extends a first height above the deck surface (B83106).

A second longitudinal row of staple cavities (B83220) extends alongside the first longitudinal row of staple cavities (B83210) on the first side of the longitudinal slot (B83110). A second projection (B83320) surrounds at least a portion of a staple cavity (B83220) within the second longitudinal row. The second projection (B83320) extends a second height above the deck surface (B83106). As shown in FIG. 67, the first height is different than the second height. More specifically, the first height is greater than the second height.

A third longitudinal row of staple cavities (B83230) extends alongside the second longitudinal row of staple cavities (B83220) on the first side of the longitudinal slot (B83110). A third projection (B83330) surrounds at least a portion of a staple cavity (B83230) within the third longitudinal row. The third projection (B83330) extends a third height above the deck surface (B83106). As shown in FIG. 67, the first projection (B83310) is discrete from or otherwise extends from the deck surface independent of the second projection (B83320) which is discrete from or otherwise extends from the deck surface independent of the third projection (B83330). The third height is different than the second height, and the third height is different than the first height. More specifically, the third height is less than the second height and the first height.

P. Sixteenth Example of a Cartridge Body

Figure 68:
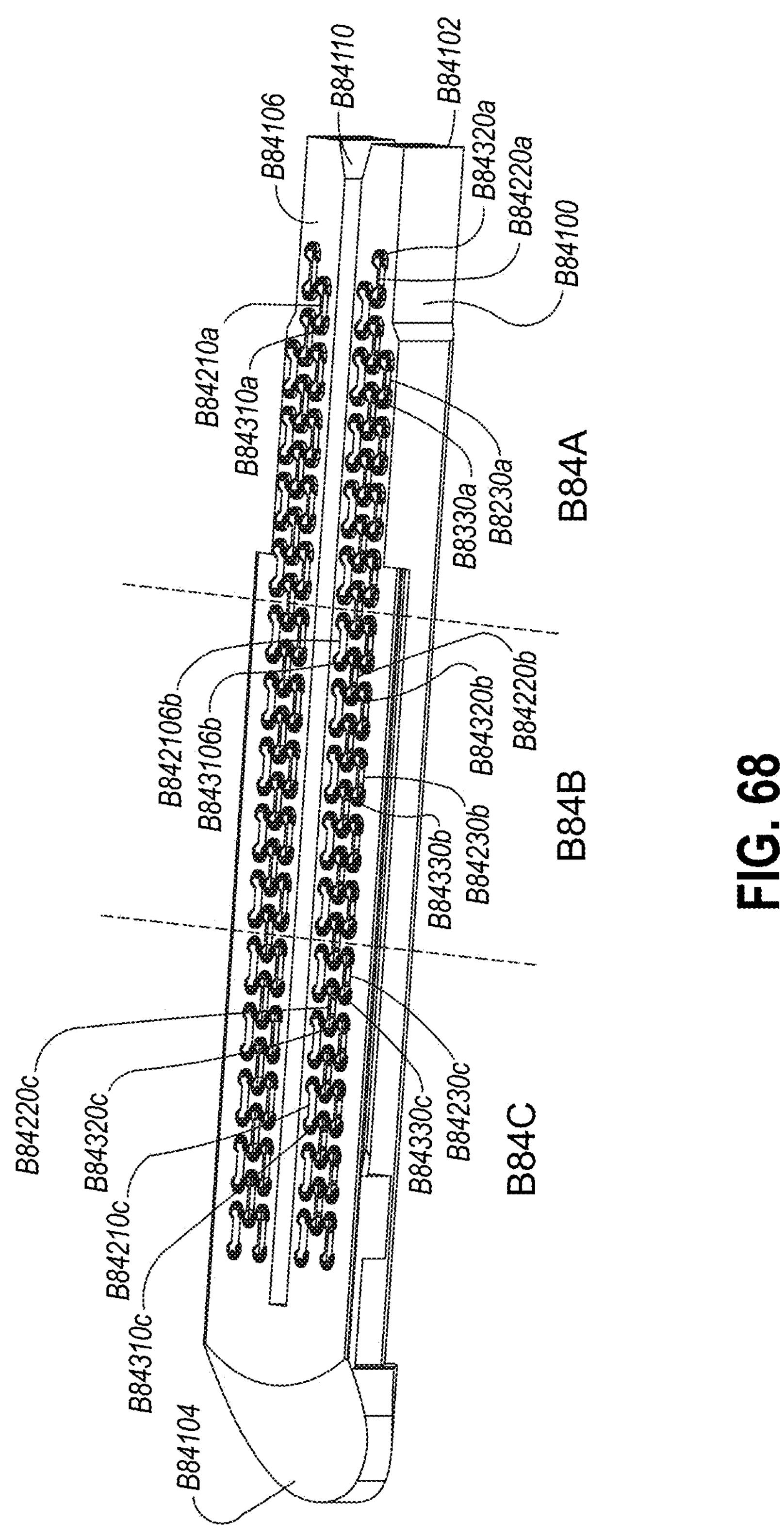
FIG. 68 depicts a perspective view of another example of a cartridge body configured to be incorporated into the staple cartridge of FIG. 24 and the end effector of FIG. 2, the cartridge body including projections extending above a deck surface.
Figure 69:
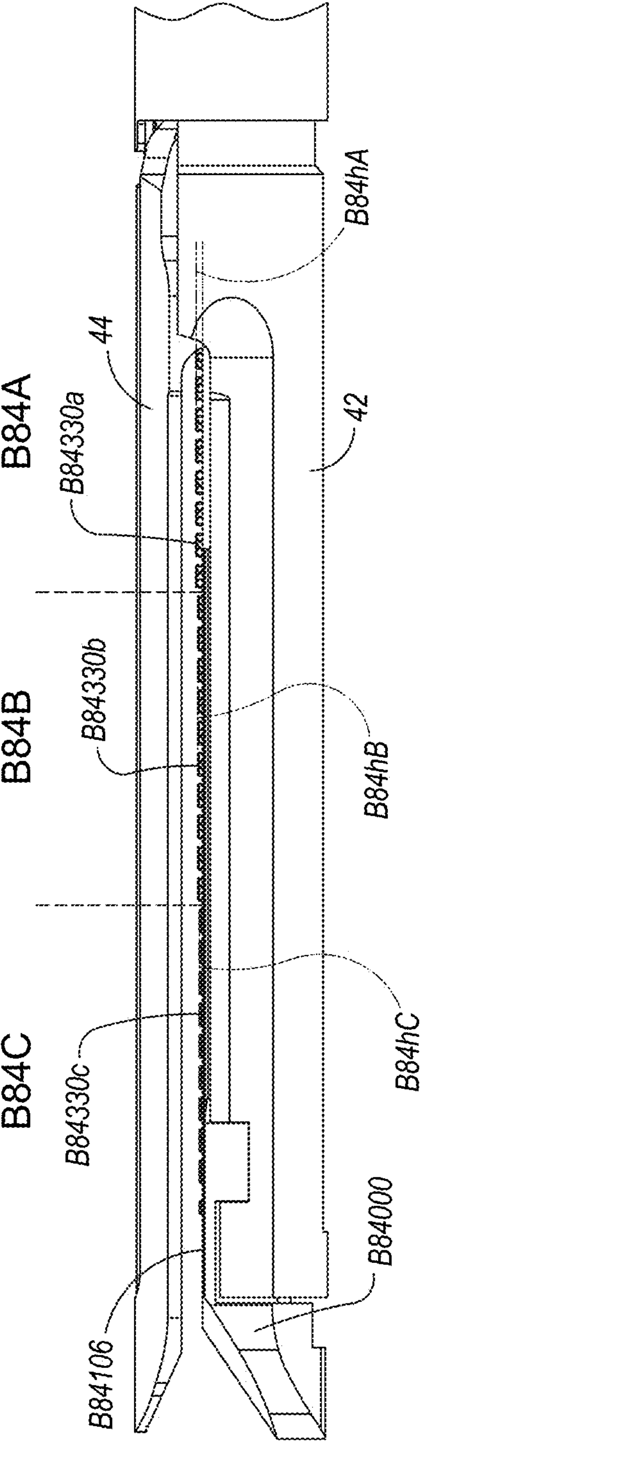
FIG. 69 depicts an elevational view of the cartridge body of FIG. 68 seated in a cartridge jaw of a surgical end effector and opposing an anvil when the surgical end effector is in a closed position.

FIGS. 68 and 69 show a cartridge body (B84100) that is similar in many respects to cartridge bodies (B80100, B81100, B82100, B83100) described above. Cartridge body (B84100) includes a deck surface (B84106) and a longitudinal slot (B84110). Longitudinal slot (B84110) is defined in the cartridge body (B84100) and extends from a proximal end (B84102) toward a distal end (B84104). A first longitudinal row (B84210) of staple cavities extends alongside the longitudinal slot (B84110), a second longitudinal row (B84220) of staple cavities extends alongside the first longitudinal row (B84210), and a third longitudinal row (B84230) of staple cavities extends alongside the second longitudinal row (B84220). The first, second, and third longitudinal rows (B84210, B84220, B84230) of staple cavities are defined on a first side of the longitudinal slot (B84110). For brevity, the topography with respect to a first side of the longitudinal slot is discussed herein in detail; however, it is envisioned that the topography of the deck surface on the first side of the longitudinal slot is mirrored onto the deck surface on the second side of the longitudinal slot. Other arrangements are contemplated wherein the topography of the deck surface on one side of the longitudinal slot differs from the topography of the deck surface on the other side of the longitudinal slot.

As shown in FIG. 68, the deck surface (B84106) has been divided into a proximal portion (B84A), a middle portion (B84B) and a distal portion (B84C). The proximal portion (B84A) of the deck surface (B84106) contains "proximal" segments of the first longitudinal row (B84210), the second longitudinal row (B84220), and the third longitudinal row (B84230). The proximal segment of the first longitudinal row (B84210) includes a plurality of proximal staple cavities (B84210*a*). The proximal segment of the second longitudinal row (B84220) includes a plurality of second proximal staple cavities (B84220*a*). The proximal segment of the third longitudinal row (B84230) includes a plurality of third proximal staple cavities (B84230*a*).

The middle portion (B84B) of the deck surface (B84106) contains "middle" segments of the first longitudinal row (B84210), the second longitudinal row (B84220), and the third longitudinal row (B84230) of staple cavities. The middle segment of the first longitudinal row (B84210) includes a plurality of middle staple cavities (B84210*b*). The middle segment of the second longitudinal row (B84220) includes a plurality of second middle staple cavities (B84220*b*). The middle segment of the third longitudinal row (B84230) contains a plurality of third middle staple cavities (B84230*b*).

The distal portion (B84C) of the deck surface (B84106) contains "distal" segments of the first longitudinal row (B84210), the second longitudinal row (B84220), and the third longitudinal row (B84230). The distal segment of the first longitudinal row (B84210) includes a plurality of distal staple cavities (B84210*c*). The distal segment of the second longitudinal row (B84220) includes a plurality of second distal staple cavities (B84220*c*). The distal segment of the third longitudinal row (B84230) includes a plurality of third distal staple cavities (B84230*c*).

In accordance with at least one embodiment, projections extend from the deck surface (B84106) and surround at least a portion of individual staple cavities. In the illustrated arrangement, each proximal staple cavity (B84210*a*) comprises a corresponding proximal projection configuration (B84211*a*). Each proximal projection configuration comprises a first projection (B84310*a*) that surrounds the corresponding proximal staple cavity (B84210*a*) in the proximal segment of the first longitudinal row (B84210) in the proximal portion (B84A) of cartridge body (84100). The first projection (B84310*a*) extends to a first height above the deck surface (B84106). Other arrangements are contemplated wherein the first projection (B84310*a*) only partially surrounds a corresponding staple cavity (B84210*a*). Each of the middle staple cavities (B84210*b*) comprises a corresponding middle projection configuration (B84211*b*). Each middle projection configuration (B84211*b*) comprises a second projection (B84310*b*) that surrounds the corresponding middle staple cavity 84210*b* in the middle segment of the first longitudinal row 84210 in a middle portion (B84B) of the cartridge body (B84100). The second projection (B84310*b*) extends to a second height above the deck surface (B84106). The second height is different than the first height. More specifically, the first height is greater than the second height. Other arrangements are contemplated wherein the second projection (B84310*b*) only partially surrounds a corresponding middle staple cavity (B84210*b*). Each, or at least a plurality of the distal staple cavities (B84210*c*) comprise a corresponding distal projection configuration (B84211*c*.). Each proximal projection configuration (B84211*c*) comprises a third projection (B84310*c*) surrounds the corresponding distal staple cavity (B84210*c*) in the distal segment (B84210D) of the first longitudinal row (B84210) in a distal portion (B84C) of the cartridge body (B84100). The third projection (B84310*c*) extends to a third height above the deck surface (B84106). The third height is different than the second height, and the third height is different than the first height. More specifically, the first height is greater than the third height, and the second height is greater than the third height. Other arrangements are contemplated wherein the third projection (B84310*c*) only partially surrounds a corresponding staple cavity (B84210*c*).

As can be further seen in FIG. 68, each second proximal staple cavity (B84220*a*) comprises a second proximal projection configuration (B84221*a*). Each second proximal projection configuration (B84221*a*) comprises a first projection (B84320*a*) that surrounds the corresponding second proximal staple cavity (B84220*a*) in the proximal segment of the second longitudinal row (B84220) in the proximal portion (B84A) of the cartridge body (B84100). The first projection (B84320*a*) extends to a first height above the deck surface (B84106). Other arrangements are contemplated wherein the first projection (B84320*a*) only partially surrounds a corresponding staple cavity (B84220*a*). Each second middle staple cavity (B84220*b*) comprises a second middle projection configuration (B84221*b*). Each second middle projection configuration (B84221*b*) comprises a second projection (B84320*b*) that surrounds the corresponding second middle staple cavity (B84220*b*) in the middle segment of the second longitudinal row (B84220) in a middle portion (B84B) of the cartridge body (B84100). The second projection (B84320*b*) extends to a second height above the deck surface (B84106). The second height is different than the first height. More specifically, the first height is greater than the second height. Other arrangements are contemplated wherein the second projection (B84320*b*) only partially surrounds a corresponding staple cavity (B84220*b*). Each, or at least a plurality of the second distal staple cavities (B84220*c*), comprises a second distal projection configuration (B84221*c*). Each second distal projection configuration (B84221*c*) comprises a third projection (B84320*c*) that surrounds a corresponding second distal staple cavity (B84220*c*) in the distal segment of the second longitudinal row (B84220) in the distal portion (B84C) of the cartridge body (B84100). The third projection (B84320*c*) extends to a third height above the deck surface (B84106). The third height is different than the second height, and the third height is different than the first height. More specifically, the first height is greater than the third height, and the second height is greater than the third height. Other arrangements are contemplated wherein the third projection (B84320*c*) only partially surrounds a corresponding second distal staple cavity (B84220*c*).

Still referring to FIG. 68 and FIG. 69, each third proximal staple cavity (B84230*a*) comprises a third proximal projection configuration (B84231*a*). Each third proximal projection configuration (B84231*a*) comprises a first projection (B84330*a*) that surrounds the corresponding third proximal staple cavity (B84230*a*) in the proximal segment of the third longitudinal row (B84230) in the proximal portion (B84A) of the cartridge body (B84100). The first projection (B84330*a*) extends to a first height (B84*h*A) above the deck surface (B84106). Other arrangements are contemplated wherein the first projection (B84330*a*) only partially surrounds a corresponding third proximal staple cavity (B84230*a*). Each third middle staple cavity (B84230*b*) comprises a third middle projection configuration (B84231*b*). Each third middle projection configuration (B84231*b*) comprises a second projection (B84330*b*) that surrounds a corresponding third middle staple cavity (B84230*b*) in the middle segment of the third longitudinal row (B84230) in the middle portion of the cartridge body (B84100). The second projection (B84330*b*) extends to a second height (B84*h*B) above the deck surface (B84106). The second height (B84*h*B) is different than the first height (B84*h*A). More specifically, the first height (B84*h*A) is greater than the second height (B84*h*B). Other arrangements are contemplated wherein the second projection (B84330*b*) only partially surrounds a corresponding third middle staple cavity (B84230*b*). As can be further seen in FIG. 68, each third distal staple cavity (B84230*c*) comprises a third distal projection configuration (B84231*c*). Each third distal projection configuration (B84231*a*) comprises a third projection (B84330*c*) that surrounds the corresponding third distal staple cavity (B84230*c*) in the distal segment of the third longitudinal row (B84230) in a distal portion of the cartridge body (84100). The third projection (B84330*c*) extends to a third height (B84*h*C) above the deck surface (B84106). The third height (B84*h*C) is different than the second height (B84*h*B), and the third height (B84*h*C) is different than the first height (B84*h*A). More specifically, the first height (B84*h*A) is greater than the third height B84*h*C), and the second height (B84*h*B) is greater than the third height (B84*h*C). Other arrangements are contemplated wherein the third projection (B84330*c*) only partially surrounds a corresponding staple cavity (B84230*c*).

The first heights (B84*h*A) associated with the first projections (B84310*a*, B84320*a*, B84330*a*) of the various longitudinal rows are the same. The second heights (B84*h*B) associated with the second projections (B84310*b*, B84320*b*, B84330*b*) of the various longitudinal rows are the same. The third heights (B84*h*C) associated with the third projections (B84310*c*, B84320*c*, B84330*c*) of the various longitudinal rows are the same. Stated another way, the heights of projections decrease longitudinally across the cartridge body (B84100).

In particular, the projections in a first, proximal portion (B84A) of the cartridge body (B84100) extend closer to a tissue-facing surface of anvil (44) when the end effector (40) is in a closed position than the projections in a second, middle portion (B84B) and a third, distal portion (B84C). Due to the shortened gap between the projections (B84310*a*, B84310*b*, B84310*c*) and the tissue-facing surface of the anvil (44), the patient tissue and/or adjunct layer captured between the anvil (44) and the cartridge body (B84100) in the proximal portion (B84A) experiences a greater clamping, or retention, force than the contents captured therebetween in the middle portion (B84B) and distal portion (B84C). The greater retention force aids in maintaining the captured contents in a desired position. While the patient tissue and/or adjunct layer captured between the projections (B84310*b*, B84320*b*, B84320*c*) and the tissue-facing surface of the anvil (44) is compressed to a lesser degree in the middle portion (B84B) of the cartridge body (B84100), such captured contents are compressed to a greater degree than in the distal portion (B84C) of the cartridge body (B84100).

More specifically, a gap distance is defined between a deck surface (B84106) of cartridge body (B84100) and a tissue-facing surface of an anvil (44) when end effector (40) is in a closed position. The height of the projections in the first, proximal portion (B84A) are envisioned as being greater than or equal to 80% of the gap distance while not exceeding 100% of the gap distance.

As discussed above, in at least one embodiment, the first proximal staple cavities, the first middle staple cavities, and the first distal staple cavities are longitudinally aligned and are adjacent to the longitudinal slot. The second proximal staple cavities, the second middle staple cavities and the second distal staple cavities are longitudinally aligned and are adjacent to the first proximal staple cavities, the first middle staple cavities, and the first distal staple cavities. The third proximal staple cavities, the third middle staple cavities and the third distal staple cavities are longitudinally aligned and are adjacent to the second proximal staple cavities, the second middle staple cavities, and the second distal staple cavities as well as a longitudinal edge the cartridge body.

Other arrangements are contemplated wherein the first projection configurations adjacent the longitudinal slot have heights that are greater than the second and third projection configurations. In such arrangements, for example, all of, or at least a plurality of, the first proximal staple cavities in a proximal portion (B84A) of the staple cartridge have first proximal projection configurations that have a first proximal height that is greater than the second proximal height of each of the second proximal projection configurations associated with all of, or at least a plurality of the second proximal staple cavities in the proximal portion (B84A). The third proximal projection configurations associated with all of, or at least a plurality of the third proximal staple cavities in the proximal portion (B84A) of the cartridge have a third proximal height that is less than the second proximal height. All of, or at least a plurality of, the first middle staple cavities in a middle portion (B84B) of the staple cartridge have first middle projection configurations that have a first middle height that is greater than a second middle height of each of the second middle projection configurations associated with all of, or at least a plurality of the second middle staple cavities in the middle portion (B84B). The third middle projection configurations associated with all of, or at least a plurality of the third middle staple cavities in the middle portion (B84B) of the cartridge have a third middle height that is less than the second middle height. All of, or at least a plurality of, the first distal staple cavities in a distal portion (B84C) of the staple cartridge have first distal projection configurations that have a first distal height that is greater than a second distal height of each of the second distal projection configurations associated with all of, or at least a plurality of the second distal staple cavities in the distal portion (B84C). The third distal projection configurations associated with all of, or at least a plurality of the third distal staple cavities in the distal portion (B84C) of the cartridge have a third distal height that is less than the second distal height. Thus, in one arrangement, the heights of the projection configurations closest to the longitudinal slot are the highest and decrease in magnitude with each subsequent row laterally. In another arrangement, although the heights of the projection configurations may decrease in subsequent lateral rows going laterally away from the longitudinal slot, each projection configuration in a single row may have the same height. In other arrangements, the proximal height is greater than the middle height, which is greater than the distal height of the projection configurations in each single row. Such arrangements serve to improve the gripping and retention characteristics of the staple cartridge in areas wherein the adjacent article (tissue and/or adjunct) encounters more forces/stress during firing-adjacent the longitudinal slot as well as adjacent the proximal end of the cartridge.

As used herein, the term "projection configuration" encompasses one or more of the following characteristics: projection height, width, thickness, compositions, and overall geometry and shape. In addition to the heights of the projections varying along a cartridge body, overall geometries of the projections can vary based on a specific location of a projection on the cartridge body. For example, it is preferable for projections extending from a distal portion of the cartridge body to have a smooth, or rounded profile so as to prevent damaging an adjacent article as jaws of the end effector capture the adjacent article therebetween. Furthermore, it is preferable for projections extending from a proximal portion of the cartridge body to have a profile that causes snagging and/or friction of the adjacent article to optimize retaining the adjacent article in position. Those of ordinary skill in the art will appreciate that the staple cavities of the various surgical staple cartridges herein are configured to removably support/store therein a corresponding surgical staple or fastener therein.

In this arrangement, first projections (B84310*a*) are associated with each of the proximal cavities (B84210*a*) in the proximal segment, second projections (B84310*b*) are associated with each of the middle cavities (B84210*b*) in the middle segment, and third projections (B84310*c*) are associated with each of the distal cavities (B84210*c*) in the distal segment in the manner described herein. Other arrangements are contemplated wherein the first projections (B84310*a*) are not associated with all of the proximal cavities (B84210*a*) and/or the second projections (B84310*b*) are not associated with all of the middle cavities (B84210*b*) and/or the third projections (B84310*c*) are not associated with all of the distal cavities (B84210*c*).

Likewise, first projections (B84320*a*) are associated with each of the second proximal cavities (B84220*a*) in the proximal segment, second projections (B84320*b*) are associated with each of the second middle cavities (B84220*b*) in the middle segment, and third projections (B84320*c*) are associated with each of the second middle cavities (B84220*c*) in the distal segment in the manner described herein. Other arrangements are contemplated wherein the first projections (B84320*a*) are not associated with all of the second proximal cavities (B84220*a*) and/or the second projections (B84320*b*) are not associated with all of the second middle cavities (B84220*b*) and/or the third projections (B84320*c*) are not associated with all of the second distal cavities (B84220*c*). Further to the above, first projections (B84330*a*) are associated with each of the third proximal cavities (B84230*a*) in the proximal segment, second projections (B84330*b*) are associated with each of the third middle cavities (B84230*b*) in the middle segment, and third projections (B84330*c*) are associated with each of the third distal cavities (B84230*c*) in the distal segment in the manner described herein. Other arrangements are contemplated wherein the first projections (B84330*a*) are not associated with all of the third proximal cavities (B84230*a*) and/or the second projections (B84330*b*) are not associated with all of the third middle cavities (B84230*b*) and/or the third projections (B84330*c*) are not associated with all of the third distal cavities (B84230*c*).

In one arrangement, the number of proximal cavities (B84210*a*) in the proximal segment of the first longitudinal row (B84210) is equal to the number of middle cavities (B84210*b*) in the middle segment of the first longitudinal row (B84210), and the number of distal cavities (B84210*c*) in the distal segment of the first longitudinal row (B84210), respectively. Similarly, the number of second proximal cavities (B84220*a*) in the proximal segment of the second longitudinal row (B84220) is equal to the number of second middle cavities (B84220*b*) in the middle segment of the second longitudinal row (B84220), and the number of second distal cavities (B84220*c*) in the distal segment of the second longitudinal row (B84220), respectively. Also in this arrangement, the number of third proximal cavities (B84230*a*) in the proximal segment of the third longitudinal row (B84230) is equal to the number of third middle cavities (B84230*b*) in the middle segment of the third longitudinal row (B84230), and the number of third distal cavities (B84230*c*) in the distal segment of the third longitudinal row (B84210), respectively. The number of cavities in the first longitudinal row (B84210) may be the same as the number of cavities in the second longitudinal row (B84220) and the number of cavities third longitudinal row (B84230), or they may be different.

IV. Examples of Buttress Assemblies

In some instances, it may be desirable to equip end effector (40) of surgical stapler (10) with an adjunct material, such as a buttress, to reinforce the mechanical fastening of tissue (T) provided by staples (86). Such a buttress may prevent the applied staples (86) from pulling through the tissue (T) and may otherwise reduce a risk of tissue (T) tearing at or near the site of applied staples (86). In addition to or as an alternative to providing structural support and integrity to a line of staples (86), a buttress may provide various other kinds of effects such as spacing or gap-filling, administration of therapeutic agents, and/or other effects. In some instances, a buttress may be provided on upper deck (74) of staple cartridge (70). As described above, deck (74) houses staples (86), which are driven by staple driver (84). In some other instances, a buttress may be provided on the surface of anvil (44) that faces staple cartridge (70). It should also be understood that a first buttress may be provided on upper deck (74) of staple cartridge (70) while a second buttress is provided on anvil (44) of the same end effector (40).

Various examples of forms that a buttress may take will be described in greater detail below. Various ways in which a buttress may be secured to a staple cartridge (70) or an anvil (44) will also be described in greater detail below. Illustrative buttress assemblies, illustrative materials and techniques for applying buttress assemblies, and illustrative buttress applier cartridges may be configured in accordance with at least some of the teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and/or U.S. Pat. No. 11,166,724, entitled "Adhesive Distribution on Buttress for Surgical Stapler," issued Nov. 9, 2021, the disclosures of which are incorporated by reference herein.

A. First Example of a Buttress Assembly

Figure 70:
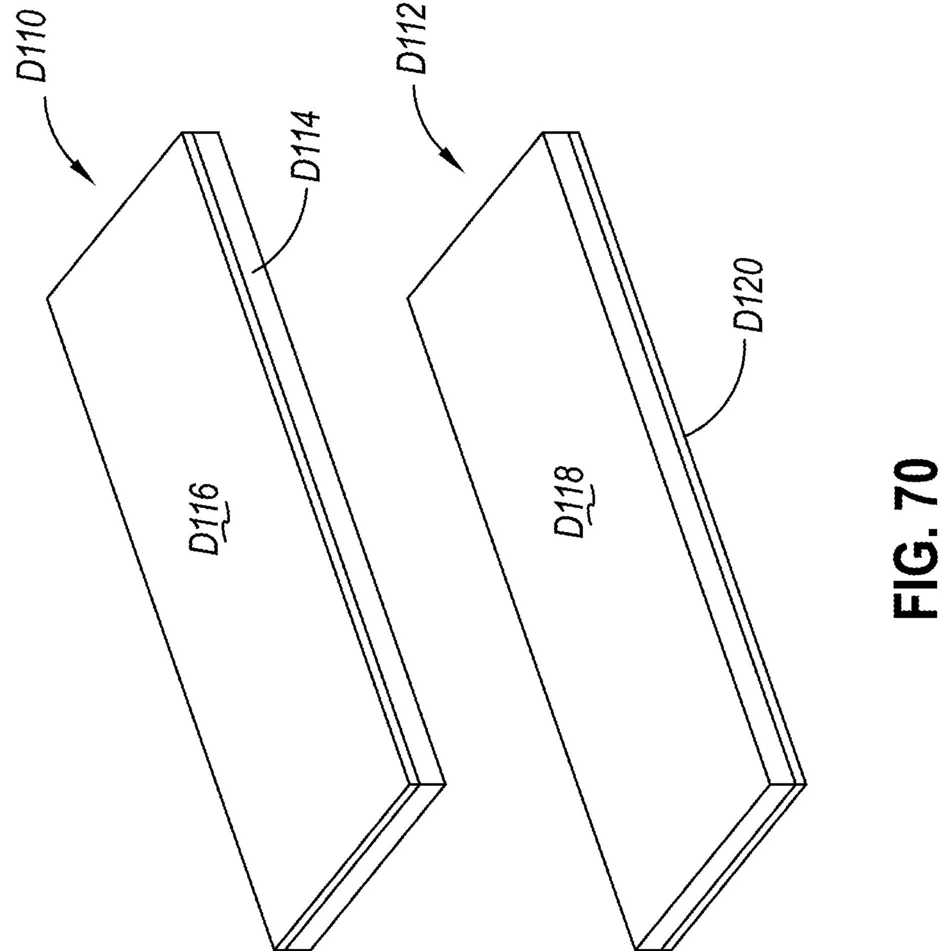
FIG. 70 depicts a perspective view of an illustrative pair of buttress assemblies, each of which may be applied to a jaw of the end effector of FIG. 2.

FIG. 70 shows an illustrative pair of buttress assemblies (D110, D112) (each also referred to individually as a "buttress"). Buttress assembly (D110) of this example comprises a buttress body (D114) and an upper adhesive layer (D116). Similarly, buttress assembly (D112) comprises a buttress body (D118) and a lower adhesive layer (D120). In the present example, each buttress body (D114, D118) comprises a strong yet flexible material configured to structurally support a line of staples (86). By way of example only, each buttress body (D114, D118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (D114, D118).

Each buttress body (D114, D118) may comprise a material including, for example, a hemostatic agent such as fibrin to assist in coagulating blood and reduce bleeding at the severed and/or stapled surgical site along tissue (T1, T2). As another merely illustrative example, each buttress body (D114, D118) may comprise other adjuncts or hemostatic agents such as thrombin may be used such that each buttress body (D114, D118) may assist to coagulate blood and reduce the amount of bleeding at the surgical site. Other adjuncts or reagents that may be incorporated into each buttress body (D114, D118) may further include but are not limited to medical fluid or matrix components.

In the present example, adhesive layer (D116) is provided on buttress body (D114) to adhere buttress body (D114) to underside (D124) of anvil (44). Similarly, adhesive layer (D120) is provided on buttress body (D118) to adhere buttress body (D118) to upper deck (74) of staple cartridge (70). Such an adhesive material may provide proper positioning of buttress body (D114, D118) before and during actuation of end effector (40); then allow buttress body (D114, D118) to separate from end effector (40) after end effector (40) has been actuated, without causing damage to buttress body (D114, D118) that is substantial enough to compromise the proper subsequent functioning of buttress body (D114, D118).

Figures 71A, 71B, 71C:
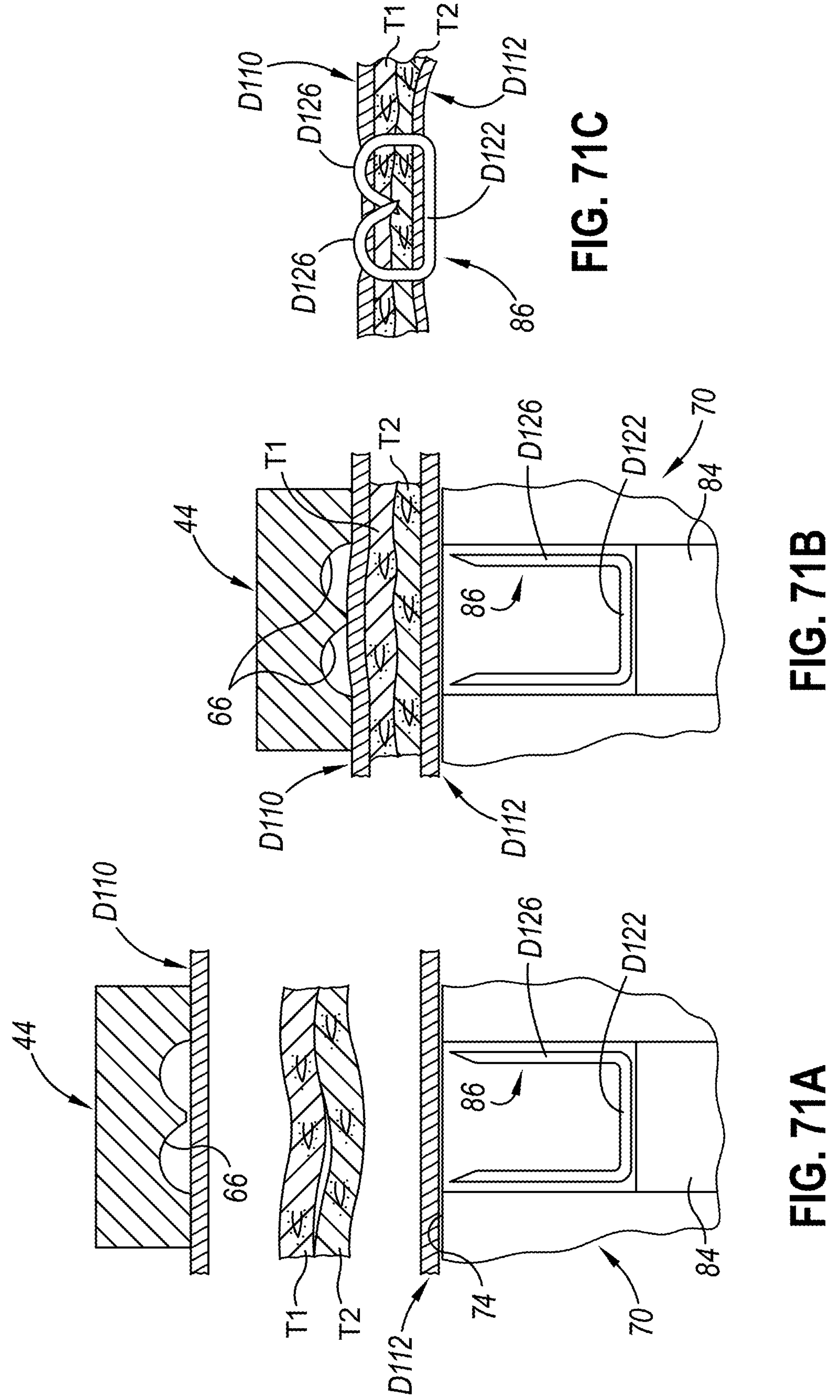
FIG. 71A depicts a cross-sectional end view of a portion of the end effector of FIG. 2 with the buttress assemblies of FIG. 70 applied to the upper and lower jaws of the end effector, showing the end effector jaws in an open state with tissue positioned between the upper and lower jaws.
FIG. 71B depicts a cross-sectional end view of the end effector and buttress assemblies of FIG. 71A, showing the end effector jaws in a closed state on the tissue.
FIG. 71C depicts a cross-sectional view of a formed staple and the buttress assemblies of FIG. 71A after having been secured to the tissue by the end effector of FIG. 2.

FIGS. 71A-71C show an illustrative sequence in which surgical stapler end effector (40), which has been loaded with buttress assemblies (D110, D112), is actuated to drive staples (86) through two opposed layers of tissue (T1, T2), with buttress assemblies (D110, D112) being secured to the same layers of tissue (T1, T2) by staples (86). In particular, FIG. 71A shows layers of tissue (T1, T2) positioned between anvil (44) and staple cartridge (70), with anvil (44) in the open position. Buttress assembly (D110) is adhered to an underside of anvil (44) via adhesive layer (D116); while buttress assembly (D112) is adhered to upper deck (74) of staple cartridge (70) via adhesive layer (D120). Layers of tissue (T1, T2) are thus interposed between buttress assemblies (D110, D112). Next, closure trigger (26) is pivoted toward pistol grip (24) to drive closure tube (34) and closure ring (36) distally. This drives anvil (44) to the closed position as shown in FIG. 71B. At this stage, layers of tissue (T1, T2) are compressed between anvil (44) and staple cartridge (70), with buttress assemblies (D110, D112) engaging opposite surfaces of tissue layers (T1, T2). End effector (40) is then actuated as described above, driving staple (86) through buttress assemblies (D110, D112) and tissue (T1, T2). As shown in FIG. 71C, crown (D122) of driven staple (86) captures and retains buttress assembly (D112) against layer of tissue (T2). Deformed legs (D126) of staple (86) capture and retain buttress assembly (D110) against layer of tissue (T1).

Figure 72:
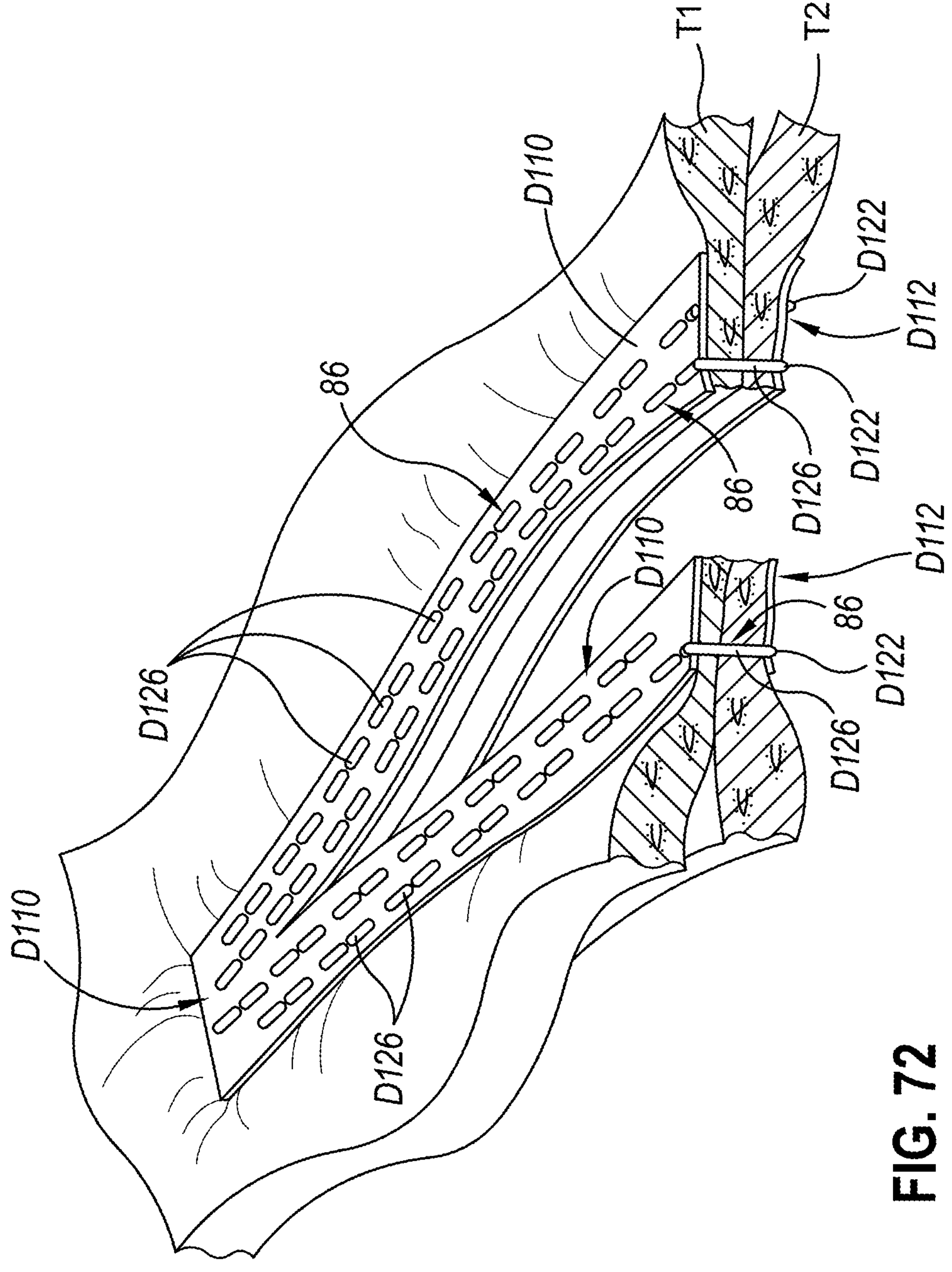
FIG. 72 depicts a perspective view of formed staples and the buttress assemblies of FIG. 71A after having been secured to the tissue by the end effector of FIG. 2.

A series of staples (86) similarly capture and retain buttress assemblies (D110, D112) against layers of tissue (T1, T2), thereby securing buttress assemblies (D110, D112) to tissue (T1, T2) as shown in FIG. 72. As end effector (40) is pulled away from tissue (T1, T2) after deploying staples (86) and buttress assemblies (D110, D112), buttress assemblies (D110, D112) disengage end effector (40) such that buttress assemblies (D110, D112) remain secured to tissue (T1, T2) with staples (86). Buttresses (D110, D112) thus provide structural reinforcement to the lines of staples (86) formed in tissue (T1, T2). As can also be seen in FIG. 72, distally presented cutting edge (58) of firing beam (46) also cuts through a centerline of buttress tissue assemblies (D110, D112), separating each buttress assembly (D110, D112) into a corresponding pair of sections, such that each section remains secured to a respective severed region of tissue (T1, T2).

B. Second Example of a Buttress Assembly

Figure 73:
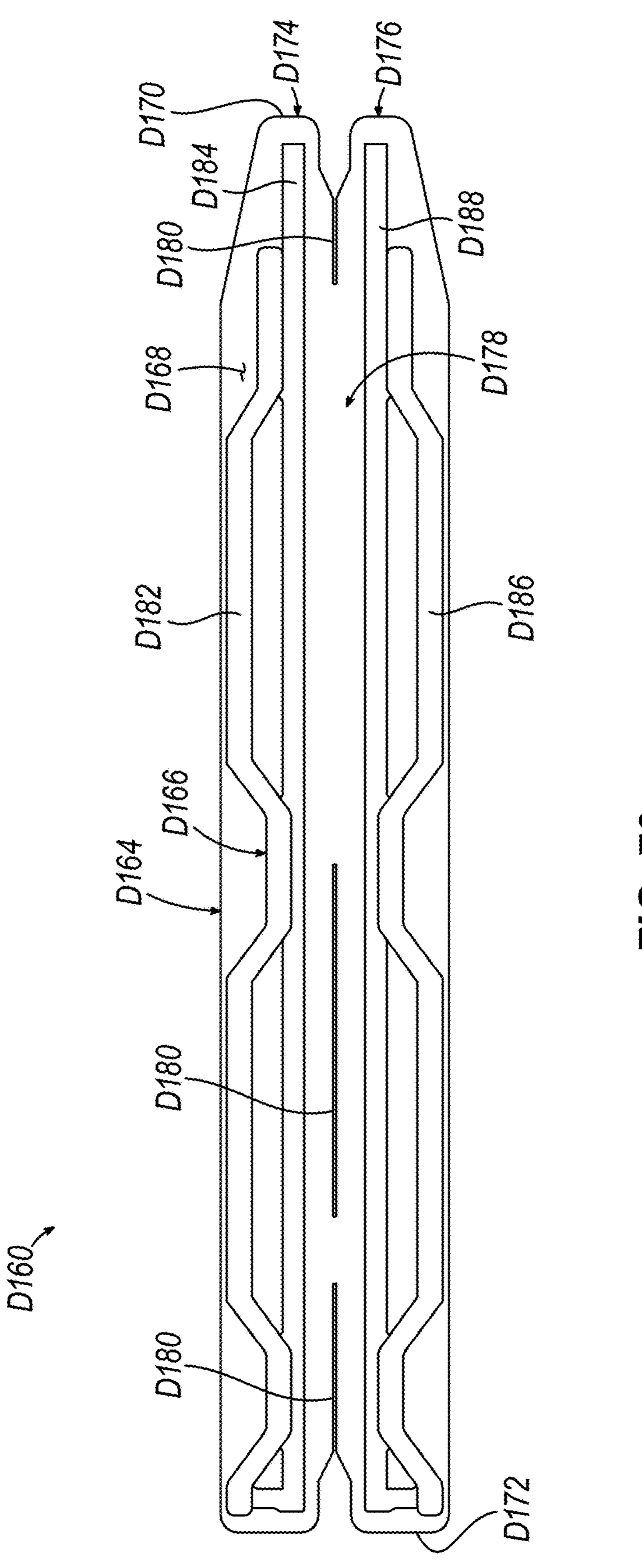
FIG. 73 depicts a top plan view of another example of a buttress assembly which may be applied to a jaw of the end effector of FIG. 2.

FIG. 73 illustrates another example of a buttress assembly (D160), which may be similar to buttress assemblies (D110, D112) described above, except as otherwise described below. In this regard, buttress assembly (D160) comprises a buttress body (D164) and an adhesive (D166) on a surface (D168) of buttress body (D164). Buttress body (D164) may comprise one or more layers of material. Where multiple layers are used the layers can be laminated together. In some examples buttress body (D164) comprises a mesh layer and one or more film layers laminated together. In some other examples buttress body (D164) comprises one or more film layers without a mesh layer. In view of the teachings herein, other various materials for one or more layers of buttress body (D164) will be apparent to those of ordinary skill in the art.

In the present example, buttress body (D164) is comprised of an absorbable material that is configured to be completely absorbed by the patient's body when used to reinforce a cut and staple site. In some examples, buttress body (D164) is comprised of polyglactin 910, which is 90% glycolide and 10% L-lactide. An example of polyglactin 910 is manufactured by Ethicon Inc. under the brand name Vicryl®. In view of the teachings herein, other absorbable synthetic materials for use with buttress body (D164) will be apparent to those of ordinary skill in the art.

Buttress body (D164) extends along a longitudinal axis between a proximal end (D170) and a distal end (D172), and defines a length extending from proximal end (D170) to distal end (D172). Buttress body (D164) includes a first edge region (D174), a second edge region (D176), and a center region (D178) between and separating first edge region (D174) and second edge region (D176). Buttress body (D164) defines a width extending orthogonal to its length as defined above, where its width extends from first edge region (D174) across center region (D178) and through second edge region (D176).

Adhesive (D166) extends from proximal end (D170) to distal end (D172) of buttress body (D164). Moreover, in the present example, adhesive (D166) extends continuously or in an uninterrupted manner. As shown in FIG. 73, adhesive (D166) is located along first edge region (D174) and second edge region (D176), with center region (D178) being substantially free of adhesive (D166). As shown in FIG. 73, center region (D178) of buttress body (D164) comprises slits (D180) that are configured to promote or facilitate cutting and separating buttress body (D164) into substantially equal halves during a cutting and stapling operation as discussed above. In the present example, the longitudinal axis of buttress body (D164) passes through slits (D180), and on each side of center region (D178), adhesive (D166) defines a pattern that is substantially symmetrical with the other side about the longitudinal axis.

Adhesive (D166) comprises a first bead (D182) and a second bead (D184) applied to first edge region (D174), and a third bead (D186) and a fourth bead (D188) applied to second edge region (D176). Each bead of adhesive (D182, D184, D186, D188) extends generally from proximal end (D170) of buttress body (D164) to distal end (D172) of buttress body (D164). Second and fourth beads of adhesive (D184, D188) extend further proximally compared to first and third beads of adhesive (D182, D186), while all four beads of adhesive (D182, D184, D186, D188) extend distally to substantially the same extent relative to buttress body (D164). As mentioned above, first and second beads of adhesive (D182, D184) are collectively symmetrical with third and fourth beads of adhesive (D186, D188) about the longitudinal axis defining the centerline of buttress body (D164). This arrangement results in more adhesive (D166) at distal end (D172) compared to proximal end (D170) of buttress body (D164). In examples like the present one where more adhesive (D166) is present at distal end (D172) of buttress body (D164), this helps buttress body (D164) stay attached and aligned to and with the respective parts of end effector (40) when aggressively manipulating end effector (40), i.e., when piercing through ostomies, sliding axially onto tissue, etc.

It will be appreciated that surgical stapler end effector (40) may be loaded with one or more buttress assemblies (D160) and actuated to drive staples (86) through two opposed layers of tissue (T1, T2), with the one or more buttress assemblies (D160) being secured to the same layers of tissue (T1, T2) by staples (86), in a manner similar to that described above in connection with FIGS. 71A-72.

V. Examples of Cartridges Having Raised Surfaces for Buttress Adhesion

In some instances, it may be desirable to increase the surface area of the regions of staple cartridge (70) that contact the adhesive layers or beads (D116, D120, D182, D184, D186, D188) of a corresponding buttress assembly (D110, D112, D160), such as in cases where staple cartridge (70) includes pocket extenders or other raised features whose height might inhibit the adhesive layers or beads (D116, D120, D182, D184, D186, D188) from reaching deck (74). For example, increasing the surface area of such regions of staple cartridge (70) may improve the adhesion of the corresponding buttress assembly (D110, D112, D160) to staple cartridge (70).

More particularly, it may be desirable to improve the adhesion of a buttress assembly (D110, D112, D160) at a distal end of staple cartridge (70). Because the distal end of staple cartridge (70) is the first part of staple cartridge (70) to contact tissue when positioning end effector (40), the distal end of staple cartridge (70) can be subject to greater forces in use compared to the proximal end of staple cartridge (70). Because of this, having stronger attachment of buttress assemblies (D110, D112, D160) at the distal end of staple cartridge (70) can be beneficial to maintaining attachment and alignment of buttress assemblies (D110, D112, D160) with respective parts of staple cartridge (70) (e.g., by inhibiting prying of the buttress assemblies (D110, D112, D160) away from staple cartridge (70) by anatomical structures encountered by the distal end of staple cartridge (70)). In addition, or alternatively, it may be desirable to improve the adhesion of a buttress assembly (D110, D112, D160) at a proximal end of staple cartridge (70). For example, such improved adhesion at the proximal end of staple cartridge (70) may inhibit movement (e.g., "plowing") of the buttress assembly (D110, D112, D160), such as by impeding the buttress assembly (D110, D112, D160) from moving distally during distal translation of firing beam (46) (e.g., during a firing stroke). In addition, or alternatively, it may be desirable to improve the adhesion of a buttress assembly (D110, D112, D160) at one or more discrete locations along the length of staple cartridge (70) between the proximal and distal ends of staple cartridge (70).

Each of the examples of staple cartridges (D210, D310, D410, D510, D610, D710, D810, D910) described below provides such functionality.

A. First Example of Staple Cartridge with Enlarged Distal Pocket Extenders

Figure 74:
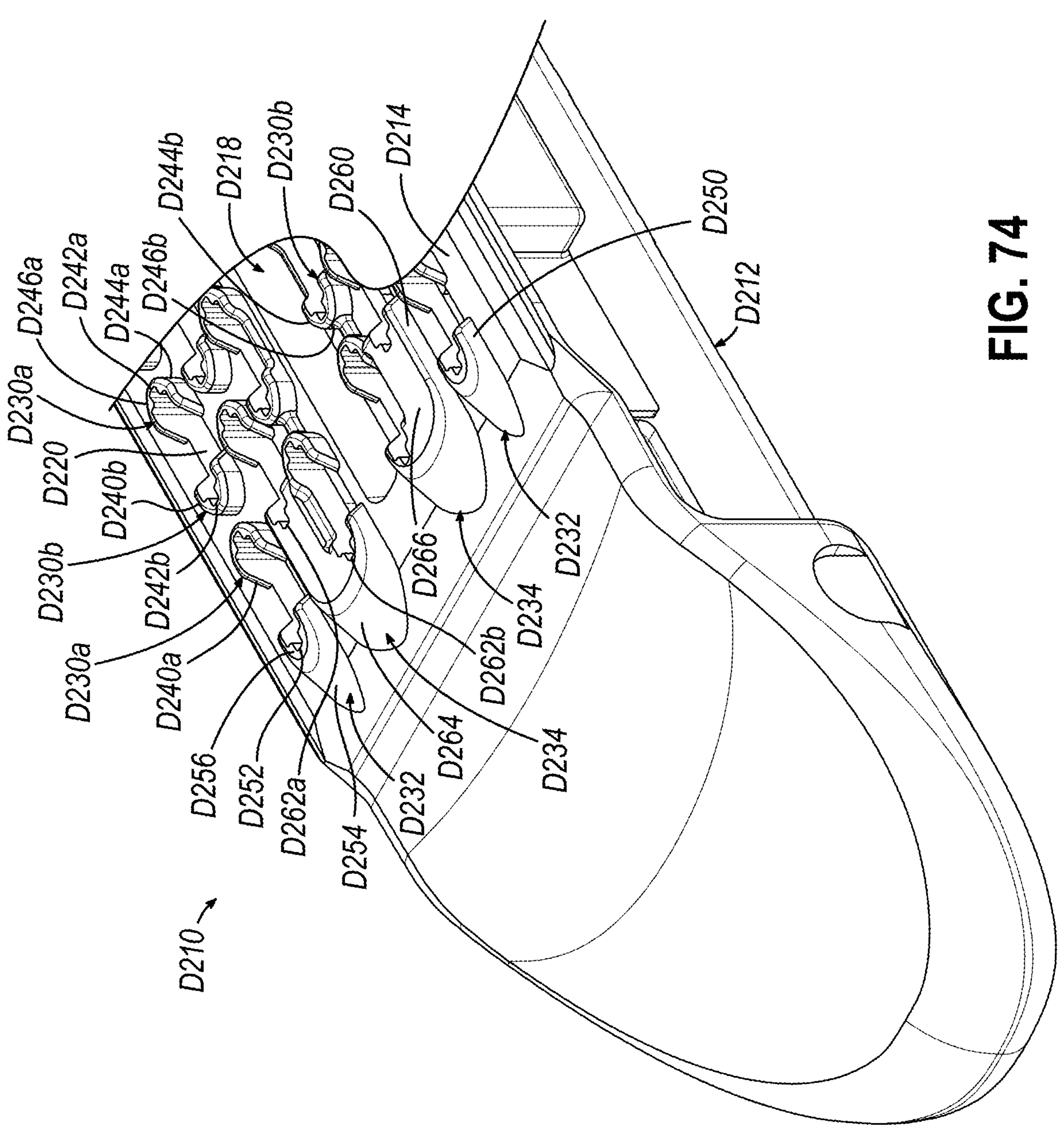
FIG. 74 depicts a partial perspective view of another example of a staple cartridge for use with the end effector of FIG. 2 and having enlarged distal pocket extenders with distal ramp surfaces that are rounded in the lateral direction, the enlarged distal pocket extenders being configured to promote adhesion of any of the buttress assemblies of FIGS. 70-73 to the staple cartridge.

FIG. 74 shows a portion of another example of a staple cartridge (D210) configured to deploy staples (86) toward corresponding staple forming pockets of an anvil (not shown), such as staple forming pockets (66) of anvil (44). Staple cartridge (D210) is configured for use with end effector (40), and is similar to staple cartridge (70) described above except as otherwise described below. In this regard, staple cartridge (D210) of the present example includes a cartridge body (D212) having an upwardly facing deck (D214), an elongate slot (D218) extending along a central axis of cartridge body (D212) and opening upwardly through deck (D214) for slidably receiving a distal knife portion of a firing beam (not shown), such as distal knife portion (50) of firing beam (46), and a plurality of cartridge pockets (D220) extending through deck (D214) on each side of knife slot (D218). In the present version, three longitudinal rows of cartridge pockets (D220) are formed through upper deck (D214) along each lateral side of knife slot (D218), including an inner row, a middle row, and an outer row on each lateral side of knife slot (D218). Each cartridge pocket (D220) slidably houses an unformed staple (86) and a respective staple driver (not shown) similar to staple drivers (84) positioned beneath staple (86). A lower tray (not shown) similar to lower tray (76) encloses an underside of cartridge body (D212) and thereby retains staples (86) and the staple drivers within cartridge body (D212). A wedge sled (not shown) similar to wedge sled (82) is slidably disposed within cartridge body (D212) and includes upwardly presented cam surfaces configured to engage the undersides of the staple drivers.

Staple cartridge (D210) of the present example further includes a plurality of raised features in the form of pocket extenders (D230*a*, D230*b*, D232, D234) that extend upwardly from deck (D214) at or near proximal and distal ends of each cartridge pocket (D220), such that each cartridge pocket (D220) is longitudinally flanked by a corresponding pair of proximal and distal pocket extenders (D230*a*, D230*b*, D232, D234). Any one or more of pocket extenders (D230*a*, D230*b*, D232, D234) may be configured to enhance the gripping of tissue (T1, T2) by staple cartridge (D210) when end effector (40) is closed (e.g., in instances when staple cartridge (D210) is not equipped with a buttress assembly (D110, D112, D160)), and/or to guide the legs (D126) of the staples (86) as the legs (D126) exit the respective cartridge pockets (D220) during deployment of the staples (86). In addition, or alternatively, any one or more of pocket extenders (D230*a*, D230*b*, D232, D234) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D210).

In the example shown, the plurality of pocket extenders (D230*a*, D230*b*, D232, D234) include a plurality of first pocket extenders (D230*a*, D230*b*) having a first configuration, a plurality of second pocket extenders (D232) having a second configuration different from the first configuration, and a plurality of third pocket extenders (D234) having a third configuration different from the first and second configurations. First pocket extenders (D230*a*, D230*b*) include proximal first pocket extenders (D230*a*) that are positioned at or near the proximal ends of each cartridge pocket (D220) of each row, and further include distal first pocket extenders (D230*b*) that are positioned at or near the distal ends of each cartridge pocket (D220) of each row, except for the distalmost cartridge pocket (D220) of each row. In this regard, second pocket extenders (D232) are positioned at or near the distal ends of the distalmost cartridge pockets (D220) of the outer rows, and third pocket extenders (D234) are positioned at or near the distal ends of the distalmost cartridge pockets (D220) of the inner and middle rows such that each third pocket extender (D234) spans laterally across two rows of cartridge pockets (D220) on the respective lateral side of knife slot (D218) (e.g., the respective inner and middle rows of cartridge pockets (D220)).

As shown, each first pocket extender (D230*a*, D230*b*) includes a generally U-shaped body (D240*a*, D240*b*) that defines a staple leg receptacle (D242*a*, D242*b*) for receiving a corresponding leg (D126) of the staple (86) slidably housed within the respective cartridge pocket (D220). In this regard, each staple leg receptacle (D242*a*, D242*b*) may be sized and configured to slidably receive the corresponding leg (D126) for vertically guiding the corresponding leg (D126) out of the respective cartridge pocket (D220) toward the corresponding staple forming pockets (66) as staples (86) are driven outwardly from cartridge pockets (D220) by the staple drivers. The body (D240*a*) of each proximal first pocket extender (D230*a*) also defines a proximally-facing outer surface (D244*a*) that extends substantially orthogonally relative to deck (D214), while the body (D240*b*) of each distal first pocket extender (D230*b*) also defines a distally-facing outer surface (D244*b*) that extends substantially orthogonally relative to deck (D214). The body (D240*a*, D240*b*) of each first pocket extender (D230*a*, D230*b*) further defines an upwardly-facing top (e.g., uppermost) surface (D246*a*, D246*b*) that extends substantially parallel relative to deck (D214). Top surfaces (D246*a*, D246*b*) may be positioned at a substantially uniform height above deck (D214).

Each second pocket extender (D232) includes a generally U-shaped body (D250) that defines a staple leg receptacle (D252) for receiving a corresponding leg (D126) of the staple (86) slidably housed within the respective distalmost, outer cartridge pocket (D220). In this regard, each staple leg receptacle (D252) may be sized and configured to slidably receive the corresponding leg (D126) for vertically guiding the corresponding leg (D126) out of the respective cartridge pocket (D220) toward the corresponding staple forming pockets (66) as staples (86) are driven outwardly from cartridge pockets (D220) by the staple drivers. The body (D250) of each second pocket extender (D232) also defines a distally-facing outer surface (D254) that extends substantially obliquely relative to deck (D214). In the example shown, the outer surface (D254) of each second pocket extender (D232) is rounded in the lateral direction. By extending substantially obliquely relative to deck (D214) and/or by being rounded in the lateral direction, the outer surface (D254) of each second pocket extender (D232) may have a substantially atraumatic configuration so that each outer surface (D254) may avoid inflicting trauma to tissue contacted by the outer surface (D254). For example, each outer surface (D254) may define a distal ramp for gently lifting such tissue upwardly relative to deck (D214).

The body (D250) of each second pocket extender (D232) further defines an upwardly-facing top surface (D256) that extends substantially parallel relative to deck (D214). Top surfaces (D256) may be positioned at a substantially same height above deck (D214) as that of top surfaces (D246*a*, D246*b*). In some other versions, top surfaces (D256) may be positioned at a lower height above deck (D214) than that of top surfaces (D246*a*, D246*b*). In the example shown, the top surface (D256) of each second pocket extender (D232) has a surface area that is greater than that of the top surface (D246*a*, D246*b*) of each first pocket extender (D230*a*, D230*b*). The top surface (D256) of each second pocket extender (D232) may also extend further distally compared to the top surface (D246*b*) of a distal first pocket extender (D230*b*) if such a distal first pocket extender (D230*b*) were substituted for the respective second pocket extender (D232). By having a greater surface area and/or extending further distally compared to the top surface (D246*a*, D246*b*) of each first pocket extender (D230*a*, D230*b*), the top surface (D256) of each second pocket extender (D232) may be configured to provide improved contact with the adhesive layers or beads (D116, D120, D182, D184, D186, D188) of a corresponding buttress assembly (D110, D112, D160), at least relative to the top surface (D246*a*, D246*b*) of each first pocket extender (D230*a*, D230*b*). For example, the further distal extension of the top surface (D256) of each second pocket extender (D232) may allow the top surface (D256) to vertically align with more adhesive (D166) at distal end (D172) of buttress body (D164) compared to the top surface (D246*b*) of a distal first pocket extender (D230*b*) if such a distal first pocket extender (D230*b*) were substituted for the respective second pocket extender (D232), and may thereby provide stronger, localized attachment of buttress assembly (D160) at the distal end of staple cartridge (D210).

As noted above, each third pocket extender (D234) spans laterally across the respective inner and middle rows of cartridge pockets (D220), and is positioned at or near the distal ends of the distalmost cartridge pockets (D220) of the respective inner and middle rows. Each third pocket extender (D234) includes a generally J-shaped body (D260) that defines proximal and distal staple leg receptacles (D262*a*, D262*b*) for receiving corresponding legs (D126) of the staples (86) slidably housed within the respective distalmost, inner and middle cartridge pockets (D220). In this regard, each staple leg receptacle (D262*a*, D262*b*) may be sized and configured to slidably receive the corresponding leg (D126) for vertically guiding the corresponding leg (D126) out of the respective cartridge pocket (D220) toward the corresponding staple forming pockets (66) as staples (86) are driven outwardly from cartridge pockets (D220) by the staple drivers.

The body (D260) of each third pocket extender (D234) also defines a distally-facing outer surface (D264) that extends substantially obliquely relative to deck (D214). In the example shown, the outer surface (D264) of each third pocket extender (D234) is rounded in the lateral direction. By extending substantially obliquely relative to deck (D214) and/or by being rounded in the lateral direction, the outer surface (D264) of each third pocket extender (D234) may have a substantially atraumatic configuration so that each outer surface (D264) may avoid inflicting trauma to tissue contacted by the outer surface (D264). For example, each outer surface (D264) may define a distal ramp for gently lifting such tissue upwardly relative to deck (D214). Due to the spanning of each third pocket extender (D234) laterally across the respective inner and middle rows of cartridge pockets (D220), each outer surface (D264) may be configured to lift the portions of such tissue that are aligned with both the respective inner and middle rows of cartridge pockets (D220), and to do so substantially simultaneously with the lifting of the portions of such tissue that are aligned with the respective outer row of cartridge pockets (D220) by the outer surface (D254) of the corresponding second pocket extender (D232).

The body (D260) of each third pocket extender (D234) further defines an upwardly-facing top surface (D266) that extends substantially parallel relative to deck (D214). Top surfaces (D266) may be positioned at a substantially same height above deck (D214) as that of top surfaces (D246*a*, D246*b*). In some other versions, top surfaces (D266) may be positioned at a lower height above deck (D214) than that of top surfaces (D246*a*, D246*b*). In the example shown, the top surface (D266) of each third pocket extender (D234) has a surface area that is greater than that of the top surface (D246*a*, D246*b*) of each first pocket extender (D230*a*, D230*b*). The top surface (D266) of each third pocket extender (D234) may also extend further distally compared to the top surfaces (D246*b*) of a pair of distal first pocket extenders (D230*b*) if such a pair of distal first pocket extenders (D230*b*) were substituted for the respective third pocket extender (D234). By having a greater surface area and/or extending further distally compared to the top surface (D246*a*, D246*b*) of each first pocket extender (D230*a*, D230*b*), the top surface (D266) of each third pocket extender (D234) may be configured to provide improved contact with the adhesive layers or beads (D116, D120, D182, D184, D186, D188) of a corresponding buttress assembly (D110, D112, D160), at least relative to the top surface (D246*a*, D246*b*) of each first pocket extender (D230*a*, D230*b*). For example, the further distal extension of the top surface (D266) of each third pocket extender (D234) may allow the top surface (D266) to vertically align with more adhesive (D166) at distal end (D172) of buttress body (D164) compared to the top surfaces (D246*b*) of a pair of distal first pocket extenders (D230*b*) if such a pair of distal first pocket extenders (D230*b*) were substituted for the respective third pocket extender (D234), and may thereby provide stronger, localized attachment of buttress assembly (D160) at the distal end of staple cartridge (D210).

Due to the spanning of each third pocket extender (D234) laterally across the respective inner and middle rows of cartridge pockets (D220), the surface area of the top surface (D266) of each third pocket extender (D234) may also be greater than that of the top surface (D256) of each second pocket extender (D232). By having a greater surface area compared to the top surface (D256) of each second pocket extender (D232), the top surface (D256) of each second pocket extender (D232) may be configured to provide improved contact with the adhesive layers or beads (D116, D120, D182, D184, D186, D188) of a corresponding buttress assembly (D110, D112, D160), at least relative to the top surface (D256) of each second pocket extender (D232) as well.

While each third pocket extender (D234) is shown spanning laterally across the respective inner and middle rows of cartridge pockets (D220), each third pocket extender (D234) may alternatively span laterally across the respective middle and outer rows of cartridge pockets (D220), and/or may span laterally across all three respective rows of cartridge pockets (D220).

B. Second Example of Staple Cartridge with Enlarged Distal Pocket Extenders

Figure 75:
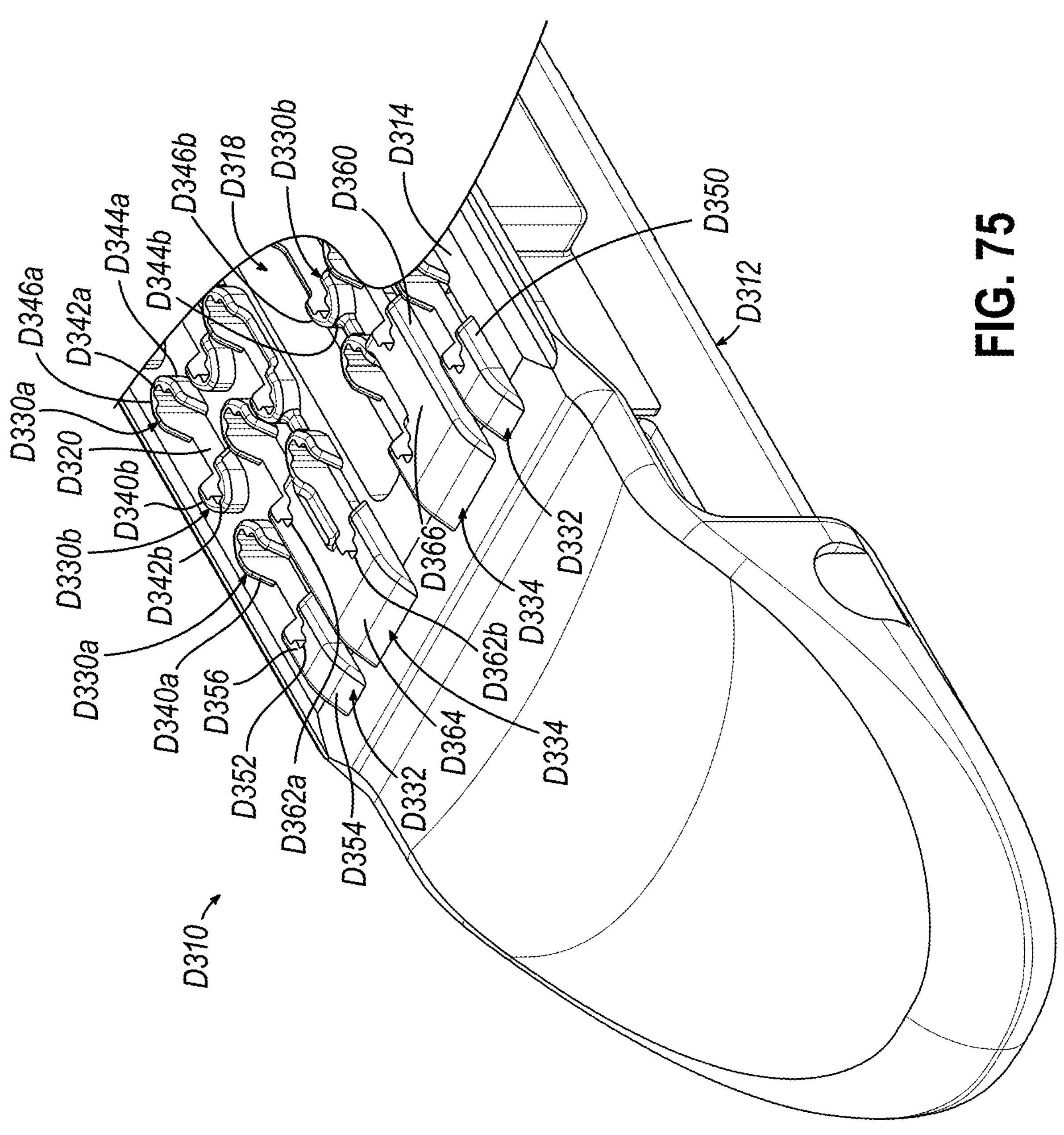
FIG. 75 depicts a partial perspective view of another example of a staple cartridge for use with the end effector of FIG. 2 and having enlarged distal pocket extenders with distal ramp surfaces that are rounded in the longitudinal direction, the enlarged distal pocket extenders being configured to promote adhesion of any of the buttress assemblies of FIGS. 70-73 to the staple cartridge.

FIG. 75 shows a portion of another example of a staple cartridge (D310) configured to deploy staples (86) toward corresponding staple forming pockets of an anvil (not shown), such as staple forming pockets (66) of anvil (44). Staple cartridge (D310) is configured for use with end effector (40), and is similar to staple cartridge (70) described above except as otherwise described below. In this regard, staple cartridge (D310) of the present example includes a cartridge body (D312) having an upwardly facing deck (D314), an elongate slot (D318) extending along a central axis of cartridge body (D312) and opening upwardly through deck (D314) for slidably receiving a distal knife portion of a firing beam (not shown), such as distal knife portion (50) of firing beam (46), and a plurality of cartridge pockets (D320) extending through deck (D314) on each side of knife slot (D318). In the present version, three longitudinal rows of cartridge pockets (D320) are formed through upper deck (D314) along each lateral side of knife slot (D318), including an inner row, a middle row, and an outer row on each lateral side of knife slot (D318). Each cartridge pocket (D320) slidably houses an unformed staple (86) and a respective staple driver (not shown) similar to staple drivers (84) positioned beneath staple (86). A lower tray (not shown) similar to lower tray (76) encloses an underside of cartridge body (D312) and thereby retains staples (86) and the staple drivers within cartridge body (D312). A wedge sled (not shown) similar to wedge sled (82) is slidably disposed within cartridge body (D312) and includes upwardly presented cam surfaces configured to engage the undersides of the staple drivers.

Staple cartridge (D310) of the present example further includes a plurality of raised features in the form of pocket extenders (D330*a*, D330*b*, D332, D334) that extend upwardly from deck (D314) at or near proximal and distal ends of each cartridge pocket (D320), such that each cartridge pocket (D320) is longitudinally flanked by a corresponding pair of proximal and distal pocket extenders (D330*a*, D330*b*, D332, D334). Any one or more of pocket extenders (D330*a*, D330*b*, D332, D334) may be configured to enhance the gripping of tissue (T1, T2) by staple cartridge (D310) when end effector (40) is closed (e.g., in instances when staple cartridge (D310) is not equipped with a buttress assembly (D110, D112, D160)), and/or to guide the legs (D126) of the staples (86) as the legs (D126) exit the respective cartridge pockets (D320) during deployment of the staples (86). In addition, or alternatively, any one or more of pocket extenders (D330*a*, D330*b*, D332, D334) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D310).

In the example shown, the plurality of pocket extenders (D330*a*, D330*b*, D332, D334) include a plurality of first pocket extenders (D330*a*, D330*b*) having a first configuration, a plurality of second pocket extenders (D332) having a second configuration different from the first configuration, and a plurality of third pocket extenders (D334) having a third configuration different from the first and second configurations. First pocket extenders (D330*a*, D330*b*) include proximal first pocket extenders (D330*a*) that are positioned at or near the proximal ends of each cartridge pocket (D320) of each row, and further include distal first pocket extenders (D330*b*) that are positioned at or near the distal ends of each cartridge pocket (D320) of each row, except for the distalmost cartridge pocket (D320) of each row. In this regard, second pocket extenders (D332) are positioned at or near the distal ends of the distalmost cartridge pockets (D320) of the outer rows, and third pocket extenders (D334) are positioned at or near the distal ends of the distalmost cartridge pockets (D320) of the inner and middle rows such that each third pocket extender (D334) spans laterally across two rows of cartridge pockets (D320) on the respective lateral side of knife slot (D318) (e.g., the respective inner and middle rows of cartridge pockets (D320)).

As shown, each first pocket extender (D330*a*, D330*b*) includes a generally U-shaped body (D340*a*, D340*b*) that defines a staple leg receptacle (D342*a*, D342*b*) for receiving a corresponding leg (D126) of the staple (86) slidably housed within the respective cartridge pocket (D320). In this regard, each staple leg receptacle (D342*a*, D342*b*) may be sized and configured to slidably receive the corresponding leg (D126) for vertically guiding the corresponding leg (D126) out of the respective cartridge pocket (D320) toward the corresponding staple forming pockets (66) as staples (86) are driven outwardly from cartridge pockets (D320) by the staple drivers. The body (D340*a*) of each proximal first pocket extender (D330*a*) also defines a proximally-facing outer surface (D344*a*) that extends substantially orthogonally relative to deck (D314), while the body (D340*b*) of each distal first pocket extender (D330*b*) also defines a distally-facing outer surface (D344*b*) that extends substantially orthogonally relative to deck (D314). The body (D340*a*, D340*b*) of each first pocket extender (D330*a*, D330*b*) further defines an upwardly-facing top surface (D346*a*, D346*b*) that extends substantially parallel relative to deck (D314). Top surfaces (D346*a*, D346*b*) may be positioned at a substantially uniform height above deck (D314).

Each second pocket extender (D332) includes a generally U-shaped body (D350) that defines a staple leg receptacle (D352) for receiving a corresponding leg (D126) of the staple (86) slidably housed within the respective distalmost, outer cartridge pocket (D320). In this regard, each staple leg receptacle (D352) may be sized and configured to slidably receive the corresponding leg (D126) for vertically guiding the corresponding leg (D126) out of the respective cartridge pocket (D320) toward the corresponding staple forming pockets (66) as staples (86) are driven outwardly from cartridge pockets (D320) by the staple drivers. The body (D350) of each second pocket extender (D332) also defines a distally-facing outer surface (D354) that extends substantially obliquely relative to deck (D314). In the example shown, the outer surface (D354) of each second pocket extender (D332) is rounded in the longitudinal direction. By extending substantially obliquely relative to deck (D314) and/or by being rounded in the longitudinal direction, the outer surface (D354) of each second pocket extender (D332) may have a substantially atraumatic configuration so that each outer surface (D354) may avoid inflicting trauma to tissue contacted by the outer surface (D354). For example, each outer surface (D354) may define a distal ramp for gently lifting such tissue upwardly relative to deck (D314).

The body (D350) of each second pocket extender (D332) further defines an upwardly-facing top surface (D356) that extends substantially parallel relative to deck (D314). Top surfaces (D356) may be positioned at a substantially same height above deck (D314) as that of top surfaces (D346*a*, D346*b*). In some other versions, top surfaces (D356) may be positioned at a lower height above deck (D314) than that of top surfaces (D346*a*, D346*b*). In the example shown, the top surface (D356) of each second pocket extender (D332) has a surface area that is greater than that of the top surface (D346*a*, D346*b*) of each first pocket extender (D330*a*, D330*b*). The top surface (D356) of each second pocket extender (D332) may also extend further distally compared to the top surface (D346*b*) of a distal first pocket extender (D330*b*) if such a distal first pocket extender (D330*b*) were substituted for the respective second pocket extender (D332). By having a greater surface area and/or extending further distally compared to the top surface (D346*a*, D346*b*) of each first pocket extender (D330*a*, D330*b*), the top surface (D356) of each second pocket extender (D332) may be configured to provide improved contact with the adhesive layers or beads (D116, D120, D182, D184, D186, D188) of a corresponding buttress assembly (D110, D112, D160), at least relative to the top surface (D346*a*, D346*b*) of each first pocket extender (D330*a*, D330*b*). For example, the further distal extension of the top surface (D356) of each second pocket extender (D332) may allow the top surface (D356) to vertically align with more adhesive (D166) at distal end (D172) of buttress body (D164) compared to the top surface (D346*b*) of a distal first pocket extender (D330*b*) if such a distal first pocket extender (D330*b*) were substituted for the respective second pocket extender (D332), and may thereby provide stronger, localized attachment of buttress assembly (D160) at the distal end of staple cartridge (D310).

As noted above, each third pocket extender (D334) spans laterally across the respective inner and middle rows of cartridge pockets (D320), and is positioned at or near the distal ends of the distalmost cartridge pockets (D320) of the respective inner and middle rows. Each third pocket extender (D334) includes a generally L-shaped body (D360) that defines proximal and distal staple leg receptacles (D362*a*, D362*b*) for receiving corresponding legs (D126) of the staples (86) slidably housed within the respective distalmost, inner and middle cartridge pockets (D320). In this regard, each staple leg receptacle (D362*a*, D362*b*) may be sized and configured to slidably receive the corresponding leg (D126) for vertically guiding the corresponding leg (D126) out of the respective cartridge pocket (D320) toward the corresponding staple forming pockets (66) as staples (86) are driven outwardly from cartridge pockets (D320) by the staple drivers.

The body (D360) of each third pocket extender (D334) also defines a distally-facing outer surface (D364) that extends substantially obliquely relative to deck (D314). In the example shown, the outer surface (D364) of each third pocket extender (D334) is rounded in the longitudinal direction. By extending substantially obliquely relative to deck (D314) and/or by being rounded in the longitudinal direction, the outer surface (D364) of each third pocket extender (D334) may have a substantially atraumatic configuration so that each outer surface (D364) may avoid inflicting trauma to tissue contacted by the outer surface (D364). For example, each outer surface (D364) may define a distal ramp for gently lifting such tissue upwardly relative to deck (D314). Due to the spanning of each third pocket extender (D334) laterally across the respective inner and middle rows of cartridge pockets (D320), each outer surface (D364) may be configured to lift the portions of such tissue that are aligned with both the respective inner and middle rows of cartridge pockets (D320), and to do so substantially simultaneously with the lifting of the portions of such tissue that are aligned with the respective outer row of cartridge pockets (D320) by the outer surface (D354) of the corresponding second pocket extender (D332).

The body (D360) of each third pocket extender (D334) further defines an upwardly-facing top surface (D366) that extends substantially parallel relative to deck (D314). Top surfaces (D366) may be positioned at a substantially same height above deck (D314) as that of top surfaces (D346*a*, D346*b*). In some other versions, top surfaces (D366) may be positioned at a lower height above deck (D314) than that of top surfaces (D346*a*, D346*b*). In the example shown, the top surface (D366) of each third pocket extender (D334) has a surface area that is greater than that of the top surface (D346*a*, D346*b*) of each first pocket extender (D330*a*, D330*b*). The top surface (D366) of each third pocket extender (D334) may also extend further distally compared to the top surfaces (D346*b*) of a pair of distal first pocket extenders (D330*b*) if such a pair of distal first pocket extenders (D330*b*) were substituted for the respective third pocket extender (D334). By having a greater surface area and/or extending further distally compared to the top surface (D346*a*, D346*b*) of each first pocket extender (D330*a*, D330*b*), the top surface (D366) of each third pocket extender (D334) may be configured to provide improved contact with the adhesive layers or beads (D116, D120, D182, D184, D186, D188) of a corresponding buttress assembly (D110, D112, D160), at least relative to the top surface (D346*a*, D346*b*) of each first pocket extender (D330*a*, D330*b*). For example, the further distal extension of the top surface (D366) of each third pocket extender (D334) may allow the top surface (D366) to vertically align with more adhesive (D166) at distal end (D172) of buttress body (D164) compared to the top surfaces (D346*b*) of a pair of distal first pocket extenders (D330*b*) if such a pair of distal first pocket extenders (D330*b*) were substituted for the respective third pocket extender (D334), and may thereby provide stronger, localized attachment of buttress assembly (D160) at the distal end of staple cartridge (D310).

Due to the spanning of each third pocket extender (D334) laterally across the respective inner and middle rows of cartridge pockets (D320), the surface area of the top surface (D366) of each third pocket extender (D334) may also be greater than that of the top surface (D356) of each second pocket extender (D332). By having a greater surface area compared to the top surface (D356) of each second pocket extender (D332), the top surface (D356) of each second pocket extender (D332) may be configured to provide improved contact with the adhesive layers or beads (D116, D120, D182, D184, D186, D188) of a corresponding buttress assembly (D110, D112, D160), at least relative to the top surface (D356) of each second pocket extender (D332) as well.

While each third pocket extender (D334) is shown spanning laterally across the respective inner and middle rows of cartridge pockets (D320), each third pocket extender (D334) may alternatively span laterally across the respective middle and outer rows of cartridge pockets (D320), and/or may span laterally across all three respective rows of cartridge pockets (D320).

C. Example of Staple Cartridge with Undulating Upper Profile

Figure 76:
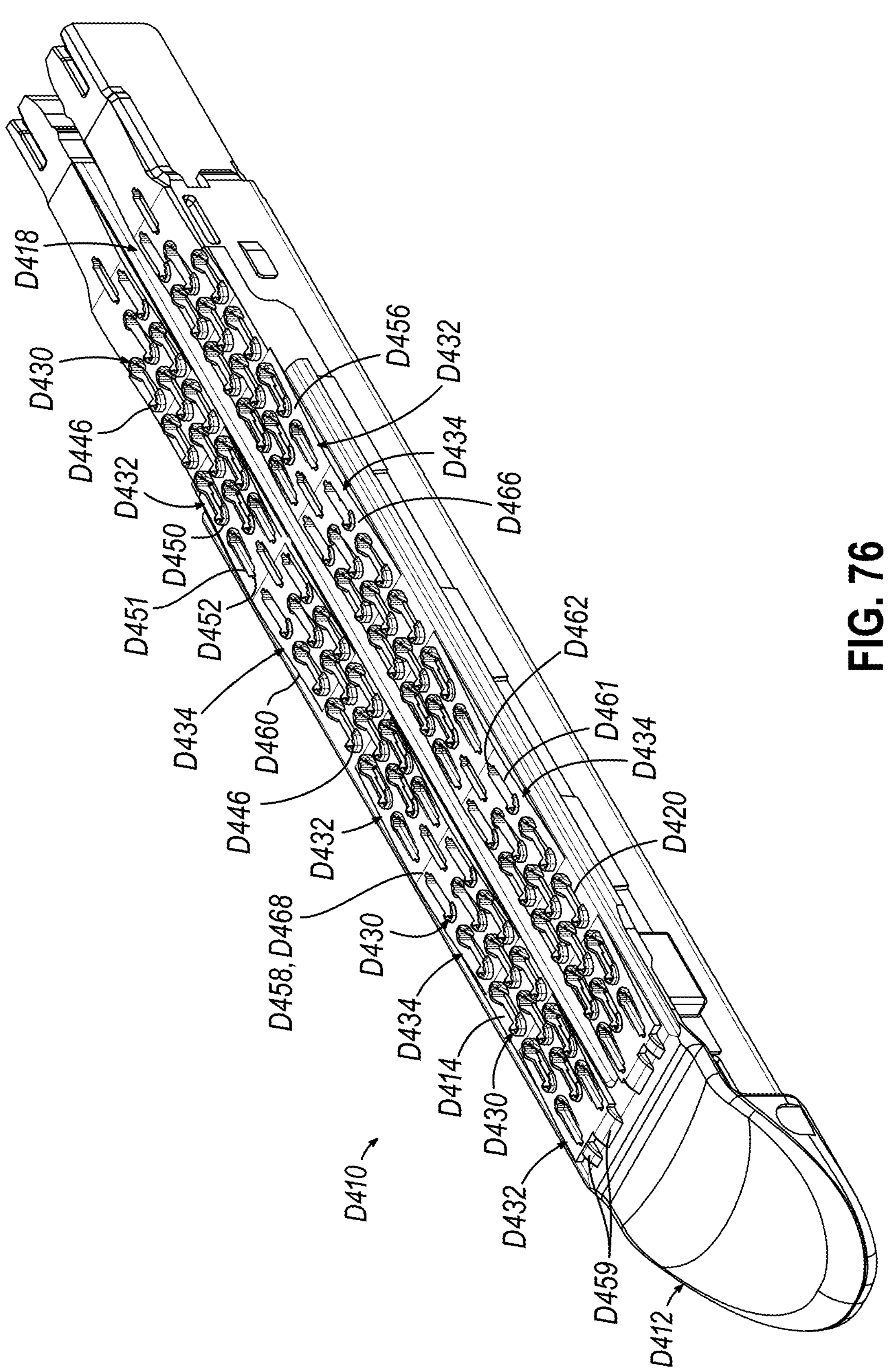
FIG. 76 depicts a perspective view of another example of a staple cartridge for use with the end effector of FIG. 2 and having an undulating upper profile configured to promote adhesion of any of the buttress assemblies of FIGS. 70-73 to the staple cartridge.
Figure 77:
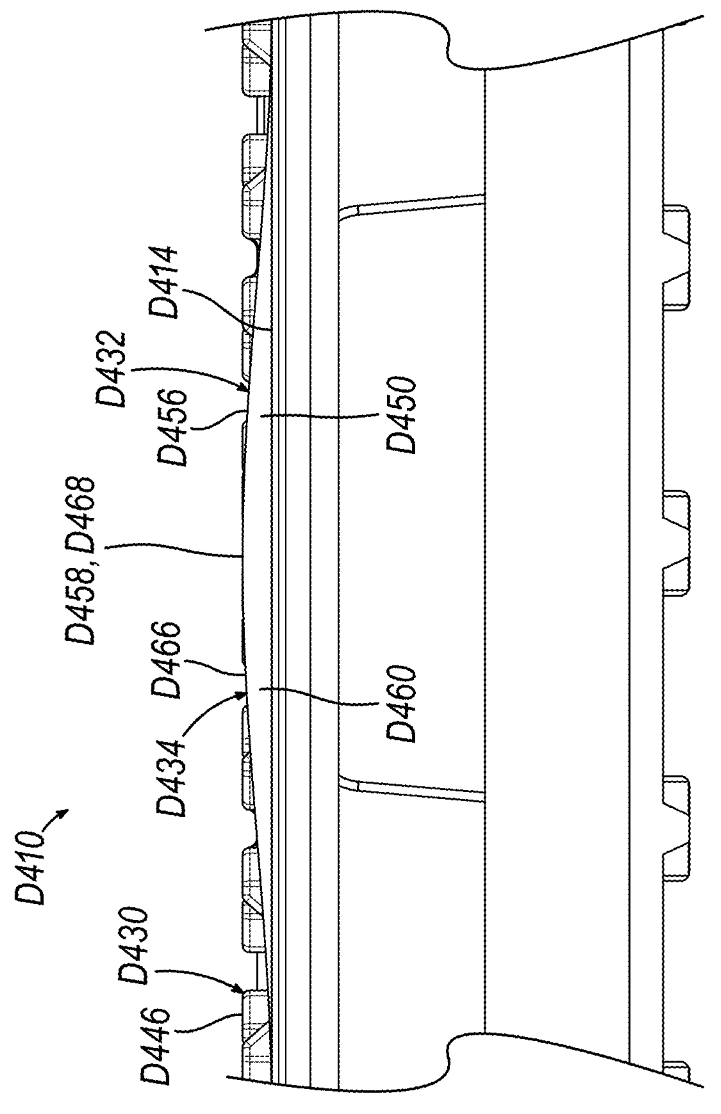
FIG. 77 depicts a partial side elevational view of the staple cartridge of FIG. 76.

FIGS. 76-77 show another example of a staple cartridge (D410) configured to deploy staples (86) toward corresponding staple forming pockets of an anvil (not shown), such as staple forming pockets (66) of anvil (44). Staple cartridge (D410) is configured for use with end effector (40), and is similar to staple cartridge (70) described above except as otherwise described below. In this regard, staple cartridge (D410) of the present example includes a cartridge body (D412) having an upwardly facing deck (D414), an elongate slot (D418) extending along a central axis of cartridge body (D412) and opening upwardly through deck (D414) for slidably receiving a distal knife portion of a firing beam (not shown), such as distal knife portion (50) of firing beam (46), and a plurality of cartridge pockets (D420) extending through deck (D414) on each side of knife slot (D418). In the present version, three longitudinal rows of cartridge pockets (D420) are formed through upper deck (D414) along each lateral side of knife slot (D418), including an inner row, a middle row, and an outer row on each lateral side of knife slot (D418). Each cartridge pocket (D420) slidably houses an unformed staple (86) and a respective staple driver (not shown) similar to staple drivers (84) positioned beneath staple (86). A lower tray (not shown) similar to lower tray (76) encloses an underside of cartridge body (D412) and thereby retains staples (86) and the staple drivers within cartridge body (D412). A wedge sled (not shown) similar to wedge sled (82) is slidably disposed within cartridge body (D412) and includes upwardly presented cam surfaces configured to engage the undersides of the staple drivers.

Staple cartridge (D410) of the present example further includes a plurality of raised features in the form of pocket extenders (D430) that extend upwardly from deck (D414) at or near proximal and distal ends of at least some cartridge pockets (D420), such that at least some cartridge pockets (D420) are each longitudinally flanked by a corresponding pair of proximal and distal pocket extenders (D430) while some other cartridge pockets (D420) are only equipped with either a corresponding proximal or distal pocket extender (D430) and while still other cartridge pockets (D420) may be equipped with neither a corresponding proximal nor distal pocket extender (D430). Any one or more of pocket extenders (D430) may be configured to enhance the gripping of tissue (T1, T2) by staple cartridge (D410) when end effector (40) is closed (e.g., in instances when staple cartridge (D410) is not equipped with a buttress assembly (D110, D112, D160)), and/or to guide the legs (D126) of the staples (86) as the legs (D126) exit the respective cartridge pockets (D420) during deployment of the staples (86). In addition, or alternatively, any one or more of pocket extenders (D430) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D410). As shown, each pocket extender (D430) includes an upwardly-facing top surface (D446) that extends substantially parallel relative to deck (D414). Top surfaces (D446) may be positioned at a substantially uniform height above deck (D414).

Staple cartridge (D410) of the present example also includes a plurality of raised features in the form of first and second wedges (D432, D434) that extend upwardly from deck (D414) on each lateral side of knife slot (D418) such that each wedge (D432, D434) spans laterally across three rows of cartridge pockets (D420) on the respective lateral side of knife slot (D418) (e.g., the respective inner, middle, and outer rows of cartridge pockets (D420)). In the example shown, first and second wedges (D432, D434) are arranged in a longitudinally-alternating manner, such that wedges (D432, D434) cooperate with each other and with deck (D414) to provide staple cartridge (D410) with a generally undulating (e.g., wavy) upper profile when viewed from the side.

Each first wedge (D432) includes a generally triangular body (D450) that defines one or more openings (D451) overlying corresponding cartridge pockets (D420) for accommodating passage of respective staples (86) therethrough. The body (D450) of each first wedge (D432) further defines one or more staple leg receptacles (D452) at or near proximal and distal ends of cartridge pockets (D420) that lack a pocket extender (D430) for receiving a corresponding leg (D126) of the staple (86) slidably housed within the respective cartridge pocket (D420). In this regard, each staple leg receptacle (D452) may be sized and configured to slidably receive the corresponding leg (D126) for vertically guiding the corresponding leg (D126) out of the respective cartridge pocket (D420) toward the corresponding staple forming pockets (66) as staples (86) are driven outwardly from cartridge pockets (D420) by the staple drivers. The body (D450) of each first wedge (D432) also defines an upwardly and/or proximally-facing top surface (D456) that tapers and/or curves upwardly and distally from deck (D414) to a peak (D458). Peaks (D458) may be positioned at a substantially same height above deck (D414) as that of top surfaces (D446). In some other versions, peaks (D458) may be positioned at a lower height above deck (D414) than that of top surfaces (D446).

In the example shown, a pair of atraumatic distal ramps (D459) taper and/or curve upwardly and proximally from deck (D414) to the peak (D458) of each distalmost first wedge (D432) for gently lifting tissue upwardly relative to deck (D414). As shown, at least one such distal ramp (D459) may span laterally at least partially across the respective inner and middle rows of cartridge pockets (D420) for lifting the portions of such tissue that are aligned with both the respective inner and middle rows of cartridge pockets (D420) substantially simultaneously with the lifting of the portions of such tissue that are aligned with the respective outer row of cartridge pockets (D420) via the other distal ramp (D459) on the same lateral side of knife slot (D418).

Each second wedge (D434) includes a generally triangular body (D460) that defines one or more openings (D461) overlying corresponding cartridge pockets (D420) for accommodating passage of respective staples (86) therethrough. The body (D460) of each second wedge (D434) further defines one or more staple leg receptacles (D462) at or near proximal and distal ends of cartridge pockets (D420) that lack a pocket extender (D430) for receiving a corresponding leg (D126) of the staple (86) slidably housed within the respective cartridge pocket (D420). In this regard, each staple leg receptacle (D462) may be sized and configured to slidably receive the corresponding leg (D126) for vertically guiding the corresponding leg (D126) out of the respective cartridge pocket (D420) toward the corresponding staple forming pockets (66) as staples (86) are driven outwardly from cartridge pockets (D420) by the staple drivers. The body (D460) of each second wedge (D434) also defines an upwardly and/or distally-facing top surface (D466) that tapers and/or curves upwardly and proximally from deck (D414) to a peak (D468). In some versions, top surfaces (D466) may be oriented obliquely relative to deck (D414) at a same angle as that at which top surfaces (D456) are oriented obliquely relative to deck (D414). In addition, or alternatively, peaks (D468) may be positioned at a substantially same height above deck (D414) as that of top surfaces (D446). In some other versions, peaks (D468) may be positioned at a lower height above deck (D414) than that of top surfaces (D446).

In the example shown, the peak (D468) of each second wedge (D434) coincides with the peak (D458) of a relatively proximal, longitudinally-adjacent first wedge (D432), while each second wedge (D434) is longitudinally spaced apart from a relatively distal, longitudinally-adjacent first wedge (D432) by a portion of deck (D414) that includes a pair of inner and outer cartridge pockets (D420). In some other versions, the peak (D468) of each second wedge (D434) may be longitudinally spaced apart from the peak (D458) of the relatively proximal, longitudinally-adjacent first wedge (D432) (e.g., by a raised platform extending between the two peaks (D458, D468) and having the same height as both peaks (D458, D468)), and/or each second wedge (D434) may not be longitudinally spaced apart from the relatively distal, longitudinally-adjacent first wedge (D432) (e.g., by directly interfacing with the relatively distal, longitudinally-adjacent first wedge (D432)).

By extending upwardly to peaks (D458, D468) and spanning laterally across the respective three rows of cartridge pockets (D420), the top surfaces (D456, D466) of each wedge (D432, D434) may be configured to provide improved contact with the adhesive layers or beads (D116, D120, D182, D184, D186, D188) of a corresponding buttress assembly (D110, D112, D160), at least relative to the top surface (D446) of each pocket extender (D430). For example, the lateral spanning of each wedge (D432, D434) across the respective three rows of cartridge pockets (D420) may allow each peak (D458, D468) and/or the longitudinally adjacent region(s) of the respective wedge(s) (D432, D434) to contact substantially all of the adhesive (D166) spanning laterally across buttress body (D164) at the corresponding longitudinal position along buttress body (D164), and may thereby provide stronger, localized attachment of buttress assembly (D160) at such longitudinal positions. As a more particular example, the lateral spanning of each distalmost first wedge (D432) across the respective three rows of cartridge pockets (D420) may allow the peak (D458) of each distalmost first wedge (D432) to contact substantially all of the adhesive (D166) spanning laterally across distal end (D172) of buttress body (D164), and may thereby provide stronger, localized attachment of buttress assembly (D160) at the distal end of staple cartridge (D410).

While each wedge (D432, D434) is shown spanning laterally across all three respective rows of cartridge pockets (D420), each wedge (D432, D434) may alternatively span laterally across only the respective inner and middle rows of cartridge pockets (D420), or only the respective middle and outer rows of cartridge pockets (D420).

It will be appreciated that the particular positions of wedges (D432, D434), including the particular positions of peaks (D458, D468), may be selected to achieve both a desired amount of tissue compression and a desired adhesion of a corresponding buttress assembly (D110, D112, D160) to staple cartridge (D410). For example, the particular positions of wedges (D432, D434), including the particular positions of peaks (D458, D468), may be selected to correspond to the position(s) of adhesive (D166) on buttress body (D164) so that wedges (D434, D434) may achieve the desired adhesion of buttress assembly (D160) to staple cartridge (D410) while limiting any increases in tissue compression that might be caused by wedges (D432, D434) to the regions in which wedges (D434, D434) are present.

D. Example of Staple Cartridge with Dome-Shaped Contact Pads

Figure 78:
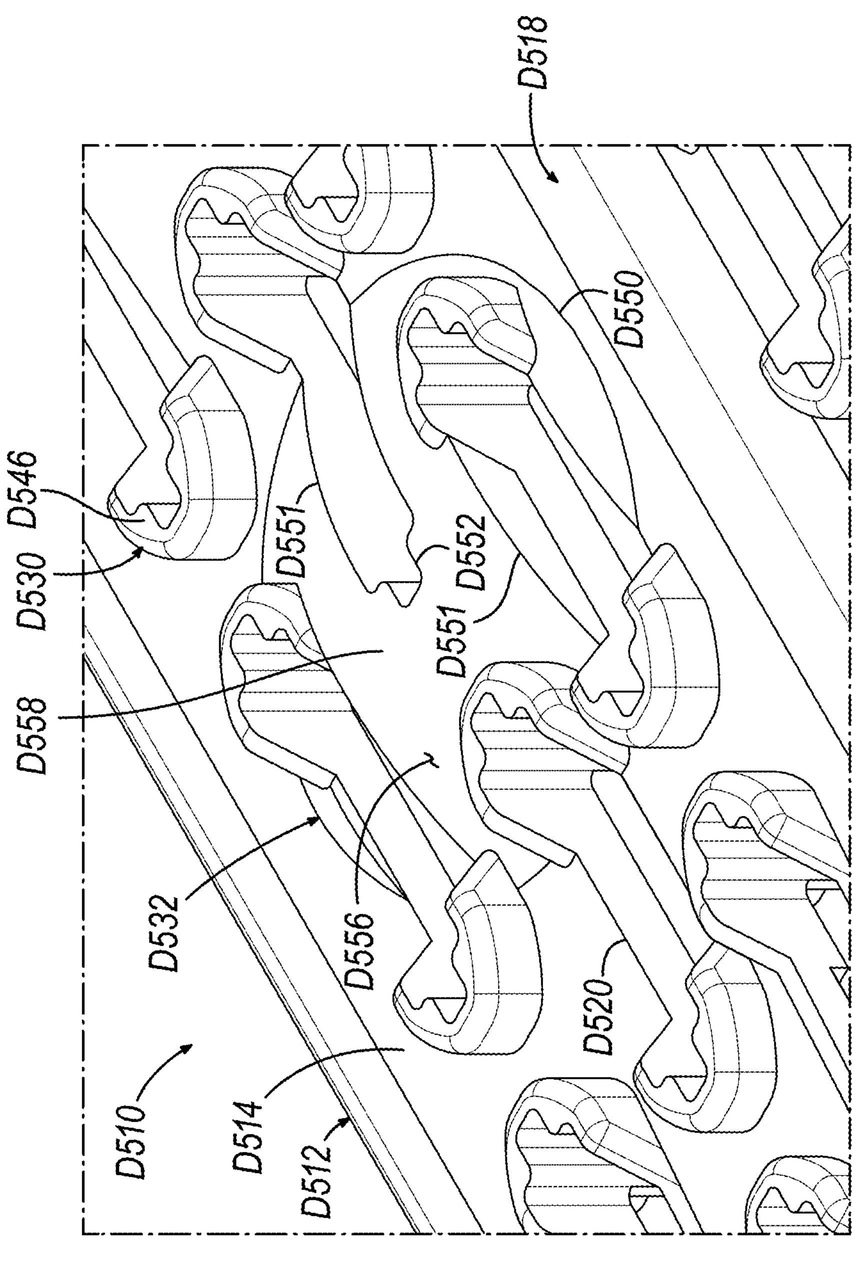
FIG. 78 depicts a partial perspective view of another example of a staple cartridge for use with the end effector of FIG. 2 and having dome-shaped contact pads configured to promote adhesion of any of the buttress assemblies of FIGS. 70-73 to the staple cartridge.

FIG. 78 shows a portion of another example of a staple cartridge (D510) configured to deploy staples (86) toward corresponding staple forming pockets of an anvil (not shown), such as staple forming pockets (66) of anvil (44). Staple cartridge (D510) is configured for use with end effector (40), and is similar to staple cartridge (70) described above except as otherwise described below. In this regard, staple cartridge (D510) of the present example includes a cartridge body (D512) having an upwardly facing deck (D514), an elongate slot (D518) extending along a central axis of cartridge body (D512) and opening upwardly through deck (D514) for slidably receiving a distal knife portion of a firing beam (not shown), such as distal knife portion (50) of firing beam (46), and a plurality of cartridge pockets (D520) extending through deck (D514) on each side of knife slot (D518). In the present version, three longitudinal rows of cartridge pockets (D520) are formed through upper deck (D514) along each lateral side of knife slot (D518), including an inner row, a middle row, and an outer row on each lateral side of knife slot (D518). Each cartridge pocket (D520) slidably houses an unformed staple (86) and a respective staple driver (not shown) similar to staple drivers (84) positioned beneath staple (86). A lower tray (not shown) similar to lower tray (76) encloses an underside of cartridge body (D512) and thereby retains staples (86) and the staple drivers within cartridge body (D512). A wedge sled (not shown) similar to wedge sled (82) is slidably disposed within cartridge body (D512) and includes upwardly presented cam surfaces configured to engage the undersides of the staple drivers.

Staple cartridge (D510) of the present example further includes a plurality of raised features in the form of pocket extenders (D530) that extend upwardly from deck (D514) at or near proximal and distal ends of at least some cartridge pockets (D520), such that at least some cartridge pockets (D520) are each longitudinally flanked by a corresponding pair of proximal and distal pocket extenders (D530) while some other cartridge pockets (D520) are only equipped with either a corresponding proximal or distal pocket extender (D530). Any one or more of pocket extenders (D530) may be configured to enhance the gripping of tissue (T1, T2) by staple cartridge (D510) when end effector (40) is closed (e.g., in instances when staple cartridge (D510) is not equipped with a buttress assembly (D110, D112, D160)), and/or to guide the legs (D126) of the staples (86) as the legs (D126) exit the respective cartridge pockets (D520) during deployment of the staples (86). In addition, or alternatively, any one or more of pocket extenders (D530) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D510). As shown, each pocket extender (D530) includes an upwardly-facing top surface (D546) that extends substantially parallel relative to deck (D514). Top surfaces (D546) may be positioned at a substantially uniform height above deck (D514).

Staple cartridge (D510) of the present example also includes a plurality of raised features in the form of contact pads (D532) that extend upwardly from deck (D514) on each lateral side of knife slot (D518) such that each contact pad (D532) spans laterally across three rows of cartridge pockets (D520) on the respective lateral side of knife slot (D518) (e.g., the respective inner, middle, and outer rows of cartridge pockets (D520)). While only one contact pad (D532) is shown, it will be appreciated that a plurality of contact pads (D532) may be spaced apart from each other along the length of staple cartridge (D510) on each lateral side of knife slot (D518).

Each contact pad (D532) includes a generally dome-shaped body (D550) that defines one or more openings (D551) overlying corresponding cartridge pockets (D520) for accommodating passage of respective staples (86) therethrough. The body (D550) of each contact pad (D532) further defines one or more staple leg receptacles (D552) at or near proximal and distal ends of cartridge pockets (D520) that lack a pocket extender (D530) for receiving a corresponding leg (D126) of the staple (86) slidably housed within the respective cartridge pocket (D520). In this regard, each staple leg receptacle (D552) may be sized and configured to slidably receive the corresponding leg (D126) for vertically guiding the corresponding leg (D126) out of the respective cartridge pocket (D520) toward the corresponding staple forming pockets (66) as staples (86) are driven outwardly from cartridge pockets (D520) by the staple drivers. The body (D550) of each contact pad (D532) also defines an upwardly-facing, hemispherical top surface (D556) that curves upwardly and radially inwardly in a convex manner from deck (D514) to a peak (D558). Peaks (D558) may be positioned at a substantially same height above deck (D514) as that of top surfaces (D546). In some other versions, peaks (D558) may be positioned at a lower height above deck (D514) than that of top surfaces (D546).

By extending upwardly to peaks (D558) and spanning laterally across the respective three rows of cartridge pockets (D520), the top surfaces (D556) of each contact pad (D532) may be configured to provide improved contact with the adhesive layers or beads (D116, D120, D182, D184, D186, D188) of a corresponding buttress assembly (D110, D112, D160), at least relative to the top surface (D546) of each pocket extender (D530). For example, the lateral spanning of each contact pad (D532) across the respective three rows of cartridge pockets (D520) may allow each peak (D558) and/or the longitudinally adjacent region(s) and/or the laterally adjacent region(s) of the respective contact pad(s) (D532) to contact at least a laterally middle region of the adhesive (D166) spanning laterally across buttress body (D164) at the corresponding longitudinal position along buttress body (D164), and may thereby provide stronger, localized attachment of buttress assembly (D160) at such longitudinal positions.

While each contact pad (D532) is shown spanning laterally across all three respective rows of cartridge pockets (D520), each contact pad (D532) may alternatively span laterally across only the respective inner and middle rows of cartridge pockets (D520), or only the respective middle and outer rows of cartridge pockets (D520).

It will be appreciated that the particular positions of contact pads (D532), including the particular positions of peaks (D558), may be selected to achieve both a desired amount of tissue compression and a desired adhesion of a corresponding buttress assembly (D110, D112, D160) to staple cartridge (D510). For example, the particular positions of contact pads (D532), including the particular positions of peaks (D558), may be selected to correspond to the position(s) of adhesive (D166) on buttress body (D164) so that contact pads (D532) may achieve the desired adhesion of buttress assembly (D160) to staple cartridge (D510) while limiting any increases in tissue compression that might be caused by contact pads (D532) to the regions in which contact pads (D532) are present.

E. Example of Staple Cartridge with Tissue-Stabilizing Wedges

Figure 79:
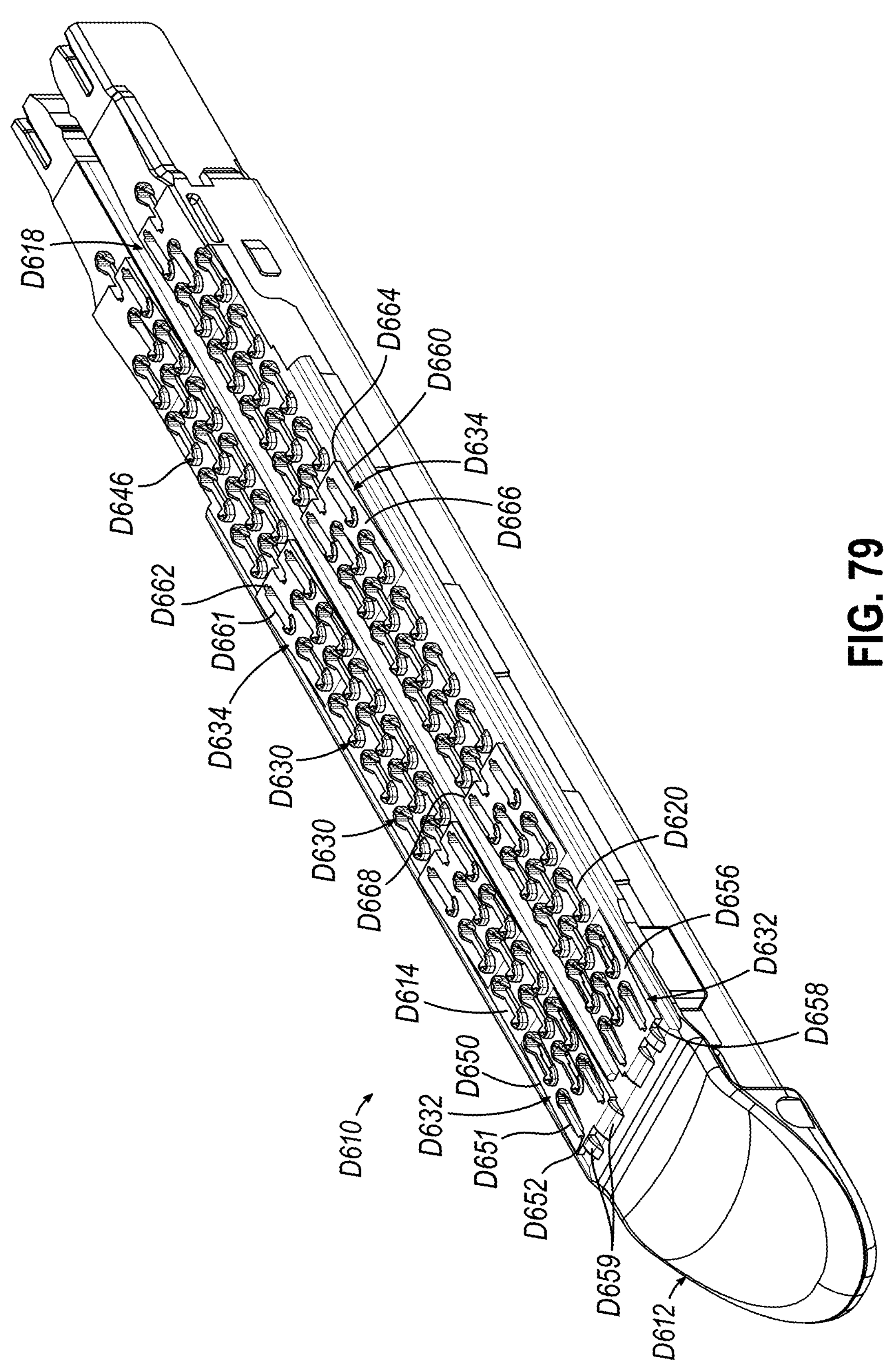
FIG. 79 depicts a perspective view of another example of a staple cartridge for use with the end effector of FIG. 2 and having tissue-stabilizing wedges configured to promote adhesion of any of the buttress assemblies of FIGS. 70-73 to the staple cartridge.
Figure 80:
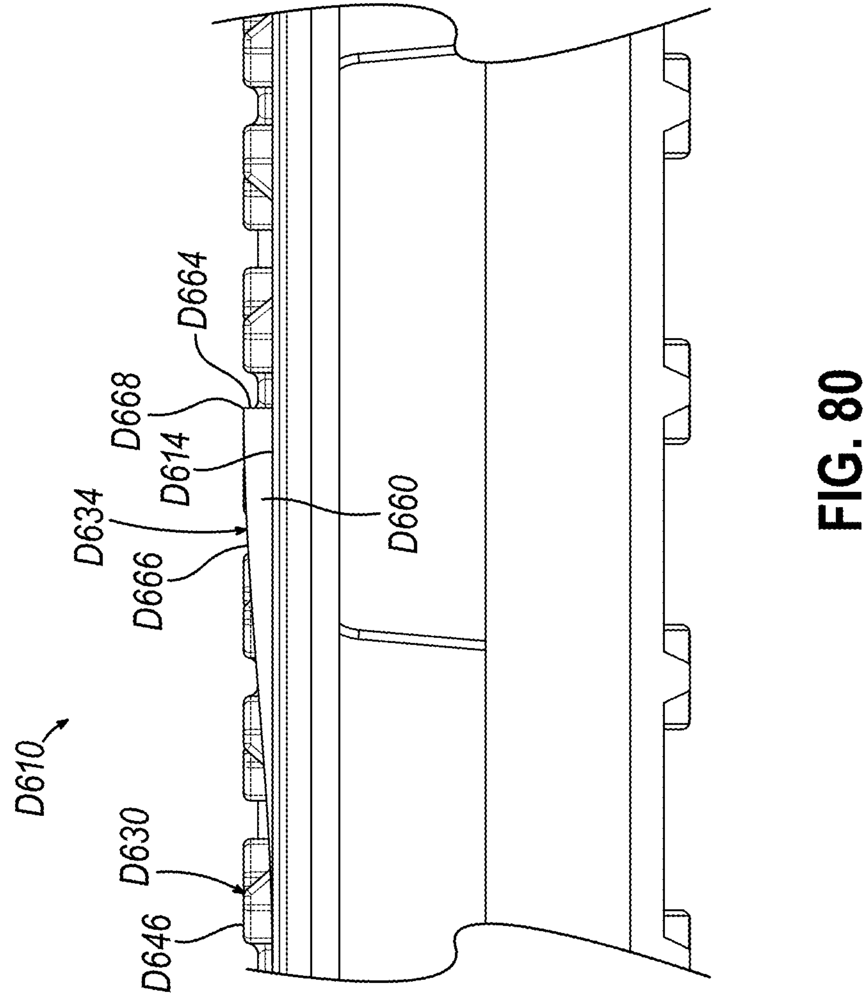
FIG. 80 depicts a partial side elevational view of the staple cartridge of FIG. 79.

FIGS. 79-80 show another example of a staple cartridge (D610) configured to deploy staples (86) toward corresponding staple forming pockets of an anvil (not shown), such as staple forming pockets (66) of anvil (44). Staple cartridge (D610) is configured for use with end effector (40), and is similar to staple cartridge (70) described above except as otherwise described below. In this regard, staple cartridge (D610) of the present example includes a cartridge body (D612) having an upwardly facing deck (D614), an elongate slot (D618) extending along a central axis of cartridge body (D612) and opening upwardly through deck (D614) for slidably receiving a distal knife portion of a firing beam (not shown), such as distal knife portion (50) of firing beam (46), and a plurality of cartridge pockets (D620) extending through deck (D614) on each side of knife slot (D618). In the present version, three longitudinal rows of cartridge pockets (D620) are formed through upper deck (D614) along each lateral side of knife slot (D618), including an inner row, a middle row, and an outer row on each lateral side of knife slot (D618). Each cartridge pocket (D620) slidably houses an unformed staple (86) and a respective staple driver (not shown) similar to staple drivers (84) positioned beneath staple (86). A lower tray (not shown) similar to lower tray (76) encloses an underside of cartridge body (D612) and thereby retains staples (86) and the staple drivers within cartridge body (D612). A wedge sled (not shown) similar to wedge sled (82) is slidably disposed within cartridge body (D612) and includes upwardly presented cam surfaces configured to engage the undersides of the staple drivers.

Staple cartridge (D610) of the present example further includes a plurality of raised features in the form of pocket extenders (D630) that extend upwardly from deck (D614) at or near proximal and distal ends of at least some cartridge pockets (D620), such that at least some cartridge pockets (D620) are each longitudinally flanked by a corresponding pair of proximal and distal pocket extenders (D630) while some other cartridge pockets (D620) are only equipped with either a corresponding proximal or distal pocket extender (D630). Any one or more of pocket extenders (D630) may be configured to enhance the gripping of tissue (T1, T2) by staple cartridge (D610) when end effector (40) is closed (e.g., in instances when staple cartridge (D610) is not equipped with a buttress assembly (D110, D112, D160)), and/or to guide the legs (D126) of the staples (86) as the legs (D126) exit the respective cartridge pockets (D620) during deployment of the staples (86). In addition, or alternatively, any one or more of pocket extenders (D630) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D610). As shown, each pocket extender (D630) includes an upwardly-facing top surface (D646) that extends substantially parallel relative to deck (D614). Top surfaces (D646) may be positioned at a substantially uniform height above deck (D614).

Staple cartridge (D610) of the present example also includes a plurality of raised features in the form of first and second wedges (D632, D634) that extend upwardly from deck (D614) on each lateral side of knife slot (D618) such that each wedge (D632, D634) spans laterally across three rows of cartridge pockets (D620) on the respective lateral side of knife slot (D618) (e.g., the respective inner, middle, and outer rows of cartridge pockets (D620)). In the example shown, first wedges (D632) are arranged at or near the distal end of deck (D614), while second wedges (D634) are each arranged proximally of first wedges (D632).

Each first wedge (D632) includes a generally triangular body (D650) that defines one or more openings (D651) overlying corresponding cartridge pockets (D620) for accommodating passage of respective staples (86) therethrough. The body (D650) of each first wedge (D632) further defines one or more staple leg receptacles (D652) at or near proximal and distal ends of cartridge pockets (D620) that lack a pocket extender (D630) for receiving a corresponding leg (D126) of the staple (86) slidably housed within the respective cartridge pocket (D620). In this regard, each staple leg receptacle (D652) may be sized and configured to slidably receive the corresponding leg (D126) for vertically guiding the corresponding leg (D126) out of the respective cartridge pocket (D620) toward the corresponding staple forming pockets (66) as staples (86) are driven outwardly from cartridge pockets (D620) by the staple drivers. The body (D650) of each first wedge (D632) also defines an upwardly and/or proximally-facing top surface (D656) that tapers and/or curves upwardly and distally from deck (D614) to a peak (D658). Peaks (D658) may be positioned at a substantially same height above deck (D614) as that of top surfaces (D646). In some other versions, peaks (D658) may be positioned at a lower height above deck (D614) than that of top surfaces (D646).

In the example shown, a pair of atraumatic distal ramps (D659) taper and/or curve upwardly and proximally from deck (D614) to the peak (D658) of each first wedge (D632) for gently lifting tissue upwardly relative to deck (D614). As shown, at least one such distal ramp (D659) may span laterally at least partially across the respective inner and middle rows of cartridge pockets (D620) for lifting the portions of such tissue that are aligned with both the respective inner and middle rows of cartridge pockets (D620) substantially simultaneously with the lifting of the portions of such tissue that are aligned with the respective outer row of cartridge pockets (D620) via the other distal ramp (D659) on the same lateral side of knife slot (D618).

Each second wedge (D634) includes a generally triangular body (D660) that defines one or more openings (D661) overlying corresponding cartridge pockets (D620) for accommodating passage of respective staples (86) therethrough. The body (D660) of each second wedge (D634) further defines one or more staple leg receptacles (D662) at or near proximal and distal ends of cartridge pockets (D620) that lack a pocket extender (D630) for receiving a corresponding leg (D126) of the staple (86) slidably housed within the respective cartridge pocket (D620). In this regard, each staple leg receptacle (D662) may be sized and configured to slidably receive the corresponding leg (D126) for vertically guiding the corresponding leg (D126) out of the respective cartridge pocket (D620) toward the corresponding staple forming pockets (66) as staples (86) are driven outwardly from cartridge pockets (D620) by the staple drivers.

The body (D660) of each second wedge (D634) also defines a proximally-facing end surface (D664) that extends substantially orthogonally relative to deck (D614) from deck (D614) to a peak (D668). By extending substantially orthogonally relative to deck (D614), the end surface (D664) of each second wedge (D634) may be configured to stabilize the tissue being severed and stapled, such as by inhibiting movement (e.g., "flow") of the tissue being severed and stapled. For example, the end surface (D664) of each second wedge (D634) may impede such tissue from moving distally during distal translation of firing beam (46) (e.g., during a firing stroke).

The body (D660) of each second wedge (D634) further defines an upwardly and/or distally-facing top surface (D666) that tapers and/or curves upwardly and proximally from deck (D614) to a respective peak (D668). In some versions, top surfaces (D666) may be oriented obliquely relative to deck (D614) at a same angle as that at which top surfaces (D656) are oriented obliquely relative to deck (D614). In addition, or alternatively, peaks (D668) may be positioned at a substantially same height above deck (D614) as that of top surfaces (D646). In some other versions, peaks (D668) may be positioned at a lower height above deck (D614) than that of top surfaces (D646).

In the example shown, each second wedge (D634) is longitudinally spaced apart from the longitudinally-adjacent second wedge(s) (D634) by a portion of deck (D614) that includes three pairs of inner and outer cartridge pockets (D620), while the distalmost second wedges (D634) are longitudinally spaced apart from the respective first wedges (D632) by a portion of deck (D614) that includes one pair of inner and outer cartridge pockets (D620). In some other versions, each second wedge (D634) may not be longitudinally spaced apart from the longitudinally-adjacent second wedge(s) (D634) (e.g., by directly interfacing with the longitudinally-adjacent second wedge(s) (D634)), and/or the distalmost second wedges (D634) may not be longitudinally spaced apart from the respective first wedges (D632) (e.g., by directly interfacing with the respective first wedges (D632)).

By extending upwardly to peaks (D658, D668) and spanning laterally across the respective three rows of cartridge pockets (D620), the top surfaces (D656, D666) of each wedge (D632, D634) may be configured to provide improved contact with the adhesive layers or beads (D116, D120, D182, D184, D186, D188) of a corresponding buttress assembly (D110, D112, D160), at least relative to the top surface (D646) of each pocket extender (D630). For example, the lateral spanning of each wedge (D632, D634) across the respective three rows of cartridge pockets (D620) may allow each peak (D658, D668) and/or the longitudinally adjacent region(s) of the respective wedge(s) (D632, D634) to contact substantially all of the adhesive (D166) spanning laterally across buttress body (D164) at the corresponding longitudinal position along buttress body (D164), and may thereby provide stronger, localized attachment of buttress assembly (D160) at such longitudinal positions. As a more particular example, the lateral spanning of each first wedge (D632) across the respective three rows of cartridge pockets (D620) may allow the peak (D658) of each first wedge (D632) to contact substantially all of the adhesive (D166) spanning laterally across distal end (D172) of buttress body (D164), and may thereby provide stronger, localized attachment of buttress assembly (D160) at the distal end of staple cartridge (D610).

While each wedge (D632, D634) is shown spanning laterally across all three respective rows of cartridge pockets (D620), each wedge (D632, D634) may alternatively span laterally across only the respective inner and middle rows of cartridge pockets (D620), or only the respective middle and outer rows of cartridge pockets (D620).

It will be appreciated that the particular positions of wedges (D632, D634), including the particular positions of peaks (D658, D668), may be selected to achieve both a desired amount of tissue compression and a desired adhesion of a corresponding buttress assembly (D110, D112, D160) to staple cartridge (D610). For example, the particular positions of wedges (D632, D634), including the particular positions of peaks (D658, D668), may be selected to correspond to the position(s) of adhesive (D166) on buttress body (D164) so that wedges (D634, D634) may achieve the desired adhesion of buttress assembly (D160) to staple cartridge (D610) while limiting any increases in tissue compression that might be caused by wedges (D632, D634) to the regions in which wedges (D634, 634) are present.

F. Example of Staple Cartridge with Distal Contact Pads

Figure 81:
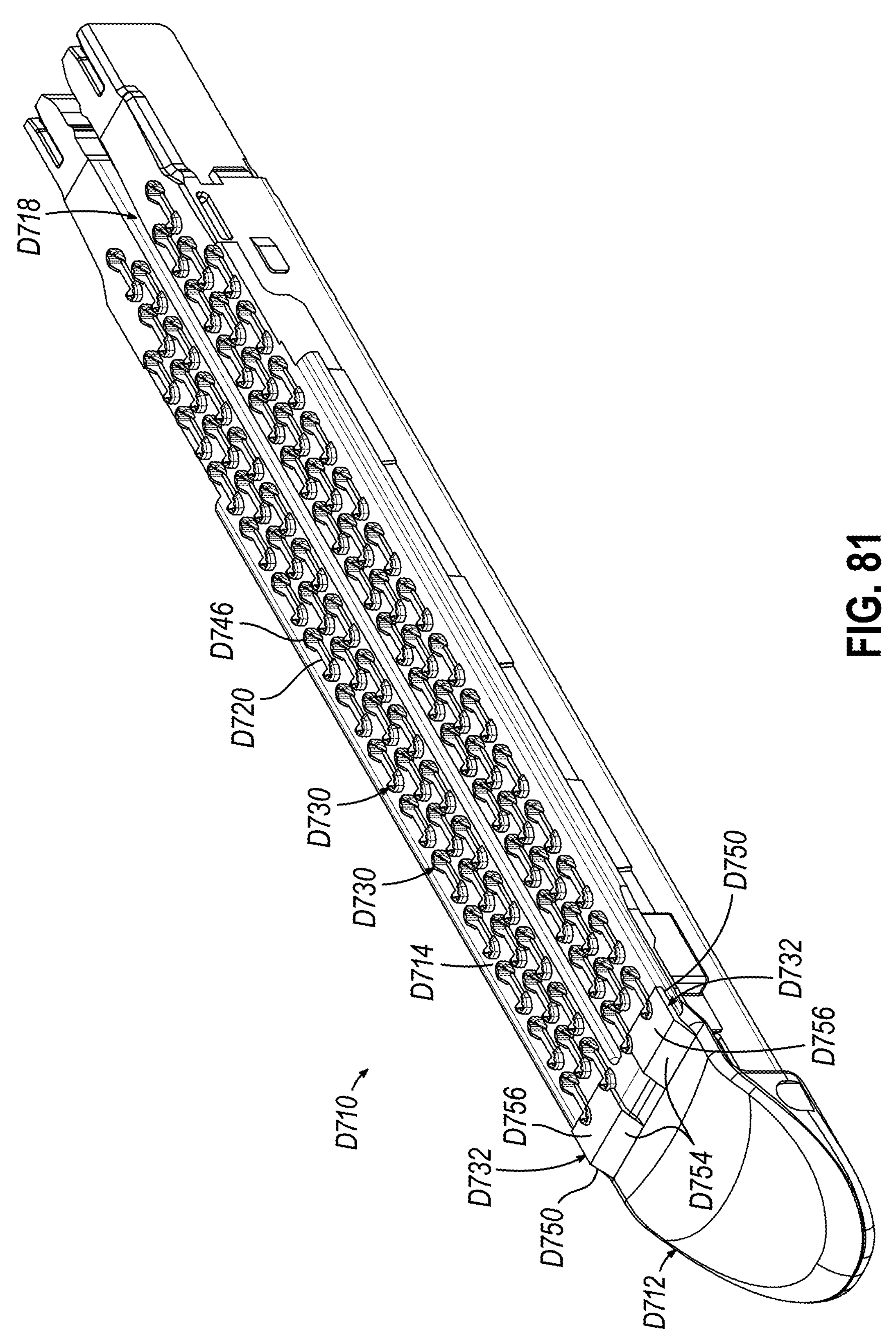
FIG. 81 depicts a perspective view of another example of a staple cartridge for use with the end effector of FIG. 2 and having distal contact pads configured to promote adhesion of any of the buttress assemblies of FIGS. 70-73 to the staple cartridge.
Figures 82, 83:
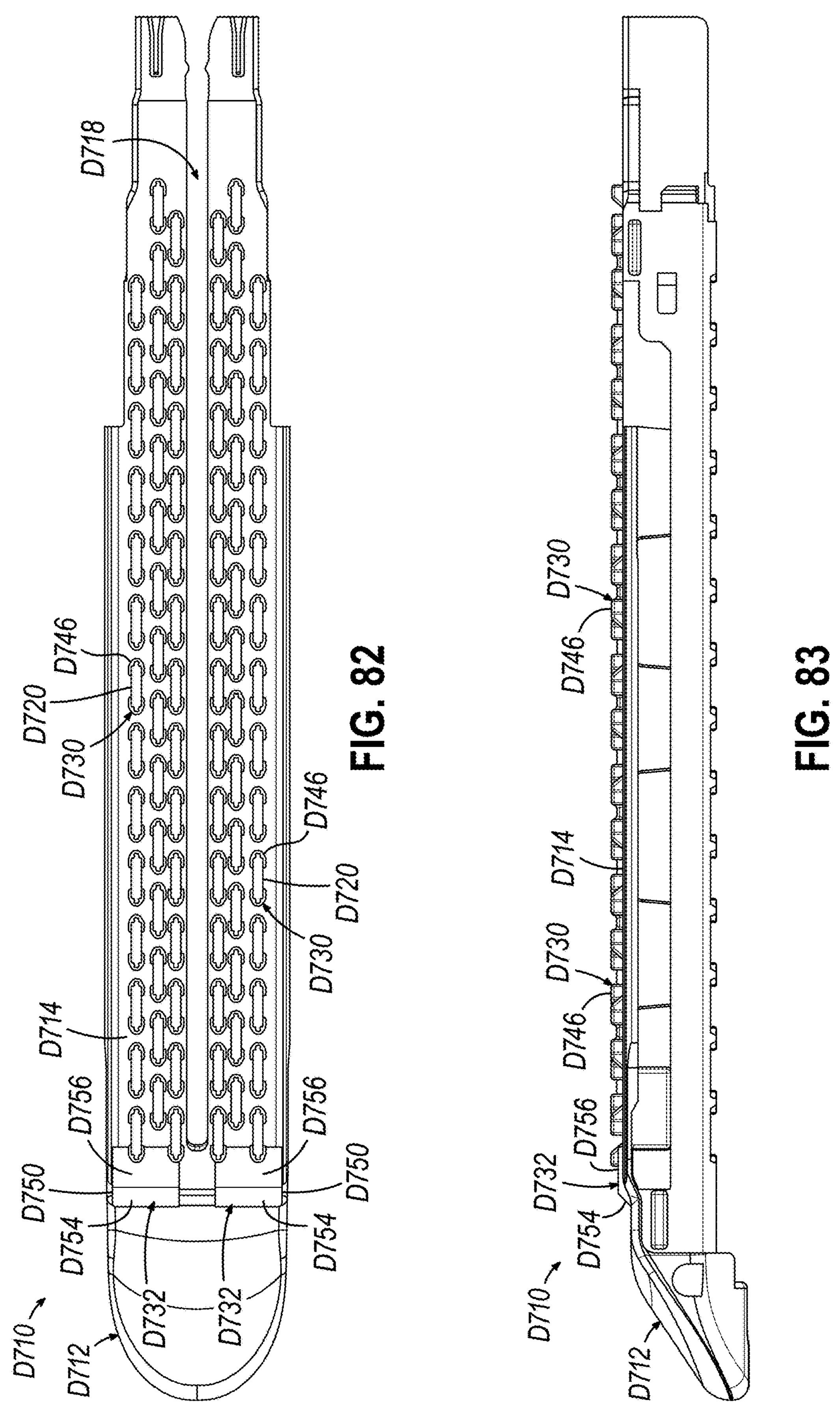
FIG. 82 depicts a top plan view of the staple cartridge of FIG. 81.
FIG. 83 depicts a side elevational view of the staple cartridge of FIG. 81.

FIGS. 81-83 show another example of a staple cartridge (D710) configured to deploy staples (86) toward corresponding staple forming pockets of an anvil (not shown), such as staple forming pockets (66) of anvil (44). Staple cartridge (D710) is configured for use with end effector (40), and is similar to staple cartridge (70) described above except as otherwise described below. In this regard, staple cartridge (D710) of the present example includes a cartridge body (D712) having an upwardly facing deck (D714), an elongate slot (D718) extending along a central axis of cartridge body (D712) and opening upwardly through deck (D714) for slidably receiving a distal knife portion of a firing beam (not shown), such as distal knife portion (50) of firing beam (46), and a plurality of cartridge pockets (D720) extending through deck (D714) on each side of knife slot (D718). In the present version, three longitudinal rows of cartridge pockets (D720) are formed through upper deck (D714) along each lateral side of knife slot (D718), including an inner row, a middle row, and an outer row on each lateral side of knife slot (D718). Each cartridge pocket (D720) slidably houses an unformed staple (86) and a respective staple driver (not shown) similar to staple drivers (84) positioned beneath staple (86). A lower tray (not shown) similar to lower tray (76) encloses an underside of cartridge body (D712) and thereby retains staples (86) and the staple drivers within cartridge body (D712). A wedge sled (not shown) similar to wedge sled (82) is slidably disposed within cartridge body (D712) and includes upwardly presented cam surfaces configured to engage the undersides of the staple drivers.

Staple cartridge (D710) of the present example further includes a plurality of raised features in the form of pocket extenders (D730) that extend upwardly from deck (D714) at or near proximal and distal ends of each cartridge pocket (D720), such that each cartridge pocket (D720) is longitudinally flanked by a corresponding pair of proximal and distal pocket extenders (D730). Any one or more of pocket extenders (D730) may be configured to enhance the gripping of tissue (T1, T2) by staple cartridge (D710) when end effector (40) is closed (e.g., in instances when staple cartridge (D710) is not equipped with a buttress assembly (D110, D112, D160)), and/or to guide the legs (D126) of the staples (86) as the legs (D126) exit the respective cartridge pockets (D720) during deployment of the staples (86). In addition, or alternatively, any one or more of pocket extenders (D730) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D710). As shown, each pocket extender (D730) includes an upwardly-facing top surface (D746) that extends substantially parallel relative to deck (D714). Top surfaces (D746) may be positioned at a substantially uniform height above deck (D714).

Staple cartridge (D710) of the present example also includes a plurality of raised features in the form of a pair of distal contact pads (D732) that extend upwardly from deck (D714) on each lateral side of knife slot (D718) such that each distal contact pad (D732) spans laterally at least partially across three rows of cartridge pockets (D720) on the respective lateral side of knife slot (D718) (e.g., the respective inner, middle, and outer rows of cartridge pockets (D720)). As shown, distal contact pads (D732) are each positioned at or near the distal end of deck (D714).

Each distal contact pad (D732) includes a generally angled body (D750) that defines a distally-facing end surface (D754) that extends substantially obliquely relative to deck (D714). In the example shown, the end surface (D754) of each distal contact pad (D732) tapers and/or curves downwardly and distally from the distal end of deck (D714). By extending substantially obliquely relative to deck (D714), the end surface (D754) of each distal contact pad (D732) may have a substantially atraumatic configuration so that each end surface (D754) may avoid inflicting trauma to tissue contacted by the end surface (D754). For example, each end surface (D754) may define a distal ramp for gently lifting such tissue upwardly relative to deck (D714). Due to the spanning of each distal contact pad (D732) laterally across the respective inner, middle, and outer rows of cartridge pockets (D720), each end surface (D754) may be configured to lift the portions of such tissue that are aligned with all three respective rows of cartridge pockets (D720).

The body (D750) of each distal contact pad (D732) further defines an upwardly-facing top surface (D756) that extends substantially parallel relative to deck (D714). Top surfaces (D756) may be positioned at a lower height above deck (D714) than that of top surfaces (D746). In some other versions, top surfaces (D756) may be positioned at a substantially same height above deck (D714) as that of top surfaces (D746). In the example shown, the top surface (D756) of each distal contact pad (D732) has a surface area that is greater than that of the top surface (D746) of each pocket extender (D730). The top surface (D756) of each distal contact pad (D732) may also extend further distally compared to the top surface (D746) of the distalmost pocket extenders (D730). By having a greater surface area and/or extending further distally compared to the top surface (D746) of the distalmost pocket extenders (D730), the top surface (D756) of each distal contact pad (D732) may be configured to provide improved contact with the adhesive layers or beads (D116, D120, D182, D184, D186, D188) of a corresponding buttress assembly (D110, D112, D160), at least relative to the top surface (D746) of each pocket extender (D730). For example, the further distal extension of the top surface (D756) of each distal contact pad (D732) may allow the top surface (D756) to vertically align with more adhesive (D166) at distal end (D172) of buttress body (D164) compared to the top surface (D746) of each distal-most pocket extender (D730), and may thereby provide stronger, localized attachment of buttress assembly (D160) at the distal end of staple cartridge (D710).

While each distal contact pad (D732) is shown spanning laterally at least partially across all three respective rows of cartridge pockets (D720), each distal contact pad (D732) may alternatively span laterally at least partially across only the respective inner and middle rows of cartridge pockets (D720), or only the respective middle and outer rows of cartridge pockets (D720).

G. Example of Staple Cartridge with Distal and Proximal Contact Pads

Figure 84:
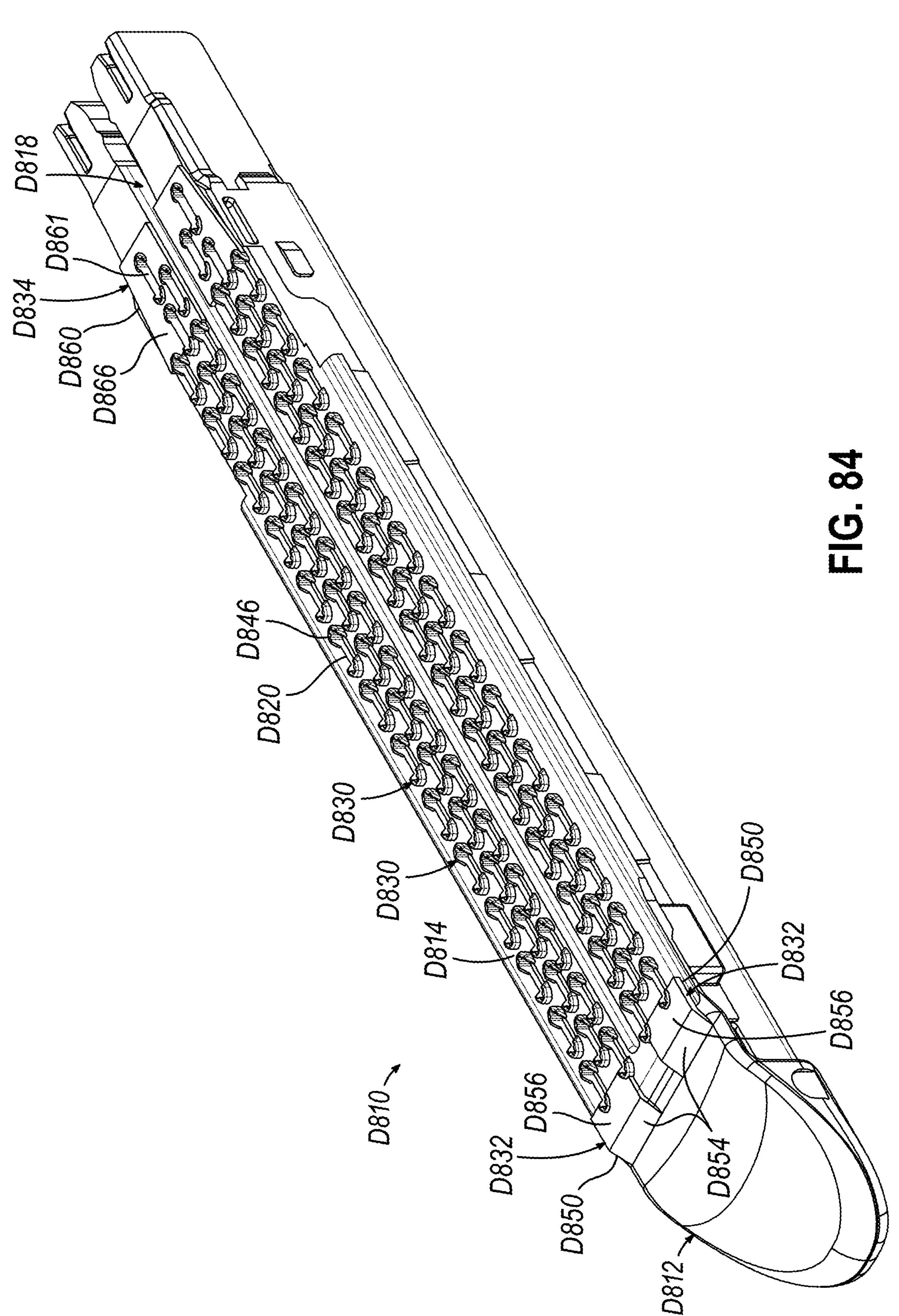
FIG. 84 depicts a perspective view of another example of a staple cartridge for use with the end effector of FIG. 2 and having distal and proximal contact pads configured to promote adhesion of any of the buttress assemblies of FIGS. 70-73 to the staple cartridge.
Figures 85, 86:
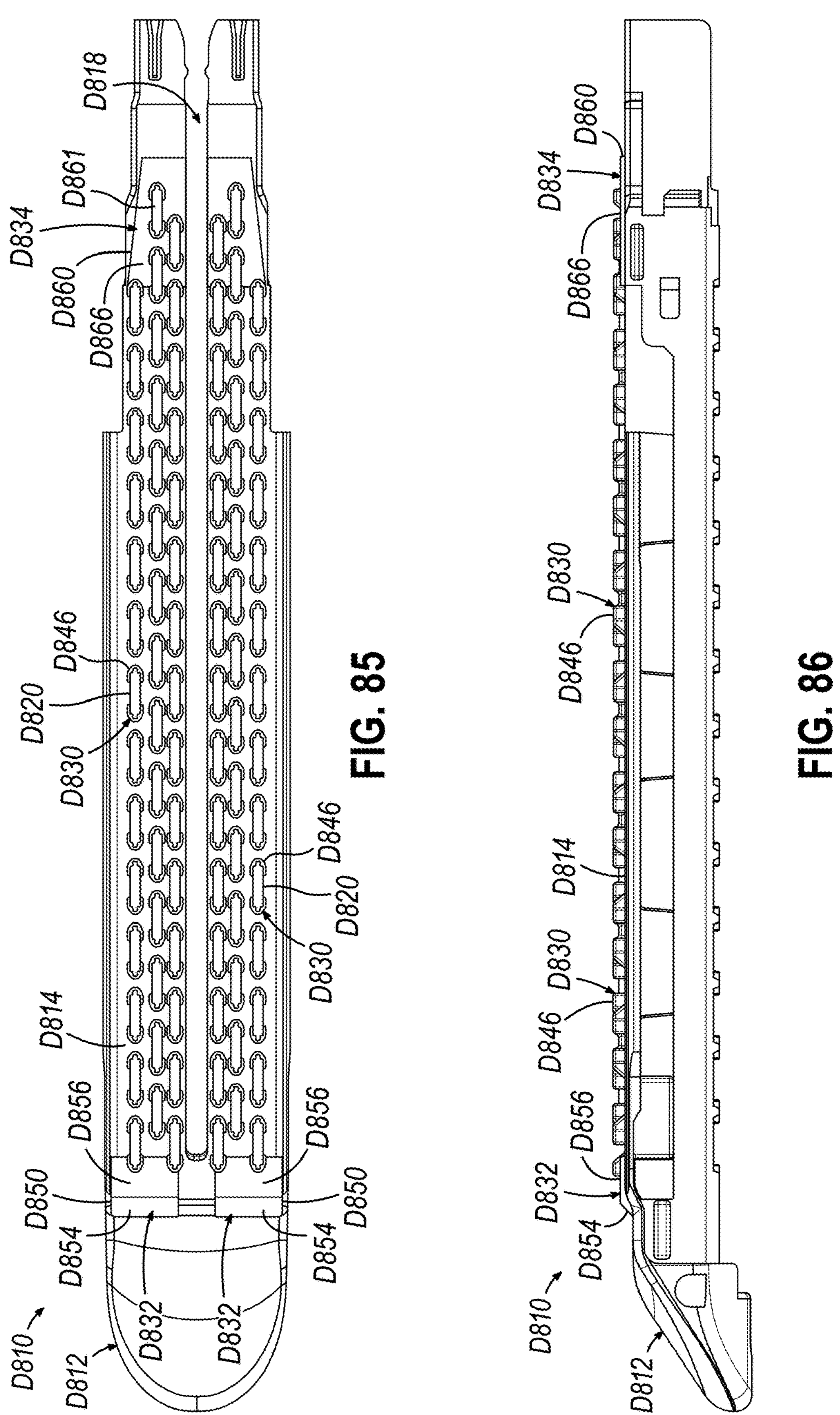
FIG. 85 depicts a top plan view of the staple cartridge of FIG. 84.
FIG. 86 depicts a side elevational view of the staple cartridge of FIG. 84.

FIGS. 84-86 show another example of a staple cartridge (D810) configured to deploy staples (86) toward corresponding staple forming pockets of an anvil (not shown), such as staple forming pockets (66) of anvil (44). Staple cartridge (D810) is configured for use with end effector (40), and is similar to staple cartridge (70) described above except as otherwise described below. In this regard, staple cartridge (D810) of the present example includes a cartridge body (D812) having an upwardly facing deck (D814), an elongate slot (D818) extending along a central axis of cartridge body (D812) and opening upwardly through deck (D814) for slidably receiving a distal knife portion of a firing beam (not shown), such as distal knife portion (50) of firing beam (46), and a plurality of cartridge pockets (D820) extending through deck (D814) on each side of knife slot (D818). In the present version, three longitudinal rows of cartridge pockets (D820) are formed through upper deck (D814) along each lateral side of knife slot (D818), including an inner row, a middle row, and an outer row on each lateral side of knife slot (D818). Each cartridge pocket (D820) slidably houses an unformed staple (86) and a respective staple driver (not shown) similar to staple drivers (84) positioned beneath staple (86). A lower tray (not shown) similar to lower tray (76) encloses an underside of cartridge body (D812) and thereby retains staples (86) and the staple drivers within cartridge body (D812). A wedge sled (not shown) similar to wedge sled (82) is slidably disposed within cartridge body (D812) and includes upwardly presented cam surfaces configured to engage the undersides of the staple drivers.

Staple cartridge (D810) of the present example further includes a plurality of raised features in the form of pocket extenders (D830) that extend upwardly from deck (D814) at or near proximal and distal ends of each cartridge pocket (D820), such that each cartridge pocket (D820) is longitudinally flanked by a corresponding pair of proximal and distal pocket extenders (D830). Any one or more of pocket extenders (D830) may be configured to enhance the gripping of tissue (T1, T2) by staple cartridge (D810) when end effector (40) is closed (e.g., in instances when staple cartridge (D810) is not equipped with a buttress assembly (D110, D112, D160)), and/or to guide the legs (D126) of the staples (86) as the legs (D126) exit the respective cartridge pockets (D820) during deployment of the staples (86). In addition, or alternatively, any one or more of pocket extenders (D830) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D810).

As shown, each pocket extender (D830) includes a generally U-shaped body (D840) that defines a staple leg receptacle (D842) for receiving a corresponding leg (D126) of the staple (86) slidably housed within the respective cartridge pocket (D820). In this regard, each staple leg receptacle (D842) may be sized and configured to slidably receive the corresponding leg (D126) for vertically guiding the corresponding leg (D126) out of the respective cartridge pocket (D820) toward the corresponding staple forming pockets (66) as staples (86) are driven outwardly from cartridge pockets (D820) by the staple drivers. The body (D840) of each pocket extender (D830) also defines a proximally-facing or distally-facing outer surface (D844) that extends substantially orthogonally relative to deck (D814). The body (D840) of each first pocket extender (D830) further defines an upwardly-facing top surface (D846) that extends substantially parallel relative to deck (D814). Top surfaces (D846) may be positioned at a substantially uniform height above deck (D814).

Staple cartridge (D810) of the present example also includes a plurality of raised features in the form of pair of distal contact pads (D832) that extend upwardly from deck (D814) on each lateral side of knife slot (D818) such that each distal contact pad (D832) spans laterally at least partially across three rows of cartridge pockets (D820) on the respective lateral side of knife slot (D818) (e.g., the respective inner, middle, and outer rows of cartridge pockets (D820)). As shown, distal contact pads (D832) are each positioned at or near the distal end of deck (D814). Staple cartridge (D810) of the present example also includes another plurality of raised features in the form of a pair of proximal contact pads (D834) that extend upwardly from deck (D814) on each lateral side of knife slot (D818) such that each proximal contact pad (D834) spans laterally at least partially across three rows of cartridge pockets (D820) on the respective lateral side of knife slot (D818) (e.g., the respective inner, middle, and outer rows of cartridge pockets (D820)). As shown, proximal contact pads (D834) are each positioned at or near the proximal end of deck (D814).

Each distal contact pad (D832) includes a generally angled body (D850) that defines a distally-facing end surface (D854) that extends substantially obliquely relative to deck (D814). In the example shown, the end surface (D854) of each distal contact pad (D832) tapers and/or curves downwardly and distally from the distal end of deck (D814). By extending substantially obliquely relative to deck (D814), the end surface (D854) of each distal contact pad (D832) may have a substantially atraumatic configuration so that each end surface (D854) may avoid inflicting trauma to tissue contacted by the end surface (D854). For example, each end surface (D854) may define a distal ramp for gently lifting such tissue upwardly relative to deck (D814). Due to the spanning of each distal contact pad (D832) laterally across the respective inner, middle, and outer rows of cartridge pockets (D820), each end surface (D854) may be configured to lift the portions of such tissue that are aligned with all three respective rows of cartridge pockets (D820).

The body (D850) of each distal contact pad (D832) further defines an upwardly-facing top surface (D856) that extends substantially parallel relative to deck (D814). Top surfaces (D856) may be positioned at a lower height above deck (D814) than that of top surfaces (D846). In some other versions, top surfaces (D856) may be positioned at a substantially same height above deck (D814) as that of top surfaces (D846). In the example shown, the top surface (D856) of each distal contact pad (D832) has a surface area that is greater than that of the top surface (D846) of each pocket extender (D830). The top surface (D856) of each distal contact pad (D832) may also extend further distally compared to the top surface (D846) of the distalmost pocket extenders (D830). By having a greater surface area and/or extending further distally compared to the top surface (D846) of the distalmost pocket extenders (D830), the top surface (D856) of each distal contact pad (D832) may be configured to provide improved contact with the adhesive layers or beads (D116, D120, D182, D184, D186, D188) of a corresponding buttress assembly (D110, D112, D160), at least relative to the top surface (D846) of each pocket extender (D830). For example, the further distal extension of the top surface (D856) of each distal contact pad (D832) may allow the top surface (D856) to vertically align with more adhesive (D166) at distal end (D172) of buttress body (D164) compared to the top surface (D846) of each distalmost pocket extender (D830), and may thereby provide stronger, localized attachment of buttress assembly (D160) at the distal end of staple cartridge (D810).

Each proximal contact pad (D834) includes a generally planar body (D860) that defines one or more openings (D861) overlying corresponding cartridge pockets (D820) for accommodating passage of respective staples (86) therethrough. The body (D860) of each proximal contact pad (D834) also defines an upwardly-facing top surface (D866) that extends substantially parallel relative to deck (D814). Top surfaces (D866) may be positioned at a lower height above deck (D814) than that of top surfaces (D846). In some other versions, top surfaces (D866) may be positioned at a substantially same height above deck (D814) as that of top surfaces (D846). In addition, or alternatively, top surfaces (D866) may be positioned at a substantially same height above deck (D814) as that of top surfaces (D856). In the example shown, the top surface (D866) of each proximal contact pad (D834) has a surface area that is greater than that of the top surface (D846) of each pocket extender (D830). The top surface (D866) of each proximal contact pad (D834) may also extend further proximally compared to the top surface (D846) of the proximal-most pocket extenders (D830). By having a greater surface area and/or extending further proximally compared to the top surface (D846) of the proximal-most pocket extenders (D830), the top surface (D866) of each proximal contact pad (D834) may be configured to provide improved contact with the adhesive layers or beads (D116, D120, D182, D184, D186, D188) of a corresponding buttress assembly (D110, D112, D160), at least relative to the top surface (D846) of each pocket extender (D830). For example, the further proximal extension of the top surface (D866) of each proximal contact pad (D834) may allow the top surface (D866) to vertically align with more adhesive (D166) at proximal end (D170) of buttress body (D164) compared to the top surface (D846) of each proximal-most pocket extender (D830), and may thereby provide stronger, localized attachment of buttress assembly (D160) at the proximal end of staple cartridge (D810).

While each contact pad (D832, D834) is shown spanning laterally at least partially across all three respective rows of cartridge pockets (D820), each contact pad (D832, D834) may alternatively span laterally at least partially across only the respective inner and middle rows of cartridge pockets (D820), or only the respective middle and outer rows of cartridge pockets (D820).

H. Example of Staple Cartridge with Adhesive Pattern-Shaped Contact Pads

FIGS. 87-90 show another example of a staple cartridge (D910) configured to deploy staples (86) toward corresponding staple forming pockets of an anvil (not shown), such as staple forming pockets (66) of anvil (44). Staple cartridge (D910) is configured for use with end effector (40), and is similar to staple cartridge (70) described above except as otherwise described below. In this regard, staple cartridge (D910) of the present example includes a cartridge body (D912) having an upwardly facing deck (D914), an elongate slot (D918) extending along a central axis of cartridge body (D912) and opening upwardly through deck (D914) for slidably receiving a distal knife portion of a firing beam (not shown), such as distal knife portion (50) of firing beam (46), and a plurality of cartridge pockets (D920) extending through deck (D914) on each side of knife slot (D918). In the present version, three longitudinal rows of cartridge pockets (D920) are formed through upper deck (D914) along each lateral side of knife slot (D918), including an inner row, a middle row, and an outer row on each lateral side of knife slot (D918). Each cartridge pocket (D920) slidably houses an unformed staple (86) and a respective staple driver (not shown) similar to staple drivers (84) positioned beneath staple (86). A lower tray (not shown) similar to lower tray (76) encloses an underside of cartridge body (D912) and thereby retains staples (86) and the staple drivers within cartridge body (D912). A wedge sled (not shown) similar to wedge sled (82) is slidably disposed within cartridge body (D912) and includes upwardly presented cam surfaces configured to engage the undersides of the staple drivers.

Figure 90:
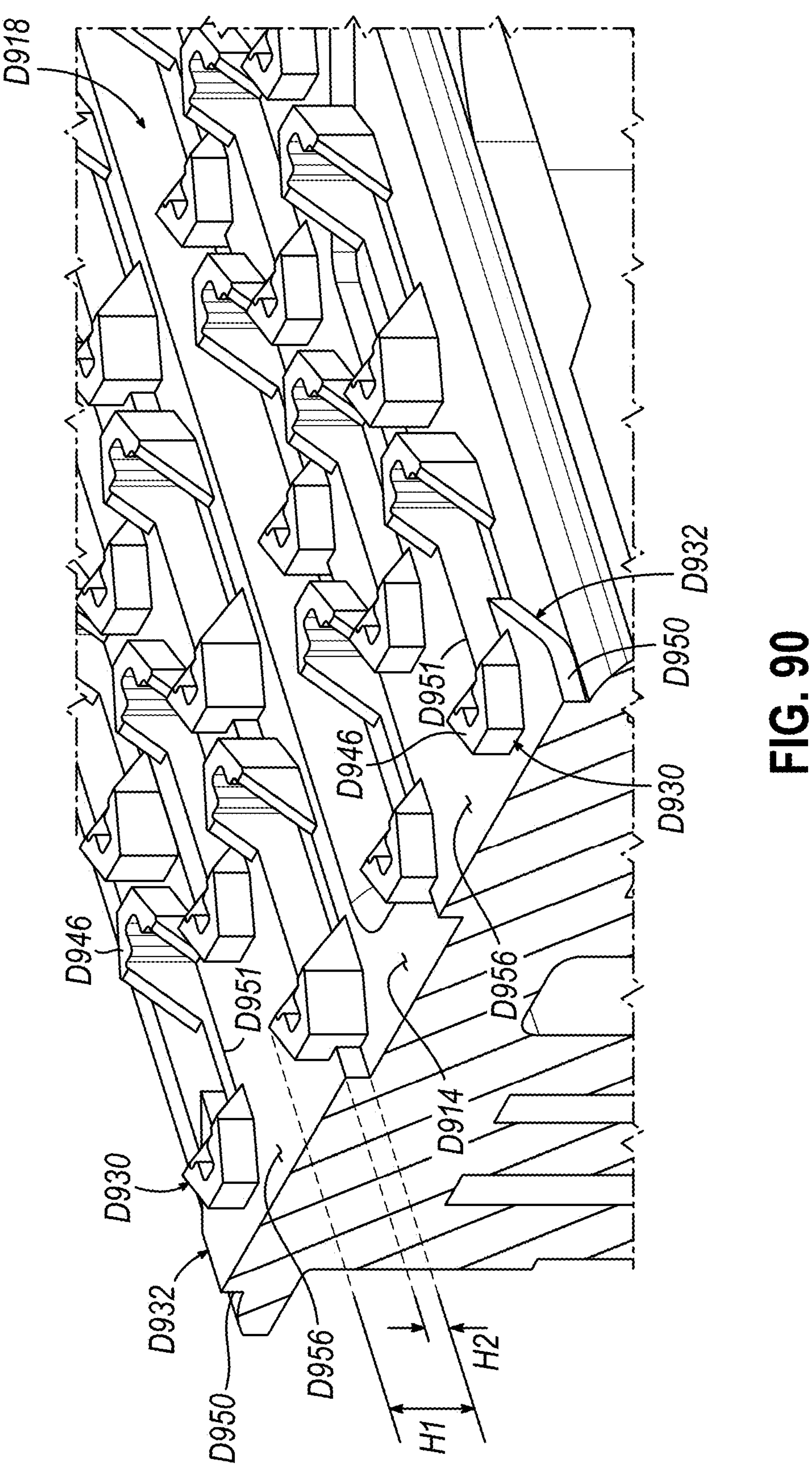
FIG. 90 depicts a partial perspective view of the staple cartridge of FIG. 87.

Staple cartridge (D910) of the present example further includes a plurality of raised features in the form of pocket extenders (D930) that extend upwardly from deck (D914) at or near proximal and distal ends of each cartridge pocket (D920), such that each cartridge pocket (D920) is longitudinally flanked by a corresponding pair of proximal and distal pocket extenders (D930). Any one or more of pocket extenders (D930) may be configured to enhance the gripping of tissue (T1, T2) by staple cartridge (D910) when end effector (40) is closed (e.g., in instances when staple cartridge (D910) is not equipped with a buttress assembly (D110, D112, D160)), and/or to guide the legs (D126) of the staples (86) as the legs (D126) exit the respective cartridge pockets (D920) during deployment of the staples (86). In addition, or alternatively, any one or more of pocket extenders (D930) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D910). As shown, each pocket extender (D930) includes an upwardly-facing top surface (D946) that extends substantially parallel relative to deck (D914). Top surfaces (D946) may be positioned at a substantially uniform first height (H1) above deck (D914), as shown in FIG. 90.

Staple cartridge (D910) of the present example also includes a plurality of raised features in the form of a pair of elongate contact pads (D932) that extend upwardly from deck (D914) on each lateral side of knife slot (D918) such that each contact pad (D932) spans laterally at least partially across three rows of cartridge pockets (D920) on the respective lateral side of knife slot (D918) (e.g., the respective inner, middle, and outer rows of cartridge pockets (D920)).

Figure 87:
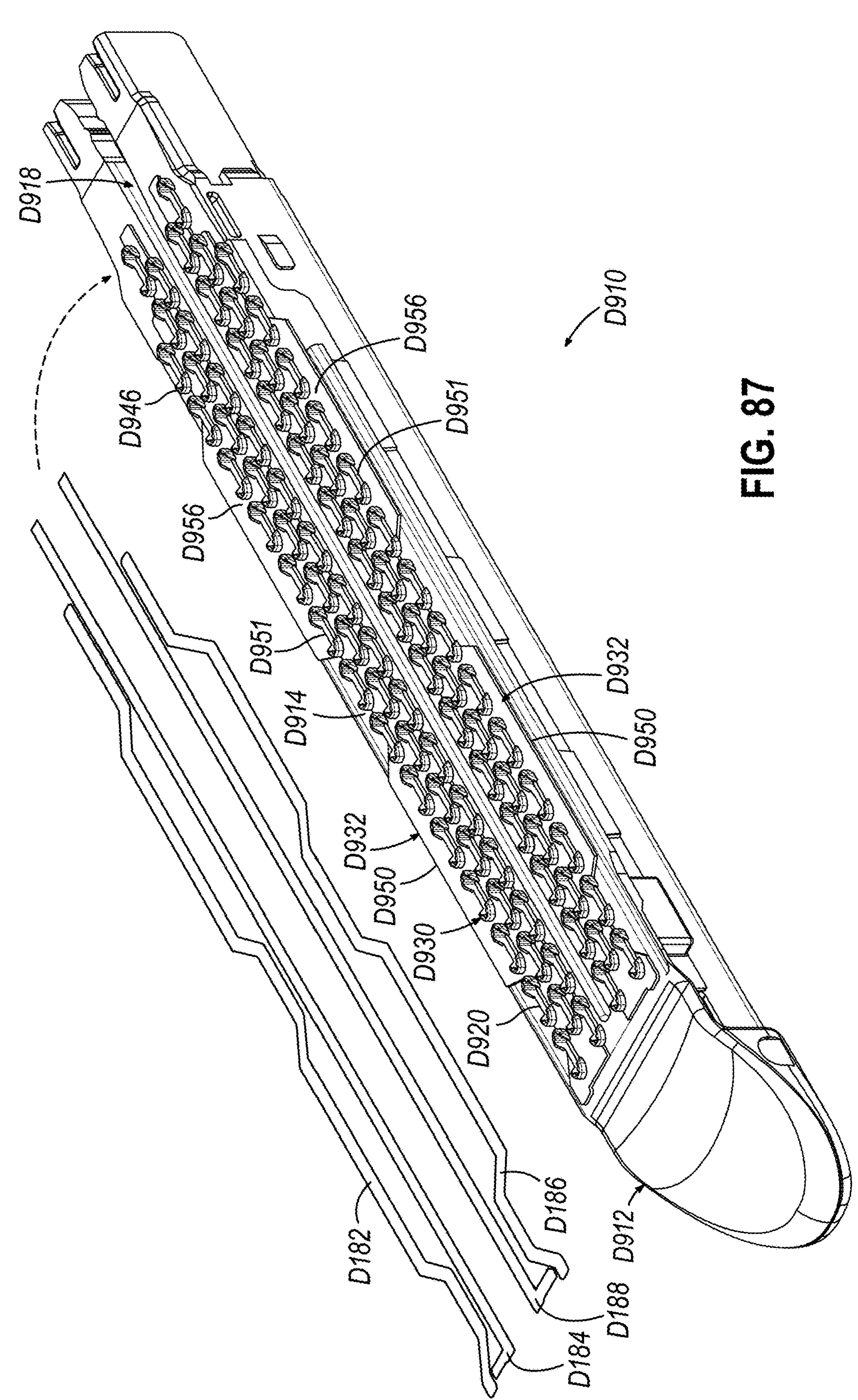
FIG. 87 depicts a perspective view of another example of a staple cartridge for use with the end effector of FIG. 2 and having adhesive pattern-shaped contact pads configured to promote adhesion of any of the buttress assemblies of FIGS. 70-73 to the staple cartridge.
Figures 88, 89:
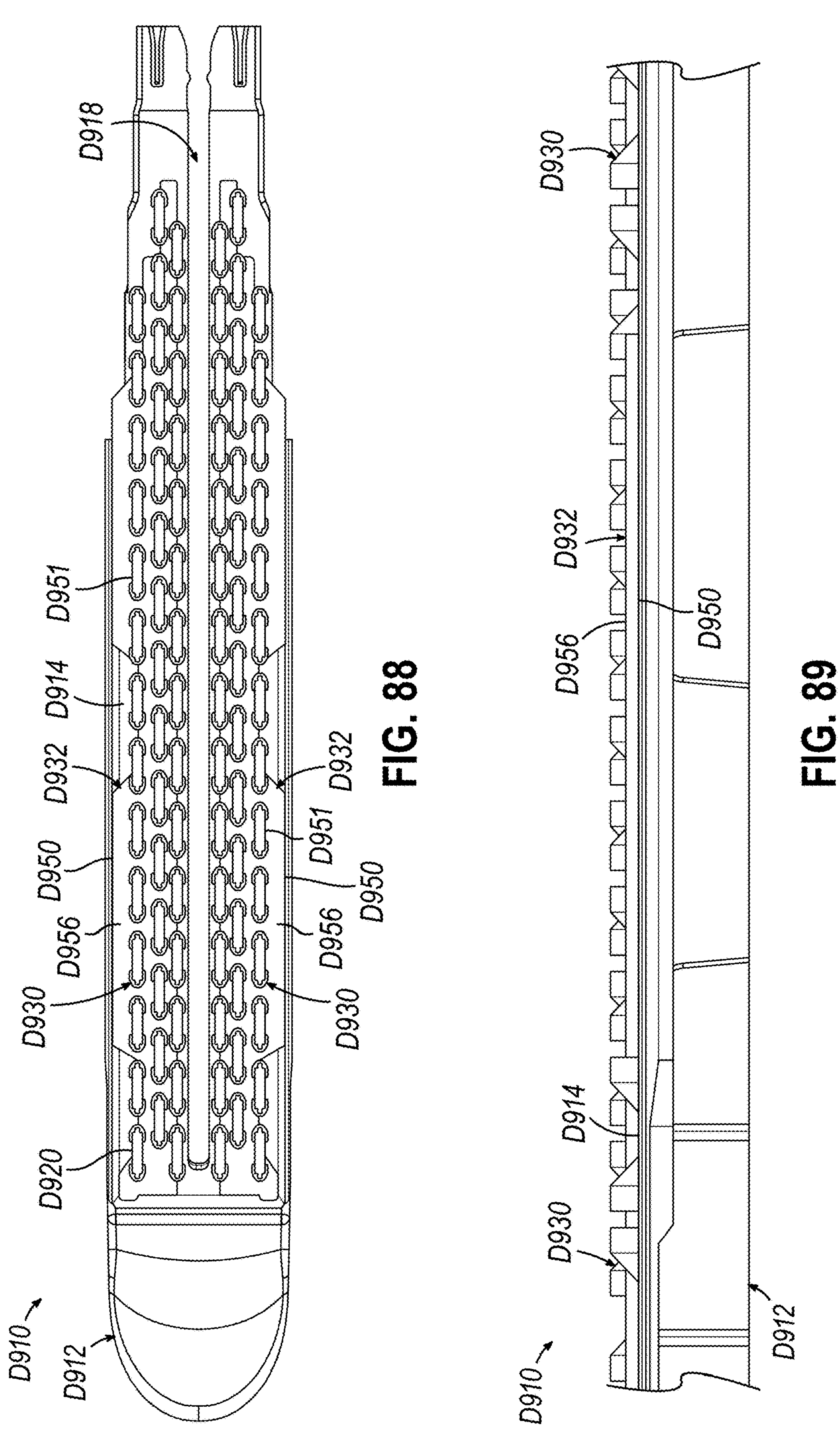
FIG. 88 depicts a top plan view of the staple cartridge of FIG. 87.
FIG. 89 depicts a side elevational view of the staple cartridge of FIG. 87.

Each contact pad (D932) includes a generally adhesive pattern-shaped body (D950). More particularly, the body (D950) of each contact pad (D932) is shaped to substantially match the pattern of adhesive (D166) of buttress assembly (D160). For example, the outer periphery of each body (D950) may substantially track the outer periphery of the corresponding adhesive beads (D182, D184, D186, D188), such that substantially all of adhesive (D166) may fit within a horizontal envelope defined by the outer periphery of the respective body (D950), as shown in FIG. 87. The body (D950) of each contact pad (D932) defines a plurality of openings (D951) overlying corresponding cartridge pockets (D920) for accommodating passage of respective staples (86) therethrough.

The body (D950) of each contact pad (D932) also defines an upwardly-facing top surface (D956) that extends substantially parallel relative to deck (D914). As shown in FIG. 90, top surfaces (D956) may be positioned at a second height (H2) above deck (D914) that is lower than the first height (H1) of top surfaces (D946). In some other versions, top surfaces (D956) may be positioned at a substantially same height above deck (D914) as that of top surfaces (D946). In the example shown, the top surface (D956) of each contact pad (D932) has a surface area that is greater than that of the top surface (D946) of each pocket extender (D930). The top surface (D956) of each contact pad (D932) may also extend further distally compared to the top surface (D946) of the distalmost pocket extenders (D930), further proximally compared to the top surface (D946) of the proximal-most pocket extenders (D930), and/or further laterally outwardly relative to the central axis of cartridge body (D912) compared to the top surface (D946) of the outer pocket extenders (D930). By having a greater surface area, extending further distally compared to the top surface (D946) of the distalmost pocket extenders (D930), extending further proximally compared to the top surface (D946) of the proximal-most pocket extenders (D930), and/or extending further laterally outwardly compared to the top surface (D946) of the outer pocket extenders (D930), the top surface (D956) of each contact pad (D932) may be configured to provide improved contact with the adhesive layers or beads (D116, D120, D182, D184, D186, D188) of a corresponding buttress assembly (D110, D112, D160), at least relative to the top surface (D946) of each pocket extender (D930). For example, the further distal extension of the top surface (D956) of each contact pad (D932) may allow the top surface (D956) to vertically align with more adhesive (D166) at distal end (D172) of buttress body (D164) compared to the top surface (D946) of each distalmost pocket extender (D930), and may thereby provide stronger, localized attachment of buttress assembly (D160) at the distal end of staple cartridge (D910).

It will also be appreciated that the adhesive-pattern shape of the body (D950) of each contact pad (D932) may allow the top surface (D956) of each contact pad (D932) to vertically align with substantially all of the adhesive (D166) along the entire length of buttress assembly (D160), and may thereby provide stronger attachment of buttress assembly (D160) along the entire length of staple cartridge (D910).

While the shape of the body (D950) of each contact pad (D932) is based on the pattern of adhesive (D166) of buttress assembly (D160), it will be appreciated that contact pads (D932) may also provide improved attachment of other types of buttress assemblies, such as buttress assemblies (D110, D112), to staple cartridge (D910). It will also be appreciated that the shape of the body (D950) of each contact pad (D932) may be based on the pattern of adhesive of any other buttress assembly desired to be attached to staple cartridge (D910).

VI. Examples of Cartridges Having Distal Raised Gripping Features

Figure 91:
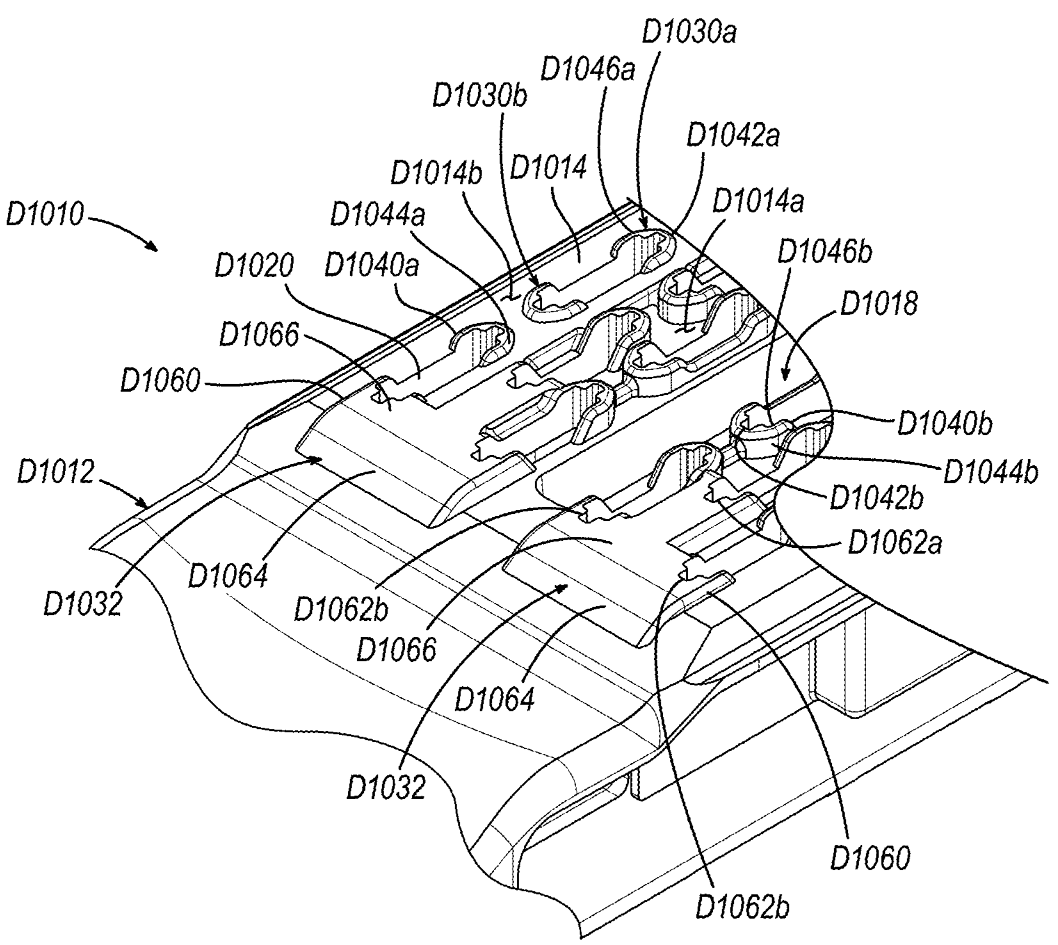
FIG. 91 depicts a partial perspective view of another example of a staple cartridge for use with the end effector of FIG. 2 and having distal raised gripping features that each span across three rows of pockets.

A. Example of Staple Cartridge with Distal Raised Gripping Feature Spanning Across Three Rows of Pockets FIG. 91 shows another example of a staple cartridge (D1010) configured to deploy staples (86) toward corresponding staple forming pockets of an anvil (not shown), such as staple forming pockets (66) of anvil (44). Staple cartridge (D1010) is configured for use with end effector (40), and is similar to staple cartridge (70) described above except as otherwise described below. In this regard, staple cartridge (D1010) of the present example includes a cartridge body (D1012) having an upwardly facing, multi-level deck (D1014), an elongate slot (D1018) extending along a central axis of cartridge body (D1012) and opening upwardly through deck (D1014) for slidably receiving a distal knife portion of a firing beam (not shown), such as distal knife portion (50) of firing beam (46), and a plurality of cartridge pockets (D1020) extending through deck (D1014) on each side of knife slot (D1018). In the present version, three longitudinal rows of cartridge pockets (D1020) are formed through upper deck (D1014) along each lateral side of knife slot (D1018), including an inner row, a middle row, and an outer row on each lateral side of knife slot (D1018). Each cartridge pocket (D1020) slidably houses an unformed staple (86) and a respective staple driver (not shown) similar to staple drivers (84) positioned beneath staple (86). A lower tray (not shown) similar to lower tray (76) encloses an underside of cartridge body (D1012) and thereby retains staples (86) and the staple drivers within cartridge body (D1012). A wedge sled (not shown) similar to wedge sled (82) is slidably disposed within cartridge body (D1012) and includes upwardly presented cam surfaces configured to engage the undersides of the staple drivers.

Multi-level deck (D1014) of the present example includes a lower deck surface (D1014*a*) spanning across at least the inner and middle rows of cartridge pockets (D1020) on each lateral side of knife slot (D1018), and an upper deck surface (D1014*b*) provided along at least a distal region of the outer row of cartridge pockets (D1020) on each lateral side of knife slot (D1018).

Staple cartridge (D1010) of the present example further includes a plurality of raised features in the form of pocket extenders (D1030*a*, D1030*b*, D1032) that extend upwardly from deck (D1014) at or near proximal and distal ends of each cartridge pocket (D1020), such that each cartridge pocket (D1020) is longitudinally flanked by a corresponding pair of proximal and distal pocket extenders (D1030*a*, D1030*b*, D1032). Any one or more of pocket extenders (D1030*a*, D1030*b*, D1032) may be configured to enhance the gripping of tissue (T1, T2) by staple cartridge (D1010) when end effector (40) is closed (e.g., in instances when staple cartridge (D1010) is not equipped with a buttress assembly (D110, D112, D160)), and/or to guide the legs (D126) of the staples (86) as the legs (D126) exit the respective cartridge pockets (D1020) during deployment of the staples (86). In addition, or alternatively, any one or more of pocket extenders (D1030*a*, D1030*b*, D1032) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1010).

In the example shown, the plurality of pocket extenders (D1030*a*, D1030*b*, D1032) include a plurality of first pocket extenders (D1030*a*, D1030*b*) having a first configuration, and a plurality of second pocket extenders (D1032) having a second configuration different from the first configuration. First pocket extenders (D1030*a*, D1030*b*) include proximal first pocket extenders (D1030*a*) that are positioned at or near the proximal ends of each cartridge pocket (D1020) of each row, and further include distal first pocket extenders (D1030*b*) that are positioned at or near the distal ends of each cartridge pocket (D1020) of each row, except for the distalmost cartridge pocket (D1020) of each row. In this regard, second pocket extenders (D1032) are positioned at or near the distal ends of the distalmost cartridge pockets (D1020) of the inner, middle, and outer rows such that each second pocket extender (D1032) spans laterally across three rows of cartridge pockets (D1020) on the respective lateral side of knife slot (D1018) (e.g., the respective inner, middle, and outer rows of cartridge pockets (D1020)).

As shown, each first pocket extender (D1030*a*, D1030*b*) includes a generally U-shaped body (D1040*a*, D1040*b*) that defines a staple leg receptacle (D1042*a*, D1042*b*) for receiving a corresponding leg (D126) of the staple (86) slidably housed within the respective cartridge pocket (D1020). In this regard, each staple leg receptacle (D1042*a*, D1042*b*) may be sized and configured to slidably receive the corresponding leg (D126) for vertically guiding the corresponding leg (D126) out of the respective cartridge pocket (D1020) toward the corresponding staple forming pockets (66) as staples (86) are driven outwardly from cartridge pockets (D1020) by the staple drivers. The body (D1040*a*) of each proximal first pocket extender (D1030*a*) also defines a proximally-facing outer surface (D1044*a*) that extends substantially orthogonally relative to deck (D1014), while the body (D1040*b*) of each distal first pocket extender (D1030*b*) also defines a distally-facing outer surface (D1044*b*) that extends substantially orthogonally relative to deck (D1014). The body (D1040*a*, D1040*b*) of each first pocket extender (D1030*a*, D1030*b*) further defines an upwardly-facing top surface (D1046*a*, D1046*b*) that extends substantially parallel relative to deck (D1014). Top surfaces (D1046*a*, D1046*b*) may be positioned at a substantially uniform height above a reference surface of deck (D1014) (e.g., either deck surface (D1014*a*, D1014*b*)).

As noted above, each second pocket extender (D1032) spans laterally across the respective inner, middle, and outer rows of cartridge pockets (D1020), and is positioned at or near the distal ends of the distalmost cartridge pockets (D1020) of the respective inner, middle, and outer rows. Each second pocket extender (D1032) includes a generally T-shaped body (D1060) that defines one proximal and a pair of distal staple leg receptacles (D1062*a*, D1062*b*) for receiving corresponding legs (D126) of the staples (86) slidably housed within the respective distalmost inner, middle, and outer cartridge pockets (D1020). In this regard, each staple leg receptacle (D1062*a*, D1062*b*) may be sized and configured to slidably receive the corresponding leg (D126) for vertically guiding the corresponding leg (D126) out of the respective cartridge pocket (D1020) toward the corresponding staple forming pockets (66) as staples (86) are driven outwardly from cartridge pockets (D1020) by the staple drivers.

The body (D1060) of each second pocket extender (D1032) also defines a distally-facing outer surface (D1064) that extends substantially obliquely relative to deck (D1014). In the example shown, the outer surface (D1064) of each second pocket extender (D1032) is rounded in the longitudinal direction. In addition, or alternatively, the outer surface (D1064) of each second pocket extender (D1032) may be rounded in the lateral direction, such as in a manner similar to that shown and described above in connection with FIG. 74. By extending substantially obliquely relative to deck (D1014) and/or by being rounded in the longitudinal and/or lateral direction, the outer surface (D1064) of each second pocket extender (D1032) may have a substantially atraumatic configuration so that each outer surface (D1064) may avoid inflicting trauma to tissue contacted by the outer surface (D1064). For example, each outer surface (D1064) may define a distal ramp for gently lifting such tissue upwardly relative to deck (D1014). Due to the spanning of each second pocket extender (D1032) laterally across the respective inner, middle, and outer rows of cartridge pockets (D1020), each outer surface (D1064) may be configured to lift the portions of such tissue that are aligned with the respective inner, middle, and outer rows of cartridge pockets (D1020).

The body (D1060) of each second pocket extender (D1032) further defines an upwardly-facing top surface (D1066) that extends substantially parallel relative to a reference surface of deck (D1014) (e.g., either deck surface (D1014*a*, D1014*b*)). Top surfaces (D1066) may be positioned above upper deck surface (D1014*b*), and/or at a substantially same height above lower deck surface (D1014*a*) as that of top surfaces (D1046*a*, D1046*b*). In some other versions, top surfaces (D1066) may be positioned at a different height above lower deck surface (D1014*a*) from that of top surfaces (D1046*a*, D1046*b*).

Due to the spanning of each second pocket extender (D1032) laterally across the respective inner, middle, and outer rows of cartridge pockets (D1020), the outer surface (1064) and top surface (D1066) of each second pocket extender (D1032) may provide a continuous interaction anti-snag surface to provide improved lifting of tissue without snagging such tissue. By having a different profile from that of first pocket extenders (D1030*a*, 1030*b*), second pocket extenders (D1032) may prevent inadvertent excessive tissue holding while still maintaining a desired degree of tissue gripping.

Figure 92:
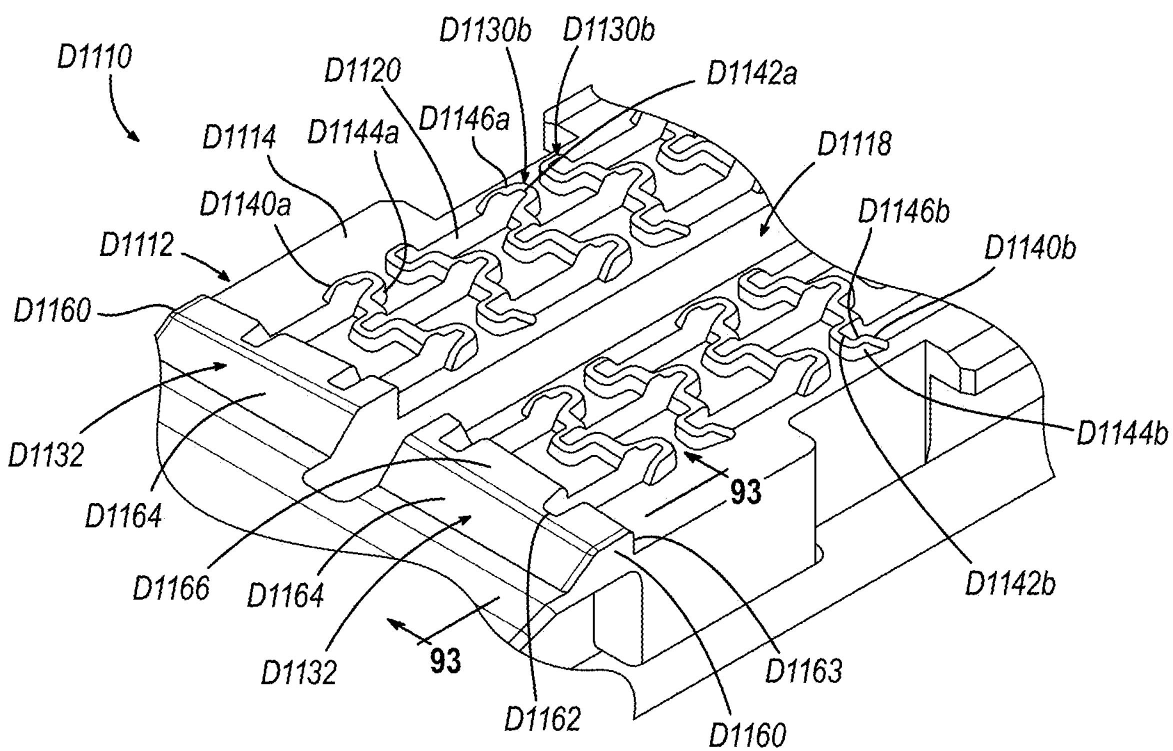
FIG. 92 depicts a partial perspective view of another example of a staple cartridge for use with the end effector of FIG. 2 and having distal raised gripping features that are ramped in multiple directions.
Figure 93:
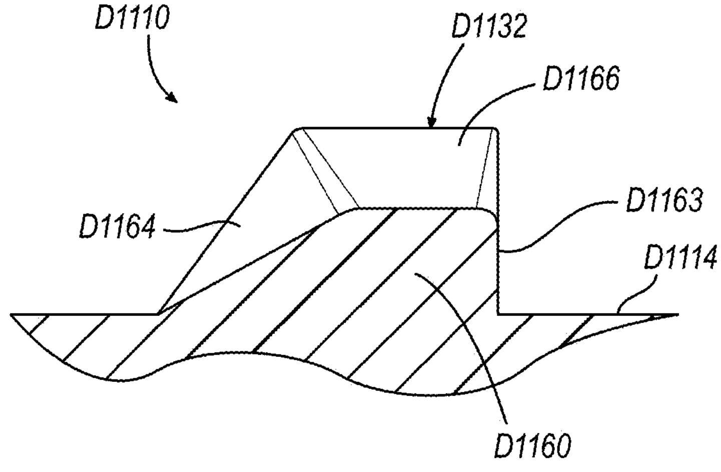
FIG. 93 depicts a cross-sectional view of the staple cartridge of FIG. 92, taken along line 93-93 in FIG. 92.

B. Example of Staple Cartridge with Distal Raised Gripping Feature Ramped in Multiple Directions FIGS. 92-93 show another example of a staple cartridge (D1110) configured to deploy staples (86) toward corresponding staple forming pockets of an anvil (not shown), such as staple forming pockets (66) of anvil (44). Staple cartridge (D1110) is configured for use with end effector (40), and is similar to staple cartridge (70) described above except as otherwise described below. In this regard, staple cartridge (D1110) of the present example includes a cartridge body (D1112) having an upwardly facing deck (D1114), an elongate slot (D1118) extending along a central axis of cartridge body (D1112) and opening upwardly through deck (D1114) for slidably receiving a distal knife portion of a firing beam (not shown), such as distal knife portion (50) of firing beam (46), and a plurality of cartridge pockets (D1120) extending through deck (D1114) on each side of knife slot (D1118). In the present version, three longitudinal rows of cartridge pockets (D1120) are formed through upper deck (D1114) along each lateral side of knife slot (D1118), including an inner row, a middle row, and an outer row on each lateral side of knife slot (D1118). Each cartridge pocket (D1120) slidably houses an unformed staple (86) and a respective staple driver (not shown) similar to staple drivers (84) positioned beneath staple (86). A lower tray (not shown) similar to lower tray (76) encloses an underside of cartridge body (D1112) and thereby retains staples (86) and the staple drivers within cartridge body (D1112). A wedge sled (not shown) similar to wedge sled (82) is slidably disposed within cartridge body (D1112) and includes upwardly presented cam surfaces configured to engage the undersides of the staple drivers.

Staple cartridge (D1110) of the present example further includes a plurality of raised features in the form of pocket extenders (D1130*a*, D1130*b*, D1132) that extend upwardly from deck (D1114) at or near proximal and distal ends of each cartridge pocket (D1120), such that each cartridge pocket (D1120) is longitudinally flanked by a corresponding pair of proximal and distal pocket extenders (D1130*a*, D1130*b*, D1132). Any one or more of pocket extenders (D1130*a*, D1130*b*, D1132) may be configured to enhance the gripping of tissue (T1, T2) by staple cartridge (D1110) when end effector (40) is closed (e.g., in instances when staple cartridge (D1110) is not equipped with a buttress assembly (D110, D112, D160)), and/or to guide the legs (D126) of the staples (86) as the legs (D126) exit the respective cartridge pockets (D1120) during deployment of the staples (86). In addition, or alternatively, any one or more of pocket extenders (D1130*a*, D1130*b*, D1132) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1110).

In the example shown, the plurality of pocket extenders (D1130*a*, D1130*b*, D1132) include a plurality of first pocket extenders (D1130*a*, D1130*b*) having a first configuration, and a plurality of second pocket extenders (D1132) having a second configuration different from the first configuration. First pocket extenders (D1130*a*, D1130*b*) include proximal first pocket extenders (D1130*a*) that are positioned at or near the proximal ends of each cartridge pocket (D1120) of each row, and further include distal first pocket extenders (D1130*b*) that are positioned at or near the distal ends of each cartridge pocket (D1120) of each row, except for the distalmost cartridge pocket (D1120) of the inner and outer rows. In this regard, second pocket extenders (D1132) are positioned at or near the distal ends of the distalmost cartridge pockets (D1120) of the inner and outer rows such that each second pocket extender (D1132) spans laterally across three rows of cartridge pockets (D1120) on the respective lateral side of knife slot (D1118) (e.g., the respective inner, middle, and outer rows of cartridge pockets (D1120)).

As shown, each first pocket extender (D1130*a*, D1130*b*) includes a generally U-shaped body (D1140*a*, D1140*b*) that defines a staple leg receptacle (D1142*a*, D1142*b*) for receiving a corresponding leg (D126) of the staple (86) slidably housed within the respective cartridge pocket (D1120). In this regard, each staple leg receptacle (D1142*a*, D1142*b*) may be sized and configured to slidably receive the corresponding leg (D126) for vertically guiding the corresponding leg (D126) out of the respective cartridge pocket (D1120) toward the corresponding staple forming pockets (66) as staples (86) are driven outwardly from cartridge pockets (D1120) by the staple drivers. The body (D1140*a*) of each proximal first pocket extender (D1130*a*) also defines a proximally-facing outer surface (D1144*a*) that extends substantially orthogonally relative to deck (D1114), while the body (D1140*b*) of each distal first pocket extender (D1130*b*) also defines a distally-facing outer surface (D1144*b*) that extends substantially orthogonally relative to deck (D1114). The body (D1140*a*, D1140*b*) of each first pocket extender (D1130*a*, D1130*b*) further defines an upwardly-facing top surface (D1146*a*, D1146*b*) that extends substantially parallel relative to deck (D1114). Top surfaces (D1146*a*, D1146*b*) may be positioned at a substantially uniform height above deck (D1114).

As noted above, each second pocket extender (D1132) spans laterally across the respective inner, middle, and outer rows of cartridge pockets (D1120), and is positioned at or near the distal ends of the distalmost cartridge pockets (D1120) of the respective inner and outer rows. Each second pocket extender (D1132) includes a body (D1160) that defines a pair of staple leg receptacles (D1162) for receiving corresponding legs (D126) of the staples (86) slidably housed within the respective distalmost inner and outer cartridge pockets (D1120). In this regard, each staple leg receptacle (D1162) may be sized and configured to slidably receive the corresponding leg (D126) for vertically guiding the corresponding leg (D126) out of the respective cartridge pocket (D1120) toward the corresponding staple forming pockets (66) as staples (86) are driven outwardly from cartridge pockets (D1120) by the staple drivers.

The body (D1160) of each second pocket extender (D1132) also defines a proximally-facing outer surface (D1163) that extends substantially orthogonally relative to deck (D1114), and a distally-facing outer surface (D1164) that extends substantially obliquely relative to deck (D1114). In the example shown, the outer surface (D1164) of each second pocket extender (D1132) is tapered proximally in a laterally-outward direction, such that the laterally-inner ends of outer surfaces (D1164) are distal of the laterally-outer ends of outer surfaces (D1164). By extending substantially obliquely relative to deck (D1114) and/or by being tapered proximally in the laterally-outward direction, the distally-facing outer surface (D1164) of each second pocket extender (D1132) may have a substantially atraumatic configuration so that each outer surface (D1164) may avoid inflicting trauma to tissue contacted by the outer surface (D1164). For example, each outer surface (D1164) may define a distal ramp for gently lifting such tissue upwardly relative to deck (D1114). Due to the spanning of each second pocket extender (D1132) laterally across the respective inner, middle, and outer rows of cartridge pockets (D1120), each outer surface (D1164) may be configured to lift the portions of such tissue that are aligned with the respective inner, middle, and outer rows of cartridge pockets (D1120). By extending substantially orthogonally relative to deck (D1114), the proximally-facing outer surface (D1163) of each second pocket extender (D1132) may be configured to apply a higher drag force and/or frictional force to tissue (T1, T2) than that applied to tissue (T1, T2) by the respective distally-facing outer surface (D1164), to thereby provide a higher pull-off load than insertion load.

The body (D1160) of each second pocket extender (D1132) further defines an upwardly-facing top surface (D1166) that extends substantially obliquely relative to deck (D1114). In the example shown, the top surface (D1166) of each second pocket extender (D1132) is tapered downwardly in the laterally-outward direction, such that the laterally-inner ends of top surfaces (D1166) are above the laterally-outer ends of top surfaces (D1166). The laterally-inner ends of top surfaces (D1166) may be positioned at a substantially same height above deck (D1114) as that of top surfaces (D1146*a*, D1146*b*). In some other versions, the laterally-inner ends of top surfaces (D1166) may be positioned at a different height above deck (D1114) from that of top surfaces (D1146*a*, D1146*b*). For example, the laterally-inner ends of top surfaces (D1166) may be positioned at a higher height above deck (D1114) than that of top surfaces (D1146*a*, D1146*b*), such that a distal tip of anvil (44) may contact the laterally-inner ends of top surfaces (D1166) before contacting top surfaces (D1146*a*, D1146*b*) during closure of end effector (40) to thereby produce an increased loading on the distal end than proximal to that location in at least a partially clamped approximation state. While the laterally-outer ends of top surfaces (D1166) are shown positioned above deck (D1114), the laterally-outer ends of top surfaces (D1166) may alternatively be positioned at a same height as deck (D1114).

In some versions, the proximally-facing outer surface (D1163) of each second pocket extender (D1132) and/or the top surface (D1166) of each second pocket extender (D1132) may be textured and/or include isolated raised features to improve frictional hold of tissue (T1, T2). For example, the proximally-facing outer surface (D1163) of each second pocket extender (D1132) may have a first surface finish (e.g., textured) that is different from a second surface finish (e.g., smooth) of the top surface (D1166) and/or distally-facing outer surface (D1164) of each second pocket extender (D1132). In addition, or alternatively, the top surface (D1166) of each second pocket extender (D1132) may have the first surface finish (e.g., textured) that is different from the second surface finish (e.g., smooth) of the distally-facing outer surface (D1164) of each second pocket extender (D1132).

VII. Examples of Cartridges Having Rails for Buttress Adhesion

A. Example of Staple Cartridge with Outer Rails

Figure 94:
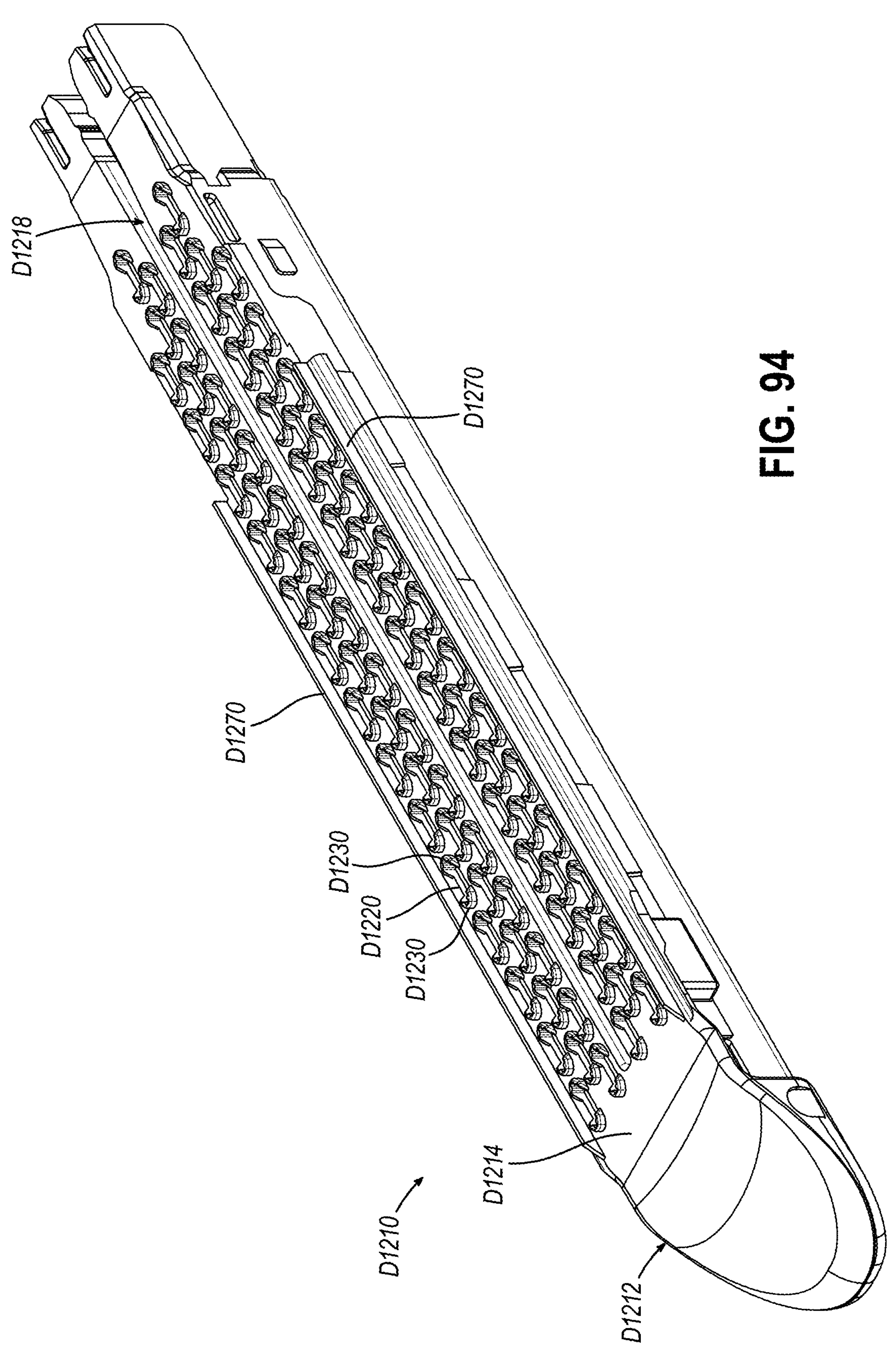
FIG. 94 depicts a perspective view of another example of a staple cartridge for use with the end effector of FIG. 2 and having laterally outer rails for buttress adhesion.

FIG. 94 shows another example of a staple cartridge (D1210) configured to deploy staples (86) toward corresponding staple forming pockets of an anvil (not shown), such as staple forming pockets (66) of anvil (44). Staple cartridge (D1210) is configured for use with end effector (40), and is similar to staple cartridge (70) described above except as otherwise described below. In this regard, staple cartridge (D1210) of the present example includes a cartridge body (D1212) having an upwardly facing deck (D1214), an elongate slot (D1218) extending along a central axis of cartridge body (D1212) and opening upwardly through deck (D1214) for slidably receiving a distal knife portion of a firing beam (not shown), such as distal knife portion (50) of firing beam (46), and a plurality of cartridge pockets (D1220) extending through deck (D1214) on each side of knife slot (D1218). In the present version, three longitudinal rows of cartridge pockets (D1220) are formed through upper deck (D1214) along each lateral side of knife slot (D1218), including an inner row, a middle row, and an outer row on each lateral side of knife slot (D1218). Each cartridge pocket (D1220) slidably houses an unformed staple (86) and a respective staple driver (not shown) similar to staple drivers (84) positioned beneath staple (86). A lower tray (not shown) similar to lower tray (76) encloses an underside of cartridge body (D1212) and thereby retains staples (86) and the staple drivers within cartridge body (D1212). A wedge sled (not shown) similar to wedge sled (82) is slidably disposed within cartridge body (D1212) and includes upwardly presented cam surfaces configured to engage the undersides of the staple drivers.

Staple cartridge (D1210) of the present example further includes a plurality of raised features in the form of pocket extenders (D1230) that extend upwardly from deck (D1214) at or near proximal and distal ends of each cartridge pocket (D1220), such that each cartridge pocket (D1220) is longitudinally flanked by a corresponding pair of proximal and distal pocket extenders (D1230). Any one or more of pocket extenders (D1230) may be configured to enhance the gripping of tissue (T1, T2) by staple cartridge (D1210) when end effector (40) is closed (e.g., in instances when staple cartridge (D1210) is not equipped with a buttress assembly (D110, D112, D160)), and/or to guide the legs (D126) of the staples (86) as the legs (D126) exit the respective cartridge pockets (D1220) during deployment of the staples (86). In addition, or alternatively, any one or more of pocket extenders (D1230) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1210).

Staple cartridge (D1210) of the present example further includes another plurality of raised features in the form of a pair of longitudinal rails (D1270) that extend upwardly from deck (D1214) along a respective lateral side of knife slot (D1218) and that are disposed laterally outwardly of the corresponding outer row of cartridge pockets (D1220). The top surfaces of rails (D1270) may be positioned at a substantially same height above deck (D1214) as that of the top surfaces of pocket extenders (D1230) such as, for example, about 0.51 mm. Any one or more of rails (D1270) may be configured to enhance the gripping of tissue (T1, T2) by staple cartridge (D1210) when end effector (40) is closed (e.g., in instances when staple cartridge (D1210) is not equipped with a buttress assembly (D110, D112, D160)). In addition, or alternatively, any one or more of rails (D1270) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1210). In some versions, any one or more of rails (D1270) may be configured to prevent the adhesive layers or beads (D116, D120, D182, D184, D186, D188) of a corresponding buttress assembly (D110, D112, D160) from spreading laterally outwardly beyond the respective rail (D1270).

Figure 95:
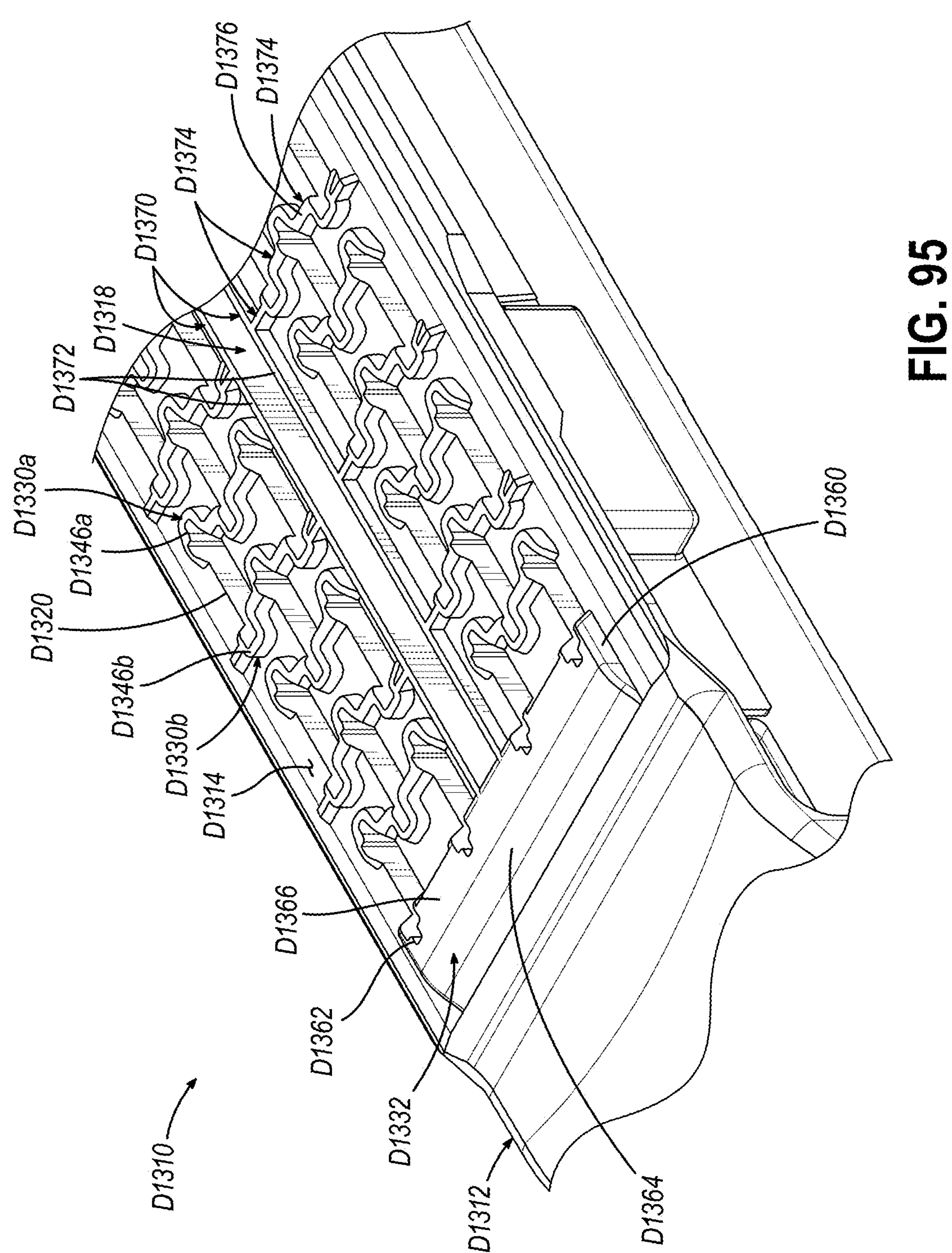
FIG. 95 depicts a partial perspective view of another example of a staple cartridge for use with the end effector of FIG. 2 and having interconnected pocket extenders and laterally inner rails for buttress adhesion.

B. Example of Staple Cartridge with Inner Rails and Interconnected Pocket Extenders FIG. 95 shows another example of a staple cartridge (D1310) configured to deploy staples (86) toward corresponding staple forming pockets of an anvil (not shown), such as staple forming pockets (66) of anvil (44). Staple cartridge (D1310) is configured for use with end effector (40), and is similar to staple cartridge (70) described above except as otherwise described below. In this regard, staple cartridge (D1310) of the present example includes a cartridge body (D1312) having an upwardly facing deck (D1314), an elongate slot (D1318) extending along a central axis of cartridge body (D1312) and opening upwardly through deck (D1314) for slidably receiving a distal knife portion of a firing beam (not shown), such as distal knife portion (50) of firing beam (46), and a plurality of cartridge pockets (D1320) extending through deck (D1314) on each side of knife slot (D1318). In the present version, three longitudinal rows of cartridge pockets (D1320) are formed through upper deck (D1314) along each lateral side of knife slot (D1318), including an inner row, a middle row, and an outer row on each lateral side of knife slot (D1318). Each cartridge pocket (D1320) slidably houses an unformed staple (86) and a respective staple driver (not shown) similar to staple drivers (84) positioned beneath staple (86). A lower tray (not shown) similar to lower tray (76) encloses an underside of cartridge body (D1312) and thereby retains staples (86) and the staple drivers within cartridge body (D1312). A wedge sled (not shown) similar to wedge sled (82) is slidably disposed within cartridge body (D1312) and includes upwardly presented cam surfaces configured to engage the undersides of the staple drivers.

Staple cartridge (D1310) of the present example further includes a plurality of raised features in the form of pocket extenders (D1330*a*, D1330*b*, D1332) that extend upwardly from deck (D1314) at or near proximal and distal ends of each cartridge pocket (D1320), such that each cartridge pocket (D1320) is longitudinally flanked by a corresponding pair of proximal and distal pocket extenders (D1330*a*, D1330*b*, D1332). Any one or more of pocket extenders (D1330*a*, D1330*b*, D1332) may be configured to enhance the gripping of tissue (T1, T2) by staple cartridge (D1310) when end effector (40) is closed (e.g., in instances when staple cartridge (D1310) is not equipped with a buttress assembly (D110, D112, D160)), and/or to guide the legs (D126) of the staples (86) as the legs (D126) exit the respective cartridge pockets (D1320) during deployment of the staples (86). In addition, or alternatively, any one or more of pocket extenders (D1330*a*, D1330*b*, D1332) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1310).

In the example shown, the plurality of pocket extenders (D1330*a*, D1330*b*, D1332) include a plurality of first pocket extenders (D1330*a*, D1330*b*) having a first configuration, and a second pocket extender (D1332) having a second configuration different from the first configuration. First pocket extenders (D1330*a*, D1330*b*) include proximal first pocket extenders (D1330*a*) that are positioned at or near the proximal ends of each cartridge pocket (D1320) of each row, and further include distal first pocket extenders (D1330*b*) that are positioned at or near the distal ends of each cartridge pocket (D1320) of each row, except for the distalmost cartridge pocket (D1320) of the inner and outer rows. In this regard, second pocket extender (D1332) is positioned at or near the distal ends of the distalmost cartridge pockets (D1320) of the inner and outer rows such that second pocket extender (D1332) spans laterally across all rows of cartridge pockets (D1320) on both lateral sides of knife slot (D1318) (e.g., the respective inner, middle, and outer rows of cartridge pockets (D1320)).

As shown, each first pocket extender (D1330*a*, D1330*b*) includes an upwardly-facing top surface (D1346*a*, D1346*b*) that extends substantially parallel relative to deck (D1314). Top surfaces (D1346*a*, D1346*b*) may be positioned at a substantially uniform height above deck (D1314).

As noted above, second pocket extender (D1332) spans laterally across all of the inner, middle, and outer rows of cartridge pockets (D1320), and is positioned at or near the distal ends of the distalmost cartridge pockets (D1320) of the inner and outer rows. Second pocket extender (D1332) includes a body (D1360) that defines four staple leg receptacles (D1362) for receiving corresponding legs (D126) of the staples (86) slidably housed within the distalmost inner and outer cartridge pockets (D1320). In this regard, each staple leg receptacle (D1362) may be sized and configured to slidably receive the corresponding leg (D126) for vertically guiding the corresponding leg (D126) out of the respective cartridge pocket (D1320) toward the corresponding staple forming pockets (66) as staples (86) are driven outwardly from cartridge pockets (D1320) by the staple drivers.

The body (D1360) of second pocket extender (D1332) also defines a distally-facing outer surface (D1364) that extends substantially obliquely relative to deck (D1314). In the example shown, the outer surface (D1364) of second pocket extender (D1332) is rounded in the longitudinal direction. In addition, or alternatively, the outer surface (D1364) of second pocket extender (D1332) may be rounded in the lateral direction, such as in a manner similar to that shown and described above in connection with FIG. 74. By extending substantially obliquely relative to deck (D1314) and/or by being rounded in the longitudinal and/or lateral direction, the outer surface (D1364) of second pocket extender (D1332) may have a substantially atraumatic configuration so that each outer surface (D1364) may avoid inflicting trauma to tissue contacted by the outer surface (D1364). For example, outer surface (D1364) may define a distal ramp for gently lifting such tissue upwardly relative to deck (D1314). Due to the spanning of each second pocket extender (D1332) laterally across all of the inner, middle, and outer rows of cartridge pockets (D1320), outer surface (D1364) may be configured to lift the portions of such tissue that are aligned with any one or more of the inner, middle, and outer rows of cartridge pockets (D1320).

The body (D1360) of second pocket extender (D1332) further defines an upwardly-facing top surface (D1366) that extends substantially parallel relative to deck (D1314). Top surface (D1366) may be positioned above deck (D1314) as that of top surfaces (D1346*a*, D1346*b*).

Due to the spanning of second pocket extender (D1332) laterally across all of the inner, middle, and outer rows of cartridge pockets (D1320), the outer surface (1064) and top surface (D1366) of second pocket extender (D1332) may provide a continuous interaction anti-snag surface to provide improved lifting of tissue without snagging such tissue.

Staple cartridge (D1310) of the present example further includes another plurality of raised features in the form of a pair of longitudinal rails (D1370) that extend upwardly from deck (D1314) and proximally from second pocket extender (D1332) along a respective lateral side of knife slot (D1318), and that are disposed laterally inwardly of the corresponding inner row of cartridge pockets (D1320). Top surfaces (D1372) of rails (D1370) may be positioned at a substantially same height above deck (D1314) as that of top surfaces (D1346*a*, D1346*b*, D1366) of pocket extenders (D1330*a*, D1330*b*, D1332) such as, for example, about 0.51 mm. Any one or more of rails (D1370) may be configured to enhance the gripping of tissue (T1, T2) by staple cartridge (D1310) when end effector (40) is closed (e.g., in instances when staple cartridge (D1310) is not equipped with a buttress assembly (D110, D112, D160)). In addition, or alternatively, any one or more of rails (D1370) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1310).

Staple cartridge (D1310) of the present example also includes another plurality of raised features in the form of bridges (D1374) that extend upwardly from deck (D1314) and laterally inwardly and/or outwardly from respective first pocket extenders (D1330*a*, D1330*b*). Top surfaces (D1376) of bridges (D1374) may be positioned at a substantially same height above deck (D1314) as that of top surfaces (D1346*a*, D1346*b*, D1366) of pocket extenders (D1330*a*, D1330*b*, D1332) and/or as that of top surfaces (D1372) of rails (D1370) such as, for example, about 0.51 mm. Any one or more of bridges (D1374) may be configured to enhance the gripping of tissue (T1, T2) by staple cartridge (D1310) when end effector (40) is closed (e.g., in instances when staple cartridge (D1310) is not equipped with a buttress assembly (D110, D112, D160)). In addition, or alternatively, any one or more of bridges (D1374) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1310).

In the example shown, bridges (D1374) interconnect various first pocket extenders (D1330*a*, D1330*b*) with each other and/or with rails (D1370), such that various top surfaces (D1346*a*, D1346*b*, D1366, D1372, D1376) are continuous with each other. As shown, the top surfaces (D1346*a*, D1346*b*) of at least some first pocket extenders (D1330*a*, D1330*b*) cooperate with the top surfaces (1376) of the corresponding bridges (D1374) to define a continuous, generally serpentine surface extending from the top surface (D1372) of the respective rail (D1370) to the respective laterally outer edge of deck (D1314).

In the example shown, pocket extenders (D1330*a*, D1330*b*, D1332), rails (D1370), and/or bridges (D1374) also collectively define a continuous lattice structure to provide staple cartridge (D1310) with improved lateral stability (e.g., during squeezing of tissue (T1, T2)).

VIII. Example of Cartridge Having Receptacles for Buttress Adhesion

Figure 96:
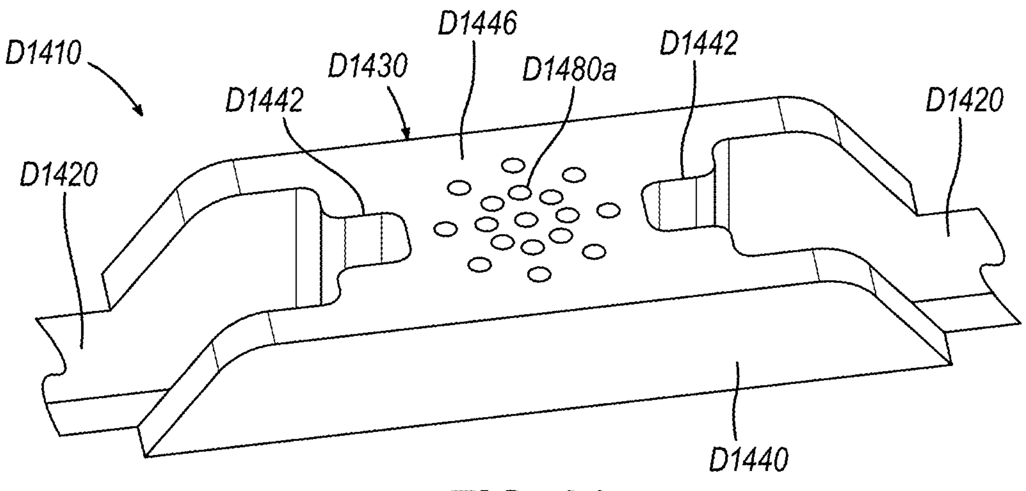
FIG. 96 depicts a partial perspective view of another example of a staple cartridge for use with the end effector of FIG. 2 and having circular receptacles for buttress adhesion.
Figure 97:
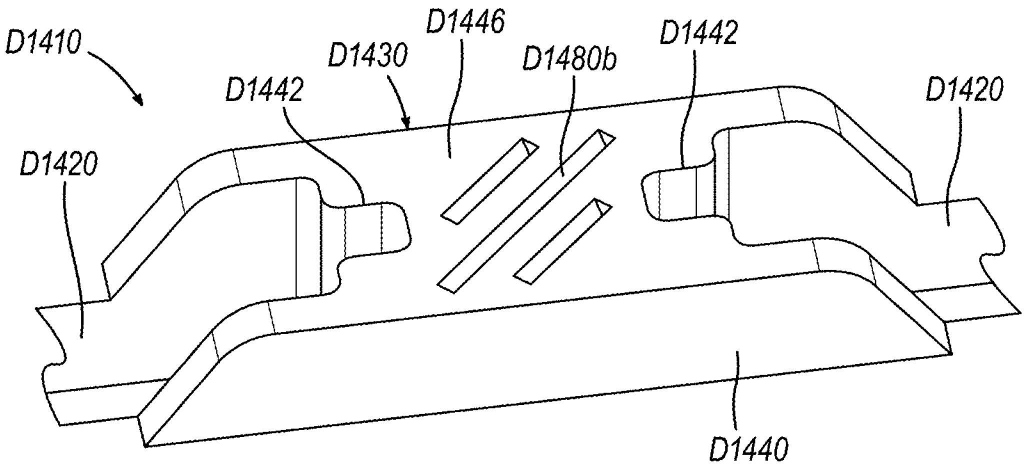
FIG. 97 depicts another partial perspective view of the staple cartridge of FIG. 96, showing linear receptacles for buttress adhesion.
Figure 98:
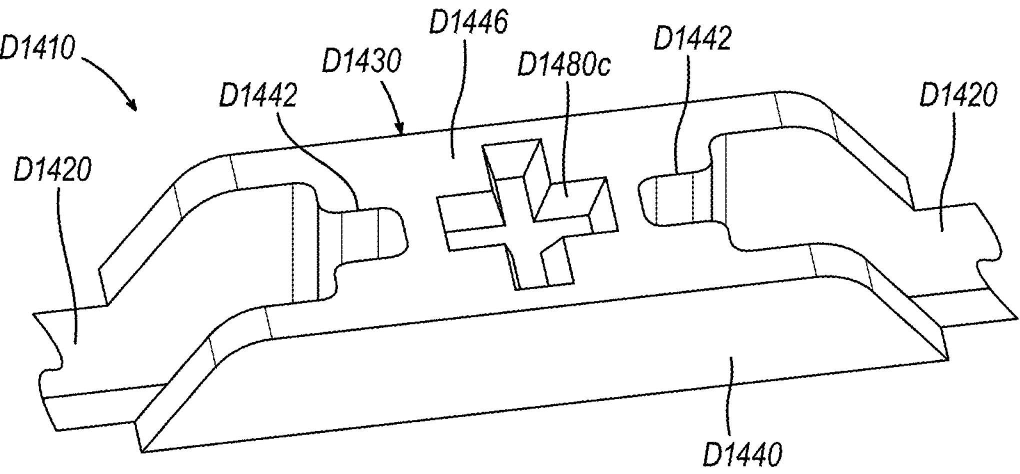
FIG. 98 depicts another partial perspective view of the staple cartridge of FIG. 96, showing a "+" shaped receptacle for buttress adhesion.

FIGS. 96-98 show portions of another example of a staple cartridge (D1410) configured to deploy staples (86) toward corresponding staple forming pockets of an anvil (not shown), such as staple forming pockets (66) of anvil (44). Staple cartridge (D1410) is configured for use with end effector (40), and is similar to staple cartridge (70) described above except as otherwise described below. In this regard, staple cartridge (D1410) of the present example includes a plurality of cartridge pockets (D1420) formed through an upper deck (not shown) on each lateral side of a knife slot (not shown). Each cartridge pocket (D1420) slidably houses an unformed staple (86) and a respective staple driver (not shown) similar to staple drivers (84) positioned beneath staple (86).

Staple cartridge (D1410) of the present example further includes a plurality of raised features in the form of pocket extenders (D1430) that extend upwardly from the deck at or near proximal and distal ends of each cartridge pocket (D1420), such that each cartridge pocket (D1420) is longitudinally flanked by a corresponding pair of pocket extenders (D1430). Any one or more of pocket extenders (D1430) may be configured to enhance the gripping of tissue (T1, T2) by staple cartridge (D1410) when end effector (40) is closed (e.g., in instances when staple cartridge (D1410) is not equipped with a buttress assembly (D110, D112, D160)), and/or to guide the legs (D126) of the staples (86) as the legs (D126) exit the respective cartridge pockets (D1420) during deployment of the staples (86). In addition, or alternatively, any one or more of pocket extenders (D1430) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1410).

As shown, each pocket extender (D1430) includes a body (D1440) that defines proximal and distal staple leg receptacles (D1442) for receiving corresponding legs (D126) of the staples (86) slidably housed within the respective cartridge pockets (D1420). The body (D1440) of each pocket extender (D1430) further defines an upwardly-facing top surface (D1446) that extends substantially parallel relative to the deck.

Staple cartridge (D1410) of the present example further includes a plurality of recesses (D1480*a*, D1480*b*, D1480*c*) that extend downwardly from the top surfaces (D1446) of respective pocket extenders (D1430). More particularly, a generally circular array of generally circular recesses (D1480*a*) extend downwardly from the top surface (D1446) of at least one respective pocket extender (D1430) as shown in FIG. 96; a plurality of generally linear recesses (D1480*b*) oriented obliquely relative to the knife slot extend downwardly from the top surface (D1446) of at least one respective pocket extender (D1430) as shown in FIG. 97; and a single generally "+" shaped recess (D1480*c*) extends downwardly from the top surface (D1446) of at least one respective pocket extender (D1430) as shown in FIG. 98. Any one or more of recesses (D1480*a*, D1480*b*, D1480*c*) may be configured to receive respective portions of the adhesive layers or beads (D116, D120, D182, D184, D186, D188) of a corresponding buttress assembly (D110, D112, D160) to promote attachment of the corresponding buttress assembly (D110, D112, D160) to staple cartridge (D1410).

While recesses (D1480*a*, D1480*b*, D1480*c*) have been described as being incorporated together into a single staple cartridge (D1410), it will be appreciated that any suitable type(s) of recess(es) (D1480*a*, D1480*b*, D1480*c*) may be incorporated into a particular staple cartridge. For example, only a single type of recess (D1480*a*, D1480*b*, D1480*c*) may be incorporated into a given staple cartridge. It will also be appreciated that recesses (D1480*a*, D1480*b*, D1480*c*) may be configured in any other suitable manners beyond those shown in FIGS. 96-98.

IX. Examples of Cartridges Having Raised Surfaces for Tissue Flow Control

A. Example of Staple Cartridge with Bi-Directionally Tapered Deck Surface

Figure 99:
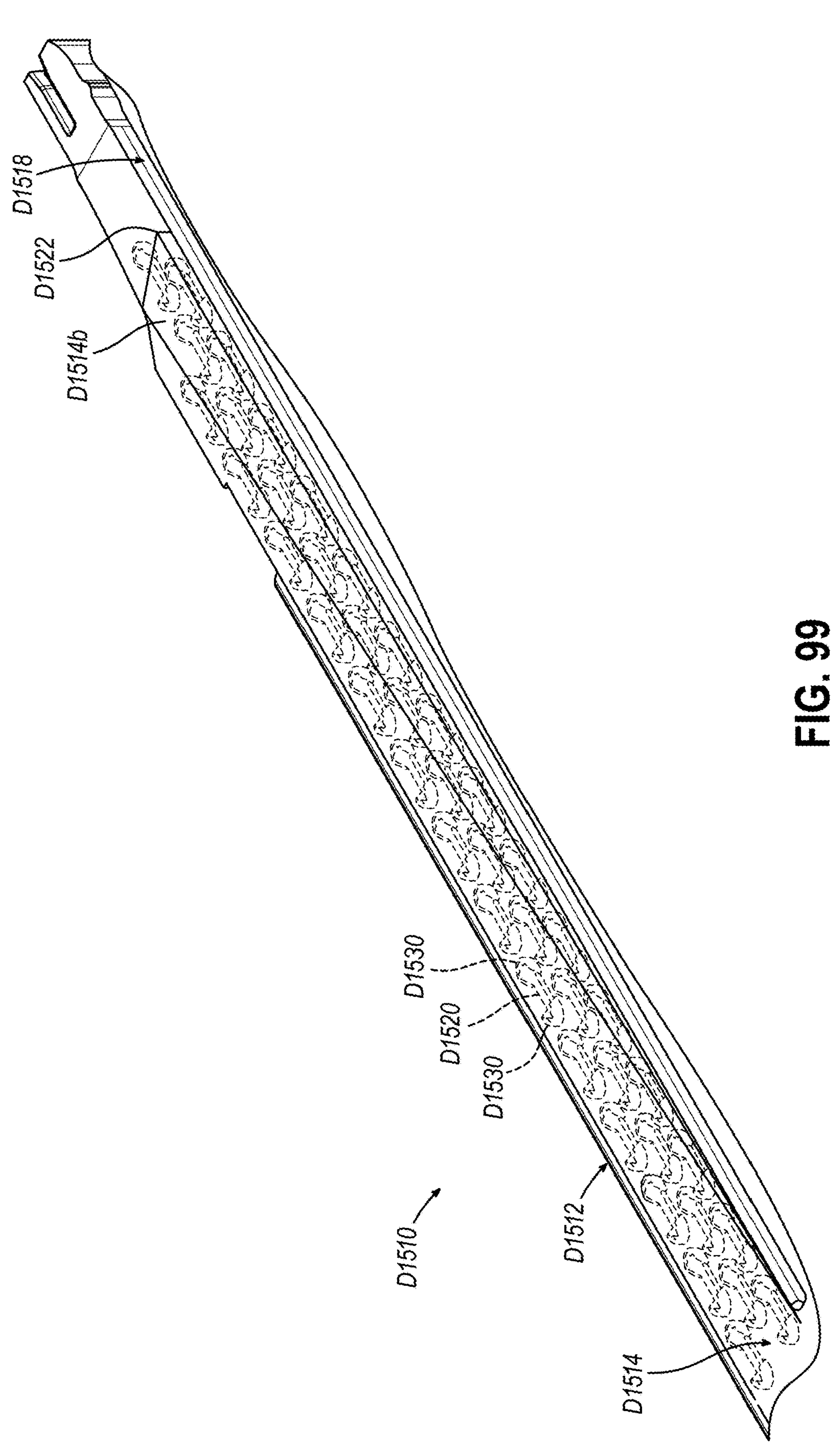
FIG. 99 depicts a partial perspective view of another example of a staple cartridge for use with the end effector of FIG. 2 and having a bi-directionally tapered deck surface for tissue flow control.
Figures 100, 101:
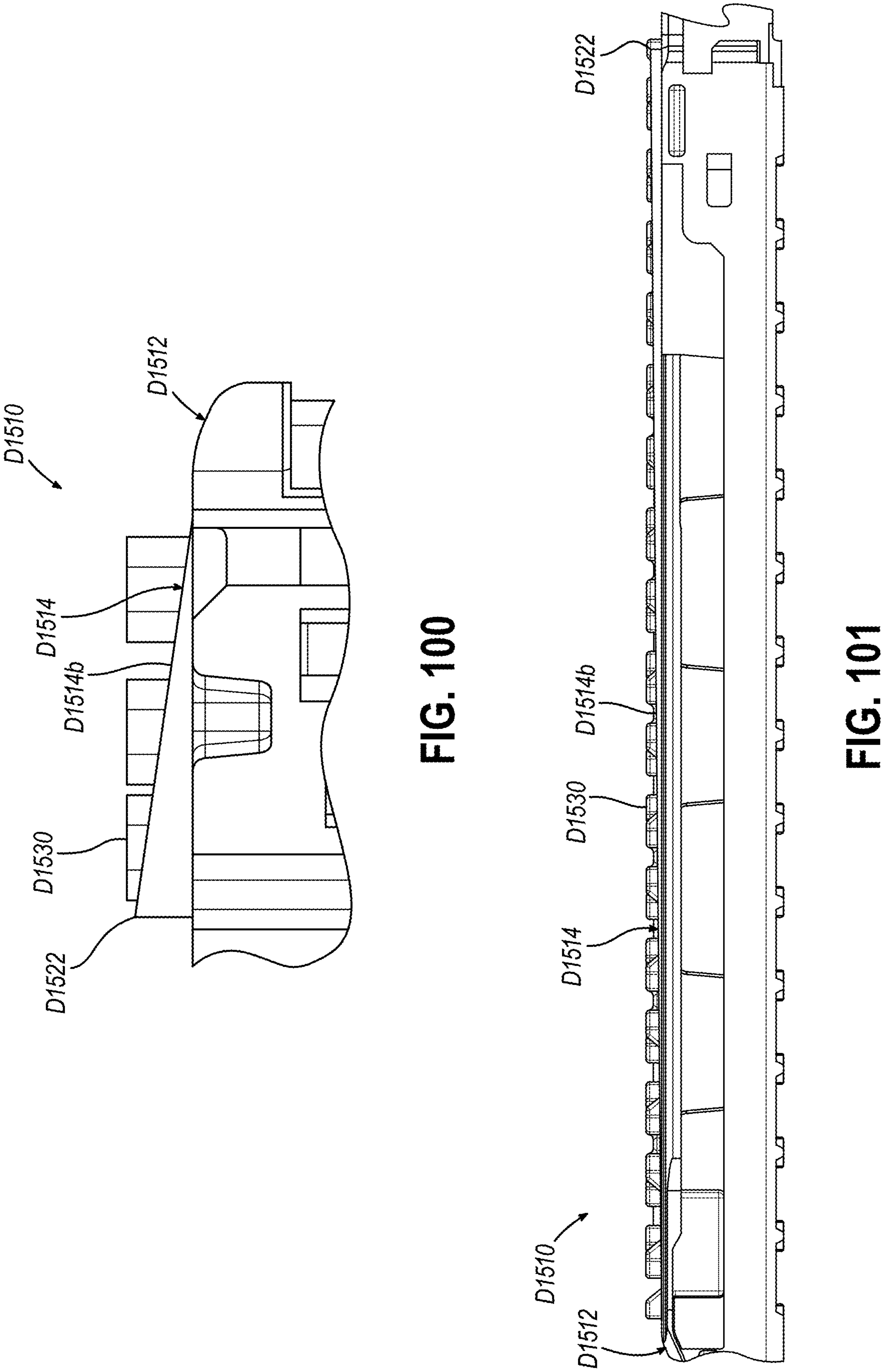
FIG. 100 depicts a rear elevational view of the staple cartridge of FIG. 99.
FIG. 101 depicts a side elevational view of the staple cartridge of FIG. 99.

FIGS. 99-101 show another example of a staple cartridge (D1510) configured to deploy staples (86) toward corresponding staple forming pockets of an anvil (not shown), such as staple forming pockets (66) of anvil (44). Staple cartridge (D1510) is configured for use with end effector (40), and is similar to staple cartridge (70) described above except as otherwise described below. In this regard, staple cartridge (D1510) of the present example includes a cartridge body (D1512) having an upwardly facing, multi-surface deck (D1514), an elongate slot (D1518) extending along a central axis of cartridge body (D1512) and opening upwardly through deck (D1514) for slidably receiving a distal knife portion of a firing beam (not shown), such as distal knife portion (50) of firing beam (46), and a plurality of cartridge pockets (D1520) extending through deck (D1514) on each side of knife slot (D1518). In the present version, three longitudinal rows of cartridge pockets (D1520) are formed through upper deck (D1514) along each lateral side of knife slot (D1518), including an inner row, a middle row, and an outer row on each lateral side of knife slot (D1518). Each cartridge pocket (D1520) slidably houses an unformed staple (86) and a respective staple driver (not shown) similar to staple drivers (84) positioned beneath staple (86). A lower tray (not shown) similar to lower tray (76) encloses an underside of cartridge body (D1512) and thereby retains staples (86) and the staple drivers within cartridge body (D1512). A wedge sled (not shown) similar to wedge sled (82) is slidably disposed within cartridge body (D1512) and includes upwardly presented cam surfaces configured to engage the undersides of the staple drivers.

Multi-surface deck (D1514) of the present example includes a flat (e.g., horizontal) base surface (D1514*a*) and a bi-directionally tapered raised surface (D1514*b*). In the example shown, raised surface (D1514*b*) tapers downwardly in both the distal and laterally outward directions. More particularly, raised surface (D1514*b*) tapers downwardly in both such directions from peaks (D1522) on each lateral side of knife slot (D1518) that define both a proximal-most and laterally-innermost portion of raised surface (D1514*b*), to base surface (D1514*a*). Peaks (D1522) of the present example are each positioned adjacent to a proximal region of knife slot (D1518). For example, peaks (D1522) may be positioned adjacent to or slightly distal of the proximal position of the wedge sled disposed within cartridge body (D1512).

Staple cartridge (D1510) of the present example further includes a plurality of raised features in the form of pocket extenders (D1530) that extend upwardly from deck (D1514) at or near proximal and distal ends of each cartridge pocket (D1520), such that each cartridge pocket (D1520) is longitudinally flanked by a corresponding pair of proximal and distal pocket extenders (D1530). Any one or more of pocket extenders (D1530) may be configured to enhance the gripping of tissue (T1, T2) by staple cartridge (D1510) when end effector (40) is closed (e.g., in instances when staple cartridge (D1510) is not equipped with a buttress assembly (D110, D112, D160)), and/or to guide the legs (D126) of the staples (86) as the legs (D126) exit the respective cartridge pockets (D1520) during deployment of the staples (86). In addition, or alternatively, any one or more of pocket extenders (D1530) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1510).

Due to the downward tapering of raised surface (D1514*b*) in both the distal and laterally outward directions, raised surface (D1514*b*) may provide tighter compression of tissue (T1, T2) adjacent to a proximal region of knife slot (D1518), thereby inhibiting dragging of tissue (T1, T2) by distal knife portion (50) upon initial contact between distal knife portion (50) and tissue (T1, T2) during distal translation of firing beam (46) (e.g., during a firing stroke), and instead promoting piercing of tissue (T1, T2) by distal knife portion (50) to provide a clean cut. In addition, or alternatively, raised surface (D1514*b*) may similarly inhibit movement (e.g., "plowing") of the buttress assembly (D110, D112, D160) and instead promote piercing of the buttress assembly (D110, D112, D160) by distal knife portion (50) to provide a clean cut. In some instances, the downward tapering of raised surface (D1514*b*) in both the distal and laterally outward directions may assist with guiding the fluid phase of clamped tissue (T1, T2) outwardly both laterally and longitudinally due to the tendency of fluid to flow in the path of least resistance, which may result in an increase in the amount of fluid evacuated from clamped tissue (T1, T2) prior to distal translation of firing beam (46) (e.g., prior to a firing stroke). This may lead to a decrease in fluid flow during distal translation of firing beam (46), thereby reducing any risk of the legs (D126) of staples (86) drifting and thus reducing any risk of staples (86) being malformed. In addition, or alternatively, the downward tapering of raised surface (D1514*b*) in both the distal and laterally outward directions may have a minimal impact on the overall compression forces applied to tissue (T1, T2), thereby reducing any risk of excessive force-to-close and/or any risk of de-cambering.

B. Example of Staple Cartridge with Convex Deck Surface

Figure 102:
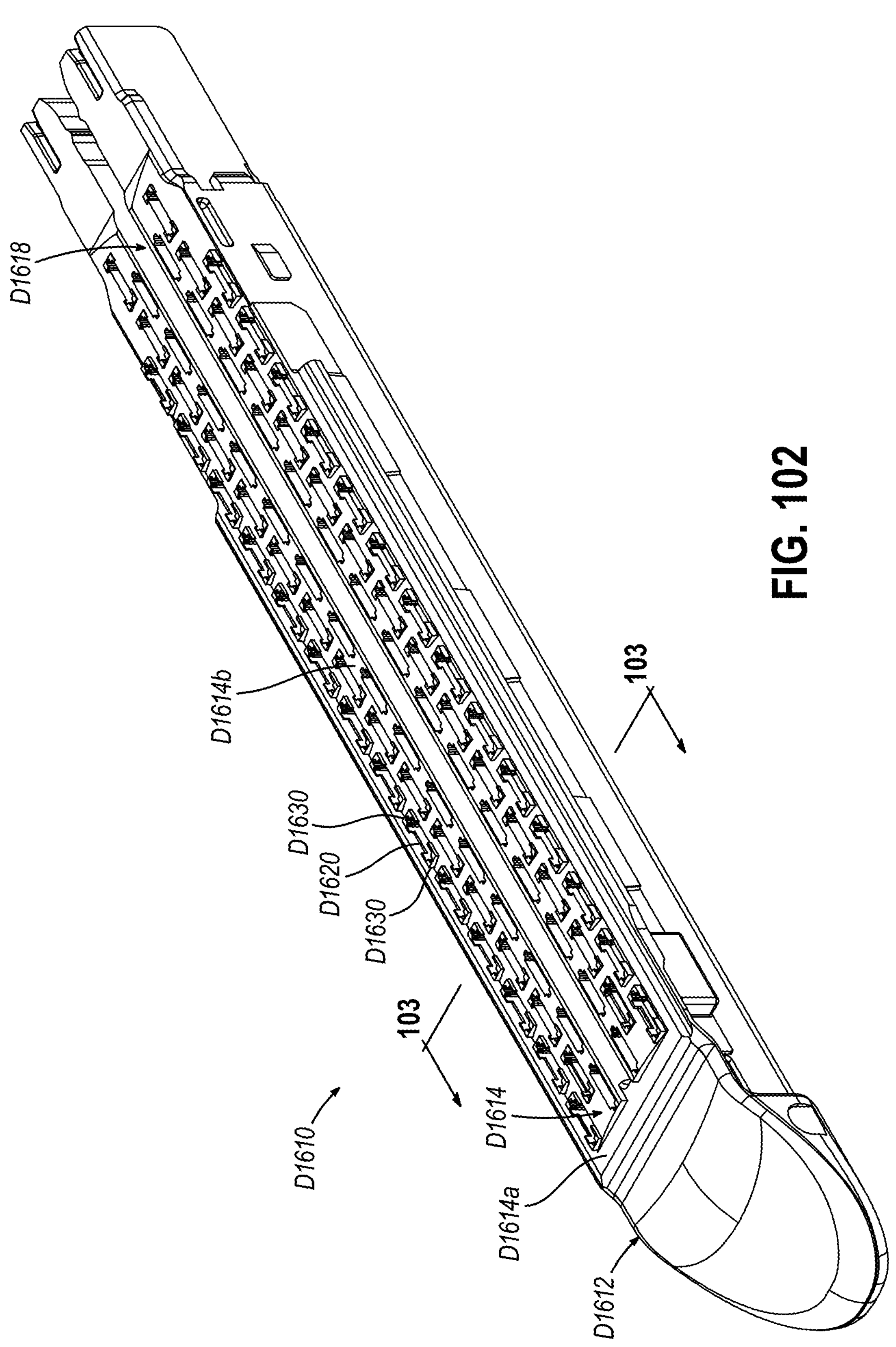
FIG. 102 depicts a perspective view of another example of a staple cartridge for use with the end effector of FIG. 2 and having a convex deck surface for tissue flow control.
Figure 103:
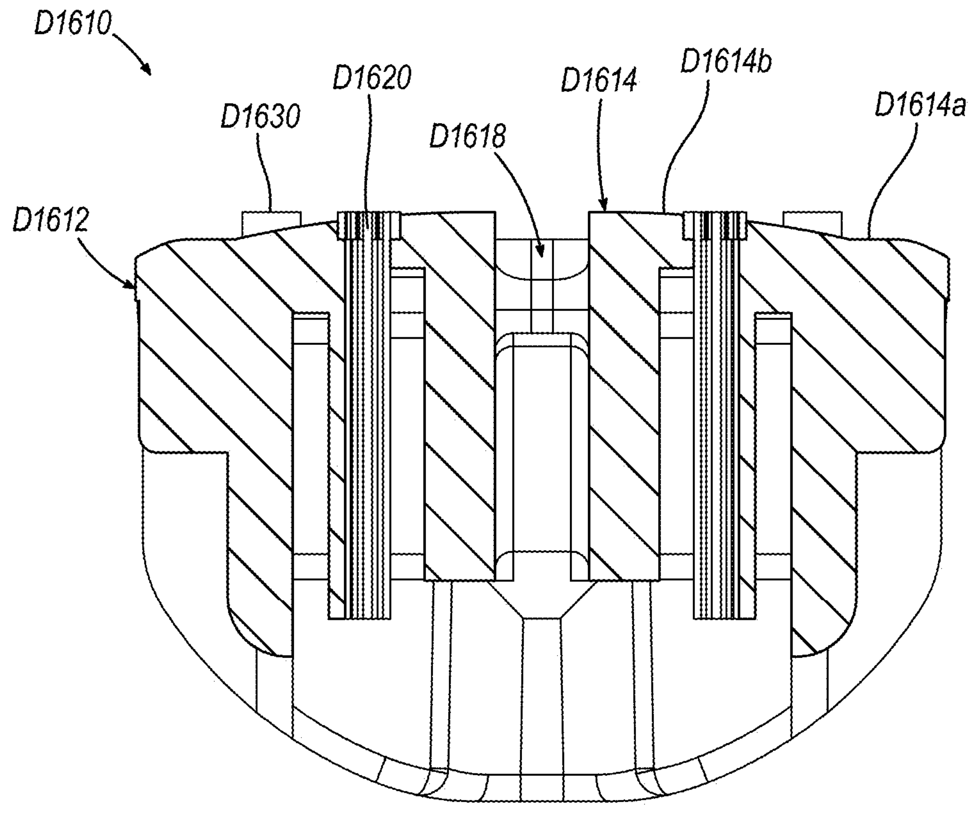
FIG. 103 depicts a cross sectional view of the staple cartridge of FIG. 102, taken along line 103-103 of FIG. 102.

FIGS. 102-103 show another example of a staple cartridge (D1610) configured to deploy staples (86) toward corresponding staple forming pockets of an anvil (not shown), such as staple forming pockets (66) of anvil (44). Staple cartridge (D1610) is configured for use with end effector (40), and is similar to staple cartridge (70) described above except as otherwise described below. In this regard, staple cartridge (D1610) of the present example includes a cartridge body (D1612) having an upwardly facing, multi-surface deck (D1614), an elongate slot (D1618) extending along a central axis of cartridge body (D1612) and opening upwardly through deck (D1614) for slidably receiving a distal knife portion of a firing beam (not shown), such as distal knife portion (50) of firing beam (46), and a plurality of cartridge pockets (D1620) extending through deck (D1614) on each side of knife slot (D1618). In the present version, three longitudinal rows of cartridge pockets (D1620) are formed through upper deck (D1614) along each lateral side of knife slot (D1618), including an inner row, a middle row, and an outer row on each lateral side of knife slot (D1618). Each cartridge pocket (D1620) slidably houses an unformed staple (86) and a respective staple driver (not shown) similar to staple drivers (84) positioned beneath staple (86). A lower tray (not shown) similar to lower tray (76) encloses an underside of cartridge body (D1612) and thereby retains staples (86) and the staple drivers within cartridge body (D1612). A wedge sled (not shown) similar to wedge sled (82) is slidably disposed within cartridge body (D1612) and includes upwardly presented cam surfaces configured to engage the undersides of the staple drivers.

Multi-surface deck (D1614) of the present example includes a flat (e.g., horizontal) base surface (D1614*a*) and a convex raised surface (D1614*b*). In the example shown, raised surface (D1614*b*) curves downwardly in the laterally outward direction. More particularly, raised surface (D1614*b*) curves downwardly in such direction from peaks (D1622) on each lateral side of knife slot (D1618) that define a laterally-innermost portion of raised surface (D1614*b*), to base surface (D1614*a*). Due to the downward curving of raised surface (D1614*b*) in the laterally outward directions, raised surface (D1614*b*) may promote flow of tissue (T1, T2) away from the cutline.

Staple cartridge (D1610) of the present example further includes a plurality of raised features in the form of pocket extenders (D1630) that extend upwardly from deck (D1614) at or near proximal and distal ends of each cartridge pocket (D1620) in the middle and outer rows, such that cartridge pockets (D1620) in the middle and outer rows are each longitudinally flanked by a corresponding pair of proximal and distal pocket extenders (D1630) while cartridge pockets (D1620) in the inner rows are equipped with neither a corresponding proximal nor distal pocket extender (D1630).

Any one or more of pocket extenders (D1630) may be configured to enhance the gripping of tissue (T1, T2) by staple cartridge (D1610) when end effector (40) is closed (e.g., in instances when staple cartridge (D1610) is not equipped with a buttress assembly (D110, D112, D160)), and/or to guide the legs (D126) of the staples (86) as the legs (D126) exit the respective cartridge pockets (D1620) during deployment of the staples (86). In addition, or alternatively, any one or more of pocket extenders (D1630) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1610).

Figure 104:
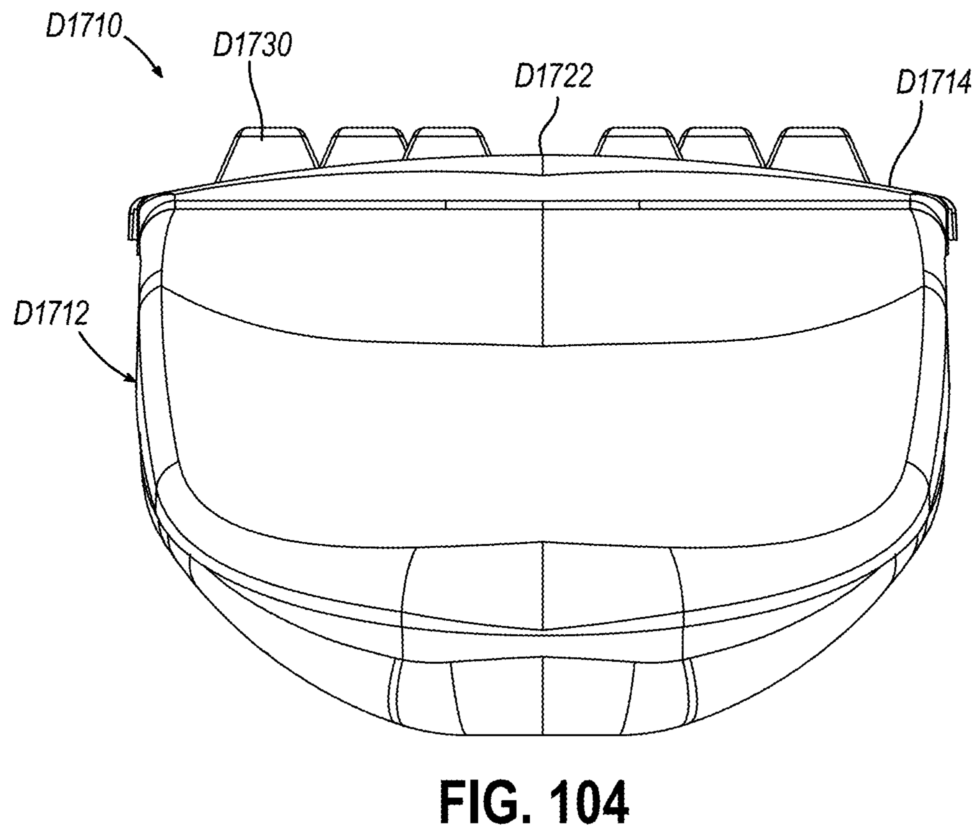
FIG. 104 depicts a front elevational view of another example of a staple cartridge for use with the end effector of FIG. 2 and having a convex deck surface and level pocket extenders.

C. Example of Staple Cartridge with Convex Deck Surface and Level Pocket Extenders FIG. 104 shows another example of a staple cartridge (D1710) configured to deploy staples (86) toward corresponding staple forming pockets of an anvil (not shown), such as staple forming pockets (66) of anvil (44). Staple cartridge (D1710) is configured for use with end effector (40), and is similar to staple cartridge (70) described above except as otherwise described below. In this regard, staple cartridge (D1710) of the present example includes a cartridge body (D1712) having an upwardly facing, convex deck (D1714), and a plurality of cartridge pockets (not shown) extending through deck (D1714) on each side of a knife slot (not shown). Convex deck (D1714) of the present example curves downwardly in the laterally outward direction on each side of the knife slot from a central peak (1722). Staple cartridge (D1710) of the present example further includes a plurality of raised features in the form of pocket extenders (D1730) that extend upwardly from deck (D1714) at or near proximal and distal ends of each cartridge pocket. In the example shown, the top surfaces of pocket extenders (D1730) are generally flat, and are generally level with each other.

Figure 105:
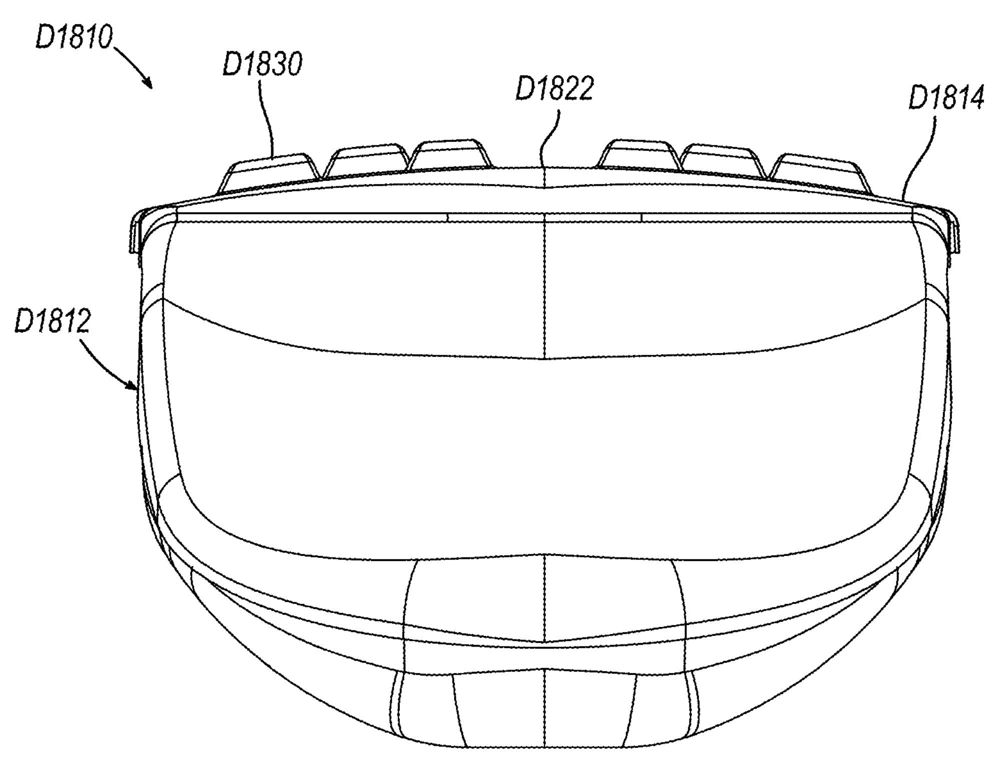
FIG. 105 depicts a front elevational view of another example of a staple cartridge for use with the end effector of FIG. 2 and having a convex deck surface and curved pocket extenders.

D. Example of Staple Cartridge with Convex Deck Surface and Curved Pocket Extenders FIG. 105 shows another example of a staple cartridge (D1810) configured to deploy staples (86) toward corresponding staple forming pockets of an anvil (not shown), such as staple forming pockets (66) of anvil (44). Staple cartridge (D1810) is configured for use with end effector (40), and is similar to staple cartridge (70) described above except as otherwise described below. In this regard, staple cartridge (D1810) of the present example includes a cartridge body (D1812) having an upwardly facing, convex deck (D1814), and a plurality of cartridge pockets (not shown) extending through deck (D1814) on each side of a knife slot (not shown). Convex deck (D1814) of the present example curves downwardly in the laterally outward direction on each side of the knife slot from a central peak (1822). Staple cartridge (D1810) of the present example further includes a plurality of raised features in the form of pocket extenders (D1830) that extend upwardly from deck (D1814) at or near proximal and distal ends of each cartridge pocket. In the example shown, the top surfaces of pocket extenders (D1830) are generally convex, and are generally arranged along an arc.

Figure 106:
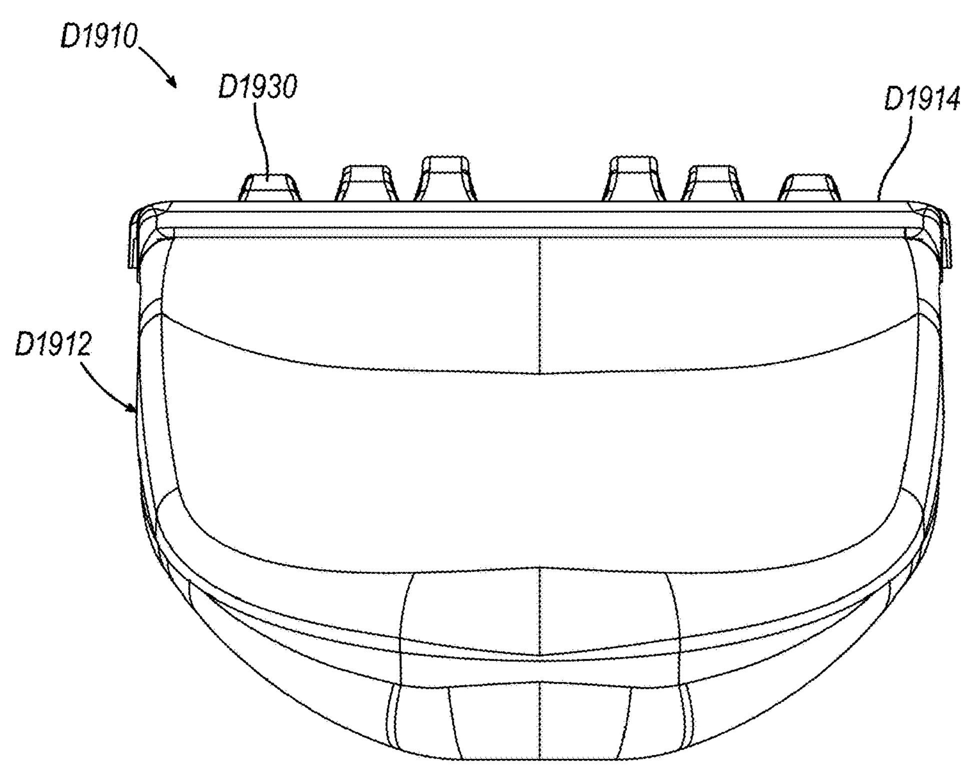
FIG. 106 depicts a front elevational view of another example of a staple cartridge for use with the end effector of FIG. 2 and having a flat deck surface and stepped pocket extenders.

E. Example of Staple Cartridge with Flat Deck Surface and Stepped Pocket Extenders FIG. 106 shows another example of a staple cartridge (D1910) configured to deploy staples (86) toward corresponding staple forming pockets of an anvil (not shown), such as staple forming pockets (66) of anvil (44). Staple cartridge (D1910) is configured for use with end effector (40), and is similar to staple cartridge (70) described above except as otherwise described below. In this regard, staple cartridge (D1910) of the present example includes a cartridge body (D1912) having an upwardly facing, flat deck (D1914), and a plurality of cartridge pockets (not shown) extending through deck (D1914) on each side of a knife slot (not shown). Staple cartridge (D1910) of the present example further includes a plurality of raised features in the form of pocket extenders (D1930) that extend upwardly from deck (D1914) at or near proximal and distal ends of each cartridge pocket. In the example shown, the top surfaces of pocket extenders (D1930) are generally flat, and are generally arranged in a stepped configuration. More particularly, the top surfaces of the pocket extenders (D1930) corresponding to an inner row of cartridge pockets are at a first height above deck (D1914), the top surfaces of the pocket extenders (D1930) corresponding to an middle row of cartridge pockets are at a second height above deck (D1914) less than the first height, and the top surfaces of the pocket extenders (D1930) corresponding to an outer row of cartridge pockets are at a third height above deck (D1914) less than the second height.

F. Example of Staple Cartridge with Stepped Deck and Stepped Pocket Extenders

Figure 107:
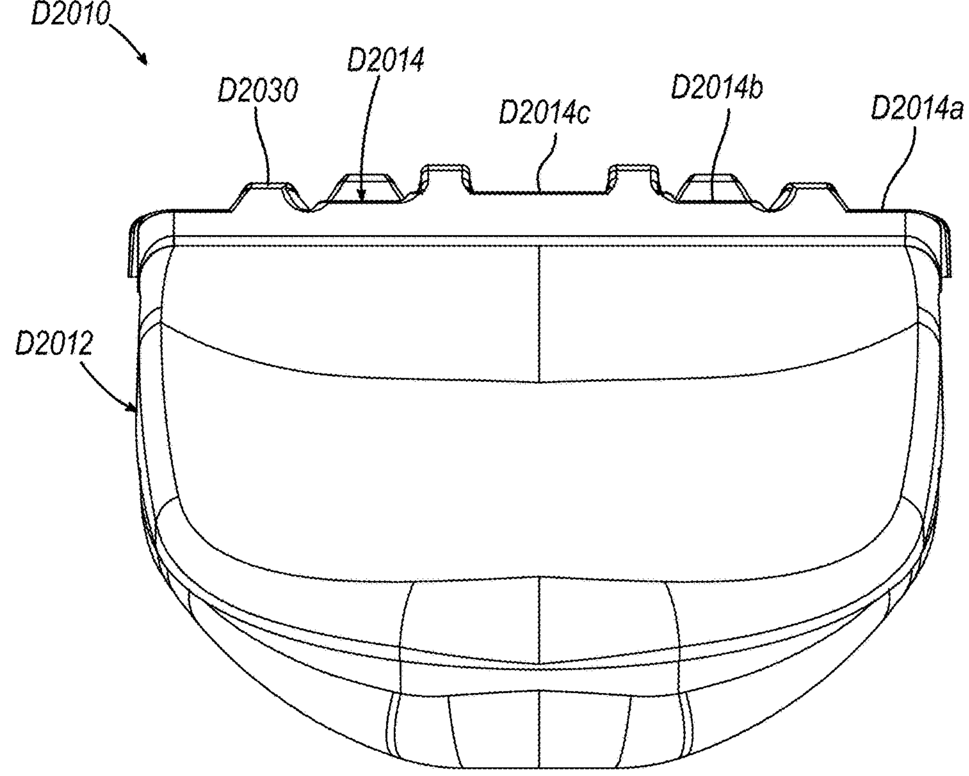
FIG. 107 depicts a front elevational view of another example of a staple cartridge for use with the end effector of FIG. 2 and having a stepped deck surface and stepped pocket extenders.

FIG. 107 shows another example of a staple cartridge (D2010) configured to deploy staples (86) toward corresponding staple forming pockets of an anvil (not shown), such as staple forming pockets (66) of anvil (44). Staple cartridge (D2010) is configured for use with end effector (40), and is similar to staple cartridge (70) described above except as otherwise described below. In this regard, staple cartridge (D2010) of the present example includes a cartridge body (D2012) having an upwardly facing, stepped deck (D2014), and a plurality of cartridge pockets (not shown) extending through deck (D2014) on each side of a knife slot (not shown).

Stepped deck (D2014) of the present example includes a lower deck surface (D2014*a*) spanning across the outer rows of cartridge pockets on each lateral side of the knife slot, an intermediate deck surface (D2014*b*) spanning across the middle rows of cartridge pockets on each lateral side of the knife slot, and an upper deck surface (D2014*c*) spanning across the inner rows of cartridge pockets on each lateral side of the knife slot.

Staple cartridge (D2010) of the present example further includes a plurality of raised features in the form of pocket extenders (D2030) that extend upwardly from deck (D2014) at or near proximal and distal ends of each cartridge pocket. In the example shown, the top surfaces of pocket extenders (D2030) are generally flat, and are generally arranged in a stepped configuration. More particularly, the top surfaces of the pocket extenders (D2030) corresponding to the inner rows of cartridge pockets are at a first height above a reference surface of deck (D2014) (e.g., lower deck surface (D2014*a*), the top surfaces of the pocket extenders (D2030) corresponding to the middle rows of cartridge pockets are at a second height above deck (D2014) less than the first height, and the top surfaces of the pocket extenders (D2030) corresponding to the outer rows of cartridge pockets are at a third height above deck (D2014) less than the second height.

G. Example of Staple Cartridge with Flat Deck and Outer Reliefs

Figure 108:
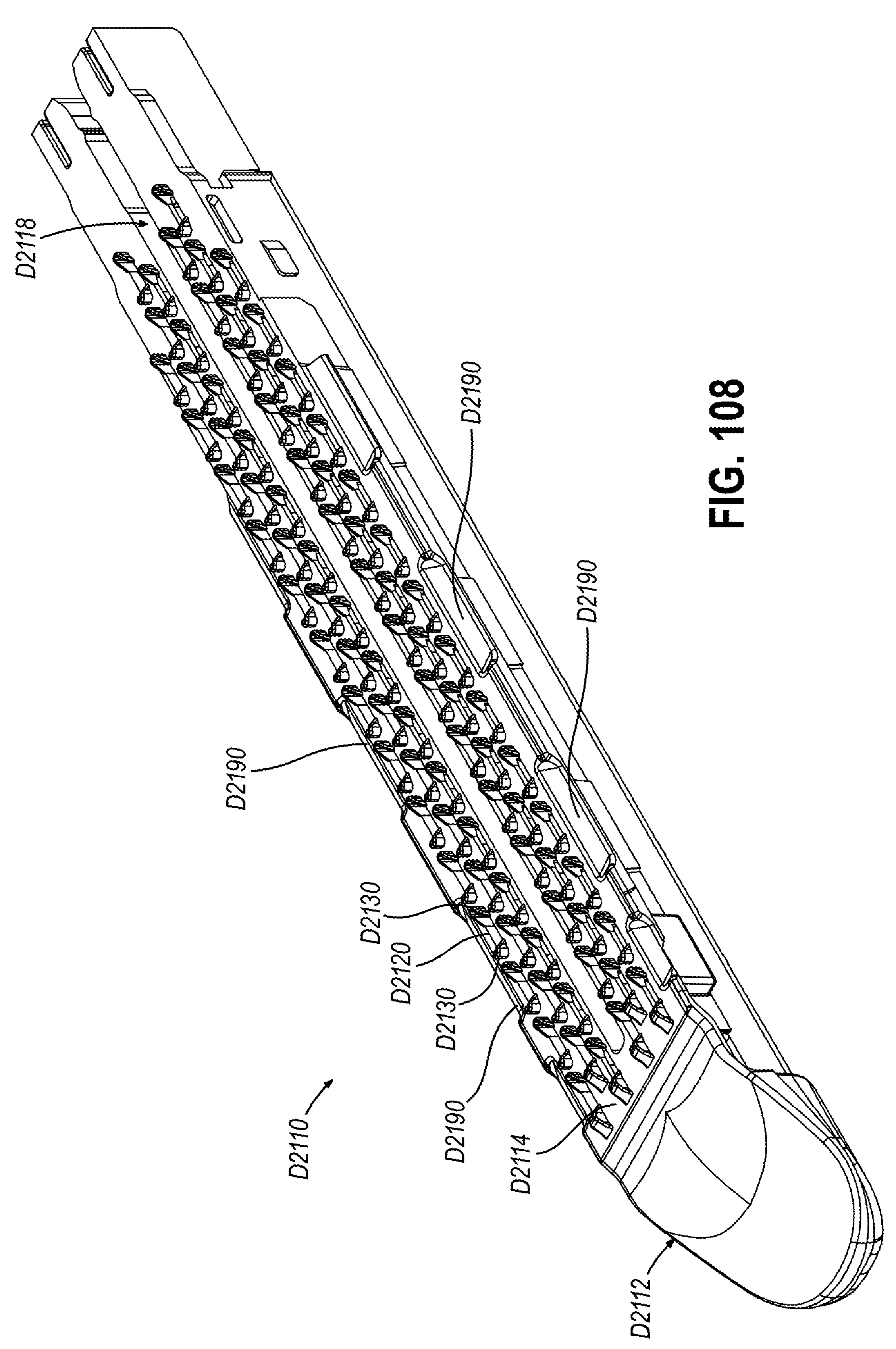
FIG. 108 depicts a front elevational view of another example of a staple cartridge for use with the end effector of FIG. 2 and having a flat deck and laterally outer reliefs.

FIG. 108 shows another example of a staple cartridge (D2110) configured to deploy staples (86) toward corresponding staple forming pockets of an anvil (not shown), such as staple forming pockets (66) of anvil (44). Staple cartridge (D2110) is configured for use with end effector (40), and is similar to staple cartridge (70) described above except as otherwise described below. In this regard, staple cartridge (D2110) of the present example includes a cartridge body (D2012) having an upwardly facing deck (D2114), and a plurality of cartridge pockets (D2120) extending through deck (D2114) on each side of a knife slot (D2118). Staple cartridge (D2110) of the present example further includes a plurality of raised features in the form of pocket extenders (D2130) that extend upwardly from deck (D2114) at or near proximal and distal ends of each cartridge pocket (D2120).

In the example shown, staple cartridge (D2110) also includes a plurality of reliefs (D2190) positioned along the laterally outer edges of deck (D2114), whereat tissue (T1, T2) may drape staple cartridge (D2110). In this regard, reliefs (D2190) may inhibit longitudinal movement (e.g., "flow") of the tissue (T1, T2) being severed and stapled.

In some versions, any one or more of the configurations shown in FIGS. 104-108 may be combined with each other.

It will be understood that while the features shown and described above are presented in the context of staple cartridges (D210, D310, D410, D510, D610, D710, D810, D910, D1010, D1110, D1210, D1310, D1410, D1510, D1610, D1710, D1810, D1910, D2010, D2110) for surgical stapler (10), such features may also be applied to staple cartridges configured for use with various other types of surgical staplers, such as linear surgical staplers.

X. Examples of Cartridge Pans Having Retention Tabs and Relief Slots

In some instances, it may be desirable to provide lower pan (76) of staple cartridge (70) with one or more retention tabs for frictionally engaging a channel of cartridge jaw (42) to resist dislodgment of staple cartridge (70) from the channel in the absence of a threshold amount of force applied between the staple cartridge (70) and the channel, at least when sled (82) is proximal of the distal fired position, such as when sled (82) is in the proximal unfired position (also referred to as the "cartridge retention force"); while avoiding undesirable increases in the threshold amount of force required to install staple cartridge (70) into the channel (also referred to as the "cartridge installation force") and/or in the threshold amount of force required to remove staple cartridge (70) from the channel when sled (82) is in the distal fired position (also referred to as the "cartridge removal force"). Each of the examples of lower pans (E110, E210, E310, E410, E510, E610, E710, E810, E910, E1010, E1110) described below provides such functionality.

A. Example of Cartridge Pan with Retention Tab Longitudinally Flanked by T-Shaped Relief Slots FIGS. 109-110 show a portion of another example of a lower pan (E110) that may be readily incorporated into staple cartridge (70) in place of lower pan (76). Lower pan (E110) may be similar to lower pan (76) described above, except as otherwise described below. In this regard, lower pan (E110) may be configured to be coupled to an underside of cartridge body (72) such that sled (82) and staple drivers (84) may be movably captured between cartridge body (72) and pan (E110). Pan (E110) of the present example includes a laterally-opposed pair of sidewalls (E112) (one shown) coupled to each other by a bottom wall (E114), such that sidewalls (E112) and bottom wall (E114) collectively define a trough (E116) that is sized and configured to securely receive a cartridge body (not shown), such as cartridge body (72). Each sidewall (E112) has a respective laterally inner side surface (E118), which may confront and/or frictionally engage a respective laterally outer side surface of cartridge body (72); and a respective laterally outer side surface (E120), which may confront and/or frictionally engage a respective laterally inner side surface (E102) of a channel (E100) of a cartridge jaw (not shown), such as cartridge jaw (42). Pan (E110) also includes a laterally-opposed pair of distal retention arms (E122) (one shown) extending upwardly and laterally inwardly toward each other from upper ends of respective sidewalls (E112) for capturing cartridge body (72) within trough (E116). While pan (E110) is shown and described for incorporation into cartridge (70) and as being used in conjunction with channel (E100), it will be appreciated that pan (E110) may be incorporated into any other suitable cartridge and/or may be used in conjunction with any other suitable channel.

In the example shown, pan (E110) also includes a retention tab (also referred to as a "protrusion" or "bump") (E130) extending laterally outwardly from each sidewall (E112) for frictionally engaging a respective laterally inner side surface (E102) of channel (E100) to removably secure staple cartridge (70) within channel (E100) (e.g., with pan (E110) incorporated into staple cartridge (70) in place of pan (76)). Each retention tab (E130) may be disposed at a relatively distal location along a length of pan (E110). For example, each retention tab (E130) may be at a substantially same position in the longitudinal direction as sled (82) when sled (82) is in the distal fired position. Each retention tab (E130) extends longitudinally between respective proximal and distal ends (E132, E134), and includes an upper, laterally inner surface (E140) extending downwardly and laterally outwardly from an upper region of the laterally inner side surface (E118) of the respective sidewall (E112); a middle, laterally inner surface (E142) extending vertically downwardly from the respective upper, laterally inner surface (E140); and a lower, laterally inner surface (E144) extending downwardly and laterally inwardly from the respective middle, laterally inner surface (E142) to a lower region of the laterally inner side surface (E118) of the respective sidewall (E112).

As shown in FIG. 110, the upper, middle, and lower laterally inner surfaces (E140, E142, E144) of each retention tab (E130) collectively define a recess (E146) that extends laterally outwardly relative to the laterally inner side surface (E118) of the respective sidewall (E112), and likewise relative to trough (E116), for permitting laterally-inward flexing of the respective retention tab (E130) into the respective recess (E146). In the example shown, each recess (E146) is open-ended. More particularly, each recess (E146) is open at the proximal and distal ends (E132, E134) of the respective retention tab (E130), by opening through the respective sidewall (E112) and/or through the respective retention tab (E130) at each of the proximal and distal ends (E132, E134) of the respective retention tab (E130).

Each retention tab (E130) also includes an upper, laterally outer surface (also referred to as an "upper ramp surface") (E150) extending downwardly and laterally outwardly from an upper region of the laterally outer side surface (E120) of the respective sidewall (E112), such that each upper, laterally outer surface (E150) is oriented obliquely (e.g., obtusely) at a first angle ($\alpha$1) relative to the laterally outer side surface (E120) of the respective sidewall (E112) and has a first length (L1) in a plane substantially orthogonal to the longitudinal direction; a middle, laterally outer surface (also referred to as an "engagement surface") (E152) extending vertically downwardly from the respective upper, laterally outer surface (E150), such that each middle, laterally outer surface (E152) is oriented substantially parallel relative to the laterally outer side surface (E120) of the respective sidewall (E112) and has a second length (L2) in the plane substantially orthogonal to the longitudinal direction; and a lower, laterally outer surface (also referred to as a "lower ramp surface") (E154) extending downwardly and laterally inwardly from the respective middle, laterally outer surface (E152) to a lower region of the laterally outer side surface (E120) of the respective sidewall (E112), such that each lower, laterally outer surface (E154) is oriented obliquely (e.g., obtusely) at a second angle ($\alpha$2) relative to the laterally outer side surface (E120) of the respective sidewall (E112) and has a third length (L3) in the plane substantially orthogonal to the longitudinal direction.

Each retention tab (E130) has a length (L) in the longitudinal direction defined between the respective proximal and distal ends (E132, E134) selected to provide a desired cartridge removal force and/or a desired cartridge installation force. For example, a greater length (L) of each retention tab (E130) may increase the removal and/or installation force(s), while a lesser length (L) of each retention tab (E130) may decrease the removal and/or installation force(s). Each retention tab (E130) also has a height (H1) in the vertical direction defined between the interface of the respective lower, laterally inner surface (E144) with the laterally inner side surface (E118) of the respective sidewall (E112), and the interface of the respective upper, laterally inner surface (E140) with the laterally inner side surface (E118) of the respective sidewall (E112). In some versions, the height (H1) of each retention tab (E130) may be selected to provide a desired cartridge removal force and/or a desired cartridge installation force. For example, a greater height (H1) of each retention tab (E130) may decrease the removal and/or installation force(s), while a lesser height (H1) of each retention tab (E130) may increase the removal and/or installation force(s). Each retention tab (E130) further has a width (W) in the lateral direction defined between the laterally outer side surface (E120) of the respective sidewall (E112) and the respective middle, laterally outer surface (E152). In some versions, the width (W) of each retention tab (E130) may be selected to provide a desired cartridge removal force and/or a desired cartridge installation force. For example, a greater width (W) of each retention tab (E130) may increase the removal and/or installation force(s), while a lesser width (W) of each retention tab (E130) may decrease the removal and/or installation force (s).

As shown, each retention tab (E130) may have a substantially uniform material thickness, and/or may have a substantially same material thickness as that of the respective sidewall (E112). For example, the material thickness defined between the respective upper, laterally inner and outer surfaces (E140, E150) may be substantially equal to each of the material thickness defined between the respective middle, laterally inner and outer surfaces (E142, E152) and the material thickness defined between the respective lower, laterally inner and outer surfaces (E144, E154), and/or may be substantially equal to the material thickness defined between the respective laterally inner and outer side surfaces (E118, 120) of the respective sidewall (E112).

In the example shown, each middle, laterally outer surface (E152) is substantially flat (e.g., planar) and is configured to be oriented substantially parallel to the respective laterally inner side surface (E102) of channel (E100) (e.g., at least when staple cartridge (70) is removably received within channel (E100)) and to frictionally engage the respective laterally inner side surface (E102) of channel (E100). In some versions, each middle, laterally outer surface (E152) may be curved in a convex manner. In addition, or alternatively, each retention tab (E130) may include one or more laterally-outwardly extending ridges and/or laterally-inwardly extending indentations provided along the respective middle, laterally outer surface (E152). It will be appreciated that such features may alter the surface area of the respective middle, laterally outer surface (E152) to adjust the cartridge retention and/or removal force(s) relative to that provided by the example shown. For example, the surface area of the respective middle, laterally outer surface (E152) may be decreased to decrease the retention and/or removal force(s), or may be increased to increase the retention and/or removal force(s). In some versions, the second length (L2) of each middle, laterally outer surface (E152) may be selected to provide a desired cartridge removal force and/or a desired cartridge installation force. For example, a greater second length (L2) of each middle, laterally outer surface (E152) may increase the removal and/or installation force(s), while a lesser second length (L2) of each middle, laterally outer surface (E152) may decrease the removal and/or installation force(s).

First and second angles ($\alpha$1, $\alpha$2) may each be selected based on one or more features of channel (E100). In this regard, channel (E100) shown in FIG. 110 includes a laterally-opposed pair of detents (E104) (one shown) extending laterally inwardly from respective laterally inner side surfaces (E102) of channel (E100) and configured to be directly above respective retention tabs (E130) when staple cartridge (70) removably received within channel (E100) to assist with inhibiting inadvertent dislodgment of staple cartridge (70) from channel (E100). Each detent (E104) includes an upper surface (E106) extending downwardly and laterally inwardly from the respective laterally inner side surface (E102) of channel, such that each upper surface (E106) is oriented obliquely (e.g., obtusely) at a third angle ($\alpha$3) relative to the respective laterally inner side surface (E102) of channel (E100); and a lower surface (E108) extending upwardly and laterally inwardly from the respective laterally inner side surface (E102) of channel toward the respective upper surface (E106), such that each lower surface (E108) is oriented obliquely (e.g., obtusely) at a fourth angle ($\alpha$4) relative to the respective laterally inner side surface (E102) of channel (E100).

In the example shown, first angle ($\alpha$1) is substantially equal to fourth angle ($\alpha$4) such that the upper, laterally outer surface (E150) of each retention tab (E130) is substantially parallel to the lower surface (E108) of the corresponding detent (E104) (e.g., at least when staple cartridge (70) is removably received within channel (E100)) to directly confront the lower surface (E108) of the corresponding detent (E104) when staple cartridge (70) is removably received within channel (E100) and thereby assist with inhibiting inadvertent dislodgment of staple cartridge (70) from channel (E100), and/or to promote a camming interaction between the upper, laterally outer surface (E150) of each retention tab (E130) and the lower surface (E108) of the corresponding detent (E104) for urging each retention tab (E130) laterally inwardly into the respective recess (E146) during removal of staple cartridge (70) from channel (E100). It will be appreciated that first angle (α1) may alternatively be substantially different from fourth angle (α4) to adjust the cartridge retention and/or removal force(s) relative to that provided by the example shown. For example, first angle (α1) may be substantially greater than fourth angle (α4) to decrease the retention and/or removal force(s), or may be substantially less than fourth angle (α4) to increase the retention and/or removal force(s). In addition, or alternatively, a greater first angle (α1) of each upper, laterally outer surface (E150) may decrease the retention and/or removal force(s), while a lesser first angle (α1) of each upper, laterally outer surface (E150) may increase the retention and/or removal force(s). In some versions, the first length (L1) of each upper, laterally outer surface (E150) may be selected to provide a desired cartridge retention force and/or a desired cartridge removal force. For example, a greater first length (L1) of each upper, laterally outer surface (E150) may increase the retention and/or removal force(s), while a lesser first length (L1) of each upper, laterally outer surface (E150) may decrease the retention and/or removal force(s).

In the example shown, second angle (α2) is substantially equal to third angle (α3) such that the lower, laterally outer surface (E154) of each retention tab (E130) is substantially parallel to the upper surface (E106) of the corresponding detent (E104) (e.g., at least when staple cartridge (70) is removably received within channel (E100)) to promote a camming interaction between the lower, laterally outer surface (E154) of each retention tab (E130) and the upper surface (E106) of the corresponding detent (E104) for urging each retention tab (E130) laterally inwardly into the respective recess (E146) during installation of staple cartridge (70) into channel (E100). It will be appreciated that second angle (α2) may alternatively be substantially different from third angle (α3) to adjust the installation force relative to that provided by the example shown. For example, second angle (α2) may be substantially greater than third angle (α3) to decrease the installation force, or may be substantially less than third angle (α3) to increase the installation force. In addition, or alternatively, a greater second angle (α2) of each lower, laterally outer surface (E154) may decrease the installation force, while a lesser second angle (α2) of each lower, laterally outer surface (E154) may increase the installation force. In some versions, the third length (L3) of each lower, laterally outer surface (E154) may be selected to provide a desired cartridge installation force. For example, a greater third length (L3) of each lower, laterally outer surface (E154) may increase the installation force, while a lesser third length (L3) of each lower, laterally outer surface (E154) may decrease the installation force.

It will be appreciated that first and second angles (α1, α2) may be substantially different from each other, such that upper and lower laterally outer surfaces (E150, E154) may have substantially different heights from each other. For example, first angle (α1) may be substantially greater than second angle (α2), such that upper laterally outer surfaces (E150) may each be substantially taller than the corresponding lower laterally outer surface (E154). While upper and lower laterally outer surfaces (E150, E154) of the present example are each substantially flat (e.g., planar), any one or more of upper or lower laterally outer surfaces (E150, E154) may alternatively be curved. For example, each upper, laterally outer surface (E150) may be defined by a first radius, and each lower, laterally outer surface (E154) may be defined by a second radius substantially different from (e.g., greater than) the first radius.

In the example shown, pan (E110) also includes a pair of relief slots (also referred to as "cutouts") (E160*a*, E160*b*) extending laterally through each sidewall (E112) from the inner side surface (E118) thereof to the laterally outer side surface (E120) thereof. Each relief slot (E160*a*, E160*b*) is positioned adjacent to a corresponding retention tab (E130) to impart the corresponding retention tab (E130) with a reduced stiffness and/or increased resilience. In this regard, each pair of relief slots (E160*a*, E160*b*) includes a proximal relief slot (E160*a*) positioned adjacent to the proximal end (E132) of the corresponding retention tab (E130), and a distal relief slot (E160*b*) positioned adjacent to the distal end (E134) of the corresponding retention tab (E130), such that each retention tab (E130) is longitudinally flanked by a corresponding pair of relief slots (E160*a*, E160*b*). Each relief slot (E160*a*, E160*b*) includes a respective vertical slot portion (E162*a*, E162*b*) extending along the respective end (E132, E134) of the corresponding retention tab (E130), and a respective horizontal slot portion (E164*a*, E164*b*) extending longitudinally from a middle region of the respective vertical slot portion (E162*a*, E162*b*), such that each relief slot (E160*a*, E160*b*) is substantially T-shaped. More particularly, the vertical slot portion (E162*a*) of each proximal relief slot (E160*a*) extends along the proximal end (E132) of the corresponding retention tab (E130), and the horizontal slot portion (E164*a*) of each proximal relief slot (E160*a*) extends proximally from the middle region of the respective vertical slot portion (E162*a*). Similarly, the vertical slot portion (E162*b*) of each distal relief slot (E160*b*) extends along the distal end (E134) of the corresponding retention tab (E130), and the horizontal slot portion (E164*b*) of each distal relief slot (E160*b*) extends distally from the middle region of the respective vertical slot portion (E162*b*). Due to each recess (E146) being open-ended as described above, vertical slot portions (E162*a*, E162*b*) of proximal and distal relief slots (E160*a*, E160*b*) may open directly into recess (E146).

By imparting the corresponding retention tab (E130) with a reduced stiffness and/or increased resilience, relief slots (E160*a*, E160*b*) may promote flexing of the corresponding retention tab (E130) laterally inwardly into the respective recess (E146), such as during installation of staple cartridge (70) into channel (E100) and/or during removal of staple cartridge (70) from channel (E100). For example, relief slots (E160*a*, E160*b*) may assist with allowing the corresponding retention tab (E130) to flex laterally inwardly into the respective recess (E146) via the camming interaction between the lower, laterally outer surface (E154) of each retention tab (E130) and the upper surface (E106) of the corresponding detent (E104) during installation of staple cartridge (70) into channel (E100), and/or may cause the corresponding retention tab (E130) to resiliently flex laterally outwardly from the respective recess (E146) in response to the corresponding retention tab (E130) disengaging the corresponding detent (e.g., when the corresponding retention tab (E130) reaches a position substantially below the corresponding detent (E104)). In addition, or alternatively, relief slots (E160*a*, E160*b*) may assist with allowing the corresponding retention tab (E130) to flex laterally inwardly into the respective recess (E146) via the camming interaction between the upper, laterally outer surface (E150) of each retention tab (E130) and the lower surface (E108) of the corresponding detent (E104) during removal of staple cartridge (70) from channel (E100), and/or may cause the corresponding retention tab (E130) to resiliently flex laterally outwardly from the respective recess (E146) in response to the corresponding retention tab (E130) disengaging the corresponding detent (E104) (e.g., when the corresponding retention tab (E130) reaches a position substantially above the corresponding detent (E104)). In other words, relief slots (E160*a*, E160*b*) may enhance the spring-like characteristics of the corresponding retention tabs (E130).

While each relief slot (E160*a*, E160*b*) of the present example is substantially T-shaped, it will be appreciated that each relief slot (E160*a*, E160*b*) may have any other suitable shape and/or size, such as any of those described elsewhere herein, and that such variations in shape and/or size may adjust the cartridge installation and/or removal force(s) relative to that provided by the example shown. For example, the size of each relief slot (E160*a*, E160*b*) may be increased to decrease the installation and/or removal force(s), or may be decreased to increase the installation and/or removal force(s). In some versions, each proximal relief slot (E160*a*) may be sized and/or shaped substantially differently from the respective distal relief slot (E160*b*) such that each pair of relief slots (E160*a*, E160*b*) may be asymmetrical relative to the respective retention tab (E130). In some other versions, either each proximal or distal relief slot (E160*a*, E160*b*) may be omitted.

In some versions, relief slots (E160*a*, E160*b*) may also improve manufacturability of pan (E110), such as by providing improved forming control of the ends (E132, E134) and/or surfaces (E140, E142, E144, E150, E152, E154) of the corresponding retention tab (E130). In this manner, the inclusion of relief slots (E160*a*, E160*b*) may reduce part-to-part variations when manufacturing multiple pans (E110).

While retention tabs (E130) and relief slots (E160*a*, E160*b*) may be arranged on sidewalls (E112) in laterally-opposed pairs with each laterally-opposed pair of retention tabs (E130) and each laterally-opposed pair of relief slots (E160*a*, E160*b*) being symmetrical relative to a longitudinal axis of pan (E110), retention tabs (E130) and/or relief slots (E160*a*, E160*b*) may alternatively be configured substantially differently on each sidewall (E112) of pan (E110) so as to be asymmetrical relative to the longitudinal axis of pan (E110). For example, the retention tab (E130) and relief slots (E160*a*, E160*b*) on one sidewall (E112) may be offset in the vertical direction and/or offset in the longitudinal direction from the retention tab (E130) and relief slots (E160*a*, E160*b*) on the other sidewall (E112). In addition, or alternatively, the retention tab (E130) and relief slots (E160*a*, E160*b*) on one sidewall (E112) may be sized and/or shaped substantially differently from the retention tab (E130) and relief slots (E160*a*, E160*b*) on the other sidewall (E112), such as by being sized and/or shaped in accordance with any of the other teachings provided herein.

B. Example of Cartridge Pan with Pair of Retention Tabs Spaced Apart by Elongate Relief Slot and Longitudinally Flanked by T-Shaped Relief Slots FIG. 111 shows a portion of another example of a lower pan (E210) that may be readily incorporated into staple cartridge (70) in place of lower pan (76). Lower pan (E210) may be similar to lower pan (E110) described above, except as otherwise described below. In this regard, lower pan (E210) may be configured to be coupled to an underside of cartridge body (72) such that sled (82) and staple drivers (84) may be movably captured between cartridge body (72) and pan (E210). Pan (E210) of the present example includes a laterally-opposed pair of sidewalls (E212) (one shown) coupled to each other by a bottom wall (E214), such that sidewalls (E212) and bottom wall (E214) collectively define a trough (not shown) similar to trough (E116) that is sized and configured to securely receive a cartridge body (not shown), such as cartridge body (72). Each sidewall (E212) has a respective laterally inner side surface (not shown) similar to laterally inner side surfaces (E118), which may confront and/or frictionally engage a respective laterally outer side surface of cartridge body (72); and a respective laterally outer side surface (E220), which may confront and/or frictionally engage a respective laterally inner side surface (E102) of a channel (E100) of a cartridge jaw (not shown), such as cartridge jaw (42). Pan (E210) also includes a laterally-opposed pair of distal retention arms (E222) (one shown) extending upwardly and laterally inwardly toward each other from upper ends of respective sidewalls (E212) for capturing cartridge body (72) within the trough. While pan (E210) is shown and described for incorporation into cartridge (70) and as being used in conjunction with channel (E100), it will be appreciated that pan (E210) may be incorporated into any other suitable cartridge and/or may be used in conjunction with any other suitable channel.

In the example shown, pan (E210) also includes a pair of retention tabs (E230*a*, E230*b*) extending laterally outwardly from each sidewall (E212). In this regard, each pair of retention tabs (E230*a*, E230*b*) includes a proximal retention tab (E230*a*) and a distal retention tab (E230*b*). Each retention tab (E230*a*, E230*b*) extends longitudinally between a respective proximal end (E232*a*, E232*b*) and a respective distal end (E234*a*, E234*b*), and includes laterally inner surfaces that collectively define a respective open-ended recess (not shown) similar to recess (E146) for permitting laterally-inward flexing of the respective retention tab (E230*a*, E230*b*) into the respective recess. Each retention tab (E230*a*, E230*b*) also includes an upper, laterally outer surface (E250*a*, E250*b*) extending downwardly and laterally outwardly from an upper region of the laterally outer side surface (E220) of the respective sidewall (E212), a middle, laterally outer surface (E252*a*, E252*b*) extending vertically downwardly from the respective upper, laterally outer surface (E250*a*, E250*b*), and a lower, laterally outer surface (E254*a*, E254*b*) extending downwardly and laterally inwardly from the respective middle, laterally outer surface (E252*a*, E252*b*) to a lower region of the laterally outer side surface (E220) of the respective sidewall (E212).

While each proximal retention tab (E230*a*) is shown as having a substantially same length as the respective distal retention tab (E230*b*), the length of each proximal retention tab (E230*a*) may alternatively be substantially different from that of the respective distal retention tab (E230*b*), such as to provide a desired cartridge removal force and/or a desired cartridge installation force.

In the example shown, pan (E210) also includes a plurality of relief slots (E260*a*, E260*b*, E260*c*) extending laterally through each sidewall (E212) from the inner side surface thereof to the laterally outer side surface (E220) thereof. Each relief slot (E260*a*, E260*b*, E260*c*) is positioned adjacent to at least one corresponding retention tab (E230*a*, E230*b*) to impart the corresponding retention tab(s) (E230*a*, E230*b*) with a reduced stiffness and/or increased resilience. In this regard, each plurality of relief slots (E260*a*, E260*b*, E260*c*) includes a proximal relief slot (E260*a*) positioned adjacent to the proximal end (E232*a*) of the proximal retention tab (E230*a*), and a distal relief slot (E260*b*) positioned adjacent to the distal end (E234*b*) of the distal retention tab (E230*b*), such that each pair of retention tabs (E230*a*, E230*b*) is longitudinally flanked by a corresponding pair of proximal and distal relief slots (E260*a*, E260*b*); and further includes an intermediate relief slot (E260*c*) positioned adjacent to and/or extending along both the distal end (E234*a*) of the proximal retention tab (E230*a*) and the proximal end (E232*b*) of the distal retention tab (E230*b*), such that each pair of retention tabs (E230*a*, E230*b*) is spaced apart from each other by the corresponding intermediate relief slot (E260*c*). Each proximal and distal relief slot (E260*a*, E260*b*) includes a respective vertical slot portion (E262*a*, E262*b*) extending along the respective end (E232*a*, E234*b*) of the corresponding retention tab (E230*a*, E230*b*), and a respective horizontal slot portion (E264*a*, E264*b*) extending longitudinally from a middle region of the respective vertical slot portion (E262*a*, E162*b*), such that each proximal and distal relief slot (E260*a*, E260*b*) is substantially T-shaped; while each intermediate relief slot (E260*c*) is substantially elongate (e.g., linear, rectangular, rectangular with rounded corners, obround, etc.). Due to the recess of each retention tab (E230*a*, E230*b*) being open-ended as described above, vertical slot portions (E262*a*, E262*b*) of proximal and distal relief slots (E260*a*, E260*b*) may each open directly into the respective recess, and each intermediate relief slot (E260*c*) may likewise open directly into both respective recesses.

As with proximal and distal relief slots (E260*a*, E260*b*), it will be appreciated that each intermediate relief slot (E260*c*) may have any other suitable shape and/or size than that shown, such as any of those described elsewhere herein, and that such variations in shape and/or size may adjust the cartridge installation and/or removal force(s) relative to that provided by the example shown.

By having multiple retention tabs (E230*a*, E230*b*) along each sidewall (E212), pan (E210) may be particularly suitable for use with a channel (E100) having a laterally inner side surface (E102) that is non-uniform along a length of the channel (E100), such as a channel (E100) having a laterally inner side surface that tapers, steps, and/or curves along the length of the channel (E100). For example, each retention tab (E230*a*, E230*b*) may be configured to frictionally engage a corresponding portion of the laterally inner side surface (E102) even in cases where such portions of the laterally inner side surface (E102) are non-uniformly spaced apart from laterally outer side surface (E220) when cartridge (70) is removably installed into the channel (E100).

In some versions, retention tabs (E230*a*, E230*b*) and relief slots (E260*a*, E260*b*, E260*c*) may be arranged on sidewalls (E212) in laterally-opposed pairs with each laterally-opposed pair of retention tabs (E230*a*, E230*b*) and each laterally-opposed pair of relief slots (E260*a*, E260*b*, E260*c*) being symmetrical relative to a longitudinal axis of pan (E210). In other versions, retention tabs (E230*a*, E230*b*) and/or relief slots (E260*a*, E260*b*, E260*c*) may alternatively be configured substantially differently on each sidewall (E212) of pan (E210) so as to be asymmetrical relative to the longitudinal axis of pan (E210). For example, the retention tab (E230*a*, E230*b*) and relief slots (E260*a*, E260*b*, E260*c*) on one sidewall (E212) may be offset in the vertical direction and/or offset in the longitudinal direction from the retention tab (E230*a*, E230*b*) and relief slots (E260*a*, E260*b*, E260*c*) on the other sidewall (E212). In addition, or alternatively, the retention tab (E230*a*, E230*b*) and relief slots (E260*a*, E260*b*, E260*c*) on one sidewall (E212) may be sized and/or shaped substantially differently from the retention tab (E230*a*, E230*b*) and relief slots (E260*a*, E260*b*, E260*c*) on the other sidewall (E212), such as by being sized and/or shaped in accordance with any of the other teachings provided herein.

C. Example of Cartridge Pan with Retention Tab Longitudinally Flanked by Elongate Relief Slots FIG. 112 shows a portion of another example of a lower pan (E310) that may be readily incorporated into staple cartridge (70) in place of lower pan (76). Lower pan (E310) may be similar to lower pan (E110) described above, except as otherwise described below. In this regard, lower pan (E310) may be configured to be coupled to an underside of cartridge body (72) such that sled (82) and staple drivers (84) may be movably captured between cartridge body (72) and pan (E310). Pan (E310) of the present example includes a laterally-opposed pair of sidewalls (E312) (one shown) coupled to each other by a bottom wall (E314), such that sidewalls (E312) and bottom wall (E314) collectively define a trough (not shown) similar to trough (E116) that is sized and configured to securely receive a cartridge body (not shown), such as cartridge body (72). Each sidewall (E312) has a respective laterally inner side surface (not shown) similar to laterally inner side surfaces (E118), which may confront and/or frictionally engage a respective laterally outer side surface of cartridge body (72); and a respective laterally outer side surface (E320), which may confront and/or frictionally engage a respective laterally inner side surface (E102) of a channel (E100) of a cartridge jaw (not shown), such as cartridge jaw (42). While pan (E310) is shown and described for incorporation into cartridge (70) and as being used in conjunction with channel (E100), it will be appreciated that pan (E310) may be incorporated into any other suitable cartridge and/or may be used in conjunction with any other suitable channel.

In the example shown, pan (E310) also includes a retention tab (E330) extending laterally outwardly from each sidewall (E312). Each retention tab (E330) extends longitudinally between a respective proximal end (E332) and a respective distal end (E334), and includes laterally inner surfaces that collectively define a respective open-ended recess (not shown) similar to recess (E146) for permitting laterally-inward flexing of the respective retention tab (E330) into the respective recess. Each retention tab (E330) also includes an upper, laterally outer surface (E350) extending downwardly and laterally outwardly from an upper region of the laterally outer side surface (E320) of the respective sidewall (E312), a middle, laterally outer surface (E352) extending vertically downwardly from the respective upper, laterally outer surface (E350), and a lower, laterally outer surface (E354) extending downwardly and laterally inwardly from the respective middle, laterally outer surface (E352) to a lower region of the laterally outer side surface (E320) of the respective sidewall (E312).

In the example shown, pan (E310) also includes a pair of relief slots (E360*a*, E360*b*) extending laterally through each sidewall (E312) from the inner side surface thereof to the laterally outer side surface (E320) thereof. Each relief slot (E360*a*, E360*b*) is positioned adjacent to a corresponding retention tab (E330) to impart the corresponding retention tab (E330) with a reduced stiffness and/or increased resilience. In this regard, each pair of relief slots (E360*a*, E360*b*) includes a proximal relief slot (E360*a*) positioned adjacent to and/or extending along the proximal end (E332) of the corresponding retention tab (E330), and a distal relief slot (E360*b*) positioned adjacent to and/or extending along the distal end (E334) of the corresponding retention tab (E330), such that each retention tab (E330) is longitudinally flanked by a corresponding pair of relief slots (E360*a*, E360*b*). Each relief slot (E360*a*, E360*b*) is substantially elongate. Due to the recess of each retention tab (E330) being open-ended as described above, relief slots (E360*a*, E360*b*) may each open directly into the respective recess.

In some versions, retention tabs (E330) and relief slots (E360*a*, E360*b*) may be arranged on sidewalls (E312) in laterally-opposed pairs with each laterally-opposed pair of retention tabs (E330) and each laterally-opposed pair of relief slots (E360*a*, E360*b*) being symmetrical relative to a longitudinal axis of pan (E310). In other versions, retention tabs (E330) and/or relief slots (E360*a*, E360*b*) may alternatively be configured substantially differently on each sidewall (E312) of pan (E310) so as to be asymmetrical relative to the longitudinal axis of pan (E310). For example, the retention tab (E330) and relief slots (E360*a*, E360*b*) on one sidewall (E312) may be offset in the vertical direction and/or offset in the longitudinal direction from the retention tab (E330) and relief slots (E360*a*, E360*b*) on the other sidewall (E312). In addition, or alternatively, the retention tab (E330) and relief slots (E360*a*, E360*b*) on one sidewall (E312) may be sized and/or shaped substantially differently from the retention tab (E330) and relief slots (E360*a*, E360*b*) on the other sidewall (E312), such as by being sized and/or shaped in accordance with any of the other teachings provided herein.

D. Example of Cartridge Pan with Retention Tab Partially Surrounded by Proximal, Distal, and Upper Elongate Relief Slots FIG. 113 shows a portion of another example of a lower pan (E410) that may be readily incorporated into staple cartridge (70) in place of lower pan (76). Lower pan (E410) may be similar to lower pan (E110) described above, except as otherwise described below. In this regard, lower pan (E410) may be configured to be coupled to an underside of cartridge body (72) such that sled (82) and staple drivers (84) may be movably captured between cartridge body (72) and pan (E410). Pan (E410) of the present example includes a laterally-opposed pair of sidewalls (E412) (one shown) coupled to each other by a bottom wall (E414), such that sidewalls (E412) and bottom wall (E414) collectively define a trough (not shown) similar to trough (E116) that is sized and configured to securely receive a cartridge body (not shown), such as cartridge body (72). Each sidewall (E412) has a respective laterally inner side surface (not shown) similar to laterally inner side surfaces (E118), which may confront and/or frictionally engage a respective laterally outer side surface of cartridge body (72); and a respective laterally outer side surface (E420), which may confront and/or frictionally engage a respective laterally inner side surface (E102) of a channel (E100) of a cartridge jaw (not shown), such as cartridge jaw (42). While pan (E410) is shown and described for incorporation into cartridge (70) and as being used in conjunction with channel (E100), it will be appreciated that pan (E410) may be incorporated into any other suitable cartridge and/or may be used in conjunction with any other suitable channel.

In the example shown, pan (E410) also includes a retention tab (E430) extending laterally outwardly from each sidewall (E412). Each retention tab (E430) extends longitudinally between a respective proximal end (E432) and a respective distal end (E434), and includes laterally inner surfaces that collectively define a respective open-ended recess (not shown) similar to recess (E146) for permitting laterally-inward flexing of the respective retention tab (E430) into the respective recess. Each retention tab (E430) also includes an upper, laterally outer surface (E450) extending downwardly and laterally outwardly from an upper region of the laterally outer side surface (E420) of the respective sidewall (E412), a middle, laterally outer surface (E452) extending vertically downwardly from the respective upper, laterally outer surface (E450), and a lower, laterally outer surface (E454) extending downwardly and laterally inwardly from the respective middle, laterally outer surface (E452) to a lower region of the laterally outer side surface (E420) of the respective sidewall (E412).

In the example shown, pan (E410) also includes a plurality of relief slots (E460*a*, E460*b*, E460*c*) extending laterally through each sidewall (E412) from the inner side surface thereof to the laterally outer side surface (E420) thereof. Each relief slot (E460*a*, E460*b*, E460*c*) is positioned adjacent to a corresponding retention tab (E430) to impart the corresponding retention tab (E430) with a reduced stiffness and/or increased resilience. In this regard, each plurality of relief slots (E460*a*, E460*b*, E460*c*) includes a proximal relief slot (E460*a*) positioned adjacent to and/or extending along the proximal end (E432) of the corresponding retention tab (E430), and a distal relief slot (E460*b*) positioned adjacent to and/or extending along the distal end (E434) of the corresponding retention tab (E430), such that each retention tab (E430) is longitudinally flanked by a corresponding pair of proximal and distal relief slots (E460*a*, E460*b*); and further includes an upper intermediate relief slot (E460*c*) positioned adjacent to and/or extending at least partially along an upper edge of the corresponding retention tab (E430) (e.g., defined by an interface between the respective upper, laterally outer surface (E450) and the laterally outer side surface (E420) of the respective sidewall (E412)). Each relief slot (E460*a*, E460*b*, E460*c*) is substantially elongate. Due to the recess of each retention tab (E430) being open-ended as described above, proximal and distal relief slots (E460*a*, E460*b*) may each open directly into the respective recess.

As shown, each upper intermediate relief slot (E460*c*) is substantially centered in the longitudinal direction along the upper edge of the corresponding retention tab (E430) and extends along a middle portion thereof. In some other versions, each upper intermediate relief slot (E460*c*) may extend along only a proximal or distal portion of the upper edge of the corresponding retention tab (E430). In still other versions, each upper intermediate relief slot (E460*c*) may extend along the entire upper edge of the corresponding retention tab (E430). While intermediate relief slot (E460*c*) of the present example is positioned adjacent to and/or along an upper edge of the corresponding retention tab (E430), intermediate relief slot (E460*c*) may alternatively be positioned adjacent to and/or along a lower edge of the corresponding retention tab (E430) (e.g., defined by an interface between the respective lower, laterally outer surface (E454) and the laterally outer side surface (E420) of the respective sidewall (E412)).

In some versions, retention tabs (E430) and relief slots (E460*a*, E460*b*, E460*c*) may be arranged on sidewalls (E412) in laterally-opposed pairs with each laterally-opposed pair of retention tabs (E430) and each laterally-opposed pair of relief slots (E460*a*, E460*b*, E460*c*) being symmetrical relative to a longitudinal axis of pan (E410). In other versions, retention tabs (E430) and/or relief slots (E460*a*, E460*b*, E460*c*) may alternatively be configured substantially differently on each sidewall (E412) of pan (E410) so as to be asymmetrical relative to the longitudinal axis of pan (E410). For example, the retention tab (E430) and relief slots (E460*a*, E460*b*, E460*c*) on one sidewall (E412) may be offset in the vertical direction and/or offset in the longitudinal direction from the retention tab (E430) and relief slots (E460*a*, E460*b*, E460*c*) on the other sidewall (E412). In addition, or alternatively, the retention tab (E430) and relief slots (E460*a*, E460*b*, E460*c*) on one sidewall (E412) may be sized and/or shaped substantially differently from the retention tab (E430) and relief slots (E460*a*, E460*b*, E460*c*) on the other sidewall (E412), such as by being sized and/or shaped in accordance with any of the other teachings provided herein.

E. Example of Cartridge Pan with Elongate Relief Slot at One End of Retention Tab FIG. 114 shows a portion of another example of a lower pan (E510) that may be readily incorporated into staple cartridge (70) in place of lower pan (76). Lower pan (E510) may be similar to lower pan (E110) described above, except as otherwise described below. In this regard, lower pan (E510) may be configured to be coupled to an underside of cartridge body (72) such that sled (82) and staple drivers (84) may be movably captured between cartridge body (72) and pan (E510). Pan (E510) of the present example includes a laterally-opposed pair of sidewalls (E512) (one shown) coupled to each other by a bottom wall (E514), such that sidewalls (E512) and bottom wall (E514) collectively define a trough (not shown) similar to trough (E116) that is sized and configured to securely receive a cartridge body (not shown), such as cartridge body (72). Each sidewall (E512) has a respective laterally inner side surface (not shown) similar to laterally inner side surfaces (E118), which may confront and/or frictionally engage a respective laterally outer side surface of cartridge body (72); and a respective laterally outer side surface (E520), which may confront and/or frictionally engage a respective laterally inner side surface (E102) of a channel (E100) of a cartridge jaw (not shown), such as cartridge jaw (42). While pan (E510) is shown and described for incorporation into cartridge (70) and as being used in conjunction with channel (E100), it will be appreciated that pan (E510) may be incorporated into any other suitable cartridge and/or may be used in conjunction with any other suitable channel.

In the example shown, pan (E510) also includes a retention tab (E530) extending laterally outwardly from each sidewall (E512). Each retention tab (E530) extends longitudinally between a respective proximal end (E532) and a respective distal end (E534), and includes laterally inner surfaces that collectively define a respective distally open-ended recess (not shown) similar to recess (E146) for permitting laterally-inward flexing of the respective retention tab (E530) into the respective recess. In the example shown, the proximal end of each recess is closed by the proximal end (E532) of the respective retention tab (E530). In other versions, each recess may be proximally open-ended and the distal end of each recess may be closed by the distal end (E534) of the respective retention tab (E530), or each recess may be open-ended both proximally and distally as described above in connection with recess (E146). Each retention tab (E530) also includes an upper, laterally outer surface (E550) extending downwardly and laterally outwardly from an upper region of the laterally outer side surface (E520) of the respective sidewall (E512), a middle, laterally outer surface (E552) extending vertically downwardly from the respective upper, laterally outer surface (E550), and a lower, laterally outer surface (E554) extending downwardly and laterally inwardly from the respective middle, laterally outer surface (E552) to a lower region of the laterally outer side surface (E520) of the respective sidewall (E512).

In the example shown, pan (E510) also includes a relief slot (E560) extending laterally through each sidewall (E512) from the inner side surface thereof to the laterally outer side surface (E520) thereof. Each relief slot (E560) is positioned adjacent to a corresponding retention tab (E530) to impart the corresponding retention tab (E530) with a reduced stiffness and/or increased resilience. In this regard, each relief slot (E560) is positioned adjacent to and/or extends along the distal end (E534) of the corresponding retention tab (E530). Each relief slot (E560) is substantially elongate. Due to the recess of each retention tab (E530) being distally open-ended as described above, relief slots (E560) may each open directly into the respective recess.

While each relief slot (E560) of the present example is positioned adjacent to and/or extends along the distal end (E534) of the corresponding retention tab (E530), each relief slot (E560) may alternatively be positioned adjacent to and/or extend along the proximal end (E532) of the corresponding retention tab (E530).

In some versions, retention tabs (E530) and relief slots (E560) may be arranged on sidewalls (E512) in laterally-opposed pairs with each laterally-opposed pair of retention tabs (E530) and each laterally-opposed pair of relief slots (E560) being symmetrical relative to a longitudinal axis of pan (E510). In other versions, retention tabs (E530) and/or relief slots (E560) may alternatively be configured substantially differently on each sidewall (E512) of pan (E510) so as to be asymmetrical relative to the longitudinal axis of pan (E510). For example, the retention tab (E530) and relief slots (E560) on one sidewall (E512) may be offset in the vertical direction and/or offset in the longitudinal direction from the retention tab (E530) and relief slots (E560) on the other sidewall (E512). In addition, or alternatively, the retention tab (E530) and relief slots (E560) on one sidewall (E512) may be sized and/or shaped substantially differently from the retention tab (E530) and relief slots (E560) on the other sidewall (E512), such as by being sized and/or shaped in accordance with any of the other teachings provided herein.

F. Example of Cartridge Pan with Retention Tab Partially Surrounded by Proximal, Distal, Upper, and Lower Elongate Relief Slots FIG. 115 shows a portion of another example of a lower pan (E610) that may be readily incorporated into staple cartridge (70) in place of lower pan (76). Lower pan (E610) may be similar to lower pan (E110) described above, except as otherwise described below. In this regard, lower pan (E610) may be configured to be coupled to an underside of cartridge body (72) such that sled (82) and staple drivers (84) may be movably captured between cartridge body (72) and pan (E610). Pan (E610) of the present example includes a laterally-opposed pair of sidewalls (E612) (one shown) coupled to each other by a bottom wall (E614), such that sidewalls (E612) and bottom wall (E614) collectively define a trough (not shown) similar to trough (E116) that is sized and configured to securely receive a cartridge body (not shown), such as cartridge body (72). Each sidewall (E612) has a respective laterally inner side surface (not shown) similar to laterally inner side surfaces (E118), which may confront and/or frictionally engage a respective laterally outer side surface of cartridge body (72); and a respective laterally outer side surface (E620), which may confront and/or frictionally engage a respective laterally inner side surface (E102) of a channel (E100) of a cartridge jaw (not shown), such as cartridge jaw (42). While pan (E610) is shown and described for incorporation into cartridge (70) and as being used in conjunction with channel (E100), it will be appreciated that pan (E610) may be incorporated into any other suitable cartridge and/or may be used in conjunction with any other suitable channel.

In the example shown, pan (E610) also includes a retention tab (E630) extending laterally outwardly from each sidewall (E612). Each retention tab (E630) extends longitudinally between a respective proximal end (E632) and a respective distal end (E634), and includes laterally inner surfaces that collectively define a respective open-ended recess (not shown) similar to recess (E146) for permitting laterally-inward flexing of the respective retention tab (E630) into the respective recess. Each retention tab (E630) also includes an upper, laterally outer surface (E650) extending downwardly and laterally outwardly from an upper region of the laterally outer side surface (E620) of the respective sidewall (E612), a middle, laterally outer surface (E652) extending vertically downwardly from the respective upper, laterally outer surface (E650), and a lower, laterally outer surface (E654) extending downwardly and laterally inwardly from the respective middle, laterally outer surface (E652) to a lower region of the laterally outer side surface (E620) of the respective sidewall (E612).

In the example shown, pan (E610) also includes a plurality of relief slots (E660*a*, E660*b*, E660*c*, E660*d*) extending laterally through each sidewall (E612) from the inner side surface thereof to the laterally outer side surface (E620) thereof. Each relief slot (E660*a*, E660*b*, E660*c*, E660*d*) is positioned adjacent to a corresponding retention tab (E630) to impart the corresponding retention tab (E630) with a reduced stiffness and/or increased resilience. In this regard, each plurality of relief slots (E660*a*, E660*b*, E660*c*, E660*d*) includes a proximal relief slot (E660*a*) positioned adjacent to and/or extending along the proximal end (E632) of the corresponding retention tab (E630), and a distal relief slot (E660*b*) positioned adjacent to and/or extending along the distal end (E634) of the corresponding retention tab (E630), such that each retention tab (E630) is longitudinally flanked by a corresponding pair of proximal and distal relief slots (E660*a*, E660*b*); and further includes an upper intermediate relief slot (E660*c*) positioned adjacent to and/or extending at least partially along an upper edge of the corresponding retention tab (E630) (e.g., defined by an interface between the respective upper, laterally outer surface (E650) and the laterally outer side surface (E620) of the respective sidewall (E612)), and a lower intermediate relief slot (E660*d*) positioned adjacent to and/or extending at least partially along a lower edge of the corresponding retention tab (E630) (e.g., defined by an interface between the respective lower, laterally outer surface (E654) and the laterally outer side surface (E620) of the respective sidewall (E612)). Each relief slot (E660*a*, E660*b*, E660*c*, E660*d*) is substantially elongate. Due to the recess of each retention tab (E630) being open-ended as described above, proximal and distal relief slots (E660*a*, E660*b*) may each open directly into the respective recess.

As shown, each upper intermediate relief slot (E660*c*) extends along only a distal portion of the upper edge of the corresponding retention tab (E630) while each lower intermediate relief slot (E660*d*) extends along only a proximal portion of the lower edge of the corresponding retention tab (E630), such that each upper intermediate relief slot (E660*c*) is disposed at a substantially different position in the longitudinal direction than the corresponding lower intermediate relief slot (E660*d*). In some other versions, each upper intermediate relief slot (E660*c*) may extend along only a proximal portion of the upper edge of the corresponding retention tab (E630) and/or each lower intermediate relief slot (E660*d*) may extend along only a proximal portion of the lower edge of the corresponding retention tab (E630). In still other versions, each upper intermediate relief slot (E660*c*) may be substantially centered in the longitudinal direction along the upper edge of the corresponding retention tab (E630) and/or each lower intermediate relief slot (E660*d*) may be substantially centered in the longitudinal direction along the lower edge of the corresponding retention tab (E630), such as in a manner similar to that described above in connection with intermediate relief slot (E460*c*). In addition, or alternatively, each upper intermediate relief slot (E660*c*) may extend along the entire upper edge of the corresponding retention tab (E630) and/or each lower intermediate relief slot (E660*d*) may extend along the entire lower edge of the corresponding retention tab (E630).

In some versions, retention tabs (E630) and relief slots (E660*a*, E660*b*, E660*c*, E660*d*) may be arranged on sidewalls (E612) in laterally-opposed pairs with each laterally-opposed pair of retention tabs (E630) and each laterally-opposed pair of relief slots (E660*a*, E660*b*, E660*c*, E660*d*) being symmetrical relative to a longitudinal axis of pan (E610). In other versions, retention tabs (E630) and/or relief slots (E660*a*, E660*b*, E660*c*, E660*d*) may alternatively be configured substantially differently on each sidewall (E612) of pan (E610) so as to be asymmetrical relative to the longitudinal axis of pan (E610). For example, the retention tab (E630) and relief slots (E660*a*, E660*b*, E660*c*, E660*d*) on one sidewall (E612) may be offset in the vertical direction and/or offset in the longitudinal direction from the retention tab (E630) and relief slots (E660*a*, E660*b*, E660*c*, E660*d*) on the other sidewall (E612). In addition, or alternatively, the retention tab (E630) and relief slots (E660*a*, E660*b*, E660*c*, E660*d*) on one sidewall (E612) may be sized and/or shaped substantially differently from the retention tab (E630) and relief slots (E660*a*, E660*b*, E660*c*, E660*d*) on the other sidewall (E612), such as by being sized and/or shaped in accordance with any of the other teachings provided herein.

G. Example of Cartridge Pan with Retention Tab Partially Surrounded by U-Shaped Relief Slot FIG. 116 shows a portion of another example of a lower pan (E710) that may be readily incorporated into staple cartridge (70) in place of lower pan (76). Lower pan (E710) may be similar to lower pan (E110) described above, except as otherwise described below. In this regard, lower pan (E710) may be configured to be coupled to an underside of cartridge body (72) such that sled (82) and staple drivers (84) may be movably captured between cartridge body (72) and pan (E710). Pan (E710) of the present example includes a laterally-opposed pair of sidewalls (E712) (one shown) coupled to each other by a bottom wall (E714), such that sidewalls (E712) and bottom wall (E714) collectively define a trough (not shown) similar to trough (E116) that is sized and configured to securely receive a cartridge body (not shown), such as cartridge body (72). Each sidewall (E712) has a respective laterally inner side surface (not shown) similar to laterally inner side surfaces (E118), which may confront and/or frictionally engage a respective laterally outer side surface of cartridge body (72); and a respective laterally outer side surface (E720), which may confront and/or frictionally engage a respective laterally inner side surface (E102) of a channel (E100) of a cartridge jaw (not shown), such as cartridge jaw (42). While pan (E710) is shown and described for incorporation into cartridge (70) and as being used in conjunction with channel (E100), it will be appreciated that pan (E710) may be incorporated into any other suitable cartridge and/or may be used in conjunction with any other suitable channel.

In the example shown, pan (E710) also includes a retention tab (E730) extending laterally outwardly from each sidewall (E712). Each retention tab (E730) extends longitudinally between a respective proximal end (E732) and a respective distal end (E734), and includes laterally inner surfaces that collectively define a respective open-ended recess (not shown) similar to recess (E146) for permitting laterally-inward flexing of the respective retention tab (E730) into the respective recess. Each retention tab (E730) also includes an upper, laterally outer surface (E750) extending downwardly and laterally outwardly from an upper region of the laterally outer side surface (E720) of the respective sidewall (E712), a middle, laterally outer surface (E752) extending vertically downwardly from the respective upper, laterally outer surface (E750), and a lower, laterally outer surface (E754) extending downwardly and laterally inwardly from the respective middle, laterally outer surface (E752) toward a lower region of the laterally outer side surface (E720) of the respective sidewall (E712).

In the example shown, pan (E710) also includes a relief slot (E760) extending laterally through each sidewall (E712) from the inner side surface thereof to the laterally outer side surface (E720) thereof. Each relief slot (E760) is positioned adjacent to a corresponding retention tab (E730) to impart the corresponding retention tab (E730) with a reduced stiffness and/or increased resilience. In this regard, each relief slot (E760) includes a proximal vertical slot portion (E762) positioned adjacent to the proximal end (E732) of the corresponding retention tab (E730), a distal vertical slot portion (E763) positioned adjacent to the distal end (E734) of the corresponding retention tab (E730), and a horizontal slot portion (E764) extending longitudinally between the lower ends of the respective vertical slot portions (E762, E763), such that each relief slot (E760) is substantially U-shaped. More particularly, the proximal vertical slot portion (E762) of each relief slot (E760) extends along the proximal end (E732) of the corresponding retention tab (E730), and the distal vertical slot portion (E763) of each relief slot (E760) extends along the distal end (E734) of the corresponding retention tab (E730), such that each retention tab (E730) is longitudinally flanked by the vertical slot portions (E762, E763) of a corresponding relief slot (E760); and the horizontal slot portion (E764) of each relief slot (E760) extends along the entire lower edge of the corresponding retention tab (E730) to thereby space apart the lower edge of the corresponding retention tab (E730) from the lower region of the laterally outer side surface (E720) of the respective sidewall (E712), such that each retention tab (E730) may be cantilevered from the upper region of the laterally outer side surface (E720) of the respective sidewall (E712). It will be appreciated that such a cantilevered configuration may further reduce the stiffness and/or increase the resilience of each retention tab (E730). Due to the recess of each retention tab (E730) being open-ended as described above, vertical slot portions (E762, E763) of each relief slot (E760) may open directly into the respective recess.

While horizontal slot portion (E764) of the present example is positioned adjacent to and/or along a lower edge of the corresponding retention tab (E730), horizontal slot portion (E764) may alternatively be positioned adjacent to and/or along an upper edge of the corresponding retention tab (E730). For example, the horizontal slot portion (E764) of each relief slot (E760) may extend along the entire upper edge of the corresponding retention tab (E730) to thereby space apart the upper edge of the corresponding retention tab (E730) from the upper region of the laterally outer side surface (E720) of the respective sidewall (E712), such that each retention tab (E730) may be cantilevered from the lower region of the laterally outer side surface (E720) of the respective sidewall (E712).

In some versions, retention tabs (E730) and relief slots (E760) may be arranged on sidewalls (E712) in laterally-opposed pairs with each laterally-opposed pair of retention tabs (E730) and each laterally-opposed pair of relief slots (E760) being symmetrical relative to a longitudinal axis of pan (E710). In other versions, retention tabs (E730) and/or relief slots (E760) may alternatively be configured substantially differently on each sidewall (E712) of pan (E710) so as to be asymmetrical relative to the longitudinal axis of pan (E710). For example, the retention tab (E730) and relief slots (E760) on one sidewall (E712) may be offset in the vertical direction and/or offset in the longitudinal direction from the retention tab (E730) and relief slots (E760) on the other sidewall (E712). In addition, or alternatively, the retention tab (E730) and relief slots (E760) on one sidewall (E712) may be sized and/or shaped substantially differently from the retention tab (E730) and relief slots (E760) on the other sidewall (E712), such as by being sized and/or shaped in accordance with any of the other teachings provided herein.

H. Example of Cartridge Pan with L-Shaped Relief Slot at One End of Retention Tab FIG. 117 shows a portion of another example of a lower pan (E810) that may be readily incorporated into staple cartridge (70) in place of lower pan (76). Lower pan (E810) may be similar to lower pan (E110) described above, except as otherwise described below. In this regard, lower pan (E810) may be configured to be coupled to an underside of cartridge body (72) such that sled (82) and staple drivers (84) may be movably captured between cartridge body (72) and pan (E810). Pan (E810) of the present example includes a laterally-opposed pair of sidewalls (E812) (one shown) coupled to each other by a bottom wall (E814), such that sidewalls (E812) and bottom wall (E814) collectively define a trough (not shown) similar to trough (E116) that is sized and configured to securely receive a cartridge body (not shown), such as cartridge body (72). Each sidewall (E812) has a respective laterally inner side surface (not shown) similar to laterally inner side surfaces (E118), which may confront and/or frictionally engage a respective laterally outer side surface of cartridge body (72); and a respective laterally outer side surface (E820), which may confront and/or frictionally engage a respective laterally inner side surface (E102) of a channel (E100) of a cartridge jaw (not shown), such as cartridge jaw (42). While pan (E810) is shown and described for incorporation into cartridge (70) and as being used in conjunction with channel (E100), it will be appreciated that pan (E810) may be incorporated into any other suitable cartridge and/or may be used in conjunction with any other suitable channel.

In the example shown, pan (E810) also includes a retention tab (E830) extending laterally outwardly from each sidewall (E812). Each retention tab (E830) extends longitudinally between a respective proximal end (E832) and a respective distal end (E834), and includes laterally inner surfaces that collectively define a respective proximally open-ended recess (not shown) similar to recess (E146) for permitting laterally-inward flexing of the respective retention tab (E830) into the respective recess. In the example shown, the distal end of each recess is closed by the distal end (E834) of the respective retention tab (E830). In other versions, each recess may be distally open-ended and the proximal end of each recess may be closed by the proximal end (E834) of the respective retention tab (E830), or each recess may be open-ended both proximally and distally as described above in connection with recess (E146). Each retention tab (E830) also includes an upper, laterally outer surface (E850) extending downwardly and laterally outwardly from an upper region of the laterally outer side surface (E820) of the respective sidewall (E812), a middle, laterally outer surface (E852) extending vertically downwardly from the respective upper, laterally outer surface (E850), and a lower, laterally outer surface (E854) extending downwardly and laterally inwardly from the respective middle, laterally outer surface (E852) to a lower region of the laterally outer side surface (E820) of the respective sidewall (E812).

In the example shown, pan (E810) also includes a relief slot (E860) extending laterally through each sidewall (E812) from the inner side surface thereof to the laterally outer side surface (E820) thereof. Each relief slot (E860) is positioned adjacent to a corresponding retention tab (E830) to impart the corresponding retention tab (E830) with a reduced stiffness and/or increased resilience. In this regard, each relief slot (E860) includes a vertical slot portion (E862) positioned adjacent to the proximal end (E832) of the corresponding retention tab (E830), and a horizontal slot portion (E864) extending longitudinally from a lower end of the respective vertical slot portion (E862), such that each relief slot (E860) is substantially L-shaped. More particularly, the vertical slot portion (E862) of each relief slot (E860) extends along the proximal end (E832) of the corresponding retention tab (E830), and the horizontal slot portion (E864) of each relief slot (E860) extends distally from the lower end of the respective vertical slot portion (E862) along a proximal portion of a lower edge of the corresponding retention tab (E830). Due to the recess of each retention tab (E830) being proximally open-ended as described above, vertical slot portion (E862) of each relief slot (E860) may open directly into the respective recess.

While horizontal slot portion (E864) of the present example is positioned adjacent to and/or along a lower edge of the corresponding retention tab (E830), horizontal slot portion (E864) may alternatively be positioned adjacent to and/or along an upper edge of the corresponding retention tab (E830). For example, the horizontal slot portion (E864) of each relief slot (E860) may extend distally from an upper end of the respective vertical slot portion (E862) along a proximal portion of an upper edge of the corresponding retention tab (E830). While vertical slot portion (E862) of the present example is positioned adjacent to and/or along the proximal end (E832) of the corresponding retention tab (E830), vertical slot portion (E862) may alternatively be positioned adjacent to and/or along the distal end (E834) of the corresponding retention tab (E830). In such cases, horizontal slot portion (E864) may extend proximally from an upper or lower end of the respective vertical slot portion (E862) along a distal portion of the upper or lower edge of the corresponding retention tab (E830), for example.

In some versions, retention tabs (E830) and relief slots (E860) may be arranged on sidewalls (E812) in laterally-opposed pairs with each laterally-opposed pair of retention tabs (E830) and each laterally-opposed pair of relief slots (E860) being symmetrical relative to a longitudinal axis of pan (E810). In other versions, retention tabs (E830) and/or relief slots (E860) may alternatively be configured substantially differently on each sidewall (E812) of pan (E810) so as to be asymmetrical relative to the longitudinal axis of pan (E810). For example, the retention tab (E830) and relief slots (E860) on one sidewall (E812) may be offset in the vertical direction and/or offset in the longitudinal direction from the retention tab (E830) and relief slots (E860) on the other sidewall (E812). In addition, or alternatively, the retention tab (E830) and relief slots (E860) on one sidewall (E812) may be sized and/or shaped substantially differently from the retention tab (E830) and relief slots (E860) on the other sidewall (E812), such as by being sized and/or shaped in accordance with any of the other teachings provided herein.

I. Example of Cartridge Pan with Retention Tab Partially Surrounded by L-Shaped Relief Slots FIG. 118 shows a portion of another example of a lower pan (E910) that may be readily incorporated into staple cartridge (70) in place of lower pan (76). Lower pan (E910) may be similar to lower pan (E110) described above, except as otherwise described below. In this regard, lower pan (E910) may be configured to be coupled to an underside of cartridge body (72) such that sled (82) and staple drivers (84) may be movably captured between cartridge body (72) and pan (E910). Pan (E910) of the present example includes a laterally-opposed pair of sidewalls (E912) (one shown) coupled to each other by a bottom wall (E914), such that sidewalls (E912) and bottom wall (E914) collectively define a trough (not shown) similar to trough (E116) that is sized and configured to securely receive a cartridge body (not shown), such as cartridge body (72). Each sidewall (E912) has a respective laterally inner side surface (not shown) similar to laterally inner side surfaces (E118), which may confront and/or frictionally engage a respective laterally outer side surface of cartridge body (72); and a respective laterally outer side surface (E920), which may confront and/or frictionally engage a respective laterally inner side surface (E102) of a channel (E100) of a cartridge jaw (not shown), such as cartridge jaw (42). While pan (E910) is shown and described for incorporation into cartridge (70) and as being used in conjunction with channel (E100), it will be appreciated that pan (E910) may be incorporated into any other suitable cartridge and/or may be used in conjunction with any other suitable channel.

In the example shown, pan (E910) also includes a retention tab (E930) extending laterally outwardly from each sidewall (E912). Each retention tab (E930) extends longitudinally between a respective proximal end (E932) and a respective distal end (E934), and includes laterally inner surfaces that collectively define a respective open-ended recess (not shown) similar to recess (E146) for permitting laterally-inward flexing of the respective retention tab (E930) into the respective recess. Each retention tab (E930) also includes an upper, laterally outer surface (E950) extending downwardly and laterally outwardly from an upper region of the laterally outer side surface (E920) of the respective sidewall (E912), a middle, laterally outer surface (E952) extending vertically downwardly from the respective upper, laterally outer surface (E950), and a lower, laterally outer surface (E954) extending downwardly and laterally inwardly from the respective middle, laterally outer surface (E952) to a lower region of the laterally outer side surface (E920) of the respective sidewall (E912).

In the example shown, pan (E910) also includes a pair of relief slots (E960*a*, E960*b*) extending laterally through each sidewall (E912) from the inner side surface thereof to the laterally outer side surface (E920) thereof. Each relief slot (E960*a*, E960*b*) is positioned adjacent to a corresponding retention tab (E930) to impart the corresponding retention tab (E930) with a reduced stiffness and/or increased resilience. In this regard, each pair of relief slots (E960*a*, E960*b*) includes a proximal relief slot (E960*a*) positioned adjacent to the proximal end (E932) of the corresponding retention tab (E930), and a distal relief slot (E960*b*) positioned adjacent to the distal end (E934) of the corresponding retention tab (E930), such that each retention tab (E930) is longitudinally flanked by a corresponding pair of relief slots (E960*a*, E960*b*). Each relief slot (E960*a*, E960*b*) includes a respective vertical slot portion (E962*a*, E962*b*) extending along the respective end (E932, E934) of the corresponding retention tab (E930), and a respective horizontal slot portion (E964*a*, E964*b*) extending longitudinally from a respective end of the respective vertical slot portion (E962*a*, E962*b*), such that each relief slot (E960*a*, E960*b*) is substantially L-shaped. More particularly, the vertical slot portion (E962*a*) of each proximal relief slot (E960*a*) extends along the proximal end (E932) of the corresponding retention tab (E930), and the horizontal slot portion (E964*a*) of each proximal relief slot (E960*a*) extends distally from the lower end of the respective vertical slot portion (E962*a*) along a proximal portion of a lower edge of the corresponding retention tab (E930). Similarly, the vertical slot portion (E962*b*) of each distal relief slot (E960*b*) extends along the distal end (E934) of the corresponding retention tab (E930), and the horizontal slot portion (E964*b*) of each distal relief slot (E960*b*) extends proximally from the upper end of the respective vertical slot portion (E962*b*) along a distal portion of an upper edge of the corresponding retention tab (E930). Due to the recess of each retention tab (E930) being open-ended as described above, vertical slot portions (E962*a*, E962*b*) of proximal and distal relief slots (E960*a*, E960*b*) may open directly into the respective recess.

While horizontal slot portion (E964*a*) of the present example is positioned adjacent to and/or along a lower edge of the corresponding retention tab (E930), horizontal slot portion (E964*a*) may alternatively be positioned adjacent to and/or along an upper edge of the corresponding retention tab (E930). For example, the horizontal slot portion (E964*a*) of each proximal relief slot (E960*a*) may extend distally from an upper end of the respective vertical slot portion (E962*a*) along a proximal portion of an upper edge of the corresponding retention tab (E930). While horizontal slot portion (E964*b*) of the present example is positioned adjacent to and/or along an upper edge of the corresponding retention tab (E930), horizontal slot portion (E964*b*) may alternatively be positioned adjacent to and/or along a lower edge of the corresponding retention tab (E930). For example, the horizontal slot portion (E964*b*) of each distal relief slot (E960*b*) may extend proximally from a lower end of the respective vertical slot portion (E962*b*) along a distal portion of a lower edge of the corresponding retention tab (E930).

In some versions, retention tabs (E930) and relief slots (E960*a*, E960*b*) may be arranged on sidewalls (E912) in laterally-opposed pairs with each laterally-opposed pair of retention tabs (E930) and each laterally-opposed pair of relief slots (E960*a*, E960*b*) being symmetrical relative to a longitudinal axis of pan (E910). In other versions, retention tabs (E930) and/or relief slots (E960*a*, E960*b*) may alternatively be configured substantially differently on each sidewall (E912) of pan (E910) so as to be asymmetrical relative to the longitudinal axis of pan (E910). For example, the retention tab (E930) and relief slots (E960*a*, E960*b*) on one sidewall (E912) may be offset in the vertical direction and/or offset in the longitudinal direction from the retention tab (E930) and relief slots (E960*a*, E960*b*) on the other sidewall (E912). In addition, or alternatively, the retention tab (E930) and relief slots (E960*a*, E960*b*) on one sidewall (E912) may be sized and/or shaped substantially differently from the retention tab (E930) and relief slots (E960*a*, E960*b*) on the other sidewall (E912), such as by being sized and/or shaped in accordance with any of the other teachings provided herein.

J. Example of Cartridge Pan with C-Shaped Relief Slot at One End of Retention Tab FIG. 119 shows a portion of another example of a lower pan (E1010) that may be readily incorporated into staple cartridge (70) in place of lower pan (76). Lower pan (E1010) may be similar to lower pan (E110) described above, except as otherwise described below. In this regard, lower pan (E1010) may be configured to be coupled to an underside of cartridge body (72) such that sled (82) and staple drivers (84) may be movably captured between cartridge body (72) and pan (E1010). Pan (E1010) of the present example includes a laterally-opposed pair of sidewalls (E1012) (one shown) coupled to each other by a bottom wall (E1014), such that sidewalls (E1012) and bottom wall (E1014) collectively define a trough (not shown) similar to trough (E116) that is sized and configured to securely receive a cartridge body (not shown), such as cartridge body (72). Each sidewall (E1012) has a respective laterally inner side surface (not shown) similar to laterally inner side surfaces (E118), which may confront and/or frictionally engage a respective laterally outer side surface of cartridge body (72); and a respective laterally outer side surface (E1020), which may confront and/or frictionally engage a respective laterally inner side surface (E102) of a channel (E100) of a cartridge jaw (not shown), such as cartridge jaw (42). While pan (E1010) is shown and described for incorporation into cartridge (70) and as being used in conjunction with channel (E100), it will be appreciated that pan (E1010) may be incorporated into any other suitable cartridge and/or may be used in conjunction with any other suitable channel.

In the example shown, pan (E1010) also includes a retention tab (E1030) extending laterally outwardly from each sidewall (E1012). Each retention tab (E1030) extends longitudinally between a respective proximal end (E1032) and a respective distal end (E1034), and includes laterally inner surfaces that collectively define a respective distally open-ended recess (not shown) similar to recess (E146) for permitting laterally-inward flexing of the respective retention tab (E1030) into the respective recess. In the example shown, the proximal end of each recess is closed by the proximal end (E1032) of the respective retention tab (E1030). In other versions, each recess may be proximally open-ended and the distal end of each recess may be closed by the distal end (E1034) of the respective retention tab (E1030), or each recess may be open-ended both proximally and distally as described above in connection with recess (E146). Each retention tab (E1030) also includes an upper, laterally outer surface (E1050) extending downwardly and laterally outwardly from an upper region of the laterally outer side surface (E1020) of the respective sidewall (E1012), a middle, laterally outer surface (E1052) extending vertically downwardly from the respective upper, laterally outer surface (E1050), and a lower, laterally outer surface (E1054) extending downwardly and laterally inwardly from the respective middle, laterally outer surface (E1052) to a lower region of the laterally outer side surface (E1020) of the respective sidewall (E1012).

In the example shown, pan (E1010) also includes a relief slot (E1060) extending laterally through each sidewall (E1012) from the inner side surface thereof to the laterally outer side surface (E1020) thereof. Each relief slot (E1060) is positioned adjacent to a corresponding retention tab (E1030) to impart the corresponding retention tab (E1030) with a reduced stiffness and/or increased resilience. In this regard, each relief slot (E1060) includes a distal vertical slot portion (E1063) positioned adjacent to the distal end (E1034) of the corresponding retention tab (E1030), an upper horizontal slot portion (E1064) extending longitudinally from an upper end of the respective vertical slot portion (E1063), and a lower horizontal slot portion (E1065) extending longitudinally from a lower end of the respective distal vertical slot portion (E1063) such that each relief slot (E1060) is substantially C-shaped. More particularly, the distal vertical slot portion (E1063) of each relief slot (E1060) extends along the distal end (E1034) of the corresponding retention tab (E1030), the upper horizontal slot portion (E1064) of each relief slot (E1060) extends proximally from the upper end of the respective vertical slot portion (E1063) along a distal portion of an upper edge of the corresponding retention tab (E1030), and the lower horizontal slot portion (E1065) of each relief slot (E1060) extends proximally from the lower end of the respective vertical slot portion (E1063) along a distal portion of a lower edge of the corresponding retention tab (E1030). Due to the recess of each retention tab (E1030) being distally open-ended as described above, vertical slot portion (E1063) of each relief slot (E1060) may open directly into the respective recess.

While vertical slot portion (E1063) of the present example is positioned adjacent to and/or along the distal end (E1034) of the corresponding retention tab (E1030), vertical slot portion (E1063) may alternatively be positioned adjacent to and/or along the proximal end (E1032) of the corresponding retention tab (E1030). In such cases, horizontal slot portions (E1064, E1065) may extend distally from respective ends of the respective vertical slot portion (E1063) along a proximal portion of the respective upper or lower edge of the corresponding retention tab (E1030), for example.

In some versions, retention tabs (E1030) and relief slots (E1060) may be arranged on sidewalls (E1012) in laterally-opposed pairs with each laterally-opposed pair of retention tabs (E1030) and each laterally-opposed pair of relief slots (E1060) being symmetrical relative to a longitudinal axis of pan (E1010). In other versions, retention tabs (E1030) and/or relief slots (E1060) may alternatively be configured substantially differently on each sidewall (E1012) of pan (E1010) so as to be asymmetrical relative to the longitudinal axis of pan (E1010). For example, the retention tab (E1030) and relief slots (E1060) on one sidewall (E1012) may be offset in the vertical direction and/or offset in the longitudinal direction from the retention tab (E1030) and relief slots (E1060) on the other sidewall (E1012). In addition, or alternatively, the retention tab (E1030) and relief slots (E1060) on one sidewall (E1012) may be sized and/or shaped substantially differently from the retention tab (E1030) and relief slots (E1060) on the other sidewall (E1012), such as by being sized and/or shaped in accordance with any of the other teachings provided herein.

K. Example of Cartridge Pan with Retention Tab Partially Surrounded by Downwardly-Extended U-Shaped Relief Slot FIG. 120 shows a portion of another example of a lower pan (E1110) that may be readily incorporated into staple cartridge (70) in place of lower pan (76). Lower pan (E1110) may be similar to lower pan (E110) described above, except as otherwise described below. In this regard, lower pan (E1110) may be configured to be coupled to an underside of cartridge body (72) such that sled (82) and staple drivers (84) may be movably captured between cartridge body (72) and pan (E1110). Pan (E1110) of the present example includes a laterally-opposed pair of sidewalls (E1112) coupled to each other by a bottom wall (E1114), such that sidewalls (E1112) and bottom wall (E1114) collectively define a trough (not shown) similar to trough (E116) that is sized and configured to securely receive a cartridge body (not shown), such as cartridge body (72). Each sidewall (E1112) has a respective laterally inner side surface (E1118), which may confront and/or frictionally engage a respective laterally outer side surface of cartridge body (72); and a respective laterally outer side surface (E1120), which may confront and/or frictionally engage a respective laterally inner side surface (E102) of a channel (E100) of a cartridge jaw (not shown), such as cartridge jaw (42). While pan (E1110) is shown and described for incorporation into cartridge (70) and as being used in conjunction with channel (E100), it will be appreciated that pan (E1110) may be incorporated into any other suitable cartridge and/or may be used in conjunction with any other suitable channel.

In the example shown, pan (E1110) also includes a retention tab (E1130) extending laterally outwardly from each sidewall (E1112). Each retention tab (E1130) extends longitudinally between a respective proximal end (E1132) and a respective distal end (E1134), and includes laterally inner surfaces that collectively define a respective open-ended recess (not shown) similar to recess (E146) for permitting laterally-inward flexing of the respective retention tab (E1130) into the respective recess. Each retention tab (E1130) also includes an upper, laterally outer surface (E1150) extending downwardly and laterally outwardly from an upper region of the laterally outer side surface (E1120) of the respective sidewall (E1112), a middle, laterally outer surface (E1152) extending vertically downwardly from the respective upper, laterally outer surface (E1150), a lower, laterally outer surface (E1154) extending downwardly and laterally inwardly from the respective middle, laterally outer surface (E1152), and a bottom surface (E1156) extending laterally inwardly from the respective lower, laterally outer surface (E1154) toward a middle region of bottom wall (E1114).

In the example shown, pan (E1110) also includes a relief slot (E1160) extending laterally through each sidewall (E1112) from the inner side surface thereof to the laterally outer side surface (E1120) thereof, and further extending vertically through bottom wall (E1114). Each relief slot (E1160) is positioned adjacent to a corresponding retention tab (E1130) to impart the corresponding retention tab (E1130) with a reduced stiffness and/or increased resilience. In this regard, each relief slot (E1160) includes a proximal vertical slot portion (E1162) positioned adjacent to the proximal end (E1132) of the corresponding retention tab (E1130), a distal vertical slot portion (E1163) positioned adjacent to the distal end (E1134) of the corresponding retention tab (E1130), and a horizontal slot portion (E1164) extending longitudinally between the lower ends of the respective vertical slot portions (E1162, E1163), such that each relief slot (E1160) is substantially U-shaped. More particularly, the proximal vertical slot portion (E1162) of each relief slot (E1160) extends along the proximal end (E1132) of the corresponding retention tab (E1130), and the distal vertical slot portion (E1163) of each relief slot (E1160) extends along the distal end (E1134) of the corresponding retention tab (E1130), such that each retention tab (E1130) is longitudinally flanked by the vertical slot portions (E1162, E1163) of a corresponding relief slot (E1160). In the example shown, vertical sot portions (E1162, E1163) each extend further downwardly than the corresponding retention tab (E1130) such that the lower ends of vertical slot portions (E1162, E1163) each extend through bottom wall (E1114); and the horizontal slot portion (E1164) of each relief slot (E1160) extends through bottom wall (E1114) along the entire lower edge of the corresponding retention tab (E1130) to thereby space apart the lower, laterally inner edge of the corresponding retention tab (E1130) from bottom wall (E1114), such that each retention tab (E1130) may be cantilevered from the upper region of the laterally outer side surface (E1120) of the respective sidewall (E1112). It will be appreciated that such a cantilevered configuration may further reduce the stiffness and/or increase the resilience of each retention tab (E1130). Due to the recess of each retention tab (E1130) being open-ended as described above, vertical slot portions (E1162, E1163) of each relief slot (E1160) may open directly into the respective recess.

In some versions, retention tabs (E1130) and relief slots (E1160) may be arranged on sidewalls (E1112) in laterally-opposed pairs with each laterally-opposed pair of retention tabs (E1130) and each laterally-opposed pair of relief slots (E1160) being symmetrical relative to a longitudinal axis of pan (E1110). In other versions, retention tabs (E1130) and/or relief slots (E1160) may alternatively be configured substantially differently on each sidewall (E1112) of pan (E1110) so as to be asymmetrical relative to the longitudinal axis of pan (E1110). For example, the retention tab (E1130) and relief slots (E1160) on one sidewall (E1112) may be offset in the vertical direction and/or offset in the longitudinal direction from the retention tab (E1130) and relief slots (E1160) on the other sidewall (E1112). In addition, or alternatively, the retention tab (E1130) and relief slots (E1160) on one sidewall (E1112) may be sized and/or shaped substantially differently from the retention tab (E1130) and relief slots (E1160) on the other sidewall (E1112), such as by being sized and/or shaped in accordance with any of the other teachings provided herein.

XI. Examples of Cartridge Bodies Having Thinned Regions to Promote Cartridge Flexing In some instances, it may be desirable to provide cartridge body (72) of staple cartridge (70) with one or more thinned regions to promote flexing of one or more portions of staple cartridge (70) when sled (82) is in the distal fired position. For example, such thinned regions may promote laterally-inward flexing of cartridge body (72) and/or lower pan (76) during removal of staple cartridge (70) from the channel of cartridge jaw (42), and may thereby reduce the cartridge removal force while minimizing any impact to the cartridge retention force. Each of the examples of cartridge bodies (E1210, E1310) described below provides such functionality.

A. Example of Cartridge Body with Thinned Distal Driver Pocket Supports

FIGS. 121-124 show another example of a cartridge body (E1210) that may be readily incorporated into staple cartridge (70) in place of cartridge body (72). Cartridge body (E1210) may be similar to cartridge body (72) described above, except as otherwise described below. In this regard, cartridge body (E1210) presents an upper deck (E1212) defining a first stapling surface, and an underside (E1213). A vertical knife slot (E1214) extends longitudinally through cartridge body (E1210) and is configured to slidably receive distal knife portion (50) of firing beam (46). In the present version, three rows of cartridge pockets (E1216) (also referred to as "staple openings," "staple apertures," or "staple cavities") are formed through upper deck (E1212) and underside (E1213) along each lateral side of knife slot (E1214). Underside (E1213) may be coupled to lower pan (E110) such that sled (82) and a plurality of staple drivers (E1218) may be movably captured between cartridge body (E1210) and pan (E110). While cartridge body (E1210) is shown and described for incorporation into cartridge (70) along with pan (E110) and as being used in conjunction with channel (E100), it will be appreciated that cartridge body (E1210) may be incorporated into any other suitable cartridge and/or may be used in conjunction with any other suitable channel. For example, cartridge body (E1210) may be incorporated into cartridge (70) while retaining pan (76), or may be incorporated into cartridge (70) along with any of the other pans (E210, E310, E410, E510, E610, E710, E810, E910, E1010, E1110) described herein.

In the example shown, cartridge body (E1210) also includes a pair of sled rail tracks (E1220, E1222) extending longitudinally on each lateral side of knife slot (E1214) for slidably receiving respective rails of sled (82). More particularly, cartridge body (E1210) includes a laterally inner sled rail track (E1220) and a laterally outer sled rail track (E1222) on each lateral side of knife slot (E1214) for slidably receiving respective laterally inner and outer rails of sled (82). In this regard each laterally outer sled rail track (E1222) is defined between a corresponding interior wall (E1224) of cartridge body and a plurality of driver pocket supports (E1230*a*, E1230*b*), with interior wall (E1224) defining a laterally inner boundary of the respective laterally outer sled rail track (E1222) and with driver pocket supports (E1230*a*, E1230*b*) collectively defining a laterally outer boundary of the respective laterally outer sled rail track (E1222).

As shown in FIG. 122, the illustrated plurality of driver pocket supports (E1230*a*, E1230*b*) includes a plurality of proximal driver pocket supports (E1230*a*) having a first thickness (Y1) and a distal (e.g., distalmost) driver pocket support (E1230*b*) having a second thickness (Y2) substantially less than the first thickness (Y1), such that a laterally inner surface of distal driver pocket support (E1230*b*) may be spaced farther apart from interior wall (E1224) than proximal driver pocket supports (E1230*a*). For example, the first thickness (Y1) may be about 0.007 in, while the second thickness (Y2) may be about 0.005 in, such that the second thickness (Y2) may be less than the first thickness (Y1) by about 0.002 in. In this manner, each laterally outer sled rail track (E1222) may have a first, proximal width (W1) and a second, distal width (W2) greater than the first width (W1)

by an amount substantially equal to the difference between the first and second thicknesses (Y1, Y2). For example, the second width (W2) may be greater than the first width (W1) by about 0.002 in.

Due to the increased second width (W2) of each laterally outer sled rail track (E1222), the laterally outer rails of sled (82) may each be spaced apart from the respective distal driver pocket support (E1230*b*) by a gap (G1) when sled (82) is in the distal fired position, as shown in FIG. 124. In this regard, the gap (G1) between each laterally outer rail of sled (82) and the respective distal driver pocket support (E1230*b*) may be substantially greater than any gap between each laterally outer rail of sled (82) and the respective proximal driver pocket supports (E1230*a*). For example, the gap (G1) between each laterally outer rail of sled (82) and the respective distal driver pocket support (E1230*b*) may be about 0.003 in, while any gap between each laterally outer rail of sled (82) and the respective proximal driver pocket supports (E1230*a*) may be about 0.001 in. The increased gap (G1) between each laterally outer rail of sled (82) and the respective distal driver pocket support (E1230*b*) may provide more space for staple cartridge (70) (e.g., cartridge body (E1210) and/or pan (E110)) to deflect laterally inwardly before contacting the laterally outer rails of sled (82), such as during removal of staple cartridge (70) from channel (E100). Such additional space for staple cartridge (70) to deflect may reduce any resistance to laterally inward flexing of staple cartridge (70) that might otherwise be caused by sled (82) being in the distal fired position, thereby reducing the cartridge removal force. For example, the laterally inward flexing of staple cartridge (70) permitted by such additional space may assist with disengaging retention tab (E130) of lower pan (E110) from channel (E100) (e.g., from detent (E104) of channel (E100)).

While distal driver pocket support (E1230*b*) of the present example has a laterally inner surface that is substantially flat (e.g., planar) and that is oriented substantially parallel to knife slot (E1214), the laterally inner surface of each distal driver pocket support (E1230*b*) may alternatively be any one or more of concave, convex, tapered in the vertical direction and/or tapered in the longitudinal direction. While only the distalmost driver pocket support (E1230*b*) has been described as having the second thickness (Y2), it will be appreciated that any suitable driver pocket supports (E1230*a*, E1230*b*) may have the second thickness (Y2), such as all driver pocket supports that are at a substantially same longitudinal position as any portion of the corresponding laterally outer rail of sled (82) when sled (82) is in the distal fired position. In this regard, it may be desirable to provide at least some proximal driver pocket supports (E1230*a*) with the first thickness (Y1) to provide a relatively tight gap between sled (82) and such proximal driver pocket supports (E1230*a*) during firing to promote proper deployment and forming of staples (86).

B. Example of Cartridge Body with Recessed Laterally Outer Surfaces

FIGS. 125-127 show another example of a cartridge body (E1310) that may be readily incorporated into staple cartridge (70) in place of cartridge body (72). Cartridge body (E1310) may be similar to cartridge body (72) described above, except as otherwise described below. In this regard, cartridge body (E1310) presents an upper deck (E1312) defining a first stapling surface, and an underside (E1313). A vertical knife slot (not shown) similar to knife slot (78) extends longitudinally through cartridge body (E1310) and is configured to slidably receive distal knife portion (50) of firing beam (46). While not shown, three rows of cartridge pockets similar to cartridge pockets (E1216) are formed through upper deck (E1312) and underside (E1313) along each lateral side of the knife slot. Underside (E1313) may be coupled to lower pan (E110) such that sled (82) and a plurality of staple drivers (not shown) similar to staple drivers (E1218) may be movably captured between cartridge body (E1310) and pan (E110). While cartridge body (E1310) is shown and described for incorporation into cartridge (70) along with pan (E110) and as being used in conjunction with channel (E100), it will be appreciated that cartridge body (E1310) may be incorporated into any other suitable cartridge and/or may be used in conjunction with any other suitable channel. For example, cartridge body (E1310) may be incorporated into cartridge (70) while retaining pan (76), or may be incorporated into cartridge (70) along with any of the other pans (E210, E310, E410, E510, E610, E710, E810, E910, E1010, E1110) described herein.

In the example shown, cartridge body (E1310) also includes a laterally-opposed pair of sidewalls (E1320) (one shown). Each sidewall (E1320) has a respective laterally inner side surface (E1322), which may partially define a laterally outer sled rail track of cartridge body (E1310); and a respective laterally outer side surface (E1324), which may confront and/or frictionally engage a respective laterally inner side surface (E118) of lower pan (E110). Cartridge body (E1310) of the present example further includes a laterally-opposed pair of recessed laterally outer surfaces (E1326) (one shown) that extend upwardly from underside (E1313) and that are recessed laterally inwardly relative to the respective laterally outer side surface (E1324). Each recessed laterally outer surface (E1326) may be disposed at a relatively distal location along a length of cartridge body (E1310). For example, each recessed laterally outer surface (E1326) may be at a substantially same position in the longitudinal direction as sled (82) when sled (82) is in the distal fired position. In the example shown, each recessed laterally outer surface (E1326) is at a substantially same position in the longitudinal direction as a corresponding retention tab (E130) of lower pan (E110). As shown in FIG. 126, each recessed laterally outer surface (E1326) has a length (L4) and a height (H2), which may be substantially equal to or greater than the length (L) and height (H1), respectively, of the corresponding retention tab (E130). For example, the length (L4) of each recessed laterally outer surface (E1326) may be about 0.185 in, and/or the height (H2) of each recessed laterally outer surface (E1326) may be about 0.094 in.

As shown in FIG. 127, the illustrated sidewall (E1320) has a first thickness (X1) defined between the respective laterally inner and outer side surfaces (E1322, E1324), and a second thickness (X2) defined between the respective laterally inner side surface (E1322) and recessed laterally outer surface (E1326) that is substantially less than the first thickness (X1), such that each recessed laterally outer surface (E1326) is recessed laterally inwardly relative to the respective laterally outer side surface (E1324) by a depth (D1). For example, the first thickness (X1) may be about 0.011 in, while the second thickness (X2) may be about 0.008 in, such that the depth (D1) may be about 0.003 in.

Due to the depth (D1) of each recessed laterally outer surface (E1326) relative to the respective laterally outer side surface (E1324), the laterally inner side surfaces (E118) of pan (E110) may each be spaced apart from the respective recessed laterally outer surface (E1326) by a localized gap defined by the same depth (D1) while the laterally inner side surfaces (E118) may each frictionally engage the respective laterally outer side surface (E1324) when pan (E110) is coupled to underside of cartridge body (E1310), as shown in FIG. 127. The gap between each laterally inner side surface (E118) of pan (E110) and the respective recessed laterally outer surface (E1326) may provide more space for staple cartridge (70) and, more particularly, pan (E110) to deflect laterally inwardly, such as during removal of staple cartridge (70) from channel (E100). Such additional space for pan (E110) to deflect may reduce any resistance to laterally inward flexing of pan (E110) that might otherwise be caused by cartridge body (E1310), thereby reducing the cartridge removal force. For example, the laterally inward flexing of pan (E110) permitted by such additional space may assist with disengaging retention tab (E130) of lower pan (E110) from channel (E100) (e.g., from detent (E104) of channel (E100)).

XII. Examples of Wedge Sleds Configured to Provide Increased Cartridge-to-Sled Gap to Promote Cartridge Flexing In some instances, it may be desirable to provide sled (82) of staple cartridge (70) with one or more features configured to increase the lateral gap between the outer rails of sled (82) and the driver pocket supports of cartridge body (72). For example, such features may promote laterally-inward flexing of cartridge body (72) and/or lower pan (76) during removal of staple cartridge (70) from the channel of cartridge jaw (42), and may thereby reduce the cartridge removal force while minimizing any impact to the cartridge retention force. Each of the examples of sleds (E1410, E1510) described below provides such functionality.

A. Example of Wedge Sled with Recessed Laterally Outer Surfaces

FIGS. 128-129 show another example of a wedge sled (E1410) that may be readily incorporated into staple cartridge (70) in place of wedge sled (82). Wedge sled (E1410) may be similar to wedge sled (82) described above, except as otherwise described below. In this regard, wedge sled (E1410) may be movably captured between cartridge body (72) and pan (76) and may be actuated longitudinally within staple cartridge (70) by distal knife portion (50) during a firing stroke. While wedge sled (E1410) is shown and described for incorporation into cartridge (70) along with pan (E110) and cartridge body (E1210), and as being used in conjunction with channel (E100), it will be appreciated that wedge sled (E1410) may be incorporated into any other suitable cartridge and/or may be used in conjunction with any other suitable channel. For example, wedge sled (E1410) may be incorporated into cartridge (70) while retaining pan (76) and/or cartridge body (72), or may be incorporated into cartridge (70) along with any of the other pans (E210, E310, E410, E510, E610, E710, E810, E910, E1010, E1110) described herein and/or along with cartridge body (E1310) described herein.

In the example shown, wedge sled (E1410) includes a base (E1412), a laterally-opposed pair of outer sled rails (E1414) extending upwardly from base (E1412), a laterally-opposed pair of inner sled rails (E1416) extending upwardly from base (E1412) between outer sled rails (E1414), and a central nose (E1418) extending upwardly and/or distally from base (E1412) between inner sled rails (E1416). Sled rails (E1414, E1416) may also be referred to as "cam ramps" or "cam wedges." In this regard, sled rails (E1414, E1416) present angled cam surfaces for camming staple drivers (84) vertically upwardly within cartridge pockets (80) to drive staples (86) upwardly above deck (74), thereby ejecting staples (86) from cartridge pockets (80) and toward anvil jaw (44) during longitudinal actuation of wedge sled (E1410). In some versions, wedge sled (E1410) may comprise a metal material. In addition, or alternatively, wedge sled (E1410) may have a substantially greater material stiffness than that of cartridge body (72).

In the example shown, each outer rail (E1414) has a respective laterally outer side surface (E1424), which may confront and/or slidingly engage the laterally inner surfaces of driver pocket supports (E1230*a*, E1230*b*) during longitudinal actuation of wedge sled (E1410). Wedge sled (E1410) of the present example further includes a laterally-opposed pair of recessed laterally outer surfaces (E1426) (one shown) that extend upwardly from base (E1412) and proximally from the distal end of the respective outer rail (E1414), and that are recessed laterally inwardly relative to the respective laterally outer side surface (E1424). Each recessed laterally outer surface (E1426) may be at a substantially same position in the longitudinal direction as the corresponding distal driver pocket support (E1230*b*) when sled (82) is in the distal fired position. As shown, each recessed laterally outer surface (E1426) is recessed laterally inwardly relative to the respective laterally outer side surface (E1424) by a depth (D2).

Due to the depth (D2) of each recessed laterally outer surface (E1426) relative to the respective laterally outer side surface (E1424), the laterally inner surfaces of at least distal driver pocket supports (E1230*b*) may each be spaced apart from the respective recessed laterally outer surface (E1426) by a localized gap defined by the same depth (D2) when sled (82) is in the distal first position, as shown in FIG. 129. The increased gap (G2) between each laterally outer rail (E1414) of sled (E1410) and the respective distal driver pocket support (E1230*b*) may provide more space for staple cartridge (70) (e.g., cartridge body (E1210) and/or pan (E110)) to deflect laterally inwardly before contacting the laterally outer rails (E1414) of sled (E1410), such as during removal of staple cartridge (70) from channel (E100). Such additional space for staple cartridge (70) to deflect may reduce any resistance to laterally inward flexing of staple cartridge (70) that might otherwise be caused by sled (82) being in the distal fired position, thereby reducing the cartridge removal force. For example, the laterally inward flexing of staple cartridge (70) permitted by such additional space may assist with disengaging retention tab (E130) of lower pan (E110) from channel (E100) (e.g., from detent (E104) of channel (E100)).

B. Example of Wedge Sled with Tapered Laterally Outer Surfaces

FIGS. 130-131 show another example of a wedge sled (E1510) that may be readily incorporated into staple cartridge (70) in place of wedge sled (82). Wedge sled (E1510) may be similar to wedge sled (82) described above, except as otherwise described below. In this regard, wedge sled (E1510) may be movably captured between cartridge body (72) and pan (76) and may be actuated longitudinally within staple cartridge (70) by distal knife portion (50) during a firing stroke. While wedge sled (E1510) is shown and described for incorporation into cartridge (70) along with pan (E110) and cartridge body (E1210), and as being used in conjunction with channel (E100), it will be appreciated that wedge sled (E1510) may be incorporated into any other suitable cartridge and/or may be used in conjunction with any other suitable channel. For example, wedge sled (E1510) may be incorporated into cartridge (70) while retaining pan (76) and/or cartridge body (72), or may be incorporated into cartridge (70) along with any of the other pans (E210, E310, E410, E510, E610, E710, E810, E910, E1010, E1110) described herein and/or along with cartridge body (E1310) described herein.

In the example shown, wedge sled (E1510) includes a base (E1512), a laterally-opposed pair of outer sled rails (E1514) extending upwardly from base (E1512), a laterally-opposed pair of inner sled rails (E1516) extending upwardly from base (E1512) between outer sled rails (E1514), and a central nose (E1518) extending upwardly and/or distally from base (E1512) between inner sled rails (E1516). Sled rails (E1514, E1516) may also be referred to as "cam ramps" or "cam wedges." In this regard, sled rails (E1514, E1516) present angled cam surfaces for camming staple drivers (84) vertically upwardly within cartridge pockets (80) to drive staples (86) upwardly above deck (74), thereby ejecting staples (86) from cartridge pockets (80) and toward anvil jaw (44) during longitudinal actuation of wedge sled (E1510). In some versions, wedge sled (E1510) may comprise a metal material. In addition, or alternatively, wedge sled (E1510) may have a substantially greater material stiffness than that of cartridge body (72).

In the example shown, each outer rail (E1514) has a respective laterally outer side surface (E1524), which may confront and/or slidingly engage the laterally inner surfaces of driver pocket supports (E1230*a*, E1230*b*) during longitudinal actuation of wedge sled (E1510). Inner rails (E1516) of the present example are substantially vertical, while outer rails (E1514) of the present example are each tilted or bent laterally outwardly from base (E1512), such that outer sled rails (E1514) are obliquely oriented relative to the horizontal plane and relative to a vertical-longitudinal plane. More particularly, each outer sled rail (E1514) is bent laterally outwardly at a same oblique angle (θ) relative to the vertical-longitudinal plane (or to any plane parallel thereto), such that wedge sled (E1510) is substantially symmetric about the vertical-longitudinal plane, at least with respect to the configurations of sled rails (E1514, E1516). In this manner, each laterally outer side surface (E1524) may be tapered laterally inwardly and downwardly at the same oblique angle (θ) relative to the vertical-longitudinal plane to provide sled (E1510) with a first, bottom width (W3) and a second, top width (W4) greater than the bottom width (W3). Each laterally outer side surface (E1524) may be at a substantially same position in the longitudinal direction as the corresponding distal driver pocket support (E1230*b*) when sled (82) is in the distal fired position.

Due to the varying widths (W3, W4) of sled (E1510), the laterally inner surfaces of driver pocket supports (E1230*a*, E1230*b*) may each be spaced apart from the respective tapered laterally outer side surface (E1524) by a gap that varies in the vertical direction when sled (82) is in the distal first position, as shown in FIG. 131. For example, the gap may be relatively large at or near base (E1512) and may be relatively small at or near the tops of outer rails (E1514) to promote proper deployment and forming of staples (86). Due to the configurations of angled cam surfaces presented by outer rails (E1514), this may result in an increased gap between each laterally outer rail (E1514) of sled (E1510) and the respective distal driver pocket support (E1230*b*). The increased gap between each laterally outer rail (E1514) of sled (E1510) and the respective distal driver pocket support (E1230*b*) may provide more space for staple cartridge (70) (e.g., cartridge body (E1210) and/or pan (E110)) to deflect laterally inwardly before contacting the laterally outer rails (E1514) of sled (E1510), such as during removal of staple cartridge (70) from channel (E100). Such additional space for staple cartridge (70) to deflect may reduce any resistance to laterally inward flexing of staple cartridge (70) that might otherwise be caused by sled (82) being in the distal fired position, thereby reducing the cartridge removal force. For example, the laterally inward flexing of staple cartridge (70) permitted by such additional space may assist with disengaging retention tab (E130) of lower pan (E110) from channel (E100) (e.g., from detent (E104) of channel (E100)).

While each laterally outer rail (E1514) of the present example tilted or bent to impart the respective laterally outer side surface (E1524) with a taper, it will be appreciated that laterally outer rails (E1514) may alternatively be substantially vertical and may have varying thicknesses to impart the respective laterally outer side surface (E1524) with a taper. While each laterally outer side surface (E1524) of the present example is tapered at a single angle (θ) relative to the vertical-longitudinal plane, it will be appreciated that each laterally outer side surface (E1524) may alternatively be tapered at more than a single angle (θ) relative to the vertical-longitudinal plane.

It will be understood that while the features shown and described above are presented in the context of staple cartridge (70) for surgical stapler (10), such features may also be applied to staple cartridges configured for use with various other types of surgical staplers, such as linear surgical staplers.

XIII. Example of Anvil Having 2D and 3D Staple Forming Pockets

In some instances, it may be desirable to arrange and configure staple forming pockets (66) of anvil jaw (44) to achieve improved sealing of severed tissue, such as by striking a desired balance between achieving tight tissue compression and good leak path resistance. FIGS. 132-135 show an example of an anvil jaw (F110) (also referred to as an "anvil") that may provide such capabilities, and that may be incorporated into end effector (40) in place of anvil jaw (44). Anvil jaw (F110) may be similar to anvil jaw (44) described above, except as otherwise described below. In this regard, anvil jaw (F110) may be configured to pivot relative to cartridge jaw (42) of end effector (40) (or cartridge jaw (42) may be configured to pivot relative to anvil jaw (F110)), to clamp tissue therebetween.

In the example shown, anvil jaw (F110) includes a body (F111) having an interior side that defines an anvil surface (F112) configured to compress tissue and having a plurality of staple forming pockets (F114*a*, F114*b*, F114*c*, F114*d*, F114*e*, F114*f*), and an opposed exterior side defining an exterior surface (F116). Anvil jaw (F110) also includes a pair of tissue stops (F118) that extend downwardly from a proximal portion of anvil jaw (F110) on opposed lateral sides such that tissue stops (F118) extend beyond anvil surface (F112). Tissue stops (F118) are configured to inhibit tissue (T) from advancing too far proximally relative to anvil jaw (F110) when tissue (T) is positioned between anvil jaw (F110) and cartridge jaw (42). More specifically, tissue stops (F118) allow tissue (T) to be proximally advanced in end effector (40) only to a predetermined position to ensure adequate engagement of staples (86*a*, 86*b*, 86*c*) (FIGS. 137-138) with tissue (T) and to ensure that anvil jaw (F110) can pivot to a closed state without binding on tissue (T).

Tissue stops (F118) are also configured to limit the lateral rotation of anvil jaw (F110) relative to lower cartridge jaw (42) by engaging lateral side portions of lower cartridge jaw (42). This can be useful for ensuring proper lateral alignment between the more proximally located staples (86*a*, 86*b*, 86*c*) and the corresponding staple forming pockets (F114*a*, F114*b*, F114*c*, F114*d*, F114*e*, F114*f*).

Anvil jaw (F110) further includes an elongate anvil slot (F122) (also referred to herein as a firing driver slot) that extends through anvil surface (F112). As shown in FIG. 133, anvil slot (F122) extends along a longitudinal axis (LA) of anvil jaw (F110). Anvil slot (F122) is configured to slidably receive upper pin (52) of firing beam (46) in a manner similar to that described above in connection with longitudinal anvil slot (62).

In the example shown, staple forming pockets (F114*a*, F114*b*, F114*c*, F114*d*, F114*e*, F114*f*) are arranged in pairs on anvil surface (F112) on each side of anvil slot (F122). Each staple forming pocket (F114*a*, F114*b*, F114*c*, F114*d*, F114*e*, F114*f*) is configured to receive and deform a respective leg of a staple (86*a*, 86*b*, 86*c*) ejected by a staple cartridge (not shown) that is received within lower cartridge jaw (42) when stapler (10) is fired. Accordingly, staple forming pockets (F114*a*, F114*b*, F114*c*, F114*d*, F114*e*, F114*f*) cooperate to form the ejected staples (86*a*, 86*b*, 86*c*) in tissue clamped between lower cartridge jaw (42) and anvil jaw (F110). In the present version, anvil jaw (F110) includes three linear (e.g., straight) rows of staple forming pockets (F114*a*, F114*b*, F114*c*, F114*d*, F114*e*, F114*f*) on each side of anvil slot (F122), though it will be appreciated that anvil jaw (F110) may include various other configurations of staple pockets (F114*a*, F114*b*, F114*c*, F114*d*, F114*e*, F114*f*) in other versions. More particularly, anvil jaw (F110) of the present version includes a laterally inner row of staple forming pockets (F114*a*, F114*b*), a laterally intermediate row of staple forming pockets (F114*c*, F114*d*), and a laterally outer row of staple forming pockets (F114*e*, F114*f*) all formed through the same anvil surface (F112) on each side of anvil slot (F122), with the laterally inner row of staple forming pockets (F114*a*, F114*b*) being closest to the longitudinal axis (LA) on the respective side of anvil slot (F122), the laterally outer row of staple forming pockets (F114*e*, F114*f*) being farthest from the longitudinal axis (LA) on the respective side of anvil slot (F122), and the laterally intermediate row of staple forming pockets (F114*c*, F114*d*) being disposed between the laterally inner row of staple forming pockets (F114*a*, F114*b*) and the laterally outer row of staple forming pockets (F114*e*, F114*f*) on the respective side of anvil slot (F122).

As described in greater detail below, each row of staple forming pockets (F114*a*, F114*b*, F114*c*, F114*d*, F114*e*, F114*f*) has a unique geometry relative to the other two rows of staple forming pockets (F114*a*, F114*b*, F114*c*, F114*d*, F114*e*, F114*f*) on the same side of the longitudinal axis (LA), such that the configurations and/or orientations of staple forming pockets (F114*a*, F114*b*, F114*c*, F114*d*, F114*e*, F114*f*) vary in the lateral direction. In this manner, each row of staple forming pockets (F114*a*, F114*b*, F114*c*, F114*d*, F114*e*, F114*f*) may be configured to form the corresponding row of staples (86*a*, 86*b*, 86*c*) with a unique configuration relative to the other two rows of staples (86*a*, 86*b*, 86*c*) on the same side of the cut line produced by cutting edge (58).

As best shown in FIGS. 133 and 134, staple forming pockets (F114*a*, F114*b*, F114*c*, F114*d*, F114*e*, F114*f*) are arranged in longitudinally adjacent pairs such that each pair is configured to receive and deform the legs of a respective staple (86*a*, 86*b*, 86*c*) and thereby transform the staple (86*a*, 86*b*, 86*c*) into a formed shape when firing beam (46) is actuated distally. More particularly, each proximal, laterally inner staple forming pocket (F114*a*) is configured to cooperate with the longitudinally adjacent distal, laterally inner staple forming pocket (F114*b*) to provide the resulting staple (86*a*) with a two-dimensional B-shape in which the crown and each bent leg of the formed staple (86*a*) lies in the same plane; each proximal, laterally intermediate staple forming pocket (F114*c*) is configured to cooperate with the longitudinally adjacent distal, laterally intermediate staple forming pocket (F114*d*) to provide the resulting staple (86*b*) with a first three-dimensional formed shape in which the crown and each bent leg of the formed staple (86*b*) lies in a different plane; and each proximal, laterally outer staple forming pocket (F114*e*) is configured to cooperate with the longitudinally adjacent distal, laterally outer staple forming pocket (F114*f*) to provide the resulting staple (86*c*) with a second three-dimensional formed shape different from the first three-dimensional formed shape in which the crown and each bent leg of the formed staple (86*c*) lies in a different plane. For example, such first and/or second three-dimensional formed shapes may be provided in accordance with any one or more teachings of U.S. Pat. No. 11,229,433, entitled "Linear Surgical Stapler," issued on Jan. 25, 2022, the disclosure of which is incorporated by reference herein.

As shown in FIG. 134, each individual staple forming pocket (F114*a*, F114*b*, F114*c*, F114*d*, F114*e*, F114*f*) of the present version includes a respective wide entry end (F130*a*, F130*b*, F130*c*, F130*d*, F130*e*, F130*f*) (also referred to as a staple catch area), and a respective narrow exit end (F132*a*, F132*b*, F132*c*, F132*d*, F132*e*, F132*f*) (also referred to as a staple forming area). Each pocket (F114*a*, F114*b*, F114*c*, F114*d*, F114*e*, F114*f*) further includes a respective concave base surface (F134*a*, F134*b*, F134*c*, F134*d*, F134*e*, F134*f*) that extends between the corresponding entry end (F130*a*, F130*b*, F130*c*, F130*d*, F130*e*, F130*f*) and exit end (F132*a*, F132*b*, F132*c*, F132*d*, F132*e*, F132*f*) such that each pocket (F114*a*, F114*b*, F114*c*, F114*d*, F114*e*, F114*f*) has a varying depth along its length.

In the example shown, entry and exit ends (F130*a*, F130*b*, F132*a*, F132*b*) of laterally inner staple forming pockets (F114*a*, F114*b*) extend substantially parallel to the longitudinal axis (LA), with the width of each proximal, laterally inner staple forming pocket (F114*a*) tapering gradually inwardly in a distal direction from the respective entry end (F130*a*) to the respective exit end (F132*a*); and the width of each distal, laterally inner staple forming pocket (F114*b*) tapering gradually inwardly in a proximal direction from the respective entry end (F130*b*) to the respective exit end (F132*b*). Entry ends (F130*a*, 130*b*) are each configured to receive and guide a staple leg in an unformed state longitudinally along the respective concave base surface (F134*a*, F134*b*) and toward the respective exit end (F132*a*, F132*b*) to be deformed. Exit ends (F132*a*, F132*b*) are each configured to guide the staple leg in a deformed state in a direction toward lower cartridge jaw (42) and into clamped tissue (T). The exit end (F132*a*) of each proximal, laterally inner staple forming pocket (F114*a*) is longitudinally adjacent to the exit end (F132*b*) of the corresponding longitudinally-paired distal, laterally inner staple forming pocket (F114*b*). In some versions, the exit ends (F132*a*, F132*b*) of longitudinally-paired laterally-inner staple forming pockets (F114*a*, F114*b*) may overlap or otherwise directly communicate with each other, such that each longitudinal pair of laterally-inner staple forming pockets (F114*a*, F114*b*) may be effectively merged to define a single corresponding laterally-inner staple forming pocket.

When end effector (40) is closed such that each pair of laterally inner pockets (F114*a*, F114*b*) is vertically aligned with a corresponding cartridge pocket (not shown) in a laterally inner row of the staple cartridge that is received within lower cartridge jaw (42), each laterally inner pocket (F114*a*, F114*b*) is symmetrical about an inner longitudinal centerline (LG1) that extends parallel to the longitudinal axis (LA) through the center points (C1) of the laterally inner cartridge pockets; and each proximal, laterally inner staple forming pocket (F114*a*) is symmetric relative to the corresponding longitudinally-paired distal, laterally inner staple forming pocket (F114*b*) about a corresponding lateral centerline (LT1) that extends perpendicular to the longitudinal axis (LA) through the center point (C1) of the corresponding laterally inner cartridge pocket.

In the example shown, entry ends (F130*c*, F130*d*) of laterally intermediate staple forming pockets (F114*c*, F114*d*) extend substantially parallel to the longitudinal axis (LA), while exit ends (F132*c*, F132*d*) of laterally intermediate staple forming pockets (F114*c*, F114*d*) extend substantially obliquely relative to the longitudinal axis (LA). In this regard, exit ends (F132*c*) of proximal, laterally intermediate staple forming pockets (F114*c*) are oriented laterally outwardly relative to the longitudinal axis (LA) at a first angle (α1), and exit ends (F132*d*) of distal, laterally intermediate staple forming pockets (F114*d*) are oriented laterally inwardly relative to the longitudinal axis (LA) at the first angle (α1). A medial portion of each laterally intermediate staple forming pocket (F114*c*, F114*d*) located between the respective entry and exit ends (F130*c*, F130*d*, F132*c*, F132*d*) includes an angled and/or curved sidewall (F136*c*, F136*d*) that faces toward the respective entry end (F130*c*, F130*d*) and which is longitudinally adjacent to the exit end (F132*c*, F132*d*) of the corresponding longitudinally-paired laterally intermediate staple forming pocket (F114*c*, F114*d*). Entry ends (F130*c*, F130*d*) are each configured to receive and guide a staple leg in an unformed state longitudinally along the respective concave base surface (F134*c*, F134*d*) and toward the respective angled sidewall (F136*c*, F136*d*) to be deformed. Exit ends (F132*c*, F132*d*) are each configured to guide the staple leg in a deformed state in a direction toward lower cartridge jaw (42) and into clamped tissue (T). The exit end (F132*c*) of each proximal, laterally intermediate staple forming pocket (F114*c*) is laterally adjacent to, and extends substantially parallel to, the exit end (F132*d*) of the corresponding longitudinally-paired distal, laterally intermediate staple forming pocket (F114*d*).

When end effector (40) is closed such that each pair of laterally intermediate pockets (F114*c*, F114*d*) is vertically aligned with a corresponding cartridge pocket (not shown) in a laterally intermediate row of the staple cartridge that is received within lower cartridge jaw (42), each laterally intermediate pocket (F114*c*, F114*d*) is asymmetrical about an intermediate longitudinal centerline (LG2) that extends parallel to the longitudinal axis (LA) through the center points (C2) of the laterally intermediate cartridge pockets; and each proximal, laterally intermediate staple forming pocket (F114*c*) is asymmetric relative to the corresponding longitudinally-paired distal, laterally intermediate staple forming pocket (F114*d*) about a corresponding lateral centerline (LT2) that extends perpendicular to the longitudinal axis (LA) through the center point (C2) of the corresponding laterally intermediate cartridge pocket.

While exit ends (F132*c*, F132*d*) of each pair of laterally intermediate pockets (F114*c*, F114*d*) may exhibit point symmetry relative to each other about the center point (C2) of the corresponding laterally intermediate cartridge pocket, entry ends (F130*c*, F130*d*) of each pair of laterally intermediate pockets (F114*c*, F114*d*) do not exhibit point symmetry relative to each other about the center point (C2) of the corresponding laterally intermediate cartridge pocket, such that each pair of laterally intermediate pockets (F114*c*, F114*d*) taken as a whole does not exhibit point symmetry relative to each other about the center point (C2) of the corresponding laterally intermediate cartridge pocket. In this regard, the entry end (F130*c*, F130*d*) of each laterally intermediate pocket (F114*c*, F114*d*) may have a first width (W1) that is asymmetric about the intermediate longitudinal centerline (LG2). For example, the first width (W1) of each entry end (F130*c*, F130*d*) may have a first width portion (WIP1) laterally inward of the intermediate longitudinal centerline (LG2), and a second width portion (W1P2) laterally outward of the intermediate longitudinal centerline (LG2) and greater than the first width portion (WIP1). Thus, each pair of laterally intermediate pockets (F114*c*, F114*d*) may be asymmetric about each of the intermediate longitudinal centerline (LG2), the corresponding intermediate lateral centerline (LT2), and the center point (C2) of the corresponding laterally intermediate cartridge pocket. Such asymmetry may enable maximizing the sizes of entry ends (F130*c*, F130*d*) within the available space provided on anvil surface (F112), thereby improving the ability of entry ends (F130*c*, F130*d*) to receive and guide the respective staple legs.

In the example shown, entry ends (F130*e*, F130*f*) of laterally outer staple forming pockets (F114*e*, F114*f*) extend substantially parallel to the longitudinal axis (LA), while exit ends (F132*e*, F132*f*) of laterally outer staple forming pockets (F114*e*, F114*f*) extend substantially obliquely relative to the longitudinal axis (LA). In this regard, exit ends (F132*e*) of proximal, laterally outer staple forming pockets (F114*e*) are oriented laterally outwardly relative to the longitudinal axis (LA) at a second angle (α2) greater than or otherwise substantially different from the first angle (α1), and exit ends (F132*f*) of distal, laterally outer staple forming pockets (F114*f*) are oriented laterally inwardly relative to the longitudinal axis (LA) at the second angle (α2). A medial portion of each laterally outer staple forming pocket (F114*e*, F114*f*) located between the respective entry and exit ends (F130*e*, F130*f*, F132*c*, F132*f*) includes an angled and/or curved sidewall (F136*e*, F136*f*) that faces toward the respective entry end (F130*e*, F130*f*) and which is longitudinally adjacent to the exit end (F132*e*, F132*f*) of the corresponding longitudinally-paired laterally outer staple forming pocket (F114*e*, F114*f*). Entry ends (F130*e*, F130*f*) are each configured to receive and guide a staple leg in an unformed state longitudinally along the respective concave base surface (F134*c*, F134*f*) and toward the respective angled sidewall (F136*e*, F136*f*) to be deformed. Exit ends (F132*e*, F132*f*) are each configured to guide the staple leg in a deformed state in a direction toward lower cartridge jaw (42) and into clamped tissue (T). The exit end (F132*e*) of each proximal, laterally outer staple forming pocket (F114*e*) is laterally adjacent to, and extends substantially parallel to, the exit end (F132*f*) of the corresponding longitudinally-paired distal, laterally outer staple forming pocket (F114*f*).

When end effector (40) is closed such that each pair of laterally outer pockets (F114*e*, F114*f*) is vertically aligned with a corresponding cartridge pocket (not shown) in a laterally outer row of the staple cartridge that is received within lower cartridge jaw (42), each laterally outer pocket (F114*e*, F114*f*) is asymmetrical about an intermediate longitudinal centerline (LG3) that extends parallel to the longitudinal axis (LA) through the center points (C3) of the laterally outer cartridge pockets; and each proximal, laterally outer staple forming pocket (F114*e*) is asymmetric relative to the corresponding longitudinally-paired distal, laterally outer staple forming pocket (F114*f*) about a corresponding lateral centerline (LT3) that extends perpendicular to the longitudinal axis (LA) through the center point (C3) of the corresponding laterally outer cartridge pocket.

While exit ends (F132*e*, F132*f*) of each pair of laterally outer pockets (F114*e*, F114*f*) may exhibit point symmetry relative to each other about the center point (C3) of the corresponding laterally outer cartridge pocket, entry ends (F130*e*, F130*f*) of each pair of laterally outer pockets (F114*e*, F114*f*) do not exhibit point symmetry relative to each other about the center point (C3) of the corresponding laterally outer cartridge pocket, such that each pair of laterally outer pockets (F114*e*, F114*f*) taken as a whole does not exhibit point symmetry relative to each other about the center point (C3) of the corresponding laterally outer cartridge pocket. In this regard, the entry end (F130*e*, F130*f*) of each laterally outer pocket (F114*e*, F114*f*) may have a second width (W2) greater than the first width (W1) that is asymmetric about the outer longitudinal centerline (LG3). For example, the second width (W2) of each entry end (F130*e*, F130*f*) may have a first width portion (W2P1) laterally inward of the outer longitudinal centerline (LG3), and a second width portion (W2P2) laterally outward of the outer longitudinal centerline (LG3) and greater than the first width portion (W2P1). Thus, each pair of laterally outer pockets (F114*e*, F114*f*) may be asymmetric about each of the outer longitudinal centerline (LG3), the corresponding outer lateral centerline (LT3), and the center point (C3) of the corresponding laterally outer cartridge pocket. Such asymmetry may enable maximizing the sizes of entry ends (F130*e*, F130*f*) within the available space provided on anvil surface (F112), thereby improving the ability of entry ends (F130*e*, F130*f*) to receive and guide the respective staple legs.

In the example shown, each proximal, laterally inner staple forming pocket (F114*a*) is substantially at a same longitudinal position as a corresponding proximal, laterally outer staple forming pocket (F114*e*), and each distal, laterally inner staple forming pocket (F114*b*) is substantially at a same longitudinal position as a corresponding distal, laterally outer staple forming pocket (F114*f*), such that each staple (86*a*) formed by each pair of laterally inner staple forming pockets (F114*a*, F114*b*) may be substantially at a same longitudinal position as the staple (86*c*) formed by the corresponding pair of laterally outer staple forming pockets (F114*e*, F114*f*). However, each proximal, laterally intermediate staple forming pocket (F114*c*) is substantially offset from each proximal, laterally inner and outer staple forming pocket (F114*a*, F114*e*), and each distal, laterally intermediate staple forming pocket (F114*d*) is substantially offset from each distal, laterally inner and outer staple forming pocket (F114*b*, F114*f*), such that each staple (86*b*) formed by each pair of laterally intermediate staple forming pockets (F114*c*, F114*d*) may be substantially offset from the staples (86*a*, 86*c*) formed by each pair of laterally inner staple forming pockets (F114*a*, F114*b*) and by each pair of outer staple forming pockets (F114*e*, F114*f*). For example, each proximal, laterally intermediate staple forming pocket (F114*c*) may be substantially at a same longitudinal position as corresponding distal, laterally inner and outer staple forming pockets (F114*b*, F114*f*), and each distal, laterally intermediate staple forming pocket (F114*d*) may be substantially at a same longitudinal position as corresponding proximal, laterally inner and outer staple forming pockets (F114*a*, F114*e*).

In this manner, the orientations of staple forming pockets (F114*a*, F114*b*, F114*c*, F114*d*, F114*e*, F114*f*) may vary in the lateral direction. More particularly, the orientations may vary from substantially parallel to the longitudinal axis (LA) in the case of each proximal, laterally inner staple forming pocket (F114*a*), to substantially skewed laterally inwardly toward the longitudinal axis (LA) in the case of the corresponding laterally-adjacent distal, laterally intermediate staple forming pocket (F114*d*) (e.g., by virtue of the orientation of the respective exit end (F132*d*)), to substantially skewed laterally outwardly away from the longitudinal axis (LA) in the case of the corresponding laterally-adjacent proximal, laterally outer staple forming pocket (F114*e*) (e.g., by virtue of the orientation of the respective exit end (F132*e*)); and may vary from substantially parallel to the longitudinal axis (LA) in the case of each distal, laterally inner staple forming pocket (F114*b*), to substantially skewed laterally outwardly away from the longitudinal axis (LA) in the case of the corresponding laterally-adjacent proximal, laterally intermediate staple forming pocket (F114*c*) (e.g., by virtue of the orientation of the respective exit end (F132*c*)), to substantially skewed laterally inwardly toward the longitudinal axis (LA) in the case of the corresponding laterally-adjacent distal, laterally outer staple forming pocket (F114*f*) (e.g., by virtue of the orientation of the respective exit end (F132*f*)).

It will be appreciated that the orientations of staple forming pockets (F114*a*, F114*b*, F114*c*, F114*d*, F114*e*, F114*f*) may vary in the lateral direction in any other suitable manner. For example, each distal, laterally intermediate staple forming pocket (F114*d*) and distal, laterally outer staple forming pocket (F114*f*) may be substantially skewed laterally outwardly away from the longitudinal axis (LA), and each proximal, laterally intermediate staple forming pocket (F114*c*) and proximal, laterally outer staple forming pocket (F114*e*) may be substantially skewed laterally inwardly toward the longitudinal axis (LA) in an inverse arrangement from that shown.

Referring now to FIG. 135, concave base surfaces (F134*a*, F134*b*) of laterally inner staple forming pockets (F114*a*, F114*b*) each have a first maximum depth (D1) relative to anvil surface (F112), concave base surfaces (F134*c*, F134*d*) of laterally intermediate staple forming pockets (F114*c*, F114*d*) each have a second maximum depth (not shown) relative to anvil surface (F112), and concave base surfaces (F134*e*, F134*f*) of laterally outer staple forming pockets (F114*e*, F114*f*) each have a third maximum depth (D3) relative to anvil surface (F112). As shown, the third maximum depth (D3) is greater than the first maximum depth (D1). In some cases, the second maximum depth may be greater than the first maximum depth (D1) and/or less than the third maximum depth (D3). In addition, or alternatively, the first maximum depth (D1) may be substantially equal to the second maximum depth and/or third maximum depth (D3). The various depths of concave base surfaces (F134*a*, F134*b*, F134*c*, F134*d*, F134*e*, F134*f*) may be selected to provide staples (86*a*, 86*b*, 86*c*) formed by staple forming pockets (F114*a*, F114*b*, F114*c*, F114*d*, F114*e*, F114*f*) with a substantially uniform height in each row. Alternatively, the various depths of concave base surfaces (F134*a*, F134*b*, F134*c*, F134*d*, F134*e*, F134*f*) may be selected to permit the different skews of by staple forming pockets (F114*a*, F114*b*, F114*c*, F114*d*, F114*e*, F114*f*) described above to impart staples (86*a*, 86*b*, 86*c*) with different heights from each other. This may be the case, for example, when the first maximum depth (D1) is substantially equal to each of the second maximum depth and third maximum depth (D3).

Entry ends (F130*a*, F130*b*, F130*c*, F130*d*, F130*e*, F130*f*) of staple forming pockets (F114*a*, F114*b*, F114*c*, F114*d*, F114*e*, F114*f*) may each be oriented downwardly relative to anvil surface (F112) (and/or relative to the longitudinal axis (LA)) in substantially different manners than the corresponding exit ends (F132*a*, F132*b*, F132*c*, F132*d*, F132*e*, F132*f*). For example, as shown in FIG. 136, the entry end (F130*e*) of each proximal, laterally outer staple forming pocket (F114*e*) is oriented downwardly relative to anvil surface (F112) (and/or relative to the longitudinal axis (LA)) at a first angle (β1), while the exit end (F132*e*) of each proximal, laterally outer staple forming pocket (F114*e*) is oriented downwardly relative to anvil surface (F112) (and/or relative to the longitudinal axis (LA)) at a second angle (β2) greater than or otherwise substantially different from the first angle (β1).

In some versions, the entry end (F130*f*) of each distal, laterally outer staple forming pocket (F114*f*) is oriented at the same first angle (β1) as the entry end (F130*e*) of each proximal, laterally outer staple forming pocket (F114*e*), and/or the exit end (F132*f*) of each distal, laterally outer staple forming pocket (F114*f*) is oriented at the same second angle (β2) as the exit end (F132*f*) of each proximal, laterally outer staple forming pocket (F114*e*). Alternatively, the entry end (F130*f*) of each distal, laterally outer staple forming pocket (F114*f*) may be oriented at a first angle substantially different from the first angle (β1) of the entry end (F130*e*) of each proximal, laterally outer staple forming pocket (F114*e*), and/or the exit end (F132*f*) of each distal, laterally outer staple forming pocket (F114*f*) may be oriented at a second angle substantially different from the second angle (β2) of the exit end (F132*f*) of each proximal, laterally outer staple forming pocket (F114*e*). Likewise, any one or more of the entry ends (F130*a*, F130*b*, F130*c*, F130*d*) of each laterally inner and/or laterally intermediate staple forming pocket (F114*a*, F114*b*, F114*c*, F114*d*) may be oriented at either the same first angle (β1) as the entry end (F130*e*) of each proximal, laterally outer staple forming pocket (F114*e*), or a first angle substantially different from the first angle (β1) of the entry end (F130*e*) of each proximal, laterally outer staple forming pocket (F114*c*); and/or any one or more of the exit ends (F132*a*, F132*b*, F132*c*, F132*d*) of each laterally inner and/or laterally intermediate staple forming pocket (F114*a*, F114*b*, F114*c*, F114*d*) may be oriented at either the same second angle (β2) as the exit end (F132*e*) of each proximal, laterally outer staple forming pocket (F114*e*), or a second angle substantially different from the second angle (β2) of the exit end (F132*e*) of each proximal, laterally outer staple forming pocket (F114*e*).

It will be appreciated that the orientations of entry ends (F130*a*, F130*b*, F130*c*, F130*d*, F130*e*, F130*f*) and exit ends (F132*a*, F132*b*, F132*c*, F132*d*, F132*e*, F132*f*) relative to anvil surface (F112) (and/or relative to the longitudinal axis (LA)), such as first and second angles (B1, B2), may affect the shape of the corresponding formed staple (86*a*, 86*b*, 86*c*), such as a radius of the corresponding formed staple (86*a*, 86*b*, 86*c*) (e.g., when viewed from the side), and may thereby impact springback and/or compression of tissue (T) within the inside area of the corresponding formed staple (86*a*, 86*b*, 86*c*). Thus, the orientations of entry ends (F130*a*, F130*b*, F130*c*, F130*d*, F130*e*, F130*f*) and exit ends (F132*a*, F132*b*, F132*c*, F132*d*, F132*e*, F132*f*) relative to anvil surface (F112) (and/or relative to the longitudinal axis (LA)), such as first and second angles (β1, β2), may be selected to impart the corresponding formed staples (86*a*, 86*b*, 86*c*) with one or more desired shapes.

FIG. 136 also shows the third maximum depth (D3) of laterally outer staple forming pockets (F114*e*, F114*f*) relative to anvil surface (F112). As noted above, the third maximum depth (D3) may be substantially different from the first maximum depth (D1) of laterally inner staple forming pockets (F114*a*, F114*b*) and/or the second maximum depth of laterally intermediate staple forming pockets (F114*c*, F114*d*). For example, the third maximum depth (D3) of laterally outer staple forming pockets (F114*e*, F114*f*) may be greater than the second maximum depth of laterally intermediate staple forming pockets (F114*c*, F114*d*).

In this manner, the depths of staple forming pockets (F114*a*, F114*b*, F114*c*, F114*d*, F114*e*, F114*f*) may vary in the lateral direction. More particularly, the depths may vary from the first maximum depth (D1) in the case of each laterally inner staple forming pocket (F114*a*, F114*b*), to the second maximum depth in the case of the corresponding laterally-adjacent, laterally intermediate staple forming pocket (F114*d*, 114*e*), to the third maximum depth (D3) in the case of the corresponding laterally-adjacent, laterally outer staple forming pocket (F114*e*, F114*f*).

As shown in FIG. 137, staple (86*a*) formed by inner staple forming pockets (F114*a*, F114*b*) and staple (86*c*) formed by outer staple forming pockets (F114*e*, F114*f*) are substantially at a same longitudinal position as each other such that staples (86*a*, 86*c*) are substantially aligned with each other, while staple (86*b*) formed by intermediate staple forming pockets (F114*c*, F114*d*) is at a substantially different (e.g., nominally different) longitudinal position from staples (86*a*, 86*c*) such that staple (86*b*) is substantially offset from staples (86*a*, 86*c*).

As shown, staple (86*a*) is formed by inner staple forming pockets (F114*a*, F114*b*) with a two-dimensional shape (also referred to as a planar shape), while staple (86*b*) is formed by intermediate staple forming pockets (F114*c*, F114*d*) with a three-dimensional shape (also referred to as a non-planar shape) and staple (86*c*) is formed by outer staple forming pockets (F114*e*, F114*f*) with another three-dimensional shape. In this regard, the crown (87*a*) and both proximal and distal legs (88*a*, 89*a*) of staple (86*a*) all lie in a same plane as each other, with the tips of legs (88*a*, 89*a*) laterally aligned with each other. Staple (86*a*) may be substantially B-shaped in the plane in which crown (87*a*) and both legs (88*a*, 89*a*) reside.

On the other hand, the proximal and distal legs (88*b*, 89*b*) of staple (86*b*) lie in different planes from each other and from crown (87*b*), with the tips of legs (88*b*, 89*b*) laterally offset from each other and from crown (87*b*) on opposed sides of crown (87*b*). More particularly, proximal leg (88*b*) skews laterally outwardly away from the longitudinal axis (LA) at the first angle (α1) relative to crown (87*b*), and distal leg (89*b*) skews laterally inwardly toward the longitudinal axis (LA) at the first angle (α1) relative to crown (87*b*).

Similarly, the proximal and distal legs (88*c*, 89*c*) of staple (86*c*) lie in different planes from each other and from crown (87*c*), with the tips of legs (88*c*, 89*c*) laterally offset from each other and from crown (87*c*) on opposed sides of crown (87*c*). More particularly, proximal leg (88*c*) skews laterally outwardly away from the longitudinal axis (LA) at the second angle (α2) relative to crown (87*c*), and distal leg (89*c*) skews laterally inwardly toward the longitudinal axis (LA) at the second angle (α2) relative to crown (87*c*). As noted above, the second angle (α2) is greater than the first angle (α1), such that the tips of legs (88*c*, 89*c*) may be laterally offset from crown (87$c$) to a greater degree than that at which the tips of legs (88$b$, 89$b$) are laterally offset from crown (87$b$). In the example shown, the crowns (87$a$, 87$b$, 87$c$) of formed staples (86$a$, 86$b$, 86$c$) are parallel to each other and to the longitudinal axis (LA), such that the crowns (87$a$, 87$b$, 87$c$) may likewise be parallel to the cut line produced by cutting edge (58). In some versions, formed staples (86$a$, 86$b$, 86$c$) may each have a same height (h) as each other in the vertical direction, as shown in FIG. 138. In addition, or alternatively, formed staples (86$a$, 86$b$, 86$c$) may each be formed from a same type of unformed staple (e.g., unformed staple (86)).

Due to the different formed shapes of staples (86$a$, 86$b$, 86$c$), formed staples (86$a$, 86$b$, 86$c$) may provide varying amounts of tissue compression and leak path resistance in the lateral direction, even in cases where formed staples (86$a$, 86$b$, 86$c$) each have a same height as each other. For example, the 2D formed configuration of staple (86$a$) with non-skewed legs (88$a$, 89$a$) may provide a tightest tissue compression and/or a lowest amount of leak path resistance relative to the other staples (86$b$, 86$c$); the 3D formed configuration of staple (86$b$) with legs (88$b$, 89$b$) skewed at the first angle ($\alpha$1) may provide looser tissue compression than staple (86$a$) and/or a greater amount of leak path resistance than staple (86$a$); and/or the 3D formed configuration of staple (86$c$) with legs (88$c$, 89$c$) skewed at the second angle ($\alpha$2) may provide a loosest tissue compression and/or a highest amount of leak path resistance relative to the other staples (86$a$, 86$b$). Thus, the rows of formed staples (86$a$, 86$b$, 86$c$) on each side of the cut line produced by cutting edge (58) may collectively achieve both tight tissue compression and good leak path resistance on each side of the cut line.

In this regard, the laterally inner row of formed staples (86$a$) on each side of the cut line may provide the tightest (e.g., localized) tissue compression near the cut line, while the laterally intermediate row of formed staples (86$b$) on each side of the cut line may provide more evenly distributed (e.g., less localized) tissue compression farther away from the cut line, and the laterally outer row of formed staples (86$c$) on each side of the cut line may provide the most evenly distributed (e.g., least localized) tissue compression farthest away from the cut line. Providing the tightest tissue compression immediately adjacent to the cut line via the innermost staples (86$a$) in this manner (e.g., rather than via the relatively outer staples (86$b$, 86$c$)) may ensure an effective seal and/or promote fast healing of the severed tissue (T) along the cut line; while providing the more evenly distributed tissue compression farther away from the cut line via the intermediate and outermost staples (86$b$, 86$c$) in this manner (e.g., rather than via the innermost staples (86$a$)) may relieve strain on the severed tissue (T) and inhibit leakage across the outer and intermediate rows of staples (86$b$, 86$c$) toward the inner row of staples (86$a$).

XIV. Example of Anvil Having Row of Staple Forming Pockets with Laterally Offset Proximal and Distal Pockets In some instances, it may be desirable to arrange and configure staple forming pockets (F114$a$, F114$b$, F114$c$, F114$d$, F114$e$, F114$f$) of anvil jaw (F110) to further improve the consistency of the formation of at least some staples (86$a$, 86$b$, 86$c$). FIG. 139 shows an example of an anvil jaw (F210) (also referred to as an "anvil") that may provide such capabilities, and that may be incorporated into end effector (40) in place of anvil jaw (44). Anvil jaw (F210) may be similar to anvil jaw (F110) described above, except as otherwise described below. In this regard, anvil jaw (F210) may be configured to pivot relative to cartridge jaw (42) of end effector (40) (or cartridge jaw (42) may be configured to pivot relative to anvil jaw (F210)), to clamp tissue therebetween.

In the example shown, anvil jaw (F210) includes a body (F211) having an interior side that defines an anvil surface (F212) configured to compress tissue and three linear (e.g., straight) rows of staple forming pockets on each side of an anvil slot (not shown), including a laterally inner row of staple forming pockets (not shown) similar to staple forming pockets (F114$a$, F114$b$), a laterally intermediate row of staple forming pockets (F214$c$, F214$d$), and a laterally outer row of staple forming pockets (not shown) similar to staple forming pockets (F114$e$, F114$f$). The laterally inner and outer rows of staple forming pockets may be configured and arranged as shown and described above in connection with FIGS. 132-136.

As shown, staple forming pockets (F214$c$, F214$d$) are arranged in longitudinally adjacent pairs such that each pair is configured to receive and deform the legs of a respective staple (86$b$) and thereby transform the staple (86$b$) into a formed shape when firing beam (46) is actuated distally. More particularly, each proximal, laterally intermediate staple forming pocket (F214$c$) is configured to cooperate with the longitudinally adjacent distal, laterally intermediate staple forming pocket (F214$d$) to provide the resulting staple (86$b$) with a three-dimensional formed shape in which the crown and each bent leg of the formed staple (86$b$) lies in a different plane.

The laterally intermediate row of staple forming pockets (F214$c$, F214$d$) may be configured and arranged in a manner similar to that shown and described above in connection with FIGS. 132-136, except that in the present version, each proximal, laterally intermediate staple forming pocket (F214$c$) is laterally offset from the longitudinally adjacent distal, laterally intermediate staple forming pocket (F214$d$). More particularly, a first longitudinal centerline (LG1) of each proximal, laterally intermediate staple forming pocket (F214$c$) is laterally offset from (e.g., laterally outward of) a second longitudinal centerline (LG2) of each distal, laterally intermediate staple forming pocket (F214$d$). In contrast, the proximal and distal laterally inner staple forming pockets may be arranged along a common, laterally inner longitudinal centerline (not shown); and/or the proximal and distal laterally outer staple forming pockets may be arranged along a common, laterally outer longitudinal centerline (not shown).

Due to the lateral offset in the laterally intermediate row of staple forming pockets (F214$c$, F214$d$), the proximal staple leg (88$b$) of each second staple (86$b$) may contact a surface of the proximal, laterally intermediate staple forming pocket (F214$c$) earlier, at least by comparison to the proximal laterally, intermediate staple forming pocket (F114$c$), to assist with ensuring that the proximal staple leg (88$b$) is angled properly to achieve the desired formation of the second staple (86$b$).

While each proximal, laterally intermediate staple forming pocket (F214$c$) is laterally offset from the longitudinally adjacent distal, laterally intermediate staple forming pocket (F214$d$) in the example shown, in some other versions the proximal and distal laterally intermediate staple forming pockets (F214$c$, F214$d$) may be arranged along a common, laterally intermediate longitudinal centerline. In such cases, the proximal and distal laterally inner staple forming pockets may be laterally offset from each other; and/or the proximal and distal laterally outer staple forming pockets may be laterally offset from each other.

XV. Examples of Staples for Anvil Having Laterally Offset Proximal and Distal Staple Forming Pockets In some instances, it may be desirable to adjust a position and/or shape of a crown (87*a*, 87*b*, 87*c*) of at least some staples (86*a*, 86*b*, 86*c*) to further improve the consistency of the formation of at least some staples (86*a*, 86*b*, 86*c*). FIGS. 140 and 141 schematically show an example of an anvil jaw (F310) (also referred to as an "anvil") that may be incorporated into end effector (40) in place of anvil jaw (44). Anvil jaw (F310) may be similar to anvil jaw (F210) described above, except as otherwise described below. In this regard, anvil jaw (F310) may be configured to pivot relative to cartridge jaw (42) of end effector (40) (or cartridge jaw (42) may be configured to pivot relative to anvil jaw (F310)), to clamp tissue therebetween.

In the example shown, anvil jaw (F310) includes three linear (e.g., straight) rows of staple forming pockets on each side of an anvil slot (not shown), including a laterally inner row of staple forming pockets (not shown) similar to staple forming pockets (F114*a*, F114*b*), a laterally intermediate row of staple forming pockets (F314*c*, F314*d*), and a laterally outer row of staple forming pockets (not shown) similar to staple forming pockets (F114*e*, F114*f*). The laterally inner and outer rows of staple forming pockets may be configured and arranged as shown and described above in connection with FIGS. 132-136.

As shown, staple forming pockets (F314*c*, F314*d*) are arranged in longitudinally adjacent pairs such that each pair is configured to receive and deform the legs of a respective staple (86*b*) and thereby transform the staple (86*b*) into a formed shape when firing beam (46) is actuated distally. More particularly, each proximal, laterally intermediate staple forming pocket (F314*c*) is configured to cooperate with the longitudinally adjacent distal, laterally intermediate staple forming pocket (F314*d*) to provide the resulting staple (86*b*) with a three-dimensional formed shape in which the crown and each bent leg of the formed staple (86*b*) lies in a different plane. In the present version, each proximal, laterally intermediate staple forming pocket (F314*c*) is laterally offset from the longitudinally adjacent distal, laterally intermediate staple forming pocket (F314*d*).

As shown in FIG. 140, the crown (87*b*) of each second staple (86*b*) may be positioned to further improve the consistency of the formation of second staples (86*b*). More particularly, the crown (87*b*) of each second staple (86*b*) may be oriented obliquely relative to the anvil slot, rather than being parallel to the anvil slot, to thereby provide the formed staple (86*b*) with an enhanced 3D shape.

As shown in FIG. 141, an alternative second staple (F386*b*) includes a generally zigzag-shaped crown (F387*b*) and a pair of legs (F388*b*, F389*b*). More particularly, the crown (F387*b*) of each second staple (F386*b*) includes a proximal segment (F390) oriented obliquely relative to the anvil slot, an intermediate segment (F391) oriented parallel to the anvil slot, and a distal segment (F392) oriented obliquely relative to the anvil slot, to thereby provide the formed staple (F386*b*) with an enhanced 3D shape.

XVI. Examples of Asymmetric Staple Patterns

In some instances, it may be desirable to adjust the arrangement of staples (86*a*, 86*b*, 86*c*) to further improve the consistency of the formation of at least some staples (86*a*, 86*b*, 86*c*) and/or to further inhibit leakage across the rows of staples (86*a*, 86*b*, 86*c*). FIGS. 142 and 143 show examples of alternative arrangements of staples (86*a*, 86*b*, 86*c*) that may provide such capabilities.

As shown in FIG. 142, staples (86*a*, 86*b*, 86*c*) are asymmetric relative to the cut line (CL) produced by cutting edge (58). More particularly, staples (86*b*, 86*c*) are oriented in a uniform manner on both sides of the cut line (CL). It will be appreciated that the arrangement of staples (86*a*, 86*b*, 86*c*) shown in FIG. 142 may be achieved using a modified version of anvil jaw (F110) that will be readily apparent to persons skilled in the art. For example, such a modified version of anvil jaw (F110) may include staple forming pockets that are arranged asymmetrically relative to anvil slot (F122).

As shown in FIG. 143, second staples (86*b*) are oriented in an inverted manner relative to third staples (86*c*). It will be appreciated that the arrangement of staples (86*a*, 86*b*, 86*c*) shown in FIG. 143 may be achieved using a modified version of anvil jaw (F110) that will be readily apparent to persons skilled in the art.

XVII. Examples of Staple Crowns with Large Compression Areas

In some instances, it may be desirable to shape a crown (87*a*, 87*b*, 87*c*) of at least some staples (86*a*, 86*b*, 86*c*) to provide an increased compression profile. FIGS. 144 and 145 show examples of staples (F486, F586) that may provide such capabilities.

As shown in FIG. 144, staple (F486) includes a generally C-shaped crown (F487) and a pair of legs (F488, F489). It will be appreciated that C-shaped crown (F487) may be either preformed prior to firing, or formed during firing (e.g., bent from a straight/linear shape).

As shown in FIG. 145, staple (F586) includes a generally S-shaped crown (F587) and a pair of legs (F588, F589). It will be appreciated that S-shaped crown (F587) may be either preformed prior to firing, or formed during firing (e.g., bent from a straight/linear shape).

It will be understood that while the features shown and described above are presented in the context of anvil jaws (F110, F210, F310) for surgical stapler (10), such features may also be applied to staple cartridges configured for use with various other types of surgical staplers, such as linear surgical staplers.

XVIII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,094, entitled "Incompatible Staple Cartridge Use Prevention Features for Surgical Stapler," filed on Feb. 27, 2024, issued as U.S. Pat.

No. 12,324,583 on Jun. 10, 2025; U.S. patent application Ser. No. 18/588,147, entitled "Surgical Stapler Cartridge Having Intermediate Raised Tissue Engagement Protrusions," filed on Feb. 27, 2024, published as U.S. Pat. Pub. No. 2024/0382197 on Nov. 21, 2024; U.S. patent application Ser. No. 18/588,175, entitled "Surgical Stapler Cartridge Having Tissue Engagement Protrusions with Enlarged Engagement Surface," filed on Feb. 27, 2024, published as U.S. Pat. Pub. No. 2024/0382196 on Nov. 21, 2024; U.S. patent application Ser. No. 18/588,206, entitled "Surgical Stapler Cartridge Having Raised Surface to Promote Buttress Adhesion," filed on Feb. 27, 2024, published as U.S. Pat. Pub. No. 2024/0382202 on Nov. 21, 2024; U.S. patent application Ser. No. 18/588,240, entitled "Surgical Stapler Cartridge Having Cartridge Retention Features," filed on Feb. 27, 2024, issued as U.S. Pat. No. 12,285,170 on Apr. 29, 2025; and/or U.S. patent application Ser. No. 18/588,269, entitled "Surgical Stapler Anvil Having Staple Forming Pockets with Laterally Varying Orientations," filed on Feb. 27, 2024, published as U.S. Pat. Pub. No. 2024/0341761 on Oct. 17, 2024. The disclosure of each of the above patent references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling assembly, comprising:

(a) a body extending along a longitudinal axis and having an upper deck that defines a stapling surface;

(b) a plurality of pockets extending through the upper deck and configured to house respective staples, wherein the pockets are arranged in a plurality of longitudinal rows;

(c) a plurality of staple drivers aligned with and movable within the pockets for driving respective staples into tissue;

(d) a staple driver actuator translatable distally relative to the body for lifting the staple drivers sequentially;

(e) a plurality of first pocket extenders extending upwardly from the upper deck, wherein each first pocket extender includes a first top surface positioned at a first height above the upper deck; and (f) at least one second pocket extender extending upwardly from the upper deck and positioned distal to the plurality of first pocket extenders, wherein the at least one second pocket extender includes:

(i) a second top surface positioned at a second height above the upper deck, wherein the second height is different from the first height, (ii) a distally-facing surface having a first profile such that the distally-facing surface is configured to apply a first frictional force to tissue, and (iii) a proximally-facing surface having a second profile that is different from the first profile such that the proximally-facing surface is configured to apply a second frictional force to tissue that is greater than the first frictional force.

2. The surgical stapling assembly of claim 1, wherein the distally-facing surface extends substantially obliquely relative to the upper deck.

3. The surgical stapling assembly of claim 1, wherein the proximally-facing surface extends substantially orthogonally relative to the upper deck.

4. The surgical stapling assembly of claim 1, wherein the proximally-facing surface spans laterally at least partially across at least two longitudinal rows of the plurality of longitudinal rows of the plurality of pockets.

5. The surgical stapling assembly of claim 4, wherein the proximally-facing surface spans laterally at least partially across three longitudinal rows of the plurality of longitudinal rows of the plurality of pockets.

6. The surgical stapling assembly of claim 1, wherein the second height is greater than the first height.

7. The surgical stapling assembly of claim 1, wherein the second top surface is configured to contact an anvil prior to the first top surface contacting the anvil during approximation of the anvil toward the stapling assembly.

8. The surgical stapling assembly of claim 1, wherein at least one of the proximally-facing surface or the second top surface has a first surface finish, wherein the distally-facing surface has a second surface finish different from the first surface finish.

9. The surgical stapling assembly of claim 8, wherein the first surface finish is textured.

10. The surgical stapling assembly of claim 8, wherein the second surface finish is smooth.

11. A surgical stapling assembly, comprising:

(a) a body extending along a longitudinal axis and having an upper deck that defines a stapling surface;

(b) a plurality of pockets extending through the upper deck and configured to house respective staples, wherein the pockets are arranged in a plurality of longitudinal rows;

(c) a plurality of staple drivers aligned with and movable within the pockets for driving respective staples into tissue;

(d) a staple driver actuator translatable distally relative to the body for lifting the staple drivers sequentially;

(e) a plurality of first pocket extenders extending upwardly from the upper deck, wherein each of the plurality of first pocket extenders includes a first top surface;

(f) at least one second pocket extender extending upwardly from the upper deck and positioned distal to the plurality of first pocket extenders, wherein the at least one second pocket extender includes:

(i) a second top surface, and (ii) a distally-facing surface extending substantially obliquely relative to the upper deck;

(g) at least one longitudinal rail extending upwardly from the upper deck and proximally from the at least one second pocket extender, wherein the at least one longitudinal rail includes a third top surface; and (h) at least one bridge extending upwardly from the upper deck and laterally between at least one of:

(i) a corresponding pair of the first pocket extenders, or (ii) the at least one longitudinal rail and a corresponding one of the first pocket extenders, wherein the at least one bridge includes a fourth top surface.

12. The surgical stapling assembly of claim 11, wherein the at least one longitudinal rail includes a pair of longitudinal rails disposed on respective lateral sides of the longitudinal axis.

13. The surgical stapling assembly of claim 11, wherein the first, second, third, and fourth top surfaces are each positioned at a same height above the upper deck.

14. The surgical stapling assembly of claim 11, wherein the first, second, third, and fourth top surfaces are continuous with each other.

15. The surgical stapling assembly of claim 11, wherein the plurality of first pocket extenders, the at least one second pocket extender, the at least one rail, and the at least one bridge collectively define a continuous lattice structure.

16. A surgical stapling assembly, comprising:

(a) a body extending along a longitudinal axis and having an upper deck that defines a stapling surface;

(b) a plurality of pockets extending through the upper deck and configured to house respective staples, wherein the pockets are arranged in a plurality of longitudinal rows;

(c) a plurality of staple drivers aligned with and movable within the pockets for driving respective staples into tissue; and (d) a staple driver actuator translatable distally relative to the body for lifting the staple drivers sequentially, wherein the upper deck extends downwardly in a laterally outward direction from a laterally inner peak toward a laterally outer edge of the upper deck.

17. The surgical stapling assembly of claim 16, wherein the upper deck tapers downwardly in the laterally outward direction from the laterally inner peak toward the laterally outer edge of the upper deck.

18. The surgical stapling assembly of claim 16, wherein the upper deck curves downwardly in the laterally outward direction from the laterally inner peak toward the laterally outer edge of the upper deck.

19. The surgical stapling assembly of claim 18, wherein the upper deck includes a convex deck surface.

20. The surgical stapling assembly of claim 16, wherein the upper deck tapers downwardly in a distal direction from the laterally inner peak toward a distal end of the upper deck.

* * * * *